US010662432B2

(12) United States Patent
Mirsky et al.

(10) Patent No.: US 10,662,432 B2
(45) Date of Patent: May 26, 2020

(54) SYNTHETIC GENE CLUSTERS

(71) Applicant: The Regents of the University of California, Oakland, CA (US)

(72) Inventors: Ethan Mirsky, San Francisco, CA (US); Karsten Temme, San Francisco, CA (US); Christopher A. Voigt, Belmont, MA (US); Dehua Zhao, Allston, MA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/706,353

(22) Filed: Sep. 15, 2017

(65) Prior Publication Data
US 2018/0073028 A1 Mar. 15, 2018

Related U.S. Application Data

(60) Division of application No. 15/288,916, filed on Oct. 7, 2016, now Pat. No. 9,957,509, which is a continuation of application No. 14/126,307, filed as application No. PCT/US2012/042502 on Jun. 14, 2012, now Pat. No. 9,512,431.

(60) Provisional application No. 61/497,781, filed on Jun. 16, 2011.

(51) Int. Cl.
*C12N 15/63* (2006.01)
*C12N 15/00* (2006.01)
*C12N 1/20* (2006.01)
*G16B 25/00* (2019.01)
*G16B 30/00* (2019.01)
*C07K 14/255* (2006.01)
*C07K 14/26* (2006.01)
*C12N 15/52* (2006.01)
*C12N 15/67* (2006.01)
*C12N 15/74* (2006.01)
*C12N 9/02* (2006.01)

(52) U.S. Cl.
CPC .......... *C12N 15/635* (2013.01); *C07K 14/255* (2013.01); *C07K 14/26* (2013.01); *C12N 9/0095* (2013.01); *C12N 15/52* (2013.01); *C12N 15/63* (2013.01); *C12N 15/67* (2013.01); *C12N 15/74* (2013.01); *C12Y 118/06001* (2013.01); *G16B 25/00* (2019.02); *G16B 30/00* (2019.02)

(58) Field of Classification Search
None
See application file for complete search history.

(56) References Cited

U.S. PATENT DOCUMENTS

| | | | |
|---|---|---|---|
| 5,916,029 A | 6/1999 | Smith et al. | |
| 6,548,289 B1 | 4/2003 | Beynon et al. | |
| 7,084,331 B2 | 8/2006 | Tsuyoshi et al. | |
| 7,470,427 B2 | 12/2008 | Cocking | |
| 8,076,142 B2 | 12/2011 | Huang et al. | |
| 8,137,665 B2 | 3/2012 | Cocking | |
| 8,268,584 B1 | 9/2012 | Harwood et al. | |
| 8,377,671 B2 | 2/2013 | Cournac et al. | |
| 9,321,697 B2 | 4/2016 | Kumar et al. | |
| 9,487,451 B2 | 8/2016 | Doty et al. | |
| 9,512,431 B2 * | 12/2016 | Mirsky | C07K 14/255 |
| 9,657,298 B2 | 5/2017 | Soto, Sr. et al. | |
| 9,975,817 B2 | 5/2018 | Temme et al. | |
| 10,384,983 B2 | 8/2019 | Temme et al. | |
| 2004/0241847 A1 | 12/2004 | Okuyama et al. | |
| 2005/0081262 A1 | 4/2005 | Cook et al. | |
| 2006/0127988 A1 | 6/2006 | Wood et al. | |
| 2006/0243011 A1 | 11/2006 | Someus | |
| 2009/0105076 A1 | 4/2009 | Stewart et al. | |
| 2010/0028870 A1 | 2/2010 | Welch | |
| 2012/0015806 A1 | 1/2012 | Paikray et al. | |
| 2014/0011261 A1 | 1/2014 | Wang et al. | |
| 2014/0230504 A1 | 8/2014 | Finlayson et al. | |
| 2014/0336050 A1 | 11/2014 | Soto, Sr. et al. | |
| 2015/0101373 A1 | 4/2015 | Munusamy et al. | |
| 2015/0239789 A1 | 8/2015 | Kang et al. | |
| 2015/0315570 A1 | 11/2015 | Zhao et al. | |
| 2016/0292355 A1 | 10/2016 | Lou et al. | |
| 2018/0290942 A1 | 10/2018 | Voigt et al. | |
| 2018/0297905 A1 | 10/2018 | Temme et al. | |
| 2018/0297906 A1 | 10/2018 | Temme et al. | |
| 2019/0039964 A1 | 2/2019 | Temme et al. | |
| 2019/0144352 A1 | 5/2019 | Temme et al. | |

FOREIGN PATENT DOCUMENTS

| | | |
|---|---|---|
| CA | 2051071 A1 | 3/1993 |
| CN | 103451130 A | 12/2013 |
| JP | H01-225483 A | 9/1989 |
| WO | 93/05154 | 3/1993 |
| WO | 99009834 A2 | 3/1999 |
| WO | 2001007567 A1 | 2/2001 |
| WO | 2006005100 A1 | 1/2006 |

(Continued)

OTHER PUBLICATIONS

Pfleger et al.; "Combinatorial engineering of intergenic regions in operons tunes expression of multiple genes"; *Nature Biotechnology*. 24(8):1027-1031 (2006).

(Continued)

*Primary Examiner* — Chaning S Mahatan
(74) *Attorney, Agent, or Firm* — Kilpatrick Townsend & Stockton LLP

(57) ABSTRACT

Methods for making synthetic gene clusters are described.

15 Claims, 93 Drawing Sheets
Specification includes a Sequence Listing.

(56) References Cited

FOREIGN PATENT DOCUMENTS

| WO | 2009060012 A2 | 5/2009 |
|---|---|---|
| WO | 2009091557 A1 | 7/2009 |
| WO | 2011099019 A1 | 8/2011 |
| WO | 2011099024 A1 | 8/2011 |
| WO | 2011154960 A1 | 12/2011 |
| WO | 2013076687 A2 | 5/2013 |
| WO | 2014042517 A2 | 3/2014 |
| WO | 2014071182 A1 | 5/2014 |

OTHER PUBLICATIONS

Sleight et al.; "Designing and engineering evolutionary robust genetic circuits"; *J. Biological Engineering*; 4:12, 2010 (20 pages).
Temme et al.; "Refactoring the nitrogen fixation gene cluster from *Klebsiella oxytoca*"; *Proc. Natl. Acad. Sci. USA*; 109(18):7085-7090 (2012) ePub Apr. 16, 2021.
"T7 RNA Polymerase Expression System for *Bacillus megaterium*"; T7 RNAP Expression System Handbook, Jan. 2010, © MoBiTec GmbH, 18 pages.
The International Search Report and Written Opinion from PCT/US2012/042502, dated Jan. 31, 2013.
Chan et al., "Refactoring bacteriophage T7," *Molecular Systems Biology*, 2005, vol. 1, No. 1, pp. E1-E10 (doi: 10.1038/msb4100025).
Fischbach et al., "Prokaryotic gene clusters: A rich toolbox for synthetic biology," *Biotechnology Journal*, 2010, 15(12): 1277-1296.
Mirsky, Ethan M. (2012) *Refactoring the Salmonella Type III Secretion System*. (Doctoral Dissertation) Apr. 12, 2012 Retrieved from web at Proquest site (media.proquest.com/media/pq/classic/doc/2644519781/fmt/aijrep/NPDF?hl=&cit:auth=Mirsky).
Temme, Karsten Louis. (2011) *Designing and Engineering Complex Behavior in Living Machines*. (Doctoral Dissertation) Oct. 1, 2011. Retrieved from the web at escholarship.org/uc/item/1r41x99s.
Voigt et al., "Genetic parts to program bacteria " *Current Opinion in Biotechnology*, 2006, 17(5):548-557.
Voigt, C. (2011) "Gaining Access: Rebuilding Genetics from the Ground Up". Institute of Medicine Board on Global Health Forum on Microbial Threats. Mar. 14, 2011 (Mar. 14, 2011). Retrieved from the web at iom.edu/~/media/Files/ActivityFiles/PublicHealth/MicrobialThreats/2011-MAR-14/Voigt.pdf.
The Extended European Search Report from EP Appl. No. 12800054.4, dated Dec. 19, 2014.
Bageshwar, et al., "An Environmentally Friendly Engineered Azotobacter Strain That Replaces a Substantial Amount of Urea Fertilizer while Sustaining the Same Wheat Yield," 2017, App. Env. Micr. Article.
Kim, et al., "Constitutive expression of nitrogenase system in *Klebsiella oxytoca* by gene targeting mutation to the chromosomal nifLA operon," Journal of Biotechnology, vol. 10, 1989, pp. 293-302.
Marx, et al. "Broad-Host-Range cre-lox System for Antibiotic Marker Recycling in Gram-Negative Bacteria," BioTechniques, vol. 33, 2002, pp. 1062-1067.
Blanco, et al., "Sequence and molecular analysis of the nifL gene of *Azotobacter vinelandii*," Molecular Microbiology, vol. 9(4), 1993, pp. 869-879.
Hidaka, et al., "Promotion of the Growth of Rice by Inoculation of Nitrogen-Fixing-Activity-Enhanced Bacteria to the Rhizosphere," In: Pedrosa F.O., Hungria M., Yates G., Newton W.E. (eds.) Nitrogen Fixation: From Molecules to Crop Productivity. Current Plant Science and Biotechnology in Agriculture, 2002, vol. 38. Springer, Dordrecht.
Bali, et al., "Excretion of Ammonium by a nifL Mutant of *Azotobacter vinelandii* fixing Nitrogen.," Applied and Environmental Microbiology, May 1992, pp. 1711-1718.
Macneil, et al., "Mutations in nif Genes That Cause *Klebsiella pneumoniae* to be Derepressed for Nitrogenase Synthesis in the Presence of Ammonium," J Bacteriol., Nov. 1980; 144(2), pp. 744-751.
Qiu, et al., "Construction of Genetically Engineered Strains of *Enterobacter cloacae* (nifL~(-)A~(c))," Acta Phytophysiologica Sinica., [Jan. 1, 1999, 25(3), pp. 269-273].
Roncato-Maccari, et al., "Endophytic *Herbaspirillum seropedicae* expresses nif genes in gramineous plant,." FEMS Microbiology Ecology, 2003; 45, pp. 39-47.

\* cited by examiner

| Promoter Name | Sequence TAATACGACTCACTANNNNNAGA | Strength |
|---|---|---|
| WT | TAATACGACTCACTATAGGGAGA | 13780 |
| Mut1 | TAATACGACTCACTACAGGCAGA | 147 |
| Mut2 | TAATACGACTCACTAGAGAGAGA | 752 |
| Mut3 | TAATACGACTCACTAATGGGAGA | 1346 |
| Mut4 | TAATACGACTCACTATAGGTAGA | 2127 |
| Mut5 | TAATACGACTCACTAAAGGGAGA | 3738 |
| Mut6 | TAATACGACTCACTATTGGGAGA | 6710 |

FIG. 3

| Strain Name | E Promoter | N Promoter | Fixation |
|---|---|---|---|
| #1 (N259) | WT | WT | 20% |
| #2 (N438) | Mut 4 | Mut 5 | 9% |
| #3 (N307) | Mut 4 | Mut 2 | 12% |
| Reflection (N319) | WT | Mut 3 | 52% |

FIG. 5

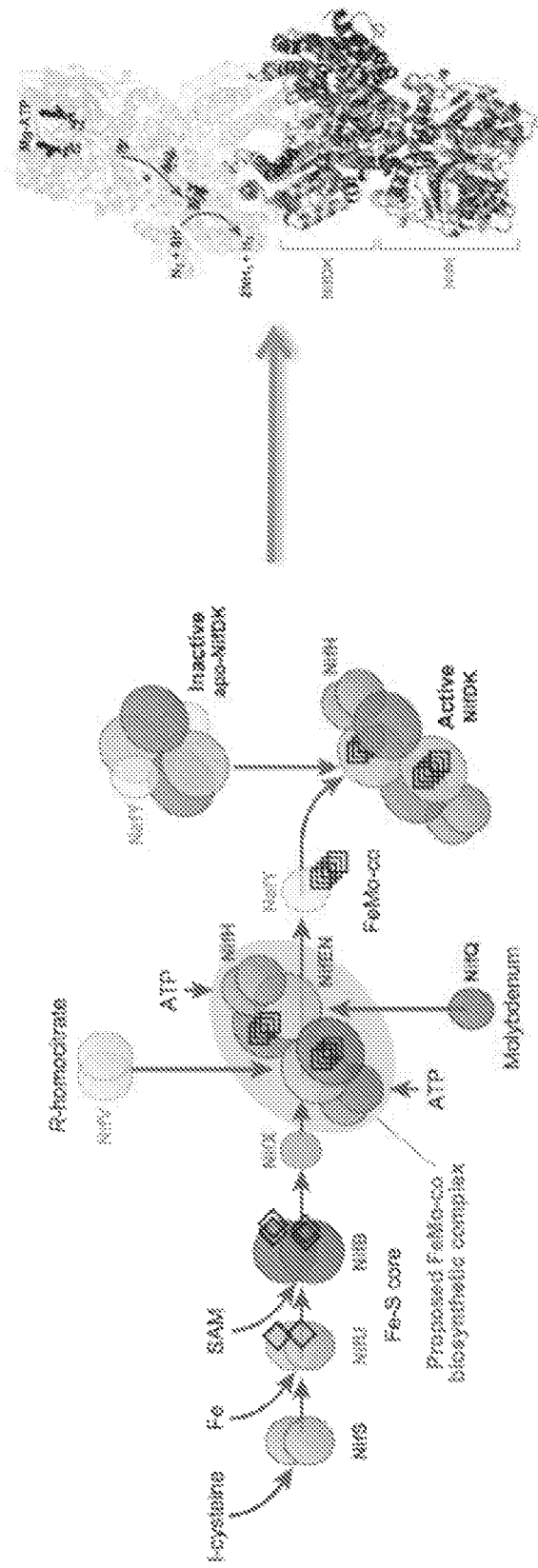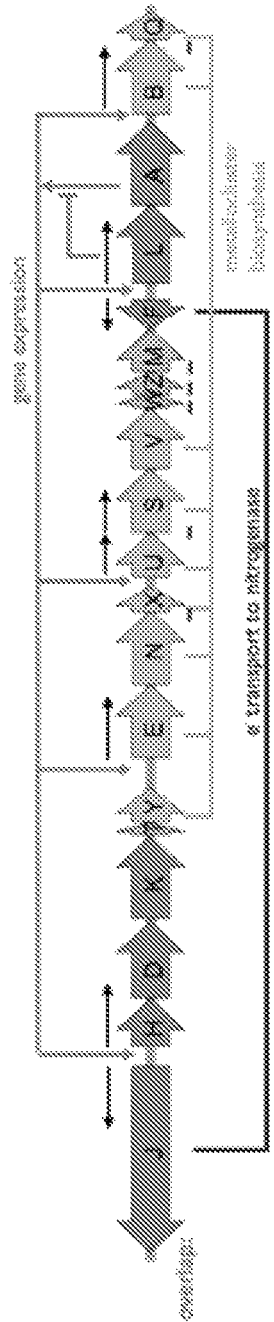
$N_2 + 8e^- + 8H^+ + 16 \text{ MgATP} \rightarrow 2 NH_3 + H_2$
Klebsiella oxytoca: 7 operons, 20 genes, 25 kb of DNA
FIG. 7

| Gene | Native RBS Strength | Synthetic RBS Strength |
|---|---|---|
| J | 254 | 104 |
| H | 21641 | 9903 |
| D | 446 | 496 |
| K | 23 | 54 |
| T | 303 | Eliminated |
| Y | 62 | 243 |
| E | 85 | 43 |
| N | 95 | 41 |
| X | 558 | Eliminated |
| U | 814 | 2832 |
| S | 686 | 174 |
| V | 11 | 5 |
| W | 39 | 43 |
| Z | 218 | 366 |
| M | 637 | 754 |
| F | 9283 | 46 |
| B | 80 | 221 |
| Q | Not Detectable | Not Detectable |

FIG. 10

| Operon | Error Location | Error |
|---|---|---|
| HDKY | H | Transposon insertion |
| USVWZM | S | Sequencing errors in Arnold NCBI entry (L110M, Q113E, S124G, R290A) |
| USVWZM | V | Sequencing errors in Arnold NCBI entry (L257S, D295H) |
| USVWZM | M | Cloning mutation |
| USVWZM | Ptac | Cloning error yielded constitutive promoter |

FIG. 12

| Operon | Function with Ptac promoter | T7 promoter | Function with T7 promoter |
|---|---|---|---|
| J | 109% | WT | 87% |
| HDKY | 39% | WT | 35% |
| EN | 75% | WT | 71% |
| USVWZM | 29% | Mut 2 | 25% |
| F | 112% | Mut 3 | 98% |
| BQ | 85% | Mut 2 | 80% |

| Gene | SEQ ID NO: | WT Sequence | Synthetic Sequence | % Nucleotide Identity | % Codon Identity |
|---|---|---|---|---|---|
| J | WT Gene J is SEQ ID NO:1<br><br>Synthetic Gene J is SEQ ID NO:2 | atgaaaacaatggatggcaacgccgcggcggcc<br>tggatctcttatgcctttaccgaggtcgcggcgattt<br>accccataaccccctccacgccgatggcggaaa<br>acgtcgacgagtgggcggcgcaggggaaaaag<br>aacctttttggccagccggtgcgcttaatggagat<br>gcagtcggaggccggcgcggcaggcgcggtcc<br>acggcgcgctgcaggccggggcgctcaccacc<br>acctatacggcctcccagggggctgctgctgatgat<br>ccccaacatgtacaaaatcgccggtgaactgctg<br>ccggcgtctttcacgtcagcgcccgggcgctgg<br>cgaccaattcgctgaatattttggcgatcaccagg<br>atgtgatggcggtccgccagaccggctgcgcgat<br>gctggcggagaacaacgtgcagcaggtgatgga<br>tttgtcggcggtggcgcatctggcggcgattaagg<br>gacgcatcccgtttgttaacttcttcgacggttttcg<br>cacctcgcacgaaattcaaaaaatcgaggtgttgg<br>aatatgagcagctggcgacgctgctggaccggc<br>ccgcgctcgacagcttccgccgtaacgcgctgca<br>tccggatcatccggtcatccgcggaacggcgcag<br>aacccggatatctacttccaggagcgggaggcg<br>ggcaaccgtttttatcaggcgctgcccgacattgtc<br>gaaagctatatgacgcaaatcagcgcgctcaccg<br>gccgggagtatcatctgttaactataccggcgcg<br>gcggatgccgaacgggtgattatcgcaatgggat<br>cggtctgcgataccgttcaggaagtggtggatac<br>gctgaacgcggcgggagagaaggtcgggctgct<br>cagcgtgcatctgtttcgcccttttttcgctggcccac<br>ttcttcgcccagctgccgaaaaccgtgcagcggat<br>tgccgtccttgaccgtaccaaagagcccggcgct<br>caggctgaaccgctgtgcctggatgtgaaaaacg<br>ccttctaccaccacgacgatgcgccgctaatcgtc<br>ggcggccgctatgcgcttggcgggaaggatgttc<br>tgcccaacgatatcgcggccgtctttgataacctca<br>ataaaccgctgccgatggacgggttaccctcgg<br>gattgtcgatgatgtaacctttacttcgttaccgccg<br>gcccagcagacgctggcggtctcgcatgacggc<br>atcaccgcctgtaaattttggggcatgggctcgga<br>cggcaccgtcggggccaataaaagcgcgatcaa<br>aattatcggcgataaaacgccgctctacgcgcag<br>gcctactttcttatgactcgaaaaaatccggcggc<br>attaccgtttcacatttacgcttcggcgaccggccg<br>atcaattcgccctacctgatccatcgggccgatttt<br>atctcctgttcgcagcagtcctacgttgagcgctac<br>gatctgctggacggattaaagccgggcgggacct<br>ttttactcaactgcagctggtccgatgcggagctg<br>gagcagcatctgccggtcggctttaaacgctatct<br>ggcgcgggaaaatatccatttttatacccctgaacg<br>ccgtggatatcgcccgcgagctcgggctgggcg<br>ggcgctttaatatgctgatgcaggcggcgttcttta<br>agctggcggcgattatcgacccgcagaccgcgg<br>cggattacctcaagcaggcggttgaaaaagcta<br>cggcagcaaaggggcggcggtgattgagatgaa | ATGAAAACTATGGACGGTAA<br>CGCTGCGGCTGCATGGATTA<br>GCTACGCCTTTACCGAAGTGG<br>CTGCGATCTACCCGATTACGC<br>CGAGCACCCCGATGGCGGAA<br>AATGTGGACGAATGGGCTGC<br>GCAGGGCAAGAAGAACCTCT<br>TCGGCCAGCCGGTGCGCCTG<br>ATGGAGATGCAGTCGGAAGC<br>GGGTGCAGCAGGTGCTGTGC<br>ATGGCGCCTTGCAAGCTGGC<br>GCACTGACGACCACCTACAC<br>CGCGTCGCAGGGCCTGTTGCT<br>GATGATCCCAAACATGTACA<br>AAATCGCGGGTGAACTGCTG<br>CCGGGTGTCTTTCATGTTTCG<br>GCACGCGCACTGGCCACCAA<br>TAGCCTCAACATCTTTGGCGA<br>TCATCAGGATGTAATGGCGG<br>TGCGCCAAACGGGCTGCGCG<br>ATGTTGGCCGAGAATAACGT<br>CCAGCAAGTTATGGATTTGTC<br>CGCGGTAGCCCACTTGGCAG<br>CGATCAAAGGTCGCATTCCGT<br>TCGTGAACTTCTTCGATGGCT<br>TTCGCACCAGCCACGAAATC<br>CAGAAGATCGAGGTTCTGGA<br>ATATGAACAGCTGGCCACCTT<br>GTTGGATCGTCCGGCCCTGGA<br>CAGCTTCCGCCGTAACGCCCT<br>TCACCCGGACCACCCGGTCAT<br>CCGTGGCACCGCCCAGAACC<br>CGGACATCTACTTCCAGGAA<br>CGTGAGGCCGGTAACCGTTTC<br>TATCAGGCGCTCCCGGATATT<br>GTGGAATCTTACATGACCCA<br>GATTTCTGCCCTGACTGGTCG<br>CGAGTATCACCTGTTTAACTA<br>CACTGGTGCTGCGGATGCGG<br>AGCGCGTGATCATCGCGATG<br>GGCTCTGTCTGTGACACCGTC<br>CAAGAGGTGGTTGACACGCT<br>GAATGCAGCGGGTGAGAAAG<br>TTGGTCTGCTCTCCGTTCATC<br>TTTTCCGCCCGTTTTCGTTAG<br>CGCACTTCTTCGCCCAACTGC<br>CGAAAACTGTACAGCGTATC<br>GCAGTATTGGACCGTACGAA<br>AGAGCCAGGTGCTCAAGCAG<br>AGCCGCTGTGCCTCGATGTGA<br>AGAATGCCTTTTACCACCATG<br>ACGATGCCCCGTTGATTGTGG | 80.8 | 48 |

FIG. 18 (cont)

| Gene | SEQ ID NO: | WT Sequence | Synthetic Sequence | % Nucleotide Identity | % Codon Identity |
|---|---|---|---|---|---|
| | | ccagcgggcgatcgagctgggcatggcctcgct gcatcaggtgacgattccggcgcactgggcgac gctggatgaacccgcggcgcaagcatcagccat gatgccggatttcatccgcgatattctgcagccgat gaaccgccagtgcggcgaccagctgccggtgag cgcgttcgtcggtatggaggacgggacctttcctt cgggcaccgccgcgtgggagaaacgcgggatc gcgctggaagtgccggtctggcagccggagggc tgcacgcagtgtaaccagtgcgcctttatctgccc gcatgcggcgatccgccggcgctgctcaacgg cgaagagcatgacgccgcgccggttgggctgct gagcaaacccgcgcagggagcgaaggagtatc actaccatctggctatctcgccgctggattgttccg gctgcggcaactgcgtggatatctgtcccgcgcg cggcaaggcgttaaaaatgcagtctctcgatagcc agcgtcagatggcgccggtctgggactatgcgct ggcgctgacgccgaagagcaatccgtttcgtaag acgacggtcaaaggcagccagtttgaaacccg ctgctggagttttccggcgcctgcgcgggatgcg gtgaaacgcctatgcccgcctgataacccagctg tttggcgaccggatgctgatcgctaacgccaccg gctgctcttctatctggggagccagcgcgccgtcg attccctataccaccaaccaccgcggccatggcc cggcatgggcgaactcgctgtttgaggataatgc ggagtttggcctcggcatgatgctcggcggccag gcggtgcgtcaacaaatcgccgatgatatgaccg ccgcgctggcgctaccggtcagcgacgaacttag cgacgcaatgcgccagtggctggcgaagcagga tgaaggcgagggcacccgcgagcgcgcggacc ggctcagcgaacggctggcggcggaaaaagag ggcgtgccgctgttggagcagctgtggcagaacc gcgactattttgttcgtcgttcgcagtggattttcgg cggcgacggctgggcctacgatatcggcttcggc ggtctcgatcacgtgctggcgagcggggaagac gtcaatattctggtgtttgacaccgaggtttactcca ataccggccggccagtcgtctaaatcgaccccggt ggcggccatcgcgaagtttgccgcgcagggcaa acgcacgcggaaaaaagatctcggcatgatggc gatgagctacggcaatgtgtacgtggcccaggtc gcgatgggcgctgataaagatcagaccctacgg gcgatcgccgaggccgaagcctggccgggacc gtcgctggtgattgcctacgccgcctgcattaacc acgggctgaaagccggtatgcgctgcagccagc gcgaggcgaaacgggcggttgaggcgggatact ggcacctgtggcgctatcatccgcagcgggaag cggaaggtaagacgccgtttatgctcgattccgaa gagccggaggagagcttccgcgacttttttgcttgg cgaagtgcgctacgcctcgctgcacaaaacgac gccgcatctggccggatgcgctctttagccgaacc gaggaggacgcgcgggcccgctttgcccagtat cggcggctggccggcgaggagtag | GTGGTCGCTATGCCTTGGGCG GTAAGGACGTGTTGCCGAAC GATATTGCGGCCGTGTTTGAT AACCTGAACAAACCGCTGCC GATGGACGGCTTCACGCTGG GTATCGTGGACGATGTTACCT TCACCTCTCTCCCGCCAGCGC AGCAGACCCTGGCGGTTTCTC ACGACGGCATCACGGCATGT AAGTTTTGGGGCATGGGCTCC GACGGCACGGTTGGTGCGAA CAAGTCCGCGATCAAGATTA TCGGCGACAAAACGCCACTG TATGCGCAAGCGTACTTTTCC TACGACTCGAAGAAGAGCGG TGGTATTACCGTCAGCCATCT GCGTTTTGGTGATCGCCCGAT CAACTCCCCGTATTTGATCCA TCGCGCGGATTTCATCTCGTG CAGCCAGCAAAGCTATGTTG AACGCTACGATCTGCTGGAT GGCCTTAAACCGGGTGGCAC CTTTCTGCTGAACTGCTCCTG GAGCGATGCCGAACTGGAGC AACATCTGCCGGTCGGTTTCA AACGTTATCTGGCACGCGAG AATATCCACTTCTACACTCTC AACGCTGTGGACATCGCCCG TGAGCTTGGTTTGGGTGGCCG TTTCAACATGCTGATGCAGGC TGCCTTCTTCAAACTGGCCGC GATCATTGACCCGCAGACTG CTGCGGACTATCTGAAGCAG GCTGTTGAGAAAGCTATGG CAGCAAAGGTGCGGCGGTCA TCGAGATGAACCAGCGTGCC ATCGAGCTTGGCATGGCCAG CCTGCACCAGGTGACGATCC CGGCACATTGGGCCACCCTG CGGCACATTGGGCCACCCTG GATGAGCCAGCGGCGCAGGC GTCCGCGATGATGCCGGACTT TATCCGCGACATCCTGCAACC GATGAACCGTCAGTGCGGCG ACCAGCTTCCGGTGTCGGCTT TTGTCGGCATGGAAGATGGC ACCTTCCCGTCCGGCACGGCC GCATGGGAGAAACGTGGCAT CGCCCTTGAGGTGCCAGTCTG GCAGCCGGAAGGCTGCACGC AGTGCAACCAGTGCGCCTTC ATTTGTCCGCACGCCGCGATT CGTCCGGCGTTGTTGAATGGC GAAGAGCATGATGCTGCCCC GGTTGGCCTGCTGAGCAAAC | | |

FIG. 18 (cont)

| Gene | SEQ ID NO: | WT Sequence | Synthetic Sequence | % Nucleotide Identity | % Codon Identity |
|---|---|---|---|---|---|
| | | | CGGCACAAGGCGCTAAAGAATATCACTATCATCTGGCGATTAGCCCGCTGGACTGCTCCGGCTGTGGCAACTGCGTTGACATTTGTCCAGCTCGTGGCAAAGCGTTGAAGATGCAGTCTCTGGATAGCCAACGCCAGATGGCTCCGGTGTGGGATTATGCGCTGGCGCTGACCCCGAAGTCTAACCCGTTTCGTAAAACCACCGTCAAAGGCTCGCAGTTCGAAACCCCGCTGCTGGAGTTTAGCGGTGCGTGCGCTGGTTGTGGCGAAACGCCGTATGCGCGCCTCATTACCCAGCTGTTTGGCGACCGCATGCTGATTGCCAATGCCACCGGCTGTTCCAGCATCTGGGGCGCATCTGCGCCGAGCATCCCGTATACCACCAATCATCGTGGTCATGGTCCGGCCTGGGCGAATAGCCTGTTTGAGGACAATGCCGAATTTGGTTTAGGTATGATGCTGGGCGGTCAAGCTGTGCGTCAACAGATCGCGGACGATATGACGGCTGCGTTAGCGCTCCCGGTTTCCGATGAGCTGAGCGACGCGATGCGCCAGTGGTTGGCGAAACAGGACGAGGGTGAAGGCACGCGTGAGCGTGCGGACCGTCTGAGCGAGCGCTTAGCCGCGGAGAAAGAGGGCGTTCCGCTGTTAGAGCAGCTGTGGCAAAATCGTGATTACTTTGTGCGTCGCAGCCAGTGGATTTTCGGCGGTGACGGCTGGGCCTATGATATTGGCTTCGGTGGCCTGGACCACGTCCTCGCCAGCGGTGAGGATGTGAACATTCTGGTATTTGACACCGAAGTCTACTCGAACACCGGCGGTCAAAGCAGCAAATCGACCCCGGTCGCGGCCATCGCCAAGTTCGCGGCTCAGGGCAAGCGCACCCGCAAGAAAGACCTGGGTATGATGGCGATGAGCTACGGCAACGTCTATGTAGCCCAGGTGGCGATGGGTGCGGATAAAGATCAAACTCTGCGCGCCATTGCGGAAGCTGAAGCGTGGCCAGGCCCGTCGCTGGTGATTGCGTATGCGGCCTGCATCAATCATGGCCTGAAGGCCGGTATGCGTTGCAGCCAACGTGAGGCGAAGCGCGCTGTTGAG | | |

FIG. 18 (cont)

| Gene | SEQ ID NO: | WT Sequence | Synthetic Sequence | % Nucleotide Identity | % Codon Identity |
|------|------------|-------------|--------------------|-----------------------|------------------|
|      |            |             | GCGGGCTACTGGCACCTGTG GCGTTATCACCCGCAGCGCG AAGCGGAAGGCAAGACGCCG TTTATGTTAGATAGCGAAGA ACCGGAAGAGTCGTTCCGTG ACTTTCTGTTGGGTGAGGTGC GCTACGCATCCCTGCACAAG ACCACCCCGCACCTCGCCGAT GCCCTTTTCAGCCGTACCGAA GAAGATGCGCGTGCGCGCTT TGCGCAATACCGTCGCCTGGC TGGCGAAGAGTAA |  |  |

FIG. 18 (cont)

| Gene | SEQ ID NO: | WT Sequence | Synthetic Sequence | % Nucleotide Identity | % Codon Identity |
|---|---|---|---|---|---|
| H | WT Gene H is SEQ ID NO:3<br><br>Synthetic Gene H is SEQ ID NO:4 | atgaccatgcgtcaatgcgctatttacggtaaagg cggtatcggtaaatccaccaccacgcagaacctc gtcgccgcgctggcggagatgggtaagaaagtg atgatcgtcggctgcgatccgaaggcggactcca cccgtctgattctgcacgccaaagcacagaacac cattatggagatggccgcggaagtcggctcggtc gaggacctcgaactcgaagacgtgctgcaaattg gctacggcgatgtgcgctgcgcggaatccggcg gcccggagccaggcgtcggctgcgcgggacgc ggcgtgatcacggcgatcaactttcttgaagaaga aggcgcctacgaggacgatctcgatttcgtgttcta tgacgtgctcggcgacgtggtctgcggcggcttc gccatgccgatccgcgaaaacaaagcccaggag atctacatcgtctgctccggcgaaatgatggcgat gtacgcggccaacaatatctccaaagggatcgtta aatacgccaaatccggcaaggtgcgcctcggcg gcctgatctgtaactcacgtcagaccgaccgtgaa gacgaactgattattgccctggcggaaaagctcg gtacccagatgatccactttgtgccccgcgacaac atcgtgcagcgcgcggagatccgccgcatgacg gttatcgagtacgaccccgcctgtaaacaggcca acgaataccgcaccctggcgcagaagatcgtcaa caacaccatgaaagtggtgccgacgccctgcacc atggatgagctggaatcgctgctgatggagttcgg catcatggaagaggaagacaccagcatcattggc aaaaccgccgccgaagaaaacgcggcctga | ATGACCATGCGTCAGTGCGC GATTTATGGCAAAGGTGGTA TTGGCAAAAGCACGACGACC CAGAACTTGGTGGCGGCCCT GGCCGAGATGGGTAAAAAGG TTATGATTGTGGGTTGCGACC CGAAGGCCGACAGCACGCGC CTGATTCTGCACGCGAAAGC ACAAAACACGATTATGGAGA TGGCTGCCGAGGTTGGTAGC GTGGAGGATCTGGAGCTGGA GGACGTTCTGCAAATTGGTTA CGGTGATGTTCGTTGCGCAGA GAGCGGTGGTCCGGAACCAG GTGTCGGCTGTGCGGGTCGTG GTGTGATTACCGCTATCAATT TCCTGGAAGAAGAGGGTGCG TACGAAGATGATCTGGATTTC GTTTTCTACGATGTGCTGGGT GATGTCGTGTGCGGTGGTTTT GCAATGCCGATTCGCGAGAA TAAGGCACAAGAAATTTACA TTGTCTGTAGCGGCGAGATG ATGGCAATGTACGCTGCTAA CAACATCAGCAAGGGTATTG TTAAATACGCAAAAAGCGGT AAGGTTCGCTTGGGTGGTTTG ATTTGCAACAGCCGTCAGAC CGACCGTGAGGACGAACTGA TCATCGCCCTGGCTGAGAAA CTGGGCACCCAAATGATCCA CTTCGTGCCACGCGATAATAT TGTTCAACGTGCAGAAATCC GCCGTATGACCGTCATTGAGT ATGACCCGGCATGCAAGCAA GCGAACGAGTACCGCACCTT GGCACAGAAAATCGTGAACA ACACCATGAAGGTTGTTCCG ACGCCGTGTACGATGGACGA GCTGGAGAGCCTGCTGATGG AGTTCGGCATTATGGAGGAG GAGGACACCAGCATTATCGG TAAGACCGCAGCGGAGGAGA ATGCGGCATAA | 79 | 41.8 |

FIG. 18 (cont)

| Gene | SEQ ID NO: | WT Sequence | Synthetic Sequence | % Nucleotide Identity | % Codon Identity |
|---|---|---|---|---|---|
| D | WT Gene D is SEQ ID NO:5<br><br>Synthetic Gene D is SEQ ID NO:6 | atgatgaccaacgcaacgggcgaacgtaatctgg cgctgatccaggaagtcctggaggtgttcccgga aaccgcgcgaaaagagcgcagaaagcacatgat ggtcagcgatccgaaaatgaagagcgtcggcaa gtgcattatctctaaccgcaaatcacaacccggcg taatgaccgtacgcggctgcgcctacgccggttc caaaggggtggtatttgggccgattaaggatatgg cccatatttcgcacggaccggctggctgcggcca gtattcccgcgccgaacgacgcaactactacacc ggagtcagcggcgtcgatagcttcggcacgctga acttcacctctgattttcaggagcgcgacatcgtctt cggcggcgataaaaagctcagcaagctgattgaa gagatggagttgctgttcccgctcaccaaagggat caccattcagtcggaatgcccggtggggctgatc ggtgatgatatcagcgcggtggccaacgccagc agcaaggcgctggataaaccggtgatcccggtac gctgcgaaggctttcgcggcgtgtcgcagtctctg gggcaccatatcgccaacgacgtggtgcgcgact ggatcctgaacaatcgcgaaggacagccgtttga aaccaccccttacgatgtggcgatcatcggcgact acaacatcggcggcgacgcctgggcctcgcgca ttctgctggaagagatggggctacgggtagtcgc gcagtggtccggcgacggcacgctggtggagat ggagaatacccattcgtcaagctgaacctggttc actgctaccgttcgatgaactatatcgcccgccata tggaggagaaacatcagattccgtggatggagta caacttcttcgggccgaccaaaatcgccgaatcg ctgcgcaaaatcgccgaccagttcgacgatacca ttcgcgcgaacgccgaagcggtgatcgcccggt atgaggggcagatggcggcgattatcgccaaata tcgcccgcgcctggagggggcgtaaggtgctgctc tatatcggaggcctgcgccgcgccacgttattgg cgcctatgaggatctcgggatggagatcatcgcc gccggctacgagtttgcccataacgatgattacga ccgcaccctgccggatctgaaagagggcacgct gctgttcgatgacgccagcagctacgagctggaa gcgttcgtcaaggcgctgaagcccgaccttatcg gctccggcatcaaggaaaaatatatcttccagaaa atgggcgtgccgttccgccagatgcactcgtggg actattccggcccgtaccacggctacgatggtttc gccattttcgcccgcgatatggatatgaccctgaa caacccggcgtggaacgaactgaccgctccgtg gctgaagtctgcgtga | atgatgactaatgctactggcgaacgtaacctgg cactgattcaagaagtactggaagtgttcccgga aaccgcgcgcaaagagcgccgtaaacacatg atggtttctgacccgaaaatgaaatctgtgggta aatgcatcatctctaatcgcaaatctcagccggg tgtcatgactgttcgtggctgtgcgtacgcaggtt ctaaaggtgtcgtattcggcccgatcaaagatat ggcgcatatctctcatggcccggcaggctgtgg ccagtactctcgcgcggaacgtcgtaactacta cacgggcgtttctggcgttgactctttcggcacg ctgaacttcacctctgacttccaggaacgtgaca tcgttttcggtggcgataaaaagctgtccaaact gatcgaagaaatggaactgctgttcccgctgact aaaggcattactatccaaagcgaatgtccggtg ggtctgatcggtgatgacatcagcgcggtcgca aacgcatcttccaaagccctggataagccggtg atcccggttcgttgcgagggcttccgcggcgttt ctcagtctctgggtcatcacatcgcaaacgatgtt gtgcgtgactggattctgaacaaccgtgaaggt cagccttttgaaaccaccccttatgacgttgcgat tattggcgactataacatcggcggcgacgcctg ggcatcccgcatcctgctggaggagatgggtct gcgtgttgtcgcacagtggtctggcgatggcac cctggttgaaatggaaaacaccccgtttgttaaa ctgaacctggttcactgctaccgctccatgaact acattgcccgtcacatggaagaaaaacatcaga tcccttggatggaatacaacttcttcggtccgact aaaatcgcagaatccctgcgtaaaatcgccgat cagtttgatgataccattcgcgcgaacgctgaag cagtaattgcgcgctacgaaggccagatggca gcaatcattgctaagtaccgtccgcgcctggaa ggtcgtaaagtgctgctgtacatgggtggtctgc gtccacgtcatgtgatcggtgcctacgaggacc tgggcatggagatcatcgcagcgggttacgaat ttgcacacaacgacgactatgatcgtacgctgc cagacctgaaagaaggtacgctgctgtttgacg acgccagctcttatgaactggaagccttcgtgaa agcgctgaaaccagacctgatcggctccggca tcaaggaaaaatacattttccagaaaatgggcgt tccgccagatgcactcctgggactactc cggtccgtaccacggctacgacggtttcgctatc ttcgctcgtgacatggatatgaccctgaataacc cagcgtggaatgaactgaccgcaccgtggctg aaatctgcataa | 82.6 | 51.2 |

FIG. 18 (cont)

| Gene | SEQ ID NO: | WT Sequence | Synthetic Sequence | % Nucleotide Identity | % Codon Identity |
|---|---|---|---|---|---|
| K | WT Gene K is SEQ ID NO:7<br><br>Synthetic Gene K is SEQ ID NO:8 | atgagccaaacgattgataaaattaatagctgttat ccgctattcgaacaggatgaataccaggagctgtt ccgcaataagcggcagctggaagaggcgcacg atgcgcagcgcgtgcaggaggtctttgcctggac caccaccgccgagtatgaagcgctgaatttccga cgcgaggcgctgaccgttgacccggcgaaagcc tgccagccgcttggcgcggtgctttgctcgctggg atttgccaacaccctgccgtatgtgcacggctctca ggggtgcgtggcctactttcgcacctattttaaccg ccatttcaaagagccgatcgcctgcgtctccgact cgatgaccgaagacgcggcggtcttcggcggca acaacaatatgaacctgggcctgcagaacgccag cgcgctgtacaaaccggagatcattgcggtgtcc accacctgcatggcggaagttatcggcgatgacc tgcaggcgtttatcgccaacgctaaaaaagatggc ttcgtcgacagcagcatcgccgtgccccacgccc atacgccaagctttatcggcagccacgtcaccgg ctgggataacatgtttgaaggcttcgccaaaacctt cactgcggactaccaggggcagccgggcaaatt gccgaagctcaatctggtgaccggctttgaaacct atctcggcaacttccgcgtattaaagcggatgatg gaacagatggcggtgccgtgcagcctgctctccg atccgtcggaagttctcgacacgcccgccgacgg tcactatcggatgtattccggcggcaccacgcagc aggagatgaaagaggcccctgacgccatcgata cgctgctcctgcagccgtggcagctgctgaagag caaaaaagtggtgcaggagatgtggaaccagcc cgccaccgaggtcgccattccgctggggctggc cgccaccgatgaactgctgatgaccgtcagccag cttagcggcaagccgattgccgacgccctcaccc ttgagcgcggccggctggttgacatgatgctcga ctcccacacctggctgcacggcaagaagtttggc ctgtacggcgatccggacttcgtgatgggcctcac ccgcttcctgctggagctgggctgcgagccaacg gtgatcctgagccataacgccaacaaacgctggc aaaaagcgatgaacaaaatgctcgatgcctcgcc gtacgggcgcgatagcgaagtgtttatcaactgcg atttgtggcacttccgttcgctgatgttcacccgtca gccggactttatgatcggcaactcctacggcaagt ttatccagcgcgataccctggcgaagggtaaagc ctttgaagtgccgcttatccgcctcggcttccgct gttcgaccgccaccatctgcaccgccagacaacc tggggttatgaaggggcgatgaacattgtgacga cgctggtgaacgccgtgctggagaaactggatag cgataccagccagctgggcaaaaaccgattacagc ttcgatctcgtccgttaa | atgtctcaaactatcgataaaatcaactcttgttac ccgctgttcgagcaggacgaatatcaggaactg ttccgtaacaaacgtcagctggaagaagcgcac gacgcacagcgcgtgcaggaagtgttcgcatg gaccaccaccgccgcggaatacgaagctctgaactt ccgtcgcgaagccctgacggttgatccggcga aagcgtgccagcctctgggtgcggttctgtgca gcctgggttttgccaacaccctgccgtatgtcca cggttccagggctgcgtagcctacttccgtacc tatttcaaccgccactttaaagaaccaatcgcgt gcgtgtccgacagcatgacggaggacgcggc agttttcggtggtaacaacaacatgaacctgggc ctgcaaaatgcttccgcactgtacaaaccggaa atcatcgcagtgtctaccacctgcatggcagag gttattggtgatgatctgcaagcatttattgccaac gcaaagaaagacggtttcgttgacagctctatcg cggttccgcacgctcataccccgtccttcatcgg ttctcacgtaactggttgggacaacatgttcgaa ggcttcgcaaaaacttttaccgcagactatcaag gccaaccgggtaaactgccgaagctgaacctg gtgaccggctttgaaacctacctgggcaactttc gtgtcctgaagcgcatgatggagcagatggcg gttccgtgttctctgctgtctgacccgtctgaggtt ctggacactccagcggacggccactatcgcat gtattctggtggcaccactcagcaggaaatgaa agaggcccagacgcgattgacaccctgctgc tgcaaccgtggcagctgctgaaaagcaagaaa gttgttcaggaaatgtggaaccagccggcaacg gaagttgcaatcccgctgggtctggcagctact gacgaactgctgatgaccgtgtcccaactgagc ggcaaaccaatcgcggatgctctgaccctgga acgcggtcgcctggtggacatgatgctggaca gccacacgtggctgcatggcaagaaatttggcc tgtacggtgacccggacttcgtaatgggcctga cccgtttcctgctggaactgggctgcgagccga ctgttatcctgtctcacaacgctaacaaacgttgg cagaaggccatgaacaaaatgctggatgcgag cccatacggccgtgatagcgaagtgttcatcaa ctgcgacctgtggcatttccgctctctgatgtttac gcgtcagccggatttcatgatcggtaactcttac ggcaaattcatccagcgtgacactctggccaaa ggcaaagcgtttgaagtgccgctgattcgtctgg gctttccgctgttcgaccgtcaccacctgcaccg ccagaccacctgggggttacgaaggcgcgatga acatcgtaactactctgtaaacgcagtactgga aaagctggacagcgatacttcccagctgggca aaaccgactattctttcgatctggttcgttaa | 82.1 | 51.2 |

FIG. 18

| Gene | SEQ ID NO: | WT Sequence | Synthetic Sequence | % Nucleotide Identity | % Codon Identity |
|---|---|---|---|---|---|
| Y | WT Gene Y is SEQ ID NO:9<br><br>Synthetic Gene Y is SEQ ID NO:10 | atgtccgacaacgatacccctattctggcgtatgctg gcgctgtttcagtctctgccggacctacagccggc gcaaatcgtcgactggctggcgcaggagagcgg cgagacgctgacgccagagcgtctggcgaccct gacccagccgcagctggccgccagctttccctcc gcgacggcggtgatgtccccgctcgctggtcgc gggtgatggcgagcctgcagggcgcgctgcccg cccatttacgcatcgttcgccctgcccagcgcacg ccgcagctgctggcggcattttgctcccaggatgg gctggtgattaacggccatttcggccagggacga ctgtttttatctacgcgttcgatgaacaaggcggct ggttgtacgatctgcgccgctatccctccgccccc caccagcaggaggccaacgaagtgcgcgcccg gcttattgaggactgtcagctgctgttttgccagga gataggcgggcccgccgccgcgcggctgatcc gccatcgcatccacccgatgaaagcgcagcccg ggacgacgattcaggcacagtgcgaggcgatca atacgctgctggccggccgtttgccgccgtggct ggcgaagcggcttaacagggataaccctctggaa gaacgcgttttttaa | ATGTCTGACAATGATACCCTG TTTTGGCGCATGCTGGCGCTG TTTCAGTCGCTGCCGGATTTG CAGCCGGCTCAAATCGTCGA TTGGCTGGCGCAGGAATCCG GCGAAACCCTGACGCCGGAG CGCCTTGCCACCCTGACCCAA CCGCAACTCGCGGCGTCGTTC CCATCCGCGACGGCAGTGAT GAGCCCGGCTCGCTGGAGCC GCGTTATGGCTTCTCTGCAAG GCGCCCTCCCAGCCCACTTGC GCATCGTACGTCCGGCGCAG CGTACCCCGCAACTGCTCGCC GCGTTTTGCAGCCAAGACGG CCTTGTTATCAATGGTCATTT CGGCCAGGGTCGTCTGTTCTT CATTTACGCCTTTGACGAGCA GGGCGGCTGGCTGTATGACTT GCGCCGCTATCCGAGCGCAC CGCACCAGCAGGAAGCGAAT GAGGTGCGTGCTCGTCTGATT GAAGATTGCCAGCTGCTGTTC TGCCAGGAGATTGGCGGTCC GGCAGCAGCGCGTCCGATCC GCCACCGCATCCATCCGATG AAGGCGCAGCCGGGTACTAC GATTCAGGCGCAGTGTGAAG CTATCAACACCCTGCTGGCCG GTCGCCTGCCGCCGTGGCTCG CCAAACGTTTGAACCGTGAT AACCCGCTGGAAGAGCGTGT GTTTTAA | 79.8 | 45.2 |

FIG. 18 (cont)

| Gene | SEQ ID NO: | WT Sequence | Synthetic Sequence | % Nucleotide Identity | % Codon Identity |
|---|---|---|---|---|---|
| E | WT Gene E is SEQ ID NO:11<br><br>Synthetic Gene E is SEQ ID NO:12 | atgaagggaaatgaaattctggcgctgctggatga accggcctgtgaacacaaccataaacaaaaatcc ggctgcagcgcgcccaaacccggcgccaccgc cgcgggctgcgcgttcgacggcgcgcagataac cctgctgcccatcgccgacgtggcgcatctggtc cacggccccatcggctgcgccggaagctcatgg gataaccgcggcagcgccagctccggccccacc cttaatcggctcgggttcaccaccgatctcaacga acaggacgtgattatgggccgcggcgaacgccg actgtttcacgccgtgcgccatatcgtcacccgcta tcatccggcggcggtctttatctacaacacctgcgt accggccatggagggcgatgacctggaagcggt atgccaggccgcgcagaccgccaccggcgtacc ggttatcgctattgacgccgccggtttctacggca gtaaaaatctcggtaaccggccggcgggcgacg tcatggtcaaacgggtcatcggccagcgcgagcc cgccccctggccggagagcacgctctttgccccg gagcagcgtcacgatattggcctgattggcgaatt caatattgccggcgagttctggcatattcagccgct gctcgacgaactggggatccgcgtgctcggcag cctctccggtgatggccgcttcgccgagatccag accatgcaccgggcgcaggccaatatgctggtct gctcgcggcgttaattaacgtcgccagagccct ggagcagcgctacggcacgccgtggttcgaagg cagcttttacgggatccgcgccacctctgacgccc tgcgccagctggcggcgctgctgggcgacgacg accttcgccagcgcaccgaagcgctgattgcgcg ggaggaacaggcggcggaactggcgctacagc cgtggcgcgaacagctgcgcgccgcaaagcg ctgctctataccggcggggtgaaatcctggtcggt ggtatcggcgctgcaggatttgggcatgaccgtg gtggcaaccggcacgcgtaaatccaccgaagag gataaacagcggatccgcgagctgatgggcgaa gaggcggtaatgctggaagagggcaacgcccg cacgctgctggatgtggtctatcgctatcaggccg acctgatgattgccggcggacgcaatatgtacacc gcctataaagccaggctgccgtttctcgatatcaat caggagcgcgaacacgccttcgctggctatcagg ggatcgtcaccctcgcccgccagctgtgtcagac catcaacagccccatcggccgcaaacccattctc gcgccccgtggcgctaa | ATGAAGGGTAACGAGATTCT TGCTCTGCTGGACGAACCGG CCTGTGAACACAACCATAAA CAGAAATCCGGCTGTAGCGC CCCAAAGCCGGGTGCGACGG CGGCTGGCTGCGCTTTCGATG GTGCGCAGATCACCCTGCTCC CGATTGCGGACGTTGCCCACC TCGTGCATGGCCCAATCGGTT GCGCAGGTAGCTCTTGGGAC AACCGTGGCAGCGCCTCCAG CGGTCCGACCCTGAATCGTTT GGGCTTTACCACTGACTTGAA TGAACAAGATGTGATCATGG GTCGCGGCGAGCGTCGCCTG TTCCACGCTGTGCGCCATATT GTCACCCGTTACCACCCAGCG GCAGTATTCATCTACAATACG TGCGTGCCGGCTATGGAAGG CGATGACCTGGAGGCCGTGT GTCAGGCAGCCCAGACTGCG ACCGGCGTCCCGGTAATCGC AATTGATGCGGCTGGCTTCTA CGGTTCGAAGAACCTGGGCA ACCGTCCGGCAGGCGATGTC ATGGTTAAACGCGTCATTGGC CAACGTGAGCCAGCGCCGTG GCCGGAGAGCACCCTGTTTG CCCCGGAGCAACGTCATGAC ATTGGCTTGATCGGTGAGTTC AACATTGCGGGCGAGTTTTG GCACATTCAGCCGCTGCTTGA TGAGCTGGGTATCCGCGTTTT GGGTTCGCTCAGCGGCGATG GTCGTTTCGCCGAGATTCAAA CCATGCACCGTGCCCAGGCG AACATGCTGGTGTGCAGCCG TGCTCTGATCAATGTTGCGCG TGCTCTGGAACAGCGCTATG GCACCCCGTGGTTTGAAGGCT CGTTCTATGGTATCCGCGCGA CCAGCGACGCCCTGCGCCAG TTAGCGGCGCTGCTGGGCGA TGACGACCTCCGTCAGCGCA CCGAGGCGCTGATCGCGCGT GAAGAACAGGCGGCTGAGCT GGCCCTGCAACCGTGGCGTG AACAGCTGCGTGGCCGCAAG GCCCTGCTCTACACGGGTGGT GTCAAAGCTGGTCTGTGGT GTCCGCGCTTCAGGATCTGGG TATGACCGTGGTTGCCACGG GCACGCGTAAGAGCACGGAA GAGGATAAACAGCGCATCCG | 80.8 | 47.6 |

FIG. 18 (cont)

| Gene | SEQ ID NO: | WT Sequence | Synthetic Sequence | % Nucleotide Identity | % Codon Identity |
|---|---|---|---|---|---|
| | | | CGAATTGATGGGCGAAGAGG CCGTGATGCTTGAAGAAGGC AACGCACGTACCTTATTGGAT GTAGTTTATCGCTATCAAGCA GACCTGATGATTGCCGGTGG CCGCAACATGTATACCGCCTA CAAAGCGCGCTTGCCGTTCCT GGACATCAACCAGGAACGCG AGCACGCGTTTGCGGGCTAC CAAGGCATCGTGACCTTAGC GCGCCAGCTGTGCCAAACGA TTAACAGCCCGATCTGGCCGC AGACTCATTCCCGCGCACCGT GGCGCTAA | | |

FIG. 18 (cont)

| Gene | SEQ ID NO: | WT Sequence | Synthetic Sequence | % Nucleotide Identity | % Codon Identity |
|---|---|---|---|---|---|
| N | WT Gene N is SEQ ID NO:13<br><br>Synthetic Gene N is SEQ ID NO:14 | atggcagacattttccgcaccgataagccgctggc ggtcagccccatcaaaaccggccagccgctcgg cgcaatcctcgccagcctcgggatcgaacacagc atccctctggtccacggcgcgcaggggtgcagc gccttcgccaaagtcttttttattcaacatttccacga cccggttcccctgcagtcgacggcgatggacccc acgtcgacgattatgggcgcggacggcaatatttt taccgccctggataccctctgccagcgcaacaatc cgcaggctatcgtactgctcagcaccgggctgtc ggaggcccagggcagcgatatttcccgcgtggtt cgccagtttcgcgaagagtatccccggcataagg gggtggcgatattgacggttaacacgccggattttt atggctccatggagaacggcttcagcgcggtgtta gagagcgtcattgagcagtgggtgccgccggcg ccgcgcccggctcagcgcaatcgccgggtcaat ctgctggtcagccatctctgttcgccgggcgatatc gagtggctgcgccgatgcgtcgaagcctttggtct gcagccgataatcctgccggacctggcgcaatcg atggacggccacctggcgcagggcgatttctcgc cgctgacccagggcgggacgccgctgcgccag atagagcagatggggcaaagcctgtgcagcttcg ccattggcgtctcccttcatcgcgcctcatcgctgc tggccccgcgctgccgcggcgaggttatcgccct gccgcacctgatgaccctcgaacgctgcgacgc ctttattcatcaactggcgaaaattccggacgcgc cgttcccgagtggctggaacgccagcgcggcca gctacaggatgcgatgatcgactgccatatgtggc tccagggccagcgcatggcgatagcggcggaa ggcgatttgctggcggcgtggtgtgatttcgccaa cagccaggggatgcagcccggcccgctggtgg cccctaccggtcatcccagcctgcgccagctgcc ggtggaacgggtggtgccggggatctggagga tctgcaaaccctgctgtgcgcgcatcccgccgac ctgctggtggcgaactcgcacgcccgcgacctg gcggagcagtttgcgctgccgctggtgcgcgcg ggttttccgctctttgacaagctcggcgaattccgc cgggtgcgacaggggtatagcgggatgcgcgat acgctgtttgagctggcaaacctgatacgcgagc gtcaccaccacctcgcccactaccgatcgccgct gcgccagaaccccgaatcgtcactctccacagga ggcgcttatgccgccgattaa | ATGGCAGACATTTTCCGCACT GATAAGCCGTTGGCTGTGTCG CCGATCAAGACCGGCCAGCC GCTGGGTGCGATCCTGGCGTC CCTGGGTATCGAGCACTCGAT TCCGCTGGTACATGGCGCGC AGGGCTGTTCGGCTTTTGCCA AGGTTTTCTTTATCCAGCACT TCCACGATCCGGTCCCGCTGC AAAGCACGGCAATGGACCCG ACCAGCACCATCATGGGCGC TGATGGTAACATCTTCACCGC GCTGGACACTCTCTGCCAACG CAATAACCCGCAAGCAATTG TGCTGCTGAGCACCGGCCTCT CCGAGGCGCAGGGCAGCGAC ATTTCCCGTGTAGTGCGTCAG TTCCGTGAAGAATATCCGCGT CATAAAGGCGTGGCGATTCT GACTGTTAACACCCCGGACTT TTACGGTAGCATGGAGAACG GCTTTTCCGCTGTCCTGGAGT CTGTGATTGAACAGTGGGTTC CGCCAGCCCCACGTCCGGCG CAGCGCAATCGTCGCGTCAA TCTTTTGGTGAGCCATCTCTG TAGCCCAGGCGATATTGAGT GGCTGCGCCGTTGCGTCGAG GCCTTCGGTCTGCAACCGATC ATTCTGCCGGATCTGGCTCAG AGCATGGACGGCCACCTTGC TCAGGGTGACTTTTCGCCGCT GACGCAGGGCGGCACGCCGT TGCGCCAAATCGAGCAGATG GGCCAGAGCCTTTGCTCTTTT GCGATTGGCGTCAGCCTGCA CCGTGCGAGCAGCCTGCTGG CTCCGCGTTGTCGTGGCGAAG TCATCGCCTTGCCGCACCTCA TGACCTTGGAACGCTGCGAC GCCTTTATCCATCAGTTGGCG AAAATCAGCGGTCGCGCCGT TCCGGAGTGGCTGGAACGCC AGCGCGGTCAGCTGCAAGAC GCCATGATCGATTGCCACATG TGGCTGCAAGGCCAGCGCAT GGCGATTGCCGCCGAAGGCG ACCTGCTGGCAGCGTGGTGC GATTTCGCGAACTCTCAAGGT ATGCAGCCGGGTCCACTGGTT GCTCCGACGGGTCATCCGAG CCTGCGTCAGTTGCCGGTGGA GCGCGTGGTGCCGGGTGATC TGGAGGATCTTCAGACCCTCT | 79.7 | 47 |

FIG. 18 (cont)

| Gene | SEQ ID NO: | WT Sequence | Synthetic Sequence | % Nucleotide Identity | % Codon Identity |
|---|---|---|---|---|---|
| | | | TATGCGCACATCCGGCCGACT TACTGGTGGCGAACTCCCAC GCCCGTGATTTAGCAGAGCA ATTCGCCCTGCCGCTGGTGCG CGCAGGCTTCCCGCTGTTTGA CAAACTGGGCGAATTTCGTC GTGTTCGCCAGGGTTATAGCG GTATGCGTGATACCCTGTTCG AGTTGGCGAACCTGATCCGT GAACGCCATCATCATCTGGCT CATTATCGCAGCCCGCTGCGC CAGAACCCAGAATCCTCGTT GTCTACGGGTGGCGCGTACG CAGCGGATTAA | | |

FIG. 18 (cont)

| Gene | SEQ ID NO: | WT Sequence | Synthetic Sequence | % Nucleotide Identity | % Codon Identity |
|---|---|---|---|---|---|
| U | WT Gene U is SEQ ID NO:15<br><br>Synthetic Gene U is SEQ ID NO:16 | atgtggaattactccgagaaagtgaaagaccatttt tttaaccccccgcaatgcgcgcgtggtggacaacg ccaacgcggtaggcgacgtcggttcgttaagctg cggcgacgccctgcgcctgatgctgcgcgtcga cccgcaaagcgaaatcattgaggaggcgggcttc cagaccttcggctgcggcagcgccatcgcctcct cctccgcgctgacggagctgattatcggccatacc ctcgccgaagccgggcagataaccaatcagcag attgccgattatctcgacggactgccgccggaga aaatgcactgctcggtgatgggccaggaggccct gcgcgcggccatcgccaactttcgcggcgaaag ccttgaagaggagcacgacgagggcaagctgat ctgcaaatgcttcggcgtcgatgaagggcatattc gccgcgcggtacagaacaacgggctgaccaccc ttgccgaggtgatcaactacaccaaagcgggcgg cggctgcacctcttgccacgaaaaaatcgagctg gccctggcggagatcctcgcccagcagccgcag acgacgccagccgtggccagcggcaaagatcc gcactggcagagcgtcgtcgataccatcgcagaa ctgcggccgcatattcaggccgacggcggcgat atggcgctactcagcgtcaccaaccaccaggtga ccgtcagcctctccggcagctgtagcggctgcat gatgaccgatatgaccctggcctggctgcagcaa aaactgatggaacgtaccggctgttatatggaagt ggtggcggcctga | ATGTGGAACTACAGCGAGAA AGTCAAGGACCATTTCTTCAA TCCGCGCAACGCGCGTGTTGT GGATAACGCAAATGCGGTGG GCGACGTCGGCAGCTTATCTT GTGGCGATGCTCTCCGCTTGA TGCTGCGCGTGGACCCGCAG AGCGAAATCATCGAAGAAGC GGGCTTTCAGACCTTCGGCTG CGGCAGCGCGATTGCGTCGT CCAGCGCACTGACGGAGCTG ATCATCGGTCACACCCTGGCG GAAGCGGGTCAGATCACCAA CCAGCAGATCGCCGACTATCT GGACGGCTTACCGCCGGAAA AGATGCACTGCTCTGTAATGG GCCAGGAAGCTCTTCGTGCG GCCATTGCTAACTTTCGCGGT GAATCGCTGGAAGAGGAGCA TGACGAGGGTAAGCTGATCT GCAAGTGCTTCGGCGTCGAT GAAGGCCATATTCGCCGTGCT GTCCAGAACAACGGTCTTAC GACTCTGGCCGAGGTGATCA ATTACACCAAGGCAGGTGGC GGTTGTACCAGCTGCCATGA GAAAATCGAGCTGGCCCTGG CCGAGATTCTCGCCCAACAG CCGCAAACCACCCCGGCAGT TGCGTCCGGTAAAGATCCGC ACTGGCAGAGCGTCGTGGAT ACCATCGCTGAACTGCGTCCA CATATCCAAGCGGACGGTGG TGACATGGCGCTGTTGTCCGT GACGAACCACCAAGTGACTG TTTCGCTGTCGGGCAGCTGTT CTGGCTGCATGATGACCGAC ATGACCCTGGCGTGGCTGCA ACAGAAATTGATGGAGCGTA CCGGCTGCTATATGGAAGTTG TTGCCGCCTAA | 82.3 | 53.5 |

FIG. 18 (cont)

| Gene | SEQ ID NO: | WT Sequence | Synthetic Sequence | % Nucleotide Identity | % Codon Identity |
|---|---|---|---|---|---|
| S | WT Gene S is SEQ ID NO:17<br><br>Synthetic Gene S is SEQ ID NO:18 | atgaaacaggtttatctcgataacaacgccaccac ccgtctggacccgatggtcctggaagcgatgatg cccttttgaccgattttacggcaaccctcgtcga tacacgattttggcattccggcccaggcggctctg gaacgcgcgcatcagcaggctgcggcgctgctg ggcgcggagtatcccagcgagatcatctttacctc ctgcgccaccgaagccaccgccaccgccatcgc ctcggcgatcgccctgctgcctgagcgtcgcgaa atcatcaccagcgtggtcgaacatccggcgacgc tggcggcctgcgagcacatggagcgcgagggct accggattcatcgcatcgcggtagatggcgaggg ggcgctggacatggcgcagttccgcgcggcgct cagcccgcgcgtcgcgttggtcagcgtgatgtgg gcgaataacgaaaccggggtgcttttcccgatcg gcgaaatggcggagctggcccatgaacaaggg gcgctgtttcactgcgatgcggtgcaggtggtcgg gaaaataccgatcgccgtgggccagacccgcat cgatatgctctcctgctcggcgcataagttccacg ggccaaaaggcgtaggctgtctttatctgcggcg gggaacgcgctttcgcccgctgctgcgcggcggt caccaggagtacggtcggcgagccgggacaga aaatatctgcggaatcgtcggcatgggcgcggcc tgcgagctggcgaatattcatctgccgggaatgac gcatatcggccaattgcgcaacaggctggagcat cgcctgctggccagcgtgccgtcggtcatggtga tgggcggcggccagccggcggtgcccggcacg gtgaatctggcctttgagtttattgaaggtgaagcc attctgctgctgttaaaccaggccgggatcgccgc ctccagcggcagcgcctgcacctcaggctcgctg gaaccctcccacgtgatgcgggcgatgaatatcc cctacaccgccgcccacggcaccatccgcttttct ctctcgcgctacacccgggagaaagagatcgatt acgtcgtcgccacgctgccgccgattatcgaccg gctgcgcgcgctgtcgccctactggcagaacgg caagccgcgcccggcggacgccgtattcacgcc ggtttacggctaa | ATGAAACAAGTGTACCTGGA CAACAACGCGACCACCCGCC TGGACCCGATGGTTCTGGAA GCGATGATGCCGTTTCTCACG GATTTCTATGGCAATCCGTCC AGCATCCATGACTTCGGCATC CCGGCACAAGCGGCGCTGGA ACGTGCGCACCAGCAAGCTG CGGCACTGCTGGGCGCAGAG TACCCGTCTGAAATCATTTTC ACGAGCTGTGCGACCGAGGC CACTGCAACCGCCATTGCGTC GGCCATCGCGTTATTGCCGGA ACGCCGCGAAATCATCACCT CGGTAGTGGAGCACCCGGCT ACGCTGGCGGCGTGCGAGCA CATGGAACGCGAAGGCTATC GCATCCATCGCATTGCGGTGG ATGGCGAAGGTGCGCTGGAC ATGGCCCAGTTCCGTGCAGC GCTCtcgCCGCGTGTCGCGTTG GTGAGCGTGATGTGGGCCAA CAACGAAACCGGCGTGCTGT TCCCGATTGGCGAAATGGCC GAGCTTGCCCACGAGCAGGG CGCTCTGTTCCACTGCGATGC CGTTCAGGTCGTTGGCAAAAT CCCAATTGCTGTTGGCCAGAC GCGCATCGACATGCTGTCTTG CTCCGCGCACAAGTTTCATGG TCCGAAGGGTGTTGGTTGCTT GTACTTACGTCGTGGCACGCG CTTTCGTCCGCTGCTTCGCGG TGGCCATCAAGAATATGGTC GCCGTGCCGGCACTGAGAAT ATCTGTGGCATCGTCGGCATG GGCGCTGCGTGCGAACTGGC GAACATCCATCTGCCGGGTAT GACCCATATTGGCCAGTTACG CAATCGCCTGGAGCACCGTCT GCTCGCCAGCGTGCCGTCCGT GATGGTTATGGGCGGTGGTC AGCCGGCTGTACCGGGTACT GTCAACCTGGCGTTCGAGTTT ATCGAAGGTGAAGCGATCCT GCTCTTGCTGAACCAGGCTGG CATTGCCGCAAGCTCCGGCTC CGCGTGTACCTCTGGCAGCTT GGAGCCGAGCCATGTGATGC GCGCCATGAACATTCCATAC ACCGCGGCTCACGGCACCAT TCGTTTTAGCCTGAGCCGTTA TACGCGCGAGAAAGAGATCG ACTACGTCGTTGCGACCCTCC | 79.1 | 43.6 |

FIG. 18 (cont)

| Gene | SEQ ID NO: | WT Sequence | Synthetic Sequence | % Nucleotide Identity | % Codon Identity |
|---|---|---|---|---|---|
| | | | CGCCAATCATTGATCGTCTGC GTGCCTTGTCCCCGTATTGGC AGAATGGTAAGCCGCGTCCG GCAGATGCAGTCTTTACCCCG GTTTACGGTTAA | | |

FIG. 18 (cont)

| Gene | SEQ ID NO: | WT Sequence | Synthetic Sequence | % Nucleotide Identity | % Codon Identity |
|---|---|---|---|---|---|
| V | WT Gene V is SEQ ID NO:19<br><br>Synthetic Gene V is SEQ ID NO:20 | atggaacgcgtgctgattaacgataccaccctgcg cgacggcgagcagagccccggcgtcgcctttcg caccagcgaaaaggtcgccattgccgaggcgctt tacgccgcaggaataacggcgatggaggtcggc accccggcgatgggcgacgaggagatcgcgcg gatccagctggtgcgtcgccagctcccgacgc gaccctgatgacctggtgtcggatgaacgcgctg gagatccgccagagcgccgatctgggcatcgact gggtggatatctcgattccggcttcggataagctg cggcagtacaaactgcgcgagccgctggcggtg ctgctggagcggctggcgatgtttatccatcttgcg catacccctcggcctgaaggtatgcatcggctgcg aggacgcctcgcgggccagcggccagaccctg cgcgctatcgccgaggtcgcgcagcaatgcgcc gccgcccgcctgcgctatgccgatacggtcggcc tgctcgacccttttaccaccgcggcgcaaatctcg gccctgcgcgacgtctggtccggcgaaatcgaaa tgcatgcccataacgatctgggtatggcgaccgc caatacgctggcggcggtaagcgccggggccac cagcgtgaatacgacggtcctcggtctcggcgag cgggcgggcaacgcggcgctggaaaccgtcgc gctgggccttgaacgctgcctgggcgtggagacc ggcgtgcattttcggcgctgcccgcgtcctgtca gaggtcgcggaagccgcgcagcgcgccatcg acccgcagcagccgctggtcggcgagctggtgtt tacccatgagtcaggtgtccacgtggcggcgctg ctgcggcacagcgagagctaccagtccatcgcc ccttccctgatgggccgcagctaccggctggtgct gggcaaacactccgggcgtcaggcggtcaacgg cgttttgaccagatgggctatcacctcaacgccg cgcagattaaccagctgctgcccgccatccgccg cttcgccgagaactggaagcgcagcccgaaaga ttacgagctggtggctatctacgacgagctgtgcg gtgaatccgctctgcgggcgagggggtaa | ATGGAGCGCGTCTTGATCAA CGATACTACCCTGCGTGATGG CGAACAATCTCCGGGCGTAG CGTTTCGTACCTCCGAGAAAG TTGCCATCGCGGAGGCACTGT ACGCTGCGGGTATCACCGCG ATGGAAGTCGGCACTCCGGC GATGGGTGATGAAGAGATCG CCCGCATTCAGCTGGTGCGTC GTCAACTGCCGGACGCGACG CTTATGACCTGGTGCCGTATG AACGCTCTGGAAATCCGTCA GAGCGCGGATCTGGGTATTG ACTGGGTGGATATCTCGATCC CAGCATCCGACAAGCTGCGT CAGTACAAGCTGCGTGAGCC GCTGGCCGTGCTGCTGGAGC GCCTTGCGATGTTTATCCATC TGGCCCACACGTTAGGCCTCA AAGTATGTATTGGTTGCGAG GATGCGAGCCGTGCGTCTGG TCAGACCCTGCGCGCCATTGC CGAGGTGGCCCAGCAATGCG CGGCTGCGCGCTTGCGTTACG CTGACACCGTGGGCCTGCTG GACCCGTTCACCACCGCAGC CCAGATCAGCGCCCTGCGTG ACGTTTGGTCGGGCGAGATC GAGATGCATGCTCACAATGA TCTGGGCATGGCTACCGCGA ACACGCTGGCGGCAGTTTCG GCTGGCGCCACGTCGGTGAA CACTACCGTCCTCGGTCTGGG TGAACGTGCAGGCAACGCAG CCCTGGAAACCGTTGCGCTG GGCCTGGAACGCTGCCTGGG CGTGGAAACCGGCGTCCATTT CAGCGCGCTCCCAGCGAGCT GTCAGCGCGTCGCGGAGGCT GCACAGCGCGCAATCGACCC GCAACAGCCGCTGGTGGGTG AATTGGTTTTCACCCACGAGT CTGGTGTTCACGTTGCGGCGC TGCTGCGCCACAGCGAATCCT ATCAATCTATTGCCCCAAGCC TCATGGGCCGTAGCTACCGTC TGGTGCTCGGCAAGCATTCG GGTCGTCAGGCTGTCAACGG TGTTTTCGACCAGATGGGTTA CCACCTGAATGCGGCGCAGA TCAATCAGTTGCTGCCGGCCA TTCGCCGCTTCGCCGAGAATT GGAAACGCTCTCCGAAAGAC TACGAACTGGTTGCGATCTAT | 80.8 | 48.3 |

FIG. 18 (cont)

| Gene | SEQ ID NO: | WT Sequence | Synthetic Sequence | % Nucleotide Identity | % Codon Identity |
|---|---|---|---|---|---|
| | | | GACGAATTGTGCGGTGAATCCGCCCTTCGTGCTCGCGGCTAA | | |

FIG. 18 (cont)

| Gene | SEQ ID NO: | WT Sequence | Synthetic Sequence | % Nucleotide Identity | % Codon Identity |
|---|---|---|---|---|---|
| W | WT Gene W is SEQ ID NO:21<br><br>Synthetic Gene W is SEQ ID NO:22 | atggagtggttttatcaaattcccggcgtggacga acttcgctccgccgaatcttttttcagtttttcgccgt ccccctatcagcccgagctgcttggccgctgcagc ctgccggtgctggcaacgtttcatcgcaaactccg cgcggaggtgccgctgcaaaaccggctcgagga taacgaccgcgcgccctggctgctggcgcgaag actgctcgcggagagctatcagcaacagtttcag gagagcggaacatga | ATGGAGTGGTTTTACCAGATT CCGGGTGTAGACGAATTGCG CAGCGCTGAATCCTTCTTTCA GTTCTTCGCGGTTCCATACCA GCCGGAACTGCTGGGCCGCT GCTCGCTTCCGGTGTTAGCGA CGTTCCACCGTAAACTGCGTG CGGAGGTCCCGCTGCAAAAC CGTCTGGAGGACAATGATCG TGCGCCGTGGCTCTTGGCGCG CCGCCTCCTGGCCGAATCTTA TCAGCAGCAATTTCAGGAGA GCGGCACCTAA | 77.9 | 43 |

FIG. 18 (cont)

| Gene | SEQ ID NO: | WT Sequence | Synthetic Sequence | % Nucleotide Identity | % Codon Identity |
|---|---|---|---|---|---|
| Z | WT Gene Z is SEQ ID NO:23<br><br>Synthetic Gene Z is SEQ ID NO:24 | atgagaccgaaattcacctttagcgaagaggtccg cgtcgtacgcgcgattcgtaacgacggcaccgtg gcgggcttcgcgcccggcgcgctgctggtcagg cgcggcagcaccggctttgtgcgcgactggggc gttttttgcaagatcagattatctaccagatccactt tccggaaaccgatcggatcatcggctgccgcgag caggagctgatccccatcacccagccgtggctgg ccggaaatttgcaatacagggatagcgtgacctg ccagatggcgctcgcggtcaacggcgatgtggtc gtgagcgccggccagcggggacgcgttgaggct accgatcggggagagctcggcgacagctacacc gtcgactttagcggccgctggttcagggtcccggt gcaggccatcgcccttatagaggaaagagaaga atga | ATGCGCCCGAAATTCACCTTC TCTGAAGAGGTCCGCGTAGTT CGCGCGATTCGTAATGATGG CACCGTGGCGGGTTTTGCGCC AGGTGCGCTGCTGGTTCGTCG CGGTTCGACGGGCTTTGTGCG TGACTGGGGTGTGTTCCTGCA AGACCAGATCATCTATCAAA TCCACTTTCCGGAAACCGACC GCATTATCGGCTGTCGCGAGC AGGAGTTAATCCCGATTACCC AGCCGTGGTTGGCTGGTAAC CTCCAGTATCGTGACAGCGTC ACGTGCCAAATGGCACTGGC TGTCAACGGTGACGTGGTTGT GAGCGCCGGTCAACGTGGCC GTGTGGAGGCCACTGATCGT GGCGAACTTGGCGATTCCTAC ACCGTGGACTTCAGCGGCCG TTGGTTCCGCGTTCCGGTCCA GGCCATCGCGCTGATTGAAG AGCGCGAAGAATAA | 80.1 | 48.3 |

FIG. 18 (cont)

| Gene | SEQ ID NO: | WT Sequence | Synthetic Sequence | % Nucleotide Identity | % Codon Identity |
|---|---|---|---|---|---|
| M | WT Gene M is SEQ ID NO:25<br><br>Synthetic Gene M is SEQ ID NO:26 | atgaacccgtggcaacgttttgcccggcagcggc tggcgcgcagccgctggaatcgcgatccggcgg ccctggatccggccgacacgccggcttttgaaca ggcctggcaacgccagtgccatatggagcagac gatcgtcgcgcgggtccctgaaggcgatattccg gcggcgttgctggagaatatcgctgcctcccttgc catctggctcgacgagggggattttgcgccgccc gagcgcgctgccatcgtgcgccatcacgcccgg ctggaactcgccttcgccgatatcgcccgccagg cgccgcagccggatctctccacggtacaggcatg gtatctgcgccaccagacgcagtttatgcgcccg gaacagcgtctgacccgccatttactgctgacggt cgataacgaccgcgaagccgtgcaccagcggat cctcggcctgtatcggcaaatcaacgcctcgcgg gacgctttcgcgccgctggcccagcgccattccc actgcccgagcgcgctggaagagggtcgtttagg ctggattagccgtggcctgctctatccgcagctcg agaccgcgctgttttcactggcggaaaacgcgct aagccttcccatcgccagcgaactgggctggcat cttttatggtgcgaagcgattcgccccgccgcgcc catggagccgcagcaggcgctggagagcgcgc gcgattatctttggcagcagagccagcagcgcca tcagcgccagtggctggaacagatgatttcccgtc agccgggactgtgcgggtag | ATGAATCCGTGGCAGCGCTTT GCCCGTCAACGCCTTGCTCGC AGCCGCTGGAACCGTGATCC GGCTGCTCTCGACCCAGCCG ATACCCCAGCGTTCGAGCAG GCGTGGCAGCGTCAATGCCA TATGGAACAAACCATCGTAG CGCGTGTCCCGGAAGGCGAT ATTCCGGCTGCCTTACTGGAA AACATCGCGGCCAGCCTGGC GATCTGGCTGGACGAGGGTG ACTTCGCTCCGCCGGAGCGC GCTGCGATTGTGCGTCATCAT GCACGTCTGGAGCTGGCGTTT GCCGACATTGCCCGCCAGGC ACCGCAACCGGATCTGAGCA CGGTTCAAGCGTGGTATCTGC GTCACCAGACTCAATTCATGC GTCCGGAGCAGCGTCTGACC CGTCACCTGCTCCTGACGGTC GATAATGATCGCGAGGCGGT GCATCAACGCATCCTTGGCCT GTATCGTCAGATCAACGCGA GCCGTGACGCCTTCGCCCCAC TGGCACAGCGCCACTCTCATT GCCCGTCCGCCTTGGAAGAA GGCCGTCTGGGCTGGATCTCC CGTGGTCTGCTGTACCCGCAG CTCGAAACCGCGTTGTTTAGC CTGGCGGAAAACGCACTGTC GCTGCCGATTGCGTCGGAATT GGGTTGGCACCTGTTATGGTG CGAGGCCATTCGTCCGGCAG CCCCGATGGAGCCGCAACAG GCCCTTGAATCTGCGCGCGAC TACTTGTGGCAGCAGAGCCA GCAGCGCCACCAGCGTCAAT GGCTGGAGCAGATGATTTCC CGCCAACCGGGCCTGTGTGG TTAA | 79.7 | 45.3 |

FIG. 18 (cont)

| Gene | SEQ ID NO: | WT Sequence | Synthetic Sequence | % Nucleotide Identity | % Codon Identity |
|---|---|---|---|---|---|
| F | WT Gene F is SEQ ID NO:27<br><br>Synthetic Gene F is SEQ ID NO:28 | atggcgaacattggtattttctttggcaccgatacc ggtaaaacccgcaaaatcgcgaaaatgatccata agcaactgggcgagctggcggatgccccggtca acattaaccgcacgacgctggacgactttatggcc tatccggtgctgctgctgggcacgccgacgctcg gcgacggccagctgccggggctggaggccgga tgcgaaagcgagtcatggagcgaatttatcagcg gcctcgacgacgccagcctgaaagggaaaaccg tggcgctgttcggcctcggcgatcagagaggcta tccggacaacttcgtcagcgggatgcgcccgctg ttcgacgccctgagcgcgcgcggcgcgcagatg attggcagctggccaaatgagggttatgaattcag cgcgtcctcggcgctggaaggcgaccgctttgtt gggctggtgctggatcaggataaccagttcgacc agaccgaagcgcgtctggcgagctggcttgagg agattaaacgcaccgtgctgtag | ATGGCGAACATCGGCATCTTC TTTGGTACGGATACCGGCAA AACCCGCAAGATTGCGAAGA TGATTCACAAACAGCTGGGC GAGCTGGCCGATGCCCCGGT TAACATCAATCGTACCACTTT GGATGACTTTATGGCTTACCC AGTCCTGTTGCTCGGCACGCC GACGCTTGGTGATGGTCAACT GCCGGGCTTAGAGGCGGGCT GCGAGAGCGAAAGCTGGTCT GAGTTTATCTCCGGTCTGGAT GACGCTTCCCTGAAGGGCAA AACCGTGGCGCTGTTTGGCCT GGGCGACCAGCGTGGTTACC CGGACAACTTCGTGTCGGGT ATGCGTCCGCTGTTCGACGCG CTGAGCGCCCGTGGCGCCCA GATGATTGGTAGCTGGCCGA ACGAAGGTTATGAGTTTAGC GCATCGTCCGCGCTGGAAGG CGACCGCTTCGTCGGCTTGGT GCTGGATCAAGACAATCAGT TCGACCAGACCGAAGCGCGC CTGGCGTCTTGGCTTGAAGAG ATCAAACGCACCGTTCTGTAA | 81.5 | 51.4 |

FIG. 18 (cont)

| Gene | SEQ ID NO: | WT Sequence | Synthetic Sequence | % Nucleotide Identity | % Codon Identity |
|---|---|---|---|---|---|
| B | WT Gene B is SEQ ID NO:29<br><br>Synthetic Gene B is SEQ ID NO:30 | atgacttcctgctcctcttttttctggcggcaaagcct gccgcccggcggatgacagcgcattgacgccgc ttgtggccgataaagctgccgcgcaccccctgctac tctcgccatgggcatcaccgtttcgcgcggatgca tctgcccgtcgcgcccgcctgcaatttgcagtgca actactgtaatcgcaaattcgattgcagcaacgagt cccgcccggggtatcgtcaacgctgctgacgcc tgaacaggcggtcgtgaaagtgcgtcaggtcgcg caggcgatcccgcagctttcggtggtgggcatcg ccggggcccggcgatccgctcgccaatatcgccc gcacctttcgcaccctggagctgatccgcgaaca gctgccggacctgaaattatgcctgtcgaccaacg gactggtgctgcctgacgcggtggaccgcctgct ggatgtcggcgttgaccacgtcacggtcaccatta acaccctcgacgcggagattgccgcgcaaatcta cgcctggctatggctggacggcgaacgctacag cgggcgcgaagcgggagagatcctgattgcccg tcagcttgagggcgtacgcaggctgaccgccaaa ggcgtgctggtgaaaataaattcggtgctgatccc cggtatcaacgatagcggcatggccggcgtgag ccgcgcgctgcggccagcggcgcgtttatccat aatattatgccgctgatcgccaggccggagcacg gcacggtgtttggcctcaacggccagccggagc cggacgccgagacgctcgccgccacccgcagc cggtgcggcgaagtgatgccgcagatgacccac tgccaccagtgtcgcgccgacgccattgggatgc tcggcgaagaccgcagccagcagtttacccagct tccggcgccagagagtctcccggcctggctgcc gatcctccaccagcgcgcgcagctgcacgccag cattgcgacccgcggcgaatctgaagccgatgac gcctgcctggtcgccgtggcgtcaagccgcggg gacgtcattgattgtcactttggtcacgccgaccgg ttctacatttacagcctctcggccgccggtatggtg ctggtcaacgagcgctttacgcccaaatattgtca ggggcgcgatgactgcgagccgcaggataacg cagcccggtttgcggcgatcctcgaactgctggc ggacgttaaagccgtattctgcgtgcgtatcggcc atacgccgtggcaacagctggaacaggaaggca ttgaaccctgcgttgacggcgcgtggcggccggt ctccgaagtgctgcccgcgtggtggcaacagcgt cggggggagctggcctgccgcgttgccgcataag ggggtcgcctga | ATGACCTCTTGTTCGTCGTTT TCTGGCGGTAAAGCGTGCCG TCCGGCCGATGACTCCGCGCT GACTCCGCTGGTGGCCGACA AGGCAGCTGCGCACCCGTGC TATAGCCGCCACGGCCATCA CCGCTTCGCGCGTATGCACCT GCCAGTCGCTCCGGCCTGCA ACTTACAATGCAACTACTGCA ACCGCAAGTTCGATTGCAGC AATGAAAGCCGTCCGGGCGT GTCCTCTACCCTGCTGACGCC GGAACAGGCTGTGGTGAAGG TGCGCCAGGTCGCCCAAGCT ATCCCGCAGCTGtcgGTGGTCG GTATTGCTGGTCCGGGCGATC CGCTTGCGAATATCGCCCGCA CCTTCCGTACCTTGGAGCTTA TTCGCGAACAGTTGCCGGAC CTGAAACTGTGCCTGAGCAC CAACGGCTTGGTGCTGCCAG ATGCCGTTGATCGTCTGCTCG ATGTGGGCGTGGATCACGTT ACCGTCACCATTAACACCCTG GACGCAGAAATCGCAGCGCA AATCTACGCGTGGTTGTGGCT GGATGGCGAACGCTACTCCG GTCGCGAAGCCGGCGAAATT CTCATTGCCCGCCAGCTGGAA GGCGTACGTCGCCTGACCGC GAAAGGTGTGCTCGTCAAGA TCAACAGCGTATTGATTCCGG GCATCAATGACAGCGGCATG GCGGGTGTTAGCCGTGCGCT GCGCGCGTCTGGTGCGTTCAT CCACAACATCATGCCACTGAT TGCGCGTCCGGAGCATGGCA CTGTTTTCGGTCTGAACGGCC AGCCGGAACCGGACGCGGAA ACCCTGGCGGCGACGCGCTC CCGCTGCGGCGAGGTTATGC CACAAATGACCCACTGCCAC CAGTGCCGTGCCGACGCGAT TGGCATGCTTGGTGAGGATC GCTCGCAACAGTTTACGCAAT TACCGGCTCCGGAGTCCCTCC CGGCCTGGCTGCCGATCCTGC ATCAGCGTGCTCAGTTGCATG CGAGCATCGCCACGCGCGGT GAGAGCGAAGCCGATGACGC CTGCCTGGTGGCCGTTGCGTC GAGCCGTGGCGATGTAATTG ACTGCCATTTCGGCCATGCCG ACCGTTTCTATATCTATAGCC | 80.2 | 45.4 |

FIG. 18 (cont)

| Gene | SEQ ID NO: | WT Sequence | Synthetic Sequence | % Nucleotide Identity | % Codon Identity |
|---|---|---|---|---|---|
| | | | TGTCTGCGGCTGGTATGGTTC TGGTTAACGAACGTTTCACCC CGAAATACTGCCAGGGTCGC GATGACTGCGAGCCGCAGGA CAATGCCGCACGCTTTGCTGC CATCCTTGAGTTGCTGGCGGA CGTCAAAGCGGTGTTTTGTGT GCGTATCGGCCATACCCCGTG GCAACAGCTGGAGCAGGAAG GCATCGAACCGTGCGTGGAT GGCGCCTGGCGTCCGGTATCC GAGGTCCTGCCGGCATGGTG GCAGCAGCGCCGTGGTAGCT GGCCGGCTGCATTGCCGCAC AAAGGCGTTGCGTAA | | |

FIG. 18 (cont)

| Gene | SEQ ID NO: | WT Sequence | Synthetic Sequence | % Nucleotide Identity | % Codon Identity |
|---|---|---|---|---|---|
| Q | WT Gene Q is SEQ ID NO:31<br><br>Synthetic Gene Q is SEQ ID NO:32 | atgccgccgctcgactggttgcggcgcttatggct gctgtaccacgcggggaaaggcagctttccgctg cgcatggggcttagcccgcgcgattggcaggcg ctgcggcggcgcctgggcgaggtggaaacgcc gctcgacggcgagacgctcacccgtcgccgcct gatggcggagctcaacgccacccgcgaagagg agcgccagcagctgggcgcctggctggcgggct ggatgcagcaggatgccgggccgatggcgcag attatcgccgaggtttcgctggcgtttaaccatctct ggcaggatcttggtctggcatcgcgcgccgaatt gcgcctgctgatgagcgactgcttccacagctgg tggtgatgaacgaacacaatatgcgctggaaaaa gttcttttatcgtcagcgctgtttgctgcaacagggg gaagttatctgccgttcgccaagctgcgacgagtg ctgggaacgcagcgcctgttttgagtag | ATGCCGCCATTGGACTGGTTG CGTCGTTTGTGGTTACTCTAT CACGCCGGCAAAGGCAGCTT TCCGCTTCGTATGGGCTTGTC GCCGCGTGACTGGCAAGCTC TGCGCCGTCGCCTGGGCGAG GTGGAAACGCCGCTGGATGG CGAAACCCTGACCCGTCGCC GTCTGATGGCGGAGCTGAAT GCGACCCGCGAAGAAGAACG CCAGCAGCTGGGTGCCTGGC TGGCCGGTTGGATGCAACAG GATGCCGGTCCGATGGCGCA GATTATCGCAGAGGTGAGCC TGGCGTTCAACCATCTCTGGC AGGACCTTGGCCTCGCGAGC CGCGCTGAACTGCGTCTGCTG ATGTCTGACTGCTTCCCGCAG CTGGTTGTTATGAACGAGCAC AACATGCGCTGGAAGAAATT CTTTTACCGCCAGCGTTGCCT GCTGCAACAGGGCGAAGTCA TCTGTCGCAGCCCGTCTTGCG ATGAATGCTGGGAACGTTCT GCGTGCTTTGAGTAA | 81.3 | 54.2 |

FIG. 19 Ptac-T7 Synthetic Controller.

Order #8-19: backbone is pincW (KT_96)

| SEQ ID NO: | Order | Name | Sequence |
|---|---|---|---|
| SEQ ID NO:33 | 1 | lacI | caattcgcgctaacttacattaattgcgttgcgctcactgcccgctttccagtcgggaaacctgtcgtgcca gctgcattaatgaatcggccaacgcgcggggagaggcggtttgcgtattgggcgccagggtggttttc ttttcaccagtgagacgggcaacagctgattgcccttcaccgcctggccctgagagagttgcagcaagc ggtccacgctggtttgccccagcaggcgaaaatcctgtttgatggtggttgacggcgggatataacatg agctgtcttcggtatcgtcgtatcccactaccgagatatccgcaccaacgcgcagcccggactcggtaat ggcgcgcattgcgcccagcgccatctgatcgttggcaaccagcatcgcagtgggaacgatgccctcat tcagcatttgcatggtttgttgaaaaccggacatggcactccagtcgccttcccgttccgctatcggctga atttgattgcgagtgagatatttatgccagccagccagacgcagacgcgccgagacagaacttaatggg cccgctaacagcgcgatttgctggtgacccaatgcgaccagatgctccacgcccagtcgcgtaccgtct tcatgggagaaaataatactgttgatgggtgtctggtcagagacatcaagaaataacgccggaacattag tgcaggcagcttccacagcaatggcatcctggtcatccagcggatagttaatgatcagcccactgacgc gttgcgcgagaagattgtgcaccgccgctttacaggcttcgacgccgcttcgttctaccatcgacaccac cacgctggcacccagttgatcggcgcgagatttaatcgccgcgacaatttgcgacggcgcgtgcaggg ccagactggaggtggcaacgccaatcagcaacgactgtttgcccgccagttgttgtgccacgcggttg ggaatgtaattcagctccgccatcgccgcttccacttttccgcgttttcgcagaaacgtggctggcctg gttcaccacgcgggaaacggtctgataagagacaccggcatactctgcgacatcgtataacgttactgg tttcac |
| SEQ ID NO:34 | 2 | lacI promoter | attcaccaccctgaattgactctcttccgggcgctatcatgccataccgcgaaaggttttgcaccattcgat ggtgtcaacgtaaatgcatgccgcttcgccttcgcgcgcgaattggccgccatgccggcgataatggcc tgcttctcgccgaaacgtttggtggcgggaccagtgacgaaggcttgagcgagggcgtgcaagattcc gaataccgcaagcgacaggccgatcatcgtcgcgctccagcgaaagcggtcctcgccgaaaatgacc cagagcgctgccggcacctgtcctacgagttgcatgataaagaagacagtcataagtgcggcgacgat agtcatgccccgcgcccaccggaaggagctgactgggttgaaggctctcaagggcatcggcggagct tatcgactgcacggtgcaccaatgcttctggcgtcaggcagccatcggaagctgtggtatggctgtgca ggtcgtaaatcactgcataattcgtgtcgctcaaggcgcactcccgttctggataatgttttttgcgccgac atcataacggttctggcaaatattctgaaatgagctg |
| SEQ ID NO:35 | 3 | tac promoter | ttgacaattaatcatcggctcgtataatgtgtggaattgtgagcggataacaatt |
| SEQ ID NO:36 | 4 | insulator 1 | TGCAGTTTTATTCTCTCGCCAGCACTGTAATAGGCACTAA |
| SEQ ID NO:37 | 5 | T7 RNAP rbs | TATCCAAACCAGTAGCTCAATTggagtCGTCTAT |
| SEQ ID NO:38 | 6 | umuD degradation tag | Gtgttgtttatcaagcctgcggatctccgcgaaattgtgacttttccgctatttagcgatcttgttcagtgtgg cttccttcaccggcagcagattacgttgaacagcgcatcgatctg |

FIG. 19 (cont)

| SEQ ID NO: | Order | Name | Sequence |
|---|---|---|---|
| SEQ ID NO:39 | 7 | T7 RNAP scaffold | ggtggcAACACGATTAACATCGCTAAGAACGACTTCTCTGACATCGAACTGGCTGCTATCCCGTTCAACACTCTGGCTGACCATTACGGTGAGCGTTTAGCTCGCGAACAGTTGGCCCTTGAGCATGAGTCTTACGAGATGGGTGAAGCACGCTTCCGCAAGATGTTTGAGCGTCAACTTAAAGCTGGTGAGGTTGCGGATAACGCTGCCGCCAAGCCTCTCATCACTACCCTACTCCCTAAGATGATTGCACGCATCAACGACTGGTTTGAGGAAGTGAAAGCTAAGCGCGGCAAGCGCCCGACAGCCTTCCAGTTCCTGCAAGAAATCAAGCCGGAAGCCGTAGCGTACATCACCATTAAGACCACTCTGGCTTGCCTAACCAGTGCTGACAATACAACCGTTCAGGCTGTAGCAAGCGCAATCGGTCGGGCCATTGAGGACGAGGCTCGCTTCGGTCGTATCCGTGACCTTGAAGCTAAGCACTTCAAGAAAAACGTTGAGGAACAACTCAACAAGCGCGTAGGGCACGTCTACAAGAAAGCATTTATGCAAGTTGTCGAGGCTGACATGCTCTCTAAGGGTCTACTCGGTGGCGAGGCGTGGTCTTCGTGGCATAAGGAAGACTCTATTCATGTAGGAGTACGCTGCATCGAGATGCTCATTGAGTCAACCGGAATGGTTAGCTTACACCGCCAAAATGCTGGCGTAGTAGGTCAAGACTCTGAGACTATCGAACTCGCACCTGAATACGCTGAGGCTATCGCAACCCGTGCAGGTGCGCTGGCTGGCATCTCTCCGATGTTCCAACCTTGCGTAGTTCCTCCTAAGCCGTGGACTGGCATTACTGGTGGTGGCTATTGGGCTAACGGTCGTCGTCCTCTGGCGCTGGTGCGTACTCACAGTAAGAAAGCACTGATGCGCTACGAAGACGTTTACATGCCTGAGGTGTACAAAGCGATTAACATTGCGCAAAACACCGCATGGAAAATCAACAAGAAAGTCCTAGCGGTCGCCAACGTAATCACCAAGTGGAAGCATTGTCCGGTCGAGGACATCCCTGCGATTGAGCGTGAAGAACTCCCGATGAAACCGGAAGACATCGACATGAATCCTGAGGCTCTCACCGCGTGGAAACGTGCTGCCGCTGCTGTGTACCGCAAGGACAAGGCTCGCAAGTCTCGCCGTATCAGCCTTGAGTTCATGCTTGAGCAAGCCAATAAGTTTGCTAACCATAAGGCCATCTGGTTCCCTTACAACATGGACTGGCGCGGTCGTGTTTACGCTGTGTCAATGTTCAACCCGCAAGGTAACGATATGACCAAAGGACTGCTTACGCTGGCGAAAGGTAAACCAATCGGTAAGGAAGGTTACTACTGGCTGAAAATCCACGGTGCAAACTGTGCGGGTGTCGACAAGGTTCCGTTCCCTGAGCGCATCAAGTTCATTGAGGAAAACCACGAGAACATCATGGCTTGCGCTAAGTCTCCACTGGAGAACACTTGGTGGGCTGAGCAAGATTCTCCGTTCTGCTTCCTTGCGTTCTGCTTTGAGTACGCTGGGGTACAGCACCACGGCCTGAGCTATAACTGCTCCCTTCCGCTGGCGTTTGACGGGTCTTGCTCTGGCATCCAGCACTTCTCCGCGATGCTCCGAGATGAGGTAGGTGGTCGCGCGGTTAACTTGCTTCCTAGTGAAACCGTTCAGGACATCTACGGGATTGTTGCTAAGAAAGTCAACGAGATTCTACAAGCAGACGCAATCAATGGGACCGATAACGAAGTAGTTACCGTGACCGATGAGAACACTGGTGAAATCTCTGAGAAAGTCAAGCTGGGCACTAAGGCACTGGCTGGTCAATGGCTGGCTTACGGTGTTACTCGCAGTGTGACTAAGAGTTCAGTCATGACGCTGGCTTACGGGTCCAAAGAGTTCGGCTTCCGTCAACAAGTGCTGGAAGATACCATTCAGCCAGCTATTGATTCCGGCAAGGGTCTGATGTTCACTCAGCCGAATCAGGCTGCTGGATACATGGCTAAGCTGATTTGGGAATCTGTGAGCGTGACGGTGGTAGCTGCGGTTGAAGCAATGAACTGGCTTAAGTCTGCTGCTAAGCTGCTGGCTGCTGAGGTCAAAGATAGAAGACTGGAGAGATTCTTCGCAAGCGTTGCGCTGTGCATTGGGTAACTCCTGATGGTTTCCCTGTGTGGCAGGAATACAAGAAGCCTATTCAGACGCGCTTGAACCTGATGTTCCTCGGTCAGTTCCGCTTACAGCCTACCATTAACACCAACAAAGATAGCGAGATTGATGCACACAAACAGGAGTCTGGTATCGCTCCTAACTTTGTACACAGCCAAGACGGTAGCCACCTTCGTAAGACTGTAGTGTGGGCACACGAGAAGTACGGAATCGAATCTTTTGCACTGATTCACGACTCCTTCGGTACGATTCCGGCTGACGCTGCGAACCTGTTCAAAGCAGTGCGCGAAACTATGGTTGACACATATGAGTCTTGTGATGTACTGGCTGATTTCTACGACCAGTTCGCTGACCAGTTGCACGAG |

FIG. 19 (cont)

| SEQ ID NO: | Order | Name | Sequence |
|---|---|---|---|
| SEQ ID NO:40 | 8 | Biobrick suffix (BBa_G00001) | Tactagtagcggccgctgcag |
| SEQ ID NO:41 | 9 | Translational stop (BBa_B0042) | ttagttagttag |
| SEQ ID NO:42 | 10 | Terminator (BBa_B0054) | attagcagaaagtcaaaagcctccgaccggaggcttttgactaaaacttcccttggggttatcattggg |
| SEQ ID NO:43 | 11 | VR primer sequence (BBa_G00102) | gctcactcaaaggcggtaat |
| SEQ ID NO:44 | 12 | Terminator (BBa_B0062) | cagataaaaaaaatccttagctttcgctaaggatgatttct |

FIG. 19 (cont)

| SEQ ID NO: | Order | Name | Sequence |
|---|---|---|---|
| SEQ ID NO:45 | 13 | pSa origin | gctagagctgtcagaccagagctccaaaccaacgttttatctataccgctacagggtatttaattcctattta atctgcgctagaatgaggcatgtttaaccgaatctgacgttttccctgcaaatgccaaaatactatgcctat ctccgggtttcgcgtgacggccaagacccggaaaaccaaaaatacggtttgctcgaatacgcgaacgc caaaggcttcgcgccgctacagatcgaggaagaaattgccagcagagcaaaggactggcgcaagcg caagctcggagcaatcatcgaaaaggccgagcgtggcgacgtgctactgacgccggagattacgcgc attgccggttccgccctcgccgccttggaaattctcaaagcggcgagcgagcgcggcctaatcgtccat gtgaccaaacagaagatcatcatggacggcagcctacaaagcgacatcatggcaaccgtgcttggctt ggctgcacagatcgagcggcatttcattcaggcacgtaccaccgaggcgctacaagtcgccagagag cgcggcaagacgctcgggcgacccaagggcagcaaatcgagcgccttgaagctggacagccgtatt gatgaagtacaggcatacgtgaaccttggcttgccgcaaagtcgcgcagccgagttgttaggcgtcag ccctcacaccttgcgcctgttcatcaaacgccggaacatcaaacccacaaacactagaccaaccatcac catgccggggagggaacaacatgcctaagaacaacaaagcccccggccatcgtatcaacgagatcat caagacgagcctcgcgctcgaaatggaggatgcccgcgaagctggcttagtcggctacatggcccgtt gccttgtgcaagcgaccatgccccacaccgacccaagaccagctactttgagcgcaccaatggcatc gtcaccttgtcgatcatgggcaagccgagcatcggcctgccctacggttctatgccgcgcaccttgcttg cttggatatgcaccgaggccgtgcgaacgaaagacccgtgttgaacccttggccggtcgcaatcggaa tttctacaaaggctcggaatgcacaccgatggccgttacacggccacccttcgcaatcaggcgcaacg cctgttttcatccatgatttcgcttgccggcgagcaaggcaatgacttcggcattgagaacgtcgtcattgc caagcgcgcttttctattctggaatcccaagcggccagaagatcgggcgctatgggatagcaccctcac cctcacaggcgatttcttcgaggaagtcacccgctcaccggttcctatcgaatcgactacctgcatgcct tgcggcagtctccgcttgcgatggacatttacacgtggctgacctatcgcgtgttcctgttgcgggccaa gggccgccccttcgtgcaaatcccttgggtcgcctgcaagcgcaattcggctcatcctatggcagccg cgcacgcaactcgcccgaactggacgataaggcccgagagcgggcagagcgggcagcactcgcca gcttcaaatacaacttcaaaaagcgcctacgcgaagtgttgattgtctatcccgaggcaagcgactgcat cgaagatgacggcgaatgcctgcgcatcaaatccacacgcctgcatgtcacccgcgcacccggcaag ggcgctcgcatcggccccctccgacttgaccaggccaacgctacgcttggcttggtcaagccttccca tccaacagcccgccgtcgagcgggctttttatcccggaagcctgtggatagagggtagttatccacgt gaaaccgctaatgccccgcaaagccttgattcacggggctttccggccccgctccaaaaactatccacgt gaaatcgctaatcagggtacgtgaaatcgctaatcggagtacgtgaaatcgctaataaggtcacgtgaa atcgctaatcaaaaaggcacgtgagaacgctaatagcccttcagatcaacagcttgcaaacacccctc gctccggcaagtagttacagcaagtagtatgttcaattagcttttcaattatgaatatatatcaattattggt cgcccttggcttgtggacaatgcgctacgcgcaccggctccgcccgtgacaaccgcaagcggttgc ccaccgtcgagcgccagcgcctttgcccacaacccggcgccgcaacagatcgttttataaatttttttt tgaaaagaaaaagcccgaaaggcggcaacctctcgggcttctggatttccgatcaacgcaggagtcg ttcggaaagtagctgttccagaattataggcgcagagacaccagattccaagatggctctgttaaattgtt gtagtatgtagtatcatacaacatactacagtacagaggcccgcaagaatggcaatcactaaacaagac atttggcgagcagccgacgaactggacgccgaaggcatccggcccactttggccgccgtgcgcaaga aactcggaagcggtagcttcacaaccatttccgatgcaatggctgaatggaaaaaccgcaagaccgcc accctgccctcatcagacccattgccggttgcagtcaacgagcatcttgccgagcttggcaatgcgctat gggctatcgccctggcgcacgccaacgcccggtttgacgaagatcggaaacagatcgaggccgaca aagcggccatcagccagcagcttgccgaagcaatcgaactagccgacaccttcacccgcgaaaacga ccagctccgcgaacgagtgaatcagctcgaacctatggaacgcgagcgcgacaagctggccgacca gcttgccgaagtgaaacgccgcagcggcgaagaactaaaccgctgcatggaaaagctcacccaacg cgataacgaggctatcgaggcccgcaaacaggccaaggaggccatcgagcgcgccgccagtctgca aggtcaggtggaagccctcaaagagcaggtcgccaatctcacagccgtcttgaaaacaggaggcaaa caatgaaaagcgccttgccgcccttcgcgcggtcgcggccgctgtcgtcctaatcgtcagtgtgcccg cttgggccgacttccggggtgaagtcgtccgaatccttgacggtgacactatcgacgttttggtgaaccg tcagaccatccgcgtgagattggccgatattgacgcaccggaaagcggccaagccttcggctcccgtg ctcgccaacgcgctcgccgacttgacctttcgccaagaggttcaagtgaccgaaaaagaggttgatcggt atggccgcactcttgggtcgtttacgcgccgttgcaataccccggcggccaaacacaactcaccaac atcaatgcgatcatggttcaagaaggcatggcctgggcttaccgttattacgcaaaccaaccgacgcg cagatgtacagtatgaaaaagaggcccgccgccaacggctcggcctttggtcagacccgaatgctca ggagccttggaaatggcgtcgcgcctcgaaaaatgccacgaactgacaccgggcacgcccttgttcg acgcgccgcaggcacgtcgaatttaccgccgggacg |

FIG. 19 (cont)

| SEQ ID NO: | Order | Name | Sequence |
|---|---|---|---|
| SEQ ID NO:46 | 14 | spectinomycin resistance | ccccctcgtcccgacacttccagatcgccatagcgcacagcgcctcgagcggtggtaacggcgcagtggcggttttcatggcttgttatgactgtttttttggggtacagtctatgcctcgggcatccaagcagcaagcgcgttacgccgtgggtcgatgtttgatgttatggagcagcaacgatgttacgcagcagggcagtcgccctaaaacaaagttaaacatcatgagggaagcggtgatcgccgaagtatcgactcaactatcagaggtagttggcgtcatcgagcgccatctcgaaccgacgttgctggccgtacatttgtacggctccgcagtggatggcggcctgaagccacacagtgatattgatttgctggttacggtgaccgtaaggcttgatgaaacaacgcggcgagctttgatcaacgaccttttggaaacttcggcttcccctggagagagcgagattctccgcgctgtagaagtcaccattgttgtgcacgacgacatcattccgtggcgttatccagctaagcgcgaactgcaatttggagaatggcagcgcaatgacattcttgcaggtatcttcgagccagccacgatcgacattgatctggctatcttgctgacaaaagcaagagaacatagcgttgccttggtaggtccagcggcggaggaactctttgatccggttcctgaacaggatctatttgaggcgctaaatgaaaccttaacgctatggaactcgccgcccgactgggctggcgatgagcgaaatgtagtgcttacgttgtcccgcatttggtacagcgcagtaaccggcaaaatcgcgccgaaggatgtcgctgccgactgggcaatggagcgcctgccggcccagtatcagcccgtcatacttgaagctagacaggcttatcttggacaagaagaagatcgcttggcctcgcgcgcagatcagttggaagaatttgtccactacgtgaaaggcgagatcaccaaggtagtcggcaaataatgtctaacaattcgttcaagccgacgccgcttcgcggcgcggcttaactcaagcgttagatgcactaagcacataattgctcacagccaaactatcaggtcaagtctgcttttattattttttaagcgtgcataataagccctacacaaatggtaccc |
| SEQ ID NO:47 | 15 | Terminator (BBa_B0053) | tccggcaaaaaaacgggcaaggtgtcaccaccctgccctttttctttaaaaccgaaaagattacttcgcgtt |
| SEQ ID NO:48 | 16 | VF2 primer sequence (BBa_G000101) | tgccacctgacgtctaagaa |
| SEQ ID NO:49 | 17 | Terminator (BBa_B0055) | aaggaatattcagcaatttgcccgtgccgaagaaaggcccacccgtgaaggtgagccagtgagttgattgctacgtaa |
| SEQ ID NO:50 | 18 | Translational stop (BBa_B0042) | ttagttagttag |
| SEQ ID NO:51 | 19 | Biobrick prefix (Bba_G00000) | gaattcgcggccgcttctagag |

FIG. 20  Parts List of Full Synthetic Cluster

Order # 57-67 have pSB4C5 backbone.

| | Order | Name | Strength (AFU) | Sequence |
|---|---|---|---|---|
| SEQ ID NO:52 | 1 | T7 promoter WT | 9000 | TAATACGACTCACTATAGGGAGA |
| SEQ ID NO:53 | 2 | nifH rbs | 5500 | ACAATAAACTAACATAAGGAGGATAAAT |
| SEQ ID NO:54 | 3 | nifH | | ATGACCATGCGTCAGTGCGCGATTTATGGCAAAGGTGGTATTG GCAAAAGCACGACGACCCAGAACTTGGTGGCGGCCCTGGCCG AGATGGGTAAAAAGGTTATGATTGTGGGTTGCGACCCGAAGG CCGACAGCACGCGCCTGATTCTGCACGCGAAAGCACAAAACA CGATTATGGAGATGGCTGCCGAGGTTGGTAGCGTGGAGGATC TGGAGCTGGAGGACGTTCTGCAAATTGGTTACGGTGATGTTCG TTGCGCAGAGAGCGGTGGTCCGGAACCAGGTGTCGGCTGTGC GGGTCGTGGTGTGATTACCGCTATCAATTTCCTGGAAGAAGAG GGTGCGTACGAAGATGATCTGGATTTCGTTTTCTACGATGTGC TGGGTGATGTCGTGTGCGGTGGTTTTGCAATGCCGATTCGCGA GAATAAGGCACAAGAAATTTACATTGTCTGTAGCGGCGAGAT GATGGCAATGTACGCTGCTAACAACATCAGCAAGGGTATTGT TAAATACGCAAAAAGCGGTAAGGTTCGCTTGGGTGGTTTGATT TGCAACAGCCGTCAGACCGACCGTGAGGACGAACTGATCATC GCCCTGGCTGAGAAACTGGGCACCCAAATGATCCACTTCGTG CCACGCGATAATATTGTTCAACGTGCAGAAATCCGCCGTATGA CCGTCATTGAGTATGACCCGGCATGCAAGCAAGCGAACGAGT ACCGCACCTTGGCACAGAAAATCGTGAACAACACCATGAAGG TTGTTCCGACGCCGTGTACGATGGACGAGCTGGAGAGCCTGCT GATGGAGTTCGGCATTATGGAGGAGGAGGACACCAGCATTAT CGGTAAGACCGCAGCGGAGGAGAATGCGGCATAA |
| SEQ ID NO:55 | 4 | insulator 1 | | GCGTGCGTACACCTTAATCACCGCTTCATGCTAAGGTCCTGGC TGCATGC |
| SEQ ID NO:56 | 5 | nifD rbs | 500 | AAAAATTCACATCCCTATCTAGCGGAGGAGCCGG |
| SEQ ID NO:57 | 6 | nifD | | atgatgactaatgctactggcgaacgtaacctggcactgattcaagaagtactggaagtgttcccggaa accgcgcgcaaagagcgccgtaaacacatgatggtttctgacccgaaaatgaaatctgtgggtaaatg catcatctctaatcgcaaatctcagccgggtgtcatgactgttcgtggctgtgcgtacgcaggttctaaag gtgtcgtattcggccccgatcaaagatatggcgcatatctctcatggcccggcaggctgtggccagtact ctcgcgcggaacgtcgtaactactacacgggcgtttctggcgttgactctttcggcacgctgaacttcac ctctgacttccaggaacgtgacatcgttttcggtggcgataaaaagctgtccaaactgatcgaagaaatg gaactgctgttcccgctgactaaaggcattactatatccaaagcgaatgtccggtgggtctgatcggtgatg acatcagcgcggtcgcaaacgcatcttccaaagccctggataagccggtgatcccggttcgttgcgag ggcttccgcggcgtttctcagtctctgggtcatcacatcgcaaacgatgttgtgcgtgactggattctgaa caaccgtgaaggtcagccttttgaaaccaccccttatgacgttgcgattattggcgactataacatcggc ggcgacgcctgggcatcccgcatcctgctggaggagatgggtctgcgtgttgtcgcacagtggtctgg cgatggcaccctggttgaaatggaaaacaccccgtttgttaaactgaacctggttcactgctaccgctcc atgaactacattgcccgtcacatggaagaaaacatcagatcccttggatggaatacaacttcttcggtc cgactaaaatcgcagaatccctgcgtaaaatcgccgatcagtttgatgataccattcgcgcgaacgctg aagcagtaattgcgcgctacgaaggccagatggcagcaatcattgctaagtaccgtccgcgcctggaa ggtcgtaaagtgctgctgtacatgggtggtctgcgtccacgtcatgtgatcggtgcctacgaggacctg ggcatggagatcatcgcagcgggttacgaatttgcacacaacgacgactatgatcgtacgctgccaga cctgaaagaaggtacgctgctgtttgacgacgccagctcttatgaactggaagccttcgtgaaagcgct gaaaccagacctgatcggctccggcatcaaggaaaaatacatttccagaaaatgggcgtgccgttcc gccagatgcactcctgggactactccggtccgtaccacggctacgacggttcgctatcttcgctcgtga |

FIG. 20 (cont)

| | | | | |
|---|---|---|---|---|
| | | | | catggatatgaccctgaataacccagcgtggaatgaactgaccgcaccgtggctgaaatctgcataa |
| SEQ ID NO:58 | 7 | insulator 2 | | CAAACACCCCATGTCGATACTGAACGAATCGACGCACACTCCCTTCCTTG |
| SEQ ID NO:59 | 8 | nifK rbs | 50 | CAATCTCATACTCTCAAAAATTAGGCGAGGTAAC |
| SEQ ID NO:60 | 9 | nifK | | atgtctcaaactatcgataaaatcaactcttgttacccgctgttcgagcaggacgaatatcaggaactgttccgtaacaaacgtcagctggaagaagcgcacgacgcacagcgcgtgcaggaagtgttcgcatggaccaccaccgcggaatacgaagctctgaacttccgtcgcgaagcccctgacggttgatccggcgaaagcgtgccagcctctgggtgcggttctgtgcagcctgggttttgccaacaccctgccgtatgtccacggttcccagggctgcgtagcctacttccgtaccatttcaaccgccacttttaaagaaccaatcgcgtgcgtgtccgacagcatgacggaggacgcggcagttttcggtggtaacaacaacatgaacctgggcctgcaaaatgcttccgcactgtacaaaccggaaatcatcgcagtgtctaccacctgcatggcagaggttattggtgatgatctgcaagcatttattgccaacgcaaagaaagacggtttcgttgacagctctatcgcggttccgcacgctcatacccgtccttcatcggttctcacgtaactggttgggacaacatgttcgaaggcttcgcaaaaacttttacgcagactatcaaggccaaccgggtaaactgccgaagctgaacctggtgaccggctttgaaacctacctgggcaactttcgtgtcctgaagcgcatgatggagcagatggcggttccgtgttctctgctgtctgacccgtctgaggttctggacactccagcggacggccactatcgcatgtattctggtggcaccactcagcaggaaatgaaagaggccccagacgcgattgacaccctgctgctgcaaccgtggcagctgctgaaaagcaagaaagttgttcaggaaatgtggaaccagccggcaacggaagttgcaatcccgctgggtctggcagctactgacgaactgctgatgaccgtgtcccaactgagcggcaaaccaatcgcggatgctctgaccctggaacgcggtcgcctggtggacatgatgctggacagccacacgtggctgcatggcaagaaatttggcctgtacggtgacccggacttcgtaatgggcctgacccgttcctgctggaactgggctgcgagccgactgttatcctgtctcacaacgctaacaaacgttggcagaaggccatgaacaaaatgctggatgcgagcccatacggccgtgatagcgaagtgttcatcaactgcgacctgtggcatttccgctctctgatgtttacgcgtcagccggatttcatgatcggtaactcttacggcaaattcatccagcgtgacactctggccaaaggcaaagcgtttgaagtgccgctgattcgtctgggctttccgctgttcgaccgtcaccacctgcaccgccagaccacctgggggttacgaaggcgcgatgaacatcgtaactactctggtaaacgcagtactggaaaagctggacagcgatacttcccagctgggcaaaaccgactattcttcgatctggttcgttaa |
| SEQ ID NO:61 | 10 | insulator 3 | | CCTGATTGTATCCGCATCTGATGCTACCGTGGTTGAGTTA |
| SEQ ID NO:62 | 11 | nifY rbs | 240 | CCATACTCACTCCCGGAGGTACTTCT |
| SEQ ID NO:63 | 12 | nifY | | ATGTCTGACAATGATACCCTGTTTTGGCGCATGCTGGCGCTGTTTCAGTCGCTGCCGGATTTGCAGCCGGCTCAAATCGTCGATTGGCTGGCGCAGGAATCCGGCGAAACCCTGACGCCGGAGCGCCTTGCCACCCTGACCCAACCGCAACTCGCGGCGTCGTTCCCATCCGCGACGGCAGTGATGAGCCCGGCTCGCTGGAGCCGCGTTATGGCTTCTCTGCAAGGCGCCCTCCCAGCCCACTTGCGCATCGTACGTCCGGCGCAGCGTACCCCGCAACTGCTCGCCGCGTTTTGCAGCCAAGACGGCCTTGTTATCAATGGTCATTTCGGCCAGGGTCGTCTGTTCTTCATTTACGCCTTTGACGAGCAGGGCGGCTGGCTGTATGACTTGCGCCGCTATCCGAGCGCACCGCACCAGCAGGAAGCGAATGAGGTGCGTGCTCGTCTGATTGAAGATTGCCAGCTGCTGTTCTGCCAGGAGATTGGCGGTCCGGCAGCAGCGCGTCCGATCCGCCACCGCATCCATCCGATGAAGGCGCAGCCGGGTACTACGATTCAGGCGCAGTGTGAAGCTATCAACACCCTGCTGGCCGGTCGCCTGCCGCCGTGGCTCGCCAAACGTTTGAACCGTGATAACCCGCTGGAAGAGCGTGTGTTTTAA |
| SEQ ID NO:64 | 13 | insulator 4 | | CATTTTTGCCTTGCGACAGACCTCCTACTTAGATTGCCAC |
| SEQ ID NO:65 | 14 | nifE rbs | 40 | ACTATTCAATACATCACTGGAGGTTATTACAA |

FIG. 20 (cont)

| | | | | |
|---|---|---|---|---|
| SEQ ID NO:66 | 15 | nifE | | ATGAAGGGTAACGAGATTCTTGCTCTGCTGGACGAACCGGCC<br>TGTGAACACAACCATAAACAGAAATCCGGCTGTAGCGCCCCA<br>AAGCCGGGTGCGACGGCGGCTGGCTGCGCTTTCGATGGTGCG<br>CAGATCACCCTGCTCCCGATTGCGGACGTTGCCCACCTCGTGC<br>ATGGCCCAATCGGTTGCGCAGGTAGCTCTTGGGACAACCGTG<br>GCAGCGCCTCCAGCGGTCCGACCCTGAATCGTTTGGGCTTTAC<br>CACTGACTTGAATGAACAAGATGTGATCATGGGTCGCGGCGA<br>GCGTCGCCTGTTCCACGCTGTGCGCCATATTGTCACCCGTTAC<br>CACCCAGCGGCAGTATTCATCTACAATACGTGCGTGCCGGCTA<br>TGGAAGGCGATGACCTGGAGGCCGTGTGTCAGGCAGCCCAGA<br>CTGCGACCGGCGTCCCGGTAATCGCAATTGATGCGGCTGGCTT<br>CTACGGTTCGAAGAACCTGGGCAACCGTCCGGCAGGCGATGT<br>CATGGTTAAACGCGTCATTGGCCAACGTGAGCCAGCGCCGTG<br>GCCGGAGAGCACCCTGTTTGCCCCGGAGCAACGTCATGACAT<br>GGCTTGATCGGTGAGTTCAACATTGCGGGCGAGTTTTGGCAC<br>ATTCAGCCGCTGCTTGATGAGCTGGGTATCCGCGTTTTGGGTT<br>CGCTCAGCGGCGATGGTCGTTTCGCCGAGATTCAAACCATGCA<br>CCGTGCCCAGGCGAACATGCTGGTGTGCAGCCGTGCTCTGATC<br>AATGTTGCGCGTGCTCTGGAACAGCGCTATGGCACCCCGTGGT<br>TTGAAGGCTCGTTCTATGGTATCCGCGCGACCAGCGACGCCCT<br>GCGCCAGTTAGCGGCGCTGCTGGGCGATGACGACCTCCGTCA<br>GCGCACCGAGGCGCTGATCGCGCGTGAAGAACAGGCGGCTGA<br>GCTGGCCCTGCAACCGTGGCGTGAACAGCTGCGTGGCCGCAA<br>GGCCCTGCTCTACACGGGTGGTGTCAAAAGCTGGTCTGTGGTG<br>TCCGCGCTTCAGGATCTGGGTATGACCGTGGTTGCCACGGGCA<br>CGCGTAAGAGCACGGAAGAGGATAAACAGCGCATCCGCGAAT<br>TGATGGGCGAAGAGGCCGTGATGCTTGAAGAAGGCAACGCAC<br>GTACCTTATTGGATGTAGTTTATCGCTATCAAGCAGACCTGAT<br>GATTGCCGGTGGCCGCAACATGTATACCGCCTACAAAGCGCG<br>CTTGCCGTTCCTGGACATCAACCAGGAACGCGAGCACGCGTTT<br>GCGGGCTACCAAGGCATCGTGACCTTAGCGCGCCAGCTGTGC<br>CAAACGATTAACAGCCCGATCTGGCCGCAGACTCATTCCCGC<br>GCACCGTGGCGCTAA |
| SEQ ID NO:67 | 16 | insulator 5 | | TGTCACGCTAGGAGGCAATTCTATAAGAATGCACACTGCA |
| SEQ ID NO:68 | 17 | infN rbs | 40 | CCTAAACCTACCACACCTGGAAGAAGTAATT |
| SEQ ID NO:69 | 18 | nifN | | ATGGCAGACATTTTCCGCACTGATAAGCCGTTGGCTGTGTCGC<br>CGATCAAGACCGGCCAGCCGCTGGGTGCGATCCTGGCGTCCC<br>TGGGTATCGAGCACTCGATTCCGCTGGTACATGGCGCGCAGG<br>GCTGTTCGGCTTTTGCCAAGGTTTTCTTTATCCAGCACTTCCAC<br>GATCCGGTCCCGCTGCAAAGCACGGCAATGGACCCGACCAGC<br>ACCATCATGGGCGCTGATGGTAACATCTTCACCGCGCTGGACA<br>CTCTCTGCCAACGCAATAACCCGCAAGCAATTGTGCTGCTGAG<br>CACCGGCCTCTCCGAGGCGCAGGGCAGCGACATTTCCCGTGT<br>AGTGCGTCAGTTCCGTGAAGAATATCCGCGTCATAAAGGCGT<br>GGCGATTCTGACTGTTAACACCCCGGACTTTTACGGTAGCATG<br>GAGAACGGCTTTTCCGCTGTCCTGGAGTCTGTGATTGAACAGT<br>GGGTTCCGCCAGCCCCACGTCCGGCGCAGCGCAATCGTCGCG<br>TCAATCTTTTGGTGAGCCATCTCTGTAGCCCAGGCGATATTGA<br>GTGGCTGCGCCGTTGCGTCGAGGCCTTCGGTCTGCAACCGATC<br>ATTCTGCCGGATCTGGCTCAGAGCATGGACGGCCACCTTGCTC<br>AGGGTGACTTTTCGCCGCTGACGCAGGGCGGCACGCCGTTGC<br>GCCAAATCGAGCAGATGGGCCAGAGCCTTTGCTCTTTTGCGAT<br>TGGCGTCAGCCTGCACCGTGCGAGCAGCCTGCTGGCTCCGCGT<br>TGTCGTGGCGAAGTCATCGCCTTGCCGCACCTCATGACCTTGG<br>AACGCTGCGACGCCTTTATCCATCAGTTGGCGAAAATCAGCG |

FIG. 20 (cont)

| | | | | GTCGCGCCGTTCCGGAGTGGCTGGAACGCCAGCGCGGTCAGC<br>TGCAAGACGCCATGATCGATTGCCACATGTGGCTGCAAGGCC<br>AGCGCATGGCGATTGCCGCCGAAGGCGACCTGCTGGCAGCGT<br>GGTGCGATTTCGCGAACTCTCAAGGTATGCAGCCGGGTCCACT<br>GGTTGCTCCGACGGGTCATCCGAGCCTGCGTCAGTTGCCGGTG<br>GAGCGCGTGGTGCCGGGTGATCTGGAGGATCTTCAGACCCTCT<br>TATGCGCACATCCGGCCGACTTACTGGTGGCGAACTCCCACGC<br>CCGTGATTTAGCAGAGCAATTCGCCCTGCCGCTGGTGCGCGCA<br>GGCTTCCCGCTGTTTGACAAACTGGGCGAATTTCGTCGTGTTC<br>GCCAGGGTTATAGCGGTATGCGTGATACCCTGTTCGAGTTGGC<br>GAACCTGATCCGTGAACGCCATCATCATCTGGCTCATTATCGC<br>AGCCCGCTGCGCCAGAACCCAGAATCCTCGTTGTCTACGGGTG<br>GCGCGTACGCAGCGGATTAA |
|---|---|---|---|---|
| SEQ ID NO:70 | 19 | nifJ rbs | 100 | ctagagattaaagaggagaaattaagc |
| SEQ ID NO:71 | 20 | nifJ | | ATGAAAACTATGGACGGTAACGCTGCGGCTGCATGGATTAGC<br>TACGCCTTTACCGAAGTGGCTGCGATCTACCCGATTACGCCGA<br>GCACCCCGATGGCGGAAAATGTGGACGAATGGGCTGCGCAGG<br>GCAAGAAGAACCTCTTCGGCCAGCCGGTGCGCCTGATGGAGA<br>TGCAGTCGGAAGCGGGTGCAGCAGGTGCTGTGCATGGCGCCT<br>TGCAAGCTGGCGCACTGACGACCACCTACACCGCGTCGCAGG<br>GCCTGTTGCTGATGATCCCAAACATGTACAAAATCGCGGGTG<br>AACTGCTGCCGGGTGTCTTTCATGTTTCGGCACGCGCACTGGC<br>CACCAATAGCCTCAACATCTTTGGCGATCATCAGGATGTAATG<br>GCGGTGCGCCAAACGGGCTGCGCGATGTTGGCCGAGAATAAC<br>GTCCAGCAAGTTATGGATTTGTCCGCGGTAGCCCACTTGGCAG<br>CGATCAAAGGTCGCATTCCGTTCGTGAACTTCTTCGATGGCTT<br>TCGCACCAGCCACGAAATCCAGAAGATCGAGGTTCTGGAATA<br>TGAACAGCTGGCCACCTTGTTGGATCGTCCGGCCCTGGACAGC<br>TTCCGCCGTAACGCCCTTCACCCGGACCACCCGGTCATCCGTG<br>GCACCGCCCAGAACCCGGACATCTACTTCCAGGAACGTGAGG<br>CCGGTAACCGTTTCTATCAGGCGCTCCCGGATATTGTGGAATC<br>TTACATGACCCAGATTTCTGCCCTGACTGGTCGCGAGTATCAC<br>CTGTTTAACTACACTGGTGCTGCGGATGCGGAGCGCGTGATCA<br>TCGCGATGGGCTCTGTCTGTGACACCGTCCAAGAGGTGGTTGA<br>CACGCTGAATGCAGCGGGTGAGAAAGTTGGTCTGCTCTCCGTT<br>CATCTTTTCCGCCCGTTTTCGTTAGCGCACTTCTTCGCCCAACT<br>GCCGAAAACTGTACAGCGTATCGCAGTATTGGACCGTACGAA<br>AGAGCCAGGTGCTCAAGCAGAGCCGCTGTGCCTCGATGTGAA<br>GAATGCCTTTTACCACCATGACGATGCCCCGTTGATTGTGGGT<br>GGTCGCTATGCCTTGGGCGGTAAGGACGTGTTGCCGAACGAT<br>ATTGCGGCCGTGTTTGATAACCTGAACAAACCGCTGCCGATGG<br>ACGGCTTCACGCTGGGTATCGTGGACGATGTTACCTTCACCTC<br>TCTCCCGCCAGCGCAGCAGACCCTGGCGGTTTCTCACGACGGC<br>ATCACGGCATGTAAGTTTTGGGGCATGGGCTCCGACGGCACG<br>GTTGGTGCGAACAAGTCCGCGATCAAGATTATCGGCGACAAA<br>ACGCCACTGTATGCGCAAGCGTACTTTTCCTACGACTCGAAGA<br>AGAGCGGTGGTATTACCGTCAGCCATCTGCGTTTTGGTGATCG<br>CCCGATCAACTCCCCGTATTTGATCCATCGCGCGGATTTCATC<br>TCGTGCAGCCAGCAAAGCTATGTTGAACGCTACGATCTGCTGG<br>ATGGCCTTAAACCGGGTGGCACCTTTCTGCTGAACTGCTCCTG<br>GAGCGATGCCGAACTGGAGCAACATCTGCCGGTCGGTTTCAA<br>ACGTTATCTGGCACGCGAGAATATCCACTTCTACACTCTCAAC<br>GCTGTGGACATCCGCCGTGAGCTTGGTTTGGGTGGCCGTTTCA<br>ACATGCTGATGCAGGCTGCCTTCTTCAAACTGGCCGCGATCAT<br>TGACCCGCAGACTGCTGCGGACTATCTGAAGCAGGCTGTTGA<br>GAAAAGCTATGGCAGCAAAGGTGCGGCGGTCATCGAGATGAA<br>CCAGCGTGCCATCGAGCTTGGCATGGCCAGCCTGCACCAGGT |

FIG. 20 (cont)

| | | | | |
|---|---|---|---|---|
| | | | | GACGATCCCGGCACATTGGGCCACCCTGGATGAGCCAGCGGC GCAGGCGTCCGCGATGATGCCGGACTTTATCCGCGACATCCTG CAACCGATGAACCGTCAGTGCGGCGACCAGCTTCCGGTGTCG GCTTTTGTCGGCATGGAAGATGGCACCTTCCCGTCCGGCACGG CCGCATGGGAGAAACGTGGCATCGCCCTTGAGGTGCCAGTCT GGCAGCCGGAAGGCTGCACGCAGTGCAACCAGTGCGCCTTCA TTTGTCCGCACGCCGCGATTCGTCCGGCGTTGTTGAATGGCGA AGAGCATGATGCTGCCCCGGTTGGCCTGCTGAGCAAACCGGC ACAAGGCGCTAAAGAATATCACTATCATCTGGCGATTAGCCC GCTGGACTGCTCCGGCTGTGGCAACTGCGTTGACATTTGTCCA GCTCGTGGCAAAGCGTTGAAGATGCAGTCTCTGGATAGCCAA CGCCAGATGGCTCCGGTGTGGGATTATGCGCTGGCGCTGACCC CGAAGTCTAACCCGTTTCGTAAAACCACCGTCAAAGGCTCGC AGTTCGAAACCCCGCTGCTGGAGTTTAGCGGTGCGTGCGCTGG TTGTGGCGAAACGCCGTATGCGCGCCTCATTACCCAGCTGTTT GGCGACCGCATGCTGATTGCCAATGCCACCGGCTGTTCCAGCA TCTGGGGCGCATCTGCGCCGAGCATCCCGTATACCACCAATCA TCGTGGTCATGGTCCGGCCTGGGCGAATAGCCTGTTTGAGGAC AATGCCGAATTTGGTTTAGGTATGATGCTGGGCGGTCAAGCTG TGCGTCAACAGATCGCGGACGATATGACGGCTGCGTTAGCGC TCCCGGTTTCCGATGAGCTGAGCGACGCGATGCGCCAGTGGTT GGCGAAACAGGACGAGGGTGAAGGCACGCGTGAGCGTGCGG ACCGTCTGAGCGAGCGCTTAGCCGCGGAGAAAGAGGGCGTTC CGCTGTTAGAGCAGCTGTGTGGCAAAATCGTGATTACTTTGTGCG TCGCAGCCAGTGGATTTTCGGCGGTGACGGCTGGGCCTATGAT ATTGGCTTCGGTGGCCTGGACCACGTCCTCGCCAGCGGTGAGG ATGTGAACATTCTGGTATTTGACACCGAAGTCTACTCGAACAC CGGCGGTCAAAGCAGCAAATCGACCCCGGTCGCGGCCATCGC CAAGTTCGCGGCTCAGGGCAAGCGCACCCGCAAGAAAGACCT GGGTATGATGGCGATGAGCTACGGCAACGTCTATGTAGCCCA GGTGGCGATGGGTGCGGATAAAGATCAAACTCTGCGCGCCAT TGCGGAAGCTGAAGCGTGGCCAGGCCCGTCGCTGGTGATTGC GTATGCGGCCTGCATCAATCATGGCCTGAAGGCCGGTATGCGT TGCAGCCAACGTGAGGCGAAGCGCGCTGTTGAGGCGGGCTAC TGGCACCTGTGGCGTTATCACCCGCAGCGCGAAGCGGAAGGC AAGACGCCGTTTATGTTAGATAGCGAAGAACCGGAAGAGTCG TTCCGTGACTTTCTGTTGGGTGAGGTGCGCTACGCATCCCTGC ACAAGACCACCCCGCACCTCGCCGATGCCCTTTTCAGCCGTAC CGAAGAAGATGCGCGTGCGCGCTTTGCGCAATACCGTCGCCT GGCTGGCAAGAGTAATAA |
| SEQ ID NO:72 | 21 | T7 terminator 25 | 1600 | TACTCTAACCCCATCGGCCGTCTTAGGGGTTTTTTGT |
| SEQ ID NO:73 | 22 | insulator 6 | | CCGTGGTTGAGTCAGCGTCGAGCACGCGGC |
| SEQ ID NO:74 | 23 | T7 promoter mut 2 | 1500 | TAATACGACTCACTAGAGAGAGA |
| SEQ ID NO:75 | 24 | insulator 7 | | CGCGACTTCCAGAGAAGAAGACTACTGACTTGAGCGTTCC |
| SEQ ID NO:76 | 25 | nifB rbs | 220 | CTCTCTGTAATACATCAAATCAATCATAGGAGGGCTAAA |
| SEQ ID NO:77 | 26 | nifB | | ATGACCTCTTGTTCGTCGTTTTCTGGCGGTAAAGCGTGCCGTC CGGCCGATGACTCCGCGCTGACTCCGCTGGTGGCCGACAAGG CAGCTGCGCACCCGTGCTATAGCCGCCACGGCCATCACCGCTT CGCGCGTATGCACCTGCCAGTCGCTCCGGCCTGCAACTTACAA TGCAACTACTGCAACCGCAAGTTCGATTGCAGCAATGAAAGC |

FIG. 20 (cont)

| | | | | |
|---|---|---|---|---|
| | | | | CGTCCGGGCGTGTCCTCTACCCTGCTGACGCCGGAACAGGCTG<br>TGGTGAAGGTGCGCCAGGTCGCCCAAGCTATCCCGCAGCTGtcg<br>GTGGTCGGTATTGCTGGTCCGGGCGATCCGCTTGCGAATATCG<br>CCCGCACCTTCCGTACCTTGGAGCTTATTCGCGAACAGTTGCC<br>GGACCTGAAACTGTGCCTGAGCACCAACGGCTTGGTGCTGCC<br>AGATGCCGTTGATCGTCTGCTCGATGTGGGCGTGGATCACGTT<br>ACCGTCACCATTAACACCCTGGACGCAGAAATCGCAGCGCAA<br>ATCTACGCGTGGTTGTGGCTGGATGGCGAACGCTACTCCGGTC<br>GCGAAGCCGGCGAAATTCTCATTGCCCGCCAGCTGGAAGGCG<br>TACGTCGCCTGACCGCGAAAGGTGTGCTCGTCAAGATCAACA<br>GCGTATTGATTCCGGGCATCAATGACAGCGGCATGGCGGGTG<br>TTAGCCGTGCGCTGCGCGCGTCTGGTGCGTTCATCCACAACAT<br>CATGCCACTGATTGCGCGTCCGGAGCATGGCACTGTTTTCGGT<br>CTGAACGGCCAGCCGGAACCGGACGCGGAAACCCTGGCGGCG<br>ACGCGCTCCCGCTGCGGCGAGGTTATGCCACAAATGACCCAC<br>TGCCACCAGTGCCGTGCCGACGCGATTGGCATGCTTGGTGAG<br>GATCGCTCGCAACAGTTTACGCAATTACCGGCTCCGGAGTCCC<br>TCCCGGCCTGGCTGCCGATCCTGCATCAGCGTGCTCAGTTGCA<br>TGCGAGCATCGCCACGCGCGGTGAGAGCGAAGCCGATGACGC<br>CTGCCTGGTGGCCGTTGCGTCGAGCCGTGGCGATGTAATTGAC<br>TGCCATTTCGGCCATGCCGACCGTTTCTATATCTATAGCCTGTC<br>TGCGGCTGGTATGGTTCTGGTTAACGAACGTTTCACCCCGAAA<br>TACTGCCAGGGTCGCGATGACTGCGAGCCGCAGGACAATGCC<br>GCACGCTTTGCTGCCATCCTTGAGTTGCTGGCGGACGTCAAAG<br>CGGTGTTTTGTGTGCGTATCGGCCATACCCCGTGGCAACAGCT<br>GGAGCAGGAAGGCATCGAACCGTGCGTGGATGGCGCCTGGCG<br>TCCGGTATCCGAGGTCCTGCCGGCATGGTGGCAGCAGCGCCG<br>TGGTAGCTGGCCGGCTGCATTGCCGCACAAAGGCGTTGCGTA<br>A |
| SEQ ID NO:78 | 27 | insulator 8 | | ACTACGAGATTTGAGGTAAACCAAATAAGCACGTAGTGGC |
| SEQ ID NO:79 | 28 | nifQ rbs | 5 | TGCGTTTAGCAGTTCCCGTAGGAATATTTCCTT |
| SEQ ID NO:80 | 29 | nifQ | | ATGCCGCCATTGGACTGGTTGCGTCGTTTGTGGTTACTCTATC<br>ACGCCGGCAAAGGCAGCTTTCCGCTTCGTATGGGCTTGTCGCC<br>GCGTGACTGGCAAGCTCTGCGCCGTCGCCTGGGCGAGGTGGA<br>AACGCCGCTGGATGCGAAACCCTGACCCGTCGCCGTCTGAT<br>GGCGGAGCTGAATGCGACCCGCGAAGAAGAACGCCAGCAGCT<br>GGGTGCCTGGCTGGCCGGTTGGATGCAACAGGATGCCGGTCC<br>GATGGCGCAGATTATCGCAGAGGTGAGCCTGGCGTTCAACCA<br>TCTCTGGCAGGACCTTGGCCTCGCGAGCCGCGCTGAACTGCGT<br>CTGCTGATGTCTGACTGCTTCCCGCAGCTGGTTGTTATGAACG<br>AGCACAACATGCGCTGGAAGAAATTCTTTTACCGCCAGCGTTG<br>CCTGCTGCAACAGGGCGAAGTCATCTGTCGCAGCCCGTCTTGC<br>GATGAATGCTGGGAACGTTCTGCGTGCTTTGAGTAA |
| SEQ ID NO:81 | 30 | T7 terminator 1 | 1300 | TACATATCGGGGGGGTAGGGGTTTTTTGT |
| SEQ ID NO:82 | 31 | insulator 9 | | GTCTGTAGCACGTGCATC |
| SEQ ID NO:83 | 32 | T7 promoter mut 3 | 2750 | TAATACGACTCACTAATGGGAGA |
| SEQ ID NO:84 | 33 | nifF rbs | 45 | GACAAGAGTCTCAATTATAAGGAGGCTTTACTAC |

FIG. 20 (cont)

| | | | | |
|---|---|---|---|---|
| SEQ ID NO:85 | 34 | nifF | | ATGGCGAACATCGGCATCTTCTTTGGTACGGATACCGGCAAA ACCCGCAAGATTGCGAAGATGATTCACAAACAGCTGGGCGAG CTGGCCGATGCCCCGGTTAACATCAATCGTACCACTTTGGATG ACTTTATGGCTTACCCAGTCCTGTTGCTCGGCACGCCGACGCT TGGTGATGGTCAACTGCCGGGCTTAGAGGCGGGCTGCGAGAG CGAAAGCTGGTCTGAGTTTATCTCCGGTCTGGATGACGCTTCC CTGAAGGGCAAAACCGTGGCGCTGTTTGGCCTGGGCGACCAG CGTGGTTACCCGGACAACTTCGTGTCGGGTATGCGTCCGCTGT TCGACGCGCTGAGCGCCCGTGGCGCCCAGATGATTGGTAGCT GGCCGAACGAAGGTTATGAGTTTAGCGCATCGTCCGCGCTGG AAGGCGACCGCTTCGTCGGCTTGGTGCTGGATCAAGACAATC AGTTCGACCAGACCGAAGCGCGCCTGGCGTCTTGGCTTGAAG AGATCAAACGCACCGTTCTGTAATAA |
| SEQ ID NO:86 | 35 | T7 terminator 1 | 1300 | TACATATCGGGGGGGTAGGGGTTTTTTGT |
| SEQ ID NO:87 | 36 | insulator 10 | | GGTCATTACAACGGTTAT |
| SEQ ID NO:88 | 37 | T7 promoter mut 2 | 1500 | TAATACGACTCACTAGAGAGAGA |
| SEQ ID NO:89 | 38 | insulator 11 | | AACATAGCGTTCCATGAGGGCTAGAATTACCTACCGGCCT |
| SEQ ID NO:90 | 39 | nifU rbs | 2800 | CAGATACTGACAAATAAACCAGCGAAGGAGGTTCCTA |
| SEQ ID NO:91 | 40 | nifU | | ATGTGGAACTACAGCGAGAAAGTCAAGGACCATTTCTTCAAT CCGCGCAACGCGCGTGTTGTGGATAACGCAAATGCGGTGGGC GACGTCGGCAGCTTATCTTGTGGCGATGCTCTCCGCTTGATGC TGCGCGTGGACCCGCAGAGCGAAATCATCGAAGAAGCGGGCT TTCAGACCTTCGGCTGCGGCAGCGCGATTGCGTCGTCCAGCGC ACTGACGGAGCTGATCATCGGTCACACCCTGGCGGAAGCGGG TCAGATCACCAACCAGCAGATCGCCGACTATCTGGACGGCTT ACCGCCGGAAAAGATGCACTGCTCTGTAATGGGCCAGGAAGC TCTTCGTGCGGCCATTGCTAACTTTCGCGGTGAATCGCTGGAA GAGGAGCATGACGAGGGTAAGCTGATCTGCAAGTGCTTCGGC GTCGATGAAGGCCATATTCGCCGTGCTGTCCAGAACAACGGT CTTACGACTCTGGCCGAGGTGATCAATTACACCAAGGCAGGT GGCGGTTGTACCAGCTGCCATGAGAAAATCGAGCTGGCCCTG GCCGAGATTCTCGCCCAACAGCCGCAAACCACCCCGGCAGTT GCGTCCGGTAAAGATCCGCACTGGCAGAGCGTCGTGGATACC ATCGCTGAACTGCGTCCACATATCCAAGCGGACGGTGGTGAC ATGGCGCTGTTGTCCGTGACGAACCACCAAGTGACTGTTTCGC TGTCGGGCAGCTGTTCTGGCTGCATGATGACCGACATGACCCT GGCGTGGCTGCAACAGAAATTGATGGAGCGTACCGGCTGCTA TATGGAAGTTGTTGCCGCCTAA |
| SEQ ID NO:92 | 41 | insulator 12 | | CATTGTAATAGCCACCAAAAGAGTGATGATAGTCATGGGT |
| SEQ ID NO:93 | 42 | nifS rbs | 175 | GATACCCGTAGACCATTCTGAAATCGAAGGAGGTTTTCC |
| SEQ ID NO:94 | 43 | nifS | | ATGAAACAAGTGTACCTGGACAACAACGCGACCACCCGCCTG GACCCGATGGTTCTGGAAGCGATGATGCCGTTTCTCACGGATT TCTATGGCAATCCGTCCAGCATCCATGACTTCGGCATCCCGGC ACAAGCGGCGCTGGAACGTGCGCACCAGCAAGCTGCGGCACT GCTGGGCGCAGAGTACCCGTCTGAAATCATTTTCACGAGCTGT GCGACCGAGGCCACTGCAACCGCCATTGCGTCGGCCATCGCG |

FIG. 20 (cont)

| | | | | |
|---|---|---|---|---|
| | | | | TTATTGCCGGAACGCCGCGAAATCATCACCTCGGTAGTGGAG CACCCGGCTACGCTGGCGGCGTGCGAGCACCTGGAACGCCAA GGCTATCGCATCCATCGCATTGCGGTGGATAGCGAAGGTGCG CTGGACATGGCCCAGTTCCGTGCAGCGCTCtcgCCGCGTGTCGC GTTGGTGAGCGTGATGTGGGCCAACAACGAAACCGGCGTGCT GTTCCCGATTGGCGAAATGGCCGAGCTTGCCCACGAGCAGGG CGCTCTGTTCCACTGCGATGCCGTTCAGGTCGTTGGCAAAATC CCAATTGCTGTTGGCCAGACGCGCATCGACATGCTGTCTTGCT CCGCGCACAAGTTTCATGGTCCGAAGGGTGTTGGTTGCTTGTA CTTACGTCGTGGCACGCGCTTTCGTCCGCTGCTTCGCGGTGGC CATCAAGAATATGGTCGCCGTGCCGGCACTGAGAATATCTGT GGCATCGTCGGCATGGGCGCTGCGTGCGAACTGGCGAACATC CATCTGCCGGGTATGACCCATATTGGCCAGTTACGCAATCGCC TGGAGCACCGTCTGCTCGCCAGCGTGCCGTCCGTGATGGTTAT GGGCGGTGGTCAGCCGcgTGTACCGGGTACTGTCAACCTGGCG TTCGAGTTTATCGAAGGTGAAGCGATCCTGCTCTTGCTGAACC AGGCTGGCATTGCCGCAAGCTCCGGCTCCGCGTGTACCTCTGG CAGCTTGGAGCCGAGCCATGTGATGCGCGCCATGAACATTCC ATACACCGCGGCTCACGGCACCATTCGTTTTAGCCTGAGCCGT TATACGCGCGAGAAAGAGATCGACTACGTCGTTGCGACCCTC CCGCCAATCATTGATCGTCTGCGTGCCTTGTCCCCGTATTGGC AGAATGGTAAGCCGCGTCCGGCAGATGCAGTCTTTACCCCGG TTTACGGTTAA |
| SEQ ID NO:95 | 44 | insulator 13 | | GAGTTACTGGCCCTGATTTCTCCGCTTCTAATACCGCACA |
| SEQ ID NO:96 | 45 | nifV rbs | 5 | GCGACTAGGAGCCTAACTCGCCACAAGGAAACAT |
| SEQ ID NO:97 | 46 | nifV | | ATGGAGCGCGTCTTGATCAACGATACTACCCTGCGTGATGGCG AACAATCTCCGGGCGTAGCGTTTCGTACCTCCGAGAAAGTTGC CATCGCGGAGGCACTGTACGCTGCGGGTATCACCGCGATGGA AGTCGGCACTCCGGCGATGGGTGATGAAGAGATCGCCCGCAT TCAGCTGGTGCGTCGTCAACTGCCGGACGCGACGCTTATGACC TGGTGCCGTATGAACGCTCTGGAAATCCGTCAGAGCGCGGAT CTGGGTATTGACTGGGTGGATATCTCGATCCCAGCATCCGACA AGCTGCGTCAGTACAAGCTGCGTGAGCCGCTGGCCGTGCTGCT GGAGCGCCTTGCGATGTTTATCCATCTGGCCCACACGTTAGGC CTCAAAGTATGTATTGGTTGCGAGGATGCGAGCCGTGCGTCTG GTCAGACCCTGCGCGCCATTGCCGAGGTGGCCCAGCAATGCG CGGCTGCGCGCTTGCGTTACGCTGACACCGTGGGCCTGCTGGA CCCGTTCACCACCGCAGCCCAGATCAGCGCCCTGCGTGACGTT TGGTCGGGCGAGATCGAGATGCATGCTCACAATGATCTGGGC ATGGCTACCGCGAACACGCTGGCGGCAGTTTCGGCTGGCGCC ACGTCGGTGAACACTACCGTCCTCGGTCTGGGTGAACGTGCA GGCAACGCAGCCCTGGAAACCGTTGCGCTGGGCCTGGAACGC TGCCTGGGCGTGGAAACCGGCGTCCATTTCAGCGCGCTCCCAG CGAGCTGTCAGCGCGTCGCGGAGGCTGCACAGCGCGCAATCG ACCCGCAACAGCCGCTGGTGGGTGAATTGGTTTTCACCCACGA GTCTGGTGTTCACGTTGCGGCGCTGCTGCGCCACAGCGAATCC TATCAATCTATTGCCCCAAGCCTCATGGGCCGTAGCTACCGTC TGGTGCTCGGCAAGCATTCGGGTCGTCAGGCTGTCAACGGTGT TTTCGACCAGATGGGTTACCACCTGAATGCGGCGCAGATCAAT CAGTTGCTGCCGGCCATTCGCCGCTTCGCCGAGAATTGGAAAC GCTCTCCGAAAGACTACGAACTGGTTGCGATCTATGACGAATT GTGCGGTGAATCCGCCCTTCGTGCTCGCGGCTAA |
| SEQ ID NO:98 | 47 | insulator 14 | | GACTCAACACGCTAGGGACGTGAAGTCGATTCCTTCGATG |

FIG. 20 (cont)

| | | | | |
|---|---|---|---|---|
| SEQ ID NO:99 | 48 | nifW rbs | 40 | CAGAAGGCGAGAACTAGATTTAAGGGCCATTATAG |
| SEQ ID NO:100 | 49 | nifW | | ATGGAGTGGTTTTACCAGATTCCGGGTGTAGACGAATTGCGCAGCGCTGAATCCTTCTTTCAGTTCTTCGCGGTTCCATACCAGCCGGAACTGCTGGGCCGCTGCTCGCTTCCGGTGTTAGCGACGTTCCACCGTAAACTGCGTGCGGAGGTCCCGCTGCAAAACCGTCTGGAGGACAATGATCGTGCGCCGTGGCTCTTGGCGCGCCGCCTCCTGGCCGAATCTTATCAGCAGCAATTTCAGGAGAGCGGCACCTAA |
| SEQ ID NO:101 | 50 | insulator 15 | | TCGAGAAACAAGGCAGTTCCGGGCTGAAAGTAGCGCCGGG |
| SEQ ID NO:102 | 51 | nifZ rbs | 365 | ACAAGTCCCGTATTATAACCGCCTAGGAGGTGTTGG |
| SEQ ID NO:103 | 52 | nifZ | | ATGCGCCCGAAATTCACCTTCTCTGAAGAGGTCCGCGTAGTTCGCGCGATTCGTAATGATGGCACCGTGGCGGGTTTTGCGCCAGGTGCGCTGCTGGTTCGTCGCGGTTCGACGGGCTTTGTGCGTGACTGGGGTGTGTTCCTGCAAGACCAGATCATCTATCAAATCCACTTTCCGGAAACCGACCGCATTATCGGCTGTCGCGAGCAGGAGTTAATCCCGATTACCCAGCCGTGGTTGGCTGGTAACCTCCAGTATCGTGACAGCGTCACGTGCCAAATGGCACTGGCTGTCAACGGTGACGTGGTTGTGAGCGCCGGTCAACGTGGCCGTGTGGAGGCCACTGATCGTGGCGAACTTGGCGATTCCTACACCGTGGACTTCAGCGGCCGTTGGTTCCGCGTTCCGGTCCAGGCCATCGCGCTGATTGAAGAGCGCGAAGAATAA |
| SEQ ID NO:104 | 53 | insulator 16 | | ACGCCACGCGTAGTGAGACATACACGTTCGTTGGGTTCAC |
| SEQ ID NO:105 | 54 | nifM rbs | 750 | TCAGAGACTGAAGTTATTACCCAGGAGGTCTATA |
| SEQ ID NO:106 | 55 | nifM | | ATGAATCCGTGGCAGCGCTTTGCCCGTCAACGCCTTGCTCGCAGCCGCTGGAACCGTGATCCGGCTGCTCTCGACCCAGCCGATACCCCAGCGTTCGAGCAGGCGTGGCAGCGTCAATGCCATATGGAACAAACCATCGTAGCGCGTGTCCCGGAAGGCGATATTCCGGCTGCCTTACTGGAAAACATCGCGGCCAGCCTGGCGATCTGGCTGACGAGGGTGACTTCGCTCCGCCGGAGCGCGCTGCGATTGTGCGTCATCATGCCACGTCTGGAGCTGGCGTTTGCCGACATTGCCCGCCAGGCACCGCCAACCGGATCTGAGCACGGTTCAAGCGTGGTATCTGCGTCACCAGACTCAATTCATGCGTCCGGAGCAGCGTCTGACCCGTCACCTGCTCCTGACGGTCGATAATGATCGCGAGGCGGTGCATCAACGCATCCTTGGCCTGTATCGTCAGATCAACGCGAGCCGTGACGCCTTCGCCCCACTGGCACAGCGCCACTCTCATTGCCCGTCCGCCTTGGAAGAAGGCCGTCTGGGCTGGATCTCCCGTGGTCTGCTGTACCCGCAGCTCGAAACCGCGTTGTTTAGCCTGGCGGAAAACGCACTGTCGCTGCCGATTGCGTCGGAATTGGGTTGGCACCTGTTATGGTGCGAGGCCATTCGTCCGGCAGCCCCGATGGAGCCGCAACAGGCCCTTGAATCTGCGCGCGACTACTTGTGGCAGCAGAGCCAGCAGCGCCACCAGCGTCAATGGCTGGAGCAGATGATTTCCCGCCAACCGGGCCTGTGTGGTTAA |
| SEQ ID NO:107 | 56 | T7 terminator WT | 1400 | TAGCATAACCCCTTGGGGCCTCTAAACGGGTCTTGAGGGGTTTTTTG |
| SEQ ID NO:108 | 57 | Biobrick suffix (BBa_G00001) | | Tactagtagcggccgctgcag |
| SEQ ID | 58 | Translational | | ttagttagttag |

FIG. 20 (cont)

| | | | | |
|---|---|---|---|---|
| NO:109 | | stop (BBa_B0042) | | |
| SEQ ID NO:110 | 59 | Terminator (BBa_B0054) | | attagcagaaagtcaaaagcctccgaccggaggcttttgactaaaacttcccttggggttatcattggg |
| SEQ ID NO:111 | 60 | VR primer sequence (BBa_G00102) | | gctcactcaaaggcggtaat |
| SEQ ID NO:112 | 61 | Terminator (BBa_B0062) | | cagataaaaaaaatccttagctttcgctaaggatgatttct |
| SEQ ID NO:113 | 62 | pSC101 origin (BBa_I50042) | | ctgtcagaccaagtttacgagctcgcttggactcctgttgatagatccagtaatgacctcagaactccatc tggatttgttcagaacgctcggttgccgccgggcgttttttattggtgagaatccaagcactagggacagt aagacgggtaagcctgttgatgataccgctgccttactgggtgcattagccagtctgaatgacctgtcac gggataatccgaagtggtcagactggaaaatcagagggcaggaactgctgaacagcaaaaagtcag atagcaccacatagcagacccgccataaaaacgccctgagaagcccgtgacgggcttttcttgtattatg ggtagtttccttgcatgaatccataaaaggcgcctgtagtgccatttaccccattcactgccagagccgt gagcgcagcgaactgaatgtcacgaaaaagacagcgactcaggtgcctgatggtcggagacaaaag gaatattcagcgatttgcccgagcttgcgagggtgctacttaagcctttagggttttaaggtctgttttgtag aggagcaaacagcgtttgcgacatccttttgtaatactgcggaactgactaaagtagtgagttatacaca gggctgggatctattcttttttatctttttttattctttattctataaattataaccacttgaatataaacaaaaa aaacacacaaaggtctagcggaatttacagagggtctagcagaatttacaagttttccagcaaaggtcta gcagaatttacagatacccacaactcaaaggaaaaggacatgtaattatcattgactagcccatctcaatt ggtatagtgattaaaatcacctagaccaattgagatgtatgtctgaattagttgttttcaaagcaaatgaact agcgattagtcgctatgacttaacggagcatgaaaccaagctaattttatgctgtgtggcactactcaacc ccacgattgaaaaccctacaaggaaagaacggacggtatcgttcacttataaccaatacgctcagatga tgaacatcagtagggaaaatgcttatggtgtattagctaaagcaaccagagagctgatgacgagaactg tggaaatcaggaatcctttggttaaaggctttgagattttccagtggacaaactatgccaagttctcaagc gaaaaattagaattagtttttagtgaagagatattgccttatctttccagttaaaaaaattcataaaatataat ctgaacatgttaagtcttttgaaaacaaatactctatgaggatttatgagtggttattaaaagaactaacac aaaagaaaactcacaaggcaaatatagagattagccttgatgaatttaagttcatgttaatgcttgaaaata actaccatgagtttaaaggcttaaccaatgggttttgaaaccaataagtaaagatttaaacacttacagc aatatgaaattggtggttgataagcgaggccgcccgactgatacgttgatttccaagttgaactagatag acaaatggatctcgtaaccgaacttgagaacaaccagataaaaatgaatggtgacaaaataccaacaa ccattacatcagattcctacctacgtaacggactaagaaaaacactacacgatgctttaactgcaaaatt cagctcaccagttttgaggcaaaattttttgagtgacatgcaaagtaagcatgatctcaatggttcgttctca tggctcacgcaaaaacaacgaaccacactagagaacatactggctaaatacgaaggatctgaggttc ttatggctcttgtatctatcagtgaagcatcaagactaacaaacaaaagtagaacaactgttcaccgttag atatcaaagggaaaactgtccatatgcacagatgaaaacggtgtaaaaaagatagatacatcagagctt ttacgagttttggtgcatttaaagctgttcaccatgaacagatcgacaatgtaac |
| SEQ ID NO:114 | 63 | chloramphenic ol resistance (BBa_P1004) | | gttgatcgggcacgtaagaggttccaactttcaccataatgaaataagatcactaccgggcgtattttttg agttatcgagattttcaggagctaaggaagctaaaatggagaaaaaaatcacgggatataccaccgttg atatatcccaatggcatcgtaaagaacattttgaggcatttcagtcagttgctcaatgtacctataaccaga ccgttcagctggatattacggcctttttaaagaccgtaaagaaaaataagcacaagttttatccggcctttt attcacattcttgcccgcctgatgaacgctcacccggagtttcgtatggccatgaaagacggtgagctggt gatctgggatagtgttcacccttgttacaccgttttccatgagcaaactgaaacgttttcgtccctctggagt gaataccacgacgatttccggcagtttctccacatatattcgcaagatgtggcgtgttacggtgaaaacct ggcctatttccctaaagggtttattgagaatatgtttttcgtctcagccaatccctgggtgagtttcaccagtt ttgatttaaacgtggccaatatggacaacttcttcgcccccgttttcacgatgggcaaatattatacgcaag gcgacaaggtgctgatgccgctggcgatccaggttcatcatgccgtttgtgatggcttccatgtcggcc gcatgcttaatgaattacaacagtactgtgatgagtggcagggcggggcgtaataa |
| SEQ ID NO:115 | 64 | Terminator (BBa_B0053) | | tccggcaaaaaaacgggcaaggtgtcaccaccctgccctttttctttaaaaccgaaaagattacttcgcg tt |
| SEQ ID NO:116 | 65 | VF2 primer sequence (BBa_G00101) | | tgccacctgacgtctaagaa |

FIG. 20 (cont)

| SEQ ID NO:117 | 66 | Terminator (BBa_B0055) | | aaggaatattcagcaatttgcccgtgccgaagaaaggcccacccgtgaaggtgagccagtgagttgattgctacgtaa |
| SEQ ID NO:118 | 67 | Translational stop (BBa_B0042) | | ttagttagttag |

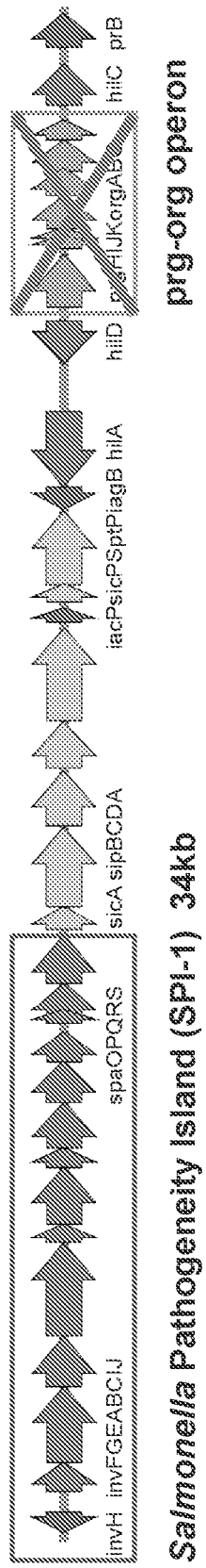
FIG. 22A
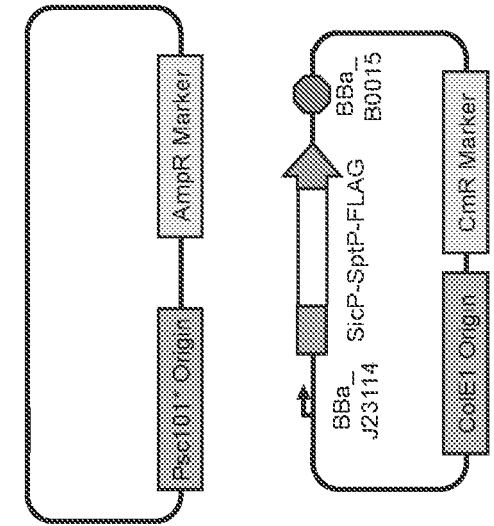
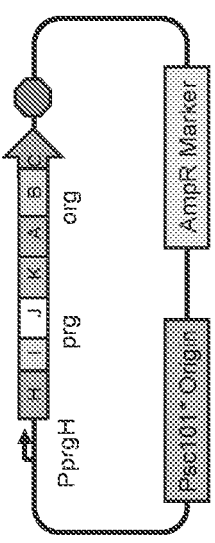
FIG. 22B

FIG. 23A
FIG. 23B
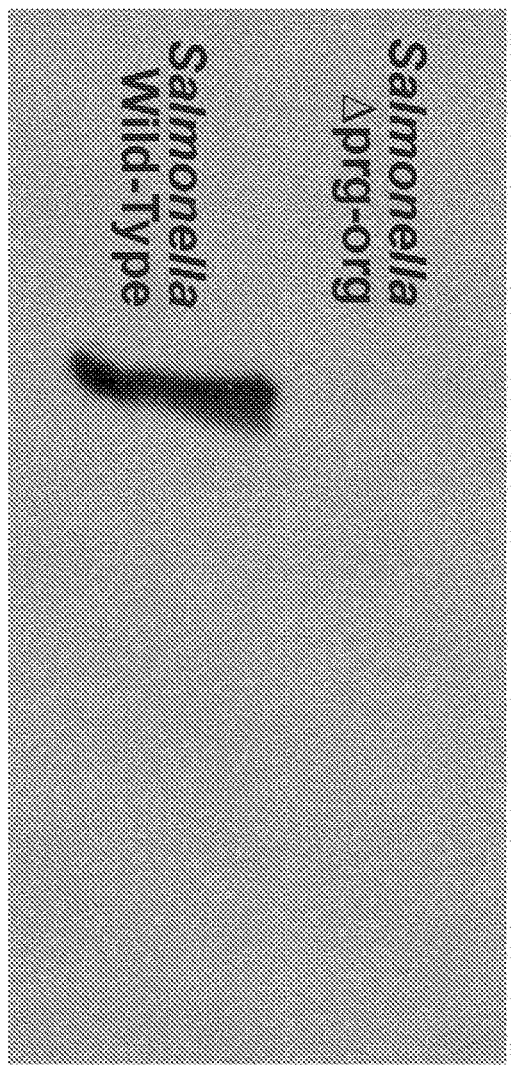
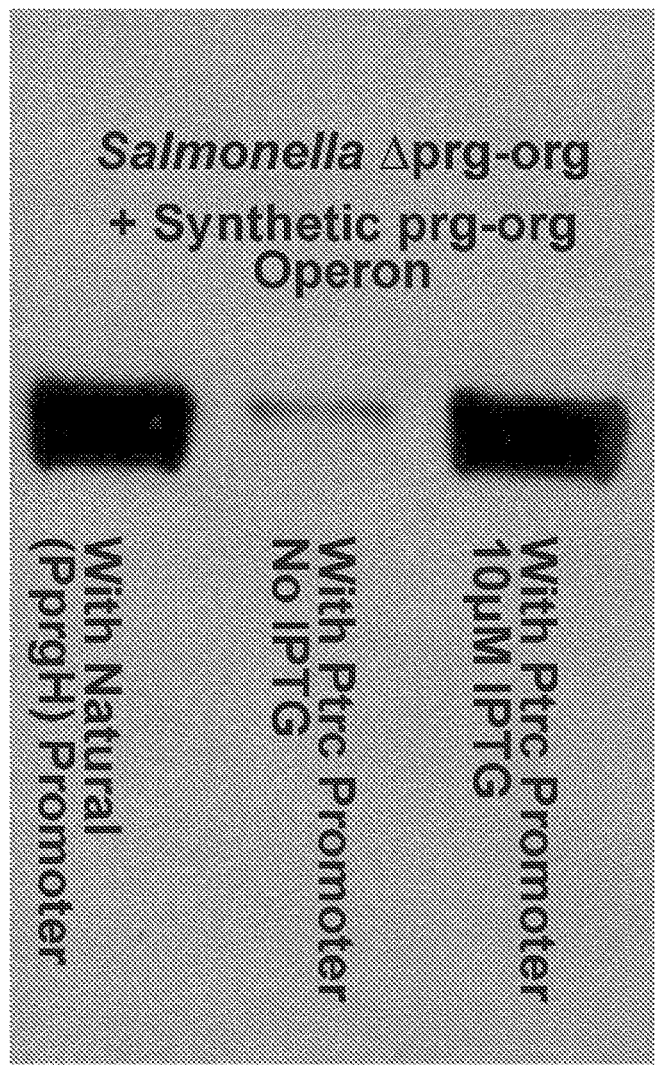

FIG. 24

| SEQ ID NO: | Name | Sequence |
|---|---|---|
| SEQ ID NO:119 | SynPrgH_RBS | ATTAAACAGGATAATAAGC |
| SEQ ID NO:120 | SynPrgH | ATGGAAACTAGCAAGGAGAAAACGATTACGTCCCCTGGTCCGTATATCGTT<br>CGTCTGTTGAACTCGTCCCTGAACGGTTGTGAATTTCCGCTGCTGACTGGTC<br>GTACGCTGTTCGTCGTGGGTCAGAGCGATGCTCTGACCGCGTCTGGTCAGCT<br>GCCGGACATTCTGCCGACTCCTTCTTCATCCCGCTGGATCATGGCGGTGTT<br>AATTTCGAGATTCAAGTGGACACTGACGCGACGGAAATCATCCTGCACGAA<br>CTGAAAGAGGGCAACTCCGAGAGCCGCTCCGTGCAACTGAACACCCCGATC<br>CAAGTTGGTGAACTGCTGATTTTGATTCGTCCGGAGAGCGAGCCGTGGGTG<br>CCGGAACAGCCGGAGAAGTTGGAAACTTCTGCAAAAAGAACGAACCGCG<br>CTTTAAAAACGGCATCGTCGCGGCACTGGCGGGTTTCTTTATCCTGGGTATC<br>GGCACGGTTGGCACCCTGTGGATTCTGAACTCGCCGCAACGTCAAGCAGCC<br>GAATTGGACAGCCTGTTGGGTCAGGAGAAGGAGCGTTTTCAGGTGCTGCCG<br>GGTCGCGACAAGATGCTGTATGTCGCCGCGCAAAACGAACGCGACACCCTG<br>TGGGCACGTCAAGTCCTGGCACGCGGCGATTACGATAAAAACGCACGCGTT<br>ATTAATGAAAATGAGGAGAATAAACGTATCAGCATCTGGCTGGACACGTAT<br>TATCCACAACTGGCATATTACCGTATCCATTTTGATGAACCACGTAAGCCGG<br>TGTTTTGGCTGTCCCGTCAACGCAACACGATGAGCAAGAAAGAGCTGGAGG<br>TGCTGTCCCAGAAATTGCGTGCGCTGATGCCGTACGCCGACAGCGTCAATAT<br>TACTCTGATGGATGACGTGACCGCAGCAGGCCAAGCCGAGGCAGGTCTGAA<br>ACAACAGGCGCTGCCATACAGCCGCCGTAACCACAAAGGTGGTGTTACGTT<br>CGTTATTCAGGGCGCCTTGGACGACGTTGAGATTCTGCGTGCGCGCCAGTTT<br>GTCGACTCCTATTATCGTACCTGGGGTGGTCGTTACGTTCAATTCGCAATTG<br>AATTGAAAGACGATTGGCTGAAAGGCCGCTCGTTCCAATACGGTGCGGAAG<br>GCTACATTAAGATGAGCCCAGGTCATTGGTATTTTCCGTCTCCTCTGTAATA<br>G |
| SEQ ID NO:121 | SynPrgI_RBS | ATTAAAGAGGAGAAATTAAGC |
| SEQ ID NO:122 | SynPrgJ_RBS | ATTAAGGAGGATAAATTAAGC |
| SEQ ID NO:123 | SynPrgJ | ATGTCTATCGCGACTATCGTGCCTGAAAATGCCGTTATTGGTCAAGCGGTGA<br>ATATTCGCAGCATGGAAACGGACATCGTCAGCTTGGACGACCGTTTGCTGC<br>AAGCATTTTCGGGCAGCGCCATCGCTACCGCCGTCGATAAGCAGACCATTA<br>CCAATCGCATTGAAGACCCTAATCTGGTTACCGATCCGAAGGAGCTGGCGA<br>TTAGCCAGGAAATGATTTCCGACTACAATCTGTACGTCAGCATGGTTAGCAC<br>CCTGACGCGTAAGGGCGTTGGCGCTGTTGAGACTTTGCTGCGTTCCTGATAG |
| SEQ ID NO:124 | SynPrgK_RBS | ATTAAACAGGATAATAAGC |
| SEQ ID NO:125 | SynPrgK | ATGATCCGCCGTTACCTGTATACCTTCTTGCTGGTTATGACTTTGGCCGGCTG<br>TAAAGATAAGGATCTGCTGAAAGGCTTGGACCAAGAGCAAGCGAATGAGG<br>TCATTGCGGTTCTGCAAATGCACAACATTGAGGCTAACAAGATTGATAGCG<br>GCAAGCTGGGTTACAGCATTACCGTCGCGGAACCGGATTTCACCGCGGCAG<br>TGTATTGGATTAAGACCTACCAGTTGCCGCCTCGCCCGCGTGTCGAAATCGC<br>CCAAATGTTTCCGGCAGACAGCCTGGTTAGCTCTCCGCGTGCGGAGAAAGC<br>ACGTCTGTACTCGGCGATTGAACAGCGCCTGGAGCAGTCGCTGCAAACGAT<br>GGAAGGTGTTCTGTCGGCCCGTGTCCACATCAGCTATGATATTGATGCGGGC<br>GAGAACGGTCGTCCGCCTAAGCCGGTGCACCTGTCGGCTTTGGCGGTGTAT<br>GAACGCGGTTCCCCTCTGGCCCATCAGATTTCGGATATTAAGCGCTTCCTGA<br>AAAACAGCTTCGCGGATGTTGACTATGATAACATCAGCGTGGTTCTGTCCGA |

FIG. 24 (cont)

| SEQ ID NO: | Name | Sequence |
|---|---|---|
| | | GCGTAGCGACGCACAGTTGCAGGCGCCGGGCACGCCGGTCAAGCGCAATAG CTTCGCTACCTCCTGGATTGTGCTGATTATCCTGTTGTCTGTTATGAGCGCGG GTTTCGGTGTCTGGTACTACAAAAATCACTATGCGCGTAATAAGAAAGGCA TTACTGCCGATGACAAGGCAAAGTCCAGCAACGAGTAATAA |
| SEQ ID NO:126 | SynOrgA_RBS | GAAAGAAGGGACAGACTAG |
| SEQ ID NO:127 | SynOrgA | ATGATTCGTCGTAACCGTCAAATGAACCGTCAACCACTGCCAATTATCTGGC AACGCATTATTTTCGACCCACTGTCCTATATTCACCCACAACGTCTGCAAAT CGCGCCGGAGATGATCGTGCGTCCGGCAGCGCGTGCGGCAGCGAATGAGCT GATTTTGGCGGCGTGGCGTTTGAAGAACGGTGAGAAGGAGTGCATTCAGAA TAGCCTGACGCAGCTGTGGTTGCGTCAATGGCGCCGTCTGCCGCAGGTTGCT TACCTGCTGGGTTGCCACAAGTTGCGTGCTGACCTGGCCCGTCAAGGTGCTT TATTGGGCCTGCCGGACTGGGCGCAGGCATTCTTGGCGATGCACCAGGGTA CGTCCTTGTCGGTTTGTAATAAGGCGCCGAACCACCGTTTCCTGCTGTCCGT TGGTTACGCCCAACTGAACGCGCTGAATGAGTTCCTGCCGGAGAGCTTGGC CCAACGCTTTCCTCTGCTGTTTCCACCGTTCATCGAGGAGGCACTGAAACAA GATGCAGTGGAGATGAGCATCCTGCTGCTGGCCCTGCAATACGCGCAAAAG TATCCTAACACCGTCCCGGCGTTTGCGTGCTAATAA |
| SEQ ID NO:128 | SynOrgB_RBS | GAAAGAAGGGACAGACTAG |
| SEQ ID NO:129 | SynOrgB | ATGTTGAAAAATATCCCGATTCCATCCCCTCTGTCTCCGGTTGAAGGTATCC TGATTAAACGCAAGACGTTGGAGCGTTACTTCTCGATTGAGCGCCTGGAAC AACAGGCGCATCAGCGTGCAAAGCGCATTTTGCGTGAGGCAGAAGAAGAA GCCAAGACCCTGCGCATGTATGCGTACCAGGAGGGCTACGAGCAGGGCATG ATTGACGCACTGCAACAGGTGGCCGCCTATTTGACCGACAACCAGACGATG GCTTGGAAATGGATGGAGAAAATTCAAATCTATGCGCGTGAGTTGTTCAGC GCGGCTGTCGATCACCCGGAAACGTTGTTGACGGTGCTGGACGAGTGGCTG CGTGATTTCGATAAGCCGGAAGGTCAGCTGTTTTTGACCCTGCCGGTGAACG CAAAGAAAGATCATCAGAAACTGATGGTGCTGCTGATGGAAAATTGGCCGG GCACCTTCAATCTGAAGTATCATCAGGAGCAACGTTTTATCATGTCCTGTGG CGATCAGATTGCCGAGTTTTCGCCGGAACAATTTGTTGAAACGGCGGTTGGT GTTATCAAGCACCATCTGGATGAGCTGCCTCAGGACTGTCGCACCATTTCGG ACAATGCGATTAACGCGCTGATTGATGAATGGAAGACGAAAACCCAAGCTG AAGTTATTCGCTGATAA |
| SEQ ID NO:130 | SynInvA_RBS | CTTGGGCACGCGTCCATTAAACAGGAGTAATTAAGC |
| SEQ ID NO:131 | SynInvA | ATGCTGCTGTCCCTGCTGAATAGCGCGCGTCTGCGTCCTGAGCTGCTGATTC TGGTTCTGATGGTTATGATCATCAGCATGTTCGTTATCCCGTTGCCGACCTAT TTGGTTGACTTCTTGATCGCTTTGAACATTGTCCTGGCAATTCTGGTGTTCAT GGGCTCCTTCTACATCGACCGCATTCTGAGCTTCAGCACCTTTCCGGCGGTT CTGCTGATCACGACTCTGTTCCGTTTGGCACTGAGCATCAGCACCAGCCGCC TGATCCTGATTGAAGCAGATGCGGGTGAGATCATCGCGACCTTTGGTCAGTT TGTGATCGGTGACAGCCTGGCGGTTGGTTTCGTCGTATTCTCCATCGTGACG GTGGTGCAGTTTATCGTTATTACCAAGGGCAGCGAACGTGTGGCGGAGGTC GCCGCTCGCTTCAGCCTGGACGGCATGCCGGGTAAACAGATGTCTATTGAT GCAGACCTGAAAGCCGGCATTATTGATGCTGATGCAGCGCGCGAGCGCCGC AGCGTCCTGGAGCGTGAAAGCCAACTGTACGGTTCCTTCGACGGTGCCATG AAGTTCATTAAAGGTGATGCGATTGCGGGCATCATTATCATCTTCGTTAACT TCATTGGCGGTATCAGCGTCGGTATGACCCGTCATGGTATGGATCTGAGCAG CGCCCTGAGCACCTACACCATGCTGACGATTGGTGATGGTCTGGTTGCCCAA ATTCCGGCGTTGCTGATCGCGATTTCTGCGGGCTTCATCGTTACCCGCGTCA |

FIG. 24 (cont)

| SEQ ID NO: | Name | Sequence |
|---|---|---|
| | | ACGGTGATAGCGATAACATGGGTCGTAACATTATGACCCAGCTGCTGAATA<br>ATCCGTTTGTCCTGGTTGTAACGGCGATTTTGACCATCAGCATGGGCACGCT<br>GCCGGGCTTTCCGTTGCCGGTTTTCGTTATTCTGTCTGTTGTGCTGTCCGTCC<br>TGTTTTACTTTAAGTTCCGCGAGGCGAAACGTAGCGCTGCGAAACCAAAAA<br>CGAGCAAGGGCGAGCAACCGTTGTCCATCGAGGAGAAGGAAGGTAGCAGC<br>CTGGGCCTGATTGGCGACCTGGATAAGGTTAGCACGGAAACCGTCCCGCTG<br>ATTTTGCTGGTGCCGAAATCGCGTCGTGAGGATCTGGAGAAAGCGCAGCTG<br>GCGGAACGTCTGCGCAGCCAATTCTTTATTGATTATGGTGTGCGTCTGCCAG<br>AAGTACTGCTGCGTGACGGTGAGGGTCTGGATGACAACTCTATCGTCCTGCT<br>GATTAATGAGATTCGCGTTGAACAGTTTACTGTCTATTTTGACCTGATGCGT<br>GTGGTTAACTACAGCGACGAGGTGGTGAGCTTTGGCATCAACCCGACCATT<br>CACCAGCAAGGTTCCAGCCAGTACTTTTGGGTGACCCATGAGGAAGGCGAA<br>AAGCTGCGCGAGCTGGGCTACGTCCTGCGTAATGCACTGGACGAACTGTAC<br>CACTGTCTGGCGGTGACGCTGGCACGCAATGTGAACGAGTATTTCGGTATCC<br>AAGAAACGAAACACATGCTGGACCAACTGGAAGCAAAGTTTCCTGACCTGC<br>TGAAGGAGGTTTTGCGCCACGCCACCGTGCAGCGCATTTCGGAAGTGCTGC<br>AACGTCTGCTGTCCGAACGCGTGAGCGTCCGTAACATGAAGCTGATCATGG<br>AAGCCCTGGCACTGTGGGCTCCGCGTGAGAAAGATGTGATCAATCTGGTGG<br>AGCACATCCGTGGTGCGATGGCGCGTTATATCTGCCACAAGTTCGCAAATG<br>GTGGTGAACTGCGTGCCGTTATGGTTTCCGCCGAAGTTGAGGATGTCATTCG<br>TAAAGGCATTCGTCAAACTTCTGGCTCCACCTTTTTGAGCTTGGACCCGGAG<br>GCTTCGGCAAATCTGATGGACCTGATCACGCTGAAGCTGGACGACCTGTTG<br>ATTGCGCATAAGGACCTGGTCCTGTTGACCAGCGTTGACGTGCGTCGTTTTA<br>TCAAGAAAATGATTGAAGGTCGTTTTCCGGATCTGGAGGTCCTGTCCTTCGG<br>TGAGATTGCAGATAGCAAAAGCGTGAATGTCATCAAAACCATCTGA |
| SEQ ID NO:132 | SynInvC_RBS | CTTGGGCACGCGTCCATTAAAGAGGACCAATTAAGC |
| SEQ ID NO:133 | SynInvC | ATGAAAACCCCACGTCTGCTGCAATACCTGGCCTACCCGCAGAAAATCACT<br>GGCCCTATCATTGAAGCAGAACTGCGTGATGTTGCAATTGGTGAATTGTGCG<br>AGATCCGTCGCGGCTGGCACCAGAAGCAGGTTGTGGCCCGTGCGCAAGTGG<br>TTGGTTTGCAGCGCGAACGTACCGTCCTGAGCCTGATCGGCAATGCCCAAG<br>GCCTGAGCCGTGATGTGGTCTTGTACCCGACCGGCCGTGCTCTGAGCGCGTG<br>GGTTGGTTACAGCGTTCTGGGCGCAGTACTGGACCCGACGGGTAAAATCGT<br>TGAACGTTTCACCCCGGAAGTCGCACCGATTTCCGAGGAGCGCGTTATCGA<br>CGTGGCACCGCCGAGCTACGCAAGCCGTGTCGGTGTGCGCGAACCGCTGAT<br>CACGGGTGTCCGCGCAATTGATGGTCTGCTGACGTGTGGTGTGGGCCAGCG<br>TATGGGTATTTTCGCAAGCGCGGGTTGTGGTAAGACCATGTTGATGCACATG<br>CTGATCGAGCAAACCGAAGCGGATGTCTTTGTTATTGGCCTGATTGGCGAGC<br>GTGGTCGTGAAGTTACCGAATTTGTAGACATGTTGCGTGCATCTCATAAGAA<br>AGAAAAATGTGTGCTGGTTTTTGCCACGTCCGACTTCCCAAGCGTTGACCGC<br>TGCAACGCTGCCCAGCTGGCAACGACGGTCGCCGAGTATTTCCGCGACCAG<br>GGTAAACGTGTTGTCCTGTTTATCGACAGCATGACCCGTTATGCACGCGCGT<br>TGCCGTGATGTCGCGCTGGCGAGCGGCGAGCGTCCGGCTCGCCGTGGTTATC<br>CGGCGTCTGTGTTCGACAATCTGCCGCGTTTGCTGGAGCGTCCGGGTGCGAC<br>GAGCGAGGGTAGCATTACCGCCTTCTATACCGTCCTGCTGGAGTCGGAAGA<br>AGAAGCGGACCCGATGCGGACGAGATCCGTTCTATTCTGGACGGTCACCT<br>GTACCTGTCCCGCAAACTGGCGGGTCAGGGTCATTACCCGGCTATCGATGTG<br>CTGAAGAGCGTGAGCCGTGTGTTTGGTCAAGTGACCACCCCGACTCACGCG<br>GAGCAAGCGAGCGCGGTCCGTAAGCTGATGACCCGTCTGGAAGAGCTGCAA<br>CTGTTCATTGACCTGGGCGAGTATCGTCCGGGCGAGAACATTGACAATGAT<br>CGTGCGATGCAAATGCGCGATAGCCTGAAGGCGTGGCTGTGTCAGCCTGTT<br>GCGCAATACAGCAGCTTCGATGATACGCTGTCCGGCATGAACGCCTTTGCG<br>GATCAGAACTGA |

FIG. 24 (cont)

| SEQ ID NO: | Name | Sequence |
|---|---|---|
| SEQ ID NO:134 | SynInvE_RBS | TACTTGGGCACGCGTCCATTAATTAGGATCAATAGC |
| SEQ ID NO:135 | SynInvE | ATGATTCCGGGCAGCACCTCCGGTATTTCCTTTAGCCGTATCCTGAGCCGTC AGACCTCCCACCAGGATGCAACCCAGCATACCGACGCACAACAAGCGGAA ATTCAACAAGCGGCGGAAGATAGCTCGCCGGGTGCGGAGGTTCAGAAATTC GTCCAGAGCACGGACGAGATGTCTGCTGCGTTGGCGCAGTTCCGCAATCGC CGTGACTATGAGAAAAAGAGCAGCAATTTGTCTAACTCCTTCGAGCGCGTT CTGGAGGACGAGGCACTGCCGAAAGCGAAGCAGATTCTGAAACTGATCAGC GTGCATGGCGGTGCGTTGGAGGATTTCCTGCGTCAGGCGCGCAGCCTGTTCC CGGACCCAAGCGATCTGGTGCTGGTTCTGCGCGAGCTGTTGCGTCGTAAGG ACCTGGAGGAGATCGTGCGTAAGAAGCTGGAGAGCCTGCTGAAGCACGTGG AGGAACAAACCGACCCGAAAACCCTGAAGGCCGGTATTAACTGCGCGCTGA AGGCGCGTCTGTTTGGCAAGACGCTGTCTCTGAAACCTGGTCTGCTGCGTGC CAGCTACCGCCAGTTCATCCAAAGCGAAAGCCACGAAGTCGAGATTTACAG CGATTGGATCGCCAGCTACGGTTATCAGCGTCGCCTGGTTGTTCTGGATTTC ATTGAAGGCAGCCTGCTGACTGACATCGATGCTAACGATGCAAGCTGCTCC CGTCTGGAGTTTGGCCAACTGCTGCGCCGTCTGACCCAGCTGAAAATGTTGC GTAGCGCCGACCTGCTGTTTGTCTCGACGTTGCTGTCTTACAGCTTCACGAA AGCATTTAACGCTGAGGAGAGCAGCTGGCTGTTGCTGATGCTGTCTTTGCTG CAACAGCCGCACGAAGTGGATAGCCTGCTGGCGGACATTATCGGTCTGAAT GCGCTGCTGTTGTCCCACAAAGAGCACGCCAGCTTCCTGCAAATCTTCTATC AGGTCTGTAAGGCAATCCCGTCTAGCCTGTTTTATGAAGAGTACTGGCAAG AAGAACTGCTGATGGCACTGCGCTCCATGACGGACATTGCTTACAAACACG AAATGGCCGAACAACGTCGTACCATCGAAAAGCTGTCCTAA |
| SEQ ID NO:136 | SynInvF_RBS | CTTGGGCACGCGTCCATTAAAAAGGAGTAATTAAGC |
| SEQ ID NO:137 | SynInvF | ATGAGCTTCAGCGAGAGCCGCCACAATGAAAACTGTCTGATTCAAGAAGGC GCACTGCTGTTTTGTGAGCAAGCAGTCGTGGCGCCTGTCAGCGGTGATCTGG TTTTTCGTCCGCTGAAAATCGAGGTCCTGAGCAAGCTGCTGGCGTTCATCGA CGGCGCAGGTCTGGTGGATACGACCTACGCGGAGTCGGACAAATGGGTTCT GCTGTCTCCGGAGTTCCGTGCTATTTGGCAAGACCGTAAACGTTGCGAATAT TGGTTTTTGCAGCAGATTATCACCCCATCTCCGGCGTTCAACAAGGTTCTGG CACTGTTGCGTAAGAGCGAAAGCTATTGGTTGGTCGGCTACTTGCTGGCCCA AAGCACCAGCGGCAATACTATGCGTATGTTGGGTGAGGATTACGGTGTTAG CTACACGCATTTCCGCCGTCTGTGCAGCCGCGCTCTGGGCGGTAAGGCGAA AAGCGAGCTGCGCAATTGGCGCATGGCCCAGTCCCTGCTGAATAGCGTGGA AGGTCATGAAAACATCACCCAGCTGGCGGTCAACCACGGTTATAGCAGCCC GTCCCACTTTAGCTCTGAAATCAAGGAGCTGATTGGTGTTTCCCCGCGTAAG CTGTCTAACATCATTCAGCTGGCCGACAAATGA |
| SEQ ID NO:138 | SynInvG_RBS | TGGGCACGCGTCCATTAATGAGGAAAAATTATTAGC |
| SEQ ID NO:139 | SynInvG | ATGAAAACGCACATTCTGTTGGCCCGTGTGCTGGCTTGCGCAGCTCTGGTGC TGGTCACCCCAGGTTATAGCTCCGAGAAGATCCCGGTTACGGGCAGCGGCT TCGTTGCAAAGGACGATTCTCTGCGCACCTTTTTCGATGCGATGGCACTGCA ATTGAAGGAGCCGGTGATTGTCAGCAAGATGGCGGCTCGCAAAAAGATTAC CGGCAATTTCGAGTTCCACGATCCAAACGCGCTGCTGGAGAAACTGTCCCT GCAACTGGGTCTGATCTGGTACTTTGATGGTCAGGCGATCTACATCTACGAC GCGAGCGAAATGCGTAATGCGGTTGTGAGCCTGCGTAATGTCAGCCTGAAC GAGTTCAACAATTTTCTGAAGCGCAGCGGCCTGTACAATAAGAACTACCCT CTGCGTGGTGATAATCGTAAAGGCACCTTCTATGTCAGCGGTCCGCCGGTGT ATGTTGATATGGTTGTAAATGCGGCCACCATGATGGACAAACAGAATGATG |

FIG. 24 (cont)

| SEQ ID NO: | Name | Sequence |
|---|---|---|
| | | GCATCGAGCTGGGTCGCCAAAAGATCGGTGTTATGCGCCTGAACAACACTT<br>TTGTGGGCGACCGCACCTACAACCTGCGTGATCAAAAGATGGTCATTCCGG<br>GTATTGCTACGGCAATTGAACGCCTGTTGCAAGGCGAAGAACAACCGCTGG<br>GTAACATTGTAAGCTCCGAGCCTCCGGCCATGCCGGCCTTTAGCGCAAACG<br>GCGAGAAAGGTAAGGCAGCGAATTACGCGGGTGGTATGAGCCTGCAAGAA<br>GCGCTGAAACAGAACGCAGCGGCAGGCAACATCAAAATTGTGGCCTATCCG<br>GACACCAACAGCCTGCTGGTGAAAGGTACGGCGGAGCAGGTGCATTTCATC<br>GAGATGCTGGTTAAAGCCCTGGACGTGGCGAAACGTCACGTTGAATTGAGC<br>CTGTGGATTGTGGATTTGAATAAGAGCGACCTGGAACGCTTGGGCACCAGC<br>TGGAGCGGTAGCATCACCATCGGCGACAAGCTGGGTGTGAGCCTGAACCAG<br>AGCAGCATCTCCACGCTGGACGGTAGCCGCTTTATTGCGGCGGTCAACGCTC<br>TGGAGGAAAAGAAACAGGCCACTGTTGTCAGCCGTCCGGTTCTGCTGACCC<br>AGGAGAATGTCCCGGCGATTTTTGACAATAATCGTACTTTCTATACCAAACT<br>GATCGGTGAACGTAATGTTGCATTGGAACACGTGACCTATGGCACCATGAT<br>CCGTGTCCTGCCGCGTTTCAGCGCGGACGGCCAGATTGAGATGAGCCTGGA<br>CATCGAAGATGGTAATGACAAAACCCCGCAGTCTGATACGACCACCTCCGT<br>TGATGCGCTGCCAGAAGTGGGTCGTACCCTGATCTCGACGATTGCACGTGTC<br>CCGCATGGTAAATCTCTGCTGGTTGGTGGCTACACGCGTGATGCAAACACG<br>GACACGGTCCAAAGCATCCCGTTCCTGGGTAAGCTGCCGCTGATTGGCTCGT<br>TGTTTCGCTACAGCAGCAAAAACAAGTCTAATGTCGTCCGTGTCTTTATGAT<br>TGAGCCGAAAGAAATCGTTGACCCGCTGACCCCGGATGCCAGCGAGAGCGT<br>TAACAACATTCTGAAACAGTCCGGTGCGTGGAGCGGTGACGATAAGCTGCA<br>AAAGTGGGTTCGTGTGTATTTGGACCGTGGTCAGGAGGCCATTAAGTAA |
| SEQ ID NO:140 | SynInvI_RBS | CTTGGGCACGCGTCCATTAAAAAGGACCAATTAAGC |
| SEQ ID NO:141 | SynInvI | ATGCACTCTCTGACTCGTATCAAGGTCCTGCAACGTCGTTGTACCGTGTTCC<br>ATTCTCAGTGCGAGTCCATTCTGTTGCGTTATCAGGACGAAGATCGCGGCTT<br>GCAGGCGGAGGAGGAGGCCATCCTGGAACAGATCGCAGGTCTGAAACTGCT<br>GTTGGACACCCTGCGTGCTGAAAATCGTCAACTGAGCCGTGAAGAAATCTA<br>TACGCTGCTGCGCAAACAGAGCATTGTTCGTCGCCAGATTAAGGATCTGGA<br>GCTGCAAATCATTCAGATTCAAGAAAAGCGTAGCGAGCTGGAAAAGAAAC<br>GTGAGGAATTTCAAAAGAAAAGCAAATACTGGCTGCGTAAAGAAGGTAACT<br>ACCAGCGCTGGATTATCCGTCAAAAACGCTTCTACATTCAACGTGAGATCCA<br>GCAAGAGGAGGCGGAGAGCGAAGAGATCATTTAA |
| SEQ ID NO:142 | SynInvJ_RBS | AAAAAAAAGCTCTAAAAGATTAAGAGGGGGTAACAT |
| SEQ ID NO:143 | SynInvJ | ATGGGTGACGTGAGCGCGGTGAGCAGCAGCGGTAACATTCTGCTGCCGCAG<br>CAGGACGAGGTTGGTGGCCTGTCCGAAGCGCTGAAGAAAGCGGTTGAAAA<br>ACACAAAACCGAATACAGCGGTGACAAGAAAGATCGTGATTATGGTGACGC<br>CTTTGTTATGCACAAGGAAACCGCGCTGCCGTTGTTGCTGGCAGCTTGGCGC<br>CACGGCGCACCGGCGAAAAGCGAGCACCATAACGGTAACGTAAGCGGTCT<br>GCATCACAACGGTAAGAGCGAGCTGCGTATTGCTGAGAAACTGCTGAAGGT<br>GACGGCGGAGAAGAGCGTTGGTCTGATTAGCGCTGAAGCGAAGGTGGATA<br>AATCTGCGGCGCTGCTGTCTAGCAAGAATCGTCCGCTGGAATCGGTCAGCG<br>GCAAAAAGTTGTCCGCCGATCTGAAAGCAGTGGAGTCCGTGTCCGAGGTCA<br>CGGATAACGCCACCGGCATTTCGGATGACAACATCAAAGCATTGCCGGGTG<br>ACAATAAGGCCATCGCCGGTGAGGGTGTGCGTAAAGAAGGTGCGCCGCTGG<br>CGCGTGACGTGGCTCCGGCACGCATGGCGGCAGCAAATACGGGCAAGCCGG<br>AGGATAAAGACCACAAGAAGGTCAAGGACGTTAGCCAGCTGCCGCTGCAA<br>CCGACTACCATCGCCGATCTGTCTCAACTGACGGGTGGCGATGAAAAGATG<br>CCGCTGGCAGCGCAGTCCAAACCGATGATGACCATTTTCCCAACCGCCGAC<br>GGCGTTAAAGGTGAGGACAGCTCTCTGACCTATCGTTTCCAGCGCTGGGGC |

FIG. 24 (cont)

| SEQ ID NO: | Name | Sequence |
|---|---|---|
| | | AACGATTACTCCGTCAATATCCAGGCACGCCAAGCGGGCGAATTTAGCCTG ATTCCTAGCAATACCCAGGTTGAACATCGTCTGCACGACCAATGGCAAAAT GGCAATCCACAACGCTGGCATTTGACGCGTGATGACCAGCAAAACCCGCAA CAGCAACAGCATCGTCAGCAGTCCGGTGAAGAGGACGACGCGTAA |
| SEQ ID NO:144 | SynSpaO_RBS | CTTGGGCACGCGTCCATGAAAGACAGGACCCACTAG |
| SEQ ID NO:145 | SynSpaO | ATGAGCTTGCGCGTACGCCAAATTGACCGCCGTGAATGGCTGCTGGCCCAG ACTGCGACCGAATGTCAGCGTCACGGTCGTGAGGCCACCCTGGAGTATCCG ACCCGTCAGGGTATGTGGGTCCGCCTGTCTGATGCCGAAAAACGCTGGTCT GCGTGGATCAAACCGGGTGATTGGTTGGAACACGTTAGCCCAGCACTGGCG GGTGCCGCGGTCAGCGCAGGCGCGGAGCACCTGGTGGTTCCGTGGCTGGCG GCAACCGAACGCCCGTTCGAGCTGCCGGTCCCGCACTTGAGCTGCCGTCGTC TGTGCGTGGAGAACCCGGTTCCGGGTTCCGCACTGCCTGAGGGCAAGCTGC TGCACATCATGTCGGATCGTGGTGGCCTGTGGTTTGAGCATCTGCCGGAGCT GCCGGCTGTTGGCGGTGGCCGTCCGAAGATGCTGCGTTGGCCGCTGCGTTTC GTTATTGGCAGCAGCGACACCCAGCGCAGCCTGCTGGGTCGTATCGGTATC GGTGATGTTCTGCTGATCCGCACCAGCCGTGCTGAGGTTTACTGTTACGCGA AGAAACTGGGCCACTTTAATCGTGTGGAAGGTGGCATTATTGTCGAAACGC TGGACATTCAACATATCGAGGAGGAGAACAACACGACGGAAACGGCGGAA ACCCTGCCGGGTCTGAATCAACTGCCGGTGAAGCTGGAGTTCGTTCTGTATC GTAAAAACGTGACGTTGGCCGAACTGGAAGCAATGGGTCAGCAACAACTGC TGTCCTTGCCAACCAATGCGGAACTGAACGTCGAAATCATGGCGAATGGCG TGCTGCTGGGTAACGGCGAACTGGTGCAGATGAATGACACCCTGGGTGTCG AGATTCATGAGTGGTTGTCCGAGAGCGGTAATGGCGAGTAG |
| SEQ ID NO:146 | SynSpaP_RBS | CTTGGGCACGCGTCCATGAAAGAAACGACATACTAG |
| SEQ ID NO:147 | SynSpaP | ATGGGTAACGATATTAGCTTGATTGCATTGCTGGCGTTTTCCACCCTGCTGC CGTTCATCATCGCGTCTGGTACTTGCTTCGTCAAATTCAGCATCGTCTTTGTG ATGGTGCGCAACGCGCTGGGTCTGCAACAAATTCCAAGCAATATGACCCTG AATGGCGTCGCACTGCTGCTGTCGATGTTTGTTATGTGGCCGATTATGCACG ACGCGTATGTGTATTTCGAGGATGAAGATGTGACCTTTAACGACATCTCCAG CCTGAGCCAAGCATGTTGATGAGGGCCTGGACGGTTATCGCGACTACCTGAT CAAGTATTCCGACCGTGAGCTGGTGCAGTTCTTTGAGAATGCCCAGTTGAAA CGTCAGTACGGTGAAGAAACGGAAACCGTTAAACGTGACAAGGACGAGAT TGAAAAGCCGAGCATTTTCGCACTGTTGCCTGCTTACGCCTTGAGCGAGATT AAGAGCGCATTCAAAATTGGTTTTTACCTGTACCTGCCGTTCGTTGTGGTCG ATCTGGTTGTCTCCAGCGTTCTGCTGGCCCTGGGCATGATGATGATGTCCCC GGTTACCATCAGCACGCCGATCAAACTGGTCCTGTTTGTGGCCCTGGATGGT TGGACGCTGCTGTCTAAAGGCCTGATCCTGCAATACATGGACATCGCGACCT AA |
| SEQ ID NO:148 | SynSpaQ_RBS | CTTGGGCACGCGTCCATTAAGAAGGAGGAATTAAGC |
| SEQ ID NO:149 | SynSpaQ | ATGGACGATCTGGTTTTCGCCGGCAACAAAGCCCTGTACTTGGTGCTGATTC TGTCCGGTTGGCCGACGATTGTCGCAACCATTATCGGTCTGCTGGTTGGTCT GTTTCAAACCGTGACGCAGTTGCAGGAGCAAACCCTGCCGTTCGGTATCAA GCTGCTGGGTGTGTGTCTGTGCCTGTTTTGCTGTCTGGCTGGTATGGCGAA GTTCTGCTGTCCTACGGCCGTCAGGTCATCTTCCTGGCTCTGGCGAAAGGTT AA |
| SEQ ID NO:150 | SynSpaR_RBS | CTTGGGCACGCGTCCATGAAAGACAGGACCCACTAG |

FIG. 24 (cont)

| SEQ ID NO: | Name | Sequence |
|---|---|---|
| SEQ ID NO:151 | SynSpaR | ATGTTCTATGCATTGTATTTTGAGATCCACCATCTGGTGGCGTCCGCGGCTC TGGGTTTTGCGCGTGTTGCTCCGATCTTTTTCTTTCTGCCGTTCCTGAATAGC GGTGTCCTGAGCGGTGCTCCGCGCAACGCGATCATCATTCTGGTGGCGCTGG GTGTATGGCCGCACGCCCTGAATGAGGCGCCACCGTTTCTGTCTGTGGCAAT GATTCCGCTGGTCCTGCAAGAGGCAGCCGTGGGTGTTATGCTGGGTTGCCTG TTGTCCTGGCCGTTTTGGGTTATGCACGCGTTGGGCTGTATCATTGATAACC AACGCGGTGCAACCCTGTCCAGCAGCATTGATCCTGCGAATGGCATCGACA CCAGCGAGATGGCCAATTTCCTGAACATGTTCGCGGCTGTCGTGTATTTGCA GAACGGTGGCTTGGTCACGATGGTGGACGTGCTGAATAAGTCTTACCAGCT GTGTGATCCGATGAACGAGTGTACGCCGAGCCTGCCTCCGTTGCTGACCTTC ATTAATCAAGTGGCCCAGAACGCACTGGTGCTGGCGTCCCCGGTCGTTCTGG TTCTGCTGCTGTCGGAAGTTTTCCTGGGCCTGCTGTCTCGTTTTGCACCGCAA ATGAACGCGTTCGCCATTAGCCTGACTGTTAAAAGCGGTATTGCGGTTTTGA TCATGCTGCTGTATTTCAGCCCCGGTCCTGCCGGACAATGTTCTGCGTCTGAG CTTTCAGGCGACCGGCCTGAGCAGCTGGTTCTACGAACGTGGCGCAACGCA TGTGCTGGAATAA |
| SEQ ID NO:152 | SynSpaS_RBS | CTTGGGCACGCGTCCATGAAAGACAGGACCCACTAG |
| SEQ ID NO:153 | SynSpaS | ATGTCCAGCAACAAAACCGAAAAACCGACTAAGAAACGTCTGGAGGATAG CGCAAAGAAAGGTCAGAGCTTCAAGAGCAAGGACCTGATTATCGCGTGCCT GACCCTGGGTGGTATCGCTTATTTGGTGAGCTACGGCAGCTTCAATGAGTTT ATGGGTATCATTAAGATTATCATCGCTGATAACTTTGATCAGTCGATGGCAG ATTATAGCCTGGCCGTGTTTGGTATTGGCCTGAAATACCTGATTCCGTTCAT GCTGCTGTGTTTGGTTTGTTCCGCACTGCCGGCACTGCTGCAAGCGGGCTTC GTTCTGGCAACCGAGGCCCTGAAGCCGAATCTGTCCGCCCTGAACCCGGTT GAAGGCGCGAAGAAACTGTTTTCCATGCGCACCGTCAAAGACACGGTCAAG ACGCTGCTGTATCTGTCGAGCTTTGTGGTTGCGGCAATCATTTGCTGGAAAA AGTATAAAGTCGAGATTTTCAGCCAACTGAACGGTAATATCGTGGGTATTG CGGTTATCTGGCGTGAATTGCTGCTGGCGTTGGTTCTGACCTGTCTGGCGTG CGCGCTGATCGTGCTGTTGCTGGATGCTATTGCCGAGTACTTTCTGACCATG AAAGATATGAAGATGGACAAAGAAGAAGTTAAACGCGAGATGAAAGAGCA GGAGGGTAACCCGGAGGTGAAGTCTAAACGTCGTGAAGTCCACATGGAAAT CCTGAGCGAACAAGTCAAGTCTGACATTGAAAATAGCCGTCTGATTGTGGC AAACCCTACGCATATTACCATCGGCATCTACTTCAAACCGGAACTGATGCCG ATTCCAATGATTAGCGTCTATGAAACCAATCAACGCGCTGGCGTCCGT GCGTACGCCGAGAAAGTGGGTGTTCCGGTTATTGTAGACATCAAGCTGGCG CGCAGCCTGTTCAAAACGCACCGTCGTTACGACCTGGTGAGCCTGGAGGAG ATCGACGAGGTTTTGCGCCTGCTGGTTTGGTTGGAAGAGGTCGAAAACGCA GGCAAGGATGTGATCCAACCGCAGGAGAATGAAGTGCGTCATTAA |
| SEQ ID NO:154 | Syn_PrgOrg_Operon | GCATGCATTAAAGAGGAGAAATTAAGCATGGCTACTCCGTGGTCTGGTTAT CTGGATGATGTTTCTGCAAAATTTGACACGGGTGTTGACAACTTGCAAACCC AAGTTACCGAAGCCCTGGACAAGCTGGCTGCGAAGCCGTCCGATCCGGCGC TGCTGGCGGCGTATCAATCCAAACTGTCTGAGTATAACTTGTACCGTAATGC GCAGTCGAACACGGTCAAGGTCTTCAAAGATATTGATGCAGCGATTATTCA GAACTTTCGTTAGTAACCTAGGATTAAGGAGGATAAATTAAGCATGTCTATC GCGACTATCGTGCCTGAAAATGCCGTTATTGGTCAAGCGGTGAATATTCGCA GCATGGAAACGGACATCGTCAGCTTGGACGACCGTTTGCTGCAAGCATTTTC GGGCAGCGCCATCGCTACCGCCGTCGATAAGCAGACCATTACCAATCGCAT TGAAGACCCTAATCTGGTTACCGATCCGAAGGAGCTGGCGATTAGCCAGGA AATGATTTCCGACTACAATCTGTACGTCAGCATGGTTAGCACCCTGACGCGT AAGGGCGTTGGCGCTGTTGAGACTTTGCTGCGTTCCTGATAGGCTAGCATTA AACAGGATAATAAGCATGGAAACTAGCAAGGAGAAAACGATTACGTCCCCT GGTCCGTATATCGTTCGTCTGTTGAACTCGTCCCTGAACGGTTGTGAATTTC |

FIG. 24 (cont)

| SEQ ID NO: | Name | Sequence |
|---|---|---|
| | | CGCTGCTGACTGGTCGTACGCTGTTCGTCGTGGGTCAGAGCGATGCTCTGAC CGCGTCTGGTCAGCTGCCGGACATTCCTGCCGACTCCTTCTTCATCCCGCTG GATCATGGCGGTGTTAATTTCGAGATTCAAGTGGACACTGACGCGACGGAA ATCATCCTGCACGAACTGAAAGAGGGCAACTCCGAGAGCCGCTCCGTGCAA CTGAACACCCCGATCCAAGTTGGTGAACTGCTGATTTTGATTCGTCCGGAGA GCGAGCCGTGGGTGCCGGAACAGCCGGAGAAGTTGGAAACTTCTGCGAAA AAGAACGAACCGCGCTTTAAAAACGGCATCGTCGCGGCACTGGCGGGTTTC TTTATCCTGGGTATCGGCACGGTTGGCACCCTGTGGATTCTGAACTCGCCGC AACGTCAAGCAGCCGAATTGGACAGCCTGTTGGGTCAGGAGAAGGAGCGTT TTCAGGTGCTGCCGGGTCGCGACAAGATGCTGTATGTCGCCGCGCAAAACG AACGCGACACCCTGTGGGCACGTCAAGTCCTGGCACGCGGCGATTACGATA AAAACGCACGCGTTATTAATGAAAATGAGGAGAATAAACGTATCAGCATCT GGCTGGACACGTATTATCCACAACTGGCATATTACCGTATCCATTTTGATGA ACCACGTAAGCCGGTGTTTTGGCTGTCCCGTCAACGCAACACGATGAGCAA GAAAGAGCTGGAGGTGCTGTCCCAGAAATTGCGTGCGCTGATGCCGTACGC CGACAGCGTCAATATTACTCTGATGGATGACGTGACCGCAGCAGGCCAAGC CGAGGCAGGTCTGAAACAACAGGCGCTGCCATACAGCCGCCGTAACCACAA AGGTGGTGTTACGTTCGTTATTCAGGGCGCCTTGGACGACGTTGAGATTCTG CGTGCGCGCCAGTTTGTCGACTCCTATTATCGTACCTGGGGTGGTCGTTACG TTCAATTCGCAATTGAATTGAAAGACGATTGGCTGAAAGGCCGCTCGTTCCA ATACGGTGCGGAAGGCTACATTAAGATGAGCCCAGGTCATTGGTATTTTCC GTCTCCTCTGTAATAGAAGCTTATTAAACAGGATAATAAGCATGATCCGCCG TTACCTGTATACCTTCTTGCTGGTTATGACTTTGGCCGGCTGTAAAGATAAG GATCTGCTGAAAGGCTTGGACCAAGAGCAAGCGAATGAGGTCATTGCGGTT CTGCAAATGCACAACATTGAGGCTAACAAGATTGATAGCGGCAAGCTGGGT TACAGCATTACCGTCGCGGAACCGGATTTCACCGCGGCAGTGTATTGGATTA AGACCTACCAGTTGCCGCCTCGCCCGCGTGTCGAAATCGCCCAAATGTTTCC GGCAGACAGCCTGGTTAGCTCTCCGCGTGCGGAGAAAGCACGTCTGTACTC GGCGATTGAACAGCGCCTGGAGCAGTCGCTGCAAACGATGGAAGGTGTTCT GTCGGCCCGTGTCCACATCAGCTATGATATTGATGCGGGCGAGAACGGTCG TCCGCCTAAGCCGGTGCACCTGTCGGCTTTGGCGGTGTATGAACGCGGTTCC CCTCTGGCCCATCAGATTTCGGATATTAAGCGCTTCCTGAAAAACAGCTTCG CGGATGTTGACTATGATAACATCAGCGTGGTTCTGTCCGAGCGTAGCGACG CACAGTTGCAGGCGCCGGGCACGCCGGTCAAGCGCAATAGCTTCGCTACCT CCTGGATTGTGCTGATTATCCTGTTGTCTGTTATGAGCGCGGGTTTCGGTGTC TGGTACTACAAAAATCACTATGCGCGTAATAAGAAAGGCATTACTGCCGAT GACAAGGCAAAGTCCAGCAACGAGTAATAAGGTACCGAAAGAAGGGACAG ACTAGATGATTCGTCGTAACCGTCAAATGAACCGTCAACCACTGCCAATTAT CTGGCAACGCATTATTTTCGACCCACTGTCCTATATTCACCCACAACGTCTG CAAATCGCGCCGGAGATGATCGTGCGTCCGGCAGCGCGTGCGGCAGCGAAT GAGCTGATTTTGGCGGCGTGGCGTTTGAAGAACGGTGAGAAGGAGTGCATT CAGAATAGCCTGACGCAGCTGTGGTTGCGTCAATGGCGCCGTCTGCCGCAG GTTGCTTACCTGCTGGGTTGCCACAAGTTGCGTGCTGACCTGGCCCGTCAAG GTGCTTTATTGGGCCTGCCGGACTGGGCGCAGGCATTCTTGGCGATGCACCA GGGTACGTCCTTGTCGGTTTGTAATAAGGCGCCGAACCACCGTTTCCTGCTG TCCGTTGGTTACGCCCAACTGAACGCGCTGAATGAGTTCCTGCCGGAGAGCT TGGCCCAACGCTTTCCTCTGCTGTTTCCACCGTTCATCGAGGAGGCACTGAA ACAAGATGCAGTGGAGATGAGCATCCTGCTGCTGGCCCTGCAATACGCGCA AAAGTATCCTAACACCGTCCCGGCGTTTGCGTGCTAATAAAGATCTGAAAG AAGGGACAGACTAGATGTTGAAAAATATCCCGATTCCATCCCCTCTGTCTCC GGTTGAAGGTATCCTGATTAAACGCAAGACGTTGGAGCGTTACTTCTCGATT GAGCGCCTGGAACAACAGGCGCATCAGCGTGCAAAGCGCATTTTGCGTGAG GCAGAAGAAGAAGCCAAGACCCTGCGCATGTATGCGTACCAGGAGGGCTA CGAGCAGGGCATGATTGACGCACTGCAACAGGTGGCCGCCTATTTGACCGA CAACCAGACGATGGCTTGGAAATGGATGGAGAAAATTCAAATCTATGCGCG TGAGTTGTTCAGCGCGGCTGTCGATCACCCGGAAACGTTGTTGACGGTGCTG |

FIG. 24 (cont)

| SEQ ID NO: | Name | Sequence |
|---|---|---|
| | | GACGAGTGGCTGCGTGATTTCGATAAGCCGGAAGGTCAGCTGTTTTTGACCC TGCCGGTGAACGCAAAGAAAGATCATCAGAAACTGATGGTGCTGCTGATGG AAAATTGGCCGGGCACCTTCAATCTGAAGTATCATCAGGAGCAACGTTTTAT CATGTCCTGTGGCGATCAGATTGCCGAGTTTTCGCCGGAACAATTTGTTGAA ACGGCGGTTGGTGTTATCAAGCACCATCTGGATGAGCTGCCTCAGGACTGTC GCACCATTTCGGACAATGCGATTAACGCGCTGATTGATGAATGGAAGACGA AAACCCAAGCTGAAGTTATTCGCTGATAAGGATCCGGCATCAAATAAAACG AAAGGCTCAGTCGAAAGACTGGGCCTTTCGTTTTATCTGTTGTTTGTCGGTG AACGCTCTCCTGAGTAGGACAAATCCGCCGCCCTAGAACTAGTccataagaatGC GGCCGC |
| SEQ ID NO:155 | Syn_InvSpa_ Operon | CTCGAGAAAAAAAAGCTCTAAAAGATTAAGAGGGGGTAACATATGGGTGA CGTGAGCGCGGTGAGCAGCAGCGGTAACATTCTGCTGCCGCAGCAGGACGA GGTTGGTGGCCTGTCCGAAGCGCTGAAGAAAGCGGTTGAAAAACACAAAAC CGAATACAGCGGTGACAAGAAAGATCGTGATTATGGTGACGCCTTTGTTAT GCACAAGGAAACCGCGCTGCCGTTGTTGCTGGCAGCTTGGCGCCACGGCGC ACCGGCGAAAAGCGAGCACCATAACGGTAACGTAAGCGGTCTGCATCACAA CGGTAAGAGCGAGCTGCGTATTGCTGAGAAACTGCTGAAGGTGACGGCGGA GAAGAGCGTTGGTCTGATTAGCGCTGAAGCGAAGGTGGATAAATCTGCGGC GCTGCTGTCTAGCAAGAATCGTCCGCTGGAATCGGTCAGCGGCAAAAAGTT GTCCGCCGATCTGAAAGCAGTGGAGTCCGTGTCCGAGGTCACGGATAACGC CACCGGCATTTCGGATGACAACATCAAAGCATTGCCGGGTGACAATAAGGC CATCGCCGGTGAGGGTGTGCGTAAAGAAGGTGCGCCGCTGGCGCGTGACGT GGCTCCGGCACGCATGGCGGCAGCAAATACGGGCAAGCCGGAGGATAAAG ACCACAAGAAGGTCAAGGACGTTAGCCAGCTGCCGCTGCAACCGACTACCA TCGCCGATCTGTCTCAACTGACGGGTGGCGATGAAAAGATGCCGCTGGCAG CGCAGTCCAAACCGATGATGACCATTTTCCCAACCGCCGACGGCGTTAAAG GTGAGGACAGCTCTCTGACCTATCGTTTCCAGCGCTGGGGCAACGATTACTC CGTCAATATCCAGGCACGCCAAGCGGGCGAATTTAGCCTGATTCCTAGCAA TACCCAGGTTGAACATCGTCTGCACGACCAATGGCAAAATGGCAATCCACA ACGCTGGCATTTGACGCGTGATGACCAGCAAAACCCGCAACAGCAACAGCA TCGTCAGCAGTCCGGTGAAGAGGACGACGCGTAACTTGGGCACGCGTCCAT TAAGAAGGAGGAATTAAGCATGGACGATCTGGTTTTCGCCGGCAACAAAGC CCTGTACTTGGTGCTGATTCTGTCCGGTTGGCCGACGATTGTCGCAACCATT ATCGGTCTGCTGGTTGGTCTGTTTCAAACCGTGACGCAGTTGCAGGAGCAAA CCCTGCCGTTCGGTATCAAGCTGCTGGGTGTGTGTCTGTGCCTGTTTTTGCTG TCTGGCTGGTATGGCGAAGTTCTGCTGTCCTACGGCCGTCAGGTCATCTTCC TGGCTCTGGCGAAAGGTTAAGACGTCCTTGGGCACGCGTCCATTAAACAGG AGTAATTAAGCATGCTGCTGTCCCTGCTGAATAGCGCGCGTCTGCGTCCTGA GCTGCTGATTCTGGTTCTGATGGTTATGATCATCAGCATGTTCGTTATCCCGT TGCCGACCTATTTGGTTGACTTCTTGATCGCTTTGAACATTGTCCTGGCAATT CTGGTGTTCATGGGCTCCTTCTACATCGACCGCATTCTGAGCTTCAGCACCT TTCCGGCGGTTCTGCTGATCACGACTCTGTTCCGTTTGGCACTGAGCATCAG CACCAGCCGCCTGATCCTGATTGAAGCAGATGCGGGTGAGATCATCGCGAC CTTTGGTCAGTTTGTGATCGGTGACAGCCTGGCGGTTGGTTTCGTCGTATTCT CCATCGTGACGGTGGTGCAGTTTATCGTTATTACCAAGGGCAGCGAACGTGT GGCGGAGGTCGCCGCTCGCTTCAGCCTGGACGGCATGCCGGGTAAACAGAT GTCTATTGATGCAGACCTGAAAGCCGGCATTATTGATGCTGATGCAGCGCG CGAGCGCCGCAGCGTCCTGGAGCGTGAAAGCCAACTGTACGGTTCCTTCGA CGGTGCCATGAAGTTCATTAAAGGTGATGCGATTGCGGGCATCATTATCATC TTCGTTAACTTCATTGGCGGTATCAGCGTCGGTATGACCCGTCATGGTATGG ATCTGAGCAGCGCCCTGAGCACCTACACCATGCTGACGATTGGTGATGGTCT GGTTGCCCAAATTCCGGCGTTGCTGATCGCGATTTCTGCGGGCTTCATCGTT ACCCGCGTCAACGGTGATAGCGATAACATGGGTCGTAACATTATGACCCAG CTGCTGAATAATCCGTTTGTCCTGGTTGTAACGGCGATTTTGACCATCAGCA TGGGCACGCTGCCGGGCTTTCCGTTGCCGGTTTTCGTTATTCTGTCTGTTGTG |

FIG. 24 (cont)

| SEQ ID NO: | Name | Sequence |
|---|---|---|
| | | CTGTCCGTCCTGTTTTACTTTAAGTTCCGCGAGGCGAAACGTAGCGCTGCGA
AACCAAAAACGAGCAAGGGCGAGCAACCGTTGTCCATCGAGGAGAAGGAA
GGTAGCAGCCTGGGCCTGATTGGCGACCTGGATAAGGTTAGCACGGAAACC
GTCCCGCTGATTTTGCTGGTGCCGAAATCGCGTCGTGAGGATCTGGAGAAA
GCGCAGCTGGCGGAACGTCTGCGCAGCCAATTCTTTATTGATTATGGTGTGC
GTCTGCCAGAAGTACTGCTGCGTGACGGTGAGGGTCTGGATGACAACTCTA
TCGTCCTGCTGATTAATGAGATTCGCGTTGAACAGTTTACTGTCTATTTTGAC
CTGATGCGTGTGGTTAACTACAGCGACGAGGTGGTGAGCTTTGGCATCAAC
CCGACCATTCACCAGCAAGGTTCCAGCCAGTACTTTTGGGTGACCCATGAG
GAAGGCGAAAAGCTGCGCGAGCTGGGCTACGTCCTGCGTAATGCACTGGAC
GAACTGTACCACTGTCTGGCGGTGACGCTGGCACGCAATGTGAACGAGTAT
TTCGGTATCCAAGAAACGAAACACATGCTGGACCAACTGGAAGCAAAGTTT
CCTGACCTGCTGAAGGAGGTTTTGCGCCACGCCACCGTGCAGCGCATTTCGG
AAGTGCTGCAACGTCTGCTGTCCGAACGCGTGAGCGTCCGTAACATGAAGC
TGATCATGGAAGCCCTGGCACTGTGGGCTCCGCGTGAGAAAGATGTGATCA
ATCTGGTGGAGCACATCCGTGGTGCGATGGCGCGTTATATCTGCCACAAGTT
CGCAAATGGTGGTGAACTGCGTGCCGTTATGGTTTCCGCCGAAGTTGAGGA
TGTCATTCGTAAAGGCATTCGTCAAACTTCTGGCTCCACCTTTTTGAGCTTG
GACCCGGAGGCTTCGGCAAATCTGATGGACCTGATCACGCTGAAGCTGGAC
GACCTGTTGATTGCGCATAAGGACCTGGTCCTGTTGACCAGCGTTGACGTGC
GTCGTTTTATCAAGAAAATGATTGAAGGTCGTTTTCCGGATCTGGAGGTCCT
GTCCTTCGGTGAGATTGCAGATAGCAAAAGCGTGAATGTCATCAAAACCAT
CTGAATTTAAATCTTGGGCACGCGTCCATTAAAAAGGAGTAATTAAGCATG
AGCTTCAGCGAGAGCCGCCACAATGAAAACTGTCTGATTCAAGAAGGCGCA
CTGCTGTTTTGTGAGCAAGCAGTCGTGGCGCCTGTCAGCGGTGATCTGGTTT
TTCGTCCGCTGAAAATCGAGGTCCTGAGCAAGCTGCTGGCGTTCATCGACG
GCGCAGGTCTGGTGGATACGACCTACGCGGAGTCGGACAAATGGGTTCTGC
TGTCTCCGGAGTTCCGTGCTATTTGGCAAGACCGTAAACGTTGCGAATATTG
GTTTTTGCAGCAGATTATCACCCCATCTCCGGCGTTCAACAAGGTTCTGGCA
CTGTTGCGTAAGAGCGAAAGCTATTGGTTGGTCGGCTACTTGCTGGCCCAAA
GCACCAGCGGCAATACTATGCGTATGTTGGGTGAGGATTACGGTGTTAGCT
ACACGCATTTCCGCCGTCTGTGCAGCCGCGCTCTGGGCGGTAAGGCGAAAA
GCGAGCTGCGCAATTGGCGCATGGCCCAGTCCCTGCTGAATAGCGTGGAAG
GTCATGAAAACATCACCCAGCTGGCGGTCAACCACGGTTATAGCAGCCCGT
CCCACTTTAGCTCTGAAATCAAGGAGCTGATTGGTGTTTCCCCGCGTAAGCT
GTCTAACATCATTCAGCTGGCCGACAAATGAATTTAAATGCTAGCCTTGGGC
ACGCGTCCATTAAAGAGGACCAATTAAGCATGAAAACCCCACGTCTGCTGC
AATACCTGGCCTACCCGCAGAAAATCACTGGCCCTATCATTGAAGCAGAAC
TGCGTGATGTTGCAATTGGTGAATTGTGCGAGATCCGTCGCGGCTGGCACCA
GAAGCAGGTTGTGGCCCGTGCGCAAGTGGTTGGTTTGCAGCGCGAACGTAC
CGTCCTGAGCCTGATCGGCAATGCCCAAGGCCTGAGCCGTGATGTGGTCTTG
TACCCGACCGGCCGTGCTCTGAGCGCGTGGGTTGGTTACAGCGTTCTGGGCG
CAGTACTGGACCCGACGGGTAAAATCGTTGAACGTTTCACCCCGGAAGTCG
CACCGATTTCCGAGGAGCGCGTTATCGACGTGGCACCGCCGAGCTACGCAA
GCCGTGTCGGTGTGCGCGAACCGCTGATCACGGGTGTCCGCGCAATTGATG
GTCTGCTGACGTGTGGTGTGGGCCAGCGTATGGGTATTTTCGCAAGCGCGG
GTTGTGGTAAGACCATGTTGATGCACATGCTGATCGAGCAAACCGAAGCGG
ATGTCTTTGTTATTGGCCTGATTGGCGAGCGTGGTCGTGAAGTTACCGAATT
TGTAGACATGTTGCGTGCATCTCATAAGAAAGAAAAATGTGTGCTGGTTTTT
GCCACGTCCGACTTCCCAAGCGTTGACCGCTGCAACGCTGCCCAGCTGGCA
ACGACGGTCGCCGAGTATTTCCGCGACCAGGGTAAACGTGTTGTCCTGTTTA
TCGACAGCATGACCCGTTATGCACGCGCGTTGCGTGATGTCGCGCTGGCGA
GCGGCGAGCGTCCGGCTCGCCGTGGTTATCCGGCGTCTGTGTTCGACAATCT
GCCGCGTTTGCTGGAGCGTCCGGGTGCGACGAGCGAGGGTAGCATTACCGC
CTTCTATACCGTCCTGCTGGAGTCGGAAGAAGAAGCGGACCCGATGGCGGA
CGAGATCCGTTCTATTCTGGACGGTCACCTGTACCTGTCCCGCAAACTGGCG |

FIG. 24 (cont)

| SEQ ID NO: | Name | Sequence |
|---|---|---|
| | | GGTCAGGGTCATTACCCGGCTATCGATGTGCTGAAGAGCGTGAGCCGTGTG
TTTGGTCAAGTGACCACCCCGACTCACGCGGAGCAAGCGAGCGCGGTCCGT
AAGCTGATGACCCGTCTGGAAGAGCTGCAACTGTTCATTGACCTGGGCGAG
TATCGTCCGGGCGAGAACATTGACAATGATCGTGCGATGCAAATGCGCGAT
AGCCTGAAGGCGTGGCTGTGTCAGCCTGTTGCGCAATACAGCAGCTTCGAT
GATACGCTGTCCGGCATGAACGCCTTTGCGGATCAGAACTGACTTGGGCAC
GCGTCCATGAAAGAAACGACATACTAGATGGGTAACGATATTAGCTTGATT
GCATTGCTGGCGTTTTCCACCCTGCTGCCGTTCATCATCGCGTCTGGTACTTG
CTTCGTCAAATTCAGCATCGTCTTTGTGATGGTGCGCAACGCGTGGGTCTG
CAACAAATTCCAAGCAATATGACCCTGAATGGCGTCGCACTGCTGCTGTCG
ATGTTTGTTATGTGGCCGATTATGCACGACGCGTATGTGTATTTCGAGGATG
AAGATGTGACCTTTAACGACATCTCCAGCCTGAGCAAGCATGTTGATGAGG
GCCTGGACGGTTATCGCGACTACCTGATCAAGTATTCCGACCGTGAGCTGGT
GCAGTTCTTTGAGAATGCCCAGTTGAAACGTCAGTACGGTGAAGAAACGGA
AACCGTTAAACGTGACAAGGACGAGATTGAAAAGCCGAGCATTTTCGCACT
GTTGCCTGCTTACGCCTTGAGCGAGATTAAGAGCGCATTCAAAATTGGTTTT
TACCTGTACCTGCCGTTCGTTGTGGTCGATCTGGTTGTCTCCAGCGTTCTGCT
GGCCCTGGGCATGATGATGATGTCCCCGGTTACCATCAGCACGCCGATCAA
ACTGGTCCTGTTTGTGGCCCTGGATGGTTGGACGCTGCTGTCTAAAGGCCTG
ATCCTGCAATACATGGACATCGCGACCTAAGAGCTCTGGGCACGCGTCCAT
TAATGAGGAAAAATTATTAGCATGAAAACGCACATTCTGTTGGCCCGTGTG
CTGGCTTGCGCAGCTCTGGTGCTGGTCACCCCAGGTTATAGCTCCGAGAAGA
TCCCGGTTACGGGCAGCGGCTTCGTTGCAAAGGACGATTCTCTGCGCACCTT
TTTCGATGCGATGGCACTGCAATTGAAGGAGCCGGTGATTGTCAGCAAGAT
GGCGGCTCGCAAAAAGATTACCGGCAATTTCGAGTTCCACGATCCAAACGC
GCTGCTGGAGAAACTGTCCCTGCAACTGGGTCTGATCTGGTACTTTGATGGT
CAGGCGATCTACATCTACGACGCGAGCGAAATGCGTAATGCGGTTGTGAGC
CTGCGTAATGTCAGCCTGAACGAGTTCAACAATTTTCTGAAGCGCAGCGGC
CTGTACAATAAGAACTACCCTCTGCGTGGTGATAATCGTAAAGGCACCTTCT
ATGTCAGCGGTCCGCCGGTGTATGTTGATATGGTTGTAAATGCGGCCACCAT
GATGGACAAACAGAATGATGGCATCGAGCTGGGTCGCCAAAAGATCGGTGT
TATGCGCCTGAACAACACTTTTGTGGGCGACCGCACCTACAACCTGCGTGAT
CAAAAGATGGTCATTCCGGGTATTGCTACGGCAATTGAACGCCTGTTGCAA
GGCGAAGAACAACCGCTGGGTAACATTGTAAGCTCCGAGCCTCCGGCCATG
CCGGCCTTTAGCGCAAACGGCGAGAAAGGTAAGGCAGCGAATTACGCGGGT
GGTATGAGCCTGCAAGAAGCGCTGAAACAGAACGCAGCGGCAGGCAACAT
CAAAATTGTGGCCTATCCGGACACCAACAGCCTGCTGGTGAAAGGTACGGC
GGAGCAGGTGCATTTCATCGAGATGCTGGTTAAAGCCCTGGACGTGGCGAA
ACGTCACGTTGAATTGAGCCTGTGGATTGTGGATTTGAATAAGAGCGACCT
GGAACGCTTGGGCACCAGCTGGAGCGGTAGCATCACCATCGGCGACAAGCT
GGGTGTGAGCCTGAACCAGAGCAGCATCTCCACGCTGGACGGTAGCCGCTT
TATTGCGGCGGTCAACGCTCTGGAGGAAAAGAAACAGGCCACTGTTGTCAG
CCGTCCGGTTCTGCTGACCCAGGAGAATGTCCCGGCGATTTTTGACAATAAT
CGTACTTTCTATACCAAACTGATCGGTGAACGTAATGTTGCATTGGAACACG
TGACCTATGGCACCATGATCCGTGTCCTGCCGCGTTTCAGCGCGGACGGCCA
GATTGAGATGAGCCTGGACATCGAAGATGGTAATGACAAAACCCCGCAGTC
TGATACGACCACCTCCGTTGATGCGCTGCCAGAAGTGGGTCGTACCCTGATC
TCGACGATTGCACGTGTCCCGCATGGTAAATCTCTGCTGGTTGGTGGCTACA
CGCGTGATGCAAACACGGACACGGTCCAAAGCATCCCGTTCCTGGGTAAGC
TGCCGCTGATTGGCTCGTTGTTTCGCTACAGCAGCAAAAACAAGTCTAATGT
CGTCCGTGTCTTTATGATTGAGCCGAAAGAAATCGTTGACCCGCTGACCCCG
GATGCCAGCGAGAGCGTTAACAACATTCTGAAACAGTCCGGTGCGTGGAGC
GGTGACGATAAGCTGCAAAAGTGGGTTCGTGTGTATTTGGACCGTGGTCAG
GAGGCCATTAAGTAACTTGGGCACGCGTCCATGAAAGACAGGACCCACTAG
ATGTCCAGCAACAAAACCGAAAAACCGACTAAGAAACGTCTGGAGGATAG
CGCAAAGAAAGGTCAGAGCTTCAAGAGCAAGGACCTGATTATCGCGTGCCT |

FIG. 24 (cont)

| SEQ ID NO: | Name | Sequence |
|---|---|---|
| | | GACCCTGGGTGGTATCGCTTATTTGGTGAGCTACGGCAGCTTCAATGAGTTT ATGGGTATCATTAAGATTATCATCGCTGATAACTTTGATCAGTCGATGGCAG ATTATAGCCTGGCCGTGTTTGGTATTGGCCTGAAATACCTGATTCCGTTCAT GCTGCTGTGTTTGGTTTGTTCCGCACTGCCGGCACTGCTGCAAGCGGGCTTC GTTCTGGCAACCGAGGCCCTGAAGCCGAATCTGTCCGCCCTGAACCCGGTT GAAGGCGCGAAGAAACTGTTTTCCATGCGCACCGTCAAAGACACGGTCAAG ACGCTGCTGTATCTGTCGAGCTTTGTGGTTGCGGCAATCATTTGCTGGAAAA AGTATAAAGTCGAGATTTTCAGCCAACTGAACGGTAATATCGTGGGTATTG CGGTTATCTGGCGTGAATTGCTGCTGGCGTTGGTTCTGACCTGTCTGGCGTG CGCGCTGATCGTGCTGTTGCTGGATGCTATTGCCGAGTACTTTCTGACCATG AAAGATATGAAGATGGACAAAGAAGAAGTTAAACGCGAGATGAAAGAGCA GGAGGGTAACCCGGAGGTGAAGTCTAAACGTCGTGAAGTCCACATGGAAAT CCTGAGCGAACAAGTCAAGTCTGACATTGAAAATAGCCGTCTGATTGTGGC AAACCCTACGCATATTACCATCGGCATCTACTTCAAACCGGAACTGATGCCG ATTCCAATGATTAGCGTCTATGAAACCAATCAACGCGCGCTGGCGGTCCGT GCGTACGCCGAGAAAGTGGGTGTTCCGGTTATTGTAGACATCAAGCTGGCG CGCAGCCTGTTCAAAACGCACCGTCGTTACGACCTGGTGAGCCTGGAGGAG ATCGACGAGGTTTTGCGCCTGCTGGTTTGGTTGGAAGAGGTCGAAAACGCA GGCAAGGATGTGATCCAACCGCAGGAGAATGAAGTGCGTCATTAACTGCAG GTTTAAACTACTTGGGCACGCGTCCATTAATTAGGATCAATAGCATGATTCC GGGCAGCACCTCCGGTATTTCCTTTAGCCGTATCCTGAGCCGTCAGACCTCC CACCAGGATGCAACCCAGCATACCGACGCACAACAAGCGGAAATTCAACA AGCGGCGGAAGATAGCTCGCCGGGTGCGGAGGTTCAGAAATTCGTCCAGAG CACGGACGAGATGTCTGCTGCGTTGGCGCAGTTCCGCAATCGCCGTGACTAT GAGAAAAAGAGCAGCAATTTGTCTAACTCCTTCGAGCGCGTTCTGGAGGAC GAGGCACTGCCGAAAGCGAAGCAGATTCTGAAACTGATCAGCGTGCATGGC GGTGCGTTGGAGGATTTCCTGCGTCAGGCGCGCAGCCTGTTCCCGGACCCA AGCGATCTGGTGCTGGTTCTGCGCGAGCTGTTGCGTCGTAAGGACCTGGAG GAGATCGTGCGTAAGAAGCTGGAGAGCCTGCTGAAGCACGTGGAGGAACA AACCGACCCGAAAACCCTGAAGGCCGGTATTAACTGCGCGCTGAAGGCGCG TCTGTTTGGCAAGACGCTGTCTCTGAAACCTGGTCTGCTGCGTGCCAGCTAC CGCCAGTTCATCCAAAGCGAAAGCCACGAAGTCGAGATTTACAGCGATTGG ATCGCCAGCTACGGTTATCAGCGTCGCCTGGTTGTTCTGGATTTCATTGAAG GCAGCCTGCTGACTGACATCGATGCTAACGATGCAAGCTGCTCCCGTCTGG AGTTTGGCCAACTGCTGCGCCGTCTGACCCAGCTGAAAATGTTGCGTAGCGC CGACCTGCTGTTTGTCTCGACGTTGCTGTCTTACAGCTTCACGAAAGCATTT AACGCTGAGGAGAGCAGCTGGCTGTTGCTGATGCTGTCTTTGCTGCAACAG CCGCACGAAGTGGATAGCCTGCTGGCGGACATTATCGGTCTGAATGCGCTG CTGTTGTCCCACAAAGAGCACGCCAGCTTCCTGCAAATCTTCTATCAGGTCT GTAAGGCAATCCCGTCTAGCCTGTTTTATGAAGAGTACTGGCAAGAAGAAC TGCTGATGGCACTGCGCTCCATGACGGACATTGCTTACAAACACGAAATGG CCGAACAACGTCGTACCATCGAAAAGCTGTCCTAAGTTTAAACCTTGGGCA CGCGTCCATGAAAGACAGGACCCACTAGATGAGCTTGCGCGTACGCCAAAT TGACCGCCGTGAATGGCTGCTGGCCCAGACTGCGACCGAATGTCAGCGTCA CGGTCGTGAGGCCACCCTGGAGTATCCGACCCGTCAGGGTATGTGGGTCCG CCTGTCTGATGCCGAAAAACGCTGGTCTGCGTGGATCAAACCGGGTGATTG GTTGGAACACGTTAGCCCAGCACTGGCGGGTGCCGCGGTCAGCGCAGGCGC GGAGCACCTGGTGGTTCCGTGGCTGGCGGCAACCGAACGCCCGTTCGAGCT GCCGGTCCCGCACTTGAGCTGCCGTCGTCTGTGCGTGGAGAACCCGGTTCCG GGTTCCGCACTGCCTGAGGGCAAGCTGCTGCACATCATGTCGGATCGTGGT GGCCTGTGGTTTGAGCATCTGCCGGAGCTGCCGGCTGTTGGCGGTGGCCGTC CGAAGATGCTGCGTTGGCCGCTGCGTTTCGTTATTGGCAGCAGCGACACCCA GCGCAGCCTGCTGGGTCGTATCGGTATCGGTGATGTTCTGCTGATCCGCACC AGCCGTGCTGAGGTTTACTGTTACGCGAAGAAACTGGGCCACTTTAATCGTG TGGAAGGTGGCATTATTGTCGAAACGCTGGACATTCAACATATCGAGGAGG AGAACAACACGACGGAAACGGCGGAAACCCTGCCGGGTCTGAATCAACTG |

FIG. 24 (cont)

| SEQ ID NO: | Name | Sequence |
|---|---|---|
| | | CCGGTGAAGCTGGAGTTCGTTCTGTATCGTAAAAACGTGACGTTGGCCGAA CTGGAAGCAATGGGTCAGCAACAACTGCTGTCCTTGCCAACCAATGCGGAA CTGAACGTCGAAATCATGGCGAATGGCGTGCTGCTGGGTAACGGCGAACTG GTGCAGATGAATGACACCCTGGGTGTCGAGATTCATGAGTGGTTGTCCGAG AGCGGTAATGGCGAGTAGAGATCTCTTGGGCACGCGTCCATTAAAAAGGAC CAATTAAGCATGCACTCTCTGACTCGTATCAAGGTCCTGCAACGTCGTTGTA CCGTGTTCCATTCTCAGTGCGAGTCCATTCTGTTGCGTTATCAGGACGAAGA TCGCGGCTTGCAGGCGGAGGAGGAGGCCATCCTGGAACAGATCGCAGGTCT GAAACTGCTGTTGGACACCCTGCGTGCTGAAAATCGTCAACTGAGCCGTGA AGAAATCTATACGCTGCTGCGCAAACAGAGCATTGTTCGTCGCCAGATTAA GGATCTGGAGCTGCAAATCATTCAGATTCAAGAAAAGCGTAGCGAGCTGGA AAAGAAACGTGAGGAATTTCAAAAGAAAAGCAAATACTGGCTGCGTAAAG AAGGTAACTACCAGCGCTGGATTATCCGTCAAAAACGCTTCTACATTCAAC GTGAGATCCAGCAAGAGGAGGCGGAGAGCGAAGAGATCATTTAACTTGGG CACGCGTCCATGAAAGACAGGACCCACTAGATGTTCTATGCATTGTATTTTG AGATCCACCATCTGGTGGCGTCCGCGGCTCTGGGTTTTGCGCGTGTTGCTCC GATCTTTTTCTTTCTGCCGTTCCTGAATAGCGGTGTCCTGAGCGGTGCTCCGC GCAACGCGATCATCATTCTGGTGGCGCTGGGTGTATGGCCGCACGCCCTGA ATGAGGCGCCACCGTTTCTGTCTGTGGCAATGATTCCGCTGGTCCTGCAAGA GGCAGCCGTGGGTGTTATGCTGGGTTGCCTGTTGTCCTGGCCGTTTTGGGTT ATGCACGCGTTGGGCTGTATCATTGATAACCAACGCGGTGCAACCCTGTCCA GCAGCATTGATCCTGCGAATGGCATCGACACCAGCGAGATGGCCAATTTCC TGAACATGTTCGCGGCTGTCGTGTATTTGCAGAACGGTGGCTTGGTCACGAT GGTGGACGTGCTGAATAAGTCTTACCAGCTGTGTGATCCGATGAACGAGTG TACGCCGAGCCTGCCTCCGTTGCTGACCTTCATTAATCAAGTGGCCCAGAAC GCACTGGTGCTGGCGTCCCCGGTCGTTCTGGTTCTGCTGCTGTCGGAAGTTT TCCTGGGCCTGCTGTCTCGTTTTGCACCGCAAATGAACGCGTTCGCCATTAG CCTGACTGTTAAAAGCGGTATTGCGGTTTTGATCATGCTGCTGTATTTCAGC CCGGTCCTGCCGGACAATGTTCTGCGTCTGAGCTTTCAGGCGACCGGCCTGA GCAGCTGGTTCTACGAACGTGGCGCAACGCATGTGCTGGAATAAGGATCCG GCATCAAATAAAACGAAAGGCTCAGTCGAAAGACTGGGCCTTTCGTTTTAT CTGTTGTTTGTCGGTGAACGCTCTCCTGAGTAGGACAAATCCGCCGCCCTAG AACTAGTccataagaatGCGGCCGC |

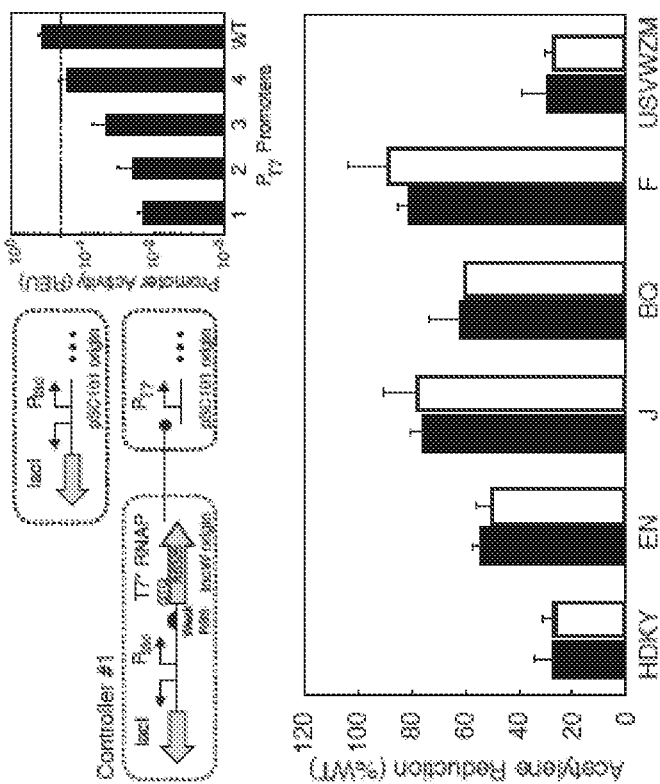
FIG. 28B
FIG. 28A
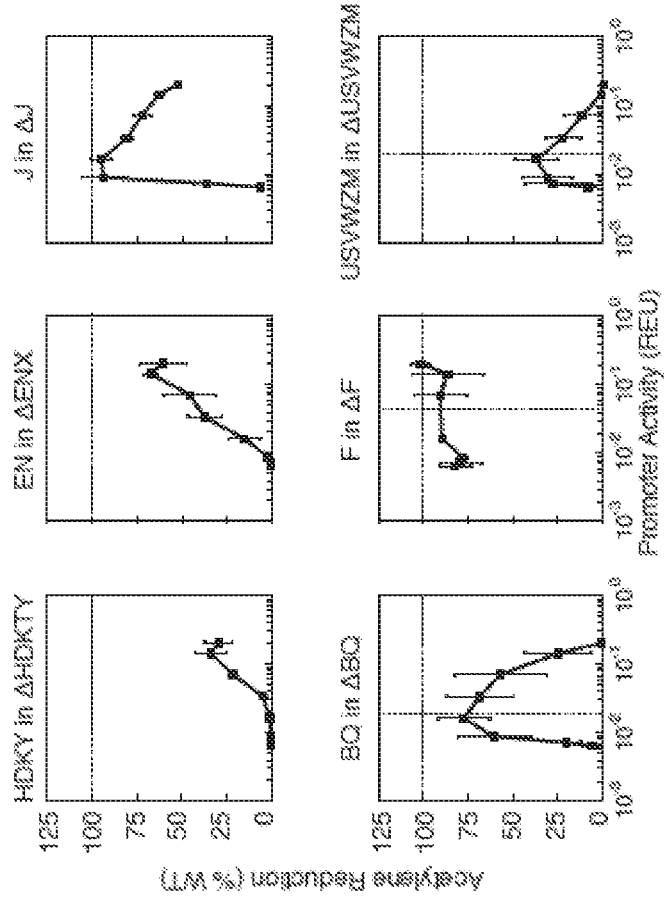
FIG. 28C

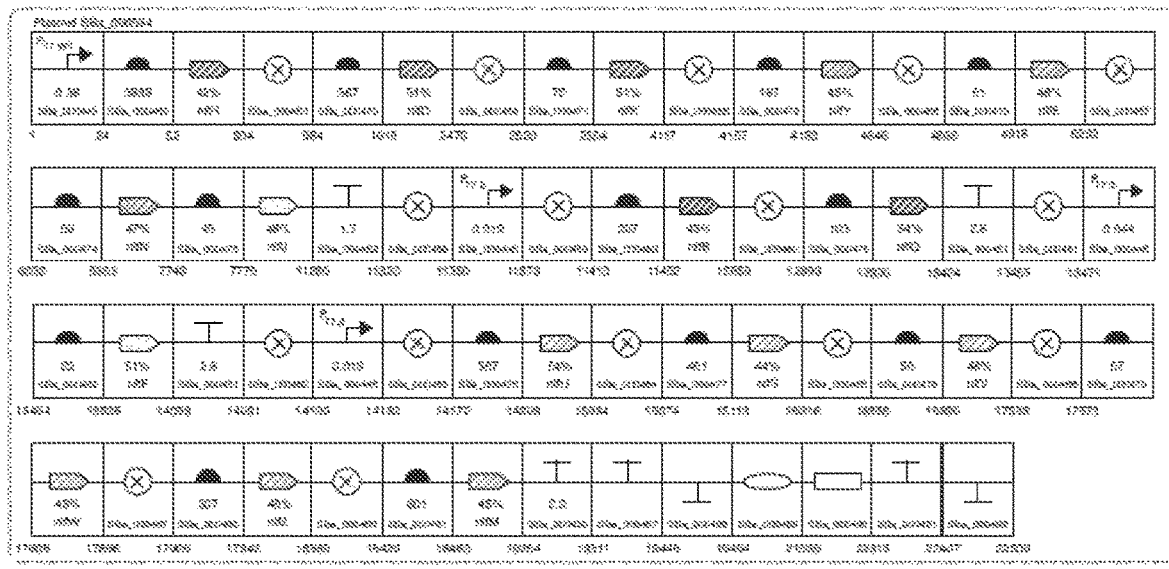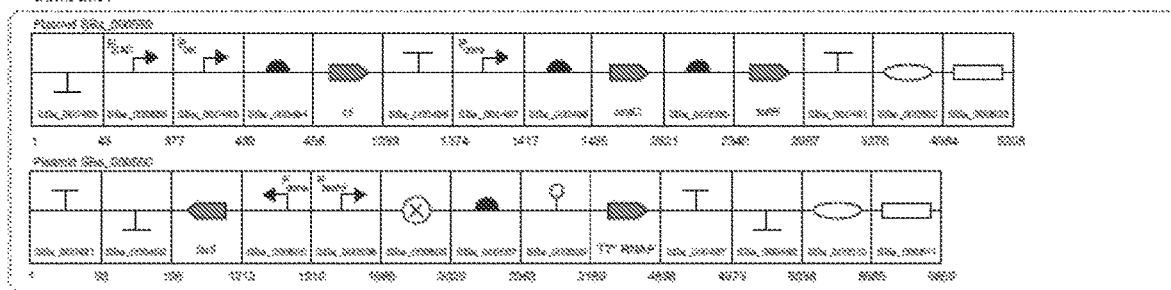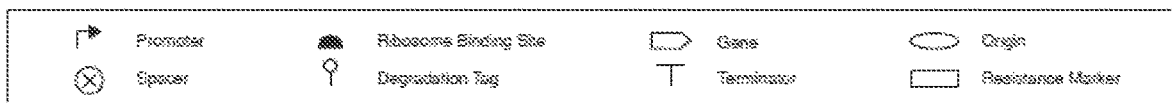
FIG. 29

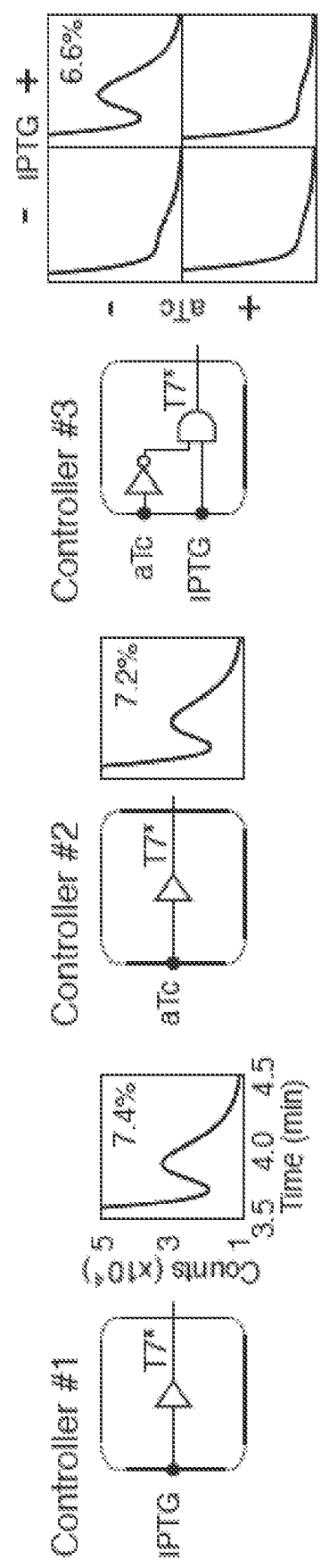
FIG. 30A
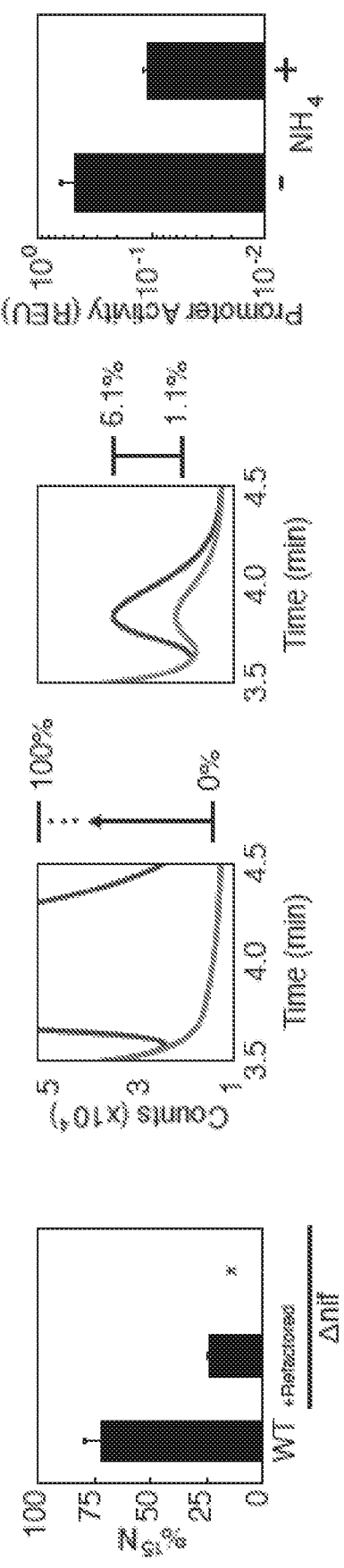
FIG. 30B
FIG. 30C
FIG. 30D

FIG. 32

| Name | Genotype | Note | Parental Strain | Allelic Exchange Plasmid[4] | DNA sequence of the deletion region[5] |
|---|---|---|---|---|---|
| NF8 | ΔnifJ, Km | operon deletion | M5aL | pNif16 | gcaggagaactaaaggcccgGCATGC<br>(Km cassette)GCATGCaagcgcccatggcccggca |
| UC12 | ΔnifHDK | in-frame deletion | M5aL | pRHB296 | cataaacaggcacggctggtGGTACCccatcaggtgcccgcgtca |
| NF9 | ΔnifHDKTY | operon deletion | M5aL | pNif9 | atggccccggcaggcgcaatGCATGCgacgctcttccccacgttac |
| UC14 | ΔnifENX | operon deletion | M5aL | pRHB294 | gacgctcttccccacgttacGCATGCgatccggacccgcgccgcta |
| UC15 | ΔnifENX | operon deletion | M5aL | pRHB295 | ctcttccccacgttacgctcGCATGCgatccggacccgcgccgcta |
| NF10 | ΔnifUSVWZM | operon deletion[1] | M5aL | pNif10 | cggacccgcgccgctagccgGCATGCatctttggcagcagagccag |
| NF11 | ΔnifUSVWZM | operon deletion | M5aL | pNif11 | cggacccgcgccgctagccgGCATGCagcctcggcggctacccgtt |
| NF12 | ΔnifF | operon deletion[2] | M5aL | pNif12 | actggttatcctgatccagcGCATGCctttgcactaccgcggccca |
| NF13 | ΔnifF | operon deletion | M5aL | pNif13 | ccgttaacgcctacagcacgGCATGCctttgcactaccgcggccca |
| NF14 | ΔnifBQ | operon deletion | M5aL | pNif14 | attcagggacgcgggttgcc------atgtgattatgcgacgtctt |
| NF24 | ΔnifJ,HDKTY, ENX | operon deletion[3] | M5aL | pNif32 | gtcaaacaccagaatattgaGAGCTCtgtcgtttctgtgacaaagc |
| NF25 | ΔnifUSVWZM,F,BQ | operon deletion | NF14 | pNif51 | cggacccgcgccgctagccgGCATGCctttgcactaccgcggccca |
| NF26 | ΔnifJ,HDKTY,ENX, USVWZM,F,LA,BQ | whole nif deletion[3] | NF24 | pNif54 | gtcaaacaccagaatattgaCTCGAGatgtgattatgcgacgtctt |

1) 83bp of *nifM* 3' retained
2) 82bp of *nifF* 3' retained
3) 500bp of *nifJ* 3' retained
4) The backbone for all allelic exchange plasmids is pDS132(1).
5) The bold region shows the restriction site sequence that replaces the deletion region. The 20 nucleotides flanking each site of the deletion region are shown.

*FIG. 35*

| Table: DNA sequence errors in *nif* cluster sequence X13303.1 | | | |
|---|---|---|---|
| Location | X13303.1 | This Study | Impact |
| 5187 | a | g | NifD K39E |
| 5193 | a | g | NifD K41E |
| 5332 | ct | tc | NifD A87V |
| 5359 | a | g | NifD E96G |
| 6137 | c | g | NifD I355M |
| 6140 | a | c | silent |
| 6749 | ga | ag | NifK R57Q |
| 7371 | t | c | silent |
| 7371 | t | c | silent |
| 8168 | cgg | ggc | *nifT* 5' UTR |
| 8919 | c | t | NifY P170L |
| 9341 | - | insert t | *nifE* 5' UTR |
| 9498 | cg | gc | NifE A35G |
| 9697 | ac | ct | silent |
| 9891 | c | t | NifE P166L |
| 12541 | ca | ac | NifX Q131T |
| 12770 | t | c | *nifU* 5' UTR |
| 13646 | gc | cg | *nifS* 5' UTR |
| 13999 | a | c | NifS M110L |
| 14008 | g | c | NifS E113Q |
| 14037 | a | g | silent |
| 14041 | g | a | NifS G124S |
| 14539 | gc | cg | NifS A290R |
| 15657 | tc | ct | NifV S257L |
| 15770 | gc | cg | NifV H295D |
| 16739 | g | a | silent |
| 16814 | c | t | silent |
| 22050 | g | a | NifB V141M |
| 22309 | g | a | NifB G227D |

FIG. 38

| Table. DNA sequences of synthetic parts | | |
|---|---|---|
| Part Number | Part Type | Sequence |
| SBa_000443 | T7 Promoter WT | taatacgactcactatagggaga |
| SBa_000444 | T7 Promoter 1 | taatacgactcactacaggcaga |
| SBa_000445 | T7 Promoter 2 | taatacgactcactagaggaga |
| SBa_000446 | T7 Promoter 3 | taatacgactcactaatgggaga |
| SBa_000447 | T7 Promoter 4 | taatacgactcactattgggaga |
| SBa_000450 | WT T7 Terminator | tagcataaccccttgggcctctaaacgggtcttgaggggttttttgt |
| SBa_000451 | T7 Terminator | tacatatcgggggggtaggggttttttgt |
| SBa_000452 | T7 Terminator | tactctaaccccatcggccgtcttaggggttttttgt |
| SBa_000453 | Insulator | gcgtgcgtacaccttaatcaccgcttcatgctaaggtcctggctgcatgc |
| SBa_000454 | Insulator | caaacaccccatgtcgatactgaacgaatcgacgcacactcccttccttg |
| SBa_000455 | Insulator | cctgattgtatccgcatctgatgctaccgtggttgagtta |
| SBa_000456 | Insulator | cattttttgccttgcgacagacctcctacttagattgccac |
| SBa_000457 | Insulator | tgtcacgctaggaggcaattctataagaatgcacactgca |
| SBa_000458 | Insulator | ccgtggttgagtcagcgtcgagcacgcggc |
| SBa_000459 | Insulator | cgcgacttccagagaagaagactactgacttgagcgttcc |
| SBa_000460 | Insulator | actacgagatttgaggtaaaccaaataagcacgtagtggc |
| SBa_000461 | Insulator | gtctgtagcacgtgcatc |
| SBa_000462 | Insulator | ggtcattacaacggttat |
| SBa_000463 | Insulator | aacatagcgttccatgagggctagaattacctaccggcct |
| SBa_000464 | Insulator | cattgtaatagccaccaaaagagtgatgatagtcatggt |
| SBa_000465 | Insulator | gagttactggccctgatttctccgcttctaataccgcaca |
| SBa_000466 | Insulator | gactcaacacgctagggacgtgaagtcgattccttcgatg |
| SBa_000467 | Insulator | tcgagaaacaaggcagttccgggctgaaagtagcgccggg |
| SBa_000468 | Insulator | acgccacgcgtagtgagacatacacgttcgttgggttcac |
| SBa_000508 | Insulator | tgcagttttattctctcgcagcactgtaataggcactaa |
| SBa_000475 | Synthetic RBS | ttaaagaggagaaattaagcATGaaaactatggacggtaacgctgcggctgcatggattagcta cgcctttaccgaagtggctgcgatctaccccgattacgccgagcacc |
| SBa_000469 | Synthetic RBS | tactagagaaataaaactaactaaggaggataaatATGaccatgcgtcagtgcgcgatttatg gcaaaggtggtattggcaaaagcacgacgacccagaacttggtggcggcctggccgagatg |
| SBa_000470 | Synthetic RBS | gcgtgcgtacaccttaatcaccgcttcatgctaaggtcctggctgcatgcaaaattcataaca ttatataggaggaggcatggATGatgactaatgctactggcgaacgtaacctggcactgattca agaagtactggaagtgttcccggaaaccgcgcgcaaagagcgcgt |
| SBa_000471 | Synthetic RBS | caaacaccccatgtcgatactgaacgaatcgacgcacactcccttccttgaatatataactct caaaatttaggcgagguaatATGtctcaaactatcgataaaatcaactcttgttaccgctgtt cgagcaggacgaatatcaggaactgttccgtaacaaacgtcagtg |
| SBa_000472 | Synthetic RBS | cctgattgtatccgcatctgatgctaccgtggttgagttacaataccaaaccggaggtacct tttaccaATGtctgacaatgatacccttgttttggcgcatgctggcgctgtttcagtcgctgccggattt gcagccggctcaaatcgtcgattggctg |
| SBa_000473 | Synthetic RBS | cattttttgccttgcgacagacctcctacttagattgccacaataattaaatatacactggagt tattacaaATGaagggtaacgagattcttgctctgctggacgaaccggcctgtgaacacaacca taaacagaaatccggctgtagcgccccaaagccg |
| SBa_000474 | Synthetic RBS | tgtcacgctaggaggcaattctataagaatgcacactgcaattaatactaccaaccggaggag agttaattATGgcagacattttccgcactgataagccgttggctgtgtcgccgatcaagaccggc cagccgctgggtgcgatcctggcgtccctgggt |
| SBa_000476 | Synthetic RBS | aacatagcgttccatgagggctagaattacctaccggccttagaattgacaaataaatcagcg aggaggtaatttATGtggaactacagcgagaaagtcaaggaccatttcttcaatccgcgcaac gcgcgtgttgtggataacgcaaatgcgtgggcgacgtc |
| SBa_000477 | Synthetic RBS | cattgtaatagccaccaaaagagtgatgatagtcatggtgatacccgtagccatcgcaaat cgaaggaggattttcATGaaacaagtgtacctggacaacaacgcgaccaccgcctggacccga tggttctggaagcgatgatgccgtttctcacggatttctat |
| SBa_000478 | Synthetic RBS | gagttactggccctgatttctccgcttctaataccgcacagtgactaggagcttaactggcaat aagaaaaccatATGgagcgctcttgatcaacgatactaccctgcgtgatggcgaacaatctccg ggcgtagcgtttcgtacctccgagaaagttgccatc |
| SBa_000479 | Synthetic RBS | gactcaacacgctagggacgtgaagtcgattccttcgatgcagaaggcgagaactagattaag ggtaattataagATGgagtggttttaccagattccgggtgtagacgaattgcgcagcgctgaatc cttctttcagttcttcgcggttccataccagccgaa |
| SBa_000480 | Synthetic RBS | tcgagaaacaaggcagttccgggctgaaagtagcgcgggaaaagtcggtattaaaacgct aggaggtgttaggATGcgcccgaaattcaccttctctgaagaggtccgcgtagttcgcgcgattc gtaatgatggcaccgtgcgggttttgcgccaggtgcg |
| SBa_000481 | Synthetic RBS | acgccacgcgtagtgagacatacacgttcgttgggttcactcagagactgaagttactacaacg gaggctataaATGaatccgtggcagcgtttgcccgtcaacgccttgctcgcagccgctggaac cgtgatccgctgctctcgacccagccgatacccca |
| SBa_000482 | Synthetic RBS | gacaagggttcaattaaaaggaggttttactaaATGgcgaacatcggcatcttctttggtacg gataccggcaaaacccgcaagattgcgaagatgattcacaaacagctgggcgagctggcc |
| SBa_000483 | Synthetic RBS | cgcgacttccagagaagaagactactgacttgagcgttccaacatgttgtaatcaataatcaat catgggaggctaaaATGacctcttgttcgtcgttttctggcggtaaagcgtgcctccggccg atgactccgcgctgactccgctggtggccgacaaggcagct |
| SBa_000475 | Synthetic RBS | aactacgagatttgaggtaaaccaaataagcacgtagtggcataaagggagaaattaagcAT Gccgccattggactggttcgctcgttttgtggttactctatcaccgcgcaaaggcagctttccg cttcgtatgggcttgtcgccgcgt |
| SBa_000561 | P$_{tac}$ Promoter and | caattcgcgctaacttacattaattgcgttgcgctcactgcccgctttccagtcgggaaacctg |

FIG. 38 (cont)

| | | |
|---|---|---|
| | lacI cassette | tcgtgccagctgcattaatgaatcggccaacgcgcggggagaggcggtttgcgtattgggcgcc<br>agggtggttttcttttcaccagtgagacgggcaacagctgattgcccttcaccgcctggccct<br>gagagagttgcagcaagcggtccacgctggtttgcccagcaggcgaaaatcctgtttgatggt<br>ggttgacggcgggatataacatgagctgtcttcggtatcgtcgtatcccactaccgagatatcc<br>gcaccaacgcgcagcccggactcggtaatggcgcgcattgcgcccagcgccatctgatcgttgg<br>caaccagcatcgcagtgggaacgatgccctcattcagcatttgcatggtttgttgaaaaccgga<br>catggcactccagtcgccttcccgttccgctatcggctgaatttgattgcgagtgagatattta<br>tgccagccagccagacgcagacgcgccgagacagaacttaatgggcccgctaacagcgcgattt<br>gctggtgacccaatgcgaccagatgctccacgcccagtcgcgtaccgtcttcatgggagaaaat<br>aatactgttgatgggtgtctggtcagagacatcaagaaataacgccggaacattagtgcaggca<br>gcttccacagcaatggcatcctgtcatccagcggatagttaatgatcagcccactgacgcgtt<br>gcgcgagaagattgtgcaccgccgctttacaggcttcgacgccgcttcgttctaccatcgacac<br>caccacgctggcacccagttgatcggcgcgagatttaatcgccgcgacaatttgcgacggcgcg<br>tgcagggccagactggaggtggcaacgccaatcagcaacgactgtttgcccgccagttgttgtg<br>ccacgcggttgggaatgtaattcagctccgccatcgccgcttccacttttcccgcgttttcgc<br>agaaacgtggctggcctggttcaccacgcgggaaacggtctgataagagacaccggcatactct<br>gcgacatcgtataacgttactggtttcacattcaccaccctgaattgactctcttccgggcgct<br>atcatgccataccgcgaaaggttttgcaccattcgatggtgtcaacgtaaatgcatgccgcttc<br>gccttcgcgcgcgaattggccgccatgccggcgataatggcctgcttctcgccgaaacgtttgg<br>tggcgggaccagtgacgaaggcttgagcgagggcgtgcaagattccgaataccgcaagcgacag<br>gccgatcatcgtcgcgctccagcgaaagcggtcctcgccgaaaatgacccagagcgctgccggc<br>acctgtcctacgagttgcatgataaagaagacagtcataagtgcggcgacgatagtcatgcccc<br>gcgcccaccggaaggagctgactgggttgaaggctctcaagggcatcggcggagcttatcgact<br>gcacggtgcaccaatgcttctggcgtcaggcagccatcggaagctgtggtatggctgtgcaggt<br>cgtaaatcactgcataattcgtgtcgctcaaggcgcactcccgttctggataatgttttttgcg<br>ccgacatcataacggttctggcaaatattctgaaatgagctgttgacaattaatcatcggctcg<br>tataatgtgtggaattgtgagcggataacaatt |
| SBa_000562 | P<sub>tet</sub> Promoter and tetR cassette | ttattaggacccactttcacatttaagttgtttttctaatccgcatatgatcaattcaaggccg<br>aataagaaggctggctctgcaccttggtgatcaaataattcgataagctgtcgtaataatggcg<br>gcatactatcagtagtaggtgtttccctttcttcttagcgacttgatgctcttgatcttccaa<br>tacgcaacctaaagtaaaatgccccacagcgctgagtgcatataatgcattctctcagtgaaaa<br>ccttgttggcataaaaaggctaattgattttcgagagtttcatactgtttttctgtaggccgtg<br>tacctaaatgtacttttgctcctcatcgcgatgacttagtaaagcacatctaaaactttttagcgtt<br>attacgtaaaaaatcttgccagctttcccccttctaaagggcaaaagtgagtatggtgcctatct<br>aacatctcaatggctaaggcgtcgagcaaagcccgcttatttttttacatgccaatacaatgtag<br>gctgctctacacctagcttctgggcgagtttacggggttgttaaaccttcgattccgacctcatt<br>aagcagctctaatgcgctgttaatcacttttatctaatcctggacatcgaggcctttcct<br>gtgtgagctagcactgtacctaggactgagctagccgtcaattttttccctatcagtgatagag<br>attgacatccctatcagtgatagatataatgagcac |
| SBa_000484 | mRFP Fluorescent Reporter | atgtccagattagataaaagtaaagttgcgagctctgaagacgttatcaaagagttcatgcgtt<br>tcaaagttcgtatggaaggttccgttaacgctcacgagttcgaaatcgaaggtgaaggtgaagg<br>tcgtccgtacgaaggtacccagaccgctaaactgaaagttaccaaaggtggtccgctgccgttc<br>gcttgggacatcctgtcccgcagttccagtacggttccaaagcttacgttaaacaccgggctg<br>acatcccggactacctgaaactgtccttccccggaaggttcaaatgggaacgtgttatgaactt<br>cgaagacggtggtgttgttaccgttacccaggactcctccctgcaagacggtgagttcatctac<br>aaagttaaactgcgtggtaccaacttcccgtccgacggtccggttatgcagaaaaaaaccatgg<br>gttgggaagcttccaccgaacgtatgtacccggaagacggtgctctgaaaggtgaaatcaaaat<br>gcgtctgaaactgaaagacggtggtcactacgacgctgaagttaaaaccacctacatggctaaa<br>aaaccggttcagctgccgggtgcttacaaaaccgacatcaaactggacatcacctcccacaacg<br>aagactacaccatcgttgaacagtacgaacgtgctgaaggtcgtcactccaccggtgcttaa |
| SBa_000514 | T7* RNAP | atgaacacgattaacatcgctaagaacgacttctctgacatcgaactggctgctatcccgttca<br>acactctggctgaccattacggtgagcgtttagctcgcgaacagttggcccttgagcatgagtc<br>ttacgagatgggtgaagcacgcttccgcaagatgtttgagcgtcaacttaaagctggtgaggtt<br>gcggataacgctgccgcaagcctctcatcactacctactcctaagatgattgcacgcatca<br>acgactggtttgaggaagtgaaagctaagcgcggcaagcgcccgacagccttccagttcctgca<br>agaaatcaagccggaagccgtagcgtacatcaccattaagaccactctggcttgcctaaccagt<br>gctgacaatacaaccgttcaggctgtagcaagcgcaatcggtcgggccattgaggacgaggctc<br>gcttcggtcgtatccgtgaccttgaagctcaagcacttcaagaaaacgctgaggaacaactcaa<br>caagcgcgtagggcacgtctacaagaaagcatttatgcaagttgtcgaggctgacatgctctct<br>aagggtctactcggtggcgaggcgtggtcttcgtggcataagaagactctattcatgtaggag<br>tacgctgcatcgagatgctcattgagtcaaccggaatggttagcttacaccgccaaaatgctgg<br>cgtagtaggtcaagctctgagactcgcacctgaatcgtgaggctatcgcaacc<br>cgtgcaggtcgcgctggctggcatctctccgatgttccaaccttgcgtagttcctcctaagccgt<br>ggactggcattactggtggtggctattgggctaacggtcgtcgtcctctggcgctggtgcgtac<br>tcacagtaagaaagcactgatgcgctacgaagacgtttacatgcctgaggtgtacaaagcgatt<br>aacattgcgcaaaaccgcatggaaaatcaacaagaaagttcctagcggtcgcaacgtaatca<br>ccaagtggaagcattgtccggtcgaggacatccctgcgattgagcgtgaagaactcccgatgaa<br>accggaagacatcgacatgaatcctgaggctctcaccgcgtgaaacgtgctgccgctgctgtg<br>taccgcaaggacaaggctcgcaagtctcgccgtatcagccttgagttcatgcttgagcaagcca<br>ataagtttgctaaccataaggccatctggttcccttacaacatggactggcgcggtcgtgttta<br>cgctgtgtcaatgttcaacccgcaaggtaacgatatgaccaaaggactgcttacgctggcgaaa<br>ggtaaaccaatcggtaaggaagttactactgctgaaaatccacggtgcaaactgtgcgggtg<br>tcgacaaggttcgttcctgagcgcatcaagttcattgaggaaaaccacgagaacatcatggc<br>ttgcgctaagtctccactggaacacttggtgggctgagcaagattctccgttctgcttcctt<br>gcgttctgctttgagtacgctggggtacagcaccacgcctgagctataactgctcccttccgc<br>tggcgtttgacgggtcttgctctggcatccagcacttctccgcgatgctccgagatgaggtagg<br>tggtcgcgcggttaacttgcttcctagtgaaaccgttcaggacatctacgggattgttgctaag<br>aaagtcaacgagattctacaagcagacgcaatcaatgggaccgcagtaacgaagtagttaccgtga<br>ccgatgagaacactggtgaaatctctgagaaagtcaaggctggccactaaggcactggctggtca<br>atgctggcttacggtgttactcgcagtgtgactaagagttcagtcatgacgctggcttacggg<br>tccaaagagttcggcttccgtcaacaagtgctggaagataccattcagccagctattgattccg |

FIG. 38 (cont)

| | | |
|---|---|---|
| | | gcaagggtctgatgttcactcagccgaatcaggcctgctggatacatggctaagctgatttggga<br>atctgtgagcgtgacggtggtagctgcggttgaagcaatgaactggcttaagtctgctgctaag<br>ctgctggctgctgaggtcaaagataagaagactggagagattcttcgcaagcgttgcgctgtgc<br>attgggtaactcctgatggtttccctgtgtggcaggaatacaagaagcctattcagacgcgctt<br>gaacctgatgttcctcggtcagttccgcttacagcctaccattaacaccaacaaagatagcgag<br>attgatgcacacaaacaggagtctggtatcgctcctaactttgtacacagccaagacggtagcc<br>accttcgtaagactgtagtgtgggcacacgagaagtacggaatcgaatcttttgcactgattca<br>cgactccttcggtacgattccggctgacgctgcgaacctgttcaaagcagtgcgcgaaactatg<br>gttgacacatatgagtcttgtgatgtactggctgatttctacgaccagttcgctgaccagttgc<br>acgagtctcaattggacaaaatgccagcacttccggctaaaggtaacttgaacctccgtgacat<br>cttagagtcggacttcgcgttcgcgtaa |
| | Synthetic *nifJ* | atgaaaactatggacggtaacgctgcggctgcatggattagctacgcctttaccgaagtggctg<br>cgatctacccgattacgccgagcaccccgatggcggaaaatgtggacgaatgggctgcgcaggg<br>caagaagaacctcttcggccagccggtgcgcctgatggagatgcagtcggaagcgggtgcagca<br>ggtgctgtgcatggcgccttgcaagctggcgcactgacgaccacctacaccgcgtcgcagggcc<br>tgttgctgatgatcccaaacatgtacaaaatcgcgggtgaactgctgccgggtgtctttcatgt<br>tccggcacgcgcactggccaccaatagcctcaacatcttttggcgatcatcaggatgtaatggcg<br>gtgcgccaaacgggctgcgcgatgttggccgagaataacgtccagcaagttatggatttgtccg<br>cggtagcccacttggcagcgatcaaaggtcgcattccgttcgtgaacttcttcgatggctttcg<br>caccagccacgaaatccagaagatcgaggttctggaatatgaacagctggccaccttgttggat<br>cgtccggcccttggacagcttccgccgtaacgcccttcaccggaccaccccggtcatccgtggca<br>ccgcccagaacccggacatctacttccaggaacgtgaggccggtaaccgtttctatcaggcgct<br>cccggatattgtggaatcttacatgacccagatttctgccctgactggtcgcgagtatcacctg<br>tttaactacactggtgctgcggatgcggagcgcgtgatcatcgcgatgggctctgtctgtgaca<br>ccgtccaagaggtggttgacacgctgaatgcacgcgggtgagaaagttggtctgctctccgttca<br>tcttttccgcccgttttcgttagcgcacttcttcgcccaactgccgaaaactgtacagcgtatc<br>gcagtattggaccgtacgaagagccaggtgctcaagcagagccgctgtgcctcgatgtgaaga<br>atgcctttaccaccatgacgatgcccgttgattgtgggtggtcgctatgccttgggcggtaa<br>ggacgtgttgccgaacgatattgcggccgtgtttgataacctgaacaaaccgctgccgatggac<br>ggcttcacgctgggtatcgtggacgatgttaccttcacctctctcccgccagcgcagcagacce<br>tggcggtttctcacgacggcatcacggcatgtaagttttgggcatgggctccgacggcacggt<br>tggtgcgaacaagtccgcgatcaagattatcggcgacaaaacgccactgtatgcgcaagcgtac<br>ttttcctacgactcgaagaagagcggtggtattaccgtcagccatctgcgttttggtgatcgcc<br>cgatcaactccccgtatttgatccatcgcgcggatttcatctcgtgcagccagcaaagctatgt<br>tgaacgctacgatctgctggatggccttaaaccgggtggcaccttctgctgaactgctcctgg<br>agcgatgccgaactggagcaacatctgccggtcggtttcaaacgttatctggcacgcgagaata<br>tccacttctacactctcaacgctgtggacatcgcccgtgagcttggtttggttgggtggccgtttcaa<br>catgctgatgcaggctgccttcttcaaactggccgcgatcattgacccgcagactgctgcggac<br>tatctgaagcaggctgttgagaaaagctatggcagcaaaggtgcggcggtcatcgagatgaacc<br>agcgtgccatcgagcttggcatggccagcctgcaccaggtgacgatcccggcacattgggccac<br>cctggatgagccagcggccaggcgtccgcgatgatgccggactttatccgcgacatcctgcaa<br>ccgatgaaccgtcagtgcggcgaccagcttccggtgtcggcttttgtcggcatggaagatggca<br>cctttccgtccggcacggccgcatgggagaaacgtggcatcgcccttgaggtgccagtctggca<br>gccggaaggctgcacgcagtgcaaccagtgcgccttcatttgtccgcacgccgcgattcgtccg<br>gcgttgttgaatgcgaagagcatgatgctgccccggttggcctgctgagcaaaccggcacaag<br>gcgctaaagaatatcactatcatctggcgattagcccgctggactgctccggctgtggcaactg<br>cgttgacatttgtccagctcgtggcaaagcgttgaagatgcagtctctggatagccaacgccag<br>atggctccggtgtgggattatgcgctggcgctgaccccgaagtctaacccgtttcgtaaaacca<br>ccgtcaaaggctcgcagttcgaaaccccgctgctggagtttagcggtgcgtgcgctggttgtgg<br>cgaaacgccgtatgcgcgcctcattacccagctgttttggcgaccgcatgctgattgccaatgcc<br>accgctgttccagcatctggggcgcatctgcgccgagcatcccgtataccaccaatcatcgtg<br>gtcatggtccggcctgggcgaatagcctgtttgaggacaatgccgaatttggttttaggtatgat<br>gctgggcggtcaagctgtgctcaacagatcgcggacgatatgacggctgcgttagcgctcccg<br>gtttccgatgagctgagcgacgcgatgcgccagtggttggcgaaacaggacgagggtgaaggca<br>cgcgtgagcgtgcggaccgtctgagcgagcgcttagccgcggagaaagagggcgttccgctgtt<br>agagcagctgtggcaaaatcgtgattactttgtcgtcgcagccagtggattttcggcggtgac<br>ggctgggcctatgatattggcttcggtggcctggaccacgtcctcgcgtggtgattgaggatgtga<br>acattctggtatttgacaccgaagtctactcgaacaccggcggtcaaagcagcaaatcgacccc<br>ggtcgcggccatcgccaagttcgcggctcagggcaagcgcacccgcaagaaagacctgggtatg<br>atggcgatgagctacggcaacgtctatgtagcccaggtggcgatgggtgcggataaagatcaaa<br>ctctgcgcgccattgcggaagctgaagcgttggccaggcccgtcgctggtgattgcgtatgcggc<br>ctgcatcaatcatggcctgaaggccggtatgcgttgcagccaacgtgaggcgaagcgcgctgtt<br>gaggcgggctactgcacctgtggcgttatcacccgcagcgcgaagcggaagcgaagacgccgt<br>ttatgttagatagcgaagaaccggaagagtcgttccgtgactttctgttgggtgaggtgcgcta<br>cgcatccctgcacaagacccaccccgcacctcgccgatgcccttttcagccgtaccgaagaagat<br>gcgcgtgcgcgctttgcgcaataccgtcgcctggctggcgaagagtaa |
| | Synthetic *nifH* | atgaccatgcgtcagtcgcgatttatggcaaaggtggtattggcaaaagcacgacgacccaga<br>acttggtggcggccctggccgagatgggtaaaaaggttatgattgtgggttgcgacccgaaggc<br>cgacagcacgcgcctgattctgcacgcgaaagcacaaaaccagcattatggagatggctgccag<br>gttggtagcgtggaggatctggagctggaggacgttctgcaaattggttacggtgatgttcgtt<br>gcgcagagagcggtggtccggaaccaggtgtcggctgtgcgggtcgtggtgtgattaccgctat<br>caatttcctggaagaagagggtgcgtacgaagatgatctggatttcgttttctacgatgtgctg<br>ggtgatgtcgtgtgcggtggttttgcaatgccgattcgcgagaataaggcacaagaaatttaca<br>ttgtctgtagcggcgagatgatggcaatgtacgctgctaacaacatcagcaaggtattgttaa<br>atacgcaaaaagcggtaaggttcgcttgggtggtttgatttgcaacagccgtcagaccgaccgt<br>gaggacgaactgatcatcgccctggctgagaaactgggcacccaaatgatccacttcgtgccac<br>gcgataatattgttcaacgtgcagaaatccgccgtatgaccgtcattgagtatgaccggcatg<br>caagcaagcgaacgagtaccgcaccttggcacagaaaatcgtgaacaacaccatgaaggttgtt<br>ccgacgccgtgtacgatgacgagctggagagcctgctgatggagttcggcattatggaggagg<br>aggacaccagcattatcggtaagaccgcagcggaggagaatgcggcataa |
| | Synthetic *nifD* | atgatgactaatgctactggcgaacgtaacctggcactgattcaagaagtactggaagtgttcc |

FIG. 38 (cont)

| | | |
|---|---|---|
| | | cggaaaccgcgcgcaaagagcgccgtaaacacatgatggtttctgacccgGaaatgGaatctgt
gggtaaatgcatcatctctaatcgcaaatctcagccgggtgtcatgactgttcgtggctgtgcg
tacgcaggttctaaaggtgtcgtattcggcccgatcaaagatatggcgcatatctctcatggcc
cggTaggctgtggccagtactctcgcgcgggGacgtcgtaactactacacgggcgtttctggcgt
tgactctttcggcacgctgaacttcacctctgacttccaggaacgtgacatcgttttcggtggc
gataaaaagctgtccaaactgatcgaagaaatggaactgctgttcccgctgactaaaggcatta
ctatccaaagcgaatgtccggtgggtctgatcggtgatgacatcagcgcggtcgcaaacgcatc
ttccaaagccctggataagccggtgatcccggttcgttgcgagggcttccgcggcgtttctcag
tctctgggtcatcacatcgcaaacgatgttgtgcgtgactggattctgaacaaccgtgaaggtc
agcctttgaaaccacccttatgacgttgcgattattggcgactataacatcggcggcgacgc
ctgggcatcccgcatcctgctgcggaggagatgggtctgcgtgttgtcgcacagtggtctggcgat
ggcaccctggttgaaatggaaaacacccccgtttgttaaactgaacctggttcactgctaccgct
ccatgaactacattgcccgtcacatgaagaaaaacatcagatcccttggatggaatacaactt
cttcggtccgactaaaatcgcagaatccctgcgtaaaatcgccgatcagtttgatgataccatt
cgcgcgaacgctgaagcagtaattgcgcgctacgaaggccagatggcagcaatcattgctaagt
accgtccgcgcctggaagtcgtaaagtgctgctgtacatgggtggtctgcgtccacgtcatgt
gatcggtgcctacgaggacctgggcatggagatcatcgcagcgggttacgaatttgcacacaac
gacgactatgatcgtacgctgccagacctgaaagaaggtacgctgctgtttgacgacgccagct
cttatgaactggaagccttcgtgaaagcgctgaaaccagacctgatcggctccggcatcaagga
aaaatacattttccagaaaatgggcgtgccgttccgccagatgcactcctgggactactccggt
ccgtaccacggctacgacggtttcgctatcttcgctcgtgacatggatatgaccctgaataacc
cagcgtggaatgaactgaccgcaccgtggctgaaatctgcataa |
| | Synthetic *nifK* | atgtctcaaactatcgataaaatcaactcttgttaccgctgttcgagcaggacgaatatcagg
aactgttccgtaacaaacgtcagctggagaagcgcacgacgcacagcgcgtgcaggaagtgtt
cgcatggaccaccaccgcggaatacgaagctctgaacttccagcgcgaagccctgacggttgat
ccggcgaaagcgtgccagcctctgggtgcggttctgtgcagcctgggttttgccaacaccctgc
cgtatgtccacggttcccagggctgcgtagcctacttccgtacctatttcaaccgccactttaa
agaaccaatcgcgtgcgtgtccgacagcatgacggaggacggacggcagttttcggtggtaacaac
aacatgaacctgggcctgcaaaatgcttccgcactgtacaaaccggaaatcatcgcagtgtcta
ccacctgcatggcagaggttattggtgatgatctgcaagcatttattgccaacgcaaagaaaga
cggtttcgttgacagctctatcgcggttccgcacgctcataccccgtccttcatcggttctcac
gtaactggttgggacaacatgttcgaaggcttcgcaaaaacttttaccgcagactatcaaggcc
aaccgggtaaactgccgaagctgaacctggtgaccggcttgaaacctacctgggcaacttcg
tgtcctgaagcgcatgatggacagatggcggttccgtgttctctgctgtctgaccgtctgag
gttctggacactccagcggacggccactatcgcatgtattctggtgcaccactcagcaggaaa
tgaaagaggccccagacgcgattgacaccctgctgctgcaaccgtggcagctgctgaaaagcaa
gaaagttgttcaggaaatgtggaaccagccggcaacggaagttgcaatcccgctgggtctggca
gctactgacgaactgctgatgaccgtgtcccaactgagcggcaaaccaatcgcggatgctctga
ccctggaacgcggtcgcctggtggacatgatgctggacagccacacgtggctgcatggcaagaa
atttggcctgtacggtgaccggacttcgtaatgggcctgaaccgacccgtttcctgctggaactgggc
tgcgagccgactgttatcctgtctcacaacgctaacaaacgttggcagaaggccatgaacaaa
tgctggatgcgagcccatacgccgtgatagcgaagtgttcatcaactgcgacctgtggcattt
ccgctctctgatgtttacgcgtcagccggatttcatgatcggtaactcttacgcaaattcatc
cagcgtgacactctggccaaaggcaaagcgtttgaagtgccgctgattcgtctgggctttccgc
tgttcgaccgtcaccacctgcaccgccagacccacctgggggttacgaaggcgcgatgaacatcgt
aactactctggtaaacgcagtactggaaaagctggacagcgatacttcccagctgggcaaaacc
gactattcttcgatctggttcgttaa |
| | Synthetic *nifY* | atgtctgacaatgatacctgttttggcgcatgctggcgctgtttcagtcgctgccggatttgc
agccggctcaaatcgtcgattggctggcgcaggaatccggcgaaacccctgacgccggagcgcct
tgccaccctgacccaaccgcaactcgcggcgtcgttcccatccgcgacggcagtgatgagcccg
gctcgctggagccgcgttatgcttctctgcaaggcgccctcccagcccacttgcgcatcgtac
gtccggcgcagcgtacccccgcaactgctcgccgcgtttgcagccaagacggccttgttatcaa
tggtcatttcggccagggtcgtctgttcttcatttacgccttttgacgagcagggcggctggctg
tatgacttgcgccgctatccgagcgcaccgcaccagcaggaagcgaatgaggtgcgtgctcgtc
tgattgaagattgccagctgctgttctgccaggagattggcggtccggcagcagcgcgtctgat
ccgccaccgcatccatccgatgaaggcgcagccgggtactacgattcaggcgcagtgtgaagct
atcaacaccctgctggccggtcgctgccgccgtggctcgccaaacgtttgaaccgtgataacc
cgctggaagagcgtgtgttttaa |
| | Synthetic *nifE* | atgaagggtaacgagattcttgctctgctggacgaaccggcctgtgaacacaaccatcaaacaga
aatccggctgtagcgccccaaagccgggtgcgacggcggctggctgcgctttcgatggtgcgca
gatcaccctgctcccgattgcggacgttgcccacctcgtgcatgcgccaatcggttgcgcaggt
agctcttgggacaaccgtggcagcgcctccagcggtccgaccctgaatcgtttgggctttacca
ctgacttgaatgaacaagatgtgatcatgggtcgcggcgagcgtcgcctgttccacgctgtgcg
ccatattgtcaccgttaccacccagcggcagtattcatctacaatacgtgcgtgccggctatg
gaaggcgatgacctggaggccgtgtgtcaggcagcccagactgcgaccggcgtcccggtaatcg
caattgatgcggctggcttctacggttcgaagaacctgggcaacctccggcaggcgatgtcat
ggttaaacgcgtcattggccaactgagccagccgtggccggagagcaccctgtttgccccg
gagcaacgtcatgacattggcttgatcggtgagttcaacattgcgggcgagttttggcacattc
agccgctgcttgatgagctgggtatccgcgtttgggttcgctcagcggcgatggtcgtttcgc
cgagattcaaaccatgcaccgtgcccaggcgaacatgctggtgtgcagccgtgctctgatcaat
gttgcgcgtgctctggaacagcgctatggcaccccgtggtttgaagctcgttctatggtatcc
gcgcgaccagcgacgccctgcgccagttagcggcgctgctgggcgatgacgacctccgtcagcg
caccgaggcgctgatcgcgcgtgaagaacaggcggctgagctggccctgcaaccgtggcgtgaa
cagctgcgtggccgcaaggccctgctctacacgggtggtgtcaaaagctggtctgtggtgtccg
cgcttcaggatctgggtatgaccgtgttgcacgggcacgcgtaagagcacggaagaggataa
acagcgcatccgcgaattgatgggcgaagaggccgtgatgcttgaagaaggcaacgcacgtacc
ttattggatgtagtttatcgctatcaagcagacctgatgattgccggtggccgcaacatgtata
ccgcctacaaagcgcgcttgccgttcctggacatcaaccaggaacgcgagcacgcgtttgcggg
ctaccaaggcatcgtgaccttagcgcgccagctgtgccaaacgattaacagcccgatctggccg
cagactcattcccgcgcaccgtggcgctaa |
| | Synthetic *nifN* | atggcagacattttccgcactgataagccgttggctgtgtcgccgatcaagaccggccagccgc |

FIG. 38 (cont)

| | | |
|---|---|---|
| | | tgggtgcgatcctggcgtccctgggtatcgagcactcgattccgctggtacatggcgcgcaggg ctgttcggcttttgccaaggttttctttatccagcacttccacgatccggtcccgctgcaaagc acggcaatggacccgaccagcaccatcatgggcgctgatggtaacatcttcaccgcgctggaca ctctctgccaacgcaataacccgcaagcaattgtgctgctgagcaccggcctctccgaggcgca gggcagcgacatttcccgtgtagtgcgtcagttccgtgaagaatatccgcgtcataaaggcgtg gcgattctgactgttaacaccccggacttttacggtagcatggagaacggcttttccgctgtcc tggagtctgtgattgaacagtgggttccgccagcccacgtccggcgcagcgcaatcgtcgcgt caatcttttggtgagccatctctgtagcccaggcgatattgagtggctgcgccgttgcgtcgag gccttcggtctgcaaccgatcattctgccggatctggctcagagcatggacggccaccttgctc agggtgacttttcgccgctgacgcagggcgggcacgccgttgcgccaaatcgagcagatgggcca gagccttgctcttttgcgattggcgtcagcctgcaccgtgcgagcagcctgctggctccgcgt tgtcgtggcgaagtcatcgccttgccgcacctcatgaccttggaacgctgcgacgccttatcc atcagttggcgaaaatcagcggtcgcgccgttccggagtggctggaacgccagccggtcagct gcaagacgccatgatcgattgccacatgtggctgcaaggccagcgcatggcgattgccgccgaa ggcgacctgctggcagcgtggtgcgatttcgcgaactctcaaggtatgcagccgggtccactgg ttgctccgacgggtcatccgagcctgcgtcagttgccggtggagcgcgtggtgccgggtgatct ggaggatcttcagaccctcttatgcgcacatccggccgacttactggtggcgaactccacgcc cgtgatttagcagagcaattcgcctgccgctggtgcgcgcaggcttcccgctgtttgacaaac tgggcgaatttcgtcgtgttcgccagggttatagcggtatgcgtgataccctgttcgagttggc gaacctgatccgtgaacgccatcatctggctcattatcgcagcccgctgcgccagaaccca gaatcctcgttgtctacgggtggcgcgtacgcagcggattaa |
| | Synthetic nifU | atgtggaactacagcgagaaagtcaaggaccatttcttcaatccgcgcaacgcgcgtgttgtgg ataacgcaaatgcggtgggcgacgtcggcagcttatcttgtggcgatgctctccgcttgatgct gcgcgtggacccgcagagcgaaatcatcgaagaagcgggctttcagaccttcggctgcggcagc gcgattgcgtcgtccagcgcactgacggagctgatcatcggtcacaccctggcggaagcgggtc agatcaccaaccagcagatcgccgactatctggacggcttaccgccggaaaagatgcactgctc tgtaatgggccaggaagctcttcgtcgcgccattgctaactttcgcggtgaatcgctggaagag gagcatgacgagggtaagctgatctgcaagtgcttcggcgtcgatgaaggccatattcgccgtg ctgtccagaacaacggtcttacgactctggccgaggtgatcaattacaccaaggcaggtggcgg ttgtaccagctgccatgagaaaatcgagctggccctggccgagattctcgcccaacagccgcaa accaccccggcagttgcgtccggtaaagatccgcactggcagagcgtcgtggataccatcgctg aactgcgtccacatatccaagcggacggtgctgacatggcgctgttgtccgtgacgaaccacca agtgactgtttcgctgtcgggcagctgttctggctgcatgatgaccgacatgacccctggcgtgg ctgcaacagaaattgatggagcgtaccggctgctatatggaagttgttgccgcctaa |
| | Synthetic nifS | atgaaacaagtgtacctggacaacaacgcgaccaccccgcctggacccgatggttctggaagcga tgatgccgtttctcacggatttctatggcaatccgtccagcatccatgacttcggcatcccggc acaagcggctggaacgtgcgcaccagcaagctgcggcactgctgctgggcgcagagtacccgtct gaaatcattttcacgagctgtgcgaccgaggccactgcaaccgccattgcgtcggccatcgcgt tattgccggaacgccgcgaaatcatcacctcggtagtggagcacccggctacgctggcggcgtg cgagcacctggaacgccaaggctatcgcatccatcgcattgcggtggatagcgaaggtgcgctg gacatggcccagttccgtgcagcgctctccgccgcgtgtcgcgttggtgagcgtgatgtgggcca acaacgaaaccggcgtgctgttccccgattggcgaaatggccgagcttgcccacgagcagggcgc tctgttccactgcgatgccgttcaggtcgttggcaaaatccaattgctgttggccagacgcgc atcgacatgctgtcttgctccgcgcacaagtttcatggtccgaagggtgttggttgcttgtact tacgtcgtggcacgcgcttcgttccgctgcttcgcggtggccatcaagaatatggtcgccgtgc cggcactgagaatatctgtggcatcgtcggcatgggcgctgcgtgcgaactggcgaacatccat ctgccgggtatgacccatattggccagttacgcaatcgcctggagcaccgtctgctcgccagcg tgccgtcgtgatggttatgggcggtggtcagccgcgtgtacccgggtactgtcaacctggcgtt cgagtttatcgaaggtgaagcgatcctgctcttgctgaaccaagctggcattgccgcaagctcc ggctccgcgtgtacctctggcagcttggagccgagccatgtgatgcgcgccatgaacattccat acaccgcggctcacggcaccattcgttttagcctgagccgttatacgcgcgagaaagagatcga ctacgtcgttgcgaccctcccgccaatcattgatcgtctgcgtgccttgtcccgtattggcag aatggtaagccgcgtccggcagatgcagtcttttaccccggtttacggttaa |
| | Synthetic nifV | atggagcgcgtcttgatcaacgatactaccctgcgtgatggcgaacaatctccgggcgtagcgt ttcgtacctccgagaaagttgccatcgccggaggcactgtacgctgcgggtatcaccgcgatgga agtcggcactccggcgatggtgatgaagagatcgcccgcattcagctggtgcgtcgtcaactg ccggacgcgacgcttatgacctggtgccgtatgaacgctctggaaatccgtcagagcgcggatc tgggtattgactgggtggatatctcgatcccagcatccgacaagctgcgtcagtacaagctgcg tgagccgctggccgtgctgctggagcgccttgcgatgtttatccatctggcccacacgttaggc ctcaaagtatgtattggttgcgaggatgcgagccgtgcgtctggtcagaccctgcgcgccattg ccgaggtggccgcagcaatgcgcggctgcgcgcttgcgttacgctgacaccgtgggcctgctgga cccgttcaccaccgcagcccagatcagcgccctgcgtgacgtttggtcgggcgagatcgagatg catgctcacaatgatctgggcatggctaccgcgaacacgctggcggcagtttcggctggcgcca cgtcggtgaacactaccgtcctcggtctgggtgaacgtgcaggcaacgcagccctggaaaccgt tgcgctgggcctggaacgctcactgggcgtggaaaccggcgtccattccagcgcgctcccagcg ctctgtcagcgcgtcgcggaggctgcacagcgcgcaatcgacccgcaacagccgctggtgggtg aattggttttcacccacgagtctggtgttcacgttgcggcgctgctgcgcgacagcgaatccta tcaatctattgccccaagcctcatgggccgtagctaccgtctggtgctcggcaagcattcggt cgtcaggctgtcaacggtgttttcgaccagatgggttaccacctgaatgcggcgcagatcaatc agttgctgccggccattcgccgcttcgccgagaattggaaacgctctccgaaagactacgaact ggttgcgatctatgacgaattgtgcgtgaatccgcccttcgtgctcgcggctaa |
| | Synthetic nifW | atggagtggttttaccagattccgggtgtagacgaattgcgcagcgctgaatccttctttcagt tcttcgcggttccataccagccggaactgctgggccgctgctcgcttccggtgttagcgacgtt ccaccgtaaactgcgtgcggaggtcccgctgcaaaaccgtctggaggacaatgatcgtcgcgcc tggctcttggcgcgccgcctcctggccgaatcttatcagcagcaatttcaggagagcggcacct aa |
| | Synthetic nifZ | atgcgcccgaaattcaccttctctgaagaggtccgcgtagttcgcgcgattcgtaatgatgca ccgtggcgggttttgcgccaggtgcgctgcttggttcgtcgacggttcgacgggcttttgtcgtga ctgggggtgtgttcctgcaagaccagatcatctatcaaatccactttccggaaaccgaccgcatt atcggctgtcgcgagcaggagttaatccccgattaccagccgtggttggctggtaacctccagt atcgtgacagcgtcacgtgccaaatggcactggctgtcaacggtgacgtggttgtgagcgccgg |

FIG. 38 (cont)

| | | |
|---|---|---|
| | | tcaacgtggccgtgtggaggccactgatcgtggcgaacttggcgattcctacaccgtggacttc<br>agcggccgttggttccgcgttccggtccaggccatcgcgctgattgaagagcgcgaagaataa |
| | Synthetic *nifM* | atgaatccgtggcagcgctttgcccgtcaacgccttgctcgcagccgctggaaccgtgatccgg<br>ctgctctcgacccagccgataccccagcgttcgagcaggcgtggcagcgtcaatgccatatgga<br>acaaaccatcgtagcgcgtgtcccggaaggcgatattccggctgccttactggaaaacatcgcg<br>gccagcctggcgatctggctggacgagggtgacttcgctccgccggagcgcgctgcgattgtgc<br>gtcatcatgcacgtctggagctggcgtttgccgacattgcccgccaggcaccgcaaccggatct<br>gagcacggttcaagcgtggtatctgcgtcaccagactcaattcatgcgtccggagcagcgtctg<br>acccgtcacctgctcctgacggtcgataatgatcgcgaggcggtgcatcaacgcatccttggcc<br>tgtatcgtcagatcaacgcgagccgtgacgccttcgcccactggcacagcgccactctcattg<br>cccgtccgccttggaagaaggccgtctgggctggatctcccgtggtctgctgtacccgcagctc<br>gaaaccgcgttgtttagcctggcggaaaacgcactgtcgctgccgattgcgtcggaattgggtt<br>ggcacctgttatggtgcgaggccattcgtccggcagccccgatggagccgcaacaggcccttga<br>atctgcgcgcgactacttgtggcagcagagccagcagcgccaccagcgtcaatggctggagcag<br>atgatttccgccaaccgggcctgtgtggttaa |
| | Synthetic *nifF* | atggcgaacatcggcatcttctttggtacggataccggcaaaacccgcaagattgcgaagatga<br>ttcacaaacagctgggcgagctggccgatgccccggttaacatcaatcgtaccactttggatga<br>ctttatggcttaccagtcctgttgctcggcacgccgacgcttggtgatggtcaactgccgggc<br>ttagaggcgggctgcgagagcgaaagctggtctgagtttatctccggtctggatgacgcttccc<br>tgaagggcaaaaccgtgcgctgtttggcctgggcgaccagcgtggttacccggacaacttcgt<br>gtcgggtatgcgtccgctgttcgacgcgctgagcgccgtggcgcccagatgattggtagctgg<br>ccgaacgaaggttatgagtttagcgcatcgtccgcgctggaaggcgaccgcttcgtcggcttgg<br>tgctggatcaagacaatcagttcgaccagaccgaagcgcgcctggcgtcttggcttgaagagat<br>caaacgcaccgttctgtaa |
| | Synthetic *nifB* | atgaccttcttgttcgtcgttttctggcggtaaagcgtgccgtccggccgatgactccgcgctga<br>ctccgctggtggccgacaaggcagctgcgcacccgtgctatagccgccacgccatcaccgctt<br>cgcgcgtatgcacctgccagtcgctccggcctgcaacttacaatgcaactactgcaaccgcaag<br>ttcgattgcagcaatgaaagccgtccgggcgtgtcctctaccctgctgacgccggaacaggctg<br>tggtgaaggtgcgccaggtcgcccaagctatcccgcagctgtcggtggtcggtattgctggtcc<br>gggcgatccgcttgcgaatatcgcccgcaccttccgtaccttggagcttattcgcgaacagttg<br>ccggacctgaaactgtgcctgagcaccaacggcttggtgctgccagatgccgttgatcgtctgc<br>tcgatgtgggcgtggatcacgttaccgtcaccattaacaccctggacgcagaaatcgcagcgca<br>aatctacgcgtggttgtggctggatggcgaacgctactccggtcgcgaagccggcgaaattctc<br>attgcccgccagctggaaggcgtacgtcgcctgaccgcgaaaggtgtgctcgtcaagatcaaca<br>gcgtattgattccgggcatcaatgacagcggcatgcgggtgttagccgtgcgctgcgcgcgtc<br>tggtgcgttcatccacaacatcatgccactgattgcgcgtccggagcatggcactgttttcggt<br>ctgaacggccagccggaaccggacgcggaaaaccctggcggcgacgcgctcccgctgcggcgagg<br>ttatgccacaaatgacccactgccaccagtgccgtgccgacgcgattggcatgcttggtgagga<br>tcgctcgcaacagtttacgcaattaccggctccggagtccctcccggcctggctgccgatcctg<br>catcagcgtgctcagttgcatgcgagcatcgccacgcgcggtgagagcgaagccgatgacgcct<br>gcctggtggccgttgcgtcgaccgtggcgcgtggatgtaattgactgccattcggccatgccgaccg<br>tttctatatctatagcctgtctgcggctggtatggttctggttaacgaacgtttcaccccgaaa<br>tactgccagggtcgcgatgactgcgagccgcaggacaatgccgcacgctttgctgccatccttg<br>agttgctggcggacgtcaaagcggtgttttgtgtgcgtatcggccataccccgtggcaacagct<br>ggagcaggaaggcatcgaaccgtgcgtggatggcgcctggcgtccggtatccgaggtcctgccg<br>gcatggtggcagcagccgccgtggtagctggccggctgcattgccgcacaaggcgttgcgtaa |
| | Synthetic *nifQ* | atgccgccattggactggttgcgtcgtttgtggttactctatcacgccggcaaaggcagctttc<br>cgcttcgtatgggcttgtccgccgcgtgactggcaagctctgcgccgtcgcctgggcgaggtgga<br>aacgccgctggatgcgaaaccctgacccgtcgccgtctgatggcggagctgaatgcgacccgc<br>gaagaagaaccgccagcagctgggtgcctggctggccggttggatgcaacaggatgccggtccga<br>tggcgcagattatcgcagaggtgagcctggcgttcaaccatctctggcaggaccttggcctcgc<br>gagccgcgctgaactgcgtctgctgatgtctgactgcttcccgcagctggttgttatgaacgag<br>cacaacatgcgctggaagaaattcttttaccgccagcgttgcctgctgcaacagggcgaagtca<br>tctgtcgcagccgtcttgcgatgaatgctgggaacgttctgcgtgctttgagtaa |

SYNTHETIC GENE CLUSTERS

CROSS-REFERENCE TO RELATED PATENT APPLICATIONS

The present application is a Division of U.S. application Ser. No. 15/288,916, filed Oct. 7, 2016, which is a Continuation of U.S. application Ser. No. 14/126,307, filed Jun. 14, 2012, which is a US National Stage (371) of International Application No. PCT/US2012/042502, filed Jun. 14, 2012, which claims benefit of priority to U.S. Provisional Patent Application No. 61/497,781, filed Jun. 16, 2011, each of which is incorporated by reference.

STATEMENT AS TO RIGHTS TO INVENTIONS MADE UNDER FEDERALLY SPONSORED RESEARCH AND DEVELOPMENT

This invention was made with government support under grant nos. CFF0943385 and EEC0540879 awarded by the National Science Foundation and grant no. R01 AI067699, awarded by the National Institutes of Health. The government has certain rights in the invention.

BACKGROUND OF THE INVENTION

Genetically programming cells require sensors to receive information, circuits to process the inputs, and actuators to link the circuit output to a cellular response (Andrianantoandro E, et al., *Mol Syst Biol* 2 (2006); Chin J W *Curr Opin Struct Biol* 16: 551-556 (2006); Voigt C A *Curr Opin Biotech* 17: 548-557 (2006); Tan C, *Mol Biosyst* 3: 343-353 (2007)). In this paradigm, sensing, signal integration, and actuation are encoded by distinct 'devices' comprised of genes and regulatory elements (Knight T K, Sussman G J Unconventional Models of Computation 257-272 (1997); Endy D *Nature* 438: 449-453 (2005)). These devices communicate with one another through changes in gene expression and activity. For example, when a sensor is stimulated, this may lead to the activation of a promoter, which then acts as the input to a circuit.

BRIEF SUMMARY OF THE INVENTION

Embodiments of the present invention provide a polynucleotide comprising a synthetic operon, wherein the operon comprises at least two coding sequences under the control of a heterologous transcriptional regulatory sequence, wherein each coding sequence is operably linked to a heterologous ribosome binding site (RBS). In some embodiments, the coding sequences are from the same native operon and the heterologous RBSs regulate translation of the coding sequences in a ratio that is substantially similar to the ratio of native translation from the native operon. In some embodiments, the coding sequences are from different native operons and the heterologous RBSs regulate translation of the coding sequences in a ratio that is substantially similar to the ratio of native translation from the native operon. In some embodiments, the coding sequences are from the same native operon and the coding sequences in the operon comprise one or more altered codon compared to the native operon. In some embodiments, codons of one or more coding sequence have been selected for maximal distance from codon usage of a corresponding coding sequence in the native operon.

In some embodiments, at least two coding sequences encode different proteins encoded by the *Klebsiella pneumoniae* nif gene cluster. In some embodiments, the proteins are selected from the group consisting of nifJ, nifH, nifD, nifK, nifY, nifE, nifN, nifU, nifS, nifV, nifW, nifZ, niM, nifF, nifB, and nifQ (e.g., wherein the coding sequences are substantially identical to those listed in FIG. 18). In some embodiments, the operon comprises coding sequences for *Klebsiella pneumoniae* nifH, nifD, nifK, and nifY. In some embodiments, the operon comprises coding sequences for *Klebsiella pneumoniae* nifE and nifN. In some embodiments, the operon comprises coding sequences for *Klebsiella pneumoniae* nifU, nifS, nifV, nifW, nifZ, and nifM. In some embodiments, the operon comprises coding sequences for *Klebsiella pneumoniae* nifB and nifQ.

In some embodiments, at least two coding sequences encode different proteins of the *Salmonella typhimurium* Type III secretion system. In some embodiments, the proteins are selected from the group consisting of PrgH, PrgI, PrgJ, PrgK, OrgA, OrgB, InvA, InvC, InvE, InvF, InvG, InvI, InvJ, SpaO, SpaP, SpaQ, SpaR, and SpaS (e.g., wherein the coding sequences are substantially identical to those listed in FIG. 24). In some embodiments, the operon comprises coding sequences for *Salmonella typhimurium* PrgH, PrgI, PrgJ, PrgK, OrgA, and OrgB. In some embodiments, the operon comprises coding sequences for *Salmonella typhimurium* InvA, InvC, InvE, InvF, InvG, InvI, InvJ, SpaO, SpaP, SpaQ, SpaR, and SpaS.

Embodiments of the present invention also provide for a host cell (optionally isolated) comprising a polynucleotide as described above or elsewhere herein. In some embodiments, the host cell is a prokaryotic or eukaryotic cell (including but not limited to a mammalian or plant or fungal cell).

Embodiments of the present invention also provide a system comprising a set of two or more different synthetic operons, the two or more operons each comprising at least two coding sequences under the control of a heterologous transcriptional regulatory sequence, wherein each coding sequence is operably linked to a heterologous ribosome binding site (RBS), wherein the transcriptional regulatory sequence of each operon in the set is controlled by the same transcriptional activator or repressor polypeptide(s).

In some embodiments, the system further comprises an expression cassette comprising a promoter operably linked to a polynucleotide encoding the transcriptional activator or repressor polypeptide(s). In some embodiments, the promoter of the expression cassette is an inducible promoter. In some embodiments, the polynucleotide in the expression cassette encodes a transcriptional repressor. In some embodiments, the polynucleotide in the expression cassette encodes a transcriptional activator. In some embodiments, the transcriptional activator is an RNA polymerase (RNAP). In some embodiments, the RNAP is T7 RNAP or is substantially similar to T7 RNAP.

In some embodiments, the transcriptional regulatory sequences of at least two of the operons are different.

In some embodiments, the coding sequences in the operons are organized such that coding sequences having substantially similar native expression are grouped into the same operon. In some embodiments, the transcriptional regulatory sequence of at least two operons have different promoters that are differentially regulated by T7 RNA polymerase and wherein the different strength of the promoters correspond to the relative strength of native promoters of the coding sequences.

In some embodiments, the expression cassette and the synthetic operons are expressed in a cell. In some embodiments, the cell is from a different species than the species from which the native operon was isolated. In some embodiments, the cell is from the same species from which the native operon was isolated.

In some embodiments, the system encodes a nitrogenase. In some embodiments, the system comprises a first operon comprising coding sequences for *Klebsiella pneumoniae* nifH, nifD, nifK, and nifY; a second operon comprising coding sequences for *Klebsiella pneumoniae* nifE and nifN; a third operon comprising coding sequences for *Klebsiella pneumoniae* nifU, nifS, nifV, nifW, nifZ, and nifM; and a fourth operon comprising coding sequences for *Klebsiella pneumoniae* nifB and nifQ. In some embodiments, the first, second, third, and fourth operon comprising a T7 RNA polymerase (RNAP) promoter and the system further comprises an expression cassette comprising a promoter operably linked to a polynucleotide encoding an RNAP substantially identical to T7 RNA polymerase (RNAP).

In some embodiments, the system encodes a type III secretion system. In some embodiments, the type III secretion system is a *Salmonella typhimurium* type III secretion system. In some embodiments, the system comprises a first operon comprising coding sequences for *Salmonella typhimurium* PrgH, PrgI, PrgJ, PrgK, OrgA, and OrgB and a second operon comprising coding sequences for *Salmonella typhimurium* InvA, InvC, InvE, InvF, InvG, InvI, InvJ, SpaO, SpaP, SpaQ, SpaR, and SpaS.

Embodiments of the present invention also provide a method for replacing native regulation of a set of genes collectively associated with a function with synthetic regulation. In some embodiments, the method comprises providing coding sequences for a set of polypeptides encoded by genes collectively associated with a function; changing codon identity within at least one coding sequence, thereby removing at least one regulatory sequence within the coding sequence; organizing the coding sequences into one or more synthetic operon(s); operably linking one or more heterologous transcriptional regulatory sequence to the operon(s), thereby controlling the magnitude of gene expression from the operon(s); and expressing the one or more synthetic operon(s) in a cell under the control of a polypeptide that binds directly or indirectly to the heterologous transcriptional regulatory sequence.

In some embodiments, the polypeptide is heterologous to the cell.

In some embodiments, the providing comprises obtaining the gene nucleotide sequences and eliminating non-coding sequences.

In some embodiments, the set of genes is from a gene cluster. In some embodiments, the set of genes are from a prokaryote. In some embodiments, the genes are from a native operon.

In some embodiments, the at least one regulatory sequence is identified using computation. In some embodiments, the computation comprises searches of coding sequences for ribosome binding sites, terminators, and/or promoters.

In some embodiments, removing the at least one regulatory sequence comprises replacement of native codons in the coding sequence with non-native synonymous codons. In some embodiments, the removing comprises selecting non-native codons having maximal distance from codons of the native coding sequence. In some embodiments, the removing comprises selecting non-native codons for optimal expression in a host cell.

In some embodiments, the method further comprises identifying and removing one or more of transposon insertion sites, sites that promote recombination, sites for cleavage by restriction endonucleases, and sites that are methylated.

In some embodiments, the organizing comprises grouping coding sequences into operons based on substantially similar native expression level.

In some embodiments, the organizing comprises ordering coding sequences within operons such that the highest expressing gene (based on native expression) occurs first and the lowest expressing gene (based on native expression) occurs last. In some embodiments, organization is based on native temporal expression, function, ease of manipulation of DNA, and/or experimental design. In some embodiments, magnitude of expression of coding sequences substantially correspond to the ratio of proteins encoded by the coding sequences as measured in the native system. In some embodiments, magnitude of expression of coding sequences is determined by computation. In some embodiments, the computation comprises a numerical optimization algorithm.

In some embodiments, the numerical optimization algorithm a Nelder-Mead algorithm, a Newton's method, a quasi-Newton method, a conjugate gradient method, an interior point method, a gradient descent, a subgradient method, a ellipsoid method, a Frank-Wolfe method, an interpolation method and pattern search methods, or an ant colony model.

In some embodiments, the heterologous transcriptional regulatory sequence(s) comprise a T7 RNAP promoter(s).

In some embodiments, the heterologous transcriptional regulatory sequence(s) comprise an inducible promoter.

In some embodiments, the method further comprises operably linking a heterologous ribosomal binding site (RBS) to one or more coding sequence in the synthetic operon. In some embodiments, different RBSs are operably linked to different coding sequences. In some embodiments, the RBSs regulate translation of the coding sequences in a ratio that is substantially similar to the ratio of native translation from the native operon.

In some embodiments, the method further comprises operably linking a heterologous transcriptional terminator sequence to one or more coding sequence in the synthetic operon. In some embodiments, the terminators are T7 RNAP terminators. In some embodiments, terminators for different operons are different.

In some embodiments, the method further comprises operably linking a buffer sequences between two functional sequences in an operon wherein the functional sequences are selected from the group consisting of a promoter, ribosome binding site, coding sequence, and terminator. In some embodiments, the buffer sequence is selected from the group consisting of a random sequence, a UP-region of a promoter, an extended 5-UTR sequence, and a RNAase cleavage site.

In some embodiments, the operons are expressed from a plasmid. In some embodiments, the plasmid has a low copy origin of replication.

In some embodiments, the polypeptide that binds directly or indirectly to the heterologous transcriptional regulatory sequence is expressed from a control expression cassette, the expression cassette comprising a control promoter operably linked to a polynucleotide sequence encoding the polypeptide. In some embodiments, the expression cassette is contained in a control plasmid separate from a plasmid containing the operons. In some embodiments, the control promoter is an inducible promoter.

In some embodiments, the heterologous polypeptide comprises an RNA polymerase (RNAP). In some embodiments, the RNAP is T7 RNAP. In some embodiments, the expression cassette is an environmental sensor.

Embodiments of the invention also provide for a method for determining an experimentation point for controlling the magnitude of expression of two or more genes (e.g., within a synthetic operon). In some embodiments, the method comprises: receiving one or more input data points, wherein the input data points provide information about one or more regulatory elements and a system property; and determining, with a computer, a next data point using a computational method, wherein the next data point provides information about the one or more regulatory elements.

In some embodiments, the method further comprises using the next data point for further experimentation to optimize expression of the two or more genes. In some embodiments, the regulatory elements include, e.g., ribosomal binding sites and/or transcriptional regulatory elements.

In some embodiments, the computational method is a numerical analysis technique. In some embodiments, the numerical optimization method is the Nelder-Mead algorithm, the Newton's method, the quasi-Newton method, a conjugate gradient method, an interior point method, a gradient descent, a subgradient method, a ellipsoid method, the Frank-Wolfe method, an interpolation method and pattern search methods, or an ant colony model. In some embodiments, the numerical optimization method used to determine the next data point for further experimentation requires considering the reflection point, expansion point, or contraction point based on the one or more input data points.

In some embodiments, the computational method is a design of experiments (DoE) method.

Embodiments of the invention also provide for a computer program product comprising a tangible computer readable medium storing a plurality of instructions for controlling a processor to perform an operation for determining an experimentation point for controlling the magnitude of expression of two or more genes, the instructions comprising receiving one or more input data points, wherein the input data points provide information about one or more regulatory elements and a system property; and determining, with a computer, a next data point using a computational method, wherein the next data point provides information about the one or more regulatory elements.

DEFINITIONS

A recitation of "a", "an" or "the" is intended to mean "one or more" unless specifically indicated to the contrary.

A polynucleotide or polypeptide sequence is "heterologous to" an organism or a second sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a T7 RNA polymerase promoter operably linked to a synthetic nifoperon).

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence. In the context of a ribosomal binding site (RBS) and coding sequences, the term refers to the functional linkage of the RBS to the coding sequence wherein the RBS recruits ribosomes for translation of the coding sequence on an RNA.

A "cognate pair" as used herein refers to a sequence-specific DNA binding polypeptide and a target DNA sequence that is bound by the particular sequence-specific DNA binding polypeptide. For sequence-specific DNA binding polypeptides that bind more than one target nucleic acid, the cognate pair can be formed with the sequence-specific DNA binding polypeptide and any one of the target DNA sequences the polypeptide binds.

"Orthogonal" transcriptional systems refer to systems (e.g., one, two, three, or more) of transcriptional regulatory elements comprising target DNA sequences regulated by their cognate sequence-specific DNA binding polypeptide such that the sequence-specific DNA binding polypeptides in the system do not have "cross-talk," i.e., the sequence-specific DNA binding polypeptides do not interfere or regulate transcriptional regulatory elements in the system other than the transcriptional regulatory elements containing the cognate target DNA sequence of the sequence-specific DNA binding polypeptide.

"Sequence-specific DNA binding polypeptides" refer to polypeptides that bind DNA in a nucleotide sequence specific manner. Exemplary sequence-specific DNA binding polypeptides include, but are not limited to transcription factors (e.g., transcriptional activators), RNA polymerases, and transcriptional repressors.

A "transcriptional activator" refers to a polypeptide, which when bound to a promoter sequence, activates or increases transcription of an RNA comprising the operably-linked coding sequence. In some embodiments, the transcriptional activator bound to a target sequence in a promoter can assist recruitment of RNA polymerase to the promoter. A "transcriptional repressor" refers to a polypeptide, which when bound to a promoter sequence, blocks or decreases transcription of an RNA comprising the operably-linked coding sequence. In some embodiments, the transcriptional repressor blocks recruitment of the RNA polymerase to the promoter or blocks the RNA polymerase's movement along the promoter.

The term "coding sequence" as used herein refers to a nucleotide sequence beginning at the codon for the first amino acid of an encoded protein and ending with the codon for the last amino acid and/or ending in a stop codon.

The term "host cell" refers to any cell capable of replicating and/or transcribing and/or translating a heterologous gene. Thus, a "host cell" refers to any prokaryotic cell (including but not limited to E. coli) or eukaryotic cell (including but not limited to yeast cells, mammalian cells, avian cells, amphibian cells, plant cells, fish cells, and insect cells), whether located in vitro or in vivo. For example, host cells may be located in a transgenic animal or transgenic plant. prokaryotic cell (including but not limited to E. coli) or eukaryotic cells (including but not limited to yeast cells, mammalian cells, avian cells, amphibian cells, plant cells, fish cells, and insect cells).

"Transcriptional regulatory elements" refer to any nucleotide sequence that influences transcription initiation and rate, or stability and/or mobility of a transcript product. Regulatory sequences include, but are not limited to, promoters, promoter control elements, protein binding sequences, 5' and 3' UTRs, transcriptional start sites, termination sequences, polyadenylation sequences, introns, etc. Such transcriptional regulatory sequences can be located either 5'-, 3'-, or within the coding region of the gene and can be either promote (positive regulatory element) or repress (negative regulatory element) gene transcription.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Examples of algorithms that are suitable for determining percent sequence identity and sequence similarity are the BLAST and BLAST 2.0 algorithms, which are described in Altschul et al., *Nucleic Acids Res.* 25:3389-3402 (1997), and Altschul et al., *J. Mol. Biol.* 215:403-410 (1990), respectively. Software for performing BLAST analyses is publicly available on the Web through the National Center for Biotechnology Information (ncbi.nlm.nih.gov). This algorithm involves first identifying high scoring sequence pairs (HSPs) by identifying short wordlength (W) in the query sequence, which either match or satisfy some positive-valued threshold score (T) when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-5787, (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity to a designated reference sequence. Alternatively, percent identity can be any integer from 25% to 100%, for example, at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. One of skill will recognize that the percent identity values above can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Percent identity of polypeptides can be any integer from 40% to 100%, for example, at least 40%, 45%, 50%, 55%, 60%, 65%, 70%, 75%, 80%, 85%, 90%, 95%, or 99%. In some embodiments, polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

BRIEF DESCRIPTION OF THE DRAWINGS

FIG. 3 illustrates a library of wild-type (SEQ ID NO:157) and mutant T7 promoters (SEQ ID NOS:158-163) and their strength to control gene expression. T7 promoter seed sequence=SEQ ID NO: 156.

FIG. 4A depicts strengths of three strains. FIG. 4B depicts the calculated Reflection coordinates.

FIG. 5 illustrates the nitrogen fixation in the Reflection strain and the initial strains.

FIG. 7 illustrates the nif gene cluster from *Klebsiella oxytoca*.

FIG. 10 illustrates the multiple clones used to identify the synthetic ribosome binding site that best matched the native ribosome binding site.

FIG. 12 lists the errors in the fully synthetic operons.

FIG. 14 shows a table of the control of the synthetic operons in the system.

FIG. 18 shows DNA sequences for native genes (SEQ ID NOS:1, 3, 5, 7, 9, 11, 13, 15, 17, 19, 21, 23, 25, 27, 29 and 31) and synthetic genes (SEQ ID NOS:2, 4, 6, 8, 10, 12, 14, 16, 18, 20, 22, 24, 26, 28, 30, and 32), as well as the percent common nucleotide and codon identities between each pair.

FIG. 19 shows the names and sequences of parts of the synthetic controller (SEQ ID NOS:33-51).

FIG. 20 lists the names, sequences and strengths of each components of the full cluster (SEQ ID NOS:52-118).

FIGS. 22A-22B depicts schematics of the inv-spa and prg-org operons and the plasmids used. FIG. 22A shows a schematic of Δprg-org *Salmonella* SL1344 knock-out strain. The inv-spa and prg-org operons are boxed. FIG. 22B shows a schematic of the prg-org operon test vector and reporter plasmid. The control plasmid and reporter plasmid are on the right.

FIGS. 23A-23B shows a western blot of secreted protein expressed from the synthetic prg-org operon in Δprg-org knock-out strain. FIG. 23A shows that the Δprg-org knock-out strain does not express the prg-org operon. FIG. 23B shows that the synthetic refactored prg-org operon in *Salmonella* Δprg-org cells can be controlled by the addition of IPTG.

FIG. 24 shows the synthetic RBS and synthetic operon sequences of the T3SS (SEQ ID NOS:119-155).

FIG. 27A The pathway for nitrogenase maturation is shown and proteins are coloured by function (FIG. 26). The metal clusters are synthesized by the biosynthetic pathway (23, 24). Nitrogen fixation catalyzed by the matured nitrogenase is shown with its in vivo electron transport chain. FIG. 27B The tolerance of nitrogenase activity to changes in the expression of component proteins are shown. Activity is measured via an acetylene reduction assay and the % compared to wild-type *K. oxytoca* is presented. Wild-type operons are expressed from a $P_{tac}$ promoter on a low copy plasmid. The promoter activity is calculated as the output of the $P_{tac}$ promoter at a given concentration of IPTG and compared to a constitutive promoter. The effect of not including NifY (-Y) and NifX (-X) are shown in red. FIG. 27C The comparison of the strength of wild-type (black) and synthetic (white) ribosome binding sites (RBSs) is shown. The RBSs were measured through an in-frame transcriptional fusion (−60 to +90) with mRFP. The strength is measured as the geometric average from a distribution of cells measured by flow cytometry. The synthetic RBSs of nifF and nifQ are not intended to match the wild-type measurement. Error bars represent the standard deviation of at least three experiments performed on different days.

FIGS. 28A-28C illustrates converting to T7* RNAP Control. FIG. 28A Nitrogenase activity is shown as a function of promoter strength for each refactored operon in respective *K. oxytoca* knockout strains (ΔnifHDKTY, ΔnifENX, ΔnifJ, ΔnifBQ, ΔnifF, and ΔnifUSVWZM). Vertical dashed lines indicate strength of the mutant T7 promoter that controls each operon in the complete refactored gene cluster. FIG. 28B A controller plasmid decouples operon expression from the inducible promoter. A T7 RNAP variant (T7*) was designed to reduce toxicity. A set of 4 mutated T7 promoters were used to control the expression of each operon (part numbers and sequences for mutants 1-4 are listed in the Materials and Methods section). Ptac activity under 1 mM IPTG induction is indicated by a dashed horizontal line. FIG. 28C Nitrogenase activity is compared for each refactored operon under the control of the $P_{tac}$ promoter at the optimal IPTG concentration (black) and the controller (part D) with 1 mM IPTG and expression controlled by different T7 promoters (white). The T7 promoters used are WT for operons HDKY, EN and J; promoter 2 for operons BQ and USVWZM; and promoter 3 for F. Error bars represent the standard deviation of at least three experiments performed on different days.

FIG. 29 shows a comprehensive schematic for the complete refactored gene cluster and controller. Each of the 89 parts is represented according to the SBOL visual standard (sbolstandard.org), and the SynBERC Registry part number (registry.synberc.org) and part activity are shown. The T7 promoter strengths are measured with red fluorescent protein (mRFP) and reported in REU (see, Materials and Methods). Terminator strengths are measured in a reporter plasmid and reported as the fold-reduction in mRFP expression when compared to a reporter without a terminator. The RBS strength is reported in as arbitrary units of expression from the induced $P_{tac}$ promoter (1 mM IPTG) and a fusion gene between the first 90 nucleotides of the gene and red fluorescent protein. The nucleotide numbers for the plasmids containing the refactored cluster and controller are shown. The codon identity of each recoded gene as compared to wild-type is shown as a percent.

FIGS. 30A-30D shows the regulation of the complete refactored gene cluster. FIG. 30A Nitrogenase activity for the three controllers are shown: IPTG-inducible, aTc-inducible, and IPTG ANDN aTc logic. The gas chromatography trace is shown for each as well as the calculated percent of wild-type activity, (7.4%±2.4%, 7.2%±1.7% and 6.6%±1.7% respectively). Standard deviation is calculated using data from at least two experiments performed on different days. FIG. 30B $^{15}N$ incorporation into cell biomass is shown. Nitrogen fixation from $N_2$ gas by the refactored gene cluster was traced using $^{15}N_2$ and measured using isotope ratio mass spectronomy (IRMS). Data are represented as the fraction of cellular nitrogen that is $^{15}N$. The standard deviation represents two experiments performed on different days. FIG. 30C The effect of ammonia on regulation of nitrogenase expression is shown. Acetylene reduction traces shown with (red) and without (blue) addition of 17.5 mM ammonium acetate for wild type cells (left) and cells bearing synthetic nif system (right). The synthetic system was induced by Controller #1 using 1 mM IPTG and exhibited nitrogenase activity of 1.1%±0.5% and 6.1%±0.4% with and without ammonium acetate respectively. FIG. 30D T7* RNAP expression of Controller #1 corresponding to Part C is shown. Strains carrying Controller #1 and a RFP reporter plasmid were characterized under 1 mM IPTG induction with or without addition of ammonium acetate.

FIG. 32 depicts a table of construction and verification of all *K. oxytoca* nif gene deletion mutants (SEQ ID NOS: 164-177).

FIG. 33A Conversion of arbitrary units into Relative Expression Units (REU). Promoters were characterized using mRFP1 fluorescent reporter protein in N155 (Measured Promoters). Data were first normalized by the fluorescence of N110 (Internal Standard) and then scaled by the fluorescence of N155(J23100) to account for RBS differences between N155 and N110 (RBS Adjustment). To directly compare our measurements to expression levels of the Kelly et al. standards, we further multiplied by the ratio of N110 fluorescence to the fluorescence of a Kelly standard plasmid expressing mRFP1 (RFP Promoter Standard). A final conversion factor is applied to compare all measurements to the Kelly et al. J23101-EGFP promoter standard based on a strong linear correlation of promoter strength (RPU) between constructs expressing mRFP and EGFP. Solid and dashed boxes were drawn to indicate which plasmids were measured at different facilities. Asterisked and non-asterisked units were measured in different facilities and correspond to the conversion factors directly above. FIG. 33B Promoter characterization for $P_{tac}$ promoter (left) and $P_{tet}$ promoter (right). The promoter strengths of Ptac promoter and $P_{tet}$ promoter were measured under varied concentrations of inducers (IPTG or aTc). The strengths of T7 promoters (WT and mutants, FIG. 28B) are shown as horizontal dotted lines.

FIG. 34A The process is shown for the identification of problem sequences within a refactored operon. After design and synthesis, the problematic DNA is crossed with wild-type to create a chimeric library, which is screened. This is done iteratively to reduce the size of the problematic region until the specific errors are identified. FIG. 34B The debugging process led to the correction of RBS strengths (red arrows), the recoded sequence of nifH, and numerous nucleotide errors found in the sequenced cluster in the database. Amino acid mutations to correct errors in the synthetic sequence are shown.

FIG. 35 depicts a table of DNA sequence errors in nif cluster sequence X13303.1.

FIG. 38 depicts a table of DNA sequences of synthetic parts (SEQ ID NOS: 178-238).

DETAILED DESCRIPTION

I. Introduction

Figure 1:
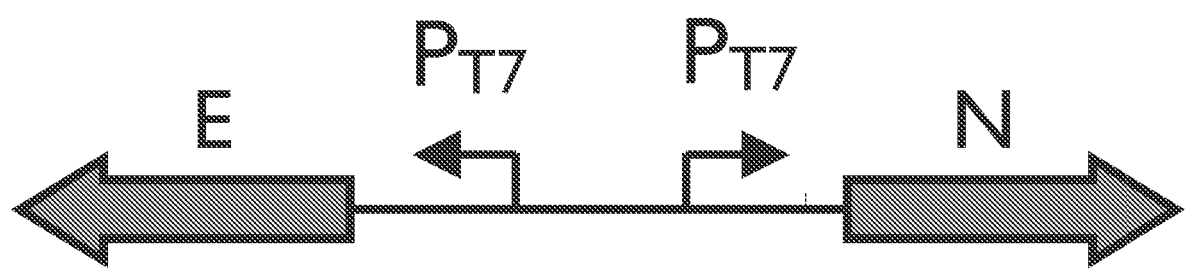
FIG. 1 depicts a scheme illustrating nifE and nifN genes under the control of unique T7 promoters.

The present invention relates to gene cluster engineering. It has been discovered how to recombinantly and computationally manipulate and select native gene cluster coding sequences and heterologous regulatory sequences such that the coding sequences are under control of heterologous regulation and produce the functional product of the gene cluster (e.g., a native operon). By eliminating native regulatory elements outside of, and within, coding sequences of gene clusters, and subsequently adding synthetic regulatory systems, the functional products of complex genetic operons and other gene clusters can be controlled and/or moved to heterologous cells, including cells of different species other than the species from which the native genes were derived.

As demonstrated below, the inventors have re-engineered the *Klebsiella oxytoca* Nif gene cluster as well as a *Salmonella* Type III protein secretion system, thereby generating functional products (e.g., nitrogen fixing enzymes and peptide secretion complexes, respectively) under control of a heterologous regulatory system. Once re-engineered, the synthetic gene clusters can be controlled by genetic circuits or other inducible regulatory systems, thereby controlling the products' expression as desired.

II. Generation of Synthetic Gene Clusters

It is believed that the methods described herein can be used and adapted to re-engineer regulation of essentially any operon or other gene cluster. Generally, the native operons or gene clusters to be engineered will have the same functional product in the native host. For example, in some embodiments, at least a majority of the gene products within the native operon or gene cluster to be re-engineered will each function to produce a specific product or function of the native host. Functional products can include, for example, multi-component enzymes, membrane-associated complexes, including but not limited to complexes that transport biological molecules across membranes, or other biologically active complexes. For example, in some embodiments, the functional products are, e.g., a Type III protein secretion system, a bacterial microcompartment, a gas vesicle, a magnetosome, a cellulosome, an alkane degradation pathway, a nitrogen fixation complex, a polybiphenyl degradation complex, a pathway for biosynthesis of Poly (3-hydroxbutyrate), nonribosomal peptide biosynthesis enzymes, polyketide biosynthesis gene cluster products, a terpenoid biosynthesis pathway, an oligosaccharide biosynthesis pathway, an indolocarbazole biosynthesis pathway, a photosynthetic light harvesting complex, a stressosome, or a quorum sensing cluster. See, Fischbach and Voigt, *Biotechnol. J.*, 5:1277-1296 (2010), which is incorporated by reference, for a detailed description and examples of each.

Native operons or gene clusters used in embodiments of the present invention can be derived (originated) from prokaryotes or eukaryotes.

As used herein, "native" is intended to refer to the host cell or host genome from which an operon or gene cluster is originally derived (e.g., as the operon is found in nature). Thus, "native expression" of an operon refers to the specific expression levels and patterns of a set of genes in an operon or gene cluster in a native host.

An operon refers to a unit of DNA comprising multiple separate coding sequences under the control of a single promoter. The separate coding sequences are typically expressed within a single RNA molecule and subsequently translated separately, e.g., with varying translation levels due to the strength of ribosomal binding sites (RBSs) associated with the particular coding sequences. Operons are most typically found in prokaryotic cells.

Gene clusters refer to sets of genes having a common function or function product. Genes are typically found within physical proximity to each other within genomic DNA (e.g., within one centiMorgan (cM)). Gene clusters can occur in prokaryotic or eukaryotic cells.

A. Coding Sequences

Once a native operon or gene cluster has been identified for re-engineering, the coding sequences to be re-engineered can be identified. Generally, it will be desirable to start with only the coding sequences from the native operon or gene cluster, thereby removing native promoters and other non-coding regulatory sequences. Depending on the function of the various gene products of the native operon or gene cluster, in some embodiments all of the coding sequences of a native operon or gene cluster are re-engineered.

Alternatively, one or more coding sequences can be omitted from the re-engineering process. For example, it may be known that one or more of the gene products in a native operon or gene cluster do not contribute to the function product of the operon or may not be necessary for generation of the operon's or cluster's product. For example, as described in the examples below, in re-engineering the Nifoperon, the nifT gene had no known function and notably it was known that elimination of nifT did not to significantly affect the ultimate function of the operon, i.e., nitrogen fixation. Thus, nifT was not included in the re-engineering process.

In some embodiments, the operon or gene cluster will include coding sequences for regulatory proteins that regulate expression or activity of one or more of the other products of the operon or gene cluster. In such embodiments, it can be desirable to omit such regulatory proteins from the re-engineering process because synthetic regulation will be employed instead. For example, as described in the examples below, in re-engineering the nifoperon, nifL and nifA were known to act as regulatory genes for the nifoperon and thus were omitted so that synthetic regulation could be instead used.

Once the set of gene products to be re-engineered has been identified, one can start with the native coding sequence, or the amino acid sequences of the gene products. For example, in some embodiments, the amino acid sequences of the gene products can be used to produce a synthetic coding sequence for expression in the host cell in which the re-engineered products are to be ultimately expressed.

In some embodiments, the native coding sequences of the set of gene products to be re-engineered are used as a starting point. In this case, in some embodiments, sequences not essential to production of the gene products is eliminated. For example, ribosome binding sites, terminators, or promoters within the coding sequences can be eliminated. In some embodiments, the nucleotide sequences of the coding sequences are analyzed using an algorithm (i.e., in a computer) to identify ribosome binding sites, terminators, or promoters within the sequence(s).

Nonessential regulatory sequences within the coding sequences can be reduced or eliminated by altering the codons of the native coding sequence(s). Regulatory sequences comprising codons can be disrupted, for example, by changing the codons to synonymous codons (i.e., encoding the same amino acid) thereby leaving the encoded amino acid sequence intact while changing the coding sequence. One or more codons of one or more coding sequences can be altered.

In some embodiments, at least 5%, 10%, 15%, 20% or more codons of one or more native coding sequence to be inserted into a synthetic operon are replaced. In some embodiments, at least 5%, 10%, 15%, 20%, 30%, 40%, 50% or more codons of each of the native coding sequences to be inserted into a synthetic operon are replaced.

In some embodiments, replacement codons can be selected, for example, to be significantly divergent from the native codons. The codon changes can result in codon optimization for the host cell, i.e., the cell in which the polynucleotide is to be expressed for testing and/or for ultimate expression. Methods of codon optimization are known (e.g., Sivaraman et al., *Nucleic Acids Res.* 36:e16 (2008); Mirzahoseini, et al., *Cell Journal* (Yakhteh) 12(4): 453 Winter 2011; U.S. Pat. No. 6,114,148) and can include reference to commonly used codons for a particular host cell. In some embodiments, one or more codon is randomized, i.e., a native codon is replaced with a random codon encoding the same amino acid. This latter approach can help to remove any cis-acting sequences involved in the native regulation of the polypeptide. In some embodiments, codons are selected to create a DNA sequence that is maximally distant from the native sequence. In some embodiments, an algorithm is used to eliminate transcriptionally functional sequences in a gene encoding the polypeptide. For example, in some embodiments, ribosome binding sites, transcriptional regulatory elements, terminators, or other DNA sequences bound by proteins are removed from the native coding sequence. Notably, the functional sequences removed can be functional in the native species (from which the sequence was originally derived), in the heterologous host cell, or both. In some embodiments, optimizing comprises removal of sequences in the native coding sequence that are functional for heterologous transcriptional activators or repressors to be used to regulate the synthetic operons to be generated.

Generation of synthetic coding sequences, as well as the remaining portions of the synthetic operon, in many cases will be performed de novo from synthetic oligonucleotides. Thus, in some embodiments, codons are selected to create a DNA sequence that does not generate difficulties for oligonucleotide production or combination. Thus, in some embodiments, codon sequences are avoided that would result in generation of oligonucleotides that form hairpins.

In some embodiments, as noted above, codon alteration will depend on the host cell used. Host cells can be any prokaryotic cell (including but not limited to *E. coli*) or eukaryotic cell (including but not limited to yeast cells, mammalian cells, avian cells, amphibian cells, plant cells, fish cells, and insect cells).

Nonessential regulatory sequences within native sequences can be identified, in some embodiments, using an algorithm performed by a processor executing instructions encoded on a computer-readable storage medium. For example, in some embodiments, ribosome binding sites are identified using a thermodynamic model that calculates the free energy of the ribosome binding to mRNA. In some embodiments, promoters are identified with an algorithm using a position weighted matrix. In some embodiments, transcriptional terminators are identified by an algorithm that identifies hairpins and/or poly-A tracks within sequences. In some embodiments, an algorithm identifies other transcriptionally functional sequences, including but not limited to transposon insertion sites, sites that promote recombination, sites for cleavage by restriction endonucleases, and/or sequences that are methylated.

In view of the alterations described above, in some embodiments, a coding sequence in a synthetic operon of the invention is less than 90, 85, 80, 75, or 70% identical to the native coding sequence. In some embodiments, the coding sequence encodes a protein sequence that is identical to the native protein or is at least 80, 85, 90 or 95% identical to the native protein. In some embodiments, less than 70%, 60%, or 50% of codons in one, two or more coding sequences in a synthetic operon are identical to the codons in the native coding sequence.

B. Organizing Coding Sequences into Synthetic Operons

Once coding sequences have been selected (e.g., and substantially "cleaned" of native or spurious regulatory sequences), the coding sequences are organized into one or more synthetic operon(s). Organization of the synthetic operon(s) includes insertion of various heterologous transcriptional and translational sequences between, before, and/or after the coding sequences so that expression of each coding sequence is controlled as desired. Thus, for example, 5' promoter sequences can be selected to drive expression of an operon RNA comprising the coding sequences of the operon. Selection of one or more terminator of appropriate strength will also affect expression levels. Moreover, the order of the coding sequences within a synthetic operon and/or selection of RBSs for the coding sequences allows for control of relative translation rates of each coding sequence, thereby allowing several levels of control for absolute and relative levels of the final protein products.

Because each synthetic operon can have its own promoter, different synthetic operons can be expressed at different strengths. Thus, in some embodiments, coding sequences are organized into different operons based on the relative native expression levels. Said another way, in some embodiments, coding sequences are organized into operons by grouping coding sequences expressed at substantially the same native level in a particular synthetic operon.

Moreover, because coding sequences at the 5' (front) end of an RNA can be expressed at a higher level than coding sequences further 3', in some embodiments, coding sequences are ordered within a synthetic operon such that the highest expressing coding sequence (in the native context) occurs first and the lowest expressing gene occurs last. In some embodiments, organization of genes within operons is based on native temporal expression, function, ease of manipulation of DNA, and/or experimental design.

In designing the transcriptional (e.g., promoters) and translational (e.g., RBSs) controls of the synthetic operons, the ratio of proteins measured in the native system can be considered. Thus, in some embodiments, two or more coding sequences that are expressed in a native context at substantially the same level and/or that are desirably expressed in an approximately 1:1 ratio to achieve functionality (e.g., where two or more members are part of a functional complex in a 1:1 ratio) are placed in proximity to each other within a synthetic operon. "Proximity" will generally mean that coding sequences are adjacent to each other in the synthetic operon.

In some embodiments, relative expression levels of coding sequences within and, in some embodiments, between synthetic operons is determined by testing one or more test operons for desired expression and/or desired functionality and then improving expression based on the initial results. While this method can be performed in a "trial and error" basis, in some embodiments, a numerical optimization method is employed to guide selection of regulatory elements in order to alter gene expression and to improve desired system properties. Such methods, for example, can be performed by a processor executing instructions encoded on a computer-readable storage medium (discussed further below). Exemplary numerical optimization methods include but are not limited to, a Nelder-Mead algorithm, a Newton's method, a quasi-Newton method, a conjugate gradient method, an interior point method, a gradient descent, a subgradient method, a ellipsoid method, a Frank-Wolfe method, an interpolation method and pattern search methods, or an ant colony model. In some embodiments, a computational design of experiments (DoE) method is employed to alter gene expression and to improve desired system properties in the synthetic operons.

Transcriptional regulatory elements, ribosomal binding sites, terminators, and other sequences affecting transcription or translation can be selected from existing collections of such sequences, and/or can be generated by screening of libraries generated by design or by random mutation. Exemplary regulatory sequences include cis-acting nucleotide sequences bound by a sequence-specific DNA binding polypeptide, e.g., a transcriptional activator or a transcriptional repressor. Exemplary transcriptional activators include, but are not limited to, sigma factors, RNA polymerases (RNAPs) and chaperone-assisted activators. In some embodiments, the transcriptional activator/cis-acting sequence cognate pair will be orthogonal to the host cell. Said another way, the regulatory sequence will not be bound by other host cells proteins except for the heterologous transcriptional activator that binds the cis-acting sequence.

i. Sigma Factors

In some embodiments, the sequence-specific DNA binding polypeptide is a sigma (σ) factor and the regulatory sequence of the synthetic operon comprises the sigma factor's cognate cis-acting nucleotide sequence. Sigma factors recruit RNA polymerase (RNAP) to specific promoter sequences to initiate transcription. The σ 70 family consist of 4 groups: Group 1 are the housekeeping σs and are essential; groups 2-4 are alternative σs that direct cellular transcription for specialized needs (Gruber and Gross, *Annu. Rev. Microbiol.*, 57:441-466 (2003)). Group 4 σs (also known as ECF σs; extracytoplasmic function) constitute the largest and most diverse group of σs, and have been classified into 43 subgroups (Staron et al., *Mol Microbiol* 74(3): 557-81 (2009)).

In some embodiments, the set of sequence-specific DNA-binding polypeptides comprise multiple sigma factors. In some embodiments, the set comprises sigma factors from Group 1, Group 2, Group 3, and/or Group 4 Sigma factors. The ECF subgroup of Group 4 is thought to recognize different promoter sequences, making these as particularly useful for constructing orthogonal σ-promoter systems. However, it will be appreciated that any group of sigma factors can be used according to the methods of the embodiments of the invention to develop cognate pairs.

TABLE 1

| Group Nr[a] | ID[b] | GI[c] | SPECIES[d] | CLASS[d] | PHYLUM[d] |
|---|---|---|---|---|---|
| ECF01 | >3473 | 109899616 | *Pseudoalteromonas atlantica* T6c | Gammaproteobacteria | Proteobacteria |
| ECF01 | >4085 | 114562024 | *Shewanella frigidimarina* NCIMB 400 | Gammaproteobacteria | Proteobacteria |
| ECF02 | >2817 | 16130498 | *Escherichia coli* K12 | Gammaproteobacteria | Proteobacteria |
| ECF02 | >915 | 119774011 | *Shewanella amazonensis* SB2B | Gammaproteobacteria | Proteobacteria |
| ECF03 | >1198 | 29350055 | *Bacteroides thetaiotaomicron* VPI-5482 | | Bacteroidetes |
| ECF03 | >1244 | 34541012 | *Porphyromonas gingivalis* W83 | | Bacteroidetes |
| ECF04 | >1609 | 21673117 | *Chlorobium tepidum* TLS | | Chlorobi |
| ECF04 | >1617 | 68549683 | *Pelodictyon phaeoclathratiforme* BU-1 | | Chlorobi |
| ECF05 | >965 | 28868416 | *Pseudomonas syringae* pv. tomato str. DC3000 | Gammaproteobacteria | Proteobacteria |
| ECF05 | >1054 | 67154316 | *Azotobacter vinelandii* AvOP | Gammaproteobacteria | Proteobacteria |
| ECF06 | >3576 | 15595669 | *Pseudomonas aeruginosa* PAO1 | Gammaproteobacteria | Proteobacteria |
| ECF06 | >853 | 26987094 | *Pseudomonas putida* KT2440 | Gammaproteobacteria | Proteobacteria |
| ECF07 | >980 | 67154823 | *Azotobacter vinelandii* AvOP | Gammaproteobacteria | Proteobacteria |
| ECF07 | >1134 | 15598606 | *Pseudomonas aeruginosa* PAO1 | Gammaproteobacteria | Proteobacteria |
| ECF08 | >3580 | 15595872 | *Pseudomonas aeruginosa* PAO1 | Gammaproteobacteria | Proteobacteria |
| ECF08 | >3627 | 70730114 | *Pseudomonas fluorescens* Pf-5 | Gammaproteobacteria | Proteobacteria |
| ECF09 | >3581 | 15597622 | *Pseudomonas aeruginosa* PAO1 | Gammaproteobacteria | Proteobacteria |
| ECF09 | >1009 | 70730971 | *Pseudomonas fluorescens* Pf-5 | Gammaproteobacteria | Proteobacteria |
| ECF10 | >3486 | 77360766 | *Pseudoalteromonas haloplanktis* TAC125 | Gammaproteobacteria | Proteobacteria |
| ECF10 | >2914 | 88706154 | gamma proteobacterium KT 71 | Gammaproteobacteria | Proteobacteria |
| ECF11 | >3726 | 28868260 | *Pseudomonas syringae* pv. tomato str. DC3000 | Gammaproteobacteria | Proteobacteria |
| ECF11 | >987 | 28899132 | *Vibrio parahaemolyticus* RIMD 2210633 | Gammaproteobacteria | Proteobacteria |
| ECF12 | >807 | 86158800 | *Anaeromyxobacter dehalogenans* 2CP-C | Deltaproteobacteria | Proteobacteria |
| ECF12 | >808 | 108762328 | *Myxococcus xanthus* DK 1622 | Deltaproteobacteria | Proteobacteria |
| ECF13 | >1146 | 33152898 | *Haemophilus ducreyi* 35000HP | Gammaproteobacteria | Proteobacteria |
| ECF13 | >1025 | 37524103 | *Photorhabdus luminescens* subsp. *laumondii* TTO1 | Gammaproteobacteria | Proteobacteria |
| ECF14 | >3200 | 15608361 | *Mycobacterium tuberculosis* H37Rv | | Actinobacteria |
| ECF14 | >1324 | 21223516 | *Streptomyces coelicolor* A3(2) | | Actinobacteria |
| ECF15 | >436 | 77464848 | *Rhodobacter sphaeroides* 2.4.1 | Alphaproteobacteria | Proteobacteria |
| ECF15 | >524 | 16127705 | *Caulobacter crescentus* CB15 | Alphaproteobacteria | Proteobacteria |
| ECF16 | >3622 | 104782321 | *Pseudomonas entomophila* L48 | Gammaproteobacteria | Proteobacteria |
| ECF16 | >973 | 161378140 | *Pseudomonas putida* KT2440 | Gammaproteobacteria | Proteobacteria |
| ECF17 | >1691 | 15607875 | *Mycobacterium tuberculosis* H37Rv | | Actinobacteria |
| ECF17 | >1458 | 21221399 | *Streptomyces coelicolor* A3(2) | | Actinobacteria |
| ECF18 | >4451 | 21230791 | *Xanthomonas campestris* pv. *campestris* str. ATCC 33913 | Gammaproteobacteria | Proteobacteria |
| ECF18 | >4438 | 21242133 | *Xanthomonas axonopodis* pv. *citri* str. 306 | Gammaproteobacteria | Proteobacteria |
| ECF19 | >3197 | 15607586 | *Mycobacterium tuberculosis* H37Rv | | Actinobacteria |
| ECF19 | >1315 | 21219164 | *Streptomyces coelicolor* A3(2) | | Actinobacteria |
| ECF20 | >992 | 70731405 | *Pseudomonas fluorescens* Pf-5 | Gammaproteobacteria | Proteobacteria |
| ECF20 | >2913 | 88706222 | gamma proteobacterium KT 71 | Gammaproteobacteria | Proteobacteria |
| ECF21 | >1280 | 29350128 | *Bacteroides thetaiotaomicron* VPI-5482 | | Bacteroidetes |
| ECF21 | >2825 | 89889680 | Flavobacteria bacterium BBFL7 | | Bacteroidetes |
| ECF22 | >4450 | 21232074 | *Xanthomonas campestris* pv. *campestris* str. ATCC 33913 | Gammaproteobacteria | Proteobacteria |
| ECF22 | >1147 | 21243541 | *Xanthomonas axonopodis* pv. *citri* str. 306 | Gammaproteobacteria | Proteobacteria |
| ECF23 | >231 | 15895043 | *Clostridium acetobutylicum* ATCC 824 | | Firmicutes |
| ECF23 | >1851 | 30261806 | *Bacillus anthracis* str. Ames | | Firmicutes |
| ECF24 | >69 | 16079737 | *Bacillus subtilis* subsp. *subtilis* str. 168 | | Firmicutes |
| ECF24 | >1034 | 32470052 | *Escherichia coli* | Gammaproteobacteria | Proteobacteria |
| ECF25 | >1645 | 170078575 | *Synechococcus* sp. PCC 7002 | | Cyanobacteria |
| ECF25 | >1643 | 17230772 | *Nostoc* sp. PCC 7120 | | Cyanobacteria |
| ECF26 | >4464 | 58581966 | *Xanthomonas oryzae* pv. *oryzae* KACC10331 | Gammaproteobacteria | Proteobacteria |
| ECF26 | >837 | 77459110 | *Pseudomonas fluorescens* PfO-1 | Gammaproteobacteria | Proteobacteria |
| ECF27 | >4265 | 21222299 | *Streptomyces coelicolor* A3(2) | | Actinobacteria |

TABLE 1-continued

| Group Nr[a] | ID[b] | GI[c] | SPECIES[d] | CLASS[d] | PHYLUM[d] |
|---|---|---|---|---|---|
| ECF27 | >1331 | 31795084 | *Mycobacterium bovis* AF2122/97 | | Actinobacteria |
| ECF28 | >1088 | 114563849 | *Shewanella frigidimarina* NCIMB 400 | Gammaproteobacteria | Proteobacteria |
| ECF28 | >1040 | 15641058 | *Vibrio cholerae* O1 biovar eltor str. N16961 | Gammaproteobacteria | Proteobacteria |
| ECF29 | >371 | 13476734 | *Mesorhizobium loti* MAFF303099 | Alphaproteobacteria | Proteobacteria |
| ECF29 | >2688 | 71281387 | *Colwellia psychrerythraea* 34H | Gammaproteobacteria | Proteobacteria |
| ECF30 | >35 | 16079766 | *Bacillus subtilis* subsp. *subtilis* str. 168 | | Firmicutes |
| ECF30 | >83 | 18309341 | *Clostridium perfringens* str. 13 | | Firmicutes |
| ECF31 | >2963 | 85713274 | *Idiomarina baltica* OS145 | Gammaproteobacteria | Proteobacteria |
| ECF31 | >34 | 16080921 | *Bacillus subtilis* subsp. *subtilis* str. 168 | | Firmicutes |
| ECF32 | >1122 | 4581629 | *Erwinia amylovora* | Gammaproteobacteria | Proteobacteria |
| ECF32 | >3724 | 28868612 | *Pseudomonas syringae* pv. tomato str. DC3000 | Gammaproteobacteria | Proteobacteria |
| ECF33 | >375 | 27378153 | *Bradyrhizobium japonicum* USDA 110 | Alphaproteobacteria | Proteobacteria |
| ECF33 | >423 | 39934888 | *Rhodopseudomonas palustris* CGA009 | Alphaproteobacteria | Proteobacteria |
| ECF34 | >3302 | 77164965 | *Nitrosococcus oceani* ATCC 19707 | Gammaproteobacteria | Proteobacteria |
| ECF34 | >1384 | 21218750 | *Streptomyces coelicolor* A3(2) | | Actinobacteria |
| ECF35 | >3582 | 15598092 | *Pseudomonas aeruginosa* PAO1 | Gammaproteobacteria | Proteobacteria |
| ECF35 | >1119 | 24375055 | *Shewanella oneidensis* MR-1 | Gammaproteobacteria | Proteobacteria |
| ECF36 | >3196 | 15609206 | *Mycobacterium tuberculosis* H37Rv | | Actinobacteria |
| ECF36 | >1595 | 21219385 | *Streptomyces coelicolor* A3(2) | | Actinobacteria |
| ECF37 | >3390 | 89094252 | *Oceanospirillum* sp. MED92 | Gammaproteobacteria | Proteobacteria |
| ECF37 | >2513 | 83718468 | *Burkholderia thailandensis* E264 | Betaproteobacteria | Proteobacteria |
| ECF38 | >1322 | 21222029 | *Streptomyces coelicolor* A3(2) | | Actinobacteria |
| ECF38 | >1442 | 152967344 | *Kineococcus radiotolerans* SRS30216 | | Actinobacteria |
| ECF39 | >1438 | 21223369 | *Streptomyces coelicolor* A3(2) | | Actinobacteria |
| ECF39 | >2973 | 84494624 | *Janibacter* sp. HTCC2649 | | Actinobacteria |
| ECF40 | >3198 | 15610550 | *Mycobacterium tuberculosis* H37Rv | | Actinobacteria |
| ECF40 | >1380 | 62389491 | *Corynebacterium glutamicum* ATCC 13032 | | Actinobacteria |
| ECF41 | >491 | 16127496 | *Caulobacter crescentus* CB15 | Alphaproteobacteria | Proteobacteria |
| ECF41 | >1141 | 77459658 | *Pseudomonas fluorescens* PfO-1 | Gammaproteobacteria | Proteobacteria |
| ECF42 | >3583 | 15596548 | *Pseudomonas aeruginosa* PAO1 | Gammaproteobacteria | Proteobacteria |
| ECF42 | >4454 | 77747962 | *Xanthomonas campestris* pv. *campestris* str. ATCC 33913 | Gammaproteobacteria | Proteobacteria |
| ECF43 | >4437 | 21244845 | *Xanthomonas axonopodis* pv. *citri* str. 306 | Gammaproteobacteria | Proteobacteria |
| ECF43 | >3477 | 109897287 | *Pseudoalteromonas atlantica* T6c | Gammaproteobacteria | Proteobacteria |

In addition to native sigma factors, chimeric or other variant sigma factors can also be used in the method of the invention. For example, in some embodiments, one or more sigma factor are submitted to mutation to generate library of sigma factor variants and the resulting library can be screen for novel DNA binding activities.

In some embodiments, chimeric sigma factors formed from portions of two or more sigma factors can be used. Accordingly, embodiments of the invention provide for generating a library of polynucleotides encoding chimeric sigma factors, wherein the chimeric sigma factors comprise a domain from at least two different sigma factors, wherein each of the domains bind to the −10 or −35 region of a regulatory element; and expressing chimeric sigma factors from the library of polynucleotides, thereby generating a library of chimeric sigma factors. For example, in some embodiments, chimeric sigma factors are generated comprising a "Region 2" from a first sigma factor and a "Region 4" from a second sigma factor, thereby generating chimeric sigma factors with novel DNA binding activities. "Region 2" of sigma factors is a conserved domain that recognizes −10 regions of promoters. "Region 4" is a conserved domain of sigma factors that recognizes −35 regions of promoters. It will be appreciated that chimeric sigma factors can be generated from any two native sigma factors that bind different target DNA sequences (e.g., different promoter sequences). It has been found that chimeric sigma factors formed from the ECF2 and ECF11 subgroups have unique DNA binding activities useful for generating orthogonal sets as described herein. Exemplary chimeric sigma factors include, but are not limited to, ECF11_ECF02 (containing amino acids 1-106 from ECF02_2817 and 122-202 from ECF11_3726) and ECF02_ECF11 (containing amino acids 1-121 from ECF11_3726 and 107-191 from ECF02_2817).

The ECF11_ECF02 amino acid sequence is as follows (SEQ ID NO:239):

```
  1  MRITASLRTFCHLSTPHSDSTTSRLWIDEVTAVARQRDRDSFMRIYDHFAPRLLRYLTGL
 61  NVPEGQAEELVQEVLLKLWHKAESFDPSKASLGTWLFRIARNLYIDSVRKDRGWVQVQNS
121  LEQLERLEAISNPENLMLSEELRQIVERTIESLPEDLRMAITLRELDGLSYEEIAAIMDC
181  PVGTVRSRIFRAREAIDNKVQPLIRR*
```

The ECF02_ECF11 amino acid sequence is as follows (SEQ ID NO:240):

```
  1  MSEQLTDQVLVERVQKGDQKAFNLLVVRYQHKVASLVSRYVPSGDVPDVVQEAFIKAYRA
 61  LDSFRGDSAFYTWLYRIAVNTAKNYLVAQGRRPPSSDVDAIEAENFEQLERLEAPVDRTL
```

```
121    DYSQRQEQQLNSAIQNLPTDQAKVLRMSYFEALSHREISERLDMPLGTVKSCLRLAFQKL

181    RSRIEES*
``` ii. RNA Polymerases

In some embodiments, the sequence-specific DNA-binding polypeptide is a polypeptide having DNA binding activity and that is a variant of the T7 RNA polymerase (RNAP) and the RNAP's cognate cis-acting sequence (e.g., a promoter recognized by the RNAP) is operably linked to the synthetic operon to control the operon's expression. The T7 RNAP amino acid sequence (SEQ ID NO:241) is as follows:

A molecular tag to promote rapid degradation of the RNAP. For example, an Lon N-terminal tag will result in rapid degradation of the tagged RNAP by the Lon protease system.

A mutated RNAP active site (e.g., within amino acids 625-655 of T7 RNAP). For example, it ha been discovered that a mutation of the position corresponding to amino acid 632 (R632) of T7 RNAP can be mutated to reduce the

```
  1    mntiniaknd  fsdielaaip  fntladhyge  rlareqlale  hesyemgear  frkmferqlk 61    agevadnaaa  kplittllpk  miarindwfe  evkakrgkrp  tafgflgeik  peavayitik 121    ttlacltsad  nttvqavasa  igraiedear  fgrirdleak  hfkknveeql  nkrvghvykk 181    afmqvveadm  lskgllggea  wsswhkedsi  hvgvrcieml  iestgmvslh  rqnagvvgqd 241    setielapey  aeaiatraga  lagispmfqp  cvvppkpwtg  itgggywang  rrplalvrth 301    skkalmryed  vympevykai  niaqntawki  nkkvlavanv  itkwkhcpve  dipaiereel 361    pmkpedidmn  pealtawkra  aaavyrkdka  rksrrislef  mleqankfan  hkaiwfpynm 421    dwrgrvyays  mfnpqgndmt  kglltlakgk  pigkegyywl  kihgancagv  dkvpfperik 481    fieenhenim  acaksplent  wwaeqdspfc  flafcfeyag  vqhhglsync  slplafdgsc 541    sgiqhfsaml  rdevggravn  llpsetvgdi  ygivakkvne  ilqadaingt  dnevvtvtde 601    ntgeisekvk  lgtkalagqw  laygvtrsvt  krsvmtlayg  skefgfrqqv  ledtiqpaid 661    sgkglmftqp  nqaagymakl  iwesysvtvv  aaveamnwlk  saakllaaev  kdkktgeilr 721    krcavhwvtp  dgfpvwqeyk  kpiqtrinlm  flggfrlqpt  intnkdseid  ahkqesgiap 781    nfvhsqdgsh  lrktvvwahe  kygiesfali  hdsfgtipad  aanlfkavre  tmvdtyescd 841    vladfydqfa  dqlhesqldk  mpalpakgnl  nlrdilesdf  afa
```

The T7 RNAP promoter has also been characterized (see, e.g., Rong et al., *Proc. Natl. Acad. Sci. USA*, 95(2):515-519 (1998)) and is well known.

Methods have been discovered for generating orthogonal pairs of RNAP variants and target promoter variants. Due to toxicity of expression of native T7 RNAP, a series of mutations and modifications can be designed such that a library of RNAP variants can be expressed and tested for activity in cells without excessive toxicity. Accordingly, embodiments of the invention provide for one or more of the following modifications (and thus, for example, an embodiment of the invention provides for host cells comprising expression cassettes, or nucleic acids comprising expression cassettes, wherein the expression cassette encodes a RNAP variant substantially identical to T7 RNAP, wherein the expression cassette comprises one or more of the following):

Expression of the T7 RNAP variant can be expressed from a low copy plasmid. Expression of the RNAP can be controlled by a separately encoded protein from a separate vector, thereby blocking expression of the RNAP until a second vector is added to the cells promoting RNAP expression;

Translational control: a GTG start codon; weak ribosomal binding sites; and/or random DNA spacers to insulate RNAP expression can be used;

RNAP's activity. In some embodiments, the RNAP contains a mutation corresponding to R632S.

Moreover, a variety of mutant T7 promoters have been discovered that can be used in a genetic circuit. Thus, in some embodiments, the regulatory sequence of a synthetic operon comprises a mutant sequence as set forth in the table below (SEQ ID NOS:156-163).

| Promoter Name | Sequence TAATACGACTCACTANNNNNAGA | Strength (2009.10.02 to 2009.10.09) |
|---|---|---|
| WT | TAATACGACTCACTATAGGGAGA | 5263 |
| Mut1 | TAATACGACTCACTACAGGCAGA | 365 |
| Mut2 | TAATACGACTCACTAGAGAGAGA | 366 |
| Mut3 | TAATACGACTCACTAATGGGAGA | 577 |
| Mut4 | TAATACGACTCACTATAGGTAGA | 1614 |
| Mut5 | TAATACGACTCACTAAAGGGAGA | 1018 |
| Mut6 | TAATACGACTCACTATTGGGAGA | 3216 |

A number of different stem loop structures that function as terminators for T7 RNAP have also been discovered. See, Table directly below (SEQ ID NOS:242-253). Accordingly, an embodiment of the invention provides for a synthetic operon comprising a promoter functional to a native T7 RNAP or an RNAP substantially identical thereto, wherein the operably linked polynucleotide comprises a terminator selected from the table directly below. Terminators with different sequences can be selected for different transcripts to avoid homologous recombination.

| Terminator Name | Sequence TANNNNAACCSSWWSSSSSTCWWW WCGSSSSSSWWSSGGTTTTTGT | Strength (2009.12.16 Assay) |
|---|---|---|
| 52 | TATAAAACGGGGGGCTAGGGGTTT TTTGT | 107 |
| 23 | TACTCGAACCCCTAGCCCGCTCTT ATCGGGCGGCTAGGGGTTTTTTGT | 714 |
| 72 | TAGCAGAACCGCTAACGGGGGCGA AGGGGTTTTTGT | 1051 |
| 48 | TACTCGAACCCCTAGCCCGCTCTT ATCGGGCGGCTAGGGGTTTTTGT | 1131 |
| 1 | TACATATCGGGGGGGTAGGGGTTT TTTGT | 1297 |
| 2 | TACATATCGGGGGGGTAGGGGTTT TTTGT | 1333 |
| WT | TAGCATAACCCCTTGGGGCCTCTA AACGGGTCTTGAGGGGTTTTTGT | 1395 |
| 31 | TACCCTAACCCCTTCCCCGGTCAA TCGGGGCGGATGGGGTTTTTGT | 1586 |
| 58 | TAGACCAACCCCTTGCGGCCTCAA TCGGGGGGGATGGGGTTTTTGT | 1608 |
| 25 | TACTCTAACCCCATCGGCCGTCTT AGGGGTTTTTGT | 1609 |
| 17 | TACCTCAACCCCTTCCGCCCTCAT ATCGCGGGCATGCGGTTTTTGT | 1887 |

In some embodiments, RNAP variants can be designed comprising an altered specificity loop (corresponding to positions between 745 and 761). Thus in some embodiments, an RNAP is provided that is identical or substantially identical to T7 or T3 RNAP but has a Loop Sequence selected from those in the tables directly below between positions 745 and 761. Loop Sequences=SEQ ID NOS:254, 255, 257 and 259. Promoter Sequences=SEQ ID NOS:157, 256, 258 and 260.

B

| | T7 promoter | T3 promoter | K1F promoter | N4 promoter |
|---|---|---|---|---|
| T7 RNAP | 2177 | 24 | 17 | 14 |
| T3 RNAP | 83 | 1062 | 14 | 14 |
| K1F RNAP | 45 | 26 | 463 | 13 |
| N4 RNAP | 51 | 147 | 46 | 2616 | iii. Activators Requiring Chaperones

In some embodiments, the set of sequence-specific DNA-binding polypeptides comprise polypeptides having DNA binding activity and that require a separate chaperone protein to bind the sequence-specific DNA-binding polypeptide for the sequence-specific DNA-binding polypeptide to be active. Exemplary transcriptional activators requiring a chaperone for activity include, but are not limited to activator is substantially similar to InvF from *Salmonella typhimurium*, MxiE from *Shigella flexneri*, and ExsA from *Pseudomonas aeruginosa*. These listed activators require binding of SicA from *Salmonella typhimurium*, IpgC from *Shigella flexneri*, or ExsC from *Psuedomonas aeruginosa*, respectively, for activation.

Sequence information for the above components are provides as follows (SEQ ID NOS:260-273):

A

| RNAP Family | Scaffold | RNAP Plasmid | Promoter Plasmid | Loop Sequence | Promoter Sequence |
|---|---|---|---|---|---|
| T7 | N249 | N249 | N155 | VWQEYKKPIQTRLNLMFLGQ FRLQPTINTNKDSEIDAHK | TAATACGACTCA CTATAGGGAGA |
| T3 | N115 | N377:115 | N352 | VWQEYKKPIQKRLDMIFLGQ FRLQPTINTNKDSEIDAHK | TAATAACCCTCA CTATAGGGAGA |
| K1F | N115 | N421:115 | N353 | VWQEYKKPIQTRLNLMFLGS FNLQPTVNTNKDSEIDAHK | TAATAACTATCA CTATAGGGAGA |
| N4 | N77 | W78 | W74 | VWQEYKKPIQTRIDCVILGT HRMALTINTNKDSEIDAHK | TAATAACCCACA CTATAGGGAGA |

| Name | Type | DNA sequence encoding the named polypeptide | Optional Mutation |
|---|---|---|---|
| sicA | Gene | atggattatcaaaataatgtcagcgaagaacgtgttgcggaaa tgatttgggatgccgttagtgaaggcgccacgctaaaagacgt tcatgggatccctcaagatatgatggacggtttatatgctcat gcttatgagttttataaccagggacgactggatgaagctgaga cgttctttcgttActttatgcatttatgattttttacaatcccgat tacaccatgggactggcggcagtatgccaactgaaaaaacaa tttcagaaagcatgtgacctttatgcagtagcgtttacgttac ttaaaaatgattatcgccccgttttttttaccgggcagtgtca attattaatgcgtaaggcagcaaaagccagacagtgttttgaa cttgtcaatgaacgtactgaagatgagtctctgcgggcaaaag cgttggtctatctggaggcgctaaaaacggcggagacagagca gcacagtgaacaagaaaaggaataa | |
| sicA* | Mutant sicA | atggattatcaaaataatgtcagcgaagaacgtgttgcggaaa tgatttgggatgccgttagtgaaggcgccacgctaaaagacgt tcatgggatccctcaagatatgatggacggtttatatgctcat gcttatgagttttataaccagggacgactggatgaagctgaga cgttattcgttacttatgcatttatgattttttacaatcccgat tacaccatgggactggcggcagtatgccaactgaaaaaacaat tcagaaagcatgtgacctttatgcagtagcgtttacgttact taaaaatgattatcgccccgtattttttaccgggcagtgtcaat tattaatgcgtaaggcagcaaaagccagacagtgttttgaact tgtcaatgaacgtactgaagatgagtctctgcgggcaaaagcg ttggtctatctggaggcgctaaaaacggcggagacagagcagc acagtgaacaagaaaaggaataa | The large "t" of the sicA sequence above was mutated to "a" by error-prone PCR. This mutation was made to reduce cross talk between SicA and MxiE. |
| invF | Gene with new start codon | atgctaaatacgcaggaagtacttaaagaaggagagaagcgga aaatccgcagcccggaagcatggtttatacagacgtgttccgc gcaaaagctgcatatgtcattttctgaaagccgacacaatgaa aattgcctgattcaggaaggcgcgctgcttttttgcgagcagg ccgttgtcgcaccagtatcaggagacctggttttttcgaccgtt aaaaattgaagtactcagcaaattactggcatttatcgatggc gcaggattagtggacacgacatatgctgaatccgataaatggg ttttgctgagtcctgagtttcgcgctatttggcaagatcgtaa acgctgcgagtactggttttgcagcaaattattacgccttct ccggccttcaataaggtactggcgctgttacgaaaaagcgaa gttactggttggttggctattactcgctcagtcaaccagcgg caacacgatgagaatgctgggagaagactatggcgtttcttat acccatttcgtcgtttgtgcagcagagcgttgggcggaaaag cgaagagtgaattacgaaactggcgtatggcgcaatcgctgct gaatagtgtagaaggccacgagaacatcacccaattagccgtt aatcatggttactcatcgccttcacattttctagtgagatca aagagctgatcggcgtttcgccgcggaaattatcaaatattat tcaattggcagacaaatga | The accepted start codon (the large "atg") was determined to be incorrect and a correct upstream start codon was found. |
| psicA | Promoter | ccacaagaaacgaggtacggcattgagccgcgtaaggcagtag cgatgtattcattgggcgtttttgaatgttcactaaccaccg tcggggtttaataactgcatcagataaacgcagtcgttaagtt ctacaaagtcggtgacagataacaggagtaagta | |
| ipgC | Gene | atgtctttaaatatcaccgaaaatgaaagcatctctactgcag taattgatgcaattaactctggcgctacactgaaagatattaa tgcaattcctgatgatatgatggatgacatttattcatatgct tatgacttttacaacaaaggaagaatagaggaagctgaagttt tcttcaggtttttatgtatatacgacttttacaatgtagacta cattatgggactcgcagctatttatcagataaaagaacagttc caacaagcagcagacctttatgctgtcgcttttgcattaggaa aaaatgactatacaccagtattccatactggacaatgtcagct tcggttgaaagcccccttaaaagctaaagagtgcttcgaactc gtaattcaacacagcaatgatgaaaaattaaaaataaaagcac aatcatacttggacgcaattcaggatatcaaggagtaa | |
| mxiE | Gene with codon optimization | atgagtaaatataaaggcctgaacaccagcaacatgactacat ctacagctctggtcatgaaccggtgaacgttgaactggtgaaa gataaagaacgtaacatcatcgaactggcaccggcgtggaaag gctttttcttttgtgcgtaaccagaacatcaaattcagcgataa cgttaactaccactaccgcttcaacatcaactcttgcgcaaaa ttcctggcgtttgggattatttagcggcgcctggttgaac attctcacgcagaaaatgcatccatttctaccacgaaaacga tctgcgtgatagctgtaatacggaatctatgctggataaactg atgctgcgcttcatttttagtagcgatcagaacgtgtctaatg ccctggcaatgatccgtatgaccgaaagttatcatctggttct gtacctgctgcgtacgattgaaaagaaaaagaagtgcgcatc aaaaagcctgaccgaacactatggcgtttctgaagcgtactttc | The wide type gene has "tttttttttt" in this enlarged sequence region. One more "t" was added to make "tttttttttt" and then the entire gene was codon optimized by GenScript. The additional "t" was added to make this ORF in-frame. In addition, the wide-type gene starts |

-continued

| Name | Type | DNA sequence encoding the named polypeptide | Optional Mutation |
|---|---|---|---|
| | | gtagtctgtgtcgcaaagcgctgggtgccaaagtgaaagaaca gctgaacacgtggcgcctggtgaatggcctgctggatgttttc ctgcataaccagaccattacgagcgcggccatgaacaatggtt atgcgtctaccagtcacttcagcaatgaaattaaaacgcgtct gggctttagtgcccgcgaactgagcaacatcaccttcctggtg aagaaaattaatgaaaaaatctaa | with "g" and this synthetic gene starts with "a." |
| pipaH9.8 | Promoter | gcgaaaatgacatcaaaaacgccattaacctgatgttctgggg aatataaatgtcaggctagggtcaaaaatcgtggcgttgacaa aatggctgcgttacgtcattgagcatatccaggactggccggc aaaccgggtacgcgatctgttgccttggaaagttgatctgacc tctcagtaaatatcaatacggttctgacgagccgcttaccgtt caaatatgaagtacgatgtttaactaaccgaaaaacaagaaca atacggtgcaaacaggccattcacggttaactgaaacagtatc gttttttttacagccaattttgtttatccttattataataaaaa agtgct | |
| pipaH9.8* | Promoter with mutation | gcgaaaatgacatcaaaaacgccattaacctgatgttctgggg aatataaatgtcaggctagggtcaaaaatcgtggcgttgacaa aatggctgcgttacgtcattgagcatatccaggactggccggc aaaccgggtacgcgatctgttgccttggaaagttgatctgacc tctcagtaaatatcaatacggttctgacgagccgcttaccgtt caaatatgaagtacgatgtttaactaaccgaaaaacaagaaca atacggtgcaaacaggccattcacggttaactgaaacagtatc gttttttttacagccaattttgtttatccttattaagataaaaa agtgct | The enlarged "ta" above of pipaH9.8 was mutated to "ag" by saturation mutagenesis. This mutation was made to reduce leaky expression of pipaH9.8. |
| exsC | Gene | atggatttaacgagcaaggtcaaccgactgcttgccgagttcg caggccgtatcggtttgccttccctgtccctcgacgaggaggg catggcgagcctcctgttcgacgaacaggtgggcgtcaccctg ttgctgctcgccgagcgcgagcgtctgttgctggaggccgatg tggcgggcatcgatgtgctgggcgaggggatattcgccagctc gccagcttcaaccgccattggcaccgtttcgatctgcattcg gcttcgacgagctgaccggcaaggtccagttgtatgcgcagat tctcgcagcgcaactgaccctcgaatgcttcgaggcgaccttg gccaatctgctcgatcacgccgagttctggcagcgcctgctgc cgtgcgacagtgatcgcgaggcggtcgctgcggtcggcatgag ggtttga | |
| exsD | Gene | atggagcaggaagacgataagcagtactcccgagaagcggtgt tcgctggcaggcgggtatccgtggtgggctcggacgcccgctc gcggggtcgggtgccgggttacgcatcgagcagtttgtatcgt gagtccggaatcatcagtgcgcggcaactggcgttgctgcagc ggatgctgccgcgcctgcggctggagcaactgttccgctgcga gtggttgcagcagcgcctggcgcgcggcctggcgctggggcgg gaagaggtgcggcagattctcctctcgcgcggcgcaggacgacg acggctggtgctccgaactgggcgaccgggtcaacctcgccgt gccgcagtcgatgatcgactgggtcctgctgccggtctatggc tggtgggaaagcctgctcgaccaggcgatccccggctggcgcc tgtcgctggtggagctggagacccagtcccggcaactgcgagt caagtccgaattctggtcccgcgtggccgagctggagccggag caggcccgcgaggaactggccagggtcgccaagtgccaggcgc gcacccaggaacaggtggccgaactggccggcaagctggagac ggcttcggcactggcgaagagcgcctggccgaactggcagcgg ggcatggcgacgctgctcgccagcggcgggctgccggcttcg agccgatcccgaggtcctcgaatgcctctggcaacctctctg ccggctggacgacgacgtcggcgcggcggacgccgtccaggcc tggctgcacgaacgcaacctgtgccaggcacaggatcacttct actggcagagctga | |
| exsA | Gene | atgcaaggagccaaatctcttggccgaaagcagataacgtctt gtcattggaacattccaactttcgaatacagggtaaacaagga agagggcgtatatgttctgctcgagggcgaactgaccgtccag gacatcgattccactttttgcctggcgcctggcgagttgcttt tcgtccgccgcggaagctatgtcgtaagtaccaagggaaagga cagccgaatactctggattccattatctgcccagtttctacaa ggcttcgtccagcgcttcggcgcgctgttgagtgaagtcgagc gttgcgacgagcccgtgccgggcatcatcgcgttcgctgccac gcctctgctggccggttgcgtcaaggggttgaaggaattgctt gtgcatgagcatccgccgatgctcgcctgcctgaagatcgagg agttgctgatgctcttcgcgttcagtccgcaggggccgctgct gatgtcggtcctgcgcgaactgagcaaccgcatgtcgagcgt ctgcagctattcatggagaagcactacctcaacgagtggaagc tgtccgactcctcccgcgagttcggcatggggctgaccaccctt caaggagctgttcggcagtgtctatgggtttcgccgcgcgcc tggatcagcgagcggagaatcctctatgcccatcagttgctgc tcaacagcgacatgagcatcgtcgacatcgccatggaggcggg | |

-continued

| Name | Type | DNA sequence encoding the named polypeptide | Optional Mutation |
|---|---|---|---|
| | | cttttccagtcagtcctatttcacccagagctatcgccgccgt ttcggctgcacgccgagccgctcgcggcagggggaaggacgaat gccgggctaaaaataactga | |
| pexsD | Promoter | gaaggacgaatgccgggctaaaaataactgacgttttttgaaa gcccggtagcggctgcatgagtagaatcggcccaaat | |
| pexsC | Promoter | gatgtggcttttttcttaaaagaaaagtctctcagtgacaaaa gcgatgcatagcccggtgctagcatgcgctgagcttt | |
| rfp | Gene | atggcttcctccgaagacgttatcaaagagttcatgcgtttca aagttcgtatggaaggttccgttaacggtcacgagttcgaaat cgaaggtgaaggtgaaggtcgtccgtacgaaggtacgcagacc gctaaactgaaagttaccaaaggtggtccgctgccgttcgctt gggacatcctgtccccgcagttccagtacggttccaaagctta cgttaaacacccggctgacatcccggactacctgaaactgtcc ttcccggaaggtttcaaatgggaacgtgttatgaacttcgaag acggtggtgttgttaccgttacccaggactcctccctgcaaga cggtgagttcatctacaaagttaaactgcgtggtactaacttc ccgtccgacggtccggttatgcagaaaaaaaccatgggttggg aagcttccaccgaacgtatgtaccggaagacggtgctctgaa aggtgaaatcaaaatgcgtctgaaactgaaagacggtggtcac tacgacgctgaagttaaaaccacctacatggctaaaaaaccgg ttcagctgccgggtgcttacaaaaccgacatcaaactggacat cacctcccacaacgaagactacaccatcgttgaacagtacgaa cgtgctgaaggtcgtcactccaccggtgctgcagcaaacgacg aaaactacgcttaa | |

C. Controlling Operon Expression

As noted above, the one or more synthetic operons are controlled by regulatory elements responsive to a sequence-specific DNA binding polypeptide (e.g., a transcriptional activator). Where more than one operon is used, it can be desirable that each operon be responsive to the same transcriptional activator, albeit with a different regulatory sequence that controls the "strength" of expression of a particular operon. As noted above, in some embodiments, the transcriptional activator is a T7 RNAP or a variant thereof.

Expression of the sequence-specific DNA binding polypeptide can be controlled on a separate expression cassette, the expression cassette comprising a promoter operably linked to a polynucleotide encoding the sequence-specific DNA binding polypeptide. In some embodiments, the promoter is inducible, thereby imparting control of expression of the operon based on the inducer. Exemplary inducible promoters (with inducer in parentheses) include, e.g., Ptac (IPTG), Ptrc (IPTG), Pbad (arabinose), Ptet (aTc), Plux (AI-1). Alternatively, in some embodiments, the promoter is constitutive.

In some embodiments, additional "buffer" nucleotide sequences are inserted between promoters and ribosomal binding sites, between coding sequences and terminators, and/or between coding sequences and a subsequent ribosomal binding site. These sequences act as "buffers" in that they reduce or eliminate regulatory cross-talk between different coding sequences. In some embodiments, the spacer forms a stem loop, is a native sequence from a metabolic pathway, or is from a 5'-UTR, e.g., obtained from a phage. In some embodiments, the stem loop is a ribozyme. In some embodiments, the ribozyme is RiboJ. In some embodiments, the buffer sequence is selected from sequences of a given length with nucleotides selected at random. In some embodiments, the buffer sequence is a UP-region of a promoters. UP regions can positively influence promoter strength and are generally centered at position −50 of a promoter (as measured from the start of transcription). See, e.g., Estrem, et al., *PNAS*, 95 (11): 9761-9766 (1988). In some embodiments, the buffer sequence is an extended 5-UTR sequence.

Exemplary buffer sequences include those listed in the table below (SEQ ID NOS:274-333, respectively):

| Sources | Sequences |
|---|---|
| T5 phage | agttcgatgagagcgataaccctctacaaataattttgtttaa |
| T5 phage | ataaattgataaacaaaaacctctacaaataattttgtttaa |
| T5 phage | ataaatttgagagaggagttcctctacaaataattttgtttaa |
| T5 phage | attaaagaggagaaattaaccctctacaaataattttgtttaa |
| T5 phage | aaacctaatggatcgaccttcctctacaaataattttgtttaa |
| T7 phage | atcgagagggacacggcgacctctacaaataattttgtttaa |
| T7 phage | gctaggtaacactagcagccctctacaaataattttgtttaa |
| T7 phage | atgaaacgacagtgagtcacctctacaaataattttgtttaa |
| T7 phage | agggagaccacaacggtttccctctacaaataattttgtttaa |

-continued

| Sources | Sequences |
|---|---|
| High-transcription escape | attaaaaaacctgctaggatcctctacaaataattttgtttaa |
| High-transcription escape | ataaaggaaaacggtcaggtcctctacaaataattttgtttaa |
| High-transcription escape | ataggttaaaagcctgtcatcctctacaaataattttgtttaa |
| Carbon utilization | acaataaaaaatcatttacatgtttcctctacaaataattttgtttaa |
| Carbon utilization | agaagcagcgcgcaaaaatcagctgcctctacaaataattttgtttaa |
| Carbon utilization | atgagttcatttcagacaggcaaatcctctacaaataattttgtttaa |
| Carbon utilization | aacttgcagttatttactgtgattacctctacaaataattttgtttaa |
| Carbon utilization | agccacaaaaaagtcatgttggttcctctacaaataattttgtttaa |
| Carbon utilization | acacagtcacttatcttttagttaaaaggtcctctacaaataattttgtttaa |
| Anti-escaping sequences | atccggaatcctcttcccggcctctacaaataattttgtttaa |
|  | aacaaaataaaaaggagtcgctcaccctctacaaataattttgtttaa |
| T5 phage | agttcgatgagagcgataacagttccagattcaggaactataa |
| T5 phage | ataaattgataaacaaaaaagttccagattcaggaactataa |
| T5 phage | ataaatttgagagaggagttagttccagattcaggaactataa |
| T5 phage | attaaagaggagaaattaacagttccagattcaggaactataa |
| T5 phage | aaacctaatggatcgaccttagttccagattcaggaactataa |
| T7 phage | atcgagagggacacggcgaagttccagattcaggaactataa |
| T7 phage | gctaggtaacactagcagcagttccagattcaggaactataa |
| T7 phage | atgaaacgacagtgagtcaagttccagattcaggaactataa |
| T7 phage | agggagaccacaacggtttcagttccagattcaggaactataa |
| High-transcription escape | attaaaaaacctgctaggatagttccagattcaggaactataa |
| High-transcription escape | ataaaggaaaacggtcaggtagttccagattcaggaactataa |
| High-transcription escape | ataggttaaaagcctgtcatagttccagattcaggaactataa |
| Carbon utilization | acaataaaaaatcatttacatgtttagttccagattcaggaactataa |
| Carbon utilization | agaagcagcgcgcaaaaatcagctgagttccagattcaggaactataa |
| Carbon utilization | atgagttcatttcagacaggcaaatagttccagattcaggaactataa |
| Carbon utilization | aacttgcagttatttactgtgattaagttccagattcaggaactataa |
| Carbon utilization | agccacaaaaaagtcatgttggttagttccagattcaggaactataa |
| Carbon utilization | acacagtcacttatatttagttaaaaggtagttccagattcaggaactataa |
| Anti-escaping sequences | atccggaatcctcttcccggagttccagattcaggaactataa |
|  | aacaaaataaaaggagtcgctcacagttccagattcaggaactataa |
| Stem loops | gatcaccaggggggatccccggtgaaggat |
| Stem loops | gatcgcccaccggcagctgccggtgggcgatcaaggat |
| Stem loops | gatcatcggtagagttaatattgagcagatcccccggtgaaggat |

| Sources | Sequences |
|---|---|
| Stem loops | attgatctggttattaaaggtaatcgggtcatttta |
| Stem loops | gttctccacgggtgggatgagcccctcgtggtggaaatgcg |
| Stem loops | agcatgaggtaaagtgtcatgcaccaa |
| Stem loops | acgtcgacttatctcgagtgagatattgttgacggtac |
| Stem loops | acgtcgacttatctcgagtgagataagttgacggtac |
| Stem loops | acgtcgacttatctcgagactgcagttcaatagagatattgttgacggtac |
| Stem loops (Ribozyme) | gactgtcaccggatgtgattccggtctgatgagtccgtgaggacgaaacag |
| Stem loops | gatcaccaggggatccccggtgaaggatcctctacaaataattngtttaa |
| Stem loops | Gatcgcccaccggcagctgccggtgggcgatcaaggatcctctacaaataattttgataa |
| Stem loops | gatcatcggtagagttaatattgagcagatcccccggtgaaggatcctctacaaataattttgtttaa |
| Stem loops | attgatctggttattaaaggtaatcgggtcattttacctctacaaataattttgtttaa |
| Stem loops | Gttctccacgggtgggatgagcccctcgtggtggaaatgcgcctctacaaataaattgtttaa |
| Stem loops | agcatgaggtaaagtgtcatgcaccaacctctacaaataattttgataa |
| Stem loops | Acgtcgacttatctcgagtgagatattgttgacggtaccctctacaaataattttgtttaa |
| Stem loops | Acgtcgacttatctcgagtgagataagttgacggtaccctctacaaataattttgtttaa |
| Stem loops | acgtcgacttatctcgagactgcagttcaatagagatattgttgacggtaccctctacaaataattttgtttaa |
| Stem loops (Ribozyme) | gactgtcaccggatgtgattccggtctgatgagtccgtgaggacgaaacagcctctacaaataattttgtttaa |

The synthetic operons and/or the expression cassette for expressing the sequence-specific DNA binding polypeptide can be carried on one or more plasmids, e.g., in a cell. In some embodiments, the operon and the expression cassette are on different plasmids. In some embodiments, the expression cassette plasmid and/or operon plasmid(s) are low copy plasmids. Low copy plasmids can include, for example, an origin of replication selected from PSC101, PSC101*, F-plasmid, R6K, or IncW.

III. Synthetic Operons

Embodiments of the present invention also provide for synthetic operons, for example as generated by the methods described herein.

IV. Systems of Synthetic Operons

Embodiments of the invention also provide for systems comprising synthetic operons and one or more controlling expression cassettes, wherein the expression cassette encodes a sequence-specific DNA binding polypeptide controlling expression of the synthetic operon(s). In some embodiments, the controlling expression cassette(s) are genetic circuits. For example, the expression cassettes can be designed to act as logic gates, pulse generators, oscillators, switches, or memory devices. In some embodiments, the controlling expression cassette are linked to a promoter such that the expression cassette functions as an environmental sensor. In some embodiments, the environmental sensor is an oxygen, temperature, touch, osmotic stress, membrane stress, or redox sensor.

As explained above, in some embodiments, the expression cassette encodes T7 RNAP or a functional variant thereof. In some embodiments, the T7 RNAP is the output of the genetic circuit(s).

The operons and expression cassettes can be expressed in a cell. Thus in some embodiments, a cell contains the systems of the invention. Any type of host cell can comprise the system.

V. Computation

In some aspects, the invention utilizes a computer program product that determines experimental values for controlling the magnitude of expression of two or more genes. This may be used for example to optimize a system property (e.g. nitrogen fixation levels). In one embodiment, the program code receives one or more input data points, wherein the input data points provide information about one or more regulatory elements and a system property. It then uses a computational method to determine a next data point. In one aspect, the computational method may be a design of experiments (DoE) method.

In some embodiments, the program code-generated next data point can then be used for further experimentation, e.g., to see if the suggested next data point results in optimized expression level for two or more genes, leading to an improvement in a desired system property. In one aspect, the generation of next data points is repeated until a desired system property level is obtained. In another aspect, the next data points are iteratively generated until the magnitude of expression of two or more genes reaches a desired level.

In some embodiments, the computer program code may use a computational method that employ numerical analysis or optimization algorithms. In some aspects, the numerical optimization methods may use the is the Nelder-Mead algorithm, the Newton's method, the quasi-Newton method, the conjugate gradient method, an interior point method, a gradient descent, a subgradient method, a ellipsoid method, the Frank-Wolfe method, an interpolation method and pattern search methods, or an ant colony model.

In one specific embodiment, the computer program to generate the next data point for experimentation uses the Nelder-Mead algorithm. The computer-implemented method will receive one or more input data points and calculate the reflection point, expansion point or contraction point to computationally determine the next data point to experiment with, based on the input data points.

In one implementation of the Nelder-Mead algorithm, the program code will take the received input data points as the simplex vertices of an n-dimensional space, having n+1 simplex vertices. Then the objective function will be evaluated for each vertex of the simplex, and the algorithm uses this information to propose a sequence of new coordinates for evaluation. New coordinates will be determined by the computer code according to the following algorithmic logic:

1. Order the simplex vertices: $f(x_1) \leq f(x_2) \leq \ldots \leq f(x_{n+1})$
2. Calculate $x_0$, the center of gravity of all points except $x_{n+1}$.
3. Calculate a Reflection coordinate: $x_r = x_o + \alpha(x_o - x_{n+1})$
4. Calculate an Expansion coordinate: $x_e = x_o + r(x_o - x_{n+1})$
5. Calculate a Contraction coordinate: $x_e = x_n + \rho(x_o - x_{n+1})$
6. Calculate Reduction coordinates: $x_i = x_1 + \sigma(x_i - x_1)$ for all $i \in \{2, \ldots, n+1\}$ The objective function is evaluated at these points and used to determine a new simplex according to the following criteria:

1. If the Reflection, Expansion or Contraction coordinates are better than the worst simplex point, $x_{n+1}$, define a new simplex by replacing the worst simplex point with the best of the three (Reflection, Expansion or Contraction).
2. Otherwise, define a new simplex by combining the best simplex point with the Reduction coordinates.

In one embodiment, a computer program product is provided comprising a tangible computer readable medium storing a plurality of instructions for controlling a processor to perform an operation for determining an experimentation point for controlling the magnitude of expression of two or more genes, the instructions comprising receiving one or more input data points, wherein the input data points provide information about one or more regulatory elements and a system property; and determining, with a computer, a next data point using a computational method, wherein the next data point provides information about the one or more regulatory elements.

Figure 25:
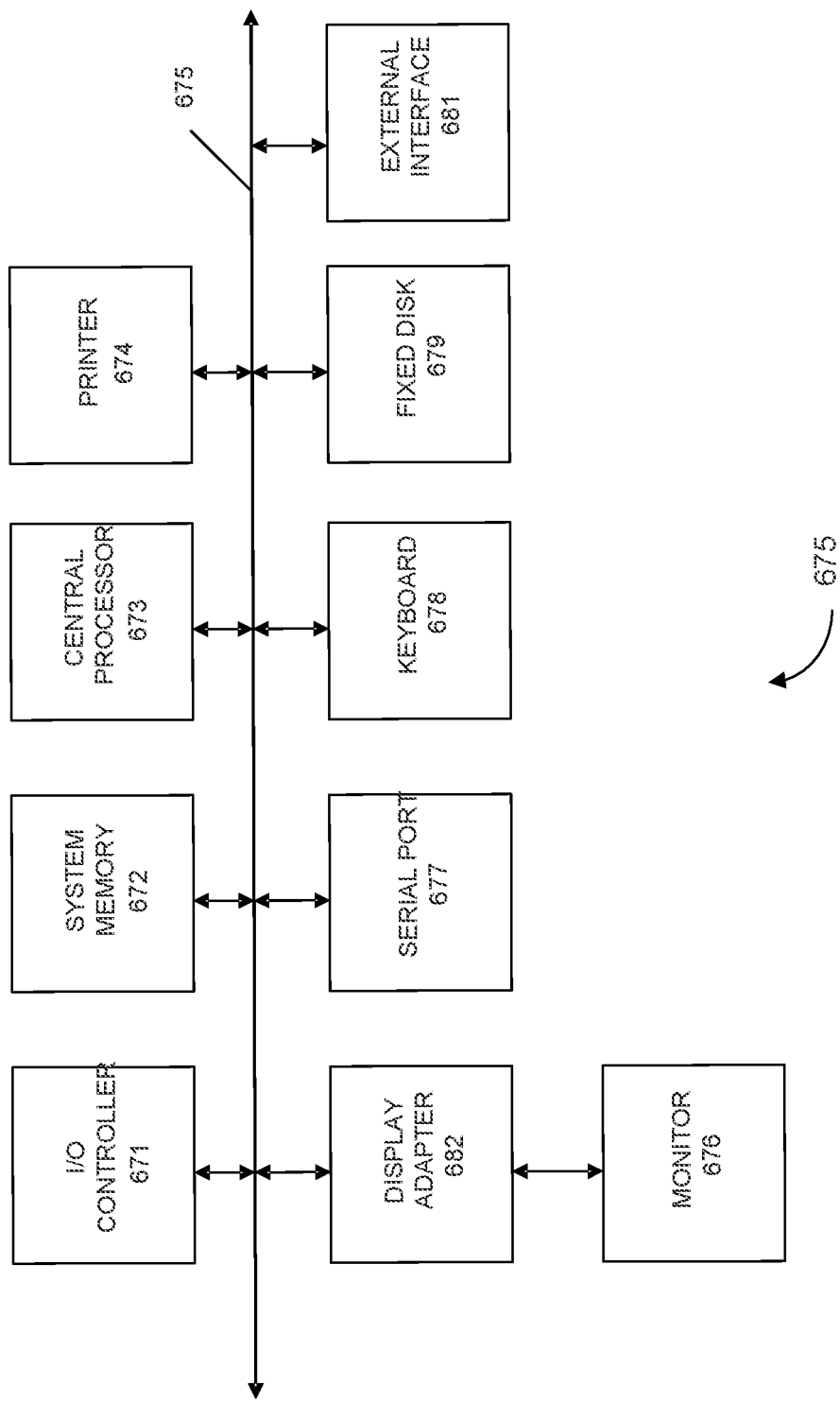
FIG. 25 shows a block diagram of a computer system.

FIG. 25 shows a block diagram of an example computer system 600 usable with system and methods according to embodiments of the present invention. The computer system 600 can be used to run the program code for various method claims according to embodiments of the present invention.

Any of the computer systems mentioned herein may utilize any suitable number of subsystems. Examples of such subsystems are shown in FIG. 25 in computer apparatus 600. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 25 are interconnected via a system bus 675. Additional subsystems such as a printer 674, keyboard 678, fixed disk 679, monitor 676, which is coupled to display adapter 682, and others are shown. Peripherals and input/output (I/O) devices, which couple to I/O controller 671, can be connected to the computer system by any number of means known in the art, such as serial port 677. For example, serial port 677 or external interface 681 can be used to connect computer system 600 to a wide area network such as the Internet, a mouse input device, or a scanner. The interconnection via system bus 675 allows the central processor 673 to communicate with each subsystem and to control the execution of instructions from system memory 672 or the fixed disk 679, as well as the exchange of information between subsystems. The system memory 672 and/or the fixed disk 679 may embody a computer readable medium. Any of the values mentioned herein can be output from one component to another component and can be output to the user.

A computer system can include a plurality of the same components or subsystems, e.g., connected together by external interface 681 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner or varied from those shown and described herein without departing from the spirit and scope of embodiments of the invention.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

EXAMPLES

The following examples are offered to illustrate, but not to limit the claimed invention.

Example 1

Use of the Nelder-Mead Method to Optimize Efficiency of Operon Discovery

This examples illustrates how to recombinant and computationally manipulate and select native gene cluster coding sequences and heterologous regulatory sequences. We have termed this process "refactoring", which comprises optimization of multiple genes, regulation of the gene cluster, and establishment of the genetic context for the biological circuit. Refactoring complex gene clusters and engineering metabolic pathways requires numerous iterations between design, construction and evaluation in order to improve a desired system property, e.g. higher product titers, lower toxicity, or improved nitrogen fixation.

One common way to affect these properties is to modify gene expression levels within the system, even if the direct relationship between gene expression and the system property is unknown. Making quantitative changes to gene expression can be achieved through the use of regulatory elements, e.g. promoters and ribosome binding sites, that exhibit rationally predictable behavior.

It is possible to utilize numerical optimization methods to guide selection of regulatory elements in order to alter gene expression and to improve desired system properties. One relevant algorithm is the Nelder-Mead method, a nonlinear optimization algorithm that minimizes an objective function in multidimensional space. We use the Nelder-Mead method to optimize a system property where each dimension in algorithmic space corresponds to expression of a gene in the engineered system. Points in this space represent a particular combination of expression levels for the genes in the system. As a result, each point may be considered a uniquely engineered strain. The algorithm is used to suggest new coordinates in space that improve the system property. New strains can be engineered by modifying regulatory elements to attain the suggested levels of gene expression. After evaluating the performance of the new strains, the algorithm can be used to predict subsequent modifications. This process iterates until the system property has been improved a desired amount.

The Nelder-Mead method relies on the concept of a simplex, which is an object in N dimensional space having N+1 vertices. The objective function is evaluated at each vertex of the simplex, and the algorithm uses this information to propose a sequence of new coordinates for evaluation. New coordinates are proposed according to the following process:

1. Order the simplex vertices: $f(x_1) \leq f(x_2) \leq \ldots \leq f(x_{n+1})$
2. Calculate $x_0$, the center of gravity of all points except $x_{n+1}$.
3. Calculate a Reflection coordinate: $x_r = x_o + \alpha(x_o - x_{n+1})$
4. Calculate an Expansion coordinate: $x_e = x_o + r(x_o - x_{n+1})$
5. Calculate a Contraction coordinate: $x_c = x_{n+1} + \rho(x_o - x_{n+1})$
6. Calculate Reduction coordinates: $x_i = x_1 + \sigma(x_i - x_1)$ for all $i \in \{2, \ldots, n+1\}$ The objective function is evaluated at these points and used to determine a new simplex according to the following criteria:

1. If the Reflection, Expansion or Contraction coordinates are better than the worst simplex point, $x_{n+1}$, define a new simplex by replacing the worst simplex point with the best of the three (Reflection, Expansion or Contraction).
2. Otherwise, define a new simplex by combining the best simplex point with the Reduction coordinates.

Figure 2:
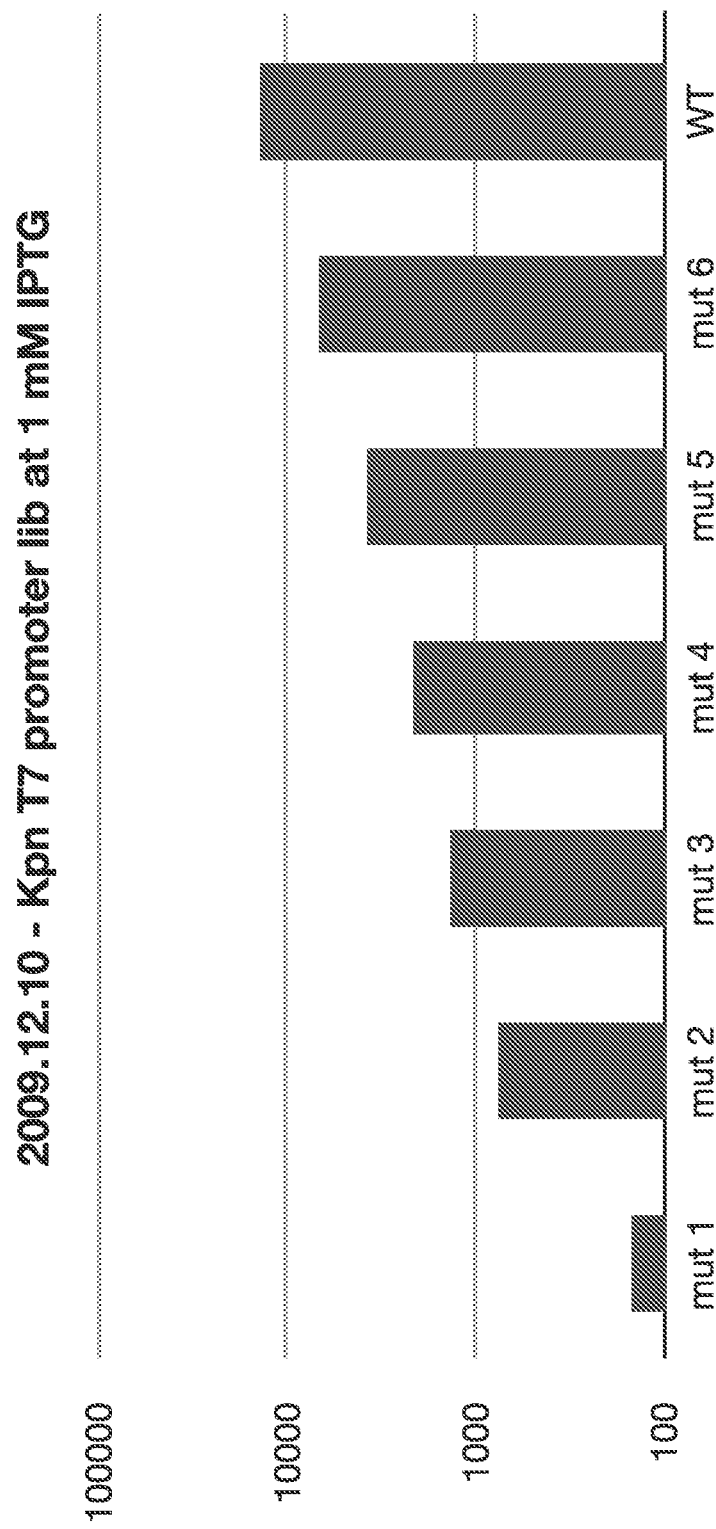
FIG. 2 illustrates the quantitatively measurement of the capacity of the synthetic operon to complement a nifEN knockout strain and recover the ability to fix nitrogen.

These steps constitute an iteration of the algorithm. The newly defined simplex becomes the seed for generating new coordinates during the next iteration of the algorithm. Iterations typically continue until one of the coordinates in the simplex crosses a desired threshold for objective function evaluation. We have optimized the performance of a nitrogen fixation operon by varying the selection of promoters that control expression of individual genes. We initially refactored the nifEN operon so that each gene was expressed under the control of a unique T7 promoter (FIG. 1). To assess the impact of refactoring the nifEN operon, we quantitatively measured the capacity of the synthetic operon to complement a nifEN knockout strain and recover the ability to fix nitrogen (FIG. 2). Our refactored system showed limited ability to fix nitrogen (20% of wild-type activity).

Figure 4A:
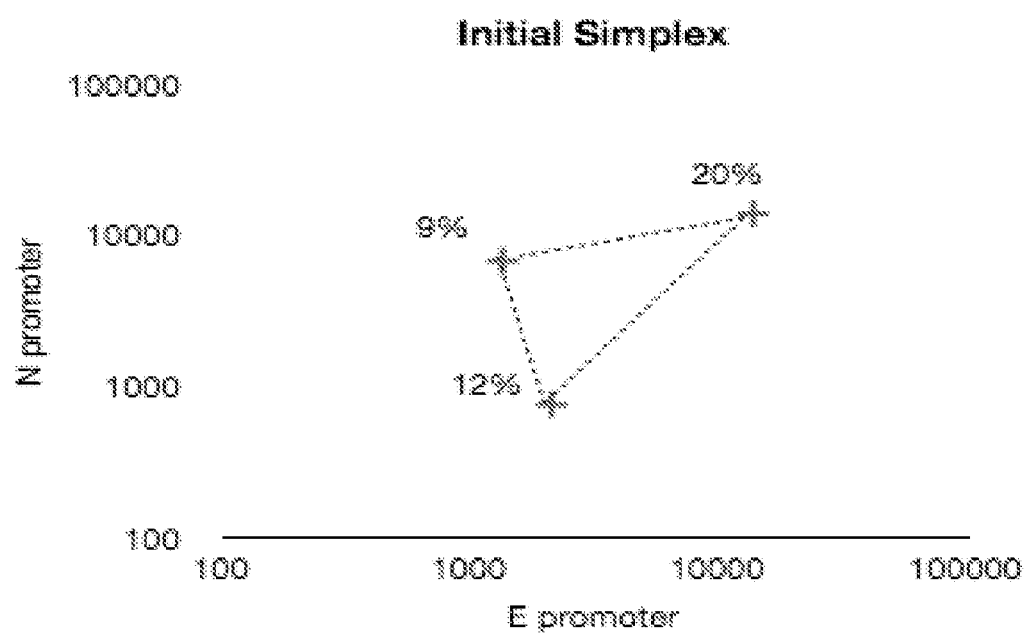
FIGS. 4A-4B illustrates strengths of T7 promoters to control nifE and nifN genes in selected mutant strains.
Figure 4B:
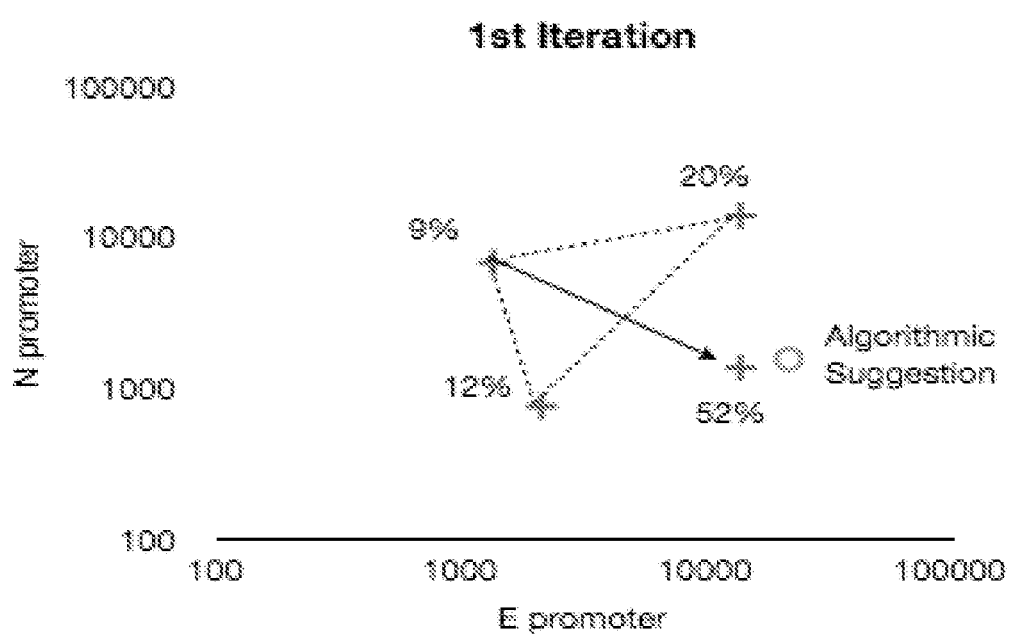
Figure 6:
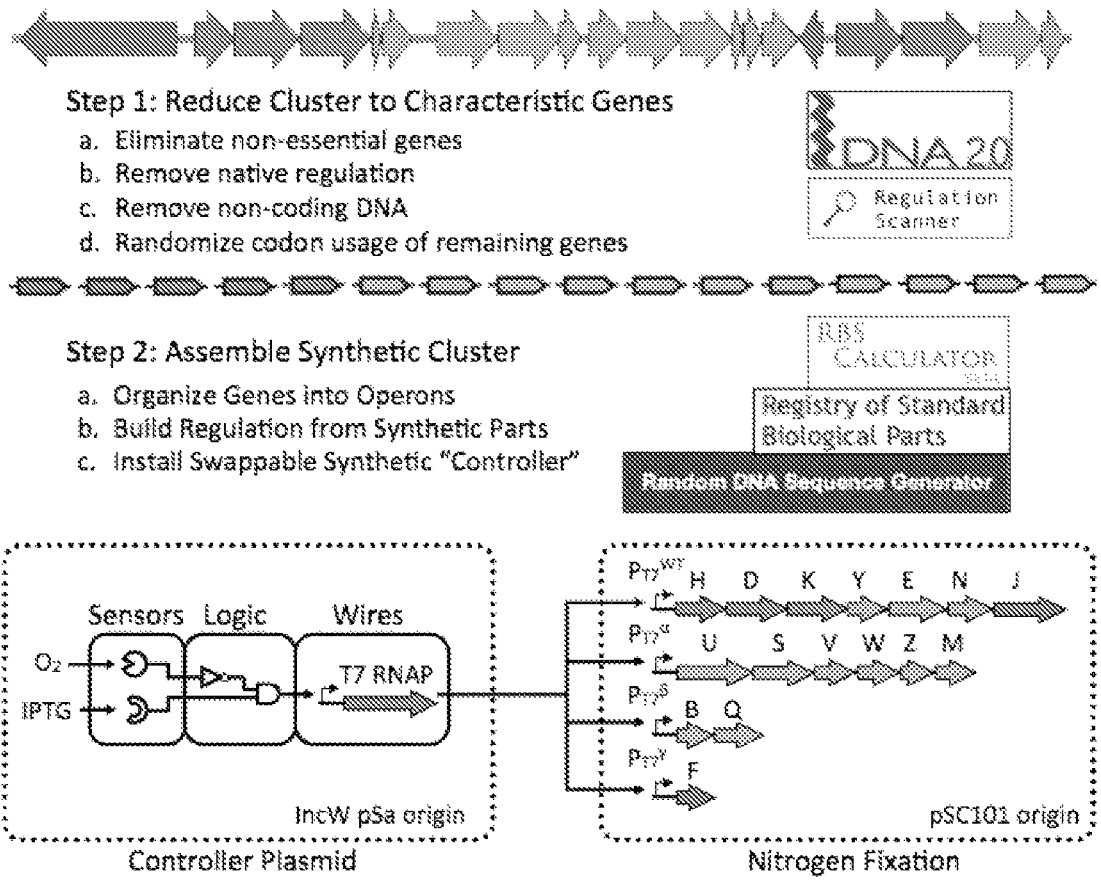
FIG. 6 illustrates the method of refactoring nitrogen fixation.

We subsequently applied the Nelder-Mead method to optimize nifE and nifN gene expression with the goal of improving nitrogen fixation rates. Our algorithmic space consisted of two dimensions, nifE and nifN expression. Our coordinate system was scaled to the strength of the promoters controlling these genes. To enable varied levels of gene expression, we generated and characterized a library of mutant T7 promoters (FIG. 3). Our library covers three order of magnitude of gene expression (This is the same library that is described in U.S. Provisional Patent Application No. 61/493,733. Here, it is characterized for behavior in *Klebsiella oxytoca*). We then randomly selected mutants from the library of T7 promoters to generate two additional strains with rationally altered levels of nifE and nifN expression. The strength of T7 promoters used in these three strains defined our initial simplex. We evaluated nitrogen fixation for each strain in the simplex (strain 1: 20%, strain 2: 9%, strain 3: 12%) and used the algorithm to calculate Reflection coordinates (FIG. 4). To construct the strain that matched the Reflection coordinates, we chose promoters from our library nearest to the coordinates in strength. We evaluated nitrogen fixation in this Reflection strain and found that it significantly outperformed (52%) our initial strains (FIG. 5).

Our improved strain had surprising results and surpassed expectations, and performed sufficiently for downstream applications. To reach higher levels of gene expression, stronger promoters can be engineered and used in the methods of the invention. Alternatively, complimentary changes to multiple regulatory elements, e.g., the promoter and ribosome binding site for a given gene, can be used to achieve desired expression levels. This involves describing the strengths of each type of element in common units of expression. This example demonstrates that new strains can be engineered by modifying regulatory elements to attain the desired levels of gene expression. The example also illustrates the use of numerical optimization methods, such as, but not limited to the Nelder-Mead method, to guide selection of regulatory elements in order to alter gene expression and to improve desired system properties.

Example 2

Refactoring Nitrogen Fixation

This example demonstrates the method of refactoring the nitrogen fixation gene cluster. The method includes steps that comprise: 1) removing host regulation and implement synthetic, orthogonal regulation; 2) tracking the contribution of each regulatory part to gene cluster function; 3) promoting modularity and integration with synthetic circuits; and 4) creating a platform amenable to rational optimization. In certain embodiments, the method of refactoring nitrogen fixation comprises reducing cluster to characteristic genes and assembling synthetic cluster.

The nif gene cluster from *Klebsiella oxytoca* has been one of the primary models for study of the nitrogenase enzyme (FIG. 7; see, Rubio and Ludden, Maturation of Nitrogenase: a Biochemical Puzzle, *J. Bacteriology*, 2005). It is a concise gene cluster, encompassing 20 genes in 7 operons within 25 kb of DNA. The nitrogenase enzyme is composed of two major units, Component I and Component II, that interact to facilitate the reduction of multiply bonded gases like $N_2$. Within the enzyme complex, multiple Fe—S clusters are responsible for active site chemistry and electron transfer to the active site. The majority of the genes in the gene cluster are involved in Fe—S cluster biosynthesis, chaperoning and insertion into the final enzyme complex.

Nearly every nif gene produces a protein with a function known to be essential to nitrogenase assembly or function (see, Simon, Homer and Roberts, Perturbation of nifT expression in *Klebsiella pneumoniae* has limited effect on nitrogen fixation, J. Bacteriology, 1996 and Gosink, Franklin and Roberts, The product of the *Klebsiella pneumoniae* nifX gene is a negative regulator of the nitrogen fixation (nif) regulon, *J Bacteriology*, 1990). Two genes, nifL and nifA, encode the master regulatory proteins. The nifT gene has no known function, and eliminating it has little effect on nitrogen fixation. Additionally, while elimination of nifX has minor effect on nitrogen fixation, its overexpression detrimentally reduces enzyme activity. For these reasons, we chose to eliminate nifL, nifA, nifT and nifX from our refactored gene cluster.

We designed synthetic genes by codon randomizing the DNA encoding each amino acid sequence. Protein coding sequences were based on the sequence deposited in the NCBI database (X13303; see, Arnold et al., Nucleotide sequence of a 24,206-base-pair DNA fragment carrying the entire nitrogen fixation gene cluster of *Klebsiella pneumoniae*. JMB, 1988). Codon selection was performed by DNA2.0 using an internal algorithm and two guiding criteria. We specified that our genes express reasonably well in both *E. coli* and *Klebsiella*. Also, we specified that our codon usage be as divergent as possible from the codon usage in the native gene. While designing synthetic genes, we scanned each proposed sequence for a list of undesired features and rejected any in which a feature was found. The feature list includes restriction enzyme recognition sites, transposon recognition sites, repetitive sequences, sigma 54 and sigma 70 promoters, cryptic ribosome binding sites, and rho independent terminators. FIG. 18 shows DNA sequences for native genes and synthetic genes, as well as the percent common nucleotide and codon identities between each pair.

Figure 8:
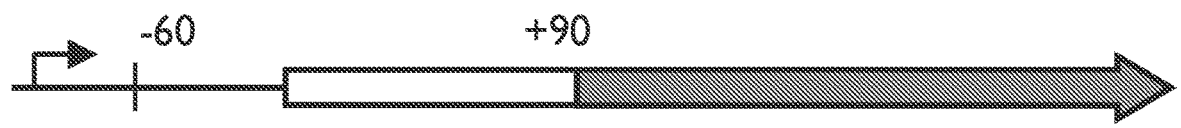
FIG. 8 depicts a scheme of a fluorescent reporter plasmid in which the 150 bp surrounding a gene's start codon (from −60 to +90) was fused to the mRFP gene and expressed under the control of the Ptac promoter.
Figure 9:
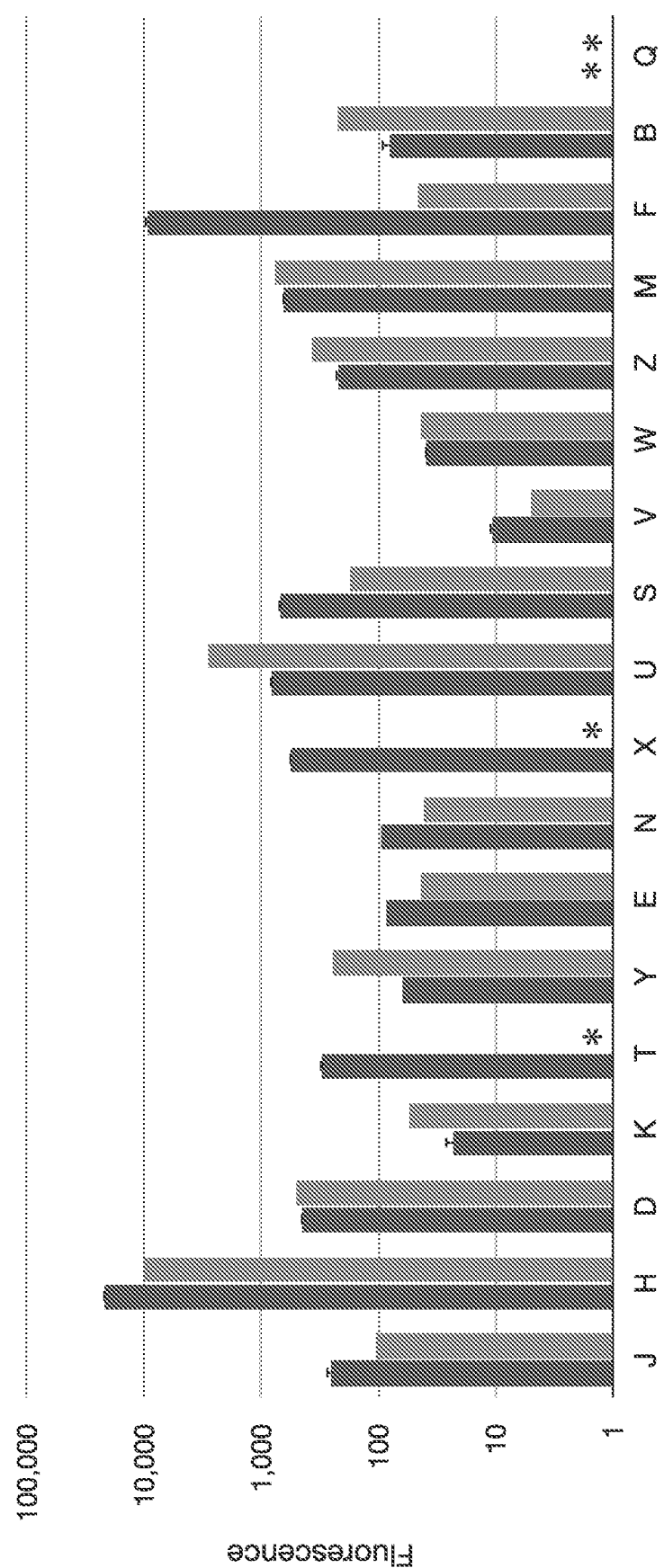
FIG. 9 illustrates the measured fluorescence by flow cytometry.

Synthetic ribosome binding sites were chosen to match the strength of each corresponding native ribosome binding site. To characterize the strength of a given native ribosome binding site, we constructed a fluorescent reporter plasmid in which the 150 bp surrounding a gene's start codon (from −60 to +90) were fused to the mRFP gene (FIG. 8). The chimera was expressed under control of the Ptac promoter, and fluorescence was measured via flow cytometry (FIG. 9). To generate synthetic ribosome binding sites, we constructed a library of reporter plasmids using 150 bp (−60 to +90) of a synthetic expression cassette. Briefly, a synthetic expression cassette consisted of a random DNA spacer, a degenerate sequence encoding an RBS library, and the coding sequence for each synthetic gene. We screened multiple clones to identify the synthetic ribosome binding site that best matched the native ribosome binding site (FIG. 10).

We constructed synthetic operons that consisted of the same genes as the native operons. This strategy enabled us to knock out a native operon from *Klebsiella* and complement the deletion using the synthetic counterpart.

Each synthetic operon consisted of a Ptac promoter followed by synthetic gene expression cassettes (random DNA spacer, synthetic rbs, synthetic coding sequence) and a transcription terminator. The random DNA spacer serves to insulate the expression of each synthetic coding sequence from preceding cassettes. Each synthetic operon was scanned to remove unintended regulatory sequences (similar to the process used during synthetic gene design and synthesis).

Figure 11:
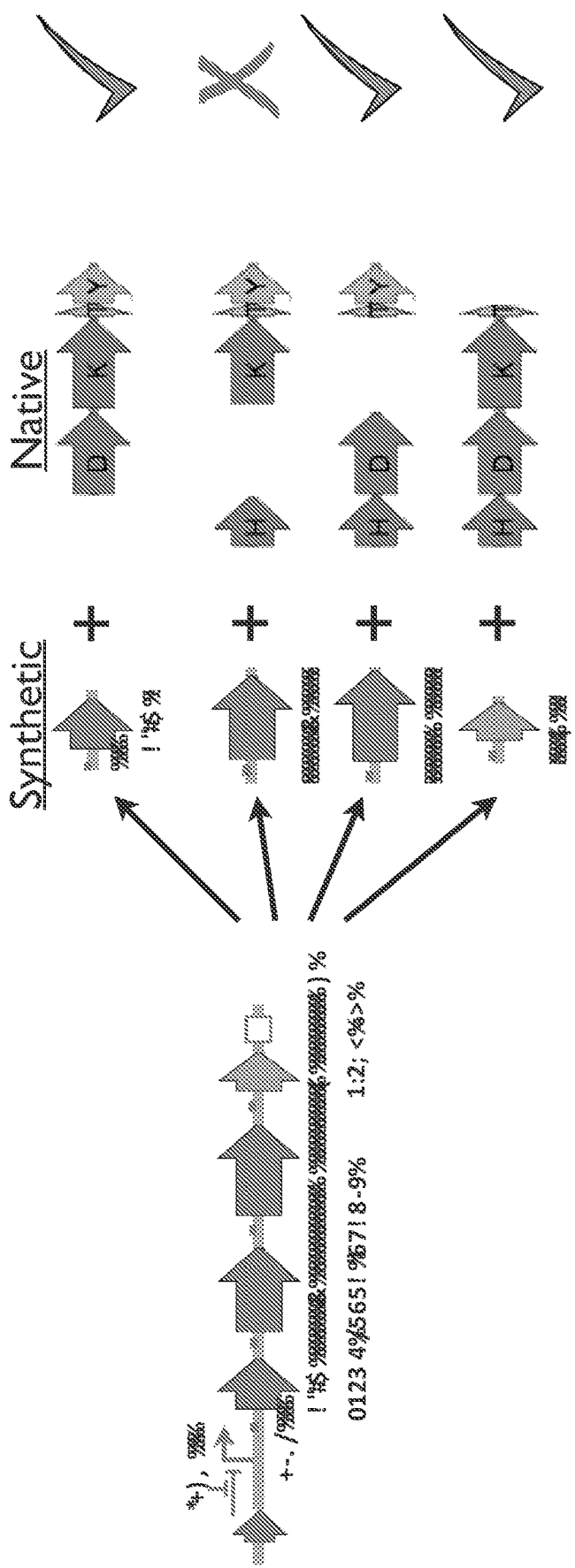
FIG. 11 illustrates the chimeric operons.

In two cases, we encountered synthetic operons that showed no functional complementation in the corresponding knockout strain (nifHDKTY and nifUSVWZM). To debug the synthetic operons, we broke the operon into constituent gene expression cassettes. We then constructed chimeric operons, wherein some cassettes had synthetic components and other cassettes were native genes and their ribosome binding sites (FIG. 11). This strategy enabled us to test each chimeric operon for functional complementation and quickly identify the problematic synthetic expression cassettes. With further analysis of problematic expression cassettes, we were able to diagnose and correct errors in the fully synthetic operons. FIG. 12 illustrates a list of errors in the two operons.

Figure 13:
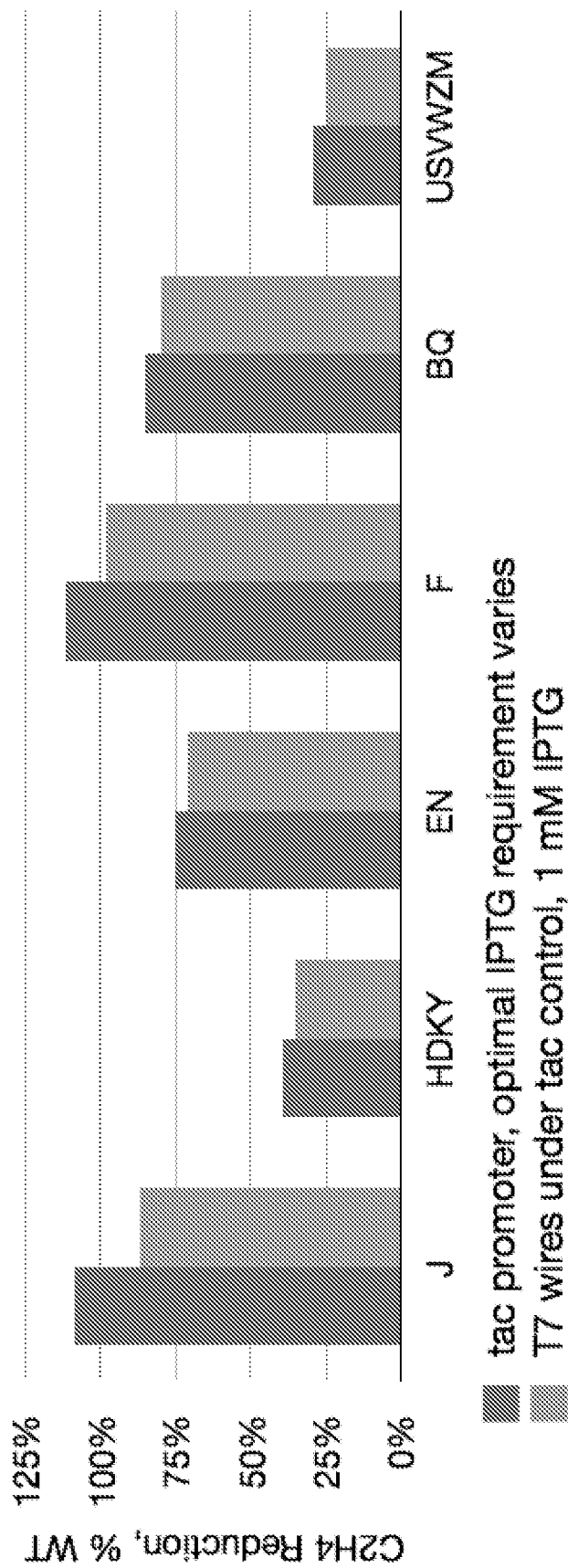
FIG. 13 shows that each synthetic operon required different levels of IPTG concentration for optimal function. It also shows the performance of individual operons in the T7 Wires system under Ptac promoter control.

Each synthetic operon was initially designed to be controlled by a Ptac inducible promoter. By titrating IPTG concentration, we could precisely specify promoter strength and corresponding synthetic operon expression. This enabled us to vary expression level to identify optimal operon function. We found that each synthetic operon required different levels of IPTG concentration for optimal function (FIG. 13).

We utilized the T7 Wires system to decouple the Ptac promoter from each synthetic operon. By inserting the wire between the promoter and transcriptional unit, we achieved two significant milestones. First, we gained the ability to modulate the transcriptional signal through the use of various mutant T7 promoters. This allowed us to shift optimal operon function to a single inducer concentration by selecting corresponding mutant T7 promoters. Second, we modularized control of the synthetic operon (FIG. 14). That is, any genetic circuit can control the synthetic operon provided that it can produce the necessary T7 RNAP concentration to drive each wire.

Figure 15:
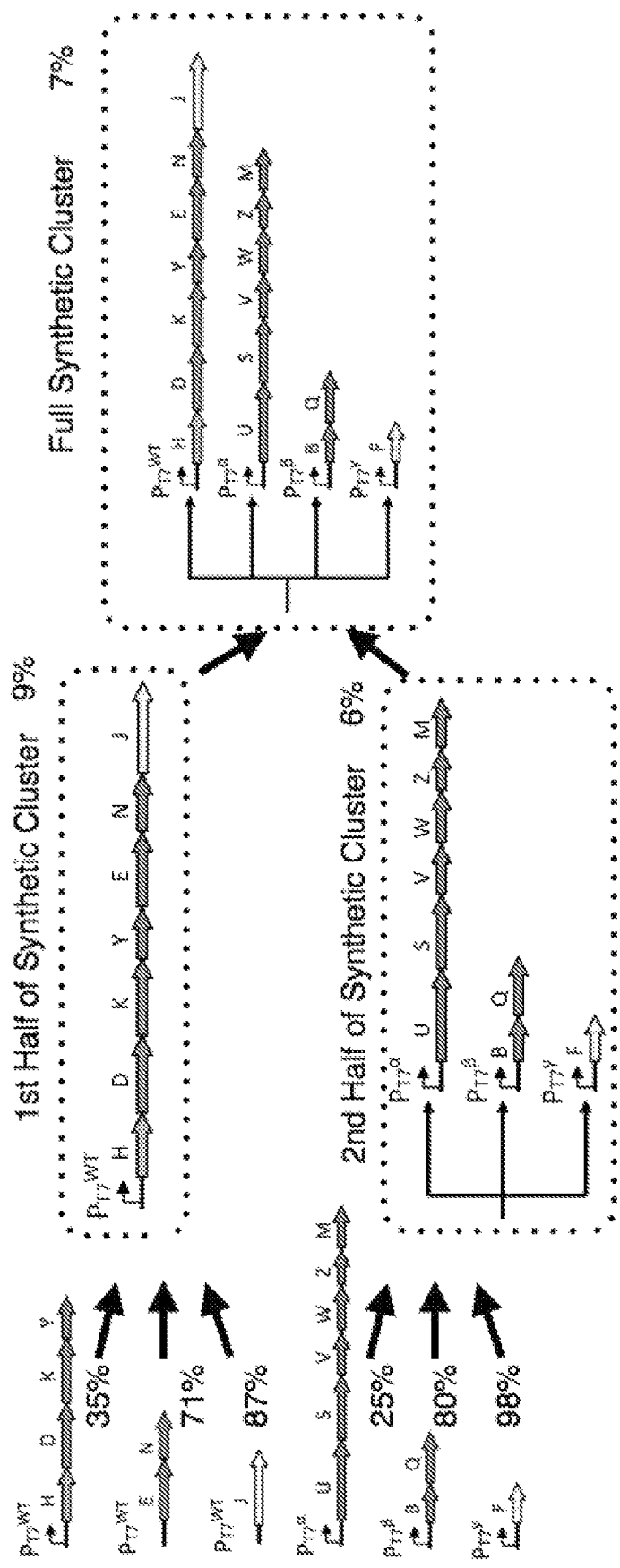
FIG. 15 shows nitrogen fixation from a full synthetic cluster expressed in a complete nif knockout strain.

We adopted a hierarchical approach to assembling individual operons into a fully synthetic cluster. First, we assembled three operons into half clusters (nifJ-nifHDKY-nifEN and nifUSVWZM-nifF-nifBQ) and demonstrated the ability of each synthetic half cluster to complement function in a corresponding knockout strain. Next, we combined the two half clusters into a full synthetic cluster and demonstrated nitrogen fixation in a complete nif knockout strain (FIG. 15).

Figure 16:
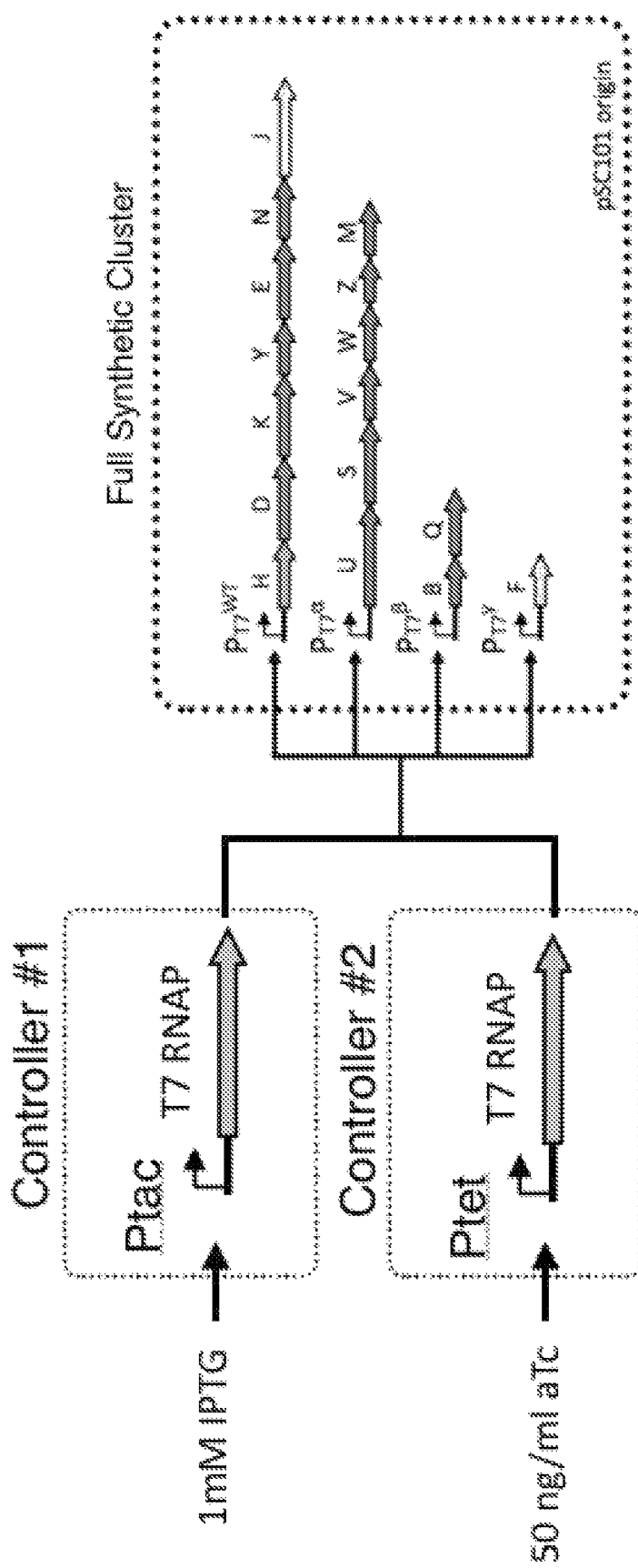
FIG. 16 illustrates the use of either controller #1 or controller #2 to produce the same performance from the full synthetic cluster.

We have shown that the use of T7 Wires produces a modular synthetic gene cluster. We have demonstrated that the use of either controller #1 or controller #2 produces the same functional performance from the synthetic cluster (FIG. 16). In controller #1, T7 RNAP is under control of the Ptac promoter. In controller #2, T7 RNAP is under control of the Ptet promoter.

Figure 17:
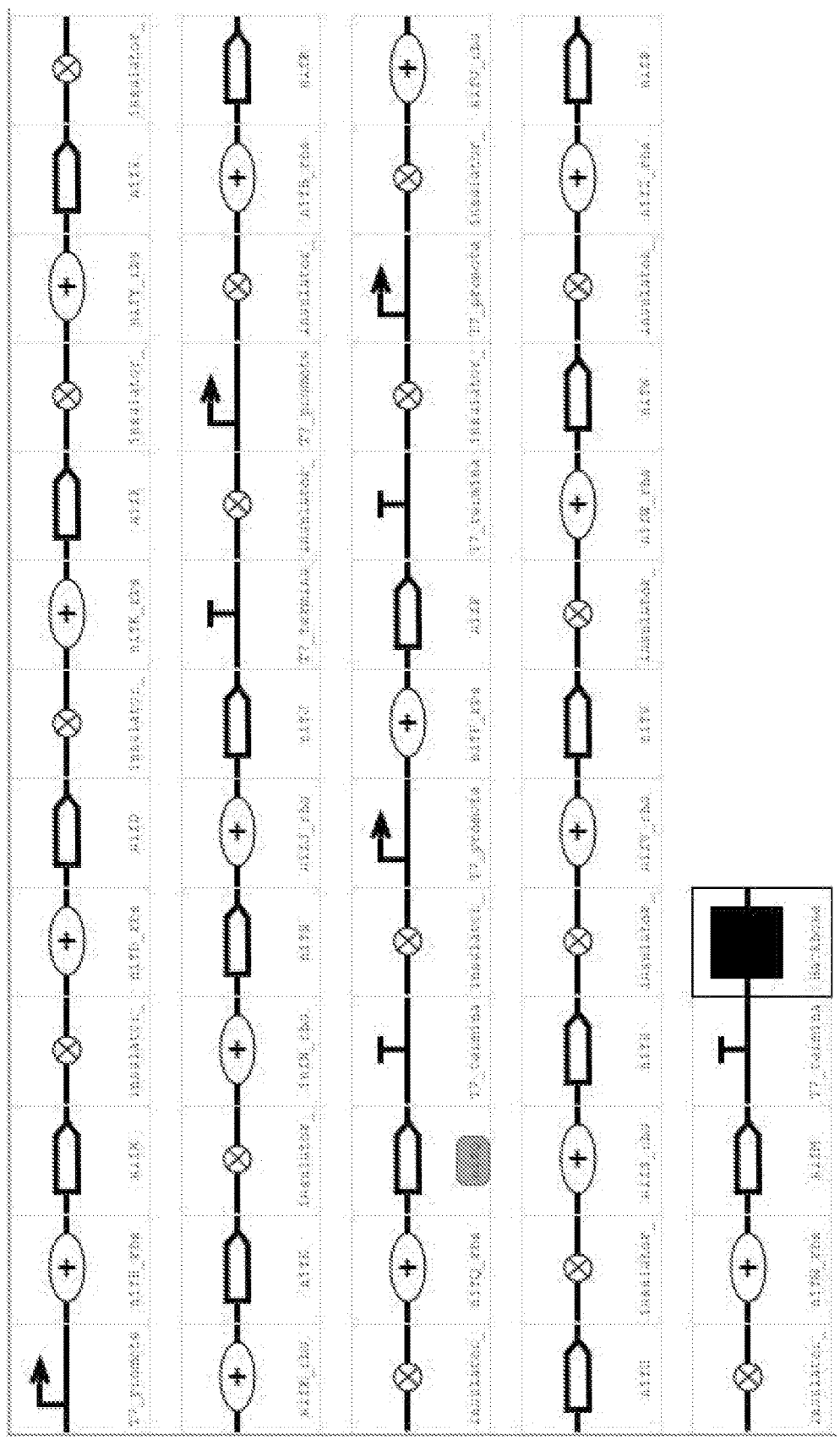
FIG. 17 depicts a detailed schematic of the full synthetic cluster.

FIG. 17 shows a schematic of the full biological cluster, with each part detailed. FIG. 19 shows the parts list of the synthetic controllers. FIG. 20 shows names, sequences and strengths of each component of the full cluster.

We have further demonstrated that complex genetic circuits can be used to produce functional performance of the synthetic gene cluster. We constructed a genetic circuit encoding the logic "A and not B" and used this circuit to control T7 RNAP. In this circuit, the "A and not B" logic corresponds to the presence or absence of the inducers, IPTG and aTc, such that the cell computes "IPTG and not aTc." The circuit was constructed by modifying controller #1 to include the cIrepressor binding sites OR1 and OR2 in the Ptac promoter to produce controller #3. Additionally, plasmid pNOR1020 (see, e.g., Tamsir and Voigt *Nature* 469:212-215 (2011)) encodes the repressor cI under control of the Ptet promoter. When pNOR1020 and controller #3 are co-transformed, they produce the logic circuit "IPTG and not aTc."

```
Ptac controller #1 promoter sequence
(SEQ ID NO: 334):
tattctgaaatgagctgttgacaattaatcatcggctcgtataatgtgt
ggaattgtgagcggataacaatt Controller #3 promoter sequence (SEQ ID NO: 335):
tattaacaccgtgcgtgttgacagctatacctctggcggttataatgct
agcggaattgtgagcggataacaatt
```

| Input | Expected Logic Output | Synthetic Nitrogen Fixation Performance (% WT) |
|---|---|---|
| No inducer | 0 | <0.5% |
| 1 mM IPTG | 1 | 9% |
| 50 ng/ml aTc | 0 | <0.5% |
| 1 mM IPTG and 50 ng/ml aTc | 0 | <0.5% |

In this experiment, we also included controller #1 as a performance reference. Under inducing conditions (1 mM IPTG), controller #1 exhibits 12% of WT fixation.

Example 3

Refactoring the Bacterial Type III Secretion System (T3SS)

This example illustrates the use of the method described herein to completely refactor the Bacterial type III secretion system (T3SS). This example also illustrates that the refactored synthetic operons of T3SS are controllable and function independently of all native control and regulation.

Bacterial type III secretion systems (T3SS) are valuable because, unlike conventionally used Sec and Tat pathways, they translocate polypeptides through both inner and outer membranes. This enables the delivery of protein directly to culture media, which can be one of the critical requirements in engineered bacterial technology. For example, toxic proteins can be removed from the cytoplasm without being allowed in the periplasm and functional enzymes (e.g., cellulases) which need to work outside the cell, can be delivered directly into the media.

However, the difficulty with utilizing T3SS in engineered bacterial systems is twofold. T3SS generally exist in pathogenic bacteria which utilize these mechanisms for invasion of host cells. Thus, T3SS are very tightly regulated in the cell and are difficult to control independently. Because of this, we chose to use methods of the present invention to completely refactor T3SS and test the function of the refactored operons in knockout cells.

The term "refactoring" refers to a process that involves optimization of multiple genes, regulation of a gene cluster, and establishment of the genetic context for a biological circuit. Refactoring complex gene clusters and engineering biological pathways requires numerous iterations between design, construction and evaluation in order to improve a desired system property. Briefly, refactoring includes breaking down a biological system into its component parts and rebuilding it synthetically. It also involves removing all native control and regulation of the biological system in order to replace it with a mechanism that provides independent control.

This example illustrates a method of recoding 18 genes of the bacterial type III secretion systems. The term "recoding" refers to a method of removing or replacing sequence of a gene in order to reduce or eliminate any native regulation elements, while also preserving the protein sequence encoded by the gene. The genes of the type III secretion system were recoded using an algorithm provided by DNA2.0 (Menlo Park, Calif.) in which individual codons of each gene are re-selected such that the gene encodes the same protein, but with maximum dissimilarity with the native sequence.

The 18 genes are arranged in two bacterial operons. Each gene is a recoded version of a native gene from *Salmonella typhimurium*. Each gene is coupled to a synthetic ribosome binding site (RBS) sequence that sets an appropriate expression level for each individual gene. Details of the synthetic RBS selection are described below. The operons can be induced with any desired promoter. In this example, simple inducible promoters are used. The recoded T3SS operons can be attached to any genetic control circuit as needed.

To select a synthetic RBS sequence that best matches the native expression level of each of the 18 genes of the bacterial type III secretion systems, we measured the expression of each gene in the natural system. We cloned the 36-base region upstream on the start codon, along with the 36-bases of coding region fused to an RFP (Red Fluorescent Protein). This was cloned into a plasmid with a constitutive promoter.

This construct was transformed into Salmonella typhimurium SL1344 and grown overnight at 37° C. in PI-1 inducing media (LB with 17 g/L NaCl). The culture was subcultured into fresh inducing media to an $OD_{260}$ of 0.025, grown for 2 hours at 37° C. until cells reached log-phase. Fluorescence was measured on a cytometer. The geometric mean of RFP fluorescence across at least 10,000 cells was used as the measure of protein expression.

To find ribosomal binding sequences to test, we utilized the Ribosome Binding Site Calculator (voigtlab.ucsf.edu/software), identified known RBS sequences from the Registry of Standard Biological Parts (partsregistry.org/Main_Page), and generated a series of randomized sequences. The randomized sequences comprise the following formats:

```
                                         (SEQ ID NO: 336)
CTTGGGCACGCGTCCATTAANNAGGANNAATTAAGC;

(SEQ ID NO: 337)
TGGGCACGCGTCCATTAANNAGGANNAATTATTAGC;

(SEQ ID NO: 338)
TACTTGGGCACGCGTCCATTAANNAGGANNAATAGC;

(SEQ ID NO: 339)
CTTGGGCACGCGTCCATTAANAAGGAGNAATTAAGC;

(SEQ ID NO: 340)
CTTGGGCACGCGTCCATTANTAAGGAGGNATTAAGC.
```

Figure 21:
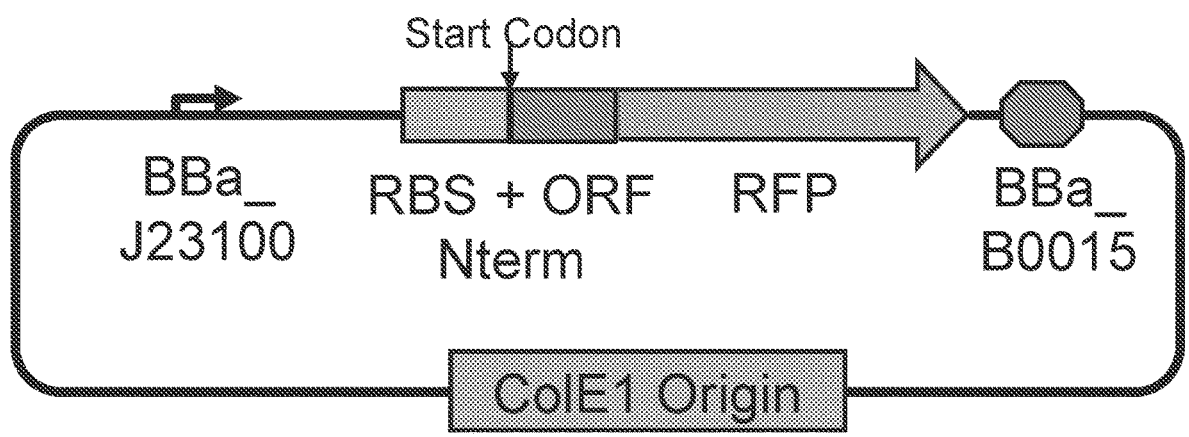
FIG. 21 shows a diagram of the RBS test vector.

All RBS sequences were cloned into the RBS test vector (FIG. 21) along with the first 36 bases of the synthetic gene they were generated to drive. We followed the same experimental procedure used to measure the expression of each gene in the natural system. Of the randomized RBS, 12-48 colonies of each randomized sequence was tested. The synthetic construct that best matched the native expression level was selected and sequenced. This sequence was then used in the construction of the refactored operons.

Two operons were assembled. The first, "prg-org" contains 6 genes, and the second "inv-spa" contains 13 genes. These genes are allocated to each operon in the same manner as in the wild-type system. However, the order of genes in each operon is arranged on the basis of measured expression level from strongest to weakest. Operons were assembled by placing the selected synthetic RBS in front of its corresponding synthetic gene sequence. Restriction enzyme binding sites were added between genes or pairs of genes in order to facilitate future manipulation. The entire sequence was synthesized by DNA2.0. The synthetic operon was cloned into a low-copy test vector and placed under the control of an inducible promoter (e.g., pTac or pBad—IPTG or Arabinose induction). A reporter plasmid was created containing a native Salmonella secretable effector protein which was fused to a FLAG epitope tag for identification. This reporter was placed under a strong constitutive promoter. FIG. 22B shows a schematic of the prg-org operon test vector and a reporter plasmid.

We also generated two operon knockout (prg-org and inv-spa) Salmonella SL1344 cell lines using the method described in Datsenko, Wanner, Proc. Natl. Acad. U.S.A., 2000. FIG. 22A shows a schematic of Δprg-org Salmonella SL1344 knock-out strain. The inv-spa and prg-org operons are boxed. FIG. 23A shows that the Δprg-org knock-out strain does not express the prg-org operon.

The test plasmid (or the control plasmid) and the reporter plasmid were transformed into the appropriate knockout strain. The strains were grown from colony overnight in low-salt media (LB with 5 g/L NaCl) at 37° C. The cultures were subcultured to an $OD_{260}$ of 0.025 in fresh low-salt media and grown for 2 hours. The cultures were diluted 1:10 into high-salt, inducting media (LB with 17 g/L of NaCl) in 50 mL unbaffled flasks and grown for 6-8 hours. 1 mL of each culture was spun down at 3000×g for 5 minutes, then the supernatant filtered through a 0.2 uM filter. This culture was then run on an SDS-PAGE gel and a western blot performed with an anti-FLAG antibody.

FIG. 23B shows that the synthetic refactored prg-org operon in Salmonella Δprg-org cells can be controlled by the addition of IPTG. The level of expression is comparable to that generated from the natural PprgH promoter.

Example 4

Refactoring Nitrogen Fixation Gene Cluster from Klebsiella oxytoca

Bacterial genes associated with a single trait are often grouped in a contiguous unit of the genome known as a gene cluster. It is difficult to genetically manipulate many gene clusters due to complex, redundant, and integrated host regulation. We have developed a systematic approach to completely specify the genetics of a gene cluster by rebuilding it from the bottom-up using only synthetic, well-characterized parts. This process removes all native regulation, including that which is undiscovered. First, all non-coding DNA, regulatory proteins, and nonessential genes are removed. The codons of essential genes are changed to create a DNA sequence as divergent as possible from the wild-type gene. Recoded genes are computationally scanned to eliminate internal regulation. They are organized into operons and placed under the control of synthetic parts (promoters, ribosome binding sites, and terminators) that are functionally separated by insulator parts. Finally, a controller consisting of genetic sensors and circuits regulates the conditions and dynamics of gene expression. We applied this approach to an agriculturally relevant gene cluster from Klebsiella oxytoca encoding the nitrogen fixation pathway for converting atmospheric $N_2$ to ammonia. The native gene cluster consists of 20 genes in 7 operons and is encoded in 23.5 kb of DNA. We constructed a refactored gene cluster that shares little DNA sequence identity with wild-type and for which the function of every genetic part is defined. This work demonstrates the potential for synthetic biology tools to rewrite the genetics encoding complex biological functions to facilitate access, engineering, and transferability.

Introduction

Many functions of interest for biotechnology are encoded in gene clusters, including metabolic pathways, nanomachines, nutrient scavenging mechanisms, and energy generators (1). Clusters typically contain internal regulation that is embedded in the global regulatory network of the organism. Promoters and 5'-UTRs are complex and integrate many regulatory inputs (2, 3). Regulation is highly redundant; for example, containing embedded feedforward and feedback loops (4). Regulation can also be internal to genes, including promoters, pause sites, and small RNAs (5, 6). Further, genes often physically overlap and regions of DNA can have multiple functions (7). The redundancy and extent of this regulation makes it difficult to manipulate a gene cluster to break its control by native environmental stimuli, optimize its function, or transfer it between organisms. As a consequence, many clusters are cryptic, meaning that laboratory conditions cannot be identified in which they are active (8).

Gene clusters have been controlled from the top-down by manipulating the native regulation or adding synthetic regulation in an otherwise wild-type background (9). For example, either knocking out a repressor or overexpressing an activator has turned on clusters encoding biosynthetic pathways (10-14). When the cluster is a single operon, it has been shown that a promoter can be inserted upstream to induce expression (15). The entire echinomycin biosynthetic cluster was transferred into *E. coli* by placing each native gene under the control of a synthetic promoter (16).

Figure 26:
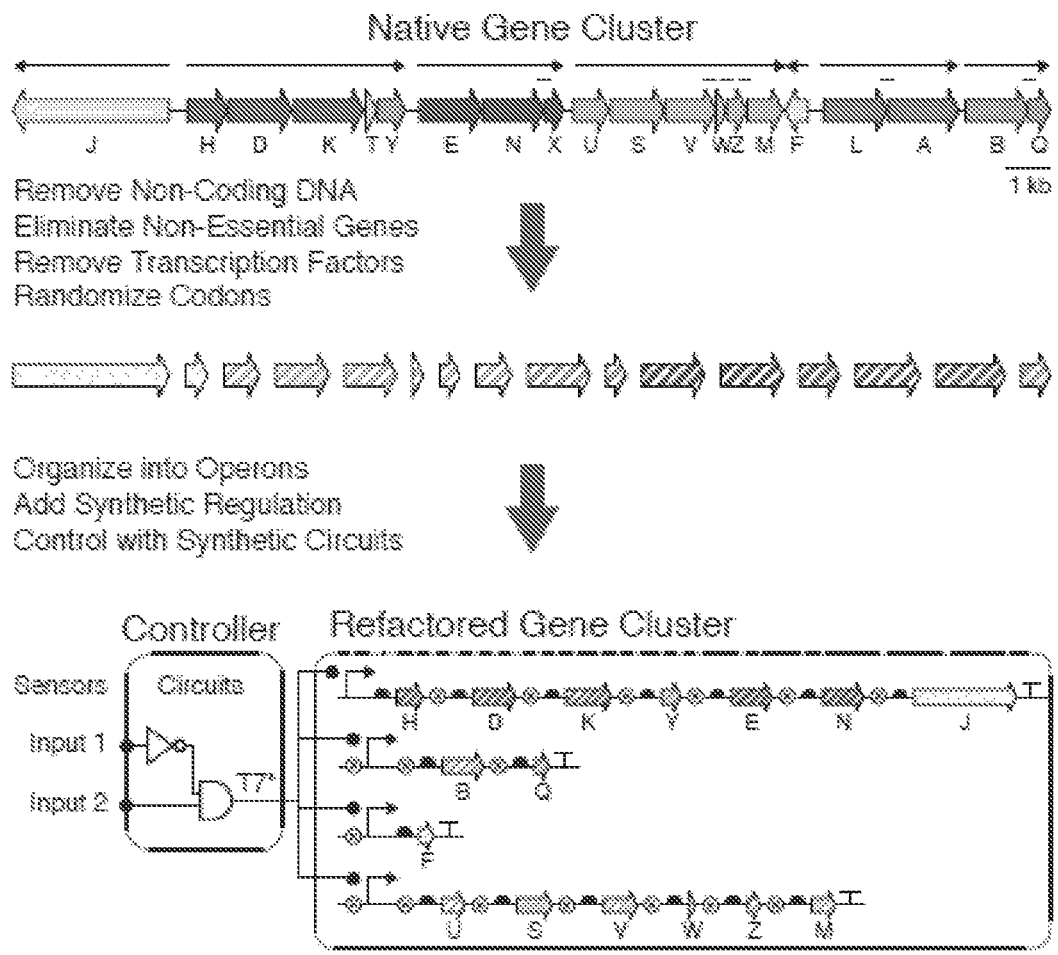
FIG. 26 illustrates the process of refactoring a gene cluster. The wild-type *K. oxytoca* nitrogen fixation gene cluster is shown at top. The genes are colored by function: blue (nitrogenase), green (co-factor biosynthesis, shading corresponds to operons), yellow (e-transport), and grey (unknown). The thin arrows show the length and orientation of the seven operons and a horizontal bar indicates overlapping genes. The recoded genes are shown as dashed lines. The symbols used to define the refactored cluster and controller are defined in FIGS. 29 and 30, respectively

In engineering, one approach to reduce the complexity of a system is to "refactor" it, a term borrowed from software development where the code underlying a program is rewritten to achieve some goal (e.g., stability) without changing functionality (17). This term was first applied to genetics to describe the top-down simplification of a phage genome by redesigning known genetic elements to be individually changeable by standard restriction digest (18). Here, we use it to refer to a comprehensive bottom-up process to systematically eliminate the native regulation of a gene cluster and replace it with synthetic genetic parts and circuits (FIG. 26). The end product is a version of the gene cluster whose DNA sequence has been rewritten, but it encodes the same function. The design process occurs on the computer, and then the resulting DNA sequence is constructed using DNA synthesis (19). The first step of the process is to remove all non-coding DNA, and regulatory genes. Next, each essential gene is recoded by selecting codons that produce a DNA sequence that is as distant as possible from the wild-type sequence. The intent is to introduce mutations throughout the gene to eliminate internal regulation (including that which is undiscovered), such as operators, promoters, mRNA secondary structure, pause sites, methylation sites, and codon regulation. Recoded sequences are further scanned by computational methods to identify putative functional sequences, which are then removed. The recoded genes are organized into artificial operons and the expression levels are controlled by synthetic ribosome binding sites (RBSs), and insulator sequences physically separate the genes. The end result is a refactored gene cluster whose native regulation has been removed and has been organized into a set of discrete, well-characterized genetic parts.

Once the native regulation has been removed, synthetic regulation can be added back to control the dynamics and conditions under which the cluster is expressed. Constructing such regulation has been a major thrust of synthetic biology and involves the design of genetic sensors and circuits and understanding how to connect them to form programs (20). In our design, we genetically separate the sensing/circuitry from the refactored pathway by carrying them on different low copy plasmids (FIG. 26). The plasmid containing the sensors and circuits is referred to as the "controller" and the output of the circuits lead to the expression of an engineered T7 polymerase (T7*). The refactored cluster is under the control of T7 promoters. One advantage of this organization is that T7 polymerase is orthogonal to native transcription and the T7 promoters are tightly off in the absence of the controller. In addition, changing the regulation is simplified to swapping the controller for one that contains different sensors and circuits, so long as the dynamic range of T7* is fixed.

Figure 27A:
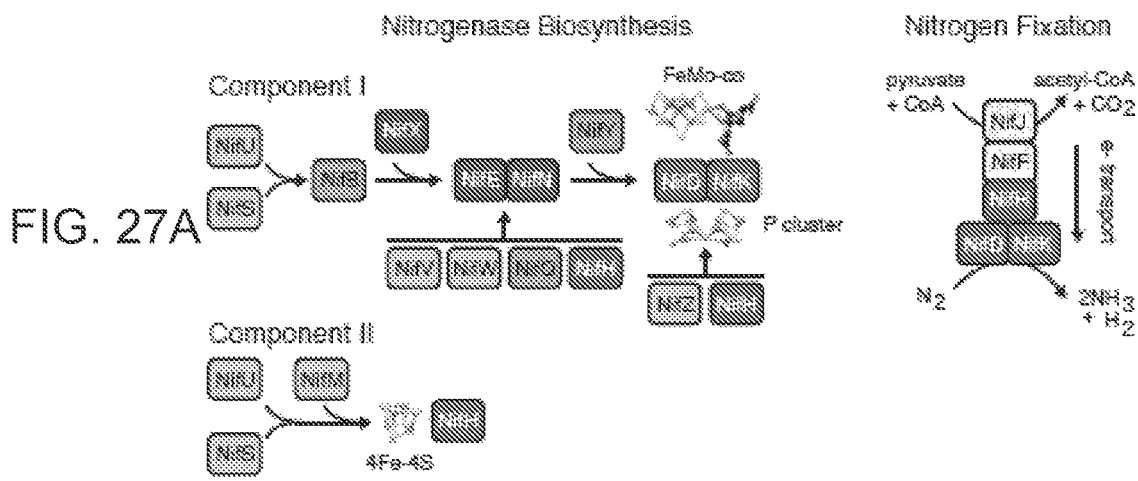
FIGS. 27A-27C illustrates the robustness of the nitrogen fixation pathway to changes in the expression of component proteins.

As a demonstration, we have applied this process to refactor the gene cluster encoding nitrogen fixation in *Klebsiella oxytoca* (21). Nitrogen fixation is the conversion of atmospheric $N_2$ to ammonia ($NH_3$), so that it can enter metabolism (22). Industrial nitrogen fixation through the Haber-Bosch process is used to produce fertilizer. Many microorganisms fix nitrogen and the necessary genes typically occur together in a gene cluster, including the nitrogenase subunits, the metallocluster biosynthetic enzymes and chaperones, e-transport, and regulators (FIG. 27A) (23, 24). The gene cluster from *K. oxytoca* has been a model system for studying nitrogen fixation and consists of 20 genes encoded in 23.5 kb of DNA (FIG. 26, top) (25). The biosynthesis of nitrogenase is tightly regulated by a two-layer transcriptional cascade in response to fixed nitrogen, oxygen, and temperature (26). The complete cluster has been transferred to *E. coli*, thus demonstrating that it has all of the genes necessary for nitrogen fixation (27). The encoding of this function is complex, many of the genes overlap, the operons are oriented in opposite directions, and there are many putative hidden regulatory elements, including internal promoters and hairpins (25). The purpose of refactoring is to reorganize the cluster, simplify its regulation, and assign a concrete function to each genetic part.

Results

Tolerance of the Native Gene Cluster to Changes in Expression

Figure 27B:
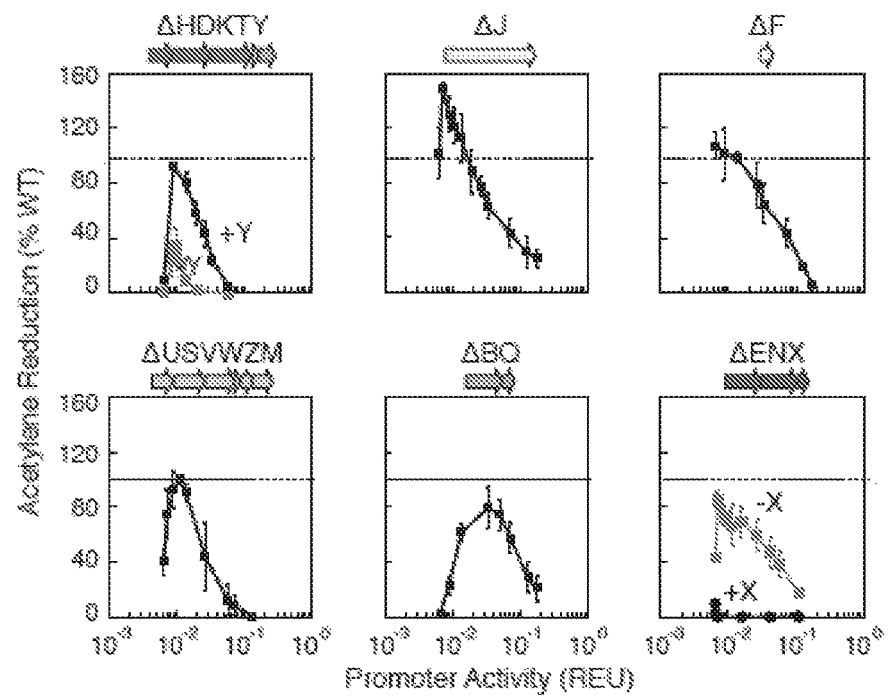

Prior to refactoring a cluster, a robustness analysis is performed to determine the tolerances of a gene or set of genes to changes in expression level (FIG. 27B). This informs the grouping of genes into operons and the selection of synthetic parts to obtain desired expression levels. In the wild-type background, genes are knocked out and complemented under inducible control. The tolerance is obtained by measuring nitrogenase activity as a function of the activity of the inducible promoter.

Nitrogenase function is notably sensitive to expression changes and each tolerance has a clear optimum (FIG. 27B). The chaperone NifY is required to achieve full activity and broadens the tolerance to changes in expression level. NifT did not have an effect on activity, as observed previously (28), and it is frequently absent from homologous clusters (29). The genes controlling electron transport (nifJ and nifF) need to be expressed at low levels, and activity falls rapidly as expression increases. The optima for genes participating in the metal cluster biosynthetic pathways vary. The nifUS-VWZM operon, which encodes proteins for early Fe—S cluster formation and proteins for component maturation, needs to be expressed at low levels, whereas nifBQ, encoding proteins for FeMo-co core synthesis and molybdenum integration, need to be expressed 10-fold higher. NifEN is tolerant to varied expression levels. However, activity is lost with the inclusion of nifX, which has been characterized as a negative regulator (30). The native cluster also includes the regulatory proteins NifL and NifA, which integrate environmental signals (26). The genes nif, nifX, and nifLA are not included in the refactored cluster.

The Complete Refactored Gene Cluster

The nitrogenase activities of the refactored operons were measured as a function of the IPTG-inducible $P_{tac}$ promoter (FIG. 28A). Each operon has a different optimum. To combine the operons, the $P_{tac}$ promoters were replaced with T7 promoters that have a strength close to the measured optimum (FIG. 28B and Materials and Methods section). The nitrogenase genes (nifHDK) are highly expressed in *Klebsiella* under fixing conditions (up to 10% of cell protein) (31), so the strongest promoter was used to control this operon (T7.WT, 0.38 REU) (32). A long operon was built to include the nifEN and nifJ genes, where the lower expression required for nifJ was achieved through transcriptional attenuation. The nifF gene was encoded separately under the control of a medium strength promoter (T7.3, 0.045 REU). Finally, the nifUSVWZM and nifBQ operons were controlled by weak promoters (T7.2, 0.019 REU). Each of the individual refactored operons under the control of a T7 promoter was able to recover the activity observed from the $P_{tac}$ promoter and corresponding optimal IPTG concentration (FIG. 28C).

Transitioning the control to T7* and T7 promoters facilitates the assembly of the complete cluster from refactored operons. We first assembled half-clusters using Gibson Assembly (33) and verified their function in strains with the corresponding genes deleted. The first half-cluster consisted of the nifHDKYENJ operon. The second half-cluster was assembled from the nifBQ, nifF, and nifUSVWZM operons. The half-clusters were able to recover 18%±0.7% and 26%±8.4% of wild-type activity, respectively. The full synthetic cluster was assembled from both half-clusters (FIG. 29), and its activity measured in a strain where the full cluster is deleted. The synthetic gene cluster recovers nitrogenase activity at 7.4%±2.4% of the wild-type (FIG. 30A). Strains carrying the synthetic gene cluster utilized ambient $N_2$ as a nitrogen source, growing 3.5-fold slower than the wild-type strain (FIG. 37) and incorporating $^{15}N$-labelled nitrogen into 24%±1.4% of their cellular nitrogen content, as measured by isotope ratio mass spectronomy (IRMS) (FIG. 30B).

The complete refactored cluster consists of 89 genetic parts, including a controller, and the function of each part is defined and characterized. Therefore, the genetics of the refactored system are complete and defined by the schematic in FIG. 29. However, the process of simplification and modularization reduces activity (18). This is an expected outcome of refactoring a highly evolved system.

Swapping Controllers to Change Regulation

The separation of the controller and the refactored cluster simplifies changing the regulation of the system. This can be achieved by transforming a different controller plasmid, as long as the dynamic range of the T7* RNAP expression is preserved. To demonstrate this, we constructed two additional controllers (FIG. 30A). Controller #2 changes the chemical that induces the system by placing the expression of T7* RNAP under the control of the aTc-inducible $P_{tet}$ promoter. When induced, Controller #2 produces nitrogenase activity identical to Controller #1 (7.2%±1.7%). The controller can also serve as a platform to encode genetic circuits to control regulatory dynamics or to integrate multiple sensors. To this end, Controller #3 contains two inducible systems (IPTG and aTc) and an ANDN gate (34, 35). In the presence of IPTG and the absence of aTc, nitrogen fixation is 6.6%±1.7% of wild-type activity. These controllers represent the simplicity by which the regulation of the refactored cluster can be changed.

In addition to making it possible to add new regulation, the process of refactoring eliminates the native regulation of the cluster. This is demonstrated through the decoupling of nitrogenase activity from the environmental signals that normally regulate its activity. For example, ammonia is a negative regulator that limits overproduction of fixed nitrogen (26). In the presence of 17.5 mM ammonia, no nitrogenase activity is observed for the wild-type cluster (FIG. 30C). In contrast, the refactored gene cluster maintains activity in the presence of ammonia (1.1%±0.5%). Interestingly, this 7-fold reduction of activity is not due to residual regulation present in the system. Rather, it occurs because the addition of ammonia to the media reduces the output of the controller by 4.5-fold (FIG. 30C). In theory, this could be fixed by increasing the expression level of T7* RNAP, but it speaks to the need to create genetic circuits that are robust to environmental context.

Discussion

The objective of refactoring is to facilitate the forward engineering of multi-gene systems encoded by complex genetics. Native gene clusters are the product of evolutionary processes; thus, they exhibit high redundancy, efficiency of information coding, and layers of regulation that rely on different biochemical mechanisms (36-38). These characteristics inhibit the quantitative alteration of function by part substitution, because the effect can become embedded in a web of interactions. Here, modularizing the cluster, physically separating and insulating the parts, and simplifying its regulation have guided the selection and analysis of part substitutions. The information gleaned from screening the permutations in a refactored system can be cleanly fed back into the design cycle.

The refactored cluster can also serve as a platform for addressing questions in basic biology. First, it allows for the impact of regulatory interactions to be quantified in isolation. For example, in the natural system, one feedback loop could be embedded in many other regulatory loops. Systematically removing such regulation provides a clean reference system (potentially less active and robust than wild-type) from which improvements can be quantified as a result of adding back regulation. It also serves as a basis for comparison of radically different regulatory programs or organizational principles; for example, to determine the importance of temporal control of gene expression (4, 39) or the need for genes to be encoded with a particular operon structure (40, 41). Second, the process of reconstruction and debugging is a discovery mechanism that is likely to reveal novel genetics and regulatory modes. In this work, the improvement from 0% to 7% revealed only minor changes: misannotations in genes and improper expression levels. However, the debugging process itself is blind to the mechanism—it simply identifies problematic regions of DNA.

One of the immediate applications of refactoring is in the access of gene clusters from genomic sequence information. This could be necessary either because the cluster is silent, meaning that it that cannot be activated in the laboratory, or because the desired cluster is from a metagenomic sample or information database and the physical DNA is unavailable (42). There are have been many elegant methods to activate a gene cluster, including the placement of inducible promoters upstream of the natural operons and the division of the cluster into individual cistrons, which can then be reassembled (43). With advances in DNA synthesis technology, it is possible to construct entire gene clusters with complete control over the identity of every nucleotide in the design. This capability eliminates the reliance on the natural physical DNA for construction and enables the simultaneous redesign of components in the complete system. Fully harnessing this technology will require the marriage of computational methods to select parts and scan designs, characterized part libraries, and methods to reduce their context dependence.

Material and Methods

Strains and Media

*E. coli* strain S17-1 was used for construction and propagation of all plasmids used in *Klebsiella oxytoca* knockout mutant construction. *K. oxytoca* strain M5al (Paul Ludden, UC Berkeley) and mutants derived from M5al were used for nitrogen fixation experiments. Luria-Bertani (LB)-Lennox was used for strain propagation. All assays were carried out in minimal medium containing (per liter) 25 g of $Na_2HPO_4$, 3 g of $KH_2PO_4$, 0.25 g of $MgSO_4.7H_2O$, 1 g of NaCl, 0.1 g of $CaCl_2.2H_2O$, 2.9 mg of $FeCl_3$, 0.25 mg of $Na_2MoO_4.2H_2O$, and 20 g of sucrose. Growth media is defined as minimal media supplemented with 6 ml (per liter) of 22% $NH_4Ac$. Derepression media is defined as minimal media supplemented with 1.5 ml (per liter) of 10% serine. The antibiotics used were 34.4 μg $ml^{-1}$ Cm, 100 μg $ml^{-1}$ Spec, 50 μg $ml^{-1}$ Kan, and/or 100 μg $ml^{-1}$ Amp.

Codon Randomization

Initial gene sequences were proposed by DNA2.0 to maximize Hamming distance from the native sequence while seeking an optimal balance between *K. oxytoca* codon usage and *E. coli* codon preferences experimentally determined by the company (44). Rare codons (<5% occurrence in *K. oxytoca*) were avoided, and mRNA structure in the translation initiation region was suppressed. Known sequence motifs, including restriction sites, transposon recognition sites, Shine-Dalgarno sequences and transcriptional terminators, were removed by the DNA2.0 algorithm.

Elimination of Undesired Regulation

Each synthetic operon was scanned prior to DNA synthesis to identify and remove undesired regulation. Multiple types of regulation were identified using publicly available software. The RBS Calculator was used (Reverse Engineering, 16S RNA: ACCTCCTTA) to identify ribosome binding sites throughout the proposed DNA sequence of the operon (45). The Prokaryotic Promoter Prediction server was used to identify putative σ70 promoter sites (e-value cutoff of 5, sigma.hmm database) (46). The PromScan algorithm was used to identify putative σ54 promoter sites using default options (47). TransTermHP software was used with default parameters to identify terminator sequences in both the forward and reverse directions (48). RBSs greater than 50 AU and all identified promoters and terminators were considered significant.

Nitrogenase Activity Assay

In vivo nitrogenase activity is determined by acetylene reduction as previously described (49). For *K. oxytoca* whole-cell nitrogenase activity assay, cells harboring the appropriate plasmids were incubated in 5 ml of growth media (supplemented with antibiotics, 30° C., 250 r.p.m.) in 50 ml conical tubes for 14 hours. The cultures were diluted into 2 ml derepression media (supplemented with antibiotics and inducers) to a final $OD_{600}$ of 0.5 in 14 ml bottles, and bottles were sealed with rubber stoppers (Sigma Z564702). Headspace in the bottles was repeatedly evacuated and flushed with $N_2$ past a copper catalyst trap using a vacuum manifold. After incubating the cultures for 5.5 hours at 30° C., 250 r.p.m, headspace was replaced by 1 atmosphere Ar. Acetylene was generated from $CaC_2$ using a Burris bottle, and 1 ml was injected into each bottle to start the reaction. Cultures were incubated for 1 hour at 30° C., 250 r.p.m before the assay was stopped by injection of 300 μl of 4M NaOH solution into each bottle. To quantify ethylene production, 50 μl of culture headspace was withdrawn through the rubber stopper with a gas tight syringe and manually injected into a HP 5890 gas chromatograph. Nitrogenase activity is reported as a percentage of wild-type activity. Briefly, ethylene production by strains was quantified by integrating area under the peak using HP Chemstation software and dividing ethylene production of experimental strains by the ethylene production of a wild type control included in each assay.

$N_2$-Dependent Growth and $^{15}N_2$ Incorporation Assay

Nitrogen fixation by synthetic nif cluster in *K. oxytoca* is further demonstrated by $N_2$-dependent growth and $^{15}N_2$ incorporation. Cells are diluted as described in the acetylene reduction assay. The headspace of the bottles is replaced by normal $N_2$ gas or by stable isotope nitrogen, $^{15}N_2$ ($^{15}N$ atom 99.9%, Icon Isotopes, Cat#: IN 5501). After incubating the cultures for 36 hours at 30° C., 250 r.p.m, $N_2$-dependent growth of the cells is determined by measuring optical density at 600 nm (OD600). To do the $^{15}N_2$ incorporation assay, the $^{15}N$-enriched cells with corresponding control cultures under normal nitrogen gas are collected by centrifugation, the cell pellets are dried in a laboratory oven at 100° C. for 12 hours. The dried pellets are analysis for $^{15}N/^{14}N$ ratio at the Center for Stable Isotope Biogeochemistry at the University of California, Berkeley using the Finnigan MAT Delta plus Isotope Ratio Mass Spectrometer.

*K. oxytoca* Knockout Strains

All *K. oxytoca* mutants are constructed from M5al by allele exchange using suicide plasmid pDS 132 carrying the corresponding nif gene deletion (pDS 132 was graciously provided by the Paul Ludden lab at UC Berkeley as a gift from Dr. Dominique Schneider at Universite Joseph Fourier) (49). We made a slight modification to a previously published protocol (50). Here, a kanamycin resistance cassette was cloned into the suicide plasmid upstream of the left homologous exchange fragment. These operon deletions in nif gene cluster span the promoter and the complete amino acid coding sequences except when specifically designated. All mutants were verified by DNA sequencing of the PCR product of the corresponding gene region to confirm physical DNA deletion and by whole-cell acetylene reduction assay to confirm the lack of nitrogenase activity.

Promoter Characterization

Figure 33A:
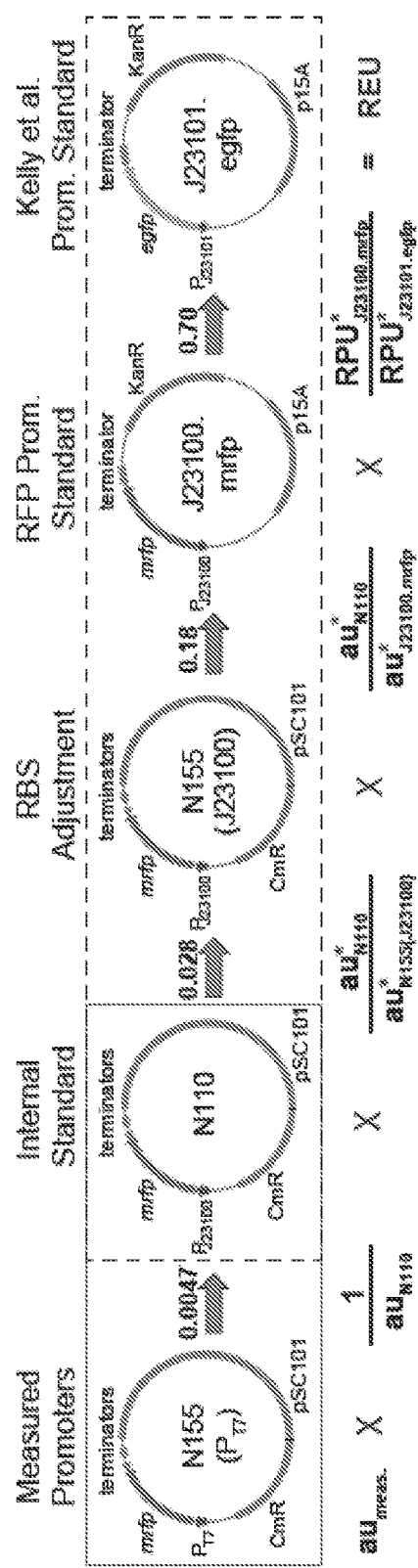
FIGS. 33A-33B shows promoter characterization using Relative Expression Units.

As described in this example, the output of promoters is reported as relative expression units (REU). This is simply a linear factor that is multiplied by the arbitrary units measured by the flow cytometer. The objective of normalizing to REU is to standardize measurements between labs and projects. The linear factor is $1.66 \times 10^{-5}$ and the division by this number back converts to the raw arbitrary units. This number was calculated to be a proxy to the RPU (relative promoter units) reported by Kelly and co-workers (51). Our original standardized measurements were made prior to the Kelly paper and involved a different reference promoter, fluorescent protein (mRFP), RBS, and plasmid backbone. Because of these differences, one cannot calculate RPU as defined by Kelly, et al. Instead, a series of plasmids was made (FIG. 33A) to estimate the relative expression of reporter protein from experimental constructs compared the standard construct in Kelly, et al. Conversion factors between constructs were measured and multiplied to obtain the linear factor above. We renamed the unit to REU (relative expression units) because it is intended to be a simple normalization of fluorescent units (akin to a fluorescent bead) and not a direct measurement of the activity of a promoter (e.g., the polymerase flux).

Cells were grown as in the Acetylene Reduction Assay with two modifications. The initial flush of headspace with N$_2$ was not performed, and the assay was halted after the 5.5 hour incubation. To halt the assay, 10 µl of cells were transferred from each bottle to a 96-well plate containing phosphate buffered saline supplemented with 2 mg ml$^{-1}$ kanamycin. Fluorescence data was collected using a BD Biosciences LSRII flow cytometer. Data were gated by forward and side scatter, and each data set consisted of at least 10,000 cells. FlowJo was used to calculate the geometric means of the fluorescence distributions. The autofluorescence value of K. oxytoca cells harboring no plasmid was subtracted from these values to give the values reported in this study. The strengths of T7 promoter mutants were characterized by swapping them in place of the P$_{tac}$ promoter in plasmid N149 (SBa_000516), co-transforming with Controller #1 (plasmid N249), and measuring fluorescence via flow cytometry under 1 mM IPTG induction.

Figure 33B:
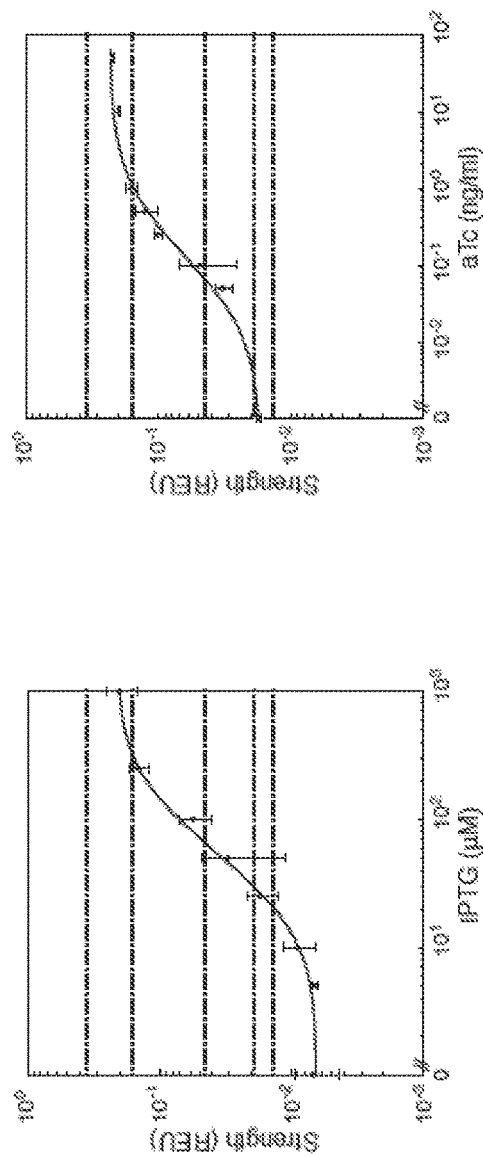

To replace the P$_{tac}$ promoter by a T7 promoter in each synthetic operon, we followed a simple process. First, we identified the IPTG concentration corresponding to the maximal functional activity of each synthetic operon. Second, we translated this IPTG concentration into REU based on characterization of the P$_{tac}$ promoter (FIG. 33B, left). Third, we selected the T7 mutant promoter with the closest strength in REU. For the synthetic nifF operon, we observed broad, robust fixation under the P$_{tac}$ promoter. We found that T7 mut 3 produced inducible functional activity with a maximum at 1 mM IPTG induction of the T7 RNAP. For the synthetic nifJ operon, our method suggests that we use a weak T7 mutant promoter. However, we found that a WT T7 promoter produced inducible activity with a maximum at 1 mM IPTG. We attribute this deviation to a change in RBS strength due to contextual differences between P$_{tac}$ and the T7 promoter.

Debugging Synthetic Operons

Figure 34B:
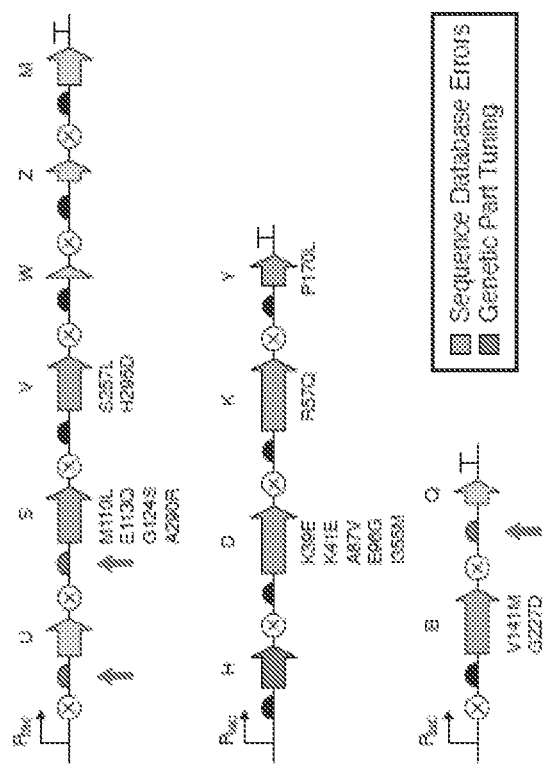
FIGS. 34A-34B illustrates debugging of the refactored operons.
Figure 34A:
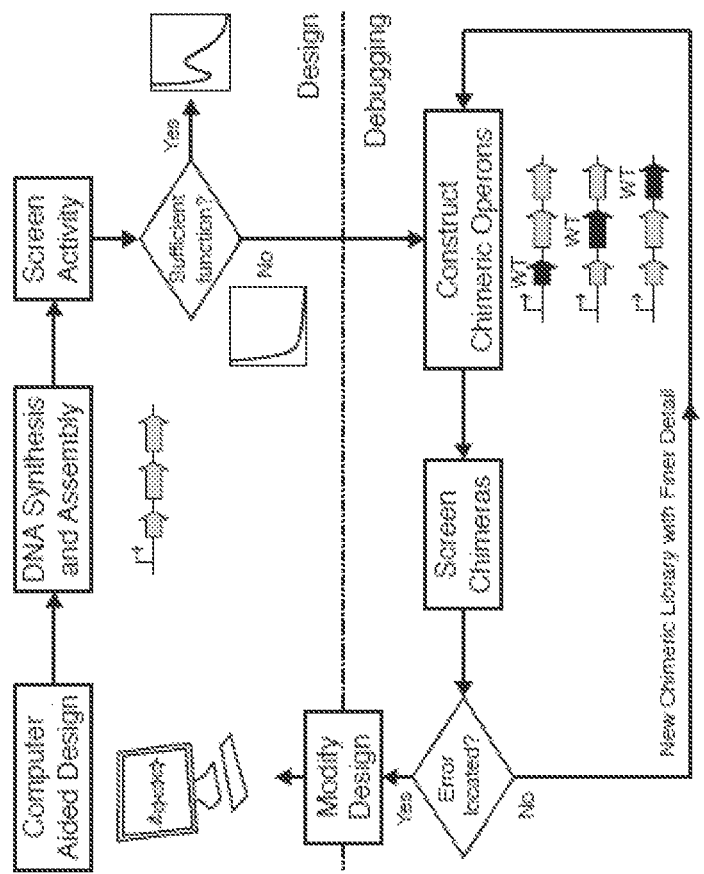
Figure 36:
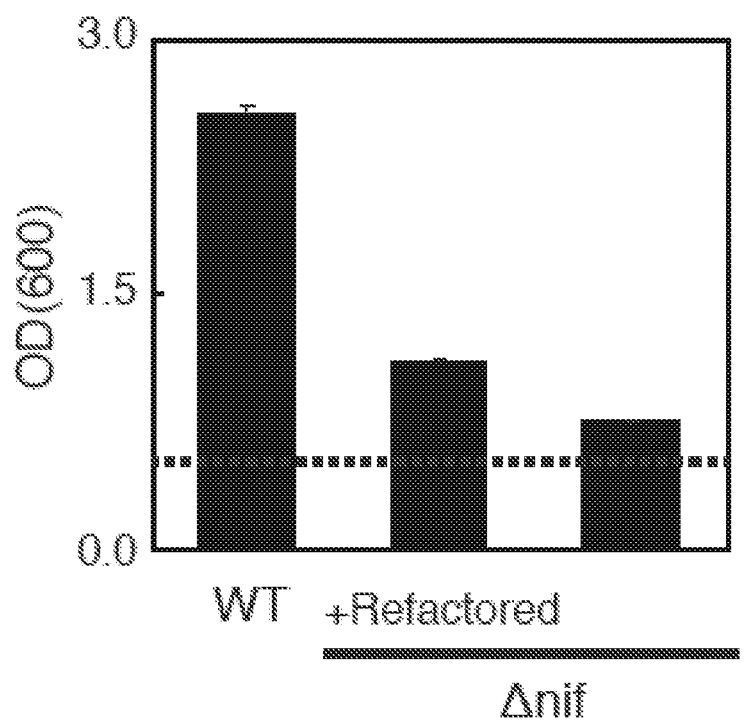
FIG. 36 shows cell growth supported by nitrogen fixation. The dotted line indicates initial seeding density of OD600 0.5. Wild-type *Klebsiella* grew to an OD600 2.57±0.07 after 36 hours of incubation in depression conditions. Eliminating the full nif cluster severely inhibited cell growth (Δnif OD600 0.76±0.02). Complementing the knockout strain with the refactored cluster and Controller #1 under 1 mM IPTG induction yielded growth of OD600 1.10±0.03.

Some of the initial designs for refactored operons showed little or no activity. When this occurs, it is challenging to identify the problem because so many genetic changes have been made simultaneously to the extent that there is almost no DNA identity with the wild-type sequence. To rapidly identify the problem, a debugging method was developed that can be generalized when refactoring different functions (FIG. 34A). Chimeric operons are created by replacing a wild-type region of DNA with its synthetic counterpart. The function of each chimera in this library is assessed to identify which region of synthetic DNA caused a loss of activity. New chimeras are then be constructed with increasingly fine-resolution changes between synthetic and wild-type DNA. This approach "zooms in" on the problematic region of DNA, which can then be fixed. The most common problem is due to errors in the reference DNA sequence (Genbank, X13303.1) (52). Refactored genes were designed using only the amino acid sequence information from the database; thus, they were sensitive to sequencing errors leading to missense mutations that reduced or eliminated activity. Indeed, 18 such mutations were identified and confirmed by carefully resequencing the wild-type cluster (FIG. 35). Fifteen of the 18 mutations occurred in refactored operons that required debugging and were corrected (FIG. 34B). This demonstrates the challenge of reconstituting biological functions using only database information and DNA synthesis (55).

Figure 27C:
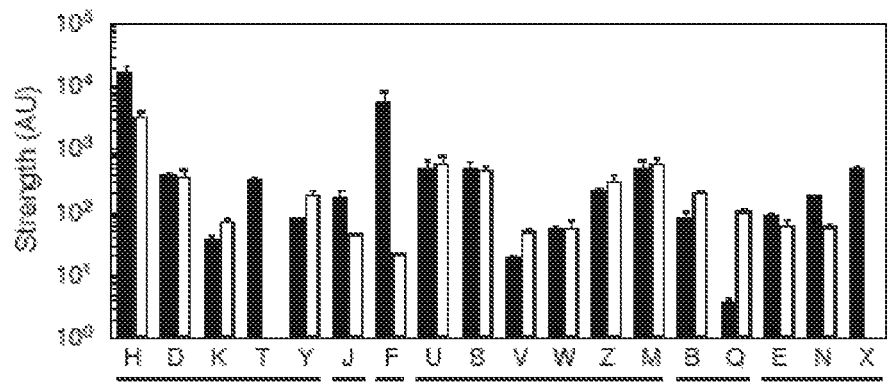
Figure 37:
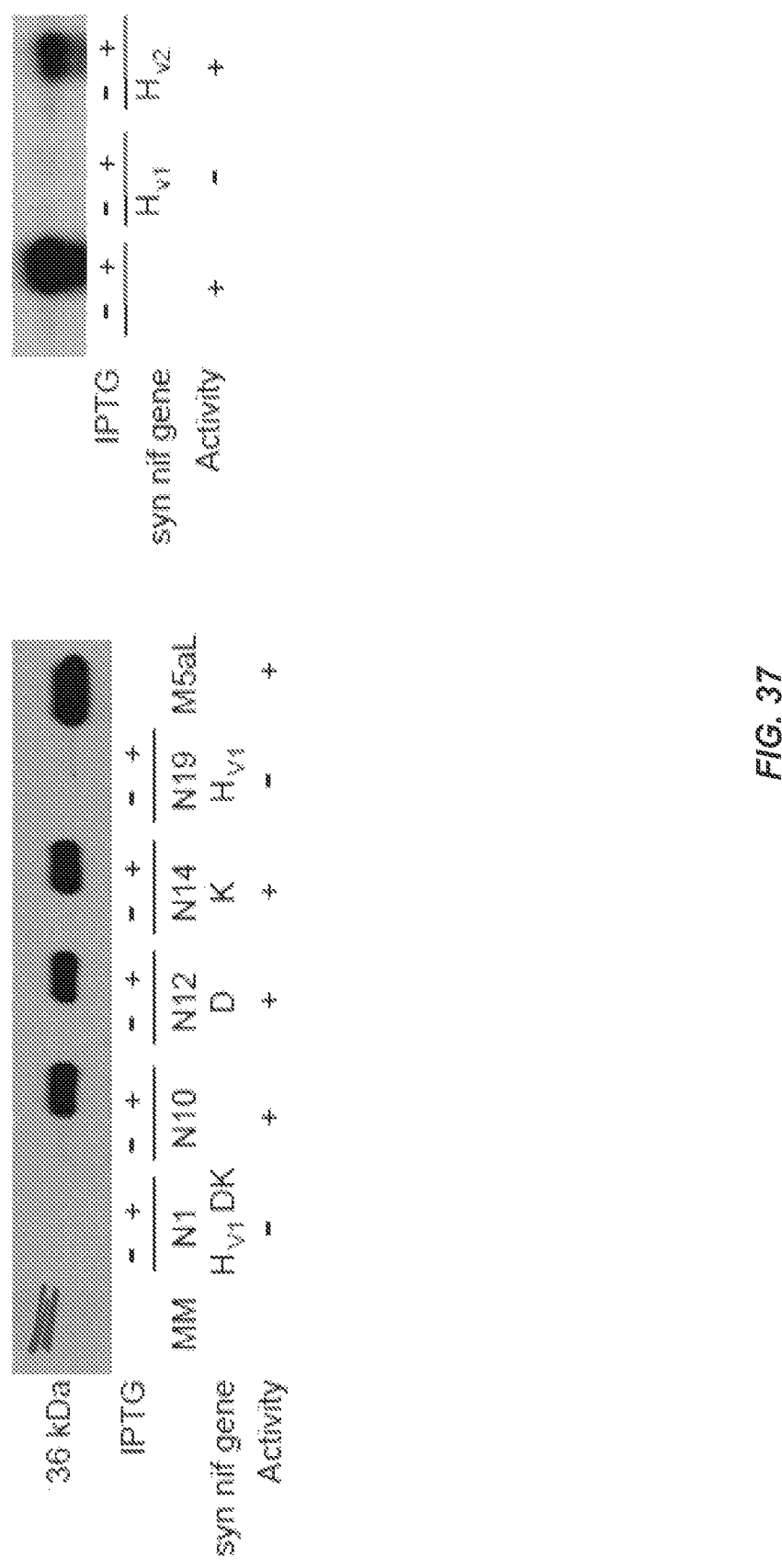
FIG. 37 shows expression of synthetic nifH variants. Western blot assay to detect the expression of synthetic $nifH_{v1}$ (left) and synthetic $nifH_{v2}$ (right). All constructs bore $P_{tac}$-nifHDK with the synthetic gene indicated. Cultures were induced with 50μM IPTG.

Modifying synthetic RBS strength was also important to debugging. The function of the synthetic nifUSVWZM operon was significantly improved by changing RBSs to match a 1:1 ratio of NifU:NifS. The initial selection of RBSs led to an observed 10:1 ratio in their respective RBS strengths. After debugging, nifU and nifS RBS strength was better balanced (1.25:1) and this improved activity. For one RBS, the measurement method proved to be inaccurate. We found the measured strength of the wild-type nifQ RBS was extremely low (FIG. 27C), and the synthetic nifBQ operon showed low activity when the synthetic nifQ RBS was matched to the measured strength. In contrast, the robustness analysis showed a requirement for high expression level of the nifBQ operon (FIG. 27B). Thus, a strong synthetic RBS near the strength of the nifB RBS was used and significantly improved nifBQ operon activity. In one case, our initial recoded nifH gene did not express well using either wild-type or synthetic regulation (FIG. 37). We designed a new synthetic gene, requiring that it diverge in DNA sequence from both the native and first synthetic DNA sequences and found that the new synthetic gene both expressed well and recovered activity.

Growth by Nitrogen Fixation

Cells capable of nitrogen fixation should exhibit measurable growth on media that lacks nitrogen by utilizing atmospheric N$_2$ as a source of nitrogen. Conversely, cells incapable of nitrogen fixation should not grow on nitrogen-free media.

In parallel to the $^{15}$N$_2$ incorporation assay, we monitored strain growth under nitrogen-limited media conditions and 100% $^{15}$N$_2$ atmosphere (Methods, N$_2$-dependent Growth Assay). Cells were grown on derepression media as used in the Nitrogenase Activity Assay. Depression media is not strictly nitrogen-free, containing 1.43 mM serine in order to promote ribosomal RNA production and hasten nitrogenase biosynthesis (54).

Strains containing Controller #1 and the refactored gene cluster grew nearly 30% as much as wild-type strains. In contrast, minimal growth was observed in Δnif strains, consistent with the limited nitrogen available from serine and cell lysis products (55). FIG. 37 illustrates cell growth supported by nitrogen fixation.

Western Blot Assay for Synthetic nifH Expression

The first synthetic nifHDK did not exhibit nitrogenase activity under induction ranging from 0 to 1 mM IPTG, and the nifJ gene (synthetic nifH$_{v1}$) was identified as a problematic part using the debugging protocol shown in FIG. 34. However there was no mutation found. Western blots were further used to confirm problematic synthetic nifJ expression.

A western blot for NifH protein in FIG. 37 (left) showed that wild type nifH expressed well with either synthetic nifD or nifK (construct N10, N12, N14), whereas synthetic nifH$_{v1}$ was not expressed regardless of the context of nifDK (construct N1 and N19). A second synthetic nifH (synthetic nifH$_{v2}$) was used to replace synthetic nifH$_{v1}$. The western blot in FIG. 37 (right) showed the synthetic nifH$_{v2}$ (construct N38) expressed well.

Samples for western blots were prepared by boiling collected K. oxytoca cells in SDS-PAGE loading buffer and run on 12% SDS-Polyacrylamide gels (Lonza Biosciences). Proteins on the gels were transferred to PVDF membranes (BioRad Cat#: 162-0177) using Trans-Blot SD Semi-Dry Transfer Cell (BioRad Cat#:#170-3940). Blocking the membrane and Antibody binding were performed using SNAP i.d. Protein Detection System (Millipore Cat#WBAVDBA). The membranes were blocked by TBST-1% BSA (TBS-Tween20). The anti-NifH and anti-NifDK antibodies (kindly provided by Paul Ludden Lab at UC-Berkeley) were used as the primary antibodies. The anti-NifH antibody was a universal anti-NifH made against a mixture of purified NifH proteins from *Azotobacter vinelandii*, *Clostridium pasteurianum*, *Rhodospirillum rubrum*, and *K. oxytoca*. The anti- NifDK antibody was made against purified NifDK protein from *Azotobacter vinelandii*. The anti-NifH and anti-NifDK antibodies were used at 1:500 and 1:2000 respectively. The secondary antibody (Goat anti-Rabbit IgG-HRP, Sigma Cat#: A0545) was used at 1:10,000. Development was done using an enhanced chemiluminescent substrate for HRP (Pierce Cat#: 32209) and captured on film (Kodak: Cat#: 178-8207).

Construction of Plasmids and Parts

Plasmids were designed in silico. Synthetic parts (promoters, RBS, terminators and insulators) were combined with the initial synthetic gene sequences proposed by DNA2.0 in ApE (A Plasmid Editor) and GeneDesigner (56) to create synthetic operons. Synthetic operons were computationally scanned to eliminate unintended regulation (Methods, "Elimination of Undesired Regulation"), and parts containing such regulation were replaced. This reiterative process continued until the synthetic operons included only designed regulation.

Physical DNA was constructed using standard manipulation techniques. Assembly methods followed published protocols and included BioBrick (57), Megawhop (58), Phusion Site-Directed Mutagenesis or Gibson Assembly methods (59). We found that Gibson Assembly was the most efficient DNA assembly method, except when making small (<10 bp) changes in plasmids under 10 kb in size. We noted assembly failures were infrequent, more common in assemblies above 15 kbp, and linked to the presence of homology within ~500 bp of part termini. In these cases, we observed annealing of unexpected parts to create non-intended junctions.

Plasmid pIncW (pSa, SpR) was generated from pEXT21 (pSa, SpR) by deletion of osa, nuc1, the Tn21 integrase gene, and ORF18 (60). Plasmid pSB4C5 (pSC101, CmR) was obtained from the Registry of Standard Biological parts and serves as the base vector for wild-type complementation, RBS characterization, and synthetic operons (57). Plasmid N58 (pSC101, CmR) was generated by inserting the $P_{tac}$ cassette (SynBERC Registry, SBa_000561) between the BioBrick prefix and BioBrick suffix of pSB4C5. Plasmid N292 (SBa_000566) was generated by inserting a terminator characterization cassette between the BioBrick prefix and BrioBrick suffix of pSB4C5. The cassette consists of the PT7 promoter, RBS (SBa_000498), GFP, the wild-type T7 terminator, RBS D103 (SBa_000563) from Salis et. al. (13), and mRFP (SBa_000484). Plasmid N149 (SBa_000516) was constructed by inserting the $P_{tac}$ promoter cassette (SBa_000563), RBS D103 (SBa_000563), and mRFP (SBa_000484) between the BioBrick prefix and BioBrick suffix of pSB4C5. Plasmid N505 (SBa_000517) was constructed by inserting the Ptet promoter cassette (SBa_000562), RBS D103 (SBa_000563), and mRFP (SBa_000484) between the BioBrick prefix and BioBrick suffix of pSB4C5. Plasmid N110 (SBa_000564) was constructed by inserting a constitutive promoter (SBa_000565), a strong RBS (SBa_000475), and mRFP (SBa_000484) between the BioBrick prefix and BioBrick suffix of pSB4C5. Plasmid N573 (SBa_000559) was constructed by inserting the AmpR resistance marker in pNOR1020 (14).

Figure 31:
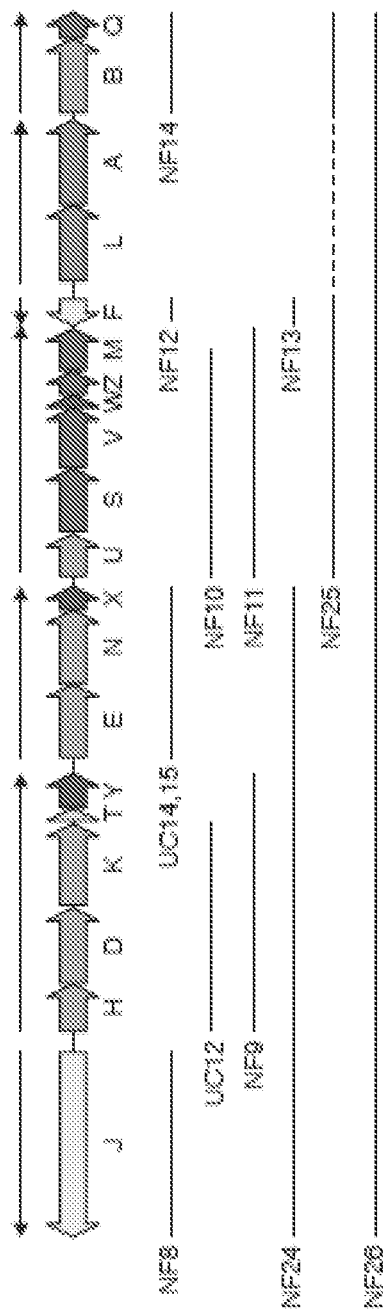
FIG. 31 shows the nifoperon deletions used in this study. The solid lines show the region of deleted nifoperons. The dashed line in NF25 shows the retained nifLA operon.

It has been shown that the multicopy expression of some nitrogen fixation genes can eliminate nitrogenase maturation and function (i.e., multicopy inhibition) (63, 64). An additional uncertainty is that the replacement of the native promoter with an inducible promoter could disrupt their function. To examine these effects, we constructed plasmids to complement the activities of the knockout strains (FIG. 31) and tested their activity under inducible control. These plasmids are also the basis for the experiments to quantify the robustness to changes in expression (FIG. 27).

Complementation plasmids were constructed by inserting the DNA encoding each wild-type operon between the $P_{tac}$ promoter and BioBrick suffix of plasmid N58 (pSC101, CmR). One exception was plasmid Nif18 which was constructed by cloning the nifHDKTY operon into the multicloning site of pEXT21 (60). Wild-type operon sequences were defined by published transcription initiation sites (65).

Wild-type RBS characterization vectors were constructed by inserting the region from −60 bp to +90 bp for each native gene and mRFP (SBa_000484) between the Ptac cassette (SBa_000561) and the BioBrick suffix of plasmid N58 (pSC101, CmR). The native gene sequence from +1 bp to +90 bp formed an in-frame fusion with mRFP. In cases where the gene transcript does not extend to −60 bp, a shorter cassette was cloned into N58. RBS strength was characterized using the Promoter Characterization Assay described herein.

Synthetic RBSs of sufficient length to capture the full ribosome footprint (~35 bp) were generated with the RBS Calculator (61). The strength of each was measured using a synthetic RBS characterization vector. These vectors were constructed similar to the wild-type RBS characterization vectors using −60 bp to +90 bp of the designed synthetic gene. This region includes part of a buffer sequence, the synthetic RBS, and the region from +1 bp to +90 bp of the synthetic gene. If the synthetic and wild-type RBSs differed by more than 3-fold in expression, new RBS sequences were generated and screened. Insulator parts consisting of −50 bp of random DNA precede each synthetic RBS (66).

Synthetic operons were cloned into the pSB4C5 (pSC101, CmR) backbone between the BioBrick prefix and BioBrick suffix.

Synthetic Part Generation

T7*RNA Polymerase: The T7 RNA polymerase was modified to be non-toxic to both *Klebsiella* and *E. coli* at high expression levels. The RNAP was expressed from a low-copy origin (pSa) under control of a weak RBS (SBa_000507, TATCCAAACCAGTAGCTCAATTG-GAGTCGTCTAT (SEQ ID NO:341)) and N-terminal degradation tag (SBa_000509, TTGTTTATCAAGCCTGCG-GATCTCCGCGAAATTGTGACTTTTCCGCTATTTAG-CGATC
TTGTTCAGTGTGGCTTTCCTTCACCGGCAGCAGAT-TACGTTGAACAGCGCATCGATC TGGGTGGC (SEQ ID NO:342)). The start codon was changed from ATG to GTG, and the active site contained a mutation (R632S).

T7 promoters: T7 promoters were generated from a random library. The T7 promoter seed sequence was TAATAC-GACTCACTANNNNNAGA (SEQ ID NO: 156). For the sequences of individual promoters, see FIG. 38.

T7 terminators: T7 terminators were generated from a random library and inserted into the terminator characterization vector N292 (SBa_000566). The T7 terminator seed sequence was TANNNAACCSSWWSSNSSSSTCWWW-CGSSSSSSWWSSGTTT (SEQ ID NO:343). Terminator plasmids were co-transformed with plasmid N249 and characterized (Methods, Fluorescence Characterization) under 1 mM IPTG induction of T7* RNAP. RFP expression was measured for each terminator, and data are reported as the fold reduction in measured fluorescence when compared to a derivative of N292 carrying no terminator. For the sequences of individual terminators, see FIG. 38

Ribosome binding sites: The RBS Calculator was used to generate an RBS that matched the measured strength of the wild-type RBS. In three cases, synthetic RBSs were selected from existing parts (SBa_000475 for nifJ and nifQ, and SBa_000469 for nifH). In cases where the strength of the initial synthetic RBS differed from the WT RBS by more than 3-fold (nifV, nifZ, and nifM), a library of synthetic RBS was constructed by replacing the 15 bp upstream of the start codon with NNNAGGAGGNNNNNN (SEQ ID NO:344). We screened mutants in each library to identify synthetic RBSs within three fold of the WT RBS strength. Ribosome binding site strength is reported in arbitrary fluorescence units measured using the fluorescence characterization assay.

Insulator sequences (spacer sequences): Insulator sequences were generated using the Random DNA Generator using a random GC content of 50% (66).

ANDN Logic: We constructed a genetic circuit encoding the logic A ANDN B and used this circuit to control T7* RNAP in Controller #3. In this circuit, the A ANDN B logic corresponds to the presence or absence of the inducers, IPTG and aTc, such that the cell computes IPTG ANDN aTc. The circuit was constructed by modifying the Ptac promoter in Controller #1 (SBa_000520) to include the cI repressor binding sites OR1 and OR2 to produce plasmid N639 (SBa_000560). Additionally, plasmid pNOR1020 encodes the repressor cI under control of the Ptet promoter (62). We modified pNOR1020 by changing the resistance marker to confer ampicillin resistance to produce N573 (SBa_000559). When N639 and N573 are co-transformed, they produce the logic circuit IPTG ANDN aTc.

```
Ptac (SBa_000512) sequence (SEQ ID NO: 334):
tattctgaaatgagctgttgacaattaatcatcggctcgtataatgt
gtggaattgtgagcggataacaatt Ptac plus OR1 and OR2 (SBa_000506) sequence
(SEQ ID NO: 335):
tattaacaccgtgcgtgttgacagctatacctctggcggttataatg
ctagcggaattgtgagcggataacaatt
```

Figure 39:
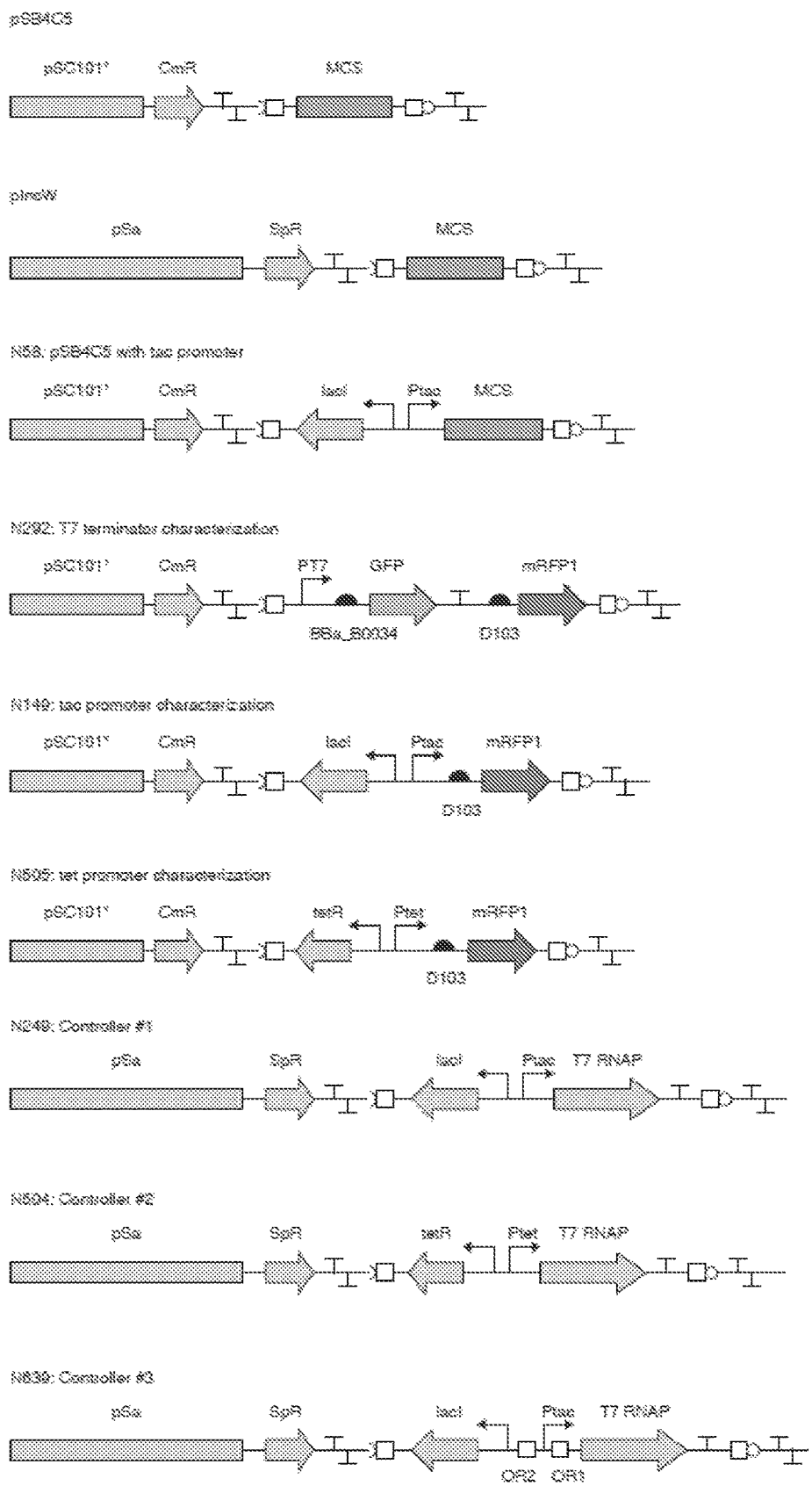
FIG. 39 shows maps of key plasmids. SBOL graphical notation is used to describe genetic parts: the BioBrick prefix and suffix are open squares, and terminators are in the shape of a T.

FIG. 39 illustrates maps for key plasmids.

The nif gene cluster in *K. oxytoca* Ma5L was re-sequenced from PCR fragments. The re-sequenced DNA sequence was compared to the reference sequence from Genbank, X13303.1 (52). Sequence differences are listed in FIG. 35. The nucleotide locations are numbered relative to X13303.1. Amino acid mutations to correct errors in the X13303.1 record are shown (Impact).

REFERENCES

1. Fischbach M, Voigt, C. A. (2010) Prokaryotic gene clusters: A rich toolbox for synthetic biology. *Biotechnol. J.* 5:1277-1296.
2. Ishihama A (2010) Prokaryotic genome regulation: multifactor promoters, multitarget regulators and hierarchic networks. *FEMS Microbiol Rev* 34(5):628-645.
3. Mandal M & Breaker R R (2004) Gene regulation by riboswitches. *Nat Rev Mol Cell Biol* 5(6):451-463.
4. Temme K, et al. (2008) Induction and relaxation dynamics of the regulatory network controlling the type III secretion system encoded within *Salmonella* pathogenicity island 1. *J Mol Biol* 377(1):47-61.
5. Georg J & Hess W R (2011) cis-antisense RNA, another level of gene regulation in bacteria. *Microbiol Mol Biol Rev* 75(2):286-300.
6. Guell M, Yus E, Lluch-Senar M, & Serrano L (2011) Bacterial transcriptomics: what is beyond the RNA horizome? *Nature reviews. Microbiology* 9(9):658-669.
7. Johnson Z I & Chisholm S W (2004) Properties of overlapping genes are conserved across microbial genomes. *Genome Res* 14(11):2268-2272.
8. Zazopoulos E, et al. (2003) A genomics-guided approach for discovering and expressing cryptic metabolic pathways. *Nat Biotechnol* 21(2): 187-190.
9. Medema M H, Breitling R, Bovenberg R, & Takano E (2011) Exploiting plug-and-play synthetic biology for drug discovery and production in microorganisms. *Nature reviews. Microbiology* 9(2):131-137.
10. Gottelt M, Koi, S., Gomez-Escribano, J. P., Bibb, M., Takano, E. (2010) Deletion of a regulatory gene within the cpk gene cluster reveals novel antibacterial activity in *Steptomyces coelicolor* A3(2). *Microbiology* 156:2343-2353.
11. Lombo F, Brana, A. F., Mendez, C., Salas, J. A. (1999) The mithramycin gene cluster of *Steptomyces argillaceus* contains a positive regulatory gene and two repeated DNA sequences that are located at both ends of the cluster. *J. Bacteriol.* 181:642-647.
12. Medema M H, Bretiling, R., Takano, E. (2011) Synthetic biology in *Steptomyces* bacteria. *Methods Enzymol* 497: 485-502.
13. Pickens L B, Tang, Y., Chooi, Y-H. (2011) Metabolic engineering for the production of natural products. *Annu. Rev. Chem. Biomol. Eng.* 2:1-26.
14. Smanski M J, Peterson, R. M., Raj ski, S. R., Shen, B. (2009) Engineered *Streptomyces platensis* strains that overproduce antibiotics platensimycin and platencin. *Antimicrob. Agents Chemother.* 53:1299-12304.
15. Biggins J B, Liu, X., Feng, Z., Brady, S. F. (2011) Metabolites from the induced expression of crypic single operons found in the genome of *Burkholderia pseudomallei. JACS* 133:1638-1641.
16. Watanabe K, Hotta, K., Praseuth, A. P., Koketsu, K., Migita, A., Boddy, C. N., Wang, C. C. C., Oguri, H., Oikawa, H. (2006) Total biosynthesis of antitumor nonribosomal peptides in *Escherichia coli. Nature Chemical Biology:* 1-6.
17. Fowler M & Beck K (1999) *Refactoring: improving the design of existing code* (Addison-Wesley, Reading, M A) pp xxl, 431 p.
18. Chan L Y, Kosuri S, & Endy D (2005) Refactoring bacteriophage T7. *Mol Syst Biol* 1:2005 0018.
19. Czar M J, Anderson J C, Bader J S, & Peccoud J (2009) Gene synthesis demystified. *Trends Biotechnol* 27(2):63-72.
20. Purnick P E & Weiss R (2009) The second wave of synthetic biology: from modules to systems. *Nat Rev Mol Cell Biol* 10(6):410-422.
21. Stacey G S, Burris R H, & Evans H J (1992) *Biological nitrogen fixation* (Chapman & Hall, New York) pp xii, 943 p.
22. Burris R H (1991) Nitrogenases. *J Biol Chem* 266(15): 9339-9342.
23. Hu Y, Fay A W, Lee C C, Yoshizawa J, & Ribbe M W (2008) Assembly of nitrogenase MoFe protein. *Biochemistry* 47(13):3973-3981.
24. Rubio L M & Ludden P W (2005) Maturation of nitrogenase: a biochemical puzzle. *J Bacteriol* 187(2): 405-414.
25. Arnold W, Rump A, Klipp W, Priefer U B, & Puhler A (1988) Nucleotide sequence of a 24,206-base-pair DNA fragment carrying the entire nitrogen fixation gene cluster of *Klebsiella pneumoniae. J Mol Biol* 203(3):715-738.

26. Dixon R & Kahn D (2004) Genetic regulation of biological nitrogen fixation. *Nat Rev Microbiol* 2(8):621-631.
27. Dixon R A & Postgate J R (1972) Genetic transfer of nitrogen fixation from *Klebsiella pneumoniae* to *Escherichia coli*. *Nature* 237(5350):102-103.
28. Simon H M, Homer M J, & Roberts G P (1996) Perturbation of nifT expression in *Klebsiella pneumoniae* has limited effect on nitrogen fixation. *J Bacteriol* 178(10):2975-2977.
29. Fani R, Gallo R, & Lio P (2000) Molecular evolution of nitrogen fixation: the evolutionary history of the nifD, nifK, nifE, and nifN genes. *J Mol Evol* 51(1):1-11.
30. Gosink M M, Franklin N M, & Roberts G P (1990) The product of the *Klebsiella pneumoniae* nifX gene is a negative regulator of the nitrogen fixation (nif) regulon. *J Bacteriol* 172(3):1441-1447.
31. Orme-Johnson W H (1985) Molecular basis of biological nitrogen fixation. *Annu Rev Biophys Biophys Chem* 14:419-459.
32. Kelly J R, et al. (2009) Measuring the activity of BioBrick promoters using an in vivo reference standard. *J Biol Eng* 3:4.
33. Gibson D G, et al. (2009) Enzymatic assembly of DNA molecules up to several hundred kilobases. *Nat Methods* 6(5):343-345.
34. Yokobayashi Y, Weiss R, & Arnold F H (2002) Directed evolution of a genetic circuit. *Proc Natl Acad Sci USA* 99(26): 16587-16591.
35. Tamsir A, Tabor J J, & Voigt C A (2011) Robust multicellular computing using genetically encoded NOR gates and chemical 'wires'. *Nature* 469(7329):212-215.
36. Alon U (2007) *An introduction to systems biology: design principles of biological circuits* (Chapman & Hall/CRC, Boca Raton, Fla.) pp xvi, 301 p., 304 p. of plates.
37. Kitano H (2002) Systems biology: a brief overview. *Science* 295(5560): 1662-1664.
38. Palsson B (2006) *Systems biology: properties of reconstructed networks* (Cambridge University Press, Cambridge; New York) pp xii, 322 p.
39. Kalir S, et al. (2001) Ordering genes in a flagella pathway by analysis of expression kinetics from living bacteria. *Science* 292(5524):2080-2083.
40. Zaslaver A, Mayo A, Ronen M, & Alon U (2006) Optimal gene partition into operons correlates with gene functional order. *Phys Biol* 3(3): 183-189.
41. Kovacs K, Hurst L D, & Papp B (2009) Stochasticity in protein levels drives colinearity of gene order in metabolic operons of *Escherichia coli*. *PLoS Biol* 7(5): e1000115.
42. Wenzel S C & Muller R (2005) Recent developments towards the heterologous expression of complex bacterial natural product biosynthetic pathways. *Curr Opin Biotechnol* 16(6):594-606.
43. Welch M, et al. (2009) Design parameters to control synthetic gene expression in *Escherichia coli*. *PLoS One* 4(9):e7002.
44. Salis H M, Mirsky E A, & Voigt C A (2009) Automated design of synthetic ribosome binding sites to control protein expression. *Nat Biotechnol* 27(10):946-950.
45. Zomer A L (2011) PPP: Perform Promoter Prediction.
46. Studholme D (2011) PromScan.
47. Kingsford C L, Ayanbule K, & Salzberg S L (2007) Rapid, accurate, computational discovery of Rho-independent transcription terminators illuminates their relationship to DNA uptake. *Genome Biol* 8(2):R22.
48. Stewart W D, Fitzgerald G P, & Burris R H (1967) In situ studies on nitrogen fixation with the acetylene reduction technique. *Science* 158(3800):536.
49. Philippe N, Alcaraz J P, Coursange E, Geiselmann J, & Schneider D (2004) Improvement of pCVD442, a suicide plasmid for gene allele exchange in bacteria. *Plasmid* 51(3):246-255.
50. Zhao D, Curatti L, & Rubio L M (2007) Evidence for nifU and nifS participation in the biosynthesis of the iron-molybdenum cofactor of nitrogenase. *J Biol Chem* 282(51):37016-37025.
51. Kelly J R, et al. (2009) Measuring the activity of BioBrick promoters using an in vivo reference standard. *J Biol Eng* 3:4.
52. Arnold W, Rump A, Klipp W, Priefer U B, & Puhler A (1988) Nucleotide sequence of a 24,206-base-pair DNA fragment carrying the entire nitrogen fixation gene cluster of *Klebsiella pneumoniae*. *J Mol Biol* 203(3):715-738.
53. Bayer T S, et al. (2009) Synthesis of Methyl Halides from Biomass Using Engineered Microbes. *J Am Chem Soc* 131(18):6508-6515.
54. Jacob G S, Schaefer J, Garbow J R, & Stejskal E O (1987) Solid-state NMR studies of *Klebsiella pneumoniae* grown under nitrogen-fixing conditions. *J Biol Chem* 262(1):254-259.
55. Mason C A & Hamer G (1987) Cryptic Growth in Klebsiella-Pneumoniae. *Appl Microbiol Biot* 25(6):577-584.
56. Villalobos A, Ness J E, Gustafsson C, Minshull J, & Govindarajan S (2006) Gene Designer: a synthetic biology tool for constructing artificial DNA segments. *BMC Bioinformatics* 7:285.
57. Shetty R P, Endy D, & Knight T F, Jr. (2008) Engineering BioBrick vectors from BioBrick parts. *J Biol Eng* 2:5.
58. Miyazaki K (2003) Creating random mutagenesis libraries by megaprimer PCR of whole plasmid (MEGAWHOP). *Methods Mol Biol* 231:23-28.
59. Gibson D G, et al. (2009) Enzymatic assembly of DNA molecules up to several hundred kilobases. *Nat Methods* 6(5):343-345.
60. Dykxhoorn D M, St Pierre R, & Linn T (1996) A set of compatible tac promoter expression vectors. *Gene* 177(1-2):133-136.
61. Salis H M, Mirsky E A, & Voigt C A (2009) Automated design of synthetic ribosome binding sites to control protein expression. *Nat Biotechnol* 27(10):946-950.
62. Tamsir A, Tabor J J, & Voigt C A (2011) Robust multicellular computing using genetically encoded NOR gates and chemical 'wires'. *Nature* 469(7329):212-215.
63. Buck M & Cannon W (1987) Frameshifts close to the *Klebsiella pneumoniae* nifH promoter prevent multicopy inhibition by hybrid nifH plasmids. *Mol Gen Genet* 207(2-3):492-498.
64. Riedel G E, Brown S E, & Ausubel F M (1983) Nitrogen fixation by *Klebsiella pneumoniae* is inhibited by certain multicopy hybrid nif plasmids. *J Bacteriol* 153(1):45-56.
65. Beynon J, Cannon M, Buchanan-Wollaston V, & Cannon F (1983) The nif promoters of *Klebsiella pneumoniae* have a characteristic primary structure. *Cell* 34(2):665-671.
66. Maduro M (2011) Random DNA Generator, faculty.ucr.edu/~mmaduro/random.htm.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of altering regulation of a plurality of native bacterial genes associated with a function in a cell, comprising:

providing a bacterial cell for expressing gene products;

providing a gene cluster having a plurality of native bacterial genes having coding sequences;

modifying the gene cluster by making at least one modification in a coding region or an intergenic region;

operably linking at least one heterologous transcriptional regulatory sequence to at least one coding sequence within the modified gene cluster wherein the at least one heterologous transcriptional regulatory sequence is from the same species as the plurality of native bacterial genes; and expressing gene products of the modified gene cluster in the bacterial cell under the control of a polypeptide that binds directly or indirectly to the at least one heterologous transcriptional regulatory sequence.

2. The method of claim 1, wherein the gene cluster modification comprises replacing at least one native codon within one of the coding sequences to modify at least one native regulatory sequence using a synonymous codon.

3. The method of claim 2, wherein at least two coding sequences of the plurality of native bacterial genes have at least one native codon replaced with a synonymous codon.

4. The method of claim 2, wherein the synonymous codon is a maximal distance from a corresponding native codon.

5. The method of claim 1, wherein the polypeptide that binds directly or indirectly to the at least one heterologous transcriptional regulatory sequence is expressed from a control expression cassette, the control expression cassette comprising a control promoter operably linked to a polynucleotide sequence encoding the polypeptide.

6. The method of claim 1, wherein the polypeptide that binds directly or indirectly to the at least one heterologous transcriptional regulatory sequence is heterologous to the cell.

7. The method of claim 1, wherein the polypeptide that binds directly or indirectly to the at least one heterologous transcriptional regulatory sequence is from the same species as the plurality of native bacterial genes.

8. The method of claim 1, further comprising: detecting the magnitude of gene expression of the expressed gene products by computation.

9. The method of claim 8, wherein the computation comprises a numerical optimization algorithm.

10. The method of claim 1, wherein modifying the gene cluster comprises replacing at least one intergenic region to remove at least one native regulatory sequence selected from the group consisting of a ribosome binding site, a terminator, and a promoter.

11. The method of claim 1, wherein modifying the gene cluster comprises: altering at least one intergenic region within the gene cluster to modify a native regulatory sequence.

12. The method of claim 11, further comprising: identifying the native regulatory sequence using computation.

13. The method of claim 11, wherein the polypeptide that binds directly or indirectly to the at least one heterologous transcriptional regulatory sequence is from the same species as the plurality of native bacterial genes.

14. The method of claim 11, wherein the polypeptide that binds directly or indirectly to the at least one heterologous transcriptional regulatory sequence is expressed from a control expression cassette, the control expression cassette comprising a control promoter operably linked to a polynucleotide sequence encoding the polypeptide.

15. The method of claim 11, further comprising: detecting the magnitude of gene expression of the expressed gene products by computation.

\* \* \* \* \*

SEQUENCE LISTING

<160> NUMBER OF SEQ ID NOS: 345

<210> SEQ ID NO 1
<211> LENGTH: 3504
<212> TYPE: DNA
<213> ORGANISM: Klebsiella pneumoniae
<220> FEATURE:
<223> OTHER INFORMATION: wild type Gene J, nifJ

<400> SEQUENCE: 1

| | | | | | | |
|---|---|---|---|---|---|---|
| atgaaaacaa | tggatggcaa | cgccgcggcg | gcctggatct | cttatgcctt | taccgaggtc | 60 |
| gcggcgattt | accccataac | cccctccacg | ccgatggcgg | aaaacgtcga | cgagtgggcg | 120 |
| gcgcagggga | aaaagaacct | ttttggccag | ccggtgcgct | taatgagat | gcagtcggag | 180 |
| gccggcgcgg | caggcgcggt | ccacggcgcg | ctgcaggccg | ggcgctcac | caccacctat | 240 |
| acggcctccc | aggggctgct | gctgatgatc | cccaacatgt | acaaaatcgc | cggtgaactg | 300 |
| ctgccgggcg | tctttcacgt | cagcgcccgg | cgctggcga | ccaattcgct | gaatatttt | 360 |
| ggcgatcacc | aggatgtgat | ggcggtccgc | cagaccggct | gcgcgatgct | ggcggagaac | 420 |
| aacgtgcagc | aggtgatgga | tttgtcggcg | gtggcgcatc | tggcggcgat | taagggacgc | 480 |
| atcccgtttg | ttaacttctt | cgacggtttt | cgcacctcgc | acgaaattca | aaaaatcgag | 540 |
| gtgttggaat | atgagcagct | ggcgacgctg | ctggaccggc | ccgcgctcga | cagcttccgc | 600 |
| cgtaacgcgc | tgcatccgga | tcatccggtc | atccgcggaa | cggcgcagaa | cccggatatc | 660 |
| tacttccagg | agcgggaggc | gggcaaccgt | ttttatcagg | cgctgcccga | cattgtcgaa | 720 |
| agctatatga | cgcaaatcag | cgcgctcacc | ggccgggagt | atcatctgtt | taactatacc | 780 |
| ggcgcggcg | atgccgaacg | ggtgattatc | gcaatgggat | cggtctgcga | taccgttcag | 840 |
| gaagtggtgg | atacgctgaa | cgcggcggga | gagaaggtcg | ggctgctcag | cgtgcatctg | 900 |
| tttcgccctt | tttcgctggc | ccacttcttc | gcccagctgc | cgaaaaccgt | gcagcggatt | 960 |
| gccgtccttg | accgtaccaa | agagcccggc | gctcaggctg | aaccgctgtg | cctggatgtg | 1020 |
| aaaaacgcct | tctaccacca | cgacgatgcg | ccgctaatcg | tcggcggccg | ctatgcgctt | 1080 |
| ggcgggaagg | atgttctgcc | caacgatatc | gcggccgtct | ttgataacct | caataaaccg | 1140 |
| ctgccgatgg | acgggtttac | cctcgggatt | gtcgatgatg | taacctttac | ttcgttaccg | 1200 |
| ccggcccagc | agacgctggc | ggtctcgcat | gacggcatca | ccgcctgtaa | attttggggc | 1260 |
| atgggctcgg | acggcaccgt | cggggccaat | aaaagcgcga | tcaaaattat | cggcgataaa | 1320 |
| acgccgctct | acgcgcaggc | ctactttcct | tatgactcga | aaaaatccgg | cggcattacc | 1380 |
| gtttcacatt | tacgcttcgg | cgaccggccg | atcaattcgc | cctacctgat | ccatcgggcc | 1440 |
| gattttatct | cctgttcgca | gcagtcctac | gttgagcgct | acgatctgct | ggacggatta | 1500 |
| aagccgggcg | ggaccttttt | actcaactgc | agctggtccg | atgcggagct | ggagcagcat | 1560 |
| ctgccggtcg | gctttaaacg | ctatctggcg | cgggaaaata | tccatttta | taccctgaac | 1620 |
| gccgtggata | tcgcccgcga | gctcgggctg | gcgggcgct | ttaatatgct | gatgcaggcg | 1680 |
| gcgttctta | agctggcggc | gattatcgac | ccgcagaccg | cggcgatta | cctcaagcag | 1740 |
| gcggttgaaa | aaagctacgg | cagcaaaggg | gcggcggtga | ttgagatgaa | ccagcgggcg | 1800 |
| atcgagctgg | gcatggcctc | gctgcatcag | gtgacgattc | cggcgcactg | ggcgacgctg | 1860 |
| gatgaacccg | cggcgcaagc | atcagccatg | atgccggatt | tcatccgcga | tattctgcag | 1920 |
| ccgatgaacc | gccagtgcgg | cgaccagctg | ccggtgagcg | cgttcgtcgg | tatggaggac | 1980 |
| gggaccttc | cttcgggcac | cgccgcgtgg | gagaaacgcg | ggatcgcgct | ggaagtgccg | 2040 |

```
gtctggcagc cggagggctg cacgcagtgt aaccagtgcg cctttatctg cccgcatgcg    2100
gcgatccgcc cggcgctgct caacggcgaa gagcatgacg ccgcgccggt tgggctgctg    2160
agcaaacccg cgcagggagc gaaggagtat cactaccatc tggctatctc gccgctggat    2220
tgttccggct gcggcaactg cgtggatatc tgtcccgcgc gcggcaaggc gttaaaaatg    2280
cagtctctcg atagccagcg tcagatggcg ccggtctggg actatgcgct ggcgctgacg    2340
ccgaagagca atccgtttcg taagacgacg gtcaaaggca gccagtttga aaccccgctg    2400
ctggagtttt ccggcgcctg cgcgggatgc ggtgaaacgc ttatgcccg cctgataacc     2460 cagctgtttg gcgaccggat gctgatcgct aacgccaccg gctgctcttc tatctgggga    2520
gccagcgcgc cgtcgattcc ctataccacc aaccaccgcg gccatggccc ggcatgggcg    2580
aactcgctgt ttgaggataa tgcggagttt ggcctcggca tgatgctcgg cggccaggcg    2640
gtgcgtcaac aaatcgccga tgatatgacc gccgcgctgg cgctaccggt cagcgacgaa    2700
cttagcgacg caatgcgcca gtggctggcg aagcaggatg aaggcgaggg cacccgcgag    2760
cgcgcggacc ggctcagcga acggctggcg gcggaaaaag agggcgtgcc gctgttggag    2820
cagctgtggc agaaccgcga ctattttgtt cgtcgttcgc agtggatttt cggcggcgac    2880
ggctgggcct acgatatcgg cttcggcggt ctcgatcacg tgctggcgag cggggaagac    2940
gtcaatattc tggtgtttga caccgaggtt tactccaata ccggcggcca gtcgtctaaa    3000
tcgaccccgg tggcggccat cgcgaagttt gccgcgcagg gcaaacgcac gcggaaaaaa    3060
gatctcggca tgatggcgat gagctacggc aatgtgtacg tggcccaggt cgcgatgggc    3120
gctgataaag atcagaccct acgggcgatc gccgaggccg aagcctggcc gggaccgtcg    3180
ctggtgattg cctacgccgc ctgcattaac cacgggctga agccggtat gcgctgcagc     3240 cagcgcgagg cgaaacgggc ggttgaggcg ggatactggc acctgtggcg ctatcatccg    3300
cagcgggaag cggaaggtaa gacgccgttt atgctcgatt ccgaagagcc ggaggagagc    3360
ttccgcgact ttttgcttgg cgaagtgcgc tacgcctcgc tgcacaaaac gacgccgcat    3420
ctggcggatg cgctctttag ccgaaccgag gaggacgcgc gggcccgctt tgcccagtat    3480
cggcggctgg ccggcgagga gtag                                           3504

<210> SEQ ID NO 2
<211> LENGTH: 3504
<212> TYPE: DNA
<213> ORGANISM: Artificial Sequence
<220> FEATURE:
<223> OTHER INFORMATION: synthetic Gene J

<400> SEQUENCE: 2
atgaaaacta tggacggtaa cgctgcggct gcatggatta gctacgcctt taccgaagtg     60
gctgcgatct acccgattac gccgagcacc ccgatggcgg aaaatgtgga cgaatgggct    120
gcgcagggca gaagaaacct cttcggccag ccggtgcgcc tgatggagat gcagtcggaa    180
gcgggtgcag caggtgctgt gcatggcgcc ttgcaagctg gcgcactgac gaccacctac    240
accgcgtcgc agggcctgtt gctgatgatc ccaaacatgt acaaaatcgc gggtgaactg    300
ctgccgggtg tcttcatgt tcggcacgc gcactggcca ccaatagcct caacatcttt      360
ggcgatcatc aggatgtaat ggcggtgcgc caaacgggct gcgcgatgtt ggccgagaat    420
aacgtccagc aagttatgga tttgtccgcg gtagcccact ggcagcgat caaaggtcgc     480 attccgttcg tgaacttctt cgatggcttt cgcaccagcc acgaaatcca gaagatcgag    540
```

```
gttctggaat atgaacagct ggccaccttg ttggatcgtc cggccctgga cagcttccgc    600
cgtaacgccc ttcacccgga ccacccggtc atccgtggca ccgccagaa cccggacatc    660 tacttccagg aacgtgaggc cggtaaccgt ttctatcagg cgctcccgga tattgtggaa    720
tcttacatga cccagatttc tgccctgact ggtcgcgagt atcacctgtt taactacact    780
ggtgctgcgg atgcggagcg cgtgatcatc gcgatgggct ctgtctgtga caccgtccaa    840
gaggtggttg acacgctgaa tgcagcgggt gagaaagttg gtctgctctc cgttcatctt    900
ttccgcccgt tttcgttagc gcacttcttc gcccaactgc gaaaactgt acagcgtatc    960 gcagtattgg accgtacgaa agagccaggt gctcaagcag agccgctgtg cctcgatgtg   1020
aagaatgcct tttaccacca tgacgatgcc ccgttgattg tgggtggtcg ctatgccttg   1080
ggcggtaagg acgtgttgcc gaacgatatt gcggccgtgt ttgataaacct gaacaaaccg   1140 ctgccgatgg acggcttcac gctgggtatc gtggacgatg ttaccttcac ctctctcccg   1200
ccagcgcagc agaccctggc ggtttctcac gacggcatca cggcatgtaa gttttgggc    1260 atgggctccg acgcacggt tggtgcgaac aagtccgcga tcaagattat cggcgacaaa   1320
acgccactgt atgcgcaagc gtacttttcc tacgactcga agaagagcgg tggtattacc   1380
gtcagccatc tgcgttttgg tgatcgcccg atcaactccc cgtatttgat ccatcgcgcg   1440
gatttcatct cgtgcagcca gcaaagctat gttgaacgct acgatctgct ggatggcctt   1500
aaaccgggtg gcacctttct gctgaactgc tcctggagcg atgccgaact ggagcaacat   1560
ctgccggtcg gtttcaaacg ttatctggca cgcgagaata tccacttcta cactctcaac   1620
gctgtggaca tcgcccgtga gcttggtttg ggtggccgtt tcaacatgct gatgcaggct   1680
gccttcttca aactggccgc gatcattgac ccgcagactg ctgcggacta tctgaagcag   1740
gctgttgaga aaagctatgg cagcaaaggt cggcggtca tcgagatgaa ccagcgtgcc   1800
atcgagcttg gcatggccag cctgcaccag gtgacgatcc cggcacattg ggccacccctg   1860 gatgagccag cggcgcaggc gtccgcgatg atgccggact ttatccgcga catcctgcaa   1920
ccgatgaacc gtcagtgcgg cgaccagctt ccggtgtcgg cttttgtcgg catggaagat   1980 ggcacccttcc cgtccggcac ggccgcatgg gagaaacgtg gcatcgccct tgaggtgcca   2040
gtctggcagc cggaaggctg cacgcagtgc aaccagtgcg ccttcatttg tccgcacgcc   2100
gcgattcgtc cggcgttgtt gaatggcgaa gagcatgatg ctgccccggt tggcctgctg   2160
agcaaaccgg cacaaggcgc taaagaatat cactatcatc tggcgattag cccgctggac   2220
tgctccggct gtggcaactg cgttgacatt tgtccagctc gtggcaaagc gttgaagatg   2280
cagtctctgg atagccaacg ccagatggct ccggtgtggg attatgcgct ggcgctgacc   2340
ccgaagtcta acccgtttcg taaaaccacc gtcaaaggct cgcagttcga aaccccgctg   2400
ctggagtttt gcggtgcgtg cgctggttgt ggcgaaacgc cgtatgcgcg cctcattacc   2460
cagctgtttg cgaccgcat gctgattgcc aatgccaccg ctgttccag catctggggc   2520 gcatctgcgc cgagcatccc gtataccacc aatcatcgtg tcatggtcc ggcctgggcg   2580 aatagcctgt ttgaggacaa tgccgaattt ggtttaggta tgatgctggg cggtcaagct   2640
gtgcgtcaac agatcgcgga cgatatgacg gctgcgttag cgctcccggt ttccgatgag   2700
ctgagcgacg cgatgcgcca gtggttggcg aaacaggacg agggtgaagg cacgcgtgag   2760
cgtgcggacc gtctgagcga gcgcttagcc gcggagaaag agggcgttcc gctgttagag   2820
cagctgtggc aaaatcgtga ttactttgtg cgtcgcagcc agtggatttt cggcggtgac   2880
ggctgggcct atgatattgg cttcggtggc ctggaccacg tcctcgccag cggtgaggat   2940
```

| | |
|---|---|
| gtgaacattc tggtatttga caccgaagtc tactcgaaca ccggcggtca aagcagcaaa | 3000 |
| tcgaccccgg tcgcggccat cgccaagttc gcggctcagg gcaagcgcac ccgcaagaaa | 3060 |
| gacctgggta tgatggcgat gagctacggc aacgtctatg tagcccaggt ggcgatgggt | 3120 |
| gcggataaag atcaaactct gcgcgccatt gcggaagctg aagcgtggcc aggcccgtcg | 3180 |
| ctggtgattg cgtatgcggc ctgcatcaat catggcctga aggccggtat gcgttgcagc | 3240 |
| caacgtgagg cgaagcgcgc tgttgaggcg ggctactggc acctgtggcg ttatcacccg | 3300 |
| cagcgcgaag cggaaggcaa gacgccgttt atgttagata gcgaagaacc ggaagagtcg | 3360 |
| ttccgtgact ttctgttggg tgaggtgcgc tacgcatccc tgcacaagac caccccgcac | 3420 |
| ctcgccgatg ccctttcag ccgtaccgaa aagatgcgc gtgcgcgctt tgcgcaatac | 3480 |
| cgtcgcctgg ctggcgaaga gtaa | 3504 |

<210> SEQ ID NO 3
<211> LENGTH: 882
<212> TYPE: DNA
<213> ORGANISM: Klebsiella pneumoniae
<220> FEATURE:
<223> OTHER INFORMATION: wild type Gene H, nifH

<400> SEQUENCE: 3

| | |
|---|---|
| atgaccatgc gtcaatgcgc tatttacggt aaaggcggta tcggtaaatc caccaccacg | 60 |
| cagaacctcg tcgccgcgct ggcggagatg ggtaagaaag tgatgatcgt cggctgcgat | 120 |
| ccgaaggcgg actccacccg tctgattctg cacgccaaag cacagaacac cattatggag | 180 |
| atggccgcgg aagtcggctc ggtcgaggac ctcgaactcg aagacgtgct gcaaattggc | 240 |
| tacggcgatg tgcgctgcgc ggaatccggc ggcccggagc caggcgtcgg ctgcgcggga | 300 |
| cgcggcgtga tcacggcgat caactttctt gaagaagaag gcgcctacga ggacgatctc | 360 |
| gatttcgtgt tctatgacgt gctcggcgac gtggtctgcg gcggcttcgc catgccgatc | 420 |
| cgcgaaaaca aagcccagga gatctacatc gtctgctccg gcgaaatgat ggcgatgtac | 480 |
| gcggccaaca tatctccaa agggatcgtt aaatacgcca aatccggcaa ggtgcgcctc | 540 |
| ggcggcctga tctgtaactc acgtcagacc gaccgtgaag acgaactgat tattgccctg | 600 |
| gcggaaaagc tcggtaccca gatgatccac tttgtgcccc gcgacaacat cgtgcagcgc | 660 |
| gcggagatcc gccgcatgac ggttatcgag tacgaccccg cctgtaaaca ggccaacgaa | 720 |
| taccgcaccc tggcgcagaa gatcgtcaac aacaccatga agtggtgcc gacgccctgc | 780 |
| accatggatg agctggaatc gctgctgatg gagttcggca tcatggaaga ggaagacacc | 840 |
| agcatcattg gcaaaaccgc cgccgaagaa aacgcggcct ga | 882 |

<210> SEQ ID NO 4
<211> LENGTH: 882
<212> TYPE: DNA
<213> ORGANISM: Artificial Sequence
<220> FEATURE:
<223> OTHER INFORMATION: synthetic Gene H

<400> SEQUENCE: 4

| | |
|---|---|
| atgaccatgc gtcagtgcgc gatttatggc aaaggtggta ttggcaaaag cacgacgacc | 60 |
| cagaacttgg tggcggccct ggccgagatg ggtaaaaagg ttatgattgt gggttgcgac | 120 |
| ccgaaggccg acagcacgcg cctgattctg cacgcgaaag cacaaaacac gattatggag | 180 |
| atggctgccg aggttggtag cgtggaggat ctggagctgg aggacgttct gcaaattggt | 240 |

```
tacggtgatg ttcgttgcgc agagagcggt ggtccggaac caggtgtcgg ctgtgcgggt      300
cgtggtgtga ttaccgctat caatttcctg gaagaagagg gtgcgtacga agatgatctg      360
gatttcgttt tctacgatgt gctgggtgat gtcgtgtgcg gtggttttgc aatgccgatt      420
cgcgagaata aggcacaaga aatttacatt gtctgtagcg gcgagatgat ggcaatgtac      480
gctgctaaca acatcagcaa gggtattgtt aaatacgcaa aaagcggtaa ggttcgcttg      540
ggtggtttga tttgcaacag ccgtcagacc gaccgtgagg acgaactgat catcgccctg      600
gctgagaaac tgggcaccca aatgatccac ttcgtgccac gcgataatat tgttcaacgt      660
gcagaaatcc gccgtatgac cgtcattgag tatgacccgg catgcaagca agcgaacgag      720
taccgcacct tggcacagaa aatcgtgaac aacaccatga aggttgttcc gacgccgtgt      780
acgatggacg agctggagag cctgctgatg gagttcggca ttatggagga ggaggacacc      840
agcattatcg gtaagaccgc agcggaggag aatgcggcat aa                         882

<210> SEQ ID NO 5
<211> LENGTH: 1452
<212> TYPE: DNA
<213> ORGANISM: Klebsiella pneumoniae
<220> FEATURE:
<223> OTHER INFORMATION: wild type Gene D, nifD

<400> SEQUENCE: 5
atgatgacca acgcaacggg cgaacgtaat ctggcgctga tccaggaagt cctggaggtg       60
ttcccggaaa ccgcgcgaaa agagcgcaga aagcacatga tggtcagcga tccgaaaatg      120
aagagcgtcg gcaagtgcat tatctctaac cgcaaatcac aacccggcgt aatgaccgta      180
cgcggctgcg cctacgccgg ttccaaaggg gtggtatttg gccgattaa ggatatggcc       240 catatttcgc acggaccggc tggctgcggc cagtattccc gcgccgaacg acgcaactac      300
tacaccggag tcagcggcgt cgatagcttc ggcacgctga acttcacctc tgattttcag      360
gagcgcgaca tcgtcttcgg cggcgataaa aagctcagca agctgattga agagatggag      420
ttgctgttcc cgctcaccaa agggatcacc attcagtcgg aatgcccggt ggggctgatc      480
ggtgatgata tcagcgcggt ggccaacgcc agcagcaagg cgctggataa accggtgatc      540
ccggtacgct gcgaaggctt tcgcggcgtg tcgcagtctc tggggcacca tatcgccaac      600
gacgtggtgc gcgactggat cctgaacaat gccgaaggac agccgtttga aaccacccct      660
tacgatgtgg cgatcatcgg cgactacaac atcggcggcg acgcctgggc ctcgcgcatt      720
ctgctggaag agatggggct acgggtagtc gcgcagtggt ccggcgacgg cacgctggtg      780
gagatggaga taccccatt cgtcaagctg aacctggttc actgctaccg ttcgatgaac       840
tatatcgccc gccatatgga ggagaaacat cagattccgt ggatggagta caacttcttc      900
gggccgacca aaatcgccga atcgctgcgc aaaatcgccg accagttcga cgataccatt      960
cgcgcgaacg ccgaagcggt gatcgcccgg tatgaggggc agatggcggc gattatcgcc     1020
aaatatcgcc cgcgcctgga ggggcgtaag gtgctgctct atatcggagg cctgcggccg     1080
cgccacgtta ttggcgccta tgaggatctc gggatggaga tcatcgccgc cggctacgag     1140
tttgcccata cgatgatta cgaccgcacc ctgccggatc tgaaagaggg cacgctgctg     1200
ttcgatgacg ccagcagcta cgagctggaa gcgttcgtca aggcgctgaa gcccgacctt     1260
atcggctccg gcatcaagga aaatatatc ttccagaaaa tgggcgtgcc gttccgccag      1320
atgcactcgt gggactattc cggccgtac cacggctacg atggtttcgc cattttcgcc      1380
cgcgatatgg atatgaccct gaacaacccg gcgtggaacg aactgaccgc tccgtggctg     1440
```
aagtctgcgt ga                                                    1452

<210> SEQ ID NO 6
<211> LENGTH: 1452
<212> TYPE: DNA
<213> ORGANISM: Artificial Sequence
<220> FEATURE:
<223> OTHER INFORMATION: synthetic Gene D

<400> SEQUENCE: 6

```
atgatgacta atgctactgg cgaacgtaac ctggcactga ttcaagaagt actggaagtg      60
ttcccggaaa ccgcgcgcaa agagcgccgt aaacacatga tggtttctga cccgaaaatg     120
aaatctgtgg gtaaatgcat catctctaat cgcaaatctc agccgggtgt catgactgtt     180
cgtggctgtg cgtacgcagg ttctaaaggt gtcgtattcg gcccgatcaa agatatggcg     240
catatctctc atggcccggc aggctgtggc cagtactctc gcgcggaacg tcgtaactac     300
tacacgggcg tttctggcgt tgactctttc ggcacgctga acttcacctc tgacttccag     360
gaacgtgaca tcgttttcgg tggcgataaa aagctgtcca actgatcga agaaatggaa     420
ctgctgttcc cgctgactaa aggcattact atccaaagcg aatgtccggt gggtctgatc     480
ggtgatgaca tcagcgcggt cgcaaacgca tcttccaaag ccctggataa gccggtgatc     540
ccggttcgtt gcgagggctt ccgcggcgtt tctcagtctc tgggtcatca catcgcaaac     600
gatgttgtgc gtgactggat tctgaacaac cgtgaaggtc agccttttga accacccct     660
tatgacgttg cgattattgg cgactataac atcggcggcg acgcctgggc atcccgcatc     720
ctgctggagg agatgggtct gcgtgttgtc gcacagtggt ctggcgatgg cacccctggtt     780
gaaatggaaa cacccgcgtt tgttaaactg aacctggttc actgctaccg ctccatgaac     840
tacattgccc gtcacatgga agaaaaacat cagatcccct tggatgaata caacttcttc     900
ggtccgacta aaatcgcaga atccctgcgt aaaatcgccg atcagtttga tgataccatt     960
cgcgcgaacg ctgaagcagt aattgcgcgc tacgaaggcc agatggcagc aatcattgct    1020
aagtaccgtc cgcgcctgga aggtcgtaaa gtgctgctgt acatgggtgg tctgcgtcca    1080
cgtcatgtga tcggtgccta cgaggacctg gcatggaga tcatcgcagc gggttacgaa    1140
tttgcacaca acgacgacta tgatcgtacg ctgccagacc tgaaagaagg tacgctgctg    1200
tttgacgacg ccagctctta tgaactggaa gccttcgtga aagcgctgaa ccagacctg    1260
atcggctccg gcatcaagga aaaatacatt ttccagaaaa tgggcgtgcc gttccgccag    1320
atgcactcct gggactactc cggtccgtac cacggctacg acgtttcgc tatcttcgct    1380
cgtgacatgg atatgaccct gaataaccca gcgtggaatg aactgaccgc accgtggctg    1440
aaatctgcat aa                                                       1452
```

<210> SEQ ID NO 7
<211> LENGTH: 1563
<212> TYPE: DNA
<213> ORGANISM: Klebsiella pneumoniae
<220> FEATURE:
<223> OTHER INFORMATION: wild type Gene K, nifK

<400> SEQUENCE: 7

```
atgagccaaa cgattgataa aattaatagc tgttatccgc tattcgaaca ggatgaatac     60
caggagctgt tccgcaataa gcggcagctg gaagaggcgc acgatgcgca gcgcgtgcag    120
gaggtctttg cctggaccac caccgccgag tatgaagcgc tgaatttccg acgcgaggcg    180
```

```
ctgaccgttg acccggcgaa agcctgccag ccgcttggcg cggtgctttg ctcgctggga    240
tttgccaaca ccctgccgta tgtgcacggc tctcagggt gcgtggccta ctttcgcacc    300
tattttaacc gccatttcaa agagccgatc gcctgcgtct ccgactcgat gaccgaagac    360
gcggcggtct tcggcggcaa caacaatatg aacctgggcc tgcagaacgc cagcgcgctg    420
tacaaaccgg agatcattgc ggtgtccacc acctgcatgg cggaagttat cggcgatgac    480
ctgcaggcgt ttatcgccaa cgctaaaaaa gatggcttcg tcgacagcag catcgccgtg    540
ccccacgccc atacgccaag ctttatcggc agccacgtca ccggctggga taacatgttt    600
gaaggcttcg ccaaaacctt cactgcggac taccaggggc agcccggcaa attgccgaag    660
ctcaatctgg tgaccggctt tgaaacctat ctcggcaact tccgcgtatt aaagcggatg    720
atggaacaga tggcggtgcc gtgcagcctg ctctccgatc cgtcggaagt tctcgacacg    780
cccgccgacg gtcactatcg gatgtattcc ggcggcacca cgcagcagga gatgaaagag    840 gccctgacg ccatcgatac gctgctcctg cagccgtggc agctgctgaa gagcaaaaaa    900
gtggtgcagg agatgtggaa ccagcccgcc accgaggtcc cattccgct ggggctggcc    960 gccaccgatg aactgctgat gaccgtcagc cagcttagcg gcaagccgat tgccgacgcc   1020
ctcacccttg agcgcggccg gctggttgac atgatgctcg actccacac ctggctgcac   1080 ggcaagaagt ttggcctgta cggcgatccg gacttcgtga tgggcctcac ccgcttcctg   1140
ctggagctgg gctgcgagcc aacggtgatc ctgagccata cgccaacaa acgctggcaa   1200 aaagcgatga acaaaatgct cgatgcctcg ccgtacgggc gcgatagcga agtgtttatc   1260
aactgcgatt tgtggcactt ccgttcgctg atgttcaccc gtcagccgga ctttatgatc   1320
ggcaactcct acggcaagtt tatccagcgc gataccctgg cgaagggtaa agcctttgaa   1380
gtgccgctta tccgcctcgg ctttccgctg ttcgaccgcc accatctgca ccgccagaca   1440
acctggggtt atgaaggggc gatgaacatt gtgacgacgc tggtgaacgc cgtgctggag   1500
aaactggata gcgataccag ccagctgggc aaaaccgatt acagcttcga tctcgtccgt   1560
taa                                                                1563

<210> SEQ ID NO 8
<211> LENGTH: 1563
<212> TYPE: DNA
<213> ORGANISM: Artificial Sequence
<220> FEATURE:
<223> OTHER INFORMATION: synthetic Gene K

<400> SEQUENCE: 8
atgtctcaaa ctatcgataa aatcaactct tgttacccgc tgttcgagca ggacgaatat     60
caggaactgt tccgtaacaa acgtcagctg gaagaagcgc acgacgcaca gcgcgtgcag    120
gaagtgttcg catggaccac caccgcggaa tacgaagctc tgaacttccg tcgcgaagcc    180
ctgacggttg atccggcgaa agcgtgccag cctctgggtg cggttctgtg cagcctgggt    240
tttgccaaca ccctgccgta tgtccacggt tcccagggct gcgtagccta cttccgtacc    300
tatttcaacc gccactttaa agaaccaatc gcgtgcgtgt ccgacagcat gacggaggac    360
gcggcagttt tcggtggtaa caacaacatg aacctgggcc tgcaaaatgc ttccgcactg    420
tacaaaccgg aaatcatcgc agtgtctacc acctgcatgg cagaggttat tggtgatgat    480
ctgcaagcat ttattgccaa cgcaaagaaa gacggtttcg ttgacagctc tatcgcggtt    540
ccgcacgctc atacccgtc cttcatcggt tctcacgtaa ctggttggga caacatgttc    600
gaaggcttcg caaaaacttt taccgcagac tatcaaggcc aaccgggtaa actgccgaag    660
```

```
ctgaacctgg tgaccggctt tgaaacctac ctgggcaact ttcgtgtcct gaagcgcatg      720
atggagcaga tggcggttcc gtgttctctg cgtctgacc cgtctgaggt tctggacact       780
ccagcggacg gccactatcg catgtattct ggtggcacca ctcagcagga aatgaaagag      840
gccccagacg cgattgacac cctgctgctg caaccgtggc agctgctgaa agcaagaaa       900 gttgttcagg aaatgtggaa ccagccggca acggaagttg caatcccgct gggtctggca      960
gctactgacg aactgctgat gaccgtgtcc caactgagcg gcaaaccaat cgcggatgct     1020
ctgaccctgg aacgcggtcg cctggtggac atgatgctgg acagccacac gtggctgcat    1080
ggcaagaaat ttggcctgta cggtgacccg gacttcgtaa tgggcctgac ccgtttcctg    1140
ctggaactgg gctgcgagcc gactgttatc ctgtctcaca cgctaacaa acgttggcag     1200 aaggccatga acaaaatgct ggatgcgagc ccatacggcc gtgatagcga agtgttcatc    1260
aactgcgacc tgtggcattt ccgctctctg atgtttacgc gtcagccgga tttcatgatc    1320
ggtaactctt acggcaaatt catccagcgt gacactctgg ccaaaggcaa agcgtttgaa    1380
gtgccgctga ttcgtctggg cttttccgctg ttcgaccgtc accacctgca ccgccagacc    1440
acctggggtt acgaaggcgc gatgaacatc gtaactactc tggtaaacgc agtactggaa     1500
aagctggaca gcgatacttc ccagctgggc aaaaccgact attctttcga tctggttcgt    1560
taa                                                                   1563

<210> SEQ ID NO 9
<211> LENGTH: 663
<212> TYPE: DNA
<213> ORGANISM: Klebsiella pneumoniae
<220> FEATURE:
<223> OTHER INFORMATION: wild type Gene Y, nifY

<400> SEQUENCE: 9
atgtccgaca acgataccct attctggcgt atgctggcgc tgtttcagtc tctgccggac       60
ctacagccgg cgcaaatcgt cgactggctg gcgcaggaga gcggcgagac gctgacgcca     120
gagcgtctgg cgaccctgac ccagccgcag ctggccgcca gctttccctc cgcgacggcg     180
gtgatgtccc ccgctcgctg gtcgcgggtg atggcgagcc tgcagggcgc gctgcccgcc     240
catttacgca tcgttcgccc tgcccagcgc acgccgcagc tgctggcggc attttgctcc     300
caggatgggc tggtgattaa cggccatttc ggccagggac gactgttttt tatctacgcg     360
ttcgatgaac aaggcggctg gttgtacgat ctgcgccgct atccctccgc cccccaccag    420
caggaggcca acgaagtgcg cgcccggctt attgaggact gtcagctgct gttttgccag    480
gagataggcg ggcccgccgc cgcgcggctg atccgccatc gcatccaccc gatgaaagcg    540
cagcccggga cgacgattca ggcacagtgc gaggcgatca atacgctgct ggccggccgt    600 tgccgccgt ggctggcgaa gcggcttaac agggataacc ctctggaaga acgcgttttt     660
taa                                                                   663

<210> SEQ ID NO 10
<211> LENGTH: 663
<212> TYPE: DNA
<213> ORGANISM: Artificial Sequence
<220> FEATURE:
<223> OTHER INFORMATION: synthetic Gene Y

<400> SEQUENCE: 10
atgtctgaca atgataccct gttttggcgc atgctggcgc tgtttcagtc gctgccggat       60
```

```
ttgcagccgg ctcaaatcgt cgattggctg gcgcaggaat ccggcgaaac cctgacgccg      120
gagcgccttg ccaccctgac ccaaccgcaa ctcgcggcgt cgttcccatc cgcgacggca      180
gtgatgagcc cggctcgctg gagccgcgtt atggcttctc tgcaaggcgc cctcccagcc      240
cacttgcgca tcgtacgtcc ggcgcagcgt accccgcaac tgctcgccgc gttttgcagc      300
caagacggcc ttgttatcaa tggtcatttc ggccagggtc gtctgttctt catttacgcc      360
tttgacgagc agggcggctg gctgtatgac ttgcgccgct atccgagcgc accgcaccag      420
caggaagcga atgaggtgcg tgctcgtctg attgaagatt gccagctgct gttctgccag      480
gagattggcg gtccggcagc agcgcgtccg atccgccacc gcatccatcc gatgaaggcg      540
cagccgggta ctacgattca ggcgcagtgt gaagctatca caccctgct ggccggtcgc       600 ctgccgccgt ggctcgccaa acgtttgaac cgtgataacc cgctggaaga gcgtgtgttt      660
taa                                                                    663

<210> SEQ ID NO 11
<211> LENGTH: 1374
<212> TYPE: DNA
<213> ORGANISM: Klebsiella pneumoniae
<220> FEATURE:
<223> OTHER INFORMATION: wild type Gene E, nifE

<400> SEQUENCE: 11
atgaagggaa atgaaattct ggcgctgctg gatgaaccgg cctgtgaaca caaccataaa       60
caaaaatccg gctgcagcgc gcccaaaccc ggcgccaccg ccgcgggctg cgcgttcgac      120
ggcgcgcaga taaccctgct gcccatcgcc gacgtggcgc atctggtcca cggccccatc      180
ggctgcgccg gaagctcatg gataaccgc ggcagcgcca gctccggccc cacccttaat       240
cggctcgggt tcaccaccga tctcaacgaa caggacgtga ttatgggccg cggcgaacgc      300
cgactgtttc acgccgtgcg ccatatcgtc accgctatc atccggcggc ggtctttatc       360
tacaacacct gcgtaccggc catggagggc gatgacctgg aagcggtatg ccaggccgcg      420
cagaccgcca ccggcgtacc ggttatcgct attgacgccg ccggtttcta cggcagtaaa      480
aatctcggta accggccggc gggcgacgtc atggtcaaac gggtcatcgg ccagcgcgag      540
cccgccccct ggccggagag cacgctcttt gccccggagc agcgtcacga tattggcctg      600
attggcgaat tcaatattgc cggcgagttc tggcatattc agccgctgct cgacgaactg      660
gggatccgcg tgctcggcag cctctccggt gatggccgct tcgccgagat ccagaccatg      720
caccgggcgc aggccaatat gctggtctgc tcgcgggcgt taattaacgt cgccagagcc      780
ctggagcagc gctacggcac gccgtggttc gaaggcagct tttacgggat ccgcgccacc      840
tctgacgccc tgcgccagct ggcggcgctg ctgggcgacg acgaccttcg ccagcgcacc      900
gaagcgctga ttgcgcggga ggaacaggcg gcggaactgg cgctacagcc gtggcgcgaa      960
cagctgcgcg ccgcaaagc gctgctctat accggcgggg tgaaatcctg gtcggtggta     1020
tcggcgctgc aggatttggg catgaccgtg gtggcaaccg gcacgcgtaa atccaccgaa     1080
gaggataaac agcggatccg cgagctgatg ggcgaagagg cggtaatgct ggaagagggc     1140
aacgcccgca cgctgctgga tgtggtctat cgctatcagg ccgacctgat gattgccggc     1200
ggacgcaata tgtacaccgc ctataaagcc aggctgccgt ttctcgatat caatcaggag     1260
cgcgaacacg ccttcgctgg ctatcagggg atcgtcaccc tcgcccgcca gctgtgtcag     1320
accatcaaca gccccatctg gccgcaaacc cattctcgcg ccccgtggcg ctaa           1374
```

<210> SEQ ID NO 12
<211> LENGTH: 1374
<212> TYPE: DNA
<213> ORGANISM: Artificial Sequence
<220> FEATURE:
<223> OTHER INFORMATION: synthetic Gene E

<400> SEQUENCE: 12

```
atgaagggta acgagattct tgctctgctg gacgaaccgg cctgtgaaca caaccataaa      60
cagaaatccg gctgtagcgc cccaaagccg ggtgcgacgg cggctggctg cgctttcgat     120
ggtgcgcaga tcaccctgct cccgattgcg gacgttgccc acctcgtgca tggcccaatc     180
ggttgcgcag gtagctcttg gacaaccgt ggcagcgcct ccagcggtcc gaccctgaat     240
cgtttgggct ttaccactga cttgaatgaa caagatgtga tcatgggtcg cggcgagcgt     300
cgcctgttcc acgctgtgcg ccatattgtc acccgttacc acccagcggc agtattcatc     360
tacaatacgt gcgtgccggc tatggaaggc gatgacctgg aggccgtgtg tcaggcagcc     420
cagactgcga ccggcgtccc ggtaatcgca attgatgcgg ctggcttcta cggttcgaag     480
aacctgggca accgtccggc aggcgatgtc atggttaaac gcgtcattgg ccaacgtgag     540
ccagcgccgt ggccggagag caccctgttt gccccggagc aacgtcatga cattggcttg     600
atcggtgagt tcaacattgc gggcgagttt tggcacattc agccgctgct tgatgagctg     660
ggtatccgcg ttttgggttc gctcagcggc gatggtcgtt tcgccgagat tcaaaccatg     720
caccgtgccc aggcgaacat gctggtgtgc agccgtgctc tgatcaatgt tgcgcgtgct     780
ctggaacagc gctatggcac cccgtggttt gaaggctcgt tctatggtat ccgcgcgacc     840
agcgacgccc tgcgccagtt agcggcgctg ctgggcgatg acgacctccg tcagcgcacc     900
gaggcgctga tcgcgcgtga gaacaggcg gctgagctgg ccctgcaacc gtggcgtgaa     960
cagctgcgtg gccgcaaggc cctgctctac acgggtggtg tcaaaagctg gtctgtggtg    1020
tccgcgcttc aggatctggg tatgaccgtg gttgccacgg gcacgcgtaa gagcacggaa    1080
gaggataaac agcgcatccg cgaattgatg ggcgaagagg ccgtgatgct tgaagaaggc    1140
aacgcacgta ccttattgga tgtagtttat cgctatcaag cagacctgat gattgccggt    1200
ggccgcaaca tgtataccgc ctacaaagcg cgcttgccgt tcctggacat caaccaggaa    1260
cgcgagcacg cgtttgcggg ctaccaaggc atcgtgacct agcgcgcca gctgtgccaa    1320
acgattaaca gcccgatctg gccgcagact cattcccgcg caccgtggcg ctaa          1374
```

<210> SEQ ID NO 13
<211> LENGTH: 1386
<212> TYPE: DNA
<213> ORGANISM: Klebsiella pneumoniae
<220> FEATURE:
<223> OTHER INFORMATION: wild type Gene N, nifN

<400> SEQUENCE: 13

```
atggcagaca ttttccgcac cgataagccg ctggcggtca gccccatcaa aaccggccag      60
ccgctcggcg caatcctcgc cagcctcggg atcgaacaca gcatccctct ggtccacggc     120
gcgcaggggt gcagcgcctt cgccaaagtc ttttttattc aacatttcca cgacccggtt     180
cccctgcagt cgacggcgat ggaccccacg tcgacgatta tgggcgcgga cggcaatatt     240
tttaccgccc tggatacccct tgccagcgc aacaatccgc aggctatcgt actgctcagc     300
accgggctgt cggaggccca gggcagcgat atttccgcg tggttcgcca gtttcgcgaa     360
gagtatcccc ggcataaggg ggtggcgata ttgacggtta acacgccgga ttttatggc     420
```

```
tccatggaga acggcttcag cgcggtgtta gagagcgtca ttgagcagtg ggtgccgccg    480
gcgccgcgcc cggctcagcg caatcgccgg gtcaatctgc tggtcagcca tctctgttcg    540
ccgggcgata tcgagtggct cgccgatgc gtcgaagcct ttggtctgca gccgataatc    600
ctgccggacc tggcgcaatc gatggacgg cacctggcgc agggcgattt ctcgccgctg    660
acccagggcg ggacgccgct cgccagata gagcagatgg ggcaaagcct gtgcagcttc    720
gccattggcg tctcccttca tcgcgcctca tcgctgctgg ccccgcgctg ccgcggcgag    780
gttatcgccc tgccgcacct gatgaccctc gaacgctgcg acgcctttat tcatcaactg    840
gcgaaaattt ccggacgcgc cgttcccgag tggctggaac gccagcgcgg ccagctacag    900
gatgcgatga tcgactgcca tatgtggctc cagggccagc gcatggcgat agcggcggaa    960
ggcgatttgc tggcggcgtg gtgtgatttc gccaacagcc aggggatgca gcccggcccg   1020
ctggtggccc ctaccggtca tcccagcctg cgccagctgc cggtggaacg ggtggtgccg   1080
ggggatctgg aggatctgca aaccctgctg tgcgcgcatc ccgccgacct gctggtggcg   1140
aactcgcacg cccgcgacct ggcggagcag tttgcgctgc cgctggtgcg cgcgggtttt   1200
ccgctctttg acaagctcgg cgaattccgc cgggtgcgac aggggtatag cgggatgcgc   1260
gatacgctgt ttgagctggc aaaacctgata cgcgagcgtc accaccacct cgcccactac   1320
cgatcgccgc tgcgccagaa ccccgaatcg tcactctcca caggaggcgc ttatgccgcc   1380
gattaa                                                               1386

<210> SEQ ID NO 14
<211> LENGTH: 1386
<212> TYPE: DNA
<213> ORGANISM: Artificial Sequence
<220> FEATURE:
<223> OTHER INFORMATION: synthetic Gene N

<400> SEQUENCE: 14
atggcagaca tttccgcac tgataagccg ttggctgtgt cgccgatcaa gaccggccag     60
ccgctgggtg cgatcctggc gtccctgggt atcgagcact cgattccgct ggtacatggc    120
gcgcagggct gttcggcttt tgccaaggtt ttctttatcc agcacttcca cgatccggtc    180
ccgctgcaaa gcacggcaat ggacccgacc agcaccatca tgggcgctga tggtaacatc    240
ttcaccgcgc tggacactct ctgccaacgc aataacccgc aagcaattgt gctgctgagc    300
accggcctct ccgaggcgca gggcagcgac atttcccgtg tagtgcgtca gttccgtgaa    360
gaatatccgc gtcataaagg cgtggcgatt ctgactgtta acaccccgga cttttacggt    420
agcatggaga acggcttttc cgctgtcctg gagtctgtga ttgaacagtg ggttccgcca    480
gccccacgtc cggcgcagcg caatcgtcgc gtcaatcttt tggtgagcca tctctgtagc    540
ccaggcgata ttgagtggct cgccgttgc gtcgaggcct tcggtctgca accgatcatt    600
ctgccggatc tggctcagag catggacggc accttgctc agggtgactt ttcgccgctg    660
acgcagggcg gcacgccgtt cgccaaatc gagcagatgg ccagagcct ttgctctttt    720
gcgattggcg tcagcctgca ccgtgcgagc agcctgctgg ctccgcgttg tcgtggcgaa    780
gtcatcgcct tgccgcacct catgacctg aacgctgcg acgcctttat ccatcagttg    840
gcgaaaatca gcggtcgcgc cgttccggag tggctggaac gccagcgcgg tcagctgcaa    900
gacgccatga tcgattgcca catgtggctg caaggccagc gcatggcgat tgccgccgaa    960
ggcgacctgc tggcagcgtg gtgcgatttc gcgaactctc aaggtatgca gccgggtcca   1020
ctggttgctc cgacgggtca tccgagcctg cgtcagttgc cggtggagcg cgtggtgccg   1080
```

```
ggtgatctgg aggatcttca gaccctctta tgcgcacatc cggccgactt actggtggcg      1140
aactcccacg cccgtgattt agcagagcaa ttcgccctgc cgctggtgcg cgcaggcttc      1200
ccgctgtttg acaaactggg cgaatttcgt cgtgttcgcc agggttatag cggtatgcgt      1260
gatacccrgt tcgagttggc gaacctgatc cgtgaacgcc atcatcatct ggctcattat      1320
cgcagcccgc tgcgccagaa cccagaatcc tcgttgtcta cgggtggcgc gtacgcagcg      1380
gattaa                                                                 1386
```

<210> SEQ ID NO 15
<211> LENGTH: 825
<212> TYPE: DNA
<213> ORGANISM: Klebsiella pneumoniae
<220> FEATURE:
<223> OTHER INFORMATION: wild type Gene U, nifU

<400> SEQUENCE: 15

```
atgtggaatt actccgagaa agtgaaagac cattttttta accccccgcaa tgcgcgcgtg       60 gtggacaacg ccaacgcggt aggcgacgtc ggttcgttaa gctgcggcga cgccctgcgc      120
ctgatgctgc gcgtcgaccc gcaaagcgaa atcattgagg aggcgggctt ccagaccttc      180
ggctgcggca gcgccatcgc ctcctcctcc gcgctgacgg agctgattat cggccatacc      240
ctcgccgaag ccgggcagat aaccaatcag cagattgccg attatctcga cggactgccg      300
ccggagaaaa tgcactgctc ggtgatgggc caggaggccc tgcgcgcggc catcgccaac      360
tttcgcggcg aaagccttga gaggagcac gacgagggca agctgatctg caaatgcttc      420
ggcgtcgatg aagggcatat tcgccgcgcg gtacagaaca acgggctgac cacccttgcc      480
gaggtgatca actacaccaa agcgggcggc ggctgcacct cttgccacga aaaaatcgag      540
ctggccctgg cggagatcct cgcccagcag ccgcagacga cgccagccgt ggccagcggc      600
aaagatccgc actggcagag cgtcgtcgat accatcgcag aactgcggcc gcatattcag      660
gccgacggcg gcgatatggc gctactcagc gtcaccaacc accaggtgac cgtcagcctc      720
tccggcagct gtagcggctg catgatgacc gatatgaccc tggcctggct gcagcaaaaa      780
ctgatggaac gtaccggctg ttatatggaa gtggtggcgg cctga                     825
```

<210> SEQ ID NO 16
<211> LENGTH: 825
<212> TYPE: DNA
<213> ORGANISM: Artificial Sequence
<220> FEATURE:
<223> OTHER INFORMATION: synthetic Gene U

<400> SEQUENCE: 16

```
atgtggaact acagcgagaa agtcaaggac catttcttca tccgcgcaa cgcgcgtgtt       60 gtggataacg caaatgcggt gggcgacgtc ggcagcttat cttgtggcga tgctctccgc      120
ttgatgctgc gcgtggaccc gcagagcgaa atcatcgaag aagcgggctt tcagaccttc      180
ggctgcggca gcgcgattgc gtcgtccagc gcactgacgg agctgatcat cggtcacacc      240
ctggcggaag cgggtcagat caccaaccag cagatcgccg actatctgga cggcttaccg      300
ccggaaaaga tgcactgctc tgtaatgggc caggaagctc ttcgtgcggc cattgctaac      360
tttcgcggtg aatcgctgga agaggagcat gacgagggta agctgatctg caagtgcttc      420
ggcgtcgatg aaggccatat tcgccgtgct gtccagaaca acggtcttac gactctggcc      480
gaggtgatca attacaccaa ggcaggtggc ggttgtacca gctgccatga gaaaatcgag      540
```

```
ctggccctgg ccgagattct cgcccaacag ccgcaaacca ccccggcagt tgcgtccggt    600
aaagatccgc actggcagag cgtcgtggat accatcgctg aactgcgtcc acatatccaa    660
gcggacggtg gtgacatggc gctgttgtcc gtgacgaacc accaagtgac tgtttcgctg    720
tcgggcagct gttctggctg catgatgacc gacatgaccc tggcgtggct gcaacagaaa    780
ttgatggagc gtaccggctg ctatatggaa gttgttgccg cctaa                    825
```

<210> SEQ ID NO 17
<211> LENGTH: 1203
<212> TYPE: DNA
<213> ORGANISM: Klebsiella pneumoniae
<220> FEATURE:
<223> OTHER INFORMATION: wild type Gene S, nifS

<400> SEQUENCE: 17

```
atgaaacagg tttatctcga taacaacgcc accacccgtc tggacccgat ggtcctggaa     60
gcgatgatgc ccttttttgac cgattttttac ggcaaccccc tcgtcgataca cgattttggc   120 attccggccc aggcggctct ggaacgcgcg catcagcagg ctgcggcgct gctgggcgcg    180
gagtatccca gcgagatcat ctttacctcc tgcgccaccg aagccaccgc caccgccatc    240
gcctcggcga tcgccctgct gcctgagcgt cgcgaaatca tcaccagcgt ggtcgaacat    300
ccggcgacgc tggcggcctg cgagcacatg gagcgcgagg ctaccggat tcatcgcatc     360 gcggtagatg gcgagggggc gctggacatg gcgcagttcc gcgcggcgct cagcccgcgc   420
gtcgcgttgg tcagcgtgat gtgggcgaat aacgaaaccg gggtgctttt cccgatcggc    480
gaaatggcgg agctggccca tgaacaaggg gcgctgtttc actgcgatgc ggtgcaggtg    540
gtcgggaaaa taccgatcgc cgtgggccag accgcatcg atatgctctc ctgctcggcg    600
cataagttcc acgggccaaa aggcgtaggc tgtctttatc tgcggcgggg aacgcgcttt    660
cgcccgctgc tgcgcggcgg tcaccaggag tacggtcggc gagccgggac agaaaatatc    720
tgcggaatcg tcggcatggg cgcggcctgc gagctggcga atattcatct gccgggaatg    780
acgcatatcg gccaattgcg caacaggctg gagcatcgcc tgctggccag cgtgccgtcg    840
gtcatggtga tgggcggcgg ccagccgcg gtgcccggca cggtgaatct ggccttttgag   900 tttattgaag gtgaagccat tctgctgctg ttaaaccagg ccgggatcgc cgcctccagc    960
ggcagcgcct gcacctcagg ctcgctggaa ccctcccacg tgatgcgggc gatgaatatc   1020
ccctacaccg ccgcccacgg caccatccgc ttttctctct cgcgctacac ccgggagaaa   1080
gagatcgatt acgtcgtcgc cacgctgccg ccgattatcg accggctgcg cgcgctgtcg   1140
ccctactggc agaacggcaa gccgcgcccg gcggacgccg tattcacgcc ggtttacggc   1200
taa                                                                 1203
```

<210> SEQ ID NO 18
<211> LENGTH: 1203
<212> TYPE: DNA
<213> ORGANISM: Artificial Sequence
<220> FEATURE:
<223> OTHER INFORMATION: synthetic Gene S

<400> SEQUENCE: 18

```
atgaaacaag tgtacctgga caacaacgcg accacccgcc tggacccgat ggttctggaa     60
gcgatgatgc cgtttctcac ggatttctat ggcaatccgt ccagcatcca tgacttcggc   120
atcccggcac aagcggcgct ggaacgtgcg caccagcaag ctgcggcact gctgggcgca   180
gagtacccgt ctgaaatcat tttcacgagc tgtgcgaccg aggccactgc aaccgccatt   240
```

```
gcgtcggcca tcgcgttatt gccggaacgc cgcgaaatca tcacctcggt agtggagcac      300
ccggctacgc tggcggcgtg cgagcacatg gaacgcgaag gctatcgcat ccatcgcatt      360
gcggtggatg gcgaaggtgc gctggacatg gcccagttcc gtgcagcgct ctcgccgcgt      420
gtcgcgttgg tgagcgtgat gtgggccaac aacgaaaccg gcgtgctgtt cccgattggc      480
gaaatggccg agcttgccca cgagcagggc gctctgttcc actgcgatgc cgttcaggtc      540
gttggcaaaa tcccaattgc tgttggccag acgcgcatcg acatgctgtc ttgctccgcg      600
cacaagtttc atggtccgaa gggtgttggt tgcttgtact acgtcgtgg cacgcgcttt       660 cgtccgctgc ttcgcggtgg ccatcaagaa tatggtcgcc gtgccggcac tgagaatatc      720
tgtggcatcg tcggcatggg cgctgcgtgc gaactggcga acatccatct gccgggtatg      780
acccatattg ccagttacg caatcgcctg gagcaccgtc tgctcgccag cgtgccgtcc       840
gtgatggtta tgggcggtgg tcagccggct gtaccgggta ctgtcaacct ggcgttcgag      900
tttatcgaag gtgaagcgat cctgctcttg ctgaaccagg ctggcattgc cgcaagctcc      960
ggctccgcgt gtacctctgg cagcttggag ccgagccatg tgatgcgcgc catgaacatt     1020
ccatacaccg cggctcacgg caccattcgt tttagcctga ccgttatac gcgcgagaaa     1080 gagatcgact acgtcgttgc gacccctccg ccaatcattg atcgtctgcg tgccttgtcc     1140
ccgtattggc agaatggtaa gccgcgtccg gcagatgcag tctttacccc ggtttacggt     1200
taa                                                                   1203
```

<210> SEQ ID NO 19
<211> LENGTH: 1143
<212> TYPE: DNA
<213> ORGANISM: Klebsiella pneumoniae
<220> FEATURE:
<223> OTHER INFORMATION: wild type Gene V, nifV

<400> SEQUENCE: 19

```
atggaacgcg tgctgattaa cgataccacc ctgcgcgacg gcgagcagag ccccggcgtc       60
gcctttcgca ccagcgaaaa ggtcgccatt gccgaggcgc tttacgccgc aggaataacg      120
gcgatggagg tcggcacccc ggcgatgggc gacgaggaga tcgcgcggat ccagctggtg      180
cgtcgccagc tgcccgacgc gaccctgatg acctggtgtc ggatgaacgc gctggagatc      240
cgccagagcg ccgatctggg catcgactgg gtggatatct cgattccggc ttcggataag      300
ctgcggcagt acaaactgcg cgagccgctg gcggtgctgc tggagcggct ggcgatgttt      360
atccatcttg cgcataccct cggcctgaag gtatgcatcg gctgcgagga cgcctcgcgg      420
gccagcggcc agaccctgcg cgctatcgcc gaggtcgcgc agcaatgcgc gccgcccgc       480 ctgcgctatg ccgatacggt cggcctgctc gacccttta ccaccgcggc gcaaatctcg       540
gccctgcgcg acgtctggtc cggcgaaatc gaaatgcatg cccataacga tctgggtatg      600
gcgaccgcca atacgctggc ggcggtaagc gccggggcca ccagcgtgaa tacgacggtc      660
ctcggtctcg gcgagcgggc gggcaacgcg gcgctggaaa ccgtcgcgct gggccttgaa      720
cgctgcctgg gcgtggagac cggcgtgcat ttttcggcgc tgcccgcgtc ctgtcagagg      780
gtcgcggaag ccgcgcagcg cgccatcgac ccgcagcagc gctggtcgg cgagctggtg       840 tttacccatg agtcaggtgt ccacgtggcg gcgctgctgc ggcacagcga gagctaccag      900
tccatcgccc cttccctgat gggccgcagc taccggctgg tgctgggcaa acactccggg      960
cgtcaggcgg tcaacggcgt ttttgaccag atgggctatc acctcaacgc cgcgcagatt     1020
```

```
aaccagctgc tgcccgccat ccgccgcttc gccgagaact ggaagcgcag cccgaaagat    1080
tacgagctgg tggctatcta cgacgagctg tgcggtgaat ccgctctgcg ggcgaggggg    1140
taa                                                                  1143

<210> SEQ ID NO 20
<211> LENGTH: 1143
<212> TYPE: DNA
<213> ORGANISM: Artificial Sequence
<220> FEATURE:
<223> OTHER INFORMATION: synthetic Gene V

<400> SEQUENCE: 20
atggagcgcg tcttgatcaa cgatactacc ctgcgtgatg cgaacaatc tccgggcgta      60 gcgtttcgta cctccgagaa agttgccatc gcggaggcac tgtacgctgc gggtatcacc    120
gcgatggaag tcggcactcc ggcgatgggt gatgaagaga tcgcccgcat tcagctggtg    180
cgtcgtcaac tgccggacgc gacgcttatg acctggtgcc gtatgaacgc tctggaaatc    240
cgtcagagcg cggatctggg tattgactgg gtggatatct cgatcccagc atccgacaag    300
ctgcgtcagt acaagctgcg tgagccgctg gccgtgctgc tggagcgcct tgcgatgttt    360
atccatctgg cccacacgtt aggcctcaaa gtatgtattg gttgcgagga tgcgagccgt    420
gcgtctggtc agaccctgcg cgccattgcc gaggtggccc agcaatgcgc ggctgcgcgc    480
ttgcgttacg ctgacaccgt gggcctgctg acccgttca ccaccgcagc ccagatcagc     540
gccctgcgtg acgtttggtc gggcgagatc gagatgcatg ctcacaatga tctgggcatg    600
gctaccgcga acacgctggc ggcagtttcg gctggcgcca cgtcggtgaa cactaccgtc    660
ctcggtctgg gtgaacgtgc aggcaacgca gccctggaaa ccgttgcgct gggcctggaa    720
cgctgcctgg gcgtggaaac cggcgtccat ttcagcgcgc tcccagcgag ctgtcagcgc    780
gtcgcggagg ctgcacagcg cgcaatcgac ccgcaacagc cgctggtggg tgaattggtt    840
ttcacccacg agtctggtgt tcacgttgcg gcgctgctgc cccacagcga atcctatcaa    900
tctattgccc caagcctcat gggccgtagc taccgtctgg tgctcggcaa gcattcgggt    960
cgtcaggctg tcaacggtgt tttcgaccag atgggttacc acctgaatgc ggcgcagatc   1020
aatcagttgc tgccggccat tcgccgcttc gccgagaatt ggaaacgctc tccgaaagac   1080
tacgaactgg ttgcgatcta tgacgaattg tgcggtgaat ccgcccttcg tgctcgcggc   1140
taa                                                                 1143

<210> SEQ ID NO 21
<211> LENGTH: 258
<212> TYPE: DNA
<213> ORGANISM: Klebsiella pneumoniae
<220> FEATURE:
<223> OTHER INFORMATION: wild type Gene W, nifW

<400> SEQUENCE: 21
atggagtggt tttatcaaat tcccggcgtg gacgaacttc gctccgccga atcttttttt     60 cagttttttcg ccgtccccta tcagcccgag ctgcttggcc gctgcagcct gccggtgctg    120
gcaacgtttc atcgcaaact ccgcgcggag gtgccgctgc aaaaccggct cgaggataac    180
gaccgcgcgc cctggctgct ggcgcgaaga ctgctcgcgg agagctatca gcaacagttt    240
caggagagcg gaacatga                                                   258

<210> SEQ ID NO 22
<211> LENGTH: 258
```

```
<212> TYPE: DNA
<213> ORGANISM: Artificial Sequence
<220> FEATURE:
<223> OTHER INFORMATION: synthetic Gene W

<400> SEQUENCE: 22
atggagtggt tttaccagat tccgggtgta gacgaattgc gcagcgctga atccttcttt     60
cagttcttcg cggttccata ccagccggaa ctgctgggcc gctgctcgct tccggtgtta    120
gcgacgttcc accgtaaact gcgtgcgagg gtcccgctgc aaaaccgtct ggaggacaat    180
gatcgtgcgc cgtggctctt ggcgcgccgc ctcctggccg aatcttatca gcagcaattt    240
caggagagcg gcacctaa                                                  258

<210> SEQ ID NO 23
<211> LENGTH: 447
<212> TYPE: DNA
<213> ORGANISM: Klebsiella pneumoniae
<220> FEATURE:
<223> OTHER INFORMATION: wild type Gene Z, nifZ

<400> SEQUENCE: 23
atgagaccga aattcacctt tagcgaagag gtccgcgtcg tacgcgcgat tcgtaacgac     60
ggcaccgtgg cgggcttcgc gcccggcgcg ctgctggtca ggcgcggcag caccggcttt    120
gtgcgcgact ggggcgtttt tttgcaagat cagattatct accagatcca ctttccggaa    180
accgatcgga tcatcggctg ccgcgagcag gagctgatcc catcaccca gccgtggctg     240 gccggaaatt tgcaatacag ggatagcgtg acctgccaga tggcgctcgc ggtcaacggc    300
gatgtggtcg tgagcgccgg ccagcgggga cgcgttgagg ctaccgatcg gggagagctc    360
ggcgacagct acaccgtcga ctttagcggc cgctggttca gggtcccggt gcaggccatc    420
gcccttatag aggaaagaga agaatga                                        447

<210> SEQ ID NO 24
<211> LENGTH: 447
<212> TYPE: DNA
<213> ORGANISM: Artificial Sequence
<220> FEATURE:
<223> OTHER INFORMATION: synthetic Gene Z

<400> SEQUENCE: 24
atgcgcccga aattcacctt ctctgaagag gtccgcgtag ttcgcgcgat tcgtaatgat     60
ggcaccgtgg cgggttttgc gccaggtgcg ctgctggttc gtcgcggttc gacgggcttt    120
gtgcgtgact ggggtgtgtt cctgcaagac cagatcatct atcaaatcca ctttccggaa    180
accgaccgca ttatcggctg tcgcgagcag gagttaatcc cgattaccca gccgtggttg    240
gctggtaacc tccagtatcg tgacagcgtc acgtgccaaa tggcactggc tgtcaacggt    300
gacgtggttg tgagcgccgg tcaacgtggc cgtgtggagg ccactgatcg tggcgaactt    360
ggcgattcct acaccgtgga cttcagcggc cgttggttcc gcgttccggt ccaggccatc    420
gcgctgattg aagagcgcga agaataa                                        447

<210> SEQ ID NO 25
<211> LENGTH: 801
<212> TYPE: DNA
<213> ORGANISM: Klebsiella pneumoniae
<220> FEATURE:
<223> OTHER INFORMATION: wild type Gene M, nifM

<400> SEQUENCE: 25
```

```
atgaacccgt ggcaacgttt tgcccggcag cggctggcgc gcagccgctg gaatcgcgat      60
ccggcggccc tggatccggc cgacacgccg gcttttgaac aggcctggca acgccagtgc     120
catatggagc agacgatcgt cgcgcgggtc cctgaaggcg atattccggc ggcgttgctg     180
gagaatatcg ctgcctccct tgccatctgg ctcgacgagg gggattttgc gccgcccgag     240
cgcgctgcca tcgtgcgcca tcacgcccgg ctggaactcg ccttcgccga tatcgcccgc     300
caggcgccgc agccggatct ctccacggta caggcatggt atctgcgcca ccagacgcag     360
tttatgcgcc cggaacagcg tctgacccgc catttactgc tgacggtcga taacgaccgc     420
gaagccgtgc accagcggat cctcggcctg tatcggcaaa tcaacgcctc gcgggacgct     480 tcgcgccgc tggcccagcg ccattcccac tgcccgagcg cgctggaaga gggtcgttta     540
ggctggatta ccgtggcct gctctatccg cagctcgaga ccgcgctgtt ttcactggcg     600
gaaaacgcgc taagccttcc catcgccagc gaactgggct ggcatctttt atggtgcgaa     660
gcgattcgcc ccgccgcgcc catggagccg cagcaggcgc tggagagcgc gcgcgattat     720
ctttggcagc agagccagca cgccatcag cgccagtggc tggaacagat gatttcccgt     780
cagccgggac tgtgcgggta g                                               801

<210> SEQ ID NO 26
<211> LENGTH: 801
<212> TYPE: DNA
<213> ORGANISM: Artificial Sequence
<220> FEATURE:
<223> OTHER INFORMATION: synthetic Gene M

<400> SEQUENCE: 26
atgaatccgt ggcagcgctt tgcccgtcaa cgccttgctc gcagccgctg gaaccgtgat      60
ccggctgctc tcgacccagc cgataccca gcgttcgagc aggcgtggca gcgtcaatgc     120
catatggaac aaaccatcgt agcgcgtgtc ccggaaggcg atattccggc tgccttactg     180
gaaaacatcg cggccagcct ggcgatctgg ctggacgagg gtgacttcgc tccgccggag     240
cgcgctgcga ttgtgcgtca tcatgcacgt ctggagctgg cgtttgccga cattgcccgc     300
caggcaccgc aaccggatct gagcacggtt caagcgtggt atctgcgtca ccagactcaa     360
ttcatgcgtc cggagcagcg tctgacccgt cacctgctcc tgacggtcga taatgatcgc     420
gaggcggtgc atcaacgcat ccttggcctg tatcgtcaga tcaacgcgag ccgtgacgcc     480
tcgcccccac tggcacagcg ccactctcat tgcccgtccg ccttggaaga aggccgtctg     540
ggctggatct cccgtggtct gctgtacccg cagctcgaaa ccgcgttgtt tagcctggcg     600
gaaaacgcac tgtcgctgcc gattgcgtcg gaattgggtt ggcacctgtt atggtgcgag     660
gccattcgtc cggcagcccc gatggagccg caacaggccc ttgaatctgc gcgcgactac     720
ttgtggcagc agagccagca cgccaccag cgtcaatggc tggagcagat gatttcccgc     780
caaccgggcc tgtgtggtta a                                               801

<210> SEQ ID NO 27
<211> LENGTH: 531
<212> TYPE: DNA
<213> ORGANISM: Klebsiella pneumoniae
<220> FEATURE:
<223> OTHER INFORMATION: wild type Gene F, nifF

<400> SEQUENCE: 27
atggcgaaca ttggtatttt ctttggcacc gataccggta aaacccgcaa aatcgcgaaa      60
atgatccata agcaactggg cgagctggcg gatgccccgg tcaacattaa ccgcacgacg     120
```

```
ctggacgact ttatggccta tccggtgctg ctgctgggca cgccgacgct cggcgacggc    180
cagctgccgg ggctggaggc cggatgcgaa agcgagtcat ggagcgaatt tatcagcggc    240
ctcgacgacg ccagcctgaa agggaaaacc gtggcgctgt tcggcctcgg cgatcagaga    300
ggctatccgg acaacttcgt cagcgggatg cgcccgctgt tcgacgccct gagcgcgcgc    360
ggcgcgcaga tgattggcag ctggccaaat gagggttatg aattcagcgc gtcctcggcg    420
ctggaaggcg accgctttgt tgggctggtg ctggatcagg ataaccagtt cgaccagacc    480
gaagcgcgtc tggcgagctg gcttgaggag attaaacgca ccgtgctgta g             531

<210> SEQ ID NO 28
<211> LENGTH: 531
<212> TYPE: DNA
<213> ORGANISM: Artificial Sequence
<220> FEATURE:
<223> OTHER INFORMATION: synthetic Gene F

<400> SEQUENCE: 28
atggcgaaca tcggcatctt ctttggtacg ataccggca aaaccgcaa gattgcgaag      60 atgattcaca acagctggg cgagctggcc gatgccccgg ttaacatcaa tcgtaccact    120
ttggatgact ttatggctta cccagtcctg ttgctcggca cgccgacgct tggtgatggt    180
caactgccgg gctagaggc gggctgcgag agcgaaagct ggtctgagtt tatctccggt    240
ctggatgacg cttccctgaa gggcaaaacc gtggcgctgt ttggcctggg cgaccagcgt    300
ggttacccgg acaacttcgt gtcgggtatg cgtccgctgt tcgacgcgct gagcgcccgt    360
ggcgcccaga tgattggtag ctggccgaac gaaggttatg agtttagcgc atcgtccgcg    420
ctggaaggcg accgcttcgt cggcttggtg ctggatcaag acaatcagtt cgaccagacc    480
gaagcgcgcc tggcgtcttg gcttgaagag atcaaacgca ccgttctgta a             531

<210> SEQ ID NO 29
<211> LENGTH: 1407
<212> TYPE: DNA
<213> ORGANISM: Klebsiella pneumoniae
<220> FEATURE:
<223> OTHER INFORMATION: wild type Gene B, nifB

<400> SEQUENCE: 29
atgacttcct gctcctcttt ttctggcggc aaagcctgcc gcccggcgga tgacagcgca     60
ttgacgccgc ttgtggccga taaagctgcc gcgcacccct gctactctcg ccatgggcat    120
caccgtttcg cgcggatgca tctgcccgtc gcgcccgcct gcaatttgca gtgcaactac    180
tgtaatcgca aattcgattg cagcaacgag tcccgccccg ggtatcgtc aacgctgctg    240 acgcctgaac aggcggtcgt gaaagtgcgt caggtcgcgc aggcgatccc gcagcttccg    300
gtggtgggca tcgccgggcc cggcgatccg ctcgccaata tcgcccgcac ctttcgcacc    360
ctggagctga tccgcaacga gctgccggac ctgaaattat gcctgtcgac caacggactg    420
gtgctgcctg acgcggtgga ccgcctgctg gatgtcggcg ttgaccacgt cacggtcacc    480
attaacaccc tcgacgcgga gattgccgcg caaatctacg cctggctatg gctggacggc    540
gaacgctaca gcgggcgcga agcgggagag atcctgattg cccgtcagct tgagggcgta    600
cgcaggctga ccgccaaagg cgtgctggtg aaaataaatt cggtgctgat ccccggtatc    660
aacgatagcg gcatggccgg cgtgagccgc gcgctgcggg ccagcggcgc gtttatccat    720
aatattatgc cgctgatcgc caggccggag cacggcacgg tgtttggcct caacggccag    780
```

```
ccggagccgg acgccgagac gctcgccgcc accgcagcc ggtgcggcga agtgatgccg      840
cagatgaccc actgccacca gtgtcgcgcc gacgccattg ggatgctcgg cgaagaccgc      900
agccagcagt ttacccagct tccggcgcca gagagtctcc cggcctggct gccgatcctc      960
caccagcgcg cgcagctgca cgccagcatt gcgaccgcg gcgaatctga agccgatgac      1020
gcctgcctgg tcgccgtggc gtcaagccgc ggggacgtca ttgattgtca ctttggtcac      1080
gccgaccggt tctacattta cagcctctcg gccgccggta tggtgctggt caacgagcgc      1140
tttacgccca aatattgtca ggggcgcgat gactgcgagc cgcaggataa cgcagcccgg      1200
tttgcggcga tcctcgaact gctggcggac gttaaagccg tattctgcgt gcgtatcggc      1260
catacgccgt ggcaacagct ggaacaggaa ggcattgaac cctgcgttga cggcgcgtgg      1320
cggccggtct ccgaagtgct gcccgcgtgg tggcaacagc gtcggggag ctggcctgcc      1380 gcgttgccgc ataagggggt cgcctga                                          1407

<210> SEQ ID NO 30
<211> LENGTH: 1407
<212> TYPE: DNA
<213> ORGANISM: Artificial Sequence
<220> FEATURE:
<223> OTHER INFORMATION: synthetic Gene B

<400> SEQUENCE: 30
atgacctctt gttcgtcgtt ttctggcggt aaagcgtgcc gtccggccga tgactccgcg      60
ctgactccgc tggtggccga caaggcagct gcgcacccgt gctatagccg ccacggccat      120
caccgcttcg cgcgtatgca cctgccagtc gctccggcct gcaacttaca atgcaactac      180
tgcaaccgca agttcgattg cagcaatgaa agccgtccgg gcgtgtcctc taccctgctg      240
acgccggaac aggctgtggt gaaggtcgcg caggtcgccc aagctatccc gcagctgtcg      300
gtggtcggta ttgctggtcc gggcgatccg cttgcgaata tcgcccgcac cttccgtacc      360
ttggagctta ttcgcgaaca gttgccggac ctgaaactgt gcctgagcac caacggcttg      420
gtgctgccag atgccgttga tcgtctgctc gatgtgggcg tggatcacgt taccgtcacc      480
attaacaccc tggacgcaga aatcgcagcg caaatctacg cgtggttgtg gctggatggc      540
gaacgctact ccggtcgcga agccggcgaa attctcattg cccgccagct ggaaggcgta      600
cgtcgcctga ccgcgaaagg tgtgctcgtc aagatcaaca gcgtattgat tccgggcatc      660
aatgacagcg gcatggcggg tgttagccgt gcgctgcgcg cgtctggtgc gttcatccac      720
aacatcatgc cactgattgc gcgtccggag catggcactg ttttcggtct gaacggccag      780
ccggaaccgg acgcggaaac cctggcggcg acgcgctccc gctgcggcga ggttatgcca      840
caaatgaccc actgccacca gtgccgtgcc gacgcgattg gcatgcttgg tgaggatcgc      900
tcgcaacagt ttacgcaatt accggctccg gagtccctcc cggcctggct gccgatcctg      960
catcagcgtg ctcagttgca tgcgagcatc gccacgcgcg gtgagagcga agccgatgac      1020
gcctgcctgg tggccgttgc gtcgagccgt ggcgatgtaa ttgactgcca tttcggccat      1080
gccgaccgtt tctatatcta tagcctgtct gcggctggta tggttctggt taacgaacgt      1140 ttcacccccga aatactgcca gggtcgcgat gactgcgagc cgcaggacaa tgccgcacgc      1200
tttgctgcca tccttgagtt gctggcggac gtcaaagcgg tgttttgtgt gcgtatcggc      1260
cataccccgt ggcaacagct ggagcaggaa ggcatcgaac cgtgcgtgga tgcgcctgg      1320 cgtccggtat ccgaggtcct gccggcatgg tggcagcagc gccgtggtag ctggccggct      1380
gcattgccgc acaaaggcgt tgcgtaa                                          1407
```

<210> SEQ ID NO 31
<211> LENGTH: 504
<212> TYPE: DNA
<213> ORGANISM: Klebsiella pneumoniae
<220> FEATURE:
<223> OTHER INFORMATION: wild type Gene Q, nifQ

<400> SEQUENCE: 31

| | | | | | | |
|---|---|---|---|---|---|---|
| atgccgccgc | tcgactggtt | gcggcgctta | tggctgctgt | accacgcggg | gaaaggcagc | 60 |
| tttccgctgc | gcatggggct | tagcccgcgc | gattggcagg | cgctgcggcg | gcgcctgggc | 120 |
| gaggtggaaa | cgccgctcga | cggcgagacg | ctcacccgtc | gccgcctgat | ggcggagctc | 180 |
| aacgccaccc | gcgaagagga | gcgccagcag | ctgggcgcct | ggctggcggg | ctggatgcag | 240 |
| caggatgccg | gccgatggc | gcagattatc | gccgaggttt | cgctggcgtt | taaccatctc | 300 |
| tggcaggatc | ttggtctggc | atcgcgcgcc | gaattgcgcc | tgctgatgag | cgactgcttt | 360 |
| ccacagctgg | tggtgatgaa | cgaacacaat | atgcgctgga | aaaagttctt | ttatcgtcag | 420 |
| cgctgtttgc | tgcaacaggg | ggaagttatc | tgccgttcgc | caagctgcga | cgagtgctgg | 480 |
| gaacgcagcg | cctgttttga | gtag | | | | 504 |

<210> SEQ ID NO 32
<211> LENGTH: 504
<212> TYPE: DNA
<213> ORGANISM: Artificial Sequence
<220> FEATURE:
<223> OTHER INFORMATION: synthetic Gene Q

<400> SEQUENCE: 32

| | | | | | | |
|---|---|---|---|---|---|---|
| atgccgccat | tggactggtt | gcgtcgtttg | tggttactct | atcacgccgg | caaaggcagc | 60 |
| tttccgcttc | gtatgggctt | gtcgccgcgt | gactggcaag | ctctgcgccg | tcgcctgggc | 120 |
| gaggtggaaa | cgccgctgga | tggcgaaacc | ctgacccgtc | gccgtctgat | ggcggagctg | 180 |
| aatgcgaccc | gcgaagaaga | acgccagcag | ctgggtgcct | ggctggccgg | ttggatgcaa | 240 |
| caggatgccg | gtccgatggc | gcagattatc | gcagaggtga | gcctggcgtt | caaccatctc | 300 |
| tggcaggacc | ttggcctcgc | gagccgcgct | gaactgcgtc | tgctgatgtc | tgactgcttc | 360 |
| ccgcagctgg | ttgttatgaa | cgagcacaac | atgcgctgga | agaaattctt | ttaccgccag | 420 |
| cgttgcctgc | tgcaacaggg | cgaagtcatc | tgtcgcagcc | gtcttgcga | tgaatgctgg | 480 |
| gaacgttctg | cgtgctttga | gtaa | | | | 504 |

<210> SEQ ID NO 33
<211> LENGTH: 1117
<212> TYPE: DNA
<213> ORGANISM: Artificial Sequence
<220> FEATURE:
<223> OTHER INFORMATION: synthetic lacI sequence of Ptac-T7 synthetic
       controller

<400> SEQUENCE: 33

| | | | | | | |
|---|---|---|---|---|---|---|
| caattcgcgc | taacttacat | taattgcgtt | gcgctcactg | cccgctttcc | agtcgggaaa | 60 |
| cctgtcgtgc | cagctgcatt | aatgaatcgg | ccaacgcgcg | gggagaggcg | gtttgcgtat | 120 |
| tgggcgccag | ggtggttttt | cttttcacca | gtgagacggg | caacagctga | ttgcccttca | 180 |
| ccgcctggcc | ctgagagagt | tgcagcaagc | ggtccacgct | ggtttgcccc | agcaggcgaa | 240 |
| aatcctgttt | gatggtggtt | gacggcggga | tataacatga | gctgtcttcg | gtatcgtcgt | 300 |
| atcccactac | cgagatatcc | gcaccaacgc | gcagcccgga | ctcggtaatg | gcgcgcattg | 360 |

```
cgcccagcgc catctgatcg ttggcaacca gcatcgcagt gggaacgatg ccctcattca    420
gcatttgcat ggtttgttga aaaccggaca tggcactcca gtcgccttcc cgttccgcta    480
tcggctgaat ttgattgcga gtgagatatt tatgccagcc agccagacgc agacgcgccg    540
agacagaact taatgggccc gctaacagcg cgatttgctg gtgacccaat gcgaccagat    600
gctccacgcc cagtcgcgta ccgtcttcat gggagaaaat aatactgttg atgggtgtct    660
ggtcagagac atcaagaaat aacgccggaa cattagtgca ggcagcttcc acagcaatgg    720
catcctggtc atccagcgga tagttaatga tcagcccact gacgcgttgc gcgagaagat    780
tgtgcaccgc cgctttacag gcttcgacgc cgcttcgttc taccatcgac accaccacgc    840
tggcacccag ttgatcggcg cgagatttaa tcgccgcgac aatttgcgac ggcgcgtgca    900
gggccagact ggaggtggca acgccaatca gcaacgactg tttgcccgcc agttgttgtg    960
ccacgcggtt gggaatgtaa ttcagctccg ccatcgccgc ttccactttt tcccgcgttt   1020
tcgcagaaac gtggctggcc tggttcacca cgcgggaaac ggtctgataa gagacaccgg   1080
catactctgc gacatcgtat aacgttactg gtttcac                           1117

<210> SEQ ID NO 34
<211> LENGTH: 589
<212> TYPE: DNA
<213> ORGANISM: Artificial Sequence
<220> FEATURE:
<223> OTHER INFORMATION: synthetic lacI promoter sequence of Ptac-T7
      synthetic controller

<400> SEQUENCE: 34
attcaccacc ctgaattgac tctcttccgg gcgctatcat gccataccgc gaaaggtttt     60
gcaccattcg atggtgtcaa cgtaaatgca tgccgcttcg ccttcgcgcg cgaattggcc    120
gccatgccgg cgataatggc ctgcttctcg ccgaaacgtt tggtggcggg accagtgacg    180
aaggcttgag cgagggcgtg caagattccg aataccgcaa gcgacaggcc gatcatcgtc    240
gcgctccagc gaaagcggtc ctcgccgaaa atgacccaga gcgctgccgg cacctgtcct    300
acgagttgca tgataaagaa gacagtcata agtgcgcgga cgatagtcat gccccgcgcc    360
caccggaagg agctgactgg gttgaaggct ctcaagggca tcggcggagc ttatcgactg    420
cacggtgcac caatgcttct ggcgtcaggc agccatcgga agctgtggta tggctgtgca    480
ggtcgtaaat cactgcataa ttcgtgtcgc tcaaggcgca ctcccgttct ggataatgtt    540
ttttgcgccg acatcataac ggttctggca aatattctga aatgagctg              589

<210> SEQ ID NO 35
<211> LENGTH: 55
<212> TYPE: DNA
<213> ORGANISM: Artificial Sequence
<220> FEATURE:
<223> OTHER INFORMATION: synthetic tac promoter sequence of Ptac-T7
      synthetic controller

<400> SEQUENCE: 35
ttgacaatta atcatcggct cgtataatgt gtggaattgt gagcggataa caatt          55

<210> SEQ ID NO 36
<211> LENGTH: 40
<212> TYPE: DNA
<213> ORGANISM: Artificial Sequence
<220> FEATURE:
<223> OTHER INFORMATION: synthetic insulator 1 sequence of Ptac-T7
      synthetic controller
```

<400> SEQUENCE: 36
tgcagtttta ttctctcgcc agcactgtaa taggcactaa                           40

<210> SEQ ID NO 37
<211> LENGTH: 34
<212> TYPE: DNA
<213> ORGANISM: Artificial Sequence
<220> FEATURE:
<223> OTHER INFORMATION: synthetic Enterobacteria phage T7 RNA
      polymerase (RNAP) ribosome binding site (rbs, RBS) sequence of
      Ptac-T7 synthetic controller

<400> SEQUENCE: 37
tatccaaacc agtagctcaa ttggagtcgt ctat                                 34

<210> SEQ ID NO 38
<211> LENGTH: 120
<212> TYPE: DNA
<213> ORGANISM: Artificial Sequence
<220> FEATURE:
<223> OTHER INFORMATION: synthetic umuD degradatiobn tag sequence of
      Ptac-T7 synthetic controller

<400> SEQUENCE: 38
gtgttgttta tcaagcctgc ggatctccgc gaaattgtga cttttccgct atttagcgat     60
cttgttcagt gtggctttcc ttcaccggca gcagattacg ttgaacagcg catcgatctg    120

<210> SEQ ID NO 39
<211> LENGTH: 2568
<212> TYPE: DNA
<213> ORGANISM: Artificial Sequence
<220> FEATURE:
<223> OTHER INFORMATION: synthetic Enterobacteria phage T7 RNA
      polymerase (RNAP) scaffold sequence of Ptac-T7 synthetic
      controller

<400> SEQUENCE: 39
ggtggcaaca cgattaacat cgctaagaac gacttctctg acatcgaact ggctgctatc     60
ccgttcaaca ctctggctga ccattacggt gagcgtttag ctcgcgaaca gttggccctt    120
gagcatgagt cttacgagat gggtgaagca cgcttccgca agatgtttga gcgtcaactt    180
aaagctggtg aggttgcgga taacgctgcc gccaagcctc tcatcactac cctactccct    240
aagatgattg cacgcatcaa cgactggttt gaggaagtga agctaagcg cggcaagcgc     300 ccgacagcct tccagttcct gcaagaaatc aagccggaag ccgtagcgta catcaccatt    360
aagaccactc tggcttgcct aaccagtgct gacaatacaa ccgttcaggc tgtagcaagc    420
gcaatcggtc gggccattga ggacgaggct cgcttcggtc gtatccgtga ccttgaagct    480
aagcacttca agaaaaacgt tgaggaacaa ctcaacaagc gcgtagggca cgtctacaag    540
aaagcattta tgcaagttgt cgaggctgac atgctctcta agggtctact cggtggcgag    600
gcgtggtctt cgtggcataa ggaagactct attcatgtag gagtacgctg catcgagatg    660
ctcattgagt caaccggaat ggttagctta caccgccaaa atgctggcgt agtaggtcaa    720
gactctgaga ctatcgaact cgcacctgaa tacgctgagg ctatcgcaac ccgtgcaggt    780
gcgctggctg gcatctctcc gatgttccaa ccttgcgtag ttcctcctaa gccgtggact    840
ggcattactg gtggtggcta ttgggctaac ggtcgtcgtc ctctggcgct ggtgcgtact    900
cacagtaaga aagcactgat gcgctacgaa gacgtttaca tgcctgaggt gtacaaagcg    960
attaacattg cgcaaaacac cgcatggaaa atcaacaaga aagtcctagc ggtcgccaac   1020

```
gtaatcacca agtggaagca ttgtccggtc gaggacatcc ctgcgattga gcgtgaagaa    1080
ctcccgatga aaccggaaga catcgacatg aatcctgagg ctctcaccgc gtggaaacgt    1140
gctgccgctg ctgtgtaccg caaggacaag gctcgcaagt ctcgccgtat cagccttgag    1200
ttcatgcttg agcaagccaa taagtttgct aaccataagg ccatctggtt cccttacaac    1260
atggactggc gcggtcgtgt ttacgctgtg tcaatgttca acccgcaagg taacgatatg    1320
accaaaggac tgcttacgct ggcgaaaggt aaaccaatcg gtaaggaagg ttactactgg    1380
ctgaaaatcc acggtgcaaa ctgtgcgggt gtcgacaagg ttccgttccc tgagcgcatc    1440
aagttcattg aggaaaacca cgagaacatc atggcttgcg ctaagtctcc actggagaac    1500
acttggtggg ctgagcaaga ttctccgttc tgcttccttg cgttctgctt tgagtacgct    1560
ggggtacagc accacggcct gagctataac tgctcccttc cgctggcgtt tgacgggtct    1620
tgctctggca tccagcactt ctccgcgatg ctccgagatg aggtaggtgg tcgcgcggtt    1680
aacttgcttc ctagtgaaac cgttcaggac atctacggga ttgttgctaa gaaagtcaac    1740
gagattctac aagcagacgc aatcaatggg accgataacg aagtagttac cgtgaccgat    1800
gagaacactg tgaaatctc tgagaaagtc aagctgggca ctaaggcact ggctggtcaa    1860
tggctggctt acggtgttac tcgcagtgtg actaagagtt cagtcatgac gctggcttac    1920
gggtccaaag agttcggctt ccgtcaacaa gtgctggaag ataccattca gccagctatt    1980
gattccggca agggtctgat gttcactcag ccgaatcagg ctgctggata catggctaag    2040
ctgatttggg aatctgtgag cgtgacggtg gtagctgcgg ttgaagcaat gaactggctt    2100
aagtctgctg ctaagctgct ggctgctgag gtcaaagata agaagactgg agagattctt    2160
cgcaagcgtt gcgctgtgca ttgggtaact cctgatggtt tccctgtgtg gcaggaatac    2220
aagaagccta ttcagacgcg cttgaacctg atgttcctcg gtcagttccg cttacagcct    2280
accattaaca ccaacaaaga tagcgagatt gatgcacaca aacaggagtc tggtatcgct    2340
cctaactttg tacacagcca agacggtagc caccttcgta agactgtagt gtgggcacac    2400
gagaagtacg gaatcgaatc ttttgcactg attcacgact ccttcggtac gattccggct    2460
gacgctgcga acctgttcaa agcagtgcgc gaaactatgg ttgacacata tgagtcttgt    2520
gatgtactgg ctgatttcta cgaccagttc gctgaccagt tgcacgag                 2568
```

<210> SEQ ID NO 40
<211> LENGTH: 21
<212> TYPE: DNA
<213> ORGANISM: Artificial Sequence
<220> FEATURE:
<223> OTHER INFORMATION: synthetic Biobrick suffix (BBa_G00001) sequence of Ptac-T7 synthetic controller

<400> SEQUENCE: 40

```
tactagtagc ggccgctgca g                                              21
```

<210> SEQ ID NO 41
<211> LENGTH: 12
<212> TYPE: DNA
<213> ORGANISM: Artificial Sequence
<220> FEATURE:
<223> OTHER INFORMATION: synthetic translational stop (BBa_B0042) sequence of Ptac-T7 synthetic controller

<400> SEQUENCE: 41

```
ttagttagtt ag                                                        12
```

```
<210> SEQ ID NO 42
<211> LENGTH: 69
<212> TYPE: DNA
<213> ORGANISM: Artificial Sequence
<220> FEATURE:
<223> OTHER INFORMATION: synthetic terminator (BBa_B0054) sequence of
      Ptac-T7 synthetic controller

<400> SEQUENCE: 42
attagcagaa agtcaaaagc ctccgaccgg aggcttttga ctaaaacttc ccttggggtt    60
atcattggg                                                            69

<210> SEQ ID NO 43
<211> LENGTH: 20
<212> TYPE: DNA
<213> ORGANISM: Artificial Sequence
<220> FEATURE:
<223> OTHER INFORMATION: synthetic VR primer (BBa_G00102) sequence of
      Ptac-T7 synthetic controller

<400> SEQUENCE: 43
gctcactcaa aggcggtaat                                                20

<210> SEQ ID NO 44
<211> LENGTH: 41
<212> TYPE: DNA
<213> ORGANISM: Artificial Sequence
<220> FEATURE:
<223> OTHER INFORMATION: synthetic terminator (BBa_B0062) sequence of
      Ptac-T7 synthetic controller

<400> SEQUENCE: 44
cagataaaaa aaatccttag ctttcgctaa ggatgatttc t                        41

<210> SEQ ID NO 45
<211> LENGTH: 3671
<212> TYPE: DNA
<213> ORGANISM: Artificial Sequence
<220> FEATURE:
<223> OTHER INFORMATION: synthetic pSa origin sequence of Ptac-T7
      synthetic controller

<400> SEQUENCE: 45
gctagagctg tcagaccaga gctccaaacc aacgttttat ctataccgct acagggtatt    60
taattcctat ttaatctgcg ctagaatgag gcatgtttaa ccgaatctga cgttttccct   120
gcaaatgcca aaatactatg cctatctccg ggtttcgcgt gacggccaag acccggaaaa   180
ccaaaaatac ggtttgctcg aatacgcgaa cgccaaaggc ttcgcgccgc tacagatcga   240
ggaagaaatt gccagcagag caaaggactg gcgcaagcgc aagctcggag caatcatcga   300
aaaggccgag cgtggcgacg tgctactgac gccggagatt acgcgcattg ccggttccgc   360
cctcgccgcc ttggaaattc tcaaagcgga gagcgagcgc ggcctaatcg tccatgtgac   420
caaacagaag atcatcatgg acggcagcct acaaagcgac atcatggcaa ccgtgcttgg   480
cttggctgca cagatcgagc ggcatttcat tcaggcacgt accaccgagg cgctacaagt   540
cgccagagag cgcggcaaga cgctcgggcg acccaagggc agcaaatcga gcgccttgaa   600
gctggacagc cgtattgatg aagtacaggc atacgtgaac cttggcttgc cgcaaagtcg   660
cgcagccgag ttgttaggcg tcagccctca caccttgcgc ctgttcatca aacgccggaa   720
catcaaaccc acaaacacta gaccaaccat caccatgccg gggagggaac aacatgccta   780
agaacaacaa agcccccggc catcgtatca acgagatcat caagacgagc ctcgcgctcg   840
```

```
aaatggagga tgcccgcgaa gctggcttag tcggctacat ggcccgttgc cttgtgcaag    900
cgaccatgcc ccacaccgac cccaagacca gctactttga gcgcaccaat ggcatcgtca    960
ccttgtcgat catgggcaag ccgagcatcg gcctgcccta cggttctatg ccgcgcacct   1020
tgcttgcttg gatatgcacc gaggccgtgc gaacgaaaga ccccgtgttg aaccttggcc   1080
ggtcgcaatc ggaatttcta caaaggctcg gaatgcacac cgatggccgt tacacggcca   1140
cccttcgcaa tcaggcgcaa cgcctgtttt catccatgat ttcgcttgcc ggcgagcaag   1200
gcaatgactt cggcattgag aacgtcgtca ttgccaagcg cgcttttcta ttctggaatc   1260
ccaagcggca agaagatcgg gcgctatggg atagcaccct caccctcaca ggcgatttct   1320
tcgaggaagt cacccgctca ccggttccta tccgaatcga ctacctgcat gccttgcggc   1380
agtctccgct tgcgatggac atttacacgt ggctgaccta tcgcgtgttc ctgttgcggg   1440
ccaagggccg cccccttcgtg caaatccctt gggtcgccct gcaagcgcaa ttcggctcat   1500
cctatggcag ccgcgcacgc aactcgcccg aactggacga taaggcccga gagcgggcag   1560
agcgggcagc actcgccagc ttcaaataca acttcaaaaa gcgcctacgc gaagtgttga   1620
ttgtctatcc cgaggcaagc gactgcatcg aagatgacgg cgaatgcctg cgcatcaaat   1680
ccacacgcct gcatgtcacc cgcgcacccg gcaagggcgc tcgcatcggc ccccctccga   1740
cttgaccagg ccaacgctac gcttggcttg gtcaagcctt cccatccaac agcccgccgt   1800
cgagcgggct tttttatccc cggaagcctg tggatagagg gtagttatcc acgtgaaacc   1860
gctaatgccc cgcaaagcct tgattcacgg ggctttccgg cccgctccaa aaactatcca   1920
cgtgaaatcg ctaatcaggg tacgtgaaat cgctaatcgg agtacgtgaa atcgctaata   1980
aggtcacgtg aaatcgctaa tcaaaaaggc acgtgagaac gctaatagcc ctttcagatc   2040
aacagcttgc aaacacccct cgctccggca agtagttaca gcaagtagta tgttcaatta   2100
gcttttcaat tatgaatata tatatcaatt attggtcgcc cttggcttgt ggacaatgcg   2160
ctacgcgcac cggctccgcc cgtggacaac cgcaagcggt tgcccaccgt cgagcgccag   2220
cgcctttgcc cacaacccgg cggccgcaac agatcgtttt ataaattttt tttttttgaaa   2280
aagaaaaagc ccgaaaggcg gcaacctctc gggcttctgg atttccgatc aacgcaggag   2340
tcgttcggaa agtagctgtt ccagaattat aggcgcagag acaccagatt ccaagatggc   2400
tctgttaaat tgttgtagta tgtagtatca tacaacatac tacagtacag aggcccgcaa   2460
gaatggcaat cactaaacaa gacatttggc gagcagccga cgaactggac gccgaaggca   2520
tccggcccac tttggccgcc gtgcgcaaga aactcggaag cggtagcttc acaaccattt   2580
ccgatgcaat ggctgaatgg aaaaaccgca agaccgccac cctgccctca tcagacccat   2640
tgccggttgc agtcaacgag catcttgccg agcttggcaa tgcgctatgg gctatcgccc   2700
tggcgcacgc caacgcccgg tttgacgaag atcggaaaca gatcgaggcc gacaaagcgg   2760
ccatcagcca gcagcttgcc gaagcaatcg aactagccga cacctccacc cgcgaaaacg   2820
accagctccg cgaacgagtg aatcagctcg aacctatgga acgcgagcgc gacaagctgg   2880
ccgaccagct tgccgaagtg aaacgccgca gcggcgaaga actaaaccgc tgcatggaaa   2940
agctcaccca acgcgataac gaggctatcg aggcccgcaa acaggccaag gaggccatcg   3000
agcgcgccgc cagtctgcaa ggtcaggtgg aagccctcaa agagcaggtc gccaatctca   3060
cagccgtctt gaaaacagga ggcaaacaat gaaaagcgcc cttgccgccc ttcgcgcggt   3120
cgcggccgct gtcgtcctaa tcgtcagtgt gcccgcttgg gccgacttcc ggggtgaagt   3180
```

```
cgtccgaatc cttgacggtg acactatcga cgttttggtg aaccgtcaga ccatccgcgt      3240
gagattggcc gatattgacg caccggaaag cggccaagcc ttcggctccc gtgctcgcca      3300
acggctcgcc gacttgacct ttcgccaaga ggttcaagtg accgaaaaag aggttgatcg      3360
gtatggccgc actcttgggg tcgtttacgc gccgttgcaa taccccggcg gccaaacaca      3420
actcaccaac atcaatgcga tcatggttca agaaggcatg gcctgggctt accgttatta      3480
cggcaaacca accgacgcgc agatgtacga gtatgaaaaa gaggcccgcc gccaacggct      3540
cggcctttgg tcagacccga atgctcagga gccttggaaa tggcgtcgcg cctcgaaaaa      3600
tgccacgaac tgacaccggg cacgccccct gttcgacgcg ccgcaggcac gtcgaattta      3660
ccgccgggac g                                                           3671
```

<210> SEQ ID NO 46
<211> LENGTH: 1175
<212> TYPE: DNA
<213> ORGANISM: Artificial Sequence
<220> FEATURE:
<223> OTHER INFORMATION: synthetic spectinomycin resistance sequence of
      Ptac-T7 synthetic controller

<400> SEQUENCE: 46

```
cccctcgtcc cgacacttcc agatcgccat agcgcacagc gcctcgagcg gtggtaacgg        60
cgcagtggcg gttttcatgg cttgttatga ctgtttttttt ggggtacagt ctatgcctcg       120
ggcatccaag cagcaagcgc gttacgccgt gggtcgatgt ttgatgttat ggagcagcaa       180
cgatgttacg cagcagggca gtcgccctaa aacaaagtta aacatcatga gggaagcggt       240
gatcgccgaa gtatcgactc aactatcaga ggtagttggc gtcatcgagc gccatctcga       300
accgacgttg ctggccgtac atttgtacgg ctccgcagtg gatggcggcc tgaagccaca       360
cagtgatatt gatttgctgg ttacggtgac cgtaaggctt gatgaaacaa cgcggcgagc       420
tttgatcaac gaccttttgg aaacttcggc ttccctgga gagagcgaga ttctccgcgc        480
tgtagaagtc accattgttg tgcacgacga catcattccg tggcgttatc cagctaagcg       540
cgaactgcaa tttggagaat ggcagcgcaa tgacattctt gcaggtatct tcgagccagc       600
cacgatcgac attgatctgg ctatcttgct gacaaaagca agagaacata gcgttgcctt       660
ggtaggtcca gcggcggagg aactctttga tccggttcct gaacaggatc tatttgaggc       720
gctaaatgaa accttaacgc tatggaactc gccgcccgac tgggctggcg atgagcgaaa       780
tgtagtgctt acgttgtccc gcatttggta cagcgcagta accggcaaaa tcgcgccgaa       840
ggatgtcgct gccgactggg caatggagcg cctgccggcc cagtatcagc ccgtcatact       900
tgaagctaga caggcttatc ttggacaaga agaagatcgc ttggcctcgc gcgcagatca       960
gttggaagaa tttgtccact acgtgaaagg cgagatcacc aaggtagtcg gcaaataatg      1020
tctaacaatt cgttcaagcc gacgccgctt cgcggcgcgg cttaactcaa gcgttagatg      1080
cactaagcac ataattgctc acagccaaac tatcaggtca agtctgcttt tattattttt      1140
aagcgtgcat aataagccct acacaaatgg taccc                                 1175
```

<210> SEQ ID NO 47
<211> LENGTH: 72
<212> TYPE: DNA
<213> ORGANISM: Artificial Sequence
<220> FEATURE:
<223> OTHER INFORMATION: synthetic terminator (BBa_B0053) sequence of
      Ptac-T7 synthetic controller

<400> SEQUENCE: 47
tccggcaaaa aaacgggcaa ggtgtcacca ccctgcccct tttctttaaa accgaaaaga    60
ttacttcgcg tt    72

<210> SEQ ID NO 48
<211> LENGTH: 20
<212> TYPE: DNA
<213> ORGANISM: Artificial Sequence
<220> FEATURE:
<223> OTHER INFORMATION: synthetic VF2 primer (BBa_G000101) sequence of
      Ptac-T7 synthetic controller

<400> SEQUENCE: 48
tgccacctga cgtctaagaa    20

<210> SEQ ID NO 49
<211> LENGTH: 78
<212> TYPE: DNA
<213> ORGANISM: Artificial Sequence
<220> FEATURE:
<223> OTHER INFORMATION: synthetic terminator (BBa_B0055) sequence of
      Ptac-T7 synthetic controller

<400> SEQUENCE: 49
aaggaatatt cagcaatttg cccgtgccga agaaaggccc acccgtgaag gtgagccagt    60
gagttgattg ctacgtaa    78

<210> SEQ ID NO 50
<211> LENGTH: 12
<212> TYPE: DNA
<213> ORGANISM: Artificial Sequence
<220> FEATURE:
<223> OTHER INFORMATION: synthetic translational stop (BBa_B0042)
      sequence of Ptac-T7 synthetic controller

<400> SEQUENCE: 50
ttagttagtt ag    12

<210> SEQ ID NO 51
<211> LENGTH: 22
<212> TYPE: DNA
<213> ORGANISM: Artificial Sequence
<220> FEATURE:
<223> OTHER INFORMATION: synthetic Biobrick prefix (BBa_G00000) sequence
      of Ptac-T7 synthetic controller

<400> SEQUENCE: 51
gaattcgcgg ccgcttctag ag    22

<210> SEQ ID NO 52
<211> LENGTH: 23
<212> TYPE: DNA
<213> ORGANISM: Artificial Sequence
<220> FEATURE:
<223> OTHER INFORMATION: synthetic Enterobacteria phage T7 wild type
      (WT) promoter of full synthetic cluster

<400> SEQUENCE: 52
taatacgact cactataggg aga    23

<210> SEQ ID NO 53
<211> LENGTH: 28
<212> TYPE: DNA
<213> ORGANISM: Artificial Sequence
<220> FEATURE:
<223> OTHER INFORMATION: synthetic nifH ribosome binding site (rbs, RBS)

of full synthetic cluster

<400> SEQUENCE: 53
acaataaact aacataagga ggataaat                                               28

<210> SEQ ID NO 54
<211> LENGTH: 882
<212> TYPE: DNA
<213> ORGANISM: Artificial Sequence
<220> FEATURE:
<223> OTHER INFORMATION: synthetic nifH of full synthetic cluster

<400> SEQUENCE: 54
atgaccatgc gtcagtgcgc gatttatggc aaaggtggta ttggcaaaag cacgacgacc        60
cagaacttgg tggcggccct ggccgagatg ggtaaaaagg ttatgattgt gggttgcgac       120
ccgaaggccg acagcacgcg cctgattctg cacgcgaaag cacaaaacac gattatggag       180
atggctgccg aggttggtag cgtggaggat ctggagctgg aggacgttct gcaaattggt       240
tacggtgatg ttcgttgcgc agagagcggt ggtccggaac caggtgtcgg ctgtgcgggt       300
cgtggtgtga ttaccgctat caatttcctg gaagaagagg gtgcgtacga agatgatctg       360
gatttcgttt tctacgatgt gctgggtgat gtcgtgtgcg gtggttttgc aatgccgatt       420
cgcgagaata aggcacaaga aatttacatt gtctgtagcg gcgagatgat ggcaatgtac       480
gctgctaaca acatcagcaa gggtattgtt aaatacgcaa aaagcggtaa ggttcgcttg       540
ggtggtttga tttgcaacag ccgtcagacc gaccgtgagg acgaactgat catcgccctg       600
gctgagaaac tgggcaccca aatgatccac ttcgtgccac gcgataatat tgttcaacgt       660
gcagaaatcc gccgtatgac cgtcattgag tatgacccgg catgcaagca agcgaacgag       720
taccgcacct tggcacagaa aatcgtgaac aacaccatga aggttgttcc gacgccgtgt       780
acgatggacg agctggagag cctgctgatg gagttcggca ttatggagga ggaggacacc       840
agcattatcg gtaagaccgc agcggaggag aatgcggcat aa                           882

<210> SEQ ID NO 55
<211> LENGTH: 50
<212> TYPE: DNA
<213> ORGANISM: Artificial Sequence
<220> FEATURE:
<223> OTHER INFORMATION: synthetic insulator 1 of full synthetic cluster

<400> SEQUENCE: 55
gcgtgcgtac accttaatca ccgcttcatg ctaaggtcct ggctgcatgc                    50

<210> SEQ ID NO 56
<211> LENGTH: 34
<212> TYPE: DNA
<213> ORGANISM: Artificial Sequence
<220> FEATURE:
<223> OTHER INFORMATION: synthetic nifD ribosome binding site (rbs, RBS)
      of full synthetic cluster

<400> SEQUENCE: 56
aaaaattcac atccctatct agcggaggag ccgg                                     34

<210> SEQ ID NO 57
<211> LENGTH: 1452
<212> TYPE: DNA
<213> ORGANISM: Artificial Sequence
<220> FEATURE:
<223> OTHER INFORMATION: synthetic nifD of full synthetic cluster

```
<400> SEQUENCE: 57
atgatgacta atgctactgg cgaacgtaac ctggcactga ttcaagaagt actggaagtg      60
ttcccggaaa ccgcgcgcaa agagcgccgt aaacacatga tggtttctga cccgaaaatg     120
aaatctgtgg gtaaatgcat catctctaat cgcaaatctc agccgggtgt catgactgtt     180
cgtggctgtg cgtacgcagg ttctaaaggt gtcgtattcg gcccgatcaa agatatggcg     240
catatctctc atggcccggc aggctgtggc cagtactctc gcgcggaacg tcgtaactac     300
tacacgggcg tttctggcgt tgactctttc ggcacgctga acttcacctc tgacttccag     360
gaacgtgaca tcgttttcgg tggcgataaa aagctgtcca aactgatcga agaaatggaa     420
ctgctgttcc cgctgactaa aggcattact atccaaagcg aatgtccggt gggtctgatc     480
ggtgatgaca tcagcgcggt cgcaaacgca tcttccaaag ccctggataa gccggtgatc     540
ccggttcgtt gcgagggctt ccgcggcgtt tctcagtctc tgggtcatca catcgcaaac     600
gatgttgtgc gtgactggat tctgaacaac cgtgaaggtc agcctttga  aaccacccct     660
tatgacgttg cgattattgg cgactataac atcggcggcg acgcctgggc atcccgcatc     720
ctgctggagg agatgggtct gcgtgttgtc gcacagtggt ctggcgatgg caccctggtt     780
gaaatggaaa cacccccgtt tgttaaactg aacctggttc actgctaccg ctccatgaac     840
tacattgccc gtcacatgga agaaaaacat cagatcccctt ggatggaata caacttcttc     900
ggtccgacta aaatcgcaga atccctgcgt aaaatcgccg atcagtttga tgataccatt     960
cgcgcgaacg ctgaagcagt aattgcgcgc tacgaaggcc agatggcagc aatcattgct    1020
aagtaccgtc cgcgcctgga aggtcgtaaa gtgctgctgt acatgggtgg tctgcgtcca    1080
cgtcatgtga tcggtgccta cgaggacctg gcatggaga  tcatcgcagc gggttacgaa    1140
tttgcacaca cgacgacta  tgatcgtacg ctgccagacc tgaaagaagg tacgctgctg    1200
tttgacgacg ccagctctta tgaactggaa gccttcgtga aagcgctgaa accagacctg    1260
atcggctccg gcatcaagga aaaatacatt ttccagaaaa tgggcgtgcc gttccgccag    1320
atgcactcct gggactactc cggtccgtac cacggctacg acggtttcgc tatcttcgct    1380
cgtgacatgg atatgaccct gaataaccca gcgtggaatg aactgaccgc accgtggctg    1440
aaatctgcat aa                                                        1452

<210> SEQ ID NO 58
<211> LENGTH: 50
<212> TYPE: DNA
<213> ORGANISM: Artificial Sequence
<220> FEATURE:
<223> OTHER INFORMATION: synthetic insulator 2 of full synthetic cluster

<400> SEQUENCE: 58
caaacacccc atgtcgatac tgaacgaatc gacgcacact cccttccttg                50

<210> SEQ ID NO 59
<211> LENGTH: 34
<212> TYPE: DNA
<213> ORGANISM: Artificial Sequence
<220> FEATURE:
<223> OTHER INFORMATION: synthetic nifK ribosome binding site (rbs, RBS)
      of full synthetic cluster

<400> SEQUENCE: 59
caatctcata ctctcaaaaa ttaggcgagg taac                                 34

<210> SEQ ID NO 60
```

<211> LENGTH: 1563
<212> TYPE: DNA
<213> ORGANISM: Artificial Sequence
<220> FEATURE:
<223> OTHER INFORMATION: synthetic nifK of full synthetic cluster

<400> SEQUENCE: 60

```
atgtctcaaa ctatcgataa aatcaactct tgttacccgc tgttcgagca ggacgaatat      60
caggaactgt tccgtaacaa acgtcagctg gaagaagcgc acgacgcaca gcgcgtgcag     120
gaagtgttcg catggaccac caccgcggaa tacgaagctc tgaacttccg tcgcgaagcc     180
ctgacggttg atccggcgaa agcgtgccag cctctgggtg cggttctgtg cagcctgggt     240
tttgccaaca ccctgccgta tgtccacggt tcccagggct gcgtagccta cttccgtacc     300
tatttcaacc gccactttaa agaaccaatc gcgtgcgtgt ccgacagcat gacggaggac     360
gcggcagttt tcggtggtaa caacaacatg aacctgggcc tgcaaaatgc ttccgcactg     420
tacaaaccgg aaatcatcgc agtgtctacc acctgcatgg cagaggttat tggtgatgat     480
ctgcaagcat ttattgccaa cgcaaagaaa gacggtttcg ttgacagctc tatcgcggtt     540
ccgcacgctc ataccccgtc cttcatcggt tctcacgtaa ctggttggga caacatgttc     600
gaaggcttcg caaaaacttt taccgcagac tatcaaggcc aaccgggtaa actgccgaag     660
ctgaacctgg tgaccggctt tgaaacctac ctgggcaact tcgtgtcct gaagcgcatg     720
atggagcaga tggcggttcc gtgttctctg ctgtctgacc cgtctgaggt tctggacact     780
ccagcggacg gccactatcg catgtattct ggtggcacca ctcagcagga aatgaaagag     840
gccccagacg cgattgacac cctgctgctg caaccgtggc agctgctgaa agcaagaaa     900
gttgttcagg aaatgtggaa ccagccggca acggaagttg caatcccgct gggtctggca     960
gctactgacg aactgctgat gaccgtgtcc caactgagcg gcaaaccaat cgcggatgct    1020
ctgacccctgg aacgcggtcg cctggtggac atgatgctgg acagccacac gtggctgcat    1080
ggcaagaaat ttggcctgta cggtgacccg gacttcgtaa tgggcctgac ccgtttcctg    1140
ctggaactgg gctgcgagcc gactgttatc ctgtctcaca acgctaacaa acgttggcag    1200
aaggccatga acaaaatgct ggatgcgagc ccatacggcc gtgatagcga agtgttcatc    1260
aactgcgacc tgtggcattt ccgctctctg atgtttacgc gtcagccgga tttcatgatc    1320
ggtaactctt acggcaaatt catccagcgt gacactctgg ccaaaggcaa agcgtttgaa    1380
gtgccgctga ttcgtctggg cttttccgctg ttcgaccgtc accacctgca ccgccagacc    1440
acctgggggtt acgaaggcgc gatgaacatc gtaactactc tggtaaacgc agtactggaa    1500
aagctggaca gcgatacttc ccagctgggc aaaaccgact attctttcga tctggttcgt    1560
taa                                                                  1563
```

<210> SEQ ID NO 61
<211> LENGTH: 40
<212> TYPE: DNA
<213> ORGANISM: Artificial Sequence
<220> FEATURE:
<223> OTHER INFORMATION: synthetic insulator 3 of full synthetic cluster

<400> SEQUENCE: 61

```
cctgattgta tccgcatctg atgctaccgt ggttgagtta                            40
```

<210> SEQ ID NO 62
<211> LENGTH: 26
<212> TYPE: DNA
<213> ORGANISM: Artificial Sequence
<220> FEATURE:
<223> OTHER INFORMATION: synthetic nifY ribosome binding site (rbs, RBS) of full synthetic cluster

<400> SEQUENCE: 62
ccatactcac tcccggaggt acttct                                              26

<210> SEQ ID NO 63
<211> LENGTH: 663
<212> TYPE: DNA
<213> ORGANISM: Artificial Sequence
<220> FEATURE:
<223> OTHER INFORMATION: synthetic nifY of full synthetic cluster

<400> SEQUENCE: 63
atgtctgaca atgataccct gttttggcgc atgctggcgc tgtttcagtc gctgccggat          60
ttgcagccgg ctcaaatcgt cgattggctg gcgcaggaat ccggcgaaac cctgacgccg         120
gagcgccttg ccaccctgac ccaaccgcaa ctcgcggcgt cgttcccatc cgcgacggca         180
gtgatgagcc cggctcgctg gagccgcgtt atggcttctc tgcaaggcgc cctcccagcc         240
cacttgcgca tcgtacgtcc ggcgcagcgt accccgcaac tgctcgccgc gttttgcagc         300
caagacggcc ttgttatcaa tggtcatttc ggccagggtc gtctgttctt catttacgcc         360
tttgacgagc agggcggctg gctgtatgac ttgcgccgct atccgagcgc accgcaccag         420
caggaagcga atgaggtgcg tgctcgtctg attgaagatt gccagctgct gttctgccag         480
gagattggcg gtccggcagc agcgcgtccg atccgccacc gcatccatcc gatgaaggcg         540
cagccgggta ctacgattca ggcgcagtgt gaagctatca acaccctgct ggccggtcgc         600
ctgccgccgt ggctcgccaa acgtttgaac cgtgataacc cgctggaaga gcgtgtgttt         660
taa                                                                      663

<210> SEQ ID NO 64
<211> LENGTH: 40
<212> TYPE: DNA
<213> ORGANISM: Artificial Sequence
<220> FEATURE:
<223> OTHER INFORMATION: synthetic insulator 4 of full synthetic cluster

<400> SEQUENCE: 64
catttttgcc ttgcgacaga cctcctactt agattgccac                                40

<210> SEQ ID NO 65
<211> LENGTH: 32
<212> TYPE: DNA
<213> ORGANISM: Artificial Sequence
<220> FEATURE:
<223> OTHER INFORMATION: synthetic nifE ribosome binding site (rbs, RBS) of full synthetic cluster

<400> SEQUENCE: 65
actattcaat acatcactgg aggttattac aa                                        32

<210> SEQ ID NO 66
<211> LENGTH: 1374
<212> TYPE: DNA
<213> ORGANISM: Artificial Sequence
<220> FEATURE:
<223> OTHER INFORMATION: synthetic nifE of full synthetic cluster

<400> SEQUENCE: 66
atgaagggta acgagattct tgctctgctg gacgaaccgg cctgtgaaca caaccataaa          60

```
cagaaatccg gctgtagcgc cccaaagccg ggtgcgacgg cggctggctg cgctttcgat      120
ggtgcgcaga tcaccctgct cccgattgcg gacgttgccc acctcgtgca tggcccaatc      180
ggttgcgcag gtagctcttg ggacaaccgt ggcagcgcct ccagcggtcc gaccctgaat      240
cgtttgggct ttaccactga cttgaatgaa caagatgtga tcatgggtcg cggcgagcgt      300
cgcctgttcc acgctgtgcg ccatattgtc acccgttacc acccagcggc agtattcatc      360
tacaatacgt gcgtgccggc tatggaaggc gatgacctgg aggccgtgtg tcaggcagcc      420
cagactgcga ccggcgtccc ggtaatcgca attgatgcgg ctggcttcta cggttcgaag      480
aacctgggca accgtccggc aggcgatgtc atggttaaac gcgtcattgg ccaacgtgag      540
ccagcgccgt ggccggagag caccctgttt gccccggagc aacgtcatga cattggcttg      600
atcggtgagt tcaacattgc gggcgagttt tggcacattc agccgctgct tgatgagctg      660
ggtatccgcg ttttgggttc gctcagcggc gatggtcgtt tcgccgagat tcaaaccatg      720
caccgtgccc aggcgaacat gctggtgtgc agccgtgctc tgatcaatgt tgcgcgtgct      780
ctggaacagc gctatggcac cccgtggttt gaaggctcgt tctatggtat ccgcgcgacc      840
agcgacgccc tgcgccagtt agcggcgctg ctgggcgatg acgacctccg tcagcgcacc      900
gaggcgctga tcgcgcgtga agaacaggcg gctgagctgg ccctgcaacc gtggcgtgaa      960
cagctgcgtg ccgcaaggc cctgctctac acgggtggtg tcaaaagctg gtctgtggtg     1020
tccgcgcttc aggatctggg tatgaccgtg gttgccacgg gcacgcgtaa gagcacggaa     1080
gaggataaac agcgcatccg cgaattgatg ggcgaagagg ccgtgatgct tgaagaaggc     1140
aacgcacgta ccttattgga tgtagtttat cgctatcaag cagacctgat gattgccggt     1200
ggccgcaaca tgtataccgc ctacaaagcg cgcttgccgt tcctggacat caaccaggaa     1260
cgcgagcacg cgtttgcggg ctaccaaggc atcgtgacct tagcgcgcca gctgtgccaa     1320
acgattaaca gcccgatctg gccgcagact cattcccgcg caccgtggcg ctaa           1374
```

<210> SEQ ID NO 67
<211> LENGTH: 40
<212> TYPE: DNA
<213> ORGANISM: Artificial Sequence
<220> FEATURE:
<223> OTHER INFORMATION: synthetic insulator 5 of full synthetic cluster

<400> SEQUENCE: 67

```
tgtcacgcta ggaggcaatt ctataagaat gcacactgca                            40
```

<210> SEQ ID NO 68
<211> LENGTH: 31
<212> TYPE: DNA
<213> ORGANISM: Artificial Sequence
<220> FEATURE:
<223> OTHER INFORMATION: synthetic nifN ribosome binding site (rbs, RBS)
    of full synthetic cluster

<400> SEQUENCE: 68

```
cctaaaccta ccacacctgg aagaagtaat t                                     31
```

<210> SEQ ID NO 69
<211> LENGTH: 1386
<212> TYPE: DNA
<213> ORGANISM: Artificial Sequence
<220> FEATURE:
<223> OTHER INFORMATION: synthetic nifN of full synthetic cluster

<400> SEQUENCE: 69

| | |
|---|---:|
| atggcagaca ttttccgcac tgataagccg ttggctgtgt cgccgatcaa gaccggccag | 60 |
| ccgctgggtg cgatcctggc gtccctgggt atcgagcact cgattccgct ggtacatggc | 120 |
| gcgcagggct gttcggcttt tgccaaggtt ttctttatcc agcacttcca cgatccggtc | 180 |
| ccgctgcaaa gcacggcaat ggacccgacc agcaccatca tgggcgctga tggtaacatc | 240 |
| ttcaccgcgc tggacactct ctgccaacgc aataaccccgc aagcaattgt gctgctgagc | 300 |
| accggcctct ccgaggcgca gggcagcgac atttcccgtg tagtgcgtca gttccgtgaa | 360 |
| gaatatccgc gtcataaagg cgtggcgatt ctgactgtta cacccccgga cttttacggt | 420 |
| agcatggaga acggcttttc cgctgtcctg gagtctgtga ttgaacagtg ggttccgcca | 480 |
| gccccacgtc cggcgcagcg caatcgtcgc gtcaatcttt tggtgagcca tctctgtagc | 540 |
| ccaggcgata ttgagtggct gcgccgttgc gtcgaggcct tcggtctgca accgatcatt | 600 |
| ctgccggatc tggctcagag catggacggc caccttgctc agggtgactt ttcgccgctg | 660 |
| acgcagggcg gcacgccgtt gcgccaaatc gagcagatgg gccagagcct ttgctctttt | 720 |
| gcgattggcg tcagcctgca ccgtgcgagc agcctgctgg ctccgcgttg tcgtggcgaa | 780 |
| gtcatcgcct gccgcaccct catgaccttg aacgctgcg acgcctttat ccatcagttg | 840 |
| gcgaaaatca gcgtcgcgc cgttccggag tggctggaaa ccagcgcgg tcagctgcaa | 900 |
| gacgccatga tcgattgcca catgtggctg caaggccagc gcatggcgat gccgccgaa | 960 |
| ggcgacctgc tggcagcgtg gtgcgatttc gcgaactctc aaggtatgca gccgggtcca | 1020 |
| ctggttgctc cgacgggtca tccgagcctg cgtcagttgc cggtggagcg cgtggtgccg | 1080 |
| ggtgatctgg aggatcttca gaccctctta tgcgcacatc cggccgactt actggtggcg | 1140 |
| aactcccacg cccgtgattt agcagagcaa ttcgccctgc cgctggtgcg cgcaggcttc | 1200 |
| ccgctgtttg acaaactggg cgaatttcgt cgtgttcgcc agggttatag cggtatgcgt | 1260 |
| gataccctgt tcgagttggc gaacctgatc cgtgaacgcc atcatcatct ggctcattat | 1320 |
| cgcagcccgc tgcgccagaa cccagaatcc tcgttgtcta cgggtggcgc gtacgcagcg | 1380 |
| gattaa | 1386 |

<210> SEQ ID NO 70
<211> LENGTH: 27
<212> TYPE: DNA
<213> ORGANISM: Artificial Sequence
<220> FEATURE:
<223> OTHER INFORMATION: synthetic nifJ ribosome binding site (rbs, RBS)
of full synthetic cluster

<400> SEQUENCE: 70

| | |
|---|---:|
| ctagagatta aagaggagaa attaagc | 27 |

<210> SEQ ID NO 71
<211> LENGTH: 3507
<212> TYPE: DNA
<213> ORGANISM: Artificial Sequence
<220> FEATURE:
<223> OTHER INFORMATION: synthetic nifJ of full synthetic cluster

<400> SEQUENCE: 71

| | |
|---|---:|
| atgaaaacta tggacggtaa cgctgcggct gcatggatta gctacgcctt taccgaagtg | 60 |
| gctgcgatct acccgattac gccgagcacc ccgatggcgg aaaatgtgga cgaatgggct | 120 |
| gcgcagggca agaagaacct cttcggccag ccggtgcgcc tgatggagat gcagtcggaa | 180 |
| gcgggtgcag caggtgctgt gcatggcgcc ttgcaagctg gcgcactgac gaccacctac | 240 |

```
accgcgtcgc agggcctgtt gctgatgatc ccaaacatgt acaaaatcgc gggtgaactg    300
ctgccgggtg tctttcatgt ttcggcacgc gcactggcca ccaatagcct caacatcttt    360
ggcgatcatc aggatgtaat ggcggtgcgc caaacgggct gcgcgatgtt ggccgagaat    420
aacgtccagc aagttatgga tttgtccgcg gtagcccact ggcagcgat caaaggtcgc     480 attccgttcg tgaacttctt cgatggcttt cgcaccagcc acgaaatcca gaagatcgag    540
gttctggaat atgaacagct ggccaccttg ttggatcgtc cggccctgga cagcttccgc    600
cgtaacgccc ttcacccgga ccacccggtc atccgtggca ccgcccagaa cccggacatc    660
tacttccagg aacgtgaggc cggtaaccgt ttctatcagg cgctcccgga tattgtggaa    720
tcttacatga cccagatttc tgccctgact ggtcgcgagt atcacctgtt taactacact    780
ggtgctgcgg atgcggagcg cgtgatcatc gcgatgggct ctgtctgtga caccgtccaa    840
gaggtggttg acacgctgaa tgcagcgggt gagaaagttg gtctgctctc cgttcatctt    900
ttccgcccgt tttcgttagc gcacttcttc gcccaactgc cgaaaactgt acagcgtatc    960
gcagtattgg accgtacgaa agagccaggt gctcaagcag agccgctgtg cctcgatgtg    1020
aagaatgcct ttaccacca tgacgatgcc ccgttgattg tgggtggtcg ctatgccttg    1080
ggcggtaagg acgtgttgcc gaacgatatt gcggccgtgt ttgataacct gaacaaaccg    1140
ctgccgatgg acggcttcac gctgggtatc gtggacgatg ttaccttcac ctctctcccg    1200
ccagcgcagc agaccctggc ggtttctcac gacggcatca cggcatgtaa gttttggggc    1260
atgggctccg acggcacggt tggtgcgaac aagtccgcga tcaagattat cggcgacaaa    1320
acgccactgt atgcgcaagc gtacttttcc tacgactcga agaagagcgg tggtattacc    1380
gtcagccatc tgcgttttgg tgatcgcccg atcaactccc cgtatttgat ccatcgcgcg    1440
gatttcatct cgtgcagcca gcaaagctat gttgaacgct acgatctgct ggatggcctt    1500
aaaccgggtg gcacctttct gctgaactgc tcctggagcg atgccgaact ggagcaacat    1560
ctgccggtcg gtttcaaacg ttatctggca cgcgagaata tccacttcta cactctcaac    1620
gctgtggaca tcgcccgtga gcttggtttg ggtggccgtt tcaacatgct gatgcaggct    1680
gccttcttca aactggccgc gatcattgac ccgcagactg ctgcggacta tctgaagcag    1740
gctgttgaga aaagctatgg cagcaaaggt gcggcggtca tcgagatgaa ccagcgtgcc    1800
atcgagcttg gcatggccag cctgcaccag gtgacgatcc cggcacattg gccaccctg     1860 gatgagccag cggcgcaggc gtccgcgatg atgccggact ttatccgcga catcctgcaa    1920
ccgatgaacc gtcagtgcgg cgaccagctt ccggtgtcgg cttttgtcgg catgaagat    1980 ggcaccttcc cgtccggcac ggccgcatgg gagaaacgtg gcatcgccct tgaggtgcca    2040
gtctggcagc cggaaggctg cacgcagtgc aaccagtgcg ccttcatttg tccgcacgcc    2100
gcgattcgtc cggcgttgtt gaatggcgaa gagcatgatg ctgccccggt tggcctgctg    2160
agcaaaccgg cacaaggcgc taaagaatat cactatcatc tggcgattag cccgctggac    2220
tgctccggct gtggcaactg cgttgacatt tgtccagctc gtggcaaagc gttgaagatg    2280
cagtctctgg atagccaacg ccagatggct ccggtgtggg attatgcgct ggcgctgacc    2340
ccgaagtcta acccgtttcg taaaaccacc gtcaaaggct cgcagttcga aaccccgctg    2400
ctggagttta gcggtgcgtg cgctggttgt ggcgaaacgc cgtatgcgcg cctcattacc    2460
cagctgtttg gcgaccgcat gctgattgcc aatgccaccg gctgttccag catctggggc    2520
gcatctgcgc cgagcatccc gtataccacc aatcatcgtg gtcatggtcc ggcctgggcg    2580
aatagcctgt ttgaggacaa tgccgaattt ggtttaggta tgatgctggg cggtcaagct    2640
```

```
gtgcgtcaac agatcgcgga cgatatgacg gctgcgttag cgctcccggt ttccgatgag    2700
ctgagcgacg cgatgcgcca gtggttggcg aaacaggacg agggtgaagg cacgcgtgag    2760
cgtgcggacc gtctgagcga gcgcttagcc gcggagaaag agggcgttcc gctgttagag    2820
cagctgtggc aaaatcgtga ttactttgtg cgtcgcagcc agtggatttt cggcggtgac    2880
ggctgggcct atgatattgg cttcggtggc ctggaccacg tcctcgccag cggtgaggat    2940
gtgaacattc tggtatttga caccgaagtc tactcgaaca ccggcggtca aagcagcaaa    3000
tcgaccccgg tcgcggccat cgccaagttc gcggctcagg gcaagcgcac ccgcaagaaa    3060
gacctgggta tgatggcgat gagctacggc aacgtctatg tagcccaggt ggcgatgggt    3120
gcggataaag atcaaactct gcgcgccatt gcggaagctg aagcgtggcc aggcccgtcg    3180
ctggtgattg cgtatgcggc ctgcatcaat catggcctga aggccggtat gcgttgcagc    3240
caacgtgagg cgaagcgcgc tgttgaggcg ggctactggc acctgtggcg ttatcacccg    3300
cagcgcgaag cggaaggcaa gacgccgttt atgttagata gcgaagaacc ggaagagtcg    3360
ttccgtgact ttctgttggg tgaggtgcgc tacgcatccc tgcacaagac caccccgcac    3420
ctcgccgatg ccctttcag ccgtaccgaa gaagatgcgc gtgcgcgctt tgcgcaatac    3480
cgtcgcctgg ctggcgaaga gtaataa                                         3507
```

<210> SEQ ID NO 72
<211> LENGTH: 37
<212> TYPE: DNA
<213> ORGANISM: Artificial Sequence
<220> FEATURE:
<223> OTHER INFORMATION: synthetic Enterobacteria phage T7 terminator 25
      of full synthetic cluster

<400> SEQUENCE: 72

```
tactctaacc ccatcggccg tcttagggt tttttgt                               37
```

<210> SEQ ID NO 73
<211> LENGTH: 30
<212> TYPE: DNA
<213> ORGANISM: Artificial Sequence
<220> FEATURE:
<223> OTHER INFORMATION: synthetic insulator 6 of full synthetic cluster

<400> SEQUENCE: 73

```
ccgtggttga gtcagcgtcg agcacgcggc                                      30
```

<210> SEQ ID NO 74
<211> LENGTH: 23
<212> TYPE: DNA
<213> ORGANISM: Artificial Sequence
<220> FEATURE:
<223> OTHER INFORMATION: synthetic Enterobacteria phage T7 promoter mut
      2 of full synthetic cluster

<400> SEQUENCE: 74

```
taatacgact cactagagag aga                                             23
```

<210> SEQ ID NO 75
<211> LENGTH: 40
<212> TYPE: DNA
<213> ORGANISM: Artificial Sequence
<220> FEATURE:
<223> OTHER INFORMATION: synthetic insulator 7 of full synthetic cluster

<400> SEQUENCE: 75
cgcgacttcc agagaagaag actactgact tgagcgttcc      40

<210> SEQ ID NO 76
<211> LENGTH: 39
<212> TYPE: DNA
<213> ORGANISM: Artificial Sequence
<220> FEATURE:
<223> OTHER INFORMATION: synthetic nifB ribosome binding site (rbs, RBS)
      of full synthetic cluster

<400> SEQUENCE: 76
ctctctgtaa tacatcaaat caatcatagg agggctaaa      39

<210> SEQ ID NO 77
<211> LENGTH: 1407
<212> TYPE: DNA
<213> ORGANISM: Artificial Sequence
<220> FEATURE:
<223> OTHER INFORMATION: synthetic nifB of full synthetic cluster

<400> SEQUENCE: 77
atgacctctt gttcgtcgtt ttctggcggt aaagcgtgcc gtccggccga tgactccgcg      60
ctgactccgc tggtggccga caaggcagct gcgcacccgt gctatagccg ccacggccat     120
caccgcttcg cgcgtatgca cctgccagtc gctccggcct gcaacttaca atgcaactac     180
tgcaaccgca agttcgattg cagcaatgaa agcgtccgg gcgtgtcctc taccctgctg     240
acgccggaac aggctgtggt gaaggtgcgc caggtcgccc aagctatccc gcagctgtcg     300
gtggtcggta ttgctggtcc gggcgatccg cttgcgaata tcgcccgcac cttccgtacc     360
ttggagctta ttcgcgaaca gttgccggac ctgaaactgt gcctgagcac caacggcttg     420
gtgctgccag atgccgttga tcgtctgctc gatgtgggcg tggatcacgt taccgtcacc     480
attaacaccc tggacgcaga atcgcagcg caaatctacg cgtggttgtg gctggatggc     540
gaacgctact ccggtcgcga agccggcgaa attctcattg cccgccagct ggaaggcgta     600
cgtcgcctga ccgcgaaagg tgtgctcgtc aagatcaaca gcgtattgat tccgggcatc     660
aatgacagcg gcatggcggg tgttagccgt gcgctgcgcg cgtctggtgc gttcatccac     720
aacatcatgc cactgattgc gcgtccggag catggcactg tttttcggtct gaacggccag     780
ccggaaccgg acgcggaaac cctggcggcg acgcgctccc gctgcggcga ggttatgcca     840
caaatgaccc actgccacca gtgccgtgcc gacgcgattg catgcttgg tgaggatcgc      900
tcgcaacagt ttacgcaatt accggctccg gagtccctcc cggcctggct gccgatcctg      960
catcagcgtg ctcagttgca tgcgagcatc gccacgcgcg gtgagagcga agccgatgac    1020
gcctgcctgg tggccgttgc gtcgagccgt ggcgatgtaa ttgactgcca tttcggccat    1080
gccgaccgtt tctatatcta tagcctgtct gcggctggta tggttctggt taacgaacgt    1140
ttcaccccga atactgccg gggtcgcgat gactgcgagc cgcaggacaa tgccgcacgc    1200
tttgctgcca tccttgagtt gctggcggac gtcaaagcgg tgttttgtgt gcgtatcggc    1260
cataccccgt ggcaacagct ggagcaggaa ggcatcgaac cgtgcgtgga tggcgcctgg    1320
cgtccggtat ccgaggtcct gccggcatgg tggcagcagc gccgtggtag ctggccggct    1380
gcattgccgc acaaaggcgt tgcgtaa                                       1407

<210> SEQ ID NO 78
<211> LENGTH: 40
<212> TYPE: DNA
<213> ORGANISM: Artificial Sequence
<220> FEATURE:

<223> OTHER INFORMATION: synthetic insulator 8 of full synthetic cluster

<400> SEQUENCE: 78
actacgagat tgaggtaaa ccaaataagc acgtagtggc                              40

<210> SEQ ID NO 79
<211> LENGTH: 33
<212> TYPE: DNA
<213> ORGANISM: Artificial Sequence
<220> FEATURE:
<223> OTHER INFORMATION: synthetic nifQ ribosome binding site (rbs, RBS)
      of full synthetic cluster

<400> SEQUENCE: 79
tgcgtttagc agttcccgta ggaatatttc ctt                                   33

<210> SEQ ID NO 80
<211> LENGTH: 504
<212> TYPE: DNA
<213> ORGANISM: Artificial Sequence
<220> FEATURE:
<223> OTHER INFORMATION: synthetic nifQ of full synthetic cluster

<400> SEQUENCE: 80
atgccgccat ggactggtt gcgtcgtttg tggttactct atcacgccgg caaaggcagc       60
tttccgcttc gtatgggctt gtcgccgcgt gactggcaag ctctgcgccg tcgcctgggc     120
gaggtggaaa cgccgctgga tgcgaaacc ctgacccgtc gccgtctgat ggcggagctg      180
aatgcgaccc gcgaagaaga acgccagcag ctgggtgcct ggctggccgg ttggatgcaa     240
caggatgccg gtccgatggc gcagattatc gcagaggtga gcctggcgtt caaccatctc    300
tggcaggacc ttggcctcgc gagccgcgct gaactgcgtc tgctgatgtc tgactgcttc    360
ccgcagctgg ttgttatgaa cgagcacaac atgcgctgga agaaaattctt ttaccgccag   420 cgttgcctgc tgcaacaggg cgaagtcatc tgtcgcagcc cgtcttgcga tgaatgctgg    480
gaacgttctg cgtgctttga gtaa                                             504

<210> SEQ ID NO 81
<211> LENGTH: 29
<212> TYPE: DNA
<213> ORGANISM: Artificial Sequence
<220> FEATURE:
<223> OTHER INFORMATION: synthetic Enterobacteria phage T7 terminator 1
      of full synthetic cluster

<400> SEQUENCE: 81
tacatatcgg gggggtaggg gttttttgt                                        29

<210> SEQ ID NO 82
<211> LENGTH: 18
<212> TYPE: DNA
<213> ORGANISM: Artificial Sequence
<220> FEATURE:
<223> OTHER INFORMATION: synthetic insulator 9 of full synthetic cluster

<400> SEQUENCE: 82
gtctgtagca cgtgcatc                                                    18

<210> SEQ ID NO 83
<211> LENGTH: 23
<212> TYPE: DNA
<213> ORGANISM: Artificial Sequence
<220> FEATURE:
<223> OTHER INFORMATION: synthetic Enterobacteria phage T7 promoter mut 3 of full synthetic cluster

<400> SEQUENCE: 83
taatacgact cactaatggg aga                                         23

<210> SEQ ID NO 84
<211> LENGTH: 34
<212> TYPE: DNA
<213> ORGANISM: Artificial Sequence
<220> FEATURE:
<223> OTHER INFORMATION: synthetic nifF ribosome binding site (rbs, RBS)
      of full synthetic cluster

<400> SEQUENCE: 84
gacaagagtc tcaattataa ggaggcttta ctac                             34

<210> SEQ ID NO 85
<211> LENGTH: 534
<212> TYPE: DNA
<213> ORGANISM: Artificial Sequence
<220> FEATURE:
<223> OTHER INFORMATION: synthetic nifF of full synthetic cluster

<400> SEQUENCE: 85
atggcgaaca tcggcatctt ctttggtacg dataccggca aaacccgcaa gattgcgaag    60
atgattcaca aacagctggg cgagctggcc gatgccccgg ttaacatcaa tcgtaccact   120
ttggatgact ttatggctta cccagtcctg ttgctcggca cgccgacgct tggtgatggt   180
caactgccgg gcttagaggc gggctgcgag agcgaaagct ggtctgagtt tatctccggt   240
ctggatgacg cttccctgaa gggcaaaacc gtggcgctgt ttggcctggg cgaccagcgt   300
ggttacccgg acaacttcgt gtcgggtatg cgtccgctgt tcgacgcgct gagcgcccgt   360
ggcgcccaga tgattggtag ctggccgaac gaaggttatg agtttagcgc atcgtccgcg   420
ctggaaggcg accgcttcgt cggcttggtg ctggatcaag acaatcagtt cgaccagacc   480
gaagcgcgcc tggcgtcttg gcttgaagag atcaaacgca ccgttctgta ataa         534

<210> SEQ ID NO 86
<211> LENGTH: 29
<212> TYPE: DNA
<213> ORGANISM: Artificial Sequence
<220> FEATURE:
<223> OTHER INFORMATION: synthetic Enterobacteria phage T7 terminator 1
      of full synthetic cluster

<400> SEQUENCE: 86
tacatatcgg gggggtaggg gttttttgt                                   29

<210> SEQ ID NO 87
<211> LENGTH: 18
<212> TYPE: DNA
<213> ORGANISM: Artificial Sequence
<220> FEATURE:
<223> OTHER INFORMATION: synthetic insulator 10 of full synthetic
      cluster

<400> SEQUENCE: 87
ggtcattaca acggttat                                               18

<210> SEQ ID NO 88
<211> LENGTH: 23
<212> TYPE: DNA
<213> ORGANISM: Artificial Sequence
<220> FEATURE:

<223> OTHER INFORMATION: synthetic Enterobacteria phage T7 promoter mut
      2 of full synthetic cluster

<400> SEQUENCE: 88
taatacgact cactagagag aga                                             23

<210> SEQ ID NO 89
<211> LENGTH: 40
<212> TYPE: DNA
<213> ORGANISM: Artificial Sequence
<220> FEATURE:
<223> OTHER INFORMATION: synthetic insulator 11 of full synthetic
      cluster

<400> SEQUENCE: 89
aacatagcgt tccatgaggg ctagaattac ctaccggcct                           40

<210> SEQ ID NO 90
<211> LENGTH: 37
<212> TYPE: DNA
<213> ORGANISM: Artificial Sequence
<220> FEATURE:
<223> OTHER INFORMATION: synthetic nifU ribosome binding site (rbs, RBS)
      of full synthetic cluster

<400> SEQUENCE: 90
cagatactga caaataaacc agcgaaggag gttccta                              37

<210> SEQ ID NO 91
<211> LENGTH: 825
<212> TYPE: DNA
<213> ORGANISM: Artificial Sequence
<220> FEATURE:
<223> OTHER INFORMATION: synthetic nifU of full synthetic cluster

<400> SEQUENCE: 91
atgtggaact acagcgagaa agtcaaggac catttcttca atccgcgcaa cgcgcgtgtt     60
gtggataacg caaatgcggt gggcgacgtc ggcagcttat cttgtggcga tgctctccgc    120
ttgatgctgc gcgtggaccc gcagagcgaa atcatcgaag aagcgggctt tcagaccttc    180
ggctgcggca gcgcgattgc gtcgtccagc gcactgacgg agctgatcat cggtcacacc    240
ctggcggaag cgggtcagat caccaaccag cagatcgccg actatctgga cggcttaccg    300
ccggaaaaga tgcactgctc tgtaatgggc caggaagctc ttcgtgcggc cattgctaac    360
tttcgcggtg aatcgctgga agaggagcat gacgagggta agctgatctg caagtgcttc    420
ggcgtcgatg aaggccatat tcgccgtgct gtccagaaca acggtcttac gactctggcc    480
gaggtgatca attacaccaa ggcaggtggc ggttgtacca gctgccatga gaaaatcgag    540
ctggccctgg ccgagattct cgcccaacag ccgcaaacca cccgggcagt tgcgtccggt    600
aaagatccgc actggcagag cgtcgtggat accatcgctg aactgcgtcc acatatccaa    660
gcggacggtg gtgacatggc gctgttgtcc gtgacgaacc accaagtgac tgtttcgctg    720
tcgggcagct gttctggctg catgatgacc gacatgaccc tggcgtggct gcaacagaaa    780
ttgatggagc gtaccggctg ctatatggaa gttgttgccg cctaa                    825

<210> SEQ ID NO 92
<211> LENGTH: 40
<212> TYPE: DNA
<213> ORGANISM: Artificial Sequence
<220> FEATURE:
<223> OTHER INFORMATION: synthetic insulator 12 of full synthetic
      cluster

<400> SEQUENCE: 92
cattgtaata gccaccaaaa gagtgatgat agtcatgggt                              40

<210> SEQ ID NO 93
<211> LENGTH: 39
<212> TYPE: DNA
<213> ORGANISM: Artificial Sequence
<220> FEATURE:
<223> OTHER INFORMATION: synthetic nifS ribosome binding site (rbs, RBS)
      of full synthetic cluster

<400> SEQUENCE: 93
gatacccgta gaccattctg aaatcgaagg aggttttcc                               39

<210> SEQ ID NO 94
<211> LENGTH: 1203
<212> TYPE: DNA
<213> ORGANISM: Artificial Sequence
<220> FEATURE:
<223> OTHER INFORMATION: synthetic nifS of full synthetic cluster

<400> SEQUENCE: 94

| | |
|---|---|
| atgaaacaag tgtacctgga caacaacgcg accacccgcc tggacccgat ggttctggaa | 60 |
| gcgatgatgc cgtttctcac ggatttctat ggcaatccgt ccagcatcca tgacttcggc | 120 |
| atcccggcac aagcggcgct ggaacgtgcg caccagcaag ctgcggcact gctgggcgca | 180 |
| gagtacccgt ctgaaatcat tttcacgagc tgtgcgaccg aggccactgc aaccgccatt | 240 |
| gcgtcggcca tcgcgttatt gccggaacgc gcgaaatca tcacctcggt agtggagcac | 300 |
| ccggctacgc tggcggcgtg cgagcacctg aacgccaag gctatcgcat ccatcgcatt | 360 |
| gcggtggata gcgaaggtgc gctggacatg gcccagttcc gtgcagcgct ctcgccgcgt | 420 |
| gtcgcgttgg tgagcgtgat gtgggccaac aacgaaaccg gcgtgctgtt cccgattggc | 480 |
| gaaatggccg agcttgccca cgagcagggc gctctgttcc actgcgatgc cgttcaggtc | 540 |
| gttggcaaaa tcccaattgc tgttggccag acgcgcatcg acatgctgtc ttgctccgcg | 600 |
| cacaagtttc atggtccgaa gggtgttggt tgcttgtact acgtcgtgg cacgcgcttt | 660 |
| cgtccgctgc ttcgcggtgg ccatcaagaa tatggtcgcc gtgccggcac tgagaatatc | 720 |
| tgtggcatcg tcggcatggg cgctgcgtgc gaactggcga acatccatct gccgggtatg | 780 |
| acccatattg gccagttacg caatcgcctg gagcaccgtc tgctcgccag cgtgccgtcc | 840 |
| gtgatggtta tgggcggtgg tcagccgcgt gtaccgggta ctgtcaacct ggcgttcgag | 900 |
| tttatcgaag gtgaagcgat cctgctcttg ctgaaccagg ctggcattgc cgcaagctcc | 960 |
| ggctccgcgt gtacctctgg cagcttggag ccgagccatg tgatgcgcgc catgaacatt | 1020 |
| ccatacaccg cggctcacgg caccattcgt tttagcctga gccgttatac gcgcgagaaa | 1080 |
| gagatcgact acgtcgttgc gaccctcccg ccaatcattg atcgtctgcg tgccttgtcc | 1140 |
| ccgtattggc agaatggtaa gccgcgtccg gcagatgcag tctttacccc ggtttacggt | 1200 |
| taa | 1203 |

<210> SEQ ID NO 95
<211> LENGTH: 40
<212> TYPE: DNA
<213> ORGANISM: Artificial Sequence
<220> FEATURE:
<223> OTHER INFORMATION: synthetic insulator 13 of full synthetic
      cluster

<400> SEQUENCE: 95
gagttactgg ccctgatttc tccgcttcta ataccgcaca            40

<210> SEQ ID NO 96
<211> LENGTH: 34
<212> TYPE: DNA
<213> ORGANISM: Artificial Sequence
<220> FEATURE:
<223> OTHER INFORMATION: synthetic nifV ribosome binding site (rbs, RBS)
      of full synthetic cluster

<400> SEQUENCE: 96
gcgactagga gcctaactcg ccacaaggaa acat            34

<210> SEQ ID NO 97
<211> LENGTH: 1143
<212> TYPE: DNA
<213> ORGANISM: Artificial Sequence
<220> FEATURE:
<223> OTHER INFORMATION: synthetic nifV of full synthetic cluster

<400> SEQUENCE: 97
atggagcgcg tcttgatcaa cgatactacc ctgcgtgatg cgaacaatc tccgggcgta      60 gcgtttcgta cctccgagaa agttgccatc gcggaggcac tgtacgctgc gggtatcacc     120
gcgatggaag tcggcactcc ggcgatgggt gatgaagaga tcgcccgcat tcagctggtg     180
cgtcgtcaac tgccggacgc gacgcttatg acctggtgcc gtatgaacgc tctggaaatc     240
cgtcagagcg cggatctggg tattgactgg gtggatatct cgatcccagc atccgacaag     300
ctgcgtcagt acaagctgcg tgagccgctg gccgtgctgc tggagcgcct tgcgatgttt     360
atccatctgg cccacacgtt aggcctcaaa gtatgtattg gttgcgagga tgcgagccgt     420
gcgtctggtc agaccctgcg cgccattgcc gaggtggccc agcaatgcgc ggctgcgcgc     480
ttgcgttacg ctgacaccgt gggcctgctg gacccgttca ccaccgcagc ccagatcagc     540
gccctgcgtg acgtttggtc gggcgagatc gagatgcatg ctcacaatga tctgggcatg     600
gctaccgcga acacgctggc ggcagtttcg gctggcgcca cgtcggtgaa cactaccgtc     660
ctcggtctgg gtgaacgtgc aggcaacgca gccctggaaa ccgttgcgct gggcctggaa     720
cgctgcctgg gcgtggaaac cggcgtccat ttcagcgcgc tcccagcgag ctgtcagcgc     780
gtcgcggagg ctgcacagcg cgcaatcgac ccgcaacagc cgctggtggg tgaattggtt     840
ttcacccacg agtctggtgt tcacgttgcg gcgctgctgc cgcacagcga atcctatcaa     900
tctattgccc caagcctcat gggccgtagc taccgtctgg tgctcggcaa gcattcgggt     960
cgtcaggctg tcaacggtgt tttcgaccag atgggttacc acctgaatgc ggcgcagatc    1020
aatcagttgc tgccggccat tcgccgcttc gccgagaatt ggaaacgctc tccgaaagac    1080
tacgaactgg ttgcgatcta tgacgaattg tgcggtgaat ccgcccttcg tgctcgcggc    1140
taa                                                                   1143

<210> SEQ ID NO 98
<211> LENGTH: 40
<212> TYPE: DNA
<213> ORGANISM: Artificial Sequence
<220> FEATURE:
<223> OTHER INFORMATION: synthetic insulator 14 of full synthetic
      cluster

<400> SEQUENCE: 98
gactcaacac gctagggacg tgaagtcgat tccttcgatg            40

<210> SEQ ID NO 99
<211> LENGTH: 35
<212> TYPE: DNA
<213> ORGANISM: Artificial Sequence
<220> FEATURE:
<223> OTHER INFORMATION: synthetic nifW ribosome binding site (rbs, RBS) of full synthetic cluster

<400> SEQUENCE: 99
cagaaggcga gaactagatt taagggccat tatag                                35

<210> SEQ ID NO 100
<211> LENGTH: 258
<212> TYPE: DNA
<213> ORGANISM: Artificial Sequence
<220> FEATURE:
<223> OTHER INFORMATION: synthetic nifW of full synthetic cluster

<400> SEQUENCE: 100
atggagtggt tttaccagat tccgggtgta gacgaattgc gcagcgctga atccttcttt      60
cagttcttcg cggttccata ccagccggaa ctgctgggcc gctgctcgct tccggtgtta     120
gcgacgttcc accgtaaact gcgtgcggag gtcccgctgc aaaaccgtct ggaggacaat     180
gatcgtgcgc cgtggctctt ggcgcgccgc ctcctggccg aatcttatca gcagcaattt     240
caggagagcg gcacctaa                                                  258

<210> SEQ ID NO 101
<211> LENGTH: 40
<212> TYPE: DNA
<213> ORGANISM: Artificial Sequence
<220> FEATURE:
<223> OTHER INFORMATION: synthetic insulator 15 of full synthetic cluster

<400> SEQUENCE: 101
tcgagaaaca aggcagttcc gggctgaaag tagcgccggg                           40

<210> SEQ ID NO 102
<211> LENGTH: 36
<212> TYPE: DNA
<213> ORGANISM: Artificial Sequence
<220> FEATURE:
<223> OTHER INFORMATION: synthetic nifZ ribosome binding site (rbs, RBS) of full synthetic cluster

<400> SEQUENCE: 102
acaagtcccg tattataacc gcctaggagg tgttgg                               36

<210> SEQ ID NO 103
<211> LENGTH: 447
<212> TYPE: DNA
<213> ORGANISM: Artificial Sequence
<220> FEATURE:
<223> OTHER INFORMATION: synthetic nifZ of full synthetic cluster

<400> SEQUENCE: 103
atgcgcccga aattcacctt ctctgaagag gtccgcgtag ttcgcgcgat tcgtaatgat      60
ggcaccgtgg cgggttttgc gccaggtgcg ctgctggttc gtcgcggttc gacgggcttt     120
gtgcgtgact ggggtgtgtt cctgcaagac cagatcatct atcaaatcca ctttccggaa     180
accgaccgca ttatcggctg tcgcgagcag gagttaatcc cgattaccca gccgtggttg     240
gctggtaacc tccagtatcg tgacagcgtc acgtgccaaa tggcactggc tgtcaacggt     300

```
gacgtggttg tgagcgccgg tcaacgtggc cgtgtggagg ccactgatcg tggcgaactt      360
ggcgattcct acaccgtgga cttcagcggc cgttggttcc gcgttccggt ccaggccatc      420
gcgctgattg aagagcgcga agaataa                                          447
```

<210> SEQ ID NO 104
<211> LENGTH: 40
<212> TYPE: DNA
<213> ORGANISM: Artificial Sequence
<220> FEATURE:
<223> OTHER INFORMATION: synthetic insulator 16 of full synthetic
      cluster

<400> SEQUENCE: 104

```
acgccacgcg tagtgagaca tacacgttcg ttgggttcac                             40
```

<210> SEQ ID NO 105
<211> LENGTH: 34
<212> TYPE: DNA
<213> ORGANISM: Artificial Sequence
<220> FEATURE:
<223> OTHER INFORMATION: synthetic nifM ribosome binding site (rbs, RBS)
      of full synthetic cluster

<400> SEQUENCE: 105

```
tcagagactg aagttattac ccaggaggtc tata                                   34
```

<210> SEQ ID NO 106
<211> LENGTH: 801
<212> TYPE: DNA
<213> ORGANISM: Artificial Sequence
<220> FEATURE:
<223> OTHER INFORMATION: synthetic nifM of full synthetic cluster

<400> SEQUENCE: 106

```
atgaatccgt ggcagcgctt tgcccgtcaa cgccttgctc gcagccgctg gaaccgtgat       60
ccggctgctc tcgacccagc cgatacccca gcgttcgagc aggcgtggca gcgtcaatgc      120
catatggaac aaaccatcgt agcgcgtgtc ccggaaggcg atattccggc tgccttactg      180
gaaaacatcg cggccagcct ggcgatctgg ctggacgagg gtgacttcgc tccgccggag      240
cgcgctgcga ttgtgcgtca tcatgcacgt ctggagctgg cgtttgccga cattgcccgc      300
caggcaccgc aaccggatct gagcacggtt caagcgtggt atctgcgtca ccagactcaa      360
ttcatgcgtc cggagcagcg tctgacccgt cacctgctcc tgacggtcga taatgatcgc      420
gaggcggtgc atcaacgcat ccttggcctg tatcgtcaga tcaacgcgag ccgtgacgcc      480
ttcgccccac tggcacagcg ccactctcat tgcccgtccg ccttggaaga aggccgtctg      540
ggctggatct cccgtggtct gctgtacccg cagctcgaaa ccgcgttgtt tagcctggcg      600
gaaaacgcac tgtcgctgcc gattgcgtcg gaattgggtt ggcacctgtt atggtgcgag      660
gccattcgtc cggcagcccc gatggagccg caacaggccc ttgaatctgc gcgcgactac      720
ttgtggcagc agagccagca gcgccaccag cgtcaatggc tggagcagat gatttcccgc      780
caaccgggcc tgtgtggtta a                                                801
```

<210> SEQ ID NO 107
<211> LENGTH: 47
<212> TYPE: DNA
<213> ORGANISM: Artificial Sequence
<220> FEATURE:
<223> OTHER INFORMATION: synthetic Enterobacteria phage T7 wild type
      (WT) terminator of full synthetic cluster

<400> SEQUENCE: 107
tagcataacc ccttggggcc tctaaacggg tcttgagggg ttttttg            47

<210> SEQ ID NO 108
<211> LENGTH: 21
<212> TYPE: DNA
<213> ORGANISM: Artificial Sequence
<220> FEATURE:
<223> OTHER INFORMATION: synthetic Biobrick suffix (BBa_G000001) of full
      synthetic cluster

<400> SEQUENCE: 108
tactagtagc ggccgctgca g                                         21

<210> SEQ ID NO 109
<211> LENGTH: 12
<212> TYPE: DNA
<213> ORGANISM: Artificial Sequence
<220> FEATURE:
<223> OTHER INFORMATION: synthetic translational stop (BBa_B0042) of
      full synthetic cluster

<400> SEQUENCE: 109
ttagttagtt ag                                                   12

<210> SEQ ID NO 110
<211> LENGTH: 69
<212> TYPE: DNA
<213> ORGANISM: Artificial Sequence
<220> FEATURE:
<223> OTHER INFORMATION: synthetic terminator (BBa_B0054) of full
      synthetic cluster

<400> SEQUENCE: 110
attagcagaa agtcaaaagc ctccgaccgg aggcttttga ctaaaacttc ccttggggtt    60
atcattggg                                                           69

<210> SEQ ID NO 111
<211> LENGTH: 20
<212> TYPE: DNA
<213> ORGANISM: Artificial Sequence
<220> FEATURE:
<223> OTHER INFORMATION: synthetic VR primer (BBa_G00102) of full
      synthetic cluster

<400> SEQUENCE: 111
gctcactcaa aggcggtaat                                           20

<210> SEQ ID NO 112
<211> LENGTH: 41
<212> TYPE: DNA
<213> ORGANISM: Artificial Sequence
<220> FEATURE:
<223> OTHER INFORMATION: synthetic terminator (BBa_B0062) of full
      synthetic cluster

<400> SEQUENCE: 112
cagataaaaa aaatccttag ctttcgctaa ggatgatttc t                   41

<210> SEQ ID NO 113
<211> LENGTH: 2037
<212> TYPE: DNA
<213> ORGANISM: Artificial Sequence
<220> FEATURE:
<223> OTHER INFORMATION: synthetic pSC101 origin (BBa_150042) of full synthetic cluster

<400> SEQUENCE: 113

```
ctgtcagacc aagtttacga gctcgcttgg actcctgttg atagatccag taatgacctc      60
agaactccat ctggatttgt tcagaacgct cggttgccgc cgggcgtttt ttattggtga     120
gaatccaagc actagggaca gtaagacggg taagcctgtt gatgataccg ctgccttact     180
gggtgcatta gccagtctga atgacctgtc acgggataat ccgaagtggt cagactggaa     240
aatcagaggg caggaactgc tgaacagcaa aaagtcagat agcaccacat agcagacccg     300
ccataaaacg ccctgagaag cccgtgacgg gcttttcttg tattatgggt agtttccttg     360
catgaatcca taaaggcgc ctgtagtgcc atttaccccc attcactgcc agagccgtga     420
gcgcagcgaa ctgaatgtca cgaaaaagac agcgactcag gtgcctgatg gtcggagaca     480
aaaggaatat tcagcgattt gcccgagctt gcgagggtgc tacttaagcc tttagggttt     540
taaggtctgt tttgtagagg agcaaacagc gtttgcgaca tccttttgta atactgcgga     600
actgactaaa gtagtgagtt atacacaggg ctgggatcta ttctttttat ctttttttat     660
tctttcttta ttctataaat tataaccact tgaatataaa caaaaaaaac acacaaaggt     720
ctagcggaat ttacagaggg tctagcagaa tttacaagtt ttccagcaaa ggtctagcag     780
aatttacaga tacccacaac tcaaaggaaa aggacatgta attatcattg actagcccat     840
ctcaattggt atagtgatta aaatcaccta gaccaattga gatgtatgtc tgaattagtt     900
gttttcaaag caaatgaact agcgattagt cgctatgact taacggagca tgaaaccaag     960
ctaatttat gctgtgtggc actactcaac cccacgattg aaaaccctac aaggaaagaa    1020
cggacggtat cgttcactta taaccaatac gctcagatga tgaacatcag tagggaaaat    1080
gcttatggtg tattagctaa agcaaccaga gagctgatga cgagaactgt ggaaatcagg    1140
aatcctttgg ttaaaggctt tgagattttc cagtggacaa actatgccaa gttctcaagc    1200
gaaaaattag aattagtttt tagtgaagag atattgcctt atcttttcca gttaaaaaaa    1260
ttcataaaat ataatctgga acatgttaag tcttttgaaa acaaatactc tatgaggatt    1320
tatgagtggt tattaaaaga actaacacaa aagaaaactc acaaggcaaa tatagagatt    1380
agccttgatg aatttaagtt catgttaatg cttgaaaata actaccatga gtttaaaagg    1440
cttaaccaat gggttttgaa accaataagt aaagatttaa acacttacag caatatgaaa    1500
ttggtggttg ataagcgagg ccgcccgact gatacgttga ttttccaagt tgaactagat    1560
agacaaatgg atctcgtaac cgaacttgag acaaccagat aaaaatgaa tggtgacaaa    1620
ataccaacaa ccattacatc agattcctac ctacgtaacg gactaagaaa aacactacac    1680
gatgctttaa ctgcaaaaat tcagctcacc agttttgagg caaattttt gagtgacatg    1740
caaagtaagc atgatctcaa tggttcgttc tcatggctca cgcaaaaaca acgaaccaca    1800
ctagagaaca tactggctaa atacggaagg atctgaggtt cttatggctc ttgtatctat    1860
cagtgaagca tcaagactaa caaacaaaag tagaacaact gttcaccgtt agatatcaaa    1920
gggaaaactg tccatatgca cagatgaaaa cggtgtaaaa aagatagata catcagagct    1980
tttacgagtt tttggtgcat ttaaagctgt tcaccatgaa cagatcgaca atgtaac      2037
```

<210> SEQ ID NO 114
<211> LENGTH: 769
<212> TYPE: DNA
<213> ORGANISM: Artificial Sequence
<220> FEATURE:
<223> OTHER INFORMATION: synthetic chloramphenicol resistance (BBa_P1004) of full synthetic cluster

<400> SEQUENCE: 114

| gttgatcggg cacgtaagag gttccaactt tcaccataat gaaataagat cactaccggg | 60 |
| cgtatttttt gagttatcga gattttcagg agctaaggaa gctaaaatgg agaaaaaat | 120 |
| cacgggatat accaccgttg atatatccca atggcatcgt aaagaacatt ttgaggcatt | 180 |
| tcagtcagtt gctcaatgta cctataacca gaccgttcag ctggatatta cggcctttt | 240 |
| aaagaccgta agaaaaata agcacaagtt ttatccggcc tttattcaca ttcttgcccg | 300 |
| cctgatgaac gctcacccgg agtttcgtat ggccatgaaa gacggtgagc tggtgatctg | 360 |
| ggatagtgtt caccttgtt acaccgtttt ccatgagcaa actgaaacgt tttcgtccct | 420 |
| ctggagtgaa taccacgacg atttccggca gtttctccac atatattcgc aagatgtggc | 480 |
| gtgttacggt gaaaacctgg cctatttccc taaagggttt attgagaata tgtttttgt | 540 |
| ctcagccaat ccctgggtga gtttcaccag ttttgattta aacgtggcca atatggacaa | 600 |
| cttcttcgcc cccgttttca cgatgggcaa atattatacg caaggcgaca aggtgctgat | 660 |
| gccgctggcg atccaggttc atcatgccgt ttgtgatggc ttccatgtcg ccgcatgct | 720 |
| taatgaatta caacagtact gtgatgagtg cagggcggg gcgtaataa | 769 |

<210> SEQ ID NO 115
<211> LENGTH: 72
<212> TYPE: DNA
<213> ORGANISM: Artificial Sequence
<220> FEATURE:
<223> OTHER INFORMATION: synthetic terminator (BBa_B0053) of full
      synthetic cluster

<400> SEQUENCE: 115

| tccggcaaaa aaacgggcaa ggtgtcacca ccctgcccct tttctttaaa accgaaaaga | 60 |
| ttacttcgcg tt | 72 |

<210> SEQ ID NO 116
<211> LENGTH: 20
<212> TYPE: DNA
<213> ORGANISM: Artificial Sequence
<220> FEATURE:
<223> OTHER INFORMATION: synthetic VF2 primer (BBa_G00101) of full
      synthetic cluster

<400> SEQUENCE: 116

| tgccacctga cgtctaagaa | 20 |

<210> SEQ ID NO 117
<211> LENGTH: 78
<212> TYPE: DNA
<213> ORGANISM: Artificial Sequence
<220> FEATURE:
<223> OTHER INFORMATION: synthetic terminator (BBa_B0055) of full
      synthetic cluster

<400> SEQUENCE: 117

| aaggaatatt cagcaatttg cccgtgccga agaaaggccc acccgtgaag gtgagccagt | 60 |
| gagttgattg ctacgtaa | 78 |

<210> SEQ ID NO 118
<211> LENGTH: 12
<212> TYPE: DNA
<213> ORGANISM: Artificial Sequence
<220> FEATURE:

<223> OTHER INFORMATION: synthetic translational stop (BBa_B0042) of
      full synthetic cluster

<400> SEQUENCE: 118
ttagttagtt ag                                                          12

<210> SEQ ID NO 119
<211> LENGTH: 19
<212> TYPE: DNA
<213> ORGANISM: Artificial Sequence
<220> FEATURE:
<223> OTHER INFORMATION: synthetic SynPrgH ribosome binding site (rbs,
      RBS) of bacterial type III secretion system (T3SS)

<400> SEQUENCE: 119
attaaacagg ataataagc                                                   19

<210> SEQ ID NO 120
<211> LENGTH: 1182
<212> TYPE: DNA
<213> ORGANISM: Artificial Sequence
<220> FEATURE:
<223> OTHER INFORMATION: synthetic SynPrgH of bacterial type III
      secretion system (T3SS)

<400> SEQUENCE: 120
atggaaacta gcaaggagaa aacgattacg tcccctggtc cgtatatcgt tcgtctgttg      60
aactcgtccc tgaacggttg tgaatttccg ctgctgactg gtcgtacgct gttcgtcgtg     120
ggtcagagcg atgctctgac cgcgtctggt cagctgccgg acattcctgc cgactccttc     180
ttcatcccgc tggatcatgg cggtgttaat ttcgagattc aagtggacac tgacgcgacg     240
gaaatcatcc tgcacgaact gaaagagggc aactccgaga gccgctccgt gcaactgaac     300
accccgatcc aagttggtga actgctgatt ttgattcgtc cggagagcga gccgtgggtg     360
ccggaacagc cggagaagtt ggaaacttct gcgaaaaaga acgaaccgcg ctttaaaaac     420
ggcatcgtcg cggcactggc gggtttcttt atcctgggta tcggcacggt tggcaccctg     480
tggattctga actcgccgca acgtcaagca gccgaattgg acagcctgtt gggtcaggag     540
aaggagcgtt tcaggtgct gccgggtcgc gacaagatgc tgtatgtcgc cgcgcaaaac     600
gaacgcgaca ccctgtgggc acgtcaagtc ctggcacgcg gcgattacga taaaaacgca     660
cgcgttatta atgaaaatga ggagaataaa cgtatcagca tctggctgga cacgtattat     720
ccacaactgg catattaccg tatccatttt gatgaaccac gtaagccggt gttttggctg     780
tcccgtcaac gcaacacgat gagcaagaaa gagctggagg tgctgtccca gaaattgcgt     840
gcgctgatgc cgtacgccga cagcgtcaat attactctga tggatgacgt gaccgcagca     900
ggccaagccg aggcaggtct gaaacaacag gcgctgccat acagccgccg taaccacaaa     960
ggtggtgtta cgttcgttat tcagggcgcc ttggacgacg ttgagattct gcgtgcgcgc    1020
cagtttgtcg actcctatta tcgtacctgg ggtggtcgtt acgttcaatt cgcaattgaa    1080
ttgaaagacg attggctgaa aggccgctcg ttccaatacg gtgcggaagg ctacattaag    1140
atgagcccag gtcattggta ttttccgtct cctctgtaat ag                       1182

<210> SEQ ID NO 121
<211> LENGTH: 21
<212> TYPE: DNA
<213> ORGANISM: Artificial Sequence
<220> FEATURE:
<223> OTHER INFORMATION: synthetic SynPrgI ribosome binding site (rbs,
      RBS) of bacterial type III secretion system (T3SS)

-continued

<400> SEQUENCE: 121
attaaagagg agaaattaag c                                                21

<210> SEQ ID NO 122
<211> LENGTH: 21
<212> TYPE: DNA
<213> ORGANISM: Artificial Sequence
<220> FEATURE:
<223> OTHER INFORMATION: synthetic SynPrgJ ribosome binding site (rbs,
      RBS) of bacterial type III secretion system (T3SS)

<400> SEQUENCE: 122
attaaggagg ataaattaag c                                                21

<210> SEQ ID NO 123
<211> LENGTH: 309
<212> TYPE: DNA
<213> ORGANISM: Artificial Sequence
<220> FEATURE:
<223> OTHER INFORMATION: synthetic SynPrgJ of bacterial type III
      secretion system (T3SS)

<400> SEQUENCE: 123
atgtctatcg cgactatcgt gcctgaaaat gccgttattg gtcaagcggt gaatattcgc      60
agcatggaaa cggacatcgt cagcttggac gaccgtttgc tgcaagcatt tcgggcagc     120 gccatcgcta ccgccgtcga taagcagacc attaccaatc gcattgaaga ccctaatctg    180
gttaccgatc cgaaggagct ggcgattagc caggaaatga tttccgacta caatctgtac    240
gtcagcatgg ttagcaccct gacgcgtaag ggcgttggcg ctgttgagac tttgctgcgt    300
tcctgatag                                                            309

<210> SEQ ID NO 124
<211> LENGTH: 19
<212> TYPE: DNA
<213> ORGANISM: Artificial Sequence
<220> FEATURE:
<223> OTHER INFORMATION: synthetic SynPrgK ribosome binding site (rbs,
      RBS) of bacterial type III secretion system (T3SS)

<400> SEQUENCE: 124
attaaacagg ataataagc                                                  19

<210> SEQ ID NO 125
<211> LENGTH: 762
<212> TYPE: DNA
<213> ORGANISM: Artificial Sequence
<220> FEATURE:
<223> OTHER INFORMATION: synthetic SynPrgK of bacterial type III
      secretion system (T3SS)

<400> SEQUENCE: 125
atgatccgcc gttacctgta taccttcttg ctggttatga ctttggccgg ctgtaaagat      60
aaggatctgc tgaaaggctt ggaccaagag caagcgaatg aggtcattgc ggttctgcaa     120
atgcacaaca ttgaggctaa caagattgat agcggcaagc tgggttacag cattaccgtc     180
gcggaaccgg atttcaccgc ggcagtgtat tggattaaga cctaccagtt gccgcctcgc     240
ccgcgtgtcg aaatcgccca aatgtttccg gcagacagcc tggttagctc tccgcgtgcg     300
gagaaagcac gtctgtactc ggcgattgaa cagcgcctgg agcagtcgct gcaaacgatg     360
gaaggtgttc tgtcggcccg tgtccacatc agctatgata ttgatgcggg cgagaacggt     420

```
cgtccgccta agccggtgca cctgtcggct ttggcggtgt atgaacgcgg ttcccctctg      480
gcccatcaga tttcggatat taagcgcttc ctgaaaaaca gcttcgcgga tgttgactat      540
gataacatca gcgtggttct gtccgagcgt agcgacgcac agttgcaggc gccgggcacg      600
ccggtcaagc gcaatagctt cgctacctcc tggattgtgc tgattatcct gttgtctgtt      660
atgagcgcgg gtttcggtgt ctggtactac aaaaatcact atgcgcgtaa taagaaaggc      720
attactgccg atgacaaggc aaagtccagc aacgagtaat aa                         762
```

<210> SEQ ID NO 126
<211> LENGTH: 19
<212> TYPE: DNA
<213> ORGANISM: Artificial Sequence
<220> FEATURE:
<223> OTHER INFORMATION: synthetic SynOrgA ribosome binding site (rbs, RBS) of bacterial type III secretion system (T3SS)

<400> SEQUENCE: 126

```
gaaagaaggg acagactag                                                   19
```

<210> SEQ ID NO 127
<211> LENGTH: 603
<212> TYPE: DNA
<213> ORGANISM: Artificial Sequence
<220> FEATURE:
<223> OTHER INFORMATION: synthetic SynOrgA of bacterial type III secretion system (T3SS)

<400> SEQUENCE: 127

```
atgattcgtc gtaaccgtca aatgaaccgt caaccactgc caattatctg gcaacgcatt      60
attttcgacc cactgtccta tattcaccca caacgtctgc aaatcgcgcc ggagatgatc      120
gtgcgtccgg cagcgcgtgc ggcagcgaat gagctgattt tggcggcgtg gcgtttgaag      180
aacggtgaga aggagtgcat tcagaatagc ctgacgcagc tgtggttgcg tcaatggcgc      240
cgtctgccgc aggttgctta cctgctgggt tgccacaagt tgcgtgctga cctgccccgt      300
caaggtgctt tatgggcct gccggactgg gcgcaggcat tcttggcgat gcaccagggt      360
acgtccttgt cggtttgtaa taaggcgccg aaccaccgtt tcctgctgtc cgttggttac      420
gcccaactga acgcgctgaa tgagttcctg ccggagagct tggcccaacg ctttcctctg      480
ctgtttccac cgttcatcga ggaggcactg aaacaagatg cagtggagat gagcatcctg      540
ctgctggccc tgcaatacgc gcaaaagtat cctaacaccg tcccggcgtt tgcgtgctaa      600
taa                                                                    603
```

<210> SEQ ID NO 128
<211> LENGTH: 19
<212> TYPE: DNA
<213> ORGANISM: Artificial Sequence
<220> FEATURE:
<223> OTHER INFORMATION: synthetic SynOrgB ribosome binding site (rbs, RBS) of bacterial type III secretion system (T3SS)

<400> SEQUENCE: 128

```
gaaagaaggg acagactag                                                   19
```

<210> SEQ ID NO 129
<211> LENGTH: 684
<212> TYPE: DNA
<213> ORGANISM: Artificial Sequence
<220> FEATURE:
<223> OTHER INFORMATION: synthetic SynOrgB of bacterial type III secretion system (T3SS)

<400> SEQUENCE: 129

```
atgttgaaaa atatcccgat tccatcccct ctgtctccgg ttgaaggtat cctgattaaa      60
cgcaagacgt tggagcgtta cttctcgatt gagcgcctgg aacaacaggc gcatcagcgt     120
gcaaagcgca ttttgcgtga ggcagaagaa gaagccaaga ccctgcgcat gtatgcgtac     180
caggagggct acgagcaggg catgattgac gcactgcaac aggtggccgc ctatttgacc     240
gacaaccaga cgatggcttg gaaatggatg gagaaaattc aaatctatgc gcgtgagttg     300
ttcagcgcgg ctgtcgatca cccggaaacg ttgttgacgg tgctggacga gtggctgcgt     360
gatttcgata agccggaagg tcagctgttt ttgaccctgc cggtgaacgc aaagaaagat     420
catcagaaac tgatggtgct gctgatggaa aattggccgg gcaccttcaa tctgaagtat     480
catcaggagc aacgttttat catgtcctgt ggcgatcaga ttgccgagtt tcgccggaa      540
caatttgttg aaacggcggt tggtgttatc aagcaccatc tggatgagct gcctcaggac     600
tgtcgcacca tttcggacaa tgcgattaac gcgctgattg atgaatggaa gacgaaaacc     660
caagctgaag ttattcgctg ataa                                            684
```

<210> SEQ ID NO 130
<211> LENGTH: 36
<212> TYPE: DNA
<213> ORGANISM: Artificial Sequence
<220> FEATURE:
<223> OTHER INFORMATION: synthetic SynInvA ribosome binding site (rbs, RBS) of bacterial type III secretion system (T3SS)

<400> SEQUENCE: 130

```
cttgggcacg cgtccattaa acaggagtaa ttaagc                                36
```

<210> SEQ ID NO 131
<211> LENGTH: 2058
<212> TYPE: DNA
<213> ORGANISM: Artificial Sequence
<220> FEATURE:
<223> OTHER INFORMATION: synthetic SynInvA of bacterial type III secretion system (T3SS)

<400> SEQUENCE: 131

```
atgctgctgt ccctgctgaa tagcgcgcgt ctgcgtcctg agctgctgat tctggttctg      60
atggttatga tcatcagcat gttcgttatc ccgttgccga cctatttggt tgacttcttg     120
atcgctttga acattgtcct ggcaattctg gtgttcatgg ctccttcta catcgaccgc      180
attctgagct tcagcaccct tccggcggtt ctgctgatca cgactctgtt ccgtttggca     240
ctgagcatca gcaccagccg cctgatcctg attgaagcag atgcgggtga tcatcgcg      300
acctttggtc agtttgtgat cggtgacagc ctggcggttg gtttcgtcgt attctccatc     360
gtgacggtgg tgcagtttat cgttattacc aagggcagcg aacgtgtggc ggaggtcgcc     420
gctcgcttca gcctggacgg catgccgggt aaacagatgt ctattgatgc agacctgaaa     480
gccggcatta ttgatgctga tgcagcgcgc gagcgccgca gcgtcctgga gcgtgaaagc     540
caactgtacg gttccttcga cggtgccatg aagttcatta aggtgatgc gattgcgggc      600
atcattatca tcttcgttaa cttcattggc ggtatcagcg tcggtatgac ccgtcatggt     660
atggatctga gcagcgccct gagcacctac accatgctga cgattggtga tggtctggtt     720
gcccaaattc cggcgttgct gatcgcgatt tctgcgggct tcatcgttac ccgcgtcaac     780
ggtgatagcg ataacatggg tcgtaacatt atgacccagc tgctgaataa tccgtttgtc     840
```

```
ctggttgtaa cggcgatttt gaccatcagc atgggcacgc tgccgggctt tccgttgccg    900
gttttcgtta ttctgtctgt tgtgctgtcc gtcctgtttt actttaagtt ccgcgaggcg    960
aaacgtagcg ctgcgaaacc aaaaacgagc aagggcgagc aaccgttgtc catcgaggag   1020
aaggaaggta gcagcctggg cctgattggc gacctggata aggttagcac ggaaaccgtc   1080
ccgctgattt tgctggtgcc gaaatcgcgt cgtgaggatc tggagaaagc gcagctggcg   1140
gaacgtctgc gcagccaatt ctttattgat tatggtgtgc gtctgccaga agtactgctg   1200
cgtgacggtg agggtctgga tgacaactct atcgtcctgc tgattaatga gattcgcgtt   1260
gaacagttta ctgtctattt tgacctgatg cgtgtggtta actacagcga cgaggtggtg   1320
agctttggca tcaacccgac cattcaccag caaggttcca gccagtactt ttgggtgacc   1380
catgaggaag gcgaaaagct gcgcgagctg ggctacgtcc tgcgtaatgc actggacgaa   1440
ctgtaccact gtctggcggt gacgctggca cgcaatgtga acgagtattt cggtatccaa   1500
gaaacgaaac acatgctgga ccaactggaa gcaaagtttc ctgacctgct gaaggaggtt   1560
ttgcgccacg ccaccgtgca cgcatttcg gaagtgctgc aacgtctgct gtccgaacgc   1620
gtgagcgtcc gtaacatgaa gctgatcatg gaagccctgg cactgtgggc tccgcgtgag   1680
aaagatgtga tcaatctggt ggagcacatc cgtggtgcga tggcgcgtta tatctgccac   1740
aagttcgcaa atggtggtga actgcgtgcc gttatggttt ccgccgaagt tgaggatgtc   1800
attcgtaaag gcattcgtca aacttctggc tccacctttt tgagcttgga cccggaggct   1860
tcggcaaatc tgatggacct gatcacgctg aagctggacg acctgttgat tgcgcataag   1920
gacctggtcc tgttgaccag cgttgacgtg cgtcgttta tcaagaaaat gattgaaggt   1980
cgttttccgg atctggaggt cctgtccttc ggtgagattg cagatagcaa aagcgtgaat   2040
gtcatcaaaa ccatctga                                                2058

<210> SEQ ID NO 132
<211> LENGTH: 36
<212> TYPE: DNA
<213> ORGANISM: Artificial Sequence
<220> FEATURE:
<223> OTHER INFORMATION: synthetic SynInvC ribosome binding site (rbs,
      RBS) of bacterial type III secretion system (T3SS)

<400> SEQUENCE: 132
cttgggcacg cgtccattaa agaggaccaa ttaagc                                36

<210> SEQ ID NO 133
<211> LENGTH: 1296
<212> TYPE: DNA
<213> ORGANISM: Artificial Sequence
<220> FEATURE:
<223> OTHER INFORMATION: synthetic SynInvC of bacterial type III
      secretion system (T3SS)

<400> SEQUENCE: 133
atgaaaaccc cacgtctgct gcaataccctg gcctacccgc agaaaatcac tggccctatc     60
attgaagcag aactgcgtga tgttgcaatt ggtgaattgt gcgagatccg tcgcggctgg    120
caccagaagc aggttgtggc ccgtgcgcaa gtggttggtt tgcagcgcga acgtaccgtc    180
ctgagcctga tcggcaatgc ccaaggcctg agccgtgatg tggtcttgta cccgaccggc    240
cgtgctctga gcgcgtgggt tggttacagc gttctgggcg cagtactgga cccgacgggt    300
aaaatcgttg aacgtttcac cccggaagtc gcaccgattt ccgaggagcg cgttatcgac    360
gtggcaccgc cgagctacgc aagccgtgtc ggtgtgcgcg aaccgctgat cacgggtgtc    420
```

-continued

```
cgcgcaattg atggtctgct gacgtgtggt gtgggccagc gtatgggtat tttcgcaagc      480
gcgggttgtg gtaagaccat gttgatgcac atgctgatcg agcaaaccga agcggatgtc      540
tttgttattg gcctgattgg cgagcgtggt cgtgaagtta ccgaatttgt agacatgttg      600
cgtgcatctc ataagaaaga aaaatgtgtg ctggttttg ccacgtccga cttcccaagc       660
gttgaccgct gcaacgctgc ccagctggca acgacggtcg ccgagtattt ccgcgaccag      720
ggtaaacgtg ttgtcctgtt tatcgacagc atgacccgtt atgcacgcgc gttgcgtgat      780
gtcgcgctgg cgagcggcga gcgtccggct cgccgtggtt atccggcgtc tgtgttcgac      840
aatctgccgc gtttgctgga gcgtccgggt gcgacgagcg agggtagcat taccgccttc      900
tataccgtcc tgctggagtc ggaagaagaa gcggacccga tggcggacga gatccgttct      960
attctggacg tcacctgta cctgtcccgc aaactggcgg tcagggtca ttacccggct       1020 atcgatgtgc tgaagagcgt gagccgtgtg tttggtcaag tgaccacccc gactcacgcg     1080
gagcaagcga gcgcggtccg taagctgatg acccgtctgg aagagctgca actgttcatt     1140
gacctgggcg agtatcgtcc gggcgagaac attgacaatg atcgtgcgat gcaaatgcgc     1200
gatagcctga aggcgtggct gtgtcagcct gttgcgcaat acagcagctt cgatgatacg     1260
ctgtccggca tgaacgcctt tgcggatcag aactga                              1296
```

<210> SEQ ID NO 134
<211> LENGTH: 36
<212> TYPE: DNA
<213> ORGANISM: Artificial Sequence
<220> FEATURE:
<223> OTHER INFORMATION: synthetic SynInvE ribosome binding site (rbs, RBS) of bacterial type III secretion system (T3SS)

<400> SEQUENCE: 134

```
tacttgggca cgcgtccatt aattaggatc aatagc                               36
```

<210> SEQ ID NO 135
<211> LENGTH: 1119
<212> TYPE: DNA
<213> ORGANISM: Artificial Sequence
<220> FEATURE:
<223> OTHER INFORMATION: synthetic SynInvE of bacterial type III secretion system (T3SS)

<400> SEQUENCE: 135

```
atgattccgg gcagcacctc cggtatttcc tttagccgta tcctgagccg tcagacctcc      60
caccaggatg caacccagca taccgacgca caacaagcgg aaattcaaca agcggcggaa     120
gatagctcgc cgggtgcgga ggttcagaaa ttcgtccaga gcacggacga gatgtctgct     180
gcgttggcgc agttccgcaa tcgccgtgac tatgagaaaa agagcagcaa tttgtctaac     240
tccttcgagc gcgttctgga ggacgaggca ctgccgaaag cgaagcagat tctgaaactg     300
atcagcgtgc atggcggtgc gttggaggat ttcctgcgtc aggcgcgcag cctgttcccg     360
gacccaagcg atctggtgct ggttctgcgc gagctgttgc gtcgtaagga cctggaggag     420
atcgtgcgta agaagctgga gagcctgctg aagcacgtgg aggaacaaac cgacccgaaa     480
accctgaagg ccggtattaa ctgcgcgctg aaggcgcgtc tgtttggcaa gacgctgtct     540
ctgaaacctg gtctgctgcg tgccagctac cgccagttca tccaaagcga aagccacgaa     600
gtcgagattt acagcgattg gatcgccagc tacggttatc agcgtcgcct ggttgttctg     660
gatttcattg aaggcagcct gctgactgac atcgatgcta acgatgcaag ctgctcccgt     720
```

```
ctggagtttg gccaactgct gcgccgtctg acccagctga aaatgttgcg tagcgccgac       780
ctgctgtttg tctcgacgtt gctgtcttac agcttcacga aagcatttaa cgctgaggag       840
agcagctggc tgttgctgat gctgtctttg ctgcaacagc cgcacgaagt ggatagcctg       900
ctggcggaca ttatcggtct gaatgcgctg ctgttgtccc acaaagagca cgccagcttc       960
ctgcaaatct tctatcaggt ctgtaaggca atcccgtcta gcctgtttta tgaagagtac      1020
tggcaagaag aactgctgat ggcactgcgc tccatgacgg acattgctta caaacacgaa      1080
atggccgaac aacgtcgtac catcgaaaag ctgtcctaa                             1119
```

<210> SEQ ID NO 136
<211> LENGTH: 36
<212> TYPE: DNA
<213> ORGANISM: Artificial Sequence
<220> FEATURE:
<223> OTHER INFORMATION: synthetic SynInvF ribosome binding site (rbs, RBS) of bacterial type III secretion system (T3SS)

<400> SEQUENCE: 136

```
cttgggcacg cgtccattaa aaaggagtaa ttaagc                                 36
```

<210> SEQ ID NO 137
<211> LENGTH: 651
<212> TYPE: DNA
<213> ORGANISM: Artificial Sequence
<220> FEATURE:
<223> OTHER INFORMATION: synthetic SynInvF of bacterial type III secretion system (T3SS)

<400> SEQUENCE: 137

```
atgagcttca gcgagagccg ccacaatgaa aactgtctga ttcaagaagg cgcactgctg        60
ttttgtgagc aagcagtcgt ggcgcctgtc agcggtgatc tggttttcg tccgctgaaa       120 atcgaggtcc tgagcaagct gctggcgttc atcgacggcg caggtctggt ggatacgacc      180
tacgcggagt cggacaaatg ggttctgctg tctccggagt tccgtgctat ttggcaagac      240
cgtaaacgtt gcgaatattg gttttgcag cagattatca ccccatctcc ggcgttcaac       300
aaggttctgg cactgttgcg taagagcgaa agctattggt tggtcggcta cttgctggcc      360
caaagcacca gcggcaatac tatgcgtatg ttgggtgagg attacggtgt tagctacacg      420
catttccgcc gtctgtgcag ccgcgctctg ggcggtaagg cgaaaagcga gctgcgcaat      480
tggcgcatgg cccagtccct gctgaatagc gtggaaggtc atgaaaacat cacccagctg      540
gcggtcaacc acggttatag cagcccgtcc cactttagct ctgaaatcaa ggagctgatt      600
ggtgtttccc cgcgtaagct gtctaacatc attcagctgg ccgacaaatg a              651
```

<210> SEQ ID NO 138
<211> LENGTH: 36
<212> TYPE: DNA
<213> ORGANISM: Artificial Sequence
<220> FEATURE:
<223> OTHER INFORMATION: synthetic SynInvG ribosome binding site (rbs, RBS) of bacterial type III secretion system (T3SS)

<400> SEQUENCE: 138

```
tgggcacgcg tccattaatg aggaaaaatt attagc                                 36
```

<210> SEQ ID NO 139
<211> LENGTH: 1689
<212> TYPE: DNA
<213> ORGANISM: Artificial Sequence
<220> FEATURE:

<223> OTHER INFORMATION: synthetic SynInvG of bacterial type III
      secretion system (T3SS)

<400> SEQUENCE: 139

```
atgaaaacgc acattctgtt ggcccgtgtg ctggcttgcg cagctctggt gctggtcacc      60
ccaggttata gctccgagaa gatcccggtt acgggcagcg gcttcgttgc aaaggacgat     120
tctctgcgca ccttttttcga tgcgatggca ctgcaattga aggagccggt gattgtcagc    180
aagatggcgg ctcgcaaaaa gattaccggc aatttcgagt ccacgatcc aaacgcgctg     240
ctggagaaac tgtccctgca actgggtctg atctggtact tgatggtca ggcgatctac     300
atctacgacg cgagcgaaat gcgtaatgcg gttgtgagcc tgcgtaatgt cagcctgaac    360
gagttcaaca attttctgaa gcgcagcggc ctgtacaata gaactaccc tctgcgtggt     420
gataatcgta aaggcacctt ctatgtcagc ggtccgccgg tgtatgttga tatggttgta    480
aatgcggcca ccatgatgga caaacagaat gatggcatcg agctgggtcg ccaaaagatc    540
ggtgttatgc gcctgaacaa cacttttgtg ggcgaccgca cctacaacct gcgtgatcaa    600
aagatggtca ttccgggtat tgctacggca attgaacgcc tgttgcaagg cgaagaacaa    660
ccgctgggta acattgtaag ctccgagcct ccggccatgc cggcctttag cgcaaacggc    720
gagaaaggta aggcagcgaa ttacgcgggt ggtatgagcc tgcaagaagc gctgaaacag    780
aacgcagcgg caggcaacat caaaattgtg gcctatccgg acaccaacag cctgctggtg    840
aaaggtacgg cggagcaggt gcatttcatc gagatgctgg ttaaagccct ggacgtggcg    900
aaacgtcacg ttgaattgag cctgtggatt gtggatttga ataagagcga cctgaacgc     960
ttgggcacca gctggagcgg tagcatcacc atcggcgaca agctgggtgt gagcctgaac   1020
cagagcagca tctccacgct ggacggtagc cgctttattg cggcggtcaa cgctctggag   1080
gaaaagaaac aggccactgt tgtcagccgt ccggttctgc tgacccagga gaatgtcccg   1140
gcgatttttg acaataatcg tactttctat accaaactga tcggtgaacg taatgttgca   1200
ttggaacacg tgacctatgg caccatgatc cgtgtcctgc cgcgtttcag cgcggacggc   1260
cagattgaga tgagcctgga catcgaagat ggtaatgaca aaaccccgca gtctgatacg   1320
accacctccg ttgatgcgct gccagaagtg ggtcgtaccc tgatctcgac gattgcacgt   1380
gtcccgcatg gtaaatctct gctggttggt ggctacacgc gtgatgcaaa cacggacacg   1440
gtccaaagca tcccgttcct gggtaagctg ccgctgattg gctcgttgtt tcgctacagc   1500
agcaaaaaca gtctaatgt cgtccgtgtc tttatgattg agccgaaaga aatcgttgac   1560
ccgctgaccc cggatgccag cgagagcgtt aacaacattc tgaaacagtc cggtgcgtgg   1620
agcggtgacg ataagctgca aaagtgggtt cgtgtgtatt tggaccgtgg tcaggaggcc   1680
attaagtaa                                                          1689
```

<210> SEQ ID NO 140
<211> LENGTH: 36
<212> TYPE: DNA
<213> ORGANISM: Artificial Sequence
<220> FEATURE:
<223> OTHER INFORMATION: synthetic SynInvI ribosome binding site (rbs,
      RBS) of bacterial type III secretion system (T3SS)

<400> SEQUENCE: 140

```
cttgggcacg cgtccattaa aaaggaccaa ttaagc                                36
```

<210> SEQ ID NO 141
<211> LENGTH: 444

```
<212> TYPE: DNA
<213> ORGANISM: Artificial Sequence
<220> FEATURE:
<223> OTHER INFORMATION: synthetic SynInvI of bacterial type III
      secretion system (T3SS)

<400> SEQUENCE: 141
atgcactctc tgactcgtat caaggtcctg caacgtcgtt gtaccgtgtt ccattctcag      60
tgcgagtcca ttctgttgcg ttatcaggac gaagatcgcg gcttgcaggc ggaggaggag     120
gccatcctgg aacagatcgc aggtctgaaa ctgctgttgg acaccctgcg tgctgaaaat     180
cgtcaactga gccgtgaaga atctatacg ctgctgcgca acagagcat tgttcgtcgc      240 cagattaagg atctggagct gcaaatcatt cagattcaag aaaagcgtag cgagctggaa     300
aagaaacgtg aggaatttca aaagaaaagc aaatactggc tgcgtaaaga aggtaactac     360
cagcgctgga ttatccgtca aaaacgcttc tacattcaac gtgagatcca gcaagaggag     420
gcggagagcg aagagatcat ttaa                                             444

<210> SEQ ID NO 142
<211> LENGTH: 36
<212> TYPE: DNA
<213> ORGANISM: Artificial Sequence
<220> FEATURE:
<223> OTHER INFORMATION: synthetic SynInvJ ribosome binding site (rbs,
      RBS) of bacterial type III secretion system (T3SS)

<400> SEQUENCE: 142
aaaaaaaagc tctaaaagat taagaggggg taacat                                36

<210> SEQ ID NO 143
<211> LENGTH: 1011
<212> TYPE: DNA
<213> ORGANISM: Artificial Sequence
<220> FEATURE:
<223> OTHER INFORMATION: synthetic SynInvJ of bacterial type III
      secretion system (T3SS)

<400> SEQUENCE: 143
atgggtgacg tgagcgcggt gagcagcagc ggtaacattc tgctgccgca gcaggacgag      60
gttggtggcc tgtccgaagc gctgaagaaa gcggttgaaa acacaaaac cgaatacagc     120 ggtgacaaga aagatcgtga ttatggtgac gcctttgtta tgcacaagga accgcgctg     180 ccgttgttgc tggcagcttg gcgccacggc gcaccggcga aaagcgagca ccataacggt     240
aacgtaagcg tctgcatca caacggtaag agcgagctgc gtattgctga aaactgctg      300 aaggtgacgg cggagaagag cgttggtctg attagcgctg aagcgaaggt ggataaatct     360
gcggcgctgc tgtctagcaa gaatcgtccg ctggaatcgg tcagcggcaa aaagttgtcc     420
gccgatctga aagcagtgga gtccgtgtcc gaggtcacgg ataacgccac cggcatttcg     480
gatgacaaca tcaaagcatt gccgggtgac aataaggcca tcgccggtga gggtgtgcgt     540
aaagaaggtg cgccgctggc gcgtgacgtg gctccggcac gcatggcggc agcaaatacg     600
ggcaagccgg aggataaaga ccacaagaag gtcaaggacg ttagccagct gccgctgcaa     660
ccgactacca tcgccgatct gtctcaactg acgggtggcc atgaaaagat gccgctggca     720
gcgcagtcca aaccgatgat gaccattttc ccaaccgccg acggcgttaa aggtgaggac     780
agctctctga cctatcgttt ccagcgctgg ggcaacgatt actccgtcaa tatccaggca     840
cgccaagcgg gcgaatttag cctgattcct agcaatacc aggttgaaca tcgtctgcac      900
gaccaatggc aaaatggcaa tccacaacgc tggcatttga cgcgtgatga ccagcaaaac     960
```
ccgcaacagc aacagcatcg tcagcagtcc ggtgaagagg acgacgcgta a      1011

<210> SEQ ID NO 144
<211> LENGTH: 36
<212> TYPE: DNA
<213> ORGANISM: Artificial Sequence
<220> FEATURE:
<223> OTHER INFORMATION: synthetic SynSpaO ribosome binding site (rbs,
      RBS) of bacterial type III secretion system (T3SS)

<400> SEQUENCE: 144
cttgggcacg cgtccatgaa agacaggacc cactag      36

<210> SEQ ID NO 145
<211> LENGTH: 912
<212> TYPE: DNA
<213> ORGANISM: Artificial Sequence
<220> FEATURE:
<223> OTHER INFORMATION: synthetic SynSpaO of bacterial type III
      secretion system (T3SS)

<400> SEQUENCE: 145
atgagcttgc gcgtacgcca aattgaccgc cgtgaatggc tgctggccca gactgcgacc      60
gaatgtcagc gtcacggtcg tgaggccacc ctggagtatc cgacccgtca gggtatgtgg     120
gtccgcctgt ctgatgccga aaacgctgg tctgcgtgga tcaaaccggg tgattggttg      180
gaacacgtta gcccagcact ggcgggtgcc gcggtcagcg caggcgcgga gcacctggtg     240
gttccgtggc tggcggcaac cgaacgcccg ttcgagctgc cggtcccgca cttgagctgc     300
cgtcgtctgt gcgtggagaa cccggttccg ggttccgcac tgcctgaggg caagctgctg     360
cacatcatgt cggatcgtgg tggcctgtgg tttgagcatc tgccggagct gccggctgtt     420
ggcggtggcc gtccgaagat gctgcgttgg ccgctgcgtt tcgttattgg cagcagcgac     480
acccagcgca gcctgctggg tcgtatcggt atcggtgatg ttctgctgat ccgcaccagc     540
cgtgctgagg tttactgtta cgcgaagaaa ctgggccact ttaatcgtgt ggaaggtggc     600
attattgtcg aaacgctgga cattcaacat atcgaggagg agaacaacac gacgaaacg      660
gcggaaaccc tgccgggtct gaatcaactg ccggtgaagc tggagttcgt tctgtatcgt     720
aaaaacgtga cgttggccga actggaagca atgggtcagc aacaactgct gtccttgcca     780
accaatgcgg aactgaacgt cgaaatcatg gcgaatggcg tgctgctggg taacggcgaa     840
ctggtgcaga tgaatgacac cctgggtgtc gagattcatg agtggttgtc cgagagcggt     900
aatggcgagt ag      912

<210> SEQ ID NO 146
<211> LENGTH: 36
<212> TYPE: DNA
<213> ORGANISM: Artificial Sequence
<220> FEATURE:
<223> OTHER INFORMATION: synthetic SynSpaP ribosome binding site (rbs,
      RBS) of bacterial type III secretion system (T3SS)

<400> SEQUENCE: 146
cttgggcacg cgtccatgaa agaaacgaca tactag      36

<210> SEQ ID NO 147
<211> LENGTH: 675
<212> TYPE: DNA
<213> ORGANISM: Artificial Sequence
<220> FEATURE:
<223> OTHER INFORMATION: synthetic SynSpaP of bacterial type III secretion system (T3SS)

<400> SEQUENCE: 147

```
atgggtaacg atattagctt gattgcattg ctggcgtttt ccaccctgct gccgttcatc      60
atcgcgtctg gtacttgctt cgtcaaattc agcatcgtct ttgtgatggt gcgcaacgcg     120
ctgggtctgc aacaaattcc aagcaatatg accctgaatg gcgtcgcact gctgctgtcg     180
atgtttgtta tgtggccgat tatgcacgac gcgtatgtgt atttcgagga tgaagatgtg     240
acctttaacg acatctccag cctgagcaag catgttgatg agggcctgga cggttatcgc     300
gactacctga tcaagtattc cgaccgtgag ctggtgcagt tctttgagaa tgcccagttg     360
aaacgtcagt acggtgaaga acggaaaacc gttaaacgtg acaaggacga gattgaaaag     420
ccgagcattt tcgcactgtt gcctgcttac gccttgagcg agattaagag cgcattcaaa     480
attggttttt acctgtacct gccgttcgtt gtggtcgatc tggttgtctc cagcgttctg     540
ctggccctgg gcatgatgat gatgtccccg gttaccatca gcacgccgat caaactggtc     600
ctgtttgtgg ccctggatgg ttggacgctg ctgtctaaag gcctgatcct gcaatacatg     660
gacatcgcga cctaa                                                      675
```

<210> SEQ ID NO 148
<211> LENGTH: 36
<212> TYPE: DNA
<213> ORGANISM: Artificial Sequence
<220> FEATURE:
<223> OTHER INFORMATION: synthetic SynSpaQ ribosome binding site (rbs, RBS) of bacterial type III secretion system (T3SS)

<400> SEQUENCE: 148

```
cttgggcacg cgtccattaa gaaggaggaa ttaagc                                36
```

<210> SEQ ID NO 149
<211> LENGTH: 261
<212> TYPE: DNA
<213> ORGANISM: Artificial Sequence
<220> FEATURE:
<223> OTHER INFORMATION: synthetic SynSpaQ of bacterial type III secretion system (T3SS)

<400> SEQUENCE: 149

```
atggacgatc tggttttcgc cggcaacaaa gccctgtact tggtgctgat tctgtccggt      60
tggccgacga ttgtcgcaac cattatcggt ctgctggttg gtctgtttca aaccgtgacg     120
cagttgcagg agcaaaccct gccgttcggt atcaagctgc tgggtgtgtg tctgtgcctg     180
tttttgctgt ctggctggta tggcgaagtt ctgctgtcct acggccgtca ggtcatcttc     240
ctggctctgg cgaaaggtta a                                               261
```

<210> SEQ ID NO 150
<211> LENGTH: 36
<212> TYPE: DNA
<213> ORGANISM: Artificial Sequence
<220> FEATURE:
<223> OTHER INFORMATION: synthetic SynSpaR ribosome binding site (rbs, RBS) of bacterial type III secretion system (T3SS)

<400> SEQUENCE: 150

```
cttgggcacg cgtccatgaa agacaggacc cactag                                36
```

<210> SEQ ID NO 151
<211> LENGTH: 792
<212> TYPE: DNA

<213> ORGANISM: Artificial Sequence
<220> FEATURE:
<223> OTHER INFORMATION: synthetic SynSpaR of bacterial type III
      secretion system (T3SS)

<400> SEQUENCE: 151

```
atgttctatg cattgtattt tgagatccac catctggtgg cgtccgcggc tctgggtttt      60
gcgcgtgttg ctccgatctt tttctttctg ccgttcctga atagcggtgt cctgagcggt     120
gctccgcgca acgcgatcat cattctggtg gcgctgggtg tatggccgca cgccctgaat     180
gaggcgccac cgtttctgtc tgtggcaatg attccgctgg tcctgcaaga ggcagccgtg     240
ggtgttatgc tgggttgcct gttgtcctgg ccgttttggg ttatgcacgc gttgggctgt     300
atcattgata accaacgcgg tgcaaccctg ccagcagca ttgatcctgc gaatggcatc      360
gacaccagcg agatggccaa tttcctgaac atgttcgcgg ctgtcgtgta tttgcagaac     420
ggtggcttgg tcacgatggt ggacgtgctg aataagtctt accagctgtg tgatccgatg     480
aacgagtgta cgccgagcct gcctccgttg ctgaccttca ttaatcaagt ggcccagaac     540
gcactggtgc tggcgtcccc ggtcgttctg gttctgctgc tgtcggaagt tttcctgggc     600
ctgctgtctc gttttgcacc gcaaatgaac gcgttcgcca ttagcctgac tgttaaaagc     660
ggtattgcgg ttttgatcat gctgctgtat ttcagcccgg tcctgccgga caatgttctg     720
cgtctgagct ttcaggcgac cggcctgagc agctggttct acgaacgtgg cgcaacgcat     780
gtgctggaat aa                                                         792
```

<210> SEQ ID NO 152
<211> LENGTH: 36
<212> TYPE: DNA
<213> ORGANISM: Artificial Sequence
<220> FEATURE:
<223> OTHER INFORMATION: synthetic SynSpaS ribosome binding site (rbs,
      RBS) of bacterial type III secretion system (T3SS)

<400> SEQUENCE: 152

```
cttgggcacg cgtccatgaa agacaggacc cactag                                36
```

<210> SEQ ID NO 153
<211> LENGTH: 1071
<212> TYPE: DNA
<213> ORGANISM: Artificial Sequence
<220> FEATURE:
<223> OTHER INFORMATION: synthetic SynSpaS of bacterial type III
      secretion system (T3SS)

<400> SEQUENCE: 153

```
atgtccagca acaaaaccga aaaccgact aagaaacgtc tggaggatag cgcaaagaaa       60
ggtcagagct tcaagagcaa ggacctgatt atcgcgtgcc tgaccctggg tggtatcgct     120
tatttggtga gctacggcag cttcaatgag tttatgggta tcattaagat tatcatcgct     180
gataactttg atcagtcgat ggcagattat agcctggccg tgtttggtat tggcctgaaa     240
tacctgattc cgttcatgct gctgtgtttg gtttgttccg cactgccggc actgctgcaa     300
gcgggcttcg ttctggcaac cgaggccctg aagccgaatc tgtccgccct gaacccggtt     360
gaaggcgcga gaaactgtt ttccatgcgc accgtcaaag acacggtcaa gacgctgctg     420
tatctgtcga gctttgtggt tgcggcaatc atttgctgga aaaagtataa agtcgagatt     480
ttcagccaac tgaacggtaa tatcgtgggt attgcggtta tctggcgtga attgctgctg     540
gcgttggttc tgacctgtct ggcgtgcgcg ctgatcgtgc tgttgctgga tgctattgcc     600
```

-continued

```
gagtactttc tgaccatgaa agatatgaag atggacaaag aagaagttaa acgcgagatg      660
aaagagcagg agggtaaccc ggaggtgaag tctaaacgtc gtgaagtcca catggaaatc      720
ctgagcgaac aagtcaagtc tgacattgaa aatagccgtc tgattgtggc aaaccctacg      780
catattacca tcggcatcta cttcaaaccg gaactgatgc cgattccaat gattagcgtc      840
tatgaaacca atcaacgcgc gctggcggtc cgtgcgtacg ccgagaaagt gggtgttccg      900
gttattgtag acatcaagct ggcgcgcagc ctgttcaaaa cgcaccgtcg ttacgacctg      960
gtgagcctgg aggagatcga cgaggttttg cgcctgctgg tttggttgga agaggtcgaa     1020
aacgcaggca aggatgtgat ccaaccgcag gagaatgaag tgcgtcatta a              1071
```

<210> SEQ ID NO 154
<211> LENGTH: 4075
<212> TYPE: DNA
<213> ORGANISM: Artificial Sequence
<220> FEATURE:
<223> OTHER INFORMATION: synthetic Syn_PrgOrg operon of bacterial type
III secretion system (T3SS)

<400> SEQUENCE: 154

```
gcatgcatta aagaggagaa attaagcatg gctactccgt ggtctggtta tctggatgat       60
gtttctgcaa aatttgacac gggtgttgac aacttgcaaa cccaagttac cgaagccctg      120
gacaagctgg ctgcgaagcc gtccgatccg gcgctgctgg cggcgtatca atccaaactg      180
tctgagtata acttgtaccg taatgcgcag tcgaacacgg tcaaggtctt caaagatatt      240
gatgcagcga ttattcagaa cttccgttag taacctagga ttaaggagga taaattaagc      300
atgtctatcg cgactatcgt gcctgaaaat gccgttattg gtcaagcggt gaatattcgc      360
agcatggaaa cggacatcgt cagcttggac gaccgttttgc tgcaagcatt ttcgggcagc      420
gccatcgcta ccgccgtcga taagcagacc attaccaatc gcattgaaga ccctaatctg      480
gttaccgatc cgaaggagct ggcgattagc caggaaatga tttccgacta caatctgtac      540
gtcagcatgg ttagcaccct gacgcgtaag ggcgttggcg ctgttgagac tttgctgcgt      600
tcctgatagg ctagcattaa acaggataat aagcatggaa actagcaagg agaaaacgat      660
tacgtcccct ggtccgtata tcgttcgtct gttgaactcg tccctgaacg gttgtgaatt      720
tccgctgctg actggtcgta cgctgttcgt cgtgggtcag agcgatgctc tgaccgcgtc      780
tggtcagctg ccggacattc ctgccgactc cttcttcatc ccgctggatc atggcggtgt      840
taatttcgag attcaagtgg acactgacgc gacggaaatc atcctgcacg aactgaaaga      900
gggcaactcc gagagccgct ccgtgcaact gaacaccccg atccaagttg gtgaactgct      960
gattttgatt cgtccggaga gcgagccgtg ggtgccggaa cagccggaga gttggaaac     1020 ttctgcgaaa agaacgaac cgcgctttaa aaacggcatc gtcgcggcac tggcgggttt     1080
ctttatcctg ggtatcggca cggttggcac cctgtggatt ctgaactcgc cgcaacgtca     1140
agcagccgaa ttggacagcc tgttgggtca ggagaaggag cgttttcagg tgctgccggg     1200
tcgcgacaag atgctgtatg tcgccgcgca aaacgaacgc gacaccctgt gggcacgtca     1260
agtcctggca cgcggcgatt acgataaaaa cgcacgcgtt attaatgaaa atgaggagaa     1320
taaacgtatc agcatctggc tggacacgta ttatccacaa ctggcatatt accgtatcca     1380
ttttgatgaa ccacgtaagc cggtgttttg gctgtcccgt caacgcaaca cgatgagcaa     1440
gaaagagctg gaggtgctgt cccagaaatt gcgtgcgctg atgccgtacg ccgacagcgt     1500
caatattact ctgatggatg acgtgaccgc agcaggccaa gccgaggcag gtctgaaaca     1560
```

```
acaggcgctg ccatacagcc gccgtaacca caaaggtggt gttacgttcg ttattcaggg    1620
cgccttggac gacgttgaga ttctgcgtgc gcgccagttt gtcgactcct attatcgtac    1680
ctggggtggt cgttacgttc aattcgcaat tgaattgaaa gacgattggc tgaaaggccg    1740
ctcgttccaa tacggtgcgg aaggctacat taagatgagc ccaggtcatt ggtattttcc    1800
gtctcctctg taatagaagc ttattaaaca ggataataag catgatccgc cgttacctgt    1860
ataccttctt gctggttatg actttggccg gctgtaaaga taaggatctg ctgaaaggct    1920
tggaccaaga gcaagcgaat gaggtcattg cggttctgca aatgcacaac attgaggcta    1980
acaagattga tagcggcaag ctgggttaca gcattaccgt cgcggaaccg gatttcaccg    2040
cggcagtgta ttggattaag acctaccagt tgccgcctcg cccgcgtgtc gaaatcgccc    2100
aaatgtttcc ggcagacagc ctggttagct ctccgcgtgc ggagaaagca cgtctgtact    2160
cggcgattga acagcgcctg gagcagtcgc tgcaaacgat ggaaggtgtt ctgtcggccc    2220
gtgtccacat cagctatgat attgatgcgg gcgagaacgg tcgtccgcct aagccggtgc    2280
acctgtcggc tttggcggtg tatgaacgcg gttcccctct ggcccatcag atttcggata    2340
ttaagcgctt cctgaaaaac agcttcgcgg atgttgacta tgataacatc agcgtggttc    2400
tgtccgagcg tagcgacgca cagttgcagg cgccgggcac gccggtcaag cgcaatagct    2460
tcgctacctc ctggattgtg ctgattatcc tgttgtctgt tatgagcgcg ggtttcggtg    2520
tctggtacta caaaaatcac tatgcgcgta ataagaaagg cattactgcc gatgacaagg    2580
caaagtccag caacgagtaa taaggtaccg aagaagggaa cagactagat gattcgtcgt    2640
aaccgtcaaa tgaaccgtca accactgcca attatctggc aacgcattat tttcgaccca    2700
ctgtcctata ttcacccaca acgtctgcaa atcgcgccgg agatgatcgt gcgtccggca    2760
gcgcgtgcgg cagcgaatga gctgattttg cggcgtggcg gtttgaagaa cggtgagaag    2820
gagtgcattc agaatagcct gacgcagctg tggttgcgtc aatggcgccg tctgccgcag    2880
gttgcttacc tgctgggttg ccacaagttg cgtgctgacc tggcccgtca aggtgcttta    2940
ttgggcctgc cggactgggc gcaggcattc ttggcgatgc accagggtac gtccttgtcg    3000
gtttgtaata aggcgccgaa ccaccgtttc ctgctgtccg ttggttacgc ccaactgaac    3060
gcgctgaatg agttcctgcc ggagagcttg gcccaacgct ttcctctgct gtttccaccg    3120
ttcatcgagg aggcactgaa acaagatgca gtggagatga gcatcctgct gctgccctg    3180 caatacgcgc aaaagtatcc taacaccgtc ccggcgtttg cgtgctaata agatctgaa    3240 agaagggaca gactagatgt tgaaaaatat cccgattcca tcccctctgt ctccggttga    3300
aggtatcctg attaaacgca agacgttgga gcgttacttc tcgattgagc gcctggaaca    3360
acaggcgcat cagcgtgcaa agcgcatttt gcgtgaggca gaagaagaag ccaagaccct    3420
gcgcatgtat gcgtaccagg agggctacga gcagggcatg attgacgcac tgcaacaggt    3480
ggccgcctat ttgaccgaca accagacgat ggcttggaaa tggatggaga aaattcaaat    3540
ctatgcgcgt gagttgttca gcgcggctgt cgatcacccg gaaacgttgt tgacggtgct    3600
ggacgagtgg ctgcgtgatt tcgataagcc ggaaggtcag ctgttttga ccctgccggt    3660 gaacgcaaag aaagatcatc agaaactgat ggtgctgctg atggaaaatt ggccgggcac    3720
cttcaatctg aagtatcatc aggagcaacg ttttatcatg tcctgtggcg atcagattgc    3780
cgagttttcg ccggaacaat tgttgaaac ggcggttggt gttatcaagc accatctgga    3840
tgagctgcct caggactgtc gcaccatttc ggacaatgcg attaacgcgc tgattgatga    3900
atggaagacg aaaacccaag ctgaagttat tcgctgataa ggatccggca tcaaataaaa    3960
```

```
cgaaaggctc agtcgaaaga ctgggccttt cgttttatct gttgtttgtc ggtgaacgct    4020
ctcctgagta ggacaaatcc gccgccctag aactagtcca taagaatgcg gccgc         4075

<210> SEQ ID NO 155
<211> LENGTH: 12614
<212> TYPE: DNA
<213> ORGANISM: Artificial Sequence
<220> FEATURE:
<223> OTHER INFORMATION: synthetic Syn_InvSpa operon of bacterial type
      III secretion system (T3SS)

<400> SEQUENCE: 155
ctcgagaaaa aaagctcta aaagattaag aggggggtaac atatgggtga cgtgagcgcg      60
gtgagcagca gcggtaacat tctgctgccg cagcaggacg aggttggtgg cctgtccgaa     120
gcgctgaaga aagcggttga aaacacaaa accgaataca gcggtgacaa gaaagatcgt     180
gattatggtg acgcctttgt tatgcacaag gaaaccgcgc tgccgttgtt gctggcagct     240
tggcgccacg gcgcaccggc gaaaagcgag caccataacg taacgtaag cggtctgcat     300 cacaacggta agagcgagct gcgtattgct gagaaactgc tgaaggtgac ggcggagaag     360
agcgttggtc tgattagcgc tgaagcgaag gtggataaat ctgcggcgct gctgtctagc     420
aagaatcgtc cgctggaatc ggtcagcggc aaaaagttgt ccgccgatct gaaagcagtg     480
gagtccgtgt ccgaggtcac ggataacgcc accggcattt cggatgacaa catcaaagca     540
ttgccgggtg acaataaggc catcgccggt gagggtgtgc gtaagaaagg tgcgccgctg     600
gcgcgtgacg tggctccggc acgcatggcg gcagcaaata cgggcaagcc ggaggataaa     660
gaccacaaga aggtcaagga cgttagccag ctgccgctgc aaccgactac catcgccgat     720
ctgtctcaac tgacgggtgg cgatgaaaag atgccgctgg cagcgcagtc caaaccgatg     780
atgaccattt cccaaccgc cgacggcgtt aaaggtgagg acagctctct gacctatcgt     840
ttccagcgct ggggcaacga ttactccgtc aatatccagg cacgccaagc gggcgaattt     900
agcctgattc ctagcaatac ccaggttgaa catcgtctgc acgaccaatg caaaatggc     960 aatccacaac gctggcattt gacgcgtgat gaccagcaaa acccgcaaca gcaacagcat    1020
cgtcagcagt ccggtgaaga ggacgacgcg taacttgggc acgcgtccat taagaaggag    1080
gaattaagca tggacgatct ggttttcgcc ggcaacaaag ccctgtactt ggtgctgatt    1140
ctgtccggtt ggccgacgat tgtcgcaacc attatcggtc tgctggttgg tctgtttcaa    1200
accgtgacgc agttgcagga gcaaaccctg ccgttcggta tcaagctgct gggtgtgtgt    1260
ctgtgcctgt ttttgctgtc tggctggtat ggcgaagttc tgctgtccta cggccgtcag    1320
gtcatcttcc tggctctggc gaaaggttaa gacgtccttg gcacgcgtc cattaaacag    1380 gagtaattaa gcatgctgct gtccctgctg aatagcgcgc gtctgcgtcc tgagctgctg    1440
attctggttc tgatggttat gatcatcagc atgttcgtta tcccgttgcc gacctatttg    1500
gttgacttct tgatcgcttt gaacattgtc ctggcaattc tggtgttcat gggctccttc    1560
tacatcgacc gcattctgag cttcagcacc tttccggcgg ttctgctgat cacgactctg    1620
ttccgtttgg cactgagcat cagcaccagc cgcctgatcc tgattgaagc agatgcgggt    1680
gagatcatcg cgacctttgg tcagtttgtg atcggtgaca gcctggcggt tggtttcgtc    1740
gtattctcca tcgtgacggt ggtgcagttt atcgttatta ccaagggcag cgaacgtgtg    1800
gcggaggtcg ccgctcgctt cagcctggac ggcatgccgg taaaacagat gtctattgat    1860
gcagacctga agccggcat tattgatgct gatgcagcgc gcgagcgccg cagcgtcctg    1920
```

```
gagcgtgaaa gccaactgta cggttccttc gacggtgcca tgaagttcat taaaggtgat    1980
gcgattgcgg gcatcattat catcttcgtt aacttcattg gcggtatcag cgtcggtatg    2040
acccgtcatg gtatggatct gagcagcgcc ctgagcacct acaccatgct gacgattggt    2100
gatggtctgg ttgcccaaat tccggcgttg ctgatcgcga tttctgcggg cttcatcgtt    2160
acccgcgtca acggtgatag cgataacatg ggtcgtaaca ttatgaccca gctgctgaat    2220
aatccgtttg tcctggttgt aacggcgatt ttgaccatca gcatgggcac gctgccgggc    2280
tttccgttgc cggttttcgt tattctgtct gttgtgctgt ccgtcctgtt ttactttaag    2340
ttccgcgagg cgaaacgtag cgctgcgaaa ccaaaaacga gcaagggcga gcaaccgttg    2400
tccatcgagg agaaggaagg tagcagcctg ggcctgattg gcgacctgga taaggttagc    2460
acggaaaccg tcccgctgat tttgctggtg ccgaaatcgc gtcgtgagga tctgagaaaa    2520
gcgcagctgg cggaacgtct gcgcagccaa ttctttattg attatggtgt gcgtctgcca    2580
gaagtactgc tgcgtgacgg tgagggtctg gatgacaact ctatcgtcct gctgattaat    2640
gagattcgcg ttgaacagtt tactgtctat tttgacctga tgcgtgtggt taactacagc    2700
gacgaggtgt gagctttgg catcaacccg accattcacc agcaaggttc cagccagtac    2760
ttttgggtga cccatgagga aggcgaaaag ctgcgcgagc tgggctacgt cctgcgtaat    2820
gcactggacg aactgtacca ctgtctggcg gtgacgctgg cacgcaatgt gaacgagtat    2880
ttcggtatcc aagaaacgaa acacatgctg gaccaactgg aagcaaagtt tcctgacctg    2940
ctgaaggagg tttgcgcca cgccaccgtg cagcgcattt cggaagtgct gcaacgtctg    3000
ctgtccgaac gcgtgagcgt ccgtaacatg aagctgatca tggaagccct ggcactgtgg    3060
gctccgcgtg agaaagatgt gatcaatctg gtggagcaca tccgtggtgc gatggcgcgt    3120
tatatctgcc acaagttcgc aaatggtggt gaactgcgtg ccgttatggt ttccgccgaa    3180
gttgaggatg tcattcgtaa aggcattcgt caaacttctg ctccaccttt tttgagcttg    3240
gacccggagg cttcggcaaa tctgatggac ctgatcacgc tgaagctgga cgacctgttg    3300
attgcgcata aggacctggt cctgttgacc agcgttgacg tgcgtcgttt tatcaagaaa    3360
atgattgaag tcgttttcc ggatctggag gtcctgtcct tcggtgagat tgcagatagc    3420
aaaagcgtga atgtcatcaa aaccatctga atttaaatct tgggcacgcg tccattaaaa    3480
aggagtaatt aagcatgagc ttcagcgaga gccgccacaa tgaaaactgt ctgattcaag    3540
aaggcgcact gctgtttttgt gagcaagcag tcgtggcgcc tgtcagcggt gatctggttt    3600
ttcgtccgct gaaaatcgag gtcctgagca agctgctggc gttcatcgac ggcgcaggtc    3660
tggtggatac gacctacgcg gagtcggaca atgggttct gctgtctccg gagttccgtg    3720
ctatttggca agaccgtaaa cgttgcgaat attggttttt gcagcagatt atcaccccat    3780
ctccggcgtt caacaaggtt ctggcactgt tgcgtaagag cgaaagctat tggttggtcg    3840
gctacttgct ggcccaaagc accagcggca atactatgcg tatgttgggt gaggattacg    3900
gtgttagcta cacgcatttc gccgtctgt gcagccgcgc tctgggcggt aaggcgaaaa    3960
gcgagctgcg caattggcgc atgggcccagt ccctgctgaa tagcgtggaa ggtcatgaaa    4020
acatcaccca gctggcggtc aaccacggtt atagcagccc gtcccacttt agctctgaaa    4080
tcaaggagct gattggtgtt tccccgcgta agctgtctaa catcattcag ctggccgaca    4140
aatgaattta aatgctagcc ttgggcacgc gtccattaaa gaggaccaat taagcatgaa    4200
aaccccacgt ctgctgcaat acctggccta cccgcagaaa atcactggcc ctatcattga    4260
```

```
agcagaactg cgtgatgttg caattggtga attgtgcgag atccgtcgcg gctggcacca   4320
gaagcaggtt gtggcccgtg cgcaagtggt tggtttgcag cgcgaacgta ccgtcctgag   4380
cctgatcggc aatgcccaag gcctgagccg tgatgtggtc ttgtacccga ccggccgtgc   4440
tctgagcgcg tggttggtt acagcgttct gggcgcagta ctggacccga cgggtaaaat   4500
cgttgaacgt tcaccccgg aagtcgcacc gatttccgag gagcgcgtta tcgacgtggc   4560
accgccgagc tacgcaagcc gtgtcggtgt gcgcgaaccg ctgatcacgg gtgtccgcgc   4620
aattgatggt ctgctgacgt gtggtgtggg ccagcgtatg ggtattttcg caagcgcggg   4680
ttgtggtaag accatgttga tgcacatgct gatcgagcaa accgaagcgg atgtctttgt   4740
tattggcctg attggcgagc gtggtcgtga agttaccgaa tttgtagaca tgttgcgtgc   4800
atctcataag aaagaaaaat gtgtgctggt ttttgccacg tccgacttcc caagcgttga   4860
ccgctgcaac gctgcccagc tggcaacgac ggtcgccgag tatttccgcg accagggtaa   4920
acgtgttgtc ctgtttatcg acagcatgac ccgttatgca cgcgcgttgc gtgatgtcgc   4980
gctggcgagc ggcgagcgtc cggctcgccg tggttatccg gcgtctgtgt tcgacaatct   5040
gccgcgtttg ctggagcgtc cgggtgcgac gagcgagggt agcattaccg ccttctatac   5100
cgtcctgctg gagtcggaag aagaagcgga cccgatggcg gacgagatcc gttctattct   5160
ggacggtcac ctgtacctgt cccgcaaact ggcgggtcag ggtcattacc cggctatcga   5220
tgtgctgaag agcgtgagcc gtgtgtttgg tcaagtgacc accccgactc acgcggagca   5280
agcgagcgcg gtccgtaagc tgatgacccg tctggaagag ctgcaactgt tcattgacct   5340
gggcgagtat cgtccgggcg agaacattga caatgatcgt gcgatgcaaa tgcgcgatag   5400
cctgaaggcg tggctgtgtc agcctgttgc gcaatacagc agcttcgatg atacgctgtc   5460
cggcatgaac gcctttgcgg atcagaactg acttgggcac gcgtccatga agaaacgac   5520
atactagatg ggtaacgata ttagcttgat tgcattgctg gcgttttcca ccctgctgcc   5580
gttcatcatc gcgtctggta cttgcttcgt caaattcagc atcgtctttg tgatggtgcg   5640
caacgcgctg ggtctgcaac aaattccaag caatatgacc ctgaatggcg tcgcactgct   5700
gctgtcgatg tttgttatgt ggccgattat gcacgacgcg tatgtgtatt tcgaggatga   5760
agatgtgacc tttaacgaca tctccagcct gagcaagcat gttgatgagg gcctggacgg   5820
ttatcgcgac tacctgatca agtattccga ccgtgagctg gtgcagttct ttgagaatgc   5880
ccagttgaaa cgtcagtacg gtgaagaaac ggaaaccgtt aaacgtgaca aggacgagat   5940
tgaaaagccg agcattttcg cactgttgcc tgcttacgcc ttgagcgaga ttaagagcgc   6000
attcaaaatt ggttttttacc tgtacctgcc gttcgttgtg gtcgatctgg ttgtctccag   6060
cgttctgctg gccctgggca tgatgatgat gtccccggtt accatcagca cgccgatcaa   6120
actggtcctg tttgtggccc tggatggttg gacgctgctg tctaaaggcc tgatcctgca   6180
atacatggac atcgcgacct aagagctctg ggcacgcgtc cattaatgag gaaaaattat   6240
tagcatgaaa acgcacattc tgttggcccg tgtgctggct tgcgcagctc tggtgctggt   6300
cacccccaggt tatagctccg agaagatccc ggttacgggc agcggcttcg ttgcaaagga   6360
cgattctctg cgcaccttt tcgatgcgat ggcactgcaa ttgaaggagc cggtgattgt   6420
cagcaagatg gcggctcgca aaaagattac cggcaatttc gagttccacg atccaaacgc   6480
gctgctggag aaactgtccc tgcaactggg tctgatctgg tactttgatg gtcaggcgat   6540
ctacatctac gacgcgagcg aaatgcgtaa tgcggttgtg agcctgcgta atgtcagcct   6600
gaacgagttc aacaattttc tgaagcgcag cggcctgtac aataagaact accctctgcg   6660
```

```
tggtgataat cgtaaaggca ccttctatgt cagcggtccg ccggtgtatg ttgatatggt    6720
tgtaaatgcg gccaccatga tggacaaaca gaatgatggc atcgagctgg gtcgccaaaa    6780
gatcggtgtt atgcgcctga acaacacttt tgtgggcgac cgcacctaca acctgcgtga    6840
tcaaaagatg gtcattccgg gtattgctac ggcaattgaa cgcctgttgc aaggcgaaga    6900
acaaccgctg ggtaacattg taagctccga gcctccggcc atgccggcct ttagcgcaaa    6960
cggcgagaaa ggtaaggcag cgaattacgc gggtggtatg agcctgcaag aagcgctgaa    7020
acagaacgca gcggcaggca acatcaaaat tgtggcctat ccggacacca acagcctgct    7080
ggtgaaaggt acgcggagc aggtgcattt catcgagatg ctggttaaag ccctggacgt    7140
ggcgaaacgt cacgttgaat tgagcctgtg gattgtggat ttgaataaga gcgacctgga    7200
acgcttgggc accagctgga gcggtagcat caccatcggc gacaagctgg gtgtgagcct    7260
gaaccagagc agcatctcca cgctggacgg tagccgcttt attgcggcgg tcaacgctct    7320
ggaggaaaag aaacaggcca ctgttgtcag ccgtccggtt ctgctgaccc aggagaatgt    7380
cccggcgatt tttgacaata atcgtacttt ctataccaaa ctgatcggtg aacgtaatgt    7440
tgcattggaa cacgtgacct atggcaccat gatccgtgtc ctgccgcgtt tcagcgcgga    7500
cggccagatt gagatgagcc tggacatcga agatggtaat gacaaaaccc cgcagtctga    7560
tacgaccacc tccgttgatg cgctgccaga agtgggtcgt accctgatct cgacgattgc    7620
acgtgtcccg catggtaaat ctctgctggt tggtggctac acgcgtgatg caaacacgga    7680
cacggtccaa agcatcccgt tcctgggtaa gctgccgctg attggctcgt tgtttcgcta    7740
cagcagcaaa aacaagtcta atgtcgtccg tgtctttatg attgagccga agaaatcgt    7800 tgacccgctg accccggatg ccagcgagag cgttaacaac attctgaaac agtccggtgc    7860
gtggagcggt gacgataagc tgcaaaagtg ggttcgtgtg tatttggacc gtggtcagga    7920
ggccattaag taacttgggc acgcgtccat gaaagacagg acccactaga tgtccagcaa    7980
caaaaccgaa aaaccgacta agaaacgtct ggaggatagc gcaaagaaag gtcagagctt    8040
caagagcaag gacctgatta tcgcgtgcct gaccctgggt ggtatcgctt atttggtgag    8100
ctacggcagc ttcaatgagt ttatgggtat cattaagatt atcatcgctg ataactttga    8160
tcagtcgatg gcagattata gcctggccgt gtttggtatt ggcctgaaat acctgattcc    8220
gttcatgctg ctgtgtttgg tttgttccgc actgccggca ctgctgcaag cgggcttcgt    8280
tctggcaacc gaggccctga agccgaatct gtccgccctg aacccggttg aaggcgcgaa    8340
gaaactgttt tccatgcgca ccgtcaaaga cacggtcaag acgctgctgt atctgtcgag    8400
ctttgtggtt gcggcaatca tttgctggaa aaagtataaa gtcgagattt tcagccaact    8460
gaacggtaat atcgtgggta ttgcggttat ctggcgtgaa ttgctgctgg cgttggttct    8520
gacctgtctg gcgtgcgcgc tgatcgtgct gttgctggat gctattgccg agtactttct    8580
gaccatgaaa gatatgaaga tggacaaaga agaagttaaa cgcgagatga aagagcagga    8640
gggtaacccg gaggtgaagt ctaaacgtcg tgaagtccac atggaaatcc tgagcgaaca    8700
agtcaagtct gacattgaaa atagccgtct gattgtggca aacccctacgc atattaccat    8760 cggcatctac ttcaaaccgg aactgatgcc gattccaatg attagcgtct atgaaaccaa    8820
tcaacgcgcg ctggcggtcc gtgcgtacgc cgagaaagtg ggtgttccgg ttattgtaga    8880
catcaagctg gcgcgcagcc tgttcaaaac gcaccgtcgt tacgacctgg tgagcctgga    8940
ggagatcgac gaggttttgc gcctgctggt ttggttggaa gaggtcgaaa acgcaggcaa    9000
```

```
ggatgtgatc caaccgcagg agaatgaagt gcgtcattaa ctgcaggttt aaactacttg    9060
ggcacgcgtc cattaattag gatcaatagc atgattccgg gcagcacctc cggtatttcc    9120
tttagccgta tcctgagccg tcagacctcc caccaggatg caacccagca taccgacgca    9180
caacaagcgg aaattcaaca agcggcggaa gatagctcgc cgggtgcgga ggttcagaaa    9240
ttcgtccaga gcacggacga gatgtctgct gcgttggcgc agttccgcaa tcgccgtgac    9300
tatgagaaaa agagcagcaa tttgtctaac tccttcgagc gcgttctgga ggacgaggca    9360
ctgccgaaag cgaagcagat tctgaaactg atcagcgtgc atggcggtgc gttggaggat    9420
ttcctgcgtc aggcgcgcag cctgttcccg gacccaagcg atctggtgct ggttctgcgc    9480
gagctgttgc gtcgtaagga cctggaggag atcgtgcgta agaagctgga gagcctgctg    9540
aagcacgtgg aggaacaaac cgacccgaaa accctgaagg ccggtattaa ctgcgcgctg    9600
aaggcgcgtc tgtttggcaa gacgctgtct ctgaaacctg gtctgctgcg tgccagctac    9660
cgccagttca tccaaagcga aagccacgaa gtcgagattt acagcgattg gatcgccagc    9720
tacggttatc agcgtcgcct ggttgttctg gatttcattg aaggcagcct gctgactgac    9780
atcgatgcta acgatgcaag ctgctcccgt ctggagtttg ccaactgct gcgccgtctg    9840 acccagctga aaatgttgcg tagcgccgac ctgctgtttg tctcgacgtt gctgtcttac    9900
agcttcacga aagcatttaa cgctgaggag agcagctggc tgttgctgat gctgtctttg    9960
ctgcaacagc cgcacgaagt ggatagcctg ctggcggaca ttatcggtct gaatgcgctg    10020
ctgttgtccc acaaagagca cgccagcttc ctgcaaatct tctatcaggt ctgtaaggca    10080
atcccgtcta gcctgtttta tgaagagtac tggcaagaag aactgctgat ggcactgcgc    10140
tccatgacgg acattgctta caaacacgaa atggccgaac aacgtcgtac catcgaaaag    10200
ctgtcctaag tttaaaccctt gggcacgcgt ccatgaaaga caggacccac tagatgagct    10260
tgcgcgtacg ccaaattgac cgccgtgaat ggctgctggc ccagactgcg accgaatgtc    10320
agcgtcacgg tcgtgaggcc accctggagt atccgacccg tcagggtatg tgggtccgcc    10380
tgtctgatgc cgaaaaacgc tggtctgcgt ggatcaaacc gggtgattgg ttggaacacg    10440
ttagcccagc actggcgggt gccgcggtca gcgcaggcgc ggagcacctg gtggttccgt    10500
ggctggcggc aaccgaacgc ccgttcgagc tgccggtccc gcacttgagc tgccgtcgtc    10560
tgtgcgtgga gaacccggtt ccgggttccg cactgcctga gggcaagctg ctgcacatca    10620
tgtcggatcg tggtggcctg tggtttgagc atctgccgga gctgccggct gttggcggtg    10680
gccgtccgaa gatgctgcgt tggccgctgc gtttcgttat tggcagcagc gacacccagc    10740
gcagcctgct gggtcgtatc ggtatcggtg atgttctgct gatccgcacc agccgtgctg    10800
aggtttactg ttacgcgaag aaactgggcc actttaatcg tgtggaaggt ggcattattg    10860
tcgaaacgct ggacattcaa catatcgagg aggagaacaa cacgacggaa acggcggaaa    10920
ccctgccggg tctgaatcaa ctgccggtga agctggagtt cgttctgtat cgtaaaaacg    10980
tgacgttggc cgaactggaa gcaatgggtc agcaacaact gctgtccttg ccaaccaatg    11040
cggaactgaa cgtcgaaatc atggcgaatg gcgtgctgct gggtaacggc gaactggtgc    11100
agatgaatga caccctgggt gtcgagattc atgagtggtt gtccgagagc ggtaatggcg    11160
agtagagatc tcttgggcac gcgtccatta aaaaggacca attaagcatg cactctctga    11220
ctcgtatcaa ggtcctgcaa cgtcgttgta ccgtgttcca ttctcagtgc gagtccattc    11280
tgttgcgtta tcaggacgaa gatcgcgcct tgcaggcgga ggaggaggcc atcctggaac    11340
agatcgcagg tctgaaactg ctgttggaca ccctgcgtgc tgaaaatcgt caactgagcc    11400
```

-continued

```
gtgaagaaat ctatacgctg ctgcgcaaac agagcattgt tcgtcgccag attaaggatc   11460
tggagctgca aatcattcag attcaagaaa agcgtagcga gctggaaaag aaacgtgagg   11520
aatttcaaaa gaaaagcaaa tactggctgc gtaaagaagg taactaccag cgctggatta   11580
tccgtcaaaa acgcttctac attcaacgtg agatccagca agaggaggcg gagagcgaag   11640
agatcattta acttgggcac gcgtccatga aagacaggac ccactagatg ttctatgcat   11700
tgtattttga gatccaccat ctggtggcgt ccgcggctct gggttttgcg cgtgttgctc   11760
cgatcttttt ctttctgccg ttcctgaata gcggtgtcct gagcggtgct ccgcgcaacg   11820
cgatcatcat tctggtggcg ctgggtgtat ggccgcacgc cctgaatgag gcgccaccgt   11880
ttctgtctgt ggcaatgatt ccgctggtcc tgcaagaggc agccgtgggt gttatgctgg   11940
gttgcctgtt gtcctggccg ttttgggtta tgcacgcgtt gggctgtatc attgataacc   12000
aacgcggtgc aaccctgtcc agcagcattg atcctgcgaa tggcatcgac accagcgaga   12060
tggccaattt cctgaacatg ttcgcggctg tcgtgtattt gcagaacggt ggcttggtca   12120
cgatggtgga cgtgctgaat aagtcttacc agctgtgtga tccgatgaac gagtgtacgc   12180
cgagcctgcc tccgttgctg accttcatta atcaagtggc ccagaacgca ctggtgctgg   12240
cgtccccggt cgttctggtt ctgctgctgt cggaagtttt cctgggcctg ctgtctcgtt   12300
ttgcaccgca aatgaacgcg ttcgccatta gcctgactgt taaaagcggt attgcggttt   12360
tgatcatgct gctgtatttc agcccggtcc tgccggacaa tgttctgcgt ctgagctttc   12420
aggcgaccgg cctgagcagc tggttctacg aacgtggcgc aacgcatgtg ctggaataag   12480
gatccggcat caaataaaac gaaaggctca gtcgaaagac tgggcctttc gttttatctg   12540
ttgtttgtcg gtgaacgctc tcctgagtag gacaaatccg ccgccctaga actagtccat   12600
aagaatgcgg ccgc                                                     12614
```

<210> SEQ ID NO 156
<211> LENGTH: 23
<212> TYPE: DNA
<213> ORGANISM: Artificial Sequence
<220> FEATURE:
<223> OTHER INFORMATION: synthetic Enterobacteria phage T7 promoter seed
      sequence
<220> FEATURE:
<221> NAME/KEY: modified_base
<222> LOCATION: (16)...(20)
<223> OTHER INFORMATION: n = g, a, c or t

<400> SEQUENCE: 156
taatacgact cactannnnn aga                                            23

<210> SEQ ID NO 157
<211> LENGTH: 23
<212> TYPE: DNA
<213> ORGANISM: Artificial Sequence
<220> FEATURE:
<223> OTHER INFORMATION: synthetic Enterobacteria phage T7 wild type
      (WT) promoter

<400> SEQUENCE: 157
taatacgact cactataggg aga                                            23

<210> SEQ ID NO 158
<211> LENGTH: 23
<212> TYPE: DNA
<213> ORGANISM: Artificial Sequence
<220> FEATURE:

<223> OTHER INFORMATION: synthetic mutant Enterobacteria phage T7
       promoter Mut1

<400> SEQUENCE: 158
taatacgact cactacaggc aga                                             23

<210> SEQ ID NO 159
<211> LENGTH: 23
<212> TYPE: DNA
<213> ORGANISM: Artificial Sequence
<220> FEATURE:
<223> OTHER INFORMATION: synthetic mutant Enterobacteria phage T7
       promoter Mut2

<400> SEQUENCE: 159
taatacgact cactagagag aga                                             23

<210> SEQ ID NO 160
<211> LENGTH: 23
<212> TYPE: DNA
<213> ORGANISM: Artificial Sequence
<220> FEATURE:
<223> OTHER INFORMATION: synthetic mutant Enterobacteria phage T7
       promoter Mut3

<400> SEQUENCE: 160
taatacgact cactaatggg aga                                             23

<210> SEQ ID NO 161
<211> LENGTH: 23
<212> TYPE: DNA
<213> ORGANISM: Artificial Sequence
<220> FEATURE:
<223> OTHER INFORMATION: synthetic mutant Enterobacteria phage T7
       promoter Mut4

<400> SEQUENCE: 161
taatacgact cactataggt aga                                             23

<210> SEQ ID NO 162
<211> LENGTH: 23
<212> TYPE: DNA
<213> ORGANISM: Artificial Sequence
<220> FEATURE:
<223> OTHER INFORMATION: synthetic mutant Enterobacteria phage T7
       promoter Mut5

<400> SEQUENCE: 162
taatacgact cactaaaggg aga                                             23

<210> SEQ ID NO 163
<211> LENGTH: 23
<212> TYPE: DNA
<213> ORGANISM: Artificial Sequence
<220> FEATURE:
<223> OTHER INFORMATION: synthetic mutant Enterobacteria phage T7
       promoter Mut6

<400> SEQUENCE: 163
taatacgact cactattggg aga                                             23

<210> SEQ ID NO 164
<211> LENGTH: 26
<212> TYPE: DNA
<213> ORGANISM: Artificial Sequence
<220> FEATURE:
<223> OTHER INFORMATION: synthetic Klebsiella oxytoca nif operon deletion mutant NF8 deletion region
<220> FEATURE:
<221> NAME/KEY: modified_base
<222> LOCATION: (26)...(26)
<223> OTHER INFORMATION: c modified by Km cassette and SEQ ID NO:163

<400> SEQUENCE: 164
gcaggagaac taaaggcccg gcatgc                                         26

<210> SEQ ID NO 165
<211> LENGTH: 26
<212> TYPE: DNA
<213> ORGANISM: Artificial Sequence
<220> FEATURE:
<223> OTHER INFORMATION: synthetic Klebsiella oxytoca nif operon
      deletion mutant NF8 deletion region
<220> FEATURE:
<221> NAME/KEY: modified_base
<222> LOCATION: (1)...(1)
<223> OTHER INFORMATION: g modified by Km cassette and SEQ ID NO:164

<400> SEQUENCE: 165
gcatgcaagc gcccatggcc ccggca                                         26

<210> SEQ ID NO 166
<211> LENGTH: 46
<212> TYPE: DNA
<213> ORGANISM: Artificial Sequence
<220> FEATURE:
<223> OTHER INFORMATION: synthetic Klebsiella oxytoca nif in-frame
      deletion mutant UC12 deletion region

<400> SEQUENCE: 166
cataaacagg cacggctggt ggtaccccat caggtgcccc gcgtca                   46

<210> SEQ ID NO 167
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF9 deletion region

<400> SEQUENCE: 167
atggccccgg caggcgcaat gcatgcgacg ctcttcccca cgttac                   46

<210> SEQ ID NO 168
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant UC14 deletion region

<400> SEQUENCE: 168
gacgctcttc cccacgttac gcatgcgatc cggacccgcg ccgcta                   46

<210> SEQ ID NO 169
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant UC15 deletion region

<400> SEQUENCE: 169
ctcttcccca cgttacgctc gcatgcgatc cggacccgcg ccgcta                   46

<210> SEQ ID NO 170
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF10 deletion region

<400> SEQUENCE: 170
cggacccgcg ccgctagccg gcatgcatct ttggcagcag agccag         46

<210> SEQ ID NO 171
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF11 deletion region

<400> SEQUENCE: 171
cggacccgcg ccgctagccg gcatgcagcc tcggcggcta cccgtt         46

<210> SEQ ID NO 172
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF12 deletion region

<400> SEQUENCE: 172
actggttatc ctgatccagc gcatgccttt gcactaccgc ggccca         46

<210> SEQ ID NO 173
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF13 deletion region

<400> SEQUENCE: 173
ccgttaacgc ctacagcacg gcatgccttt gcactaccgc ggccca         46

<210> SEQ ID NO 174
<211> LENGTH: 40
<212> TYPE: DNA
<213> ORGANISM: Artificial Sequence
<220> FEATURE:
<223> OTHER INFORMATION: synthetic Klebsiella oxytoca nif operon
      deletion mutant NF14 deletion region

<400> SEQUENCE: 174
attcagggac gcgggttgcc atgtgattat gcgacgtctt         40

<210> SEQ ID NO 175
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF24 deletion region

<400> SEQUENCE: 175
gtcaaacacc agaatattga gagctctgtc gtttctgtga caaagc         46

<210> SEQ ID NO 176
<211> LENGTH: 46
<212> TYPE: DNA
<213> ORGANISM: Artificial Sequence
<220> FEATURE:
<223> OTHER INFORMATION: synthetic Klebsiella oxytoca nif operon
      deletion mutant NF25 deletion region

<400> SEQUENCE: 176
cggacccgcg ccgctagccg gcatgcctttt gcactaccgc ggccca         46

<210> SEQ ID NO 177
<211> LENGTH: 46
<212> TYPE: DNA
<213> ORGANISM: Artificial Sequence
<220> FEATURE:
<223> OTHER INFORMATION: synthetic Klebsiella oxytoca whole nif deletion
      mutant NF26 deletion region

<400> SEQUENCE: 177
gtcaaacacc agaatattga ctcgagatgt gattatgcga cgtctt         46

<210> SEQ ID NO 178
<211> LENGTH: 23
<212> TYPE: DNA
<213> ORGANISM: Artificial Sequence
<220> FEATURE:
<223> OTHER INFORMATION: synthetic wild type (WT) Enterobacteria phage
      T7 promoter part number SBa_000443

<400> SEQUENCE: 178
taatacgact cactataggg aga         23

<210> SEQ ID NO 179
<211> LENGTH: 23
<212> TYPE: DNA
<213> ORGANISM: Artificial Sequence
<220> FEATURE:
<223> OTHER INFORMATION: synthetic Enterobacteria phage T7 promoter 1
      part number SBa_000444

<400> SEQUENCE: 179
taatacgact cactacaggc aga         23

<210> SEQ ID NO 180
<211> LENGTH: 23
<212> TYPE: DNA
<213> ORGANISM: Artificial Sequence
<220> FEATURE:
<223> OTHER INFORMATION: synthetic Enterobacteria phage T7 promoter 2
      part number SBa_000445

<400> SEQUENCE: 180
taatacgact cactagagag aga         23

<210> SEQ ID NO 181
<211> LENGTH: 23
<212> TYPE: DNA
<213> ORGANISM: Artificial Sequence
<220> FEATURE:
<223> OTHER INFORMATION: synthetic Enterobacteria phage T7 promoter 3
      part number SBa_000446

<400> SEQUENCE: 181
taatacgact cactaatggg aga         23

<210> SEQ ID NO 182

```
<211> LENGTH: 23
<212> TYPE: DNA
<213> ORGANISM: Artificial Sequence
<220> FEATURE:
<223> OTHER INFORMATION: synthetic Enterobacteria phage T7 promoter 4
      part number SBa_000447

<400> SEQUENCE: 182
taatacgact cactattggg aga                                           23

<210> SEQ ID NO 183
<211> LENGTH: 48
<212> TYPE: DNA
<213> ORGANISM: Artificial Sequence
<220> FEATURE:
<223> OTHER INFORMATION: synthetic Enterobacteria phage T7 wild type
      (WT) terminator part number SBa_000450

<400> SEQUENCE: 183
tagcataacc ccttggggcc tctaaacggg tcttgagggg ttttttgt                48

<210> SEQ ID NO 184
<211> LENGTH: 29
<212> TYPE: DNA
<213> ORGANISM: Artificial Sequence
<220> FEATURE:
<223> OTHER INFORMATION: synthetic Enterobacteria phage T7 terminator
      part number SBa_000451

<400> SEQUENCE: 184
tacatatcgg gggggtaggg gttttttgt                                     29

<210> SEQ ID NO 185
<211> LENGTH: 37
<212> TYPE: DNA
<213> ORGANISM: Artificial Sequence
<220> FEATURE:
<223> OTHER INFORMATION: synthetic Enterobacteria phage T7 terminator
      part number SBa_000452

<400> SEQUENCE: 185
tactctaacc ccatcggccg tcttaggggt tttttgt                            37

<210> SEQ ID NO 186
<211> LENGTH: 50
<212> TYPE: DNA
<213> ORGANISM: Artificial Sequence
<220> FEATURE:
<223> OTHER INFORMATION: synthetic insulator part number SBa_000453

<400> SEQUENCE: 186
gcgtgcgtac accttaatca ccgcttcatg ctaaggtcct ggctgcatgc              50

<210> SEQ ID NO 187
<211> LENGTH: 50
<212> TYPE: DNA
<213> ORGANISM: Artificial Sequence
<220> FEATURE:
<223> OTHER INFORMATION: synthetic insulator part number SBa_000454

<400> SEQUENCE: 187
caaacacccc atgtcgatac tgaacgaatc gacgcacact cccttccttg              50

<210> SEQ ID NO 188
<211> LENGTH: 40
<212> TYPE: DNA
<213> ORGANISM: Artificial Sequence
```

```
<220> FEATURE:
<223> OTHER INFORMATION: synthetic insulator part number SBa_000455

<400> SEQUENCE: 188
cctgattgta tccgcatctg atgctaccgt ggttgagtta                              40

<210> SEQ ID NO 189
<211> LENGTH: 40
<212> TYPE: DNA
<213> ORGANISM: Artificial Sequence
<220> FEATURE:
<223> OTHER INFORMATION: synthetic insulator part number SBa_000456

<400> SEQUENCE: 189 cattttgcc ttgcgacaga cctcctactt agattgccac                               40

<210> SEQ ID NO 190
<211> LENGTH: 40
<212> TYPE: DNA
<213> ORGANISM: Artificial Sequence
<220> FEATURE:
<223> OTHER INFORMATION: synthetic insulator part number SBa_000457

<400> SEQUENCE: 190
tgtcacgcta ggaggcaatt ctataagaat gcacactgca                              40

<210> SEQ ID NO 191
<211> LENGTH: 30
<212> TYPE: DNA
<213> ORGANISM: Artificial Sequence
<220> FEATURE:
<223> OTHER INFORMATION: synthetic insulator part number SBa_000458

<400> SEQUENCE: 191
ccgtggttga gtcagcgtcg agcacgcggc                                         30

<210> SEQ ID NO 192
<211> LENGTH: 40
<212> TYPE: DNA
<213> ORGANISM: Artificial Sequence
<220> FEATURE:
<223> OTHER INFORMATION: synthetic insulator part number SBa_000459

<400> SEQUENCE: 192
cgcgacttcc agagaagaag actactgact tgagcgttcc                              40

<210> SEQ ID NO 193
<211> LENGTH: 40
<212> TYPE: DNA
<213> ORGANISM: Artificial Sequence
<220> FEATURE:
<223> OTHER INFORMATION: synthetic insulator part number SBa_000460

<400> SEQUENCE: 193
actacgagat ttgaggtaaa ccaaataagc acgtagtggc                              40

<210> SEQ ID NO 194
<211> LENGTH: 18
<212> TYPE: DNA
<213> ORGANISM: Artificial Sequence
<220> FEATURE:
<223> OTHER INFORMATION: synthetic insulator part number SBa_000461

<400> SEQUENCE: 194
gtctgtagca cgtgcatc                                                      18
```

<210> SEQ ID NO 195
<211> LENGTH: 18
<212> TYPE: DNA
<213> ORGANISM: Artificial Sequence
<220> FEATURE:
<223> OTHER INFORMATION: synthetic insulator part number SBa_000462

<400> SEQUENCE: 195
ggtcattaca acgtttat                                                     18

<210> SEQ ID NO 196
<211> LENGTH: 40
<212> TYPE: DNA
<213> ORGANISM: Artificial Sequence
<220> FEATURE:
<223> OTHER INFORMATION: synthetic insulator part number SBa_000463

<400> SEQUENCE: 196
aacatagcgt tccatgaggg ctagaattac ctaccggcct                              40

<210> SEQ ID NO 197
<211> LENGTH: 40
<212> TYPE: DNA
<213> ORGANISM: Artificial Sequence
<220> FEATURE:
<223> OTHER INFORMATION: synthetic insulator part number SBa_000464

<400> SEQUENCE: 197
cattgtaata gccaccaaaa gagtgatgat agtcatgggt                              40

<210> SEQ ID NO 198
<211> LENGTH: 40
<212> TYPE: DNA
<213> ORGANISM: Artificial Sequence
<220> FEATURE:
<223> OTHER INFORMATION: synthetic insulator part number SBa_000465

<400> SEQUENCE: 198
gagttactgg ccctgatttc tccgcttcta ataccgcaca                              40

<210> SEQ ID NO 199
<211> LENGTH: 40
<212> TYPE: DNA
<213> ORGANISM: Artificial Sequence
<220> FEATURE:
<223> OTHER INFORMATION: synthetic insulator part number SBa_000466

<400> SEQUENCE: 199
gactcaacac gctagggacg tgaagtcgat tccttcgatg                              40

<210> SEQ ID NO 200
<211> LENGTH: 40
<212> TYPE: DNA
<213> ORGANISM: Artificial Sequence
<220> FEATURE:
<223> OTHER INFORMATION: synthetic insulator part number SBa_000467

<400> SEQUENCE: 200
tcgagaaaca aggcagttcc gggctgaaag tagcgccggg                              40

<210> SEQ ID NO 201
<211> LENGTH: 40
<212> TYPE: DNA
<213> ORGANISM: Artificial Sequence
<220> FEATURE:
<223> OTHER INFORMATION: synthetic insulator part number SBa_000468

<400> SEQUENCE: 201
acgccacgcg tagtgagaca tacacgttcg ttgggttcac                          40

<210> SEQ ID NO 202
<211> LENGTH: 40
<212> TYPE: DNA
<213> ORGANISM: Artificial Sequence
<220> FEATURE:
<223> OTHER INFORMATION: synthetic insulator part number SBa_000508

<400> SEQUENCE: 202
tgcagtttta ttctctcgcc agcactgtaa taggcactaa                          40

<210> SEQ ID NO 203
<211> LENGTH: 110
<212> TYPE: DNA
<213> ORGANISM: Artificial Sequence
<220> FEATURE:
<223> OTHER INFORMATION: synthetic ribosome binding site (RBS) part
      number SBa_000475

<400> SEQUENCE: 203
ttaaagagga gaaattaagc atgaaaacta tggacggtaa cgctgcggct gcatggatta    60
gctacgcctt taccgaagtg gctgcgatct acccgattac gccgagcacc              110

<210> SEQ ID NO 204
<211> LENGTH: 126
<212> TYPE: DNA
<213> ORGANISM: Artificial Sequence
<220> FEATURE:
<223> OTHER INFORMATION: synthetic ribosome binding site (RBS) part
      number SBa_000469

<400> SEQUENCE: 204
tactagagac aataaactaa cataaggagg ataaatatga ccatgcgtca gtgcgcgatt    60
tatggcaaag gtggtattgg caaaagcacg acgacccaga acttggtggc ggccctggcc   120
gagatg                                                              126

<210> SEQ ID NO 205
<211> LENGTH: 174
<212> TYPE: DNA
<213> ORGANISM: Artificial Sequence
<220> FEATURE:
<223> OTHER INFORMATION: synthetic ribosome binding site (RBS) part
      number SBa_000470

<400> SEQUENCE: 205
gcgtgcgtac accttaatca ccgcttcatg ctaaggtcct ggctgcatgc aaaaattcac    60
atccctatct agcggaggag ccggatgatg actaatgcta ctggcgaacg taacctggca   120
ctgattcaag aagtactgga agtgttcccg gaaaccgcgc gcaaagagcg ccgt         174

<210> SEQ ID NO 206
<211> LENGTH: 174
<212> TYPE: DNA
<213> ORGANISM: Artificial Sequence
<220> FEATURE:
<223> OTHER INFORMATION: synthetic ribosome binding site (RBS) part
      number SBa_000471

<400> SEQUENCE: 206
caaacacccc atgtcgatac tgaacgaatc gacgcacact cccttccttg caatctcata    60

```
ctctcaaaaa ttaggcgagg taacatgtct caaactatcg ataaaatcaa ctcttgttac      120
ccgctgttcg agcaggacga atatcaggaa ctgttccgta caaacgtca gctg             174
```

<210> SEQ ID NO 207
<211> LENGTH: 156
<212> TYPE: DNA
<213> ORGANISM: Artificial Sequence
<220> FEATURE:
<223> OTHER INFORMATION: synthetic ribosome binding site (RBS) part
      number SBa_000472

<400> SEQUENCE: 207

```
cctgattgta tccgcatctg atgctaccgt ggttgagtta ccatactcac tcccggaggt      60
acttctatgt ctgacaatga taccctgttt tggcgcatgc tggcgctgtt tcagtcgctg     120
ccggatttgc agccggctca aatcgtcgat tggctg                                156
```

<210> SEQ ID NO 208
<211> LENGTH: 162
<212> TYPE: DNA
<213> ORGANISM: Artificial Sequence
<220> FEATURE:
<223> OTHER INFORMATION: synthetic ribosome binding site (RBS) part
      number SBa_000473

<400> SEQUENCE: 208

```
cattttttgcc ttgcgacaga cctcctactt agattgccac actattcaat acatcactgg    60
aggttattac aaatgaaggg taacgagatt cttgctctgc tggacgaacc ggcctgtgaa     120
cacaaccata aacagaaatc cggctgtagc gccccaaagc cg                         162
```

<210> SEQ ID NO 209
<211> LENGTH: 161
<212> TYPE: DNA
<213> ORGANISM: Artificial Sequence
<220> FEATURE:
<223> OTHER INFORMATION: synthetic ribosome binding site (RBS) part
      number SBa_000474

<400> SEQUENCE: 209

```
tgtcacgcta ggaggcaatt ctataagaat gcacactgca cctaaaccta ccacacctga     60
ggagagtaat tatggcagac attttccgca ctgataagcc gttggctgtg tcgccgatca    120
agaccggcca gccgctgggt gcgatcctgg cgtccctggg t                         161
```

<210> SEQ ID NO 210
<211> LENGTH: 167
<212> TYPE: DNA
<213> ORGANISM: Artificial Sequence
<220> FEATURE:
<223> OTHER INFORMATION: synthetic ribosome binding site (RBS) part
      number SBa_000476

<400> SEQUENCE: 210

```
aacatagcgt tccatgaggg ctagaattac ctaccggcct cagatactga caaataaacc     60
agcgaaggag gttcctaatg tggaactaca gcgagaaagt caaggaccat tcttcaatc    120 cgcgcaacgc gcgtgttgtg gataacgcaa atgcggtggg cgacgtc                   167
```

<210> SEQ ID NO 211
<211> LENGTH: 169
<212> TYPE: DNA
<213> ORGANISM: Artificial Sequence
<220> FEATURE:
<223> OTHER INFORMATION: synthetic ribosome binding site (RBS) part number SBa_000477

<400> SEQUENCE: 211
cattgtaata gccaccaaaa gagtgatgat agtcatgggt gatacccgta gaccattctg    60
aaatcgaagg aggttttcca tgaaacaagt gtacctggac aacaacgcga ccacccgcct   120
ggacccgatg gttctggaag cgatgatgcc gtttctcacg gatttctat              169

<210> SEQ ID NO 212
<211> LENGTH: 164
<212> TYPE: DNA
<213> ORGANISM: Artificial Sequence
<220> FEATURE:
<223> OTHER INFORMATION: synthetic ribosome binding site (RBS) part
      number SBa_000478

<400> SEQUENCE: 212
gagttactgg ccctgatttc tccgcttcta ataccgcaca gcgactagga gcctaactcg    60
ccacaaggaa acatatggag cgcgtcttga tcaacgatac taccctgcgt gatggcgaac   120
aatctccggg cgtagcgttt cgtacctccg agaaagttgc catc                    164

<210> SEQ ID NO 213
<211> LENGTH: 165
<212> TYPE: DNA
<213> ORGANISM: Artificial Sequence
<220> FEATURE:
<223> OTHER INFORMATION: synthetic ribosome binding site (RBS) part
      number SBa_000479

<400> SEQUENCE: 213
gactcaacac gctagggacg tgaagtcgat tccttcgatg cagaaggcga gaactagatt    60
taagggccat tatagatgga gtggttttac cagattccgg gtgtagacga attgcgcagc   120
gctgaatcct tctttcagtt cttcgcggtt ccataccagc cggaa                   165

<210> SEQ ID NO 214
<211> LENGTH: 166
<212> TYPE: DNA
<213> ORGANISM: Artificial Sequence
<220> FEATURE:
<223> OTHER INFORMATION: synthetic ribosome binding site (RBS) part
      number SBa_000480

<400> SEQUENCE: 214
tcgagaaaca aggcagttcc gggctgaaag tagcgccggg acaagtcccg tattataacc    60
gcctaggagg tgttggatgc gcccgaaatt caccttctct gaagaggtcc gcgtagttcg   120
cgcgattcgt aatgatggca ccgtggcggg ttttgcgcca ggtgcg                  166

<210> SEQ ID NO 215
<211> LENGTH: 164
<212> TYPE: DNA
<213> ORGANISM: Artificial Sequence
<220> FEATURE:
<223> OTHER INFORMATION: synthetic ribosome binding site (RBS) part
      number SBa_000481

<400> SEQUENCE: 215
acgccacgcg tagtgagaca tacacgttcg ttgggttcac tcagagactg aagttattac    60
ccaggaggtc tataatgaat ccgtggcagc gctttgcccg tcaacgcctt gctcgcagcc   120
gctggaaccg tgatccggct gctctcgacc cagccgatac ccca                    164

<210> SEQ ID NO 216
<211> LENGTH: 124
<212> TYPE: DNA
<213> ORGANISM: Artificial Sequence
<220> FEATURE:
<223> OTHER INFORMATION: synthetic ribosome binding site (RBS) part
      number SBa_000482

<400> SEQUENCE: 216
gacaagagtc tcaattataa ggaggcttta ctacatggcg aacatcggca tcttctttgg    60
tacggatacc ggcaaaaccc gcaagattgc gaagatgatt cacaaacagc tgggcgagct   120
ggcc                                                                124

<210> SEQ ID NO 217
<211> LENGTH: 169
<212> TYPE: DNA
<213> ORGANISM: Artificial Sequence
<220> FEATURE:
<223> OTHER INFORMATION: synthetic ribosome binding site (RBS) part
      number SBa_000483

<400> SEQUENCE: 217
cgcgacttcc agagaagaag actactgact tgagcgttcc ctctctgtaa tacatcaaat    60
caatcatagg agggctaaaa tgacctcttg ttcgtcgttt tctggcggta aagcgtgccg   120
tccggccgat gactccgcgc tgactccgct ggtggccgac aaggcagct               169

<210> SEQ ID NO 218
<211> LENGTH: 152
<212> TYPE: DNA
<213> ORGANISM: Artificial Sequence
<220> FEATURE:
<223> OTHER INFORMATION: synthetic ribosome binding site (RBS) part
      number SBa_000475

<400> SEQUENCE: 218
aactacgaga tttgaggtaa accaaataag cacgtagtgg cattaaagag gagaaattaa    60
gcatgccgcc attggactgg ttgcgtcgtt tgtggttact ctatcacgcc ggcaaaggca   120
gctttccgct tcgtatgggc ttgtcgccgc gt                                 152

<210> SEQ ID NO 219
<211> LENGTH: 1761
<212> TYPE: DNA
<213> ORGANISM: Artificial Sequence
<220> FEATURE:
<223> OTHER INFORMATION: synthetic P-tac promoter and lacI cassette part
      number SBa_000561

<400> SEQUENCE: 219
caattcgcgc taacttacat taattgcgtt gcgctcactg cccgctttcc agtcgggaaa    60
cctgtcgtgc cagctgcatt aatgaatcgg ccaacgcgcg gggagaggcg gtttgcgtat   120
tgggcgccag ggtggttttt cttttcacca gtgagacggg caacagctga ttgcccttca   180
ccgcctggcc ctgagagagt tgcagcaagc ggtccacgct ggtttgcccc agcaggcgaa   240
aatcctgttt gatggtggtt gacggcggga tataacatga gctgtcttcg gtatcgtcgt   300
atcccactac cgagatatcc gcaccaacgc gcagcccgga ctcggtaatg gcgcgcattg   360
cgcccagcgc catctgatcg ttggcaacca gcatcgcagt gggaacgatg ccctcattca   420
gcatttgcat ggtttgttga aaaccggaca tggcactcca gtcgccttcc cgttccgcta   480
tcggctgaat ttgattgcga gtgagatatt tatgccagcc agccagacgc agacgcgccg   540

```
agacagaact taatgggccc gctaacagcg cgatttgctg gtgacccaat gcgaccagat    600
gctccacgcc cagtcgcgta ccgtcttcat gggagaaaat aatactgttg atgggtgtct    660
ggtcagagac atcaagaaat aacgccggaa cattagtgca ggcagcttcc acagcaatgg    720
catcctggtc atccagcgga tagttaatga tcagcccact gacgcgttgc gcgagaagat    780
tgtgcaccgc cgctttacag gcttcgacgc cgcttcgttc taccatcgac accaccacgc    840
tggcacccag ttgatcggcg cgagatttaa tcgccgcgac aatttgcgac ggcgcgtgca    900
gggccagact ggaggtggca acgccaatca gcaacgactg tttgcccgcc agttgttgtg    960
ccacgcggtt gggaatgtaa ttcagctccg ccatcgccgc ttccactttt tcccgcgttt   1020
tcgcagaaac gtggctggcc tggttcacca cgcgggaaac ggtctgataa gagacaccgg   1080
catactctgc gacatcgtat aacgttactg gtttcacatt caccaccctg aattgactct   1140
cttccgggcg ctatcatgcc ataccgcgaa aggttttgca ccattcgatg gtgtcaacgt   1200
aaatgcatgc cgcttcgcct cgcgcgcga attggccgcc atgccggcga taatggcctg   1260
cttctcgccg aaacgtttgg tggcgggacc agtgacgaag gcttgagcga gggcgtgcaa   1320
gattccgaat accgcaagcg acaggccgat catcgtcgcg ctccagcgaa agcggtcctc   1380
gccgaaaatg acccagagcg ctgccggcac ctgtcctacg agttgcatga taagaagac    1440 agtcataagt gcggcgacga tagtcatgcc ccgcgcccac cggaaggagc tgactgggtt   1500
gaaggctctc aagggcatcg gcggagctta tcgactgcac ggtgcaccaa tgcttctggc   1560
gtcaggcagc catcggaagc tgtggtatgg ctgtgcaggt cgtaaatcac tgcataattc   1620
gtgtcgctca aggcgcactc ccgttctgga taatgttttt tgcgccgaca tcataacggt   1680
tctggcaaat attctgaaat gagctgttga caattaatca tcggctcgta taatgtgtgg   1740
aattgtgagc ggataacaat t                                              1761
```

<210> SEQ ID NO 220
<211> LENGTH: 740
<212> TYPE: DNA
<213> ORGANISM: Artificial Sequence
<220> FEATURE:
<223> OTHER INFORMATION: synthetic P-tet promoter and tetR cassette part
      number SBa_000562

<400> SEQUENCE: 220

```
ttattaggac ccactttcac atttaagttg ttttttctaat ccgcatatga tcaattcaag     60
gccgaataag aaggctggct ctgcaccttg gtgatcaaat aattcgatag cttgtcgtaa    120
taatggcggc atactatcag tagtaggtgt ttcccttttct tctttagcga cttgatgctc    180
ttgatcttcc aatacgcaac ctaaagtaaa atgccccaca gcgctgagtg catataatgc    240
attctctagt gaaaaacctt gttggcataa aaaggctaat tgattttcga gagtttcata    300
ctgtttttct gtaggccgtg tacctaaatg tacttttgct ccatcgcgat gacttagtaa    360
agcacatcta aaacttttag cgttattacg taaaaaatct tgccagcttt ccccttctaa    420
agggcaaaag tgagtatggt gcctatctaa catctcaatg gctaaggcgt cgagcaaagc    480
ccgcttattt tttacatgcc aatacaatgt aggctgctct acacctagct tctgggcgag    540
tttacgggtt gttaaacctt cgattccgac ctcattaagc agctctaatg cgctgttaat    600
cactttactt ttatctaatc tggacatcga ggcctttcct gtgtgagcta gcactgtacc    660
taggactgag ctagccgtca attttttccc tatcagtgat agagattgac atccctatca    720
gtgatagata taatgagcac                                                 740
```

<210> SEQ ID NO 221
<211> LENGTH: 702
<212> TYPE: DNA
<213> ORGANISM: Artificial Sequence
<220> FEATURE:
<223> OTHER INFORMATION: synthetic red fluorescent protein (mRFP) fluorescsnt reporter part number SBa_000484

<400> SEQUENCE: 221

| | | | | | |
|---|---|---|---|---|---|
| atgtccagat | tagataaaag | taaagttgcg | agctctgaag | acgttatcaa | agagttcatg | 60 |
| cgtttcaaag | ttcgtatgga | aggttccgtt | aacggtcacg | agttcgaaat | cgaaggtgaa | 120 |
| ggtgaaggtc | gtccgtacga | aggtacccag | accgctaaac | tgaaagttac | caaaggtggt | 180 |
| ccgctgccgt | tcgcttggga | catcctgtcc | ccgcagttcc | agtacggttc | caaagcttac | 240 |
| gttaaacacc | cggctgacat | cccggactac | ctgaaactgt | ccttcccgga | aggtttcaaa | 300 |
| tgggaacgtg | ttatgaactt | cgaagacggt | ggtgttgtta | ccgttaccca | ggactcctcc | 360 |
| ctgcaagacg | gtgagttcat | ctacaaagtt | aaactgcgtg | gtaccaactt | cccgtccgac | 420 |
| ggtccggtta | tgcagaaaaa | aaccatgggt | tgggaagctt | ccaccgaacg | tatgtacccg | 480 |
| gaagacggtc | tctgaaagg | tgaaatcaaa | atgcgtctga | actgaaaga | cggtggtcac | 540 |
| tacgacgctg | aagttaaaac | cacctacatg | gctaaaaaac | cggttcagct | gccgggtgct | 600 |
| tacaaaaccg | acatcaaact | ggacatcacc | tcccacaacg | aagactacac | catcgttgaa | 660 |
| cagtacgaac | gtgctgaagg | tcgtcactcc | accggtgctt | aa | | 702 |

<210> SEQ ID NO 222
<211> LENGTH: 2652
<212> TYPE: DNA
<213> ORGANISM: Artificial Sequence
<220> FEATURE:
<223> OTHER INFORMATION: synthetic Enterobacteria phage T7* variant RNA polymerase (RNAP) part number SBa_000514

<400> SEQUENCE: 222

| | | | | | |
|---|---|---|---|---|---|
| atgaacacga | ttaacatcgc | taagaacgac | ttctctgaca | tcgaactggc | tgctatcccg | 60 |
| ttcaacactc | tggctgacca | ttacggtgag | cgtttagctc | gcgaacagtt | ggcccttgag | 120 |
| catgagtctt | acgagatggg | tgaagcacgc | ttccgcaaga | tgtttgagcg | tcaacttaaa | 180 |
| gctggtgagg | ttgcggataa | cgctgccgcc | aagcctctca | tcactaccct | actccctaag | 240 |
| atgattgcac | gcatcaacga | ctggtttgag | gaagtgaaag | ctaagcgcgg | caagcgcccg | 300 |
| acagccttcc | agttcctgca | agaaatcaag | ccggaagccg | tagcgtacat | caccattaag | 360 |
| accactctgg | cttgcctaac | cagtgctgac | aatacaaccg | ttcaggctgt | agcaagcgca | 420 |
| atcggtcggg | ccattgagga | cgaggctcgc | ttcggtcgta | tccgtgacct | tgaagctaag | 480 |
| cacttcaaga | aaaacgttga | ggaacaactc | aacaagcgcg | tagggcacgt | ctacaagaaa | 540 |
| gcatttatgc | aagttgtcga | ggctgacatg | ctctctaagg | gtctactcgg | tggcgaggcg | 600 |
| tggtcttcgt | ggcataagga | agactctatt | catgtaggag | tacgctgcat | cgagatgctc | 660 |
| attgagtcaa | ccggaatggt | tagcttacac | cgccaaaatg | ctggcgtagt | aggtcaagac | 720 |
| tctgagacta | tcgaactcgc | acctgaatac | gctgaggcta | tcgcaacccg | tgcaggtgcg | 780 |
| ctggctggca | tctctccgat | gttccaacct | tgcgtagttc | ctcctaagcc | gtggactggc | 840 |
| attactggtg | gtggctattg | ggctaacggt | cgtcgtcctc | tggcgctggt | gcgtactcac | 900 |
| agtaagaaag | cactgatgcg | ctacgaagac | gtttacatgc | ctgaggtgta | caaagcgatt | 960 |
| aacattgcgc | aaaacaccgc | atggaaaatc | aacaagaaag | tcctagcggt | cgccaacgta | 1020 |

```
atcaccaagt ggaagcattg tccggtcgag acatccctg cgattgagcg tgaagaactc    1080
ccgatgaaac cggaagacat cgacatgaat cctgaggctc tcaccgcgtg aaacgtgct    1140 gccgctgctg tgtaccgcaa ggacaaggct cgcaagtctc gccgtatcag ccttgagttc    1200
atgcttgagc aagccaataa gtttgctaac cataaggcca tctggttccc ttacaacatg    1260
gactggcgcg tcgtgttta cgctgtgtca atgttcaacc cgcaaggtaa cgatatgacc    1320
aaaggactgc ttacgctggc gaaaggtaaa ccaatcggta aggaaggtta ctactggctg    1380
aaaatccacg gtgcaaactg tgcgggtgtc gacaaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagagttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtacgat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aa                                                       2652
```

<210> SEQ ID NO 223
<211> LENGTH: 3504
<212> TYPE: DNA
<213> ORGANISM: Artificial Sequence
<220> FEATURE:
<223> OTHER INFORMATION: synthetic Klebsiella pneumoniae nifJ

<400> SEQUENCE: 223

```
atgaaaacta tggacggtaa cgctgcggct gcatggatta gctacgcctt taccgaagtg     60
gctgcgatct acccgattac gccgagcacc ccgatggcgg aaaatgtgga cgaatgggct    120
gcgcagggca agaagaacct cttcggccag ccggtgcgcc tgatggagat gcagtcggaa    180
gcgggtgcag caggtgctgt gcatggcgcc ttgcaagctg gcgcactgac gaccacctac    240
accgcgtcgc agggcctgtt gctgatgatc ccaaacatgt acaaaatcgc gggtgaactg    300 ctgccggggtg tctttcatgt ttcggcacgc gcactggcca ccaatagcct caacatcttt    360
```

```
ggcgatcatc aggatgtaat ggcggtgcgc caaacgggct gcgcgatgtt ggccgagaat       420
aacgtccagc aagttatgga tttgtccgcg gtagcccact tggcagcgat caaaggtcgc       480
attccgttcg tgaacttctt cgatggcttt cgcaccagcc acgaaatcca gaagatcgag       540
gttctggaat atgaacagct ggccaccttg ttggatcgtc cggccctgga cagcttccgc       600
cgtaacgccc ttcacccgga ccacccggtc atccgtggca ccgcccagaa cccggacatc       660
tacttccagg aacgtgaggc cggtaaccgt ttctatcagg cgctcccgga tattgtggaa       720
tcttacatga cccagatttc tgccctgact ggtcgcgagt atcacctgtt taactacact       780
ggtgctgcgg atgcggagcg cgtgatcatc gcgatgggct ctgtctgtga caccgtccaa       840
gaggtggttg acacgctgaa tgcagcgggt gagaaagttg gtctgctctc cgttcatctt       900
ttccgcccgt tttcgttagc gcacttcttc gcccaactgc cgaaaactgt acagcgtatc       960
gcagtattgg accgtacgaa agagccaggt gctcaagcag agccgctgtg cctcgatgtg      1020
aagaatgcct tttaccacca tgacgatgcc ccgttgattg tgggtggtcg ctatgccttg      1080
ggcggtaagg acgtgttgcc gaacgatatt gcggccgtgt ttgataacct gaacaaaccg      1140
ctgccgatgg acggcttcac gctgggtatc gtggacgatg ttaccttcac ctctctcccg      1200
ccagcgcagc agaccctggc ggtttctcac gacggcatca cggcatgtaa gttttggggc      1260
atgggctccg acggcacggt tggtgcgaac aagtccgcga tcaagattat cggcgacaaa      1320
acgccactgt atgcgcaagc gtacttttcc tacgactcga agaagagcgg tggtattacc      1380
gtcagccatc tgcgttttgg tgatcgcccg atcaactccc cgtatttgat ccatcgcgcg      1440
gatttcatct cgtgcagcca gcaaagctat gttgaacgct acgatctgct ggatggcctt      1500
aaaccgggtg gcacctttct gctgaactgc tcctggagcg atgccgaact ggagcaacat      1560
ctgccggtcg gtttcaaacg ttatctggca cgcgagaata tccacttcta cactctcaac      1620
gctgtggaca tcgcccgtga gcttggtttg ggtggccgtt tcaacatgct gatgcaggct      1680
gccttcttca aactggccgc gatcattgac ccgcagactg ctgcggacta tctgaagcag      1740
gctgttgaga aaagctatgg cagcaaaggt gcggcggtca tcgagatgaa ccagcgtgcc      1800
atcgagcttg gcatggccag cctgcaccag gtgacgatcc cggcacattg gccaccctg       1860 gatgagccag cggcgcaggc gtccgcgatg atgccggact ttatccgcga catcctgcaa      1920
ccgatgaacc gtcagtgcgg cgaccagctt ccggtgtcgg cttttgtcgg catgaagat      1980 ggcaccttcc cgtccggcac ggccgcatgg gagaaacgtg gcatcgccct tgaggtgcca      2040
gtctggcagc cggaaggctg cacgcagtgc aaccagtgcg ccttcatttg tccgcacgcc      2100
gcgattcgtc cggcgttgtt gaatggcgaa gagcatgatg ctgccccggt tggcctgctg      2160
agcaaaccgg cacaaggcgc taagaatat cactatcatc tggcgattag cccgctggac       2220
tgctccggct gtggcaactg cgttgacatt tgtccagctc gtggcaaagc gttgaagatg      2280
cagtctctgg atagccaacg ccagatggct ccggtgtggg attatgcgct ggcgctgacc      2340
ccgaagtcta acccgtttcg taaaaccacc gtcaaaggct cgcagttcga aaccccgctg      2400 ctggagtttta gcggtgcgtg cgctggttgt ggcgaaacgc cgtatgcgcg cctcattacc      2460
cagctgtttg gcgaccgcat gctgattgcc aatgccaccg gctgttccag catctggggc      2520
gcatctgcgc cgagcatccc gtataccacc aatcatcgtg gtcatggtcc ggcctgggcg      2580
aatagcctgt ttgaggacaa tgccgaattt ggtttaggta tgatgctggg cggtcaagct      2640
gtgcgtcaac agatcgcgga cgatatgacg gctgcgttag cgctcccggt ttccgatgag      2700
ctgagcgacg cgatgcgcca gtggttggcg aaacaggacg agggtgaagg cacgcgtgag      2760
```

| | |
|---|---|
| cgtgcggacc gtctgagcga gcgcttagcc gcggagaaag agggcgttcc gctgttagag | 2820 |
| cagctgtggc aaaatcgtga ttactttgtg cgtcgcagcc agtggatttt cggcggtgac | 2880 |
| ggctgggcct atgatattgg cttcggtggc ctggaccacg tcctcgccag cggtgaggat | 2940 |
| gtgaacattc tggtatttga caccgaagtc tactcgaaca ccggcggtca aagcagcaaa | 3000 |
| tcgaccccgg tcgcggccat cgccaagttc gcggctcagg caagcgcac ccgcaagaaa | 3060 |
| gacctgggta tgatggcgat gagctacggc aacgtctatg tagcccaggt ggcgatgggt | 3120 |
| gcggataaag atcaaactct gcgcgccatt gcggaagctg aagcgtggcc aggcccgtcg | 3180 |
| ctggtgattg cgtatgcggc ctgcatcaat catggcctga aggccggtat gcgttgcagc | 3240 |
| caacgtgagg cgaagcgcgc tgttgaggcg ggctactggc acctgtggcg ttatcacccg | 3300 |
| cagcgcgaag cggaaggcaa gacgccgttt atgttagata gcaagaaacc ggaagagtcg | 3360 |
| ttccgtgact ttctgttggg tgaggtgcgc tacgcatccc tgcacaagac caccccgcac | 3420 |
| ctcgccgatg cccttttcag ccgtaccgaa gaagatgcgc gtgcgcgctt tgcgcaatac | 3480 |
| cgtcgcctgg ctggcgaaga gtaa | 3504 |

<210> SEQ ID NO 224
<211> LENGTH: 882
<212> TYPE: DNA
<213> ORGANISM: Artificial Sequence
<220> FEATURE:
<223> OTHER INFORMATION: synthetic Klebsiella pneumoniae nifH

<400> SEQUENCE: 224

| | |
|---|---|
| atgaccatgc gtcagtgcgc gatttatggc aaaggtggta ttggcaaaag cacgacgacc | 60 |
| cagaacttgg tggcggccct ggccgagatg ggtaaaaagg ttatgattgt gggttgcgac | 120 |
| ccgaaggccg acagcacgcg cctgattctg cacgcgaaag cacaaaacac gattatggag | 180 |
| atggctgccg aggttggtag cgtggaggat ctggagctgg aggacgttct gcaaattggt | 240 |
| tacggtgatg ttcgttgcgc agagagcggt ggtccggaac caggtgtcgg ctgtgcgggt | 300 |
| cgtggtgtga ttaccgctat caatttcctg gaagaagagg gtgcgtacga agatgatctg | 360 |
| gatttcgttt tctacgatgt gctgggtgat gtcgtgtgcg gtggttttgc aatgccgatt | 420 |
| cgcgagaata aggcacaaga aatttacatt gtctgtagcg gcgagatgat ggcaatgtac | 480 |
| gctgctaaca acatcagcaa gggtattgtt aaatacgcaa aaagcggtaa ggttcgcttg | 540 |
| ggtggtttga tttgcaacag ccgtcagacc gaccgtgagg acgaactgat catcgccctg | 600 |
| gctgagaaac tgggcaccca aatgatccac ttcgtgccac gcgataatat tgttcaacgt | 660 |
| gcagaaatcc gccgtatgac cgtcattgag tatgacccgg catgcaagca agcgaacgag | 720 |
| taccgcacct tggcacagaa aatcgtgaac aacaccatga aggttgttcc gacgccgtgt | 780 |
| acgatggacg agctggagag cctgctgatg gagttcggca ttatggagga ggaggacacc | 840 |
| agcattatcg gtaagaccgc agcggaggag aatgcggcat aa | 882 |

<210> SEQ ID NO 225
<211> LENGTH: 1452
<212> TYPE: DNA
<213> ORGANISM: Artificial Sequence
<220> FEATURE:
<223> OTHER INFORMATION: synthetic Klebsiella pneumoniae nifI

<400> SEQUENCE: 225

| | |
|---|---|
| atgatgacta atgctactgg cgaacgtaac ctggcactga ttcaagaagt actggaagtg | 60 |

```
ttcccggaaa ccgcgcgcaa agagcgccgt aaacacatga tggtttctga cccggaaatg    120
gaatctgtgg gtaaatgcat catctctaat cgcaaatctc agccgggtgt catgactgtt    180
cgtggctgtg cgtacgcagg ttctaaaggt gtcgtattcg gcccgatcaa agatatggcg    240
catatctctc atggcccggt aggctgtggc cagtactctc gcgcgggacg tcgtaactac    300
tacacgggcg tttctggcgt tgactctttc ggcacgctga acttcacctc tgacttccag    360
gaacgtgaca tcgttttcgg tggcgataaa aagctgtcca aactgatcga gaaatggaa    420 ctgctgttcc cgctgactaa aggcattact atccaaagcg aatgtccggt gggtctgatc    480
ggtgatgaca tcagcgcggt cgcaaacgca tcttccaaag ccctggataa gccggtgatc    540
ccggttcgtt gcgagggctt ccgcggcgtt tctcagtctc tgggtcatca catcgcaaac    600
gatgttgtgc gtgactggat tctgaacaac cgtgaaggtc agccttttga aaccacccct    660
tatgacgttg cgattattgg cgactataac atcggcggcg acgcctgggc atcccgcatc    720
ctgctggagg agatgggtct gcgtgttgtc gcacagtggt ctggcgatgg caccctggtt    780
gaaatggaaa acaccccgtt tgttaaactg aacctggttc actgctaccg ctccatgaac    840
tacattgccc gtcacatgga agaaaaacat cagatccctt ggatggaata caacttcttc    900
ggtccgacta aaatcgcaga atccctgcgt aaaatcgccg atcagtttga tgataccatt    960
cgcgcgaacg ctgaagcagt aattgcgcgc tacgaaggcc agatggcagc aatcattgct    1020
aagtaccgtc cgcgcctgga aggtcgtaaa gtgctgctgt acatgggtgg tctgcgtcca    1080
cgtcatgtga tcggtgccta cgaggacctg ggcatggaga tcatcgcagc gggttacgaa    1140
tttgcacaca cgacgacta tgatcgtacg ctgccagacc tgaaagaagg tacgctgctg    1200
tttgacgacg ccagctctta tgaactggaa gccttcgtga aagcgctgaa accagacctg    1260
atcggctccg gcatcaagga aaaatacatt ttccagaaaa tgggcgtgcc gttccgccag    1320
atgcactcct gggactactc cggtccgtac cacggctacg acggtttcgc tatcttcgct    1380
cgtgacatgg atatgaccct gaataaccca gcgtggaatg aactgaccgc accgtggctg    1440
aaatctgcat aa    1452
```

<210> SEQ ID NO 226
<211> LENGTH: 1563
<212> TYPE: DNA
<213> ORGANISM: Artificial Sequence
<220> FEATURE:
<223> OTHER INFORMATION: synthetic Klebsiella pneumoniae nifK

<400> SEQUENCE: 226

```
atgtctcaaa ctatcgataa aatcaactct tgttacccgc tgttcgagca ggacgaatat    60
caggaactgt tccgtaacaa acgtcagctg aagaagcgc acgacgcaca gcgcgtgcag    120
gaagtgttcg catggaccac caccgcggaa tacgaagctc tgaacttcca gcgcgaagcc    180
ctgacggttg atccggcgaa agcgtgccag cctctgggtg cggttctgtg cagcctgggt    240
tttgccaaca ccctgccgta tgtccacggt tcccagggct gcgtagccta cttccgtacc    300
tatttcaacc gccactttaa agaaccaatc gcgtgcgtgt ccgacagcat gacggaggac    360
gcggcagttt cggtggtaa caacaacatg aacctgggcc tgcaaaatgc ttccgcactg    420
tacaaaccgg aaatcatcgc agtgtctacc acctgcatgg cagaggttat tggtgatgat    480
ctgcaagcat ttattgccaa cgcaaagaaa gacggtttcg ttgacagctc tatcgcggtt    540
ccgcacgctc ataccccgtc cttcatcggt tctcacgtaa ctggtggga caacatgttc    600 gaaggcttcg caaaaacttt taccgcagac tatcaaggcc aaccgggtaa actgccgaag    660
```

```
ctgaacctgg tgaccggctt tgaaacctac ctgggcaact ttcgtgtcct gaagcgcatg      720
atggagcaga tggcggttcc gtgttctctg cgtctgaccc gtctgaggt  tctggacact      780 ccagcggacg gccactatcg catgtattct ggtggcacca ctcagcagga atgaaagag       840 gccccagacg cgattgacac cctgctgctg caaccgtggc agctgctgaa agcaagaaa       900 gttgttcagg aaatgtggaa ccagccggca acggaagttg caatcccgct gggtctggca      960
gctactgacg aactgctgat gaccgtgtcc caactgagcg gcaaaccaat cgcggatgct     1020
ctgaccctgg aacgcggtcg cctggtggac atgatgctgg acagccacac gtggctgcat     1080
ggcaagaaat ttggcctgta cggtgacccg gacttcgtaa tgggcctgac ccgtttcctg     1140
ctggaactgg gctgcgagcc gactgttatc ctgtctcaca cgctaacaa  acgttggcag     1200 aaggccatga acaaaatgct ggatgcgagc ccatacggcc gtgatagcga agtgttcatc     1260
aactgcgacc tgtggcattt ccgctctctg atgtttacgc gtcagccgga tttcatgatc     1320
ggtaactctt acggcaaatt catccagcgt gacactctgg ccaaaggcaa agcgtttgaa     1380
gtgccgctga ttcgtctggg cttttccgctg ttcgaccgtc accacctgca ccgccagacc     1440
acctggggtt acgaaggcgc gatgaacatc gtaactactc tggtaaacgc agtactggaa     1500
aagctggaca gcgatacttc ccagctgggc aaaaccgact attctttcga tctggttcgt     1560
taa                                                                    1563

<210> SEQ ID NO 227
<211> LENGTH: 663
<212> TYPE: DNA
<213> ORGANISM: Artificial Sequence
<220> FEATURE:
<223> OTHER INFORMATION: synthetic Klebsiella pneumoniae nifY

<400> SEQUENCE: 227
atgtctgaca atgatacct  gttttggcgc atgctggcgc tgtttcagtc gctgccggat        60
ttgcagccgg ctcaaatcgt cgattggctg gcgcaggaat ccggcgaaac cctgacgccg      120
gagcgccttg ccaccctgac ccaaccgcaa ctcgcggcgt cgttcccatc cgcgacggca      180
gtgatgagcc cggctcgctg gagccgcgtt atggcttctc tgcaaggcgc cctcccagcc      240
cacttgcgca tcgtacgtcc ggcgcagcgt accccgcaac tgctcgccgc gttttgcagc      300
caagacggcc ttgttatcaa tggtcatttc ggccagggtc gtctgttctt catttacgcc      360
tttgacgagc agggcggctg gctgtatgac ttgcgccgct atccgagcgc accgcaccag      420
caggaagcga atgaggtgcg tgctcgtctg attgaagatt gccagctgct gttctgccag      480
gagattggcg gtccggcagc agcgcgtctg atccgccacc gcatccatcc gatgaaggcg      540
cagccgggta ctacgattca ggcgcagtgt gaagctatca acaccctgct ggccggtcgc      600
ctgccgccgt ggctcgccaa acgtttgaac cgtgataacc cgctggaaga gcgtgtgttt      660
taa                                                                    663

<210> SEQ ID NO 228
<211> LENGTH: 1374
<212> TYPE: DNA
<213> ORGANISM: Artificial Sequence
<220> FEATURE:
<223> OTHER INFORMATION: synthetic Klebsiella pneumoniae nifE

<400> SEQUENCE: 228
atgaagggta acgagattct tgctctgctg gacgaaccgg cctgtgaaca caaccataaa       60
```
cagaaatccg gctgtagcgc cccaaagccg ggtgcgacgg cggctggctg cgctttcgat 120
ggtgcgcaga tcaccctgct cccgattgcg gacgttgccc acctcgtgca tggcccaatc 180
ggttgcgcag gtagctcttg ggacaaccgt ggcagcgcct ccagcggtcc gaccctgaat 240
cgtttgggct ttaccactga cttgaatgaa caagatgtga tcatgggtcg cggcgagcgt 300
cgcctgttcc acgctgtgcg ccatattgtc acccgttacc acccagcggc agtattcatc 360
tacaatacgt gcgtgccggc tatggaaggc gatgacctgg aggccgtgtg tcaggcagcc 420
cagactgcga ccggcgtccc ggtaatcgca attgatgcgg ctggcttcta cggttcgaag 480
aacctgggca accgtccggc aggcgatgtc atggttaaac gcgtcattgg ccaacgtgag 540
ccagcgccgt ggccggagag caccctgttt gccccggagc aacgtcatga cattggcttg 600
atcggtgagt tcaacattgc gggcgagttt tggcacattc agccgctgct tgatgagctg 660
ggtatccgcg ttttgggttc gctcagcggc gatggtcgtt tcgccgagat tcaaaccatg 720
caccgtgccc aggcgaacat gctggtgtgc agccgtgctc tgatcaatgt tgcgcgtgct 780
ctggaacagc gctatggcac cccgtggttt gaaggctcgt tctatggtat ccgcgcgacc 840
agcgacgccc tgcgccagtt agcggcgctg ctgggcgatg acgacctccg tcagcgcacc 900
gaggcgctga tcgcgcgtga agaacaggcg gctgagctgg ccctgcaacc gtggcgtgaa 960
cagctgcgtg gccgcaaggc cctgctctac acgggtggtg tcaaaagctg gtctgtggtg 1020
tccgcgcttc aggatctggg tatgaccgtg gttgccacgg gcacgcgtaa gagcacggaa 1080
gaggataaac agcgcatccg cgaattgatg ggcgaagagg ccgtgatgct tgaagaaggc 1140
aacgcacgta ccttattgga tgtagtttat cgctatcaag cagacctgat gattgccggt 1200
ggccgcaaca tgtataccgc ctacaaagcg cgcttgccgt tcctggacat caaccaggaa 1260
cgcgagcacg cgtttgcggg ctaccaaggc atcgtgacct tagcgcgcca gctgtgccaa 1320
acgattaaca gcccgatctg gccgcagact cattcccgcg caccgtggcg ctaa 1374

<210> SEQ ID NO 229
<211> LENGTH: 1386
<212> TYPE: DNA
<213> ORGANISM: Artificial Sequence
<220> FEATURE:
<223> OTHER INFORMATION: synthetic Klebsiella pneumoniae nifN

<400> SEQUENCE: 229
atggcagaca ttttccgcac tgataagccg ttggctgtgt cgccgatcaa gaccggccag 60
ccgctgggtg cgatcctggc gtccctgggt atcgagcact cgattccgct ggtacatggc 120
gcgcagggct gttcggcttt tgccaaggtt ttctttatcc agcacttcca cgatccggtc 180
ccgctgcaaa gcacggcaat ggacccgacc agcaccatca tgggcgctga tggtaacatc 240
ttcaccgcgc tggacactct ctgccaacgc aataacccgc aagcaattgt gctgctgagc 300
accggcctct ccgaggcgca gggcagcgac atttcccgtg tagtgcgtca gttccgtgaa 360
gaatatccgc gtcataaagg cgtggcgatt ctgactgtta acaccccgga cttttacggt 420
agcatggaga acggcttttc cgctgtcctg gagtctgtga ttgaacagtg ggttccgcca 480
gccccacgtc cggcgcagcg caatcgtcgc gtcaatcttt tggtgagcca tctctgtagc 540
ccaggcgata ttgagtggct gcgccgttgc gtcgaggcct tcggtctgca accgatcatt 600
ctgccggatc tggctcagag catggacggc caccttgctc agggtgactt ttcgccgctg 660
acgcagggcg gcacgccgtt gcgccaaatc gagcagatgg gccagagcct ttgctctttt 720
gcgattggcg tcagcctgca ccgtgcgagc agcctgctgg ctccgcgttg tcgtggcgaa 780

```
gtcatcgcct tgccgcacct catgaccttg gaacgctgcg acgcctttat ccatcagttg    840
gcgaaaatca gcggtcgcgc cgttccggag tggctggaac gccagcgcgg tcagctgcaa    900
gacgccatga tcgattgcca catgtggctc caaggccagc gcatggcgat tgccgccgaa    960
ggcgacctgc tggcagcgtg gtgcgatttc gcgaactctc aaggtatgca gccgggtcca   1020
ctggttgctc cgacgggtca tccgagcctg cgtcagttgc cggtggagcg cgtggtgccg   1080
ggtgatctgg aggatcttca gaccctctta tgcgcacatc cggccgactt actggtggcg   1140
aactcccacg cccgtgattt agcagagcaa ttcgccctgc cgctggtgcg cgcaggcttc   1200
ccgctgtttg acaaactggg cgaatttcgt cgtgttcgcc agggttatag cggtatgcgt   1260
gataccctgt tcgagttggc gaacctgatc cgtgaacgcc atcatcatct ggctcattat   1320
cgcagcccgc tgcgccagaa cccagaatcc tcgttgtcta cgggtggcgc gtacgcagcg   1380
gattaa                                                              1386
```

<210> SEQ ID NO 230
<211> LENGTH: 825
<212> TYPE: DNA
<213> ORGANISM: Artificial Sequence
<220> FEATURE:
<223> OTHER INFORMATION: synthetic Klebsiella pneumoniae nifU

<400> SEQUENCE: 230

```
atgtggaact acagcgagaa agtcaaggac catttcttca atccgcgcaa cgcgcgtgtt     60
gtggataacg caaatgcggt gggcgacgtc ggcagcttat cttgtggcga tgctctccgc    120
ttgatgctgc gcgtggaccc gcagagcgaa atcatcgaag aagcgggctt tcagaccttc    180
ggctgcggca gcgcgattgc gtcgtccagc gcactgacgg agctgatcat cggtcacacc    240
ctggcggaag cgggtcagat caccaaccag cagatcgccg actatctgga cggcttaccg    300
ccggaaaaga tgcactgctc tgtaatgggc caggaagctc ttcgtgcggc cattgctaac    360
tttcgcggtg aatcgctgga agaggagcat gacgagggta gctgatctg caagtgcttc    420 ggcgtcgatg aaggccatat tcgccgtgct gtccagaaca acggtcttac gactctggcc    480
gaggtgatca attacaccaa ggcaggtggc ggttgtacca gctgccatga aaaatcgag    540 ctggccctgg ccgagattct cgcccaacag ccgcaaacca cccggcagt tgcgtccggt    600 aaagatccgc actggcagag cgtcgtggat accatcgctg aactgcgtcc acatatccaa    660
gcggacggtg tgacatggc gctgttgtcc gtgacgaacc accaagtgac tgtttcgctg    720
tcgggcagct gttctggctg catgatgacc gacatgaccc tggcgtggct gcaacagaaa    780
ttgatggagc gtaccggctg ctatatggaa gttgttgccg cctaa                   825
```

<210> SEQ ID NO 231
<211> LENGTH: 1203
<212> TYPE: DNA
<213> ORGANISM: Artificial Sequence
<220> FEATURE:
<223> OTHER INFORMATION: synthetic Klebsiella pneumoniae nifS

<400> SEQUENCE: 231

```
atgaaacaag tgtacctgga caacaacgcg accacccgcc tggacccgat ggttctggaa     60
gcgatgatgc cgtttctcac ggatttctat ggcaatccgt ccagcatcca tgacttcggc    120
atcccggcac aagcggcgct ggaacgtgcg caccagcaag ctgcggcact gctgggcgca    180
gagtacccgt ctgaaatcat tttcacgagc tgtgcgaccg aggccactgc aaccgccatt    240
```

```
gcgtcggcca tcgcgttatt gccggaacgc cgcgaaatca tcacctcggt agtggagcac    300
ccggctacgc tggcggcgtg cgagcacctg gaacgccaag gctatcgcat ccatcgcatt    360
gcggtggata gcgaaggtgc gctggacatg gcccagttcc gtgcagcgct ctcgccgcgt    420
gtcgcgttgg tgagcgtgat gtgggccaac aacgaaaccg gcgtgctgtt cccgattggc    480
gaaatggccg agcttgccca cgagcagggc gctctgttcc actgcgatgc cgttcaggtc    540
gttggcaaaa tcccaattgc tgttggccag acgcgcatcg acatgctgtc ttgctccgcg    600
cacaagtttc atggtccgaa gggtgttggt tgcttgtact tacgtcgtgg cacgcgcttt    660
cgtccgctgc ttcgcggtgg ccatcaagaa tatggtcgcc gtgccggcac tgagaatatc    720
tgtggcatcg tcggcatggg cgctgcgtgc gaactggcga acatccatct gccgggtatg    780
acccatattg gccagttacg caatcgcctg gagcaccgtc tgctcgccag cgtgccgtcc    840
gtgatggtta tgggcggtgg tcagccgcgt gtaccgggta ctgtcaacct ggcgttcgag    900
tttatcgaag gtgaagcgat cctgctcttg ctgaaccagg ctggcattgc cgcaagctcc    960
ggctccgcgt gtacctctgg cagcttggag ccgagccatg tgatgcgcgc catgaacatt   1020
ccatacaccg cggctcacgg caccattcgt tttagcctga gccgttatac gcgcgagaaa   1080
gagatcgact acgtcgttgc gaccctcccg ccaatcattg atcgtctgcg tgccttgtcc   1140
ccgtattggc agaatggtaa gccgcgtccg gcagatgcag tctttacccc ggtttacggt   1200
taa                                                                 1203
```

<210> SEQ ID NO 232
<211> LENGTH: 1143
<212> TYPE: DNA
<213> ORGANISM: Artificial Sequence
<220> FEATURE:
<223> OTHER INFORMATION: synthetic Klebsiella pneumoniae nifV

<400> SEQUENCE: 232

```
atggagcgcg tcttgatcaa cgatactacc ctgcgtgatg gcgaacaatc tccgggcgta     60
gcgtttcgta cctccgagaa agttgccatc gcggaggcac tgtacgctgc gggtatcacc    120
gcgatggaag tcggcactcc ggcgatgggt gatgaagaga tcgcccgcat tcagctggtg    180
cgtcgtcaac tgccggacgc gacgcttatg acctggtgcc gtatgaacgc tctggaaatc    240
cgtcagagcg cggatctggg tattgactgg gtggatatct cgatcccagc atccgacaag    300
ctgcgtcagt acaagctgcg tgagccgctg gccgtgctgc tggagcgcct tgcgatgttt    360
atccatctgg cccacacgtt aggcctcaaa gtatgtattg gttgcgagga tgcgagccgt    420
gcgtctggtc agaccctgcg cgccattgcc gaggtggccc agcaatgcgc ggctgcgcgc    480
ttgcgttacg ctgacaccgt gggcctgctg gacccgttca ccaccgcagc ccagatcagc    540
gccctgcgtg acgtttggtc gggcgagatc gagatgcatg ctcacaatga tctgggcatg    600
gctaccgcga acacgctggc ggcagtttcg gctggcgcca cgtcggtgaa cactaccgtc    660
ctcggtctgg gtgaacgtgc aggcaacgca gccctggaaa ccgttgcgct gggcctggaa    720
cgctgcctgg gcgtggaaac cggcgtccat ttcagcgcgc tcccagcgct ctgtcagcgc    780
gtcgcggagg ctgcacagcg cgcaatcgac ccgcaacagc cgctggtggg tgaattggtt    840
ttcacccacg agtctggtgt tcacgttgcg gcgctgctgc gcgacagcga atcctatcaa    900
tctattgccc caagcctcat gggccgtagc taccgtctgg tgctcggcaa gcattcgggt    960
cgtcaggctg tcaacggtgt tttcgaccag atgggttacc acctgaatgc ggcgcagatc   1020
aatcagttgc tgccggccat tcgccgcttc gccgagaatt ggaaacgctc tccgaaagac   1080
```

```
tacgaactgg ttgcgatcta tgacgaattg tgcggtgaat ccgcccttcg tgctcgcggc    1140
taa                                                                  1143

<210> SEQ ID NO 233
<211> LENGTH: 258
<212> TYPE: DNA
<213> ORGANISM: Artificial Sequence
<220> FEATURE:
<223> OTHER INFORMATION: synthetic Klebsiella pneumoniae nifW

<400> SEQUENCE: 233
atggagtggt tttaccagat tccgggtgta gacgaattgc gcagcgctga atccttcttt      60
cagttcttcg cggttccata ccagccggaa ctgctgggcc gctgctcgct tccggtgtta     120
gcgacgttcc accgtaaact gcgtgcggag gtcccgctgc aaaaccgtct ggaggacaat     180
gatcgtgcgc cgtggctctt ggcgcgccgc ctcctggccg aatcttatca gcagcaattt     240
caggagagcg gcacctaa                                                  258

<210> SEQ ID NO 234
<211> LENGTH: 447
<212> TYPE: DNA
<213> ORGANISM: Artificial Sequence
<220> FEATURE:
<223> OTHER INFORMATION: synthetic Klebsiella pneumoniae nifZ

<400> SEQUENCE: 234
atgcgcccga aattcacctt ctctgaagag gtccgcgtag ttcgcgcgat tcgtaatgat      60
ggcaccgtgg cgggttttgc gccaggtgcg ctgctggttc gtcgcggttc gacgggcttt     120
gtgcgtgact ggggtgtgtt cctgcaagac cagatcatct atcaaatcca ctttccggaa     180
accgaccgca ttatcggctg tcgcgagcag gagttaatcc cgattaccca gccgtggttg     240
gctggtaacc tccagtatcg tgacagcgtc acgtgccaaa tggcactggc tgtcaacggt     300
gacgtggttg tgagcgccgg tcaacgtggc cgtgtggagg ccactgatcg tggcgaactt     360
ggcgattcct acaccgtgga cttcagcggc cgttggttcc gcgttccggt ccaggccatc     420
gcgctgattg aagagcgcga agaataa                                        447

<210> SEQ ID NO 235
<211> LENGTH: 801
<212> TYPE: DNA
<213> ORGANISM: Artificial Sequence
<220> FEATURE:
<223> OTHER INFORMATION: synthetic Klebsiella pneumoniae nifM

<400> SEQUENCE: 235
atgaatccgt ggcagcgctt tgcccgtcaa cgccttgctc gcagccgctg gaaccgtgat      60
ccggctgctc tcgacccagc cgataccccca gcgttcgagc aggcgtggca cgtcaatgc     120 catatggaac aaaccatcgt agcgcgtgtc ccggaaggcg atattccggc tgccttactg     180
gaaaacatcg cggccagcct ggcgatctgg ctggacgagg gtgacttcgc tccgccggag     240
cgcgctgcga ttgtgcgtca tcatgcacgt ctggagctgg cgtttgccga cattgcccgc     300
caggcaccga accggatct gagcacggtt caagcgtggt atctgcgtca ccagactcaa     360
ttcatgcgtc cggagcagcg tctgacccgt cacctgctcc tgacggtcga taatgatcgc     420
gaggcggtgc atcaacgcat ccttggcctg tatcgtcaga tcaacgcgag ccgtgacgcc     480
ttcgccccac tggcacagcg ccactctcat tgcccgtccg ccttggaaga aggccgtctg     540
```

```
ggctggatct cccgtggtct gctgtacccg cagctcgaaa ccgcgttgtt tagcctggcg      600
gaaaacgcac tgtcgctgcc gattgcgtcg gaattgggtt ggcacctgtt atggtgcgag      660
gccattcgtc cggcagcccc gatggagccg caacaggccc ttgaatctgc gcgcgactac      720
ttgtggcagc agagccagca cgccaccag cgtcaatggc tggagcagat gatttcccgc       780
caaccgggcc tgtgtggtta a                                                801

<210> SEQ ID NO 236
<211> LENGTH: 531
<212> TYPE: DNA
<213> ORGANISM: Artificial Sequence
<220> FEATURE:
<223> OTHER INFORMATION: synthetic Klebsiella pneumoniae nifF

<400> SEQUENCE: 236
atggcgaaca tcggcatctt ctttggtacg ataccggca aaacccgcaa gattgcgaag        60
atgattcaca aacagctggg cgagctggcc gatgccccgg ttaacatcaa tcgtaccact      120
ttggatgact ttatggctta cccagtcctg ttgctcggca cgccgacgct tggtgatggt      180
caactgccgg gcttagaggc gggctgcgag agcgaaagct ggtctgagtt tatctccggt      240
ctggatgacg cttccctgaa gggcaaaacc gtggcgctgt ttggcctggg cgaccagcgt      300
ggttacccgg acaacttcgt gtcgggtatg cgtccgctgt tcgacgcgct gagcgcccgt      360
ggcgcccaga tgattggtag ctggccgaac gaaggttatg agtttagcgc atcgtccgcg      420
ctggaaggcg accgcttcgt cggcttggtg ctggatcaag acaatcagtt cgaccagacc      480
gaagcgcgcc tggcgtcttg gcttgaagag atcaaacgca ccgttctgta a               531

<210> SEQ ID NO 237
<211> LENGTH: 1407
<212> TYPE: DNA
<213> ORGANISM: Artificial Sequence
<220> FEATURE:
<223> OTHER INFORMATION: synthetic Klebsiella pneumoniae nifB

<400> SEQUENCE: 237
atgacctctt gttcgtcgtt ttctggcggt aaagcgtgcc gtccggccga tgactccgcg        60
ctgactccgc tggtggccga caaggcagct gcgcacccgt gctatagccg ccacggccat      120
caccgcttcg cgcgtatgca cctgccagtc gctccggcct gcaacttaca atgcaactac      180
tgcaaccgca agttcgattg cagcaatgaa agccgtccgg gcgtgtcctc taccctgctg      240
acgccggaac aggctgtggt gaaggtcgcg caggtcgccc aagctatccc gcagctgtcg      300
gtggtcggta ttgctggtcc gggcgatccg cttgcgaata tcgcccgcac cttccgtacc      360
ttggagctta ttcgcgaaca gttgccggac ctgaaactgt gcctgagcac caacggcttg      420
gtgctgccag atgccgttga tcgtctgctc gatgtgggcg tggatcacgt taccgtcacc      480
attaacaccc tggacgcaga atcgcagcg caaatctacg cgtggttgtg gctggatggc      540
gaacgctact ccggtcgcga agccggcgaa attctcattg cccgcagct ggaaggcgta       600 cgtcgcctga ccgcgaaagg tgtgctcgtc aagatcaaca gcgtattgat tccgggcatc      660
aatgacagcg gcatggcggg tgttagccgt gcgctgcgcg cgtctggtgc gttcatccac      720
aacatcatgc cactgattgc gcgtccggag catggcactg ttttcggtct gaacggccag      780
ccggaaccgg acgcggaaac cctggcggcg acgcgctccc gctgcggcga ggttatgcca      840
caaatgaccc actgccacca gtgccgtgcc gacgcgattg gcatgcttgg tgaggatcgc      900
tcgcaacagt ttacgcaatt accggctccg gagtccctcc cggcctggct gccgatcctg      960
```

-continued

```
catcagcgtg ctcagttgca tgcgagcatc gccacgcgcg gtgagagcga agccgatgac    1020
gcctgcctgg tggccgttgc gtcgagccgt ggcgatgtaa ttgactgcca tttcggccat    1080
gccgaccgtt tctatatcta tagcctgtct gcggctggta tggttctggt taacgaacgt    1140
ttcaccccga aatactgcca gggtcgcgat gactgcgagc gcaggacaa tgccgcacgc     1200 tttgctgcca tccttgagtt gctggcggac gtcaaagcgg tgttttgtgt gcgtatcggc    1260 catacccgt ggcaacagct ggagcaggaa ggcatcgaac cgtgcgtgga tggcgcctgg     1320
cgtccggtat ccgaggtcct gccggcatgg tggcagcagc gccgtggtag ctggccggct    1380
gcattgccgc acaaaggcgt tgcgtaa                                        1407
```

<210> SEQ ID NO 238
<211> LENGTH: 504
<212> TYPE: DNA
<213> ORGANISM: Artificial Sequence
<220> FEATURE:
<223> OTHER INFORMATION: synthetic Klebsiella pneumoniae nifQ

<400> SEQUENCE: 238

```
atgccgccat ggactggtt gcgtcgtttg tggttactct atcacgccgg caaaggcagc      60
tttccgcttc gtatgggctt gtcgccgcgt gactggcaag ctctgcgccg tcgcctgggc    120
gaggtggaaa cgccgctgga tggcgaaacc ctgacccgtc gccgtctgat ggcggagctg    180
aatgcgaccc gcgaagaaga acgccagcag ctgggtgcct ggctggccgg ttggatgcaa    240
caggatgccg gtccgatggc gcagattatc gcagaggtga gcctggcgtt caaccatctc    300
tggcaggacc ttggcctcgc gagccgcgct gaactgcgtc tgctgatgtc tgactgcttc    360
ccgcagctgg ttgttatgaa cgagcacaac atgcgctgga agaaattctt ttaccgccag    420
cgttgcctgc tgcaacaggg cgaagtcatc tgtcgcagcc cgtcttgcga tgaatgctgg    480
gaacgttctg cgtgctttga gtaa                                          504
```

<210> SEQ ID NO 239
<211> LENGTH: 206
<212> TYPE: PRT
<213> ORGANISM: Artificial Sequence
<220> FEATURE:
<223> OTHER INFORMATION: synthetic chimeric sigma factor ECF11_ECF02

<400> SEQUENCE: 239

```
Met Arg Ile Thr Ala Ser Leu Arg Thr Phe Cys His Leu Ser Thr Pro
1               5                   10                  15

His Ser Asp Ser Thr Thr Ser Arg Leu Trp Ile Asp Glu Val Thr Ala
            20                  25                  30

Val Ala Arg Gln Arg Asp Arg Asp Ser Phe Met Arg Ile Tyr Asp His
        35                  40                  45

Phe Ala Pro Arg Leu Leu Arg Tyr Leu Thr Gly Leu Asn Val Pro Glu
    50                  55                  60

Gly Gln Ala Glu Glu Leu Val Gln Glu Val Leu Leu Lys Leu Trp His
65                  70                  75                  80

Lys Ala Glu Ser Phe Asp Pro Ser Lys Ala Ser Leu Gly Thr Trp Leu
                85                  90                  95

Phe Arg Ile Ala Arg Asn Leu Tyr Ile Asp Ser Val Arg Lys Asp Arg
            100                 105                 110

Gly Trp Val Gln Val Gln Asn Ser Leu Glu Gln Leu Glu Arg Leu Glu
        115                 120                 125
```

Ala Ile Ser Asn Pro Glu Asn Leu Met Leu Ser Glu Leu Arg Gln
        130                 135                 140

Ile Val Phe Arg Thr Ile Glu Ser Leu Pro Glu Asp Leu Arg Met Ala
145                 150                 155                 160

Ile Thr Leu Arg Glu Leu Asp Gly Leu Ser Tyr Glu Glu Ile Ala Ala
                165                 170                 175

Ile Met Asp Cys Pro Val Gly Thr Val Arg Ser Arg Ile Phe Arg Ala
                180                 185                 190

Arg Glu Ala Ile Asp Asn Lys Val Gln Pro Leu Ile Arg Arg
            195                 200                 205

<210> SEQ ID NO 240
<211> LENGTH: 187
<212> TYPE: PRT
<213> ORGANISM: Artificial Sequence
<220> FEATURE:
<223> OTHER INFORMATION: synthetic chimeric sigma factor ECF02_ECF11

<400> SEQUENCE: 240

Met Ser Glu Gln Leu Thr Asp Gln Val Leu Val Glu Arg Val Gln Lys
1               5                   10                  15

Gly Asp Gln Lys Ala Phe Asn Leu Leu Val Val Arg Tyr Gln His Lys
            20                  25                  30

Val Ala Ser Leu Val Ser Arg Tyr Val Pro Ser Gly Asp Val Pro Asp
        35                  40                  45

Val Val Gln Glu Ala Phe Ile Lys Ala Tyr Arg Ala Leu Asp Ser Phe
    50                  55                  60

Arg Gly Asp Ser Ala Phe Tyr Thr Trp Leu Tyr Arg Ile Ala Val Asn
65                  70                  75                  80

Thr Ala Lys Asn Tyr Leu Val Ala Gln Gly Arg Arg Pro Pro Ser Ser
                85                  90                  95

Asp Val Asp Ala Ile Glu Ala Glu Asn Phe Glu Gln Leu Glu Arg Leu
            100                 105                 110

Glu Ala Pro Val Asp Arg Thr Leu Asp Tyr Ser Gln Arg Gln Glu Gln
        115                 120                 125

Gln Leu Asn Ser Ala Ile Gln Asn Leu Pro Thr Asp Gln Ala Lys Val
    130                 135                 140

Leu Arg Met Ser Tyr Phe Glu Ala Leu Ser His Arg Glu Ile Ser Glu
145                 150                 155                 160

Arg Leu Asp Met Pro Leu Gly Thr Val Lys Ser Cys Leu Arg Leu Ala
                165                 170                 175

Phe Gln Lys Leu Arg Ser Arg Ile Glu Glu Ser
            180                 185

<210> SEQ ID NO 241
<211> LENGTH: 883
<212> TYPE: PRT
<213> ORGANISM: Enterobacteria phage T7
<220> FEATURE:
<223> OTHER INFORMATION: Enterobacteria phage T7 RNA polymerase (RNAP)

<400> SEQUENCE: 241

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

```
Ala Arg Phe Arg Lys Met Phe Glu Arg Gln Leu Lys Ala Gly Glu Val
 50                  55                  60

Ala Asp Asn Ala Ala Lys Pro Leu Ile Thr Thr Leu Leu Pro Lys
 65                  70                  75                  80

Met Ile Ala Arg Ile Asn Asp Trp Phe Glu Glu Val Lys Ala Lys Arg
                     85                  90                  95

Gly Lys Arg Pro Thr Ala Phe Gln Phe Leu Gln Glu Ile Lys Pro Glu
                100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
                130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
                195                 200                 205

Ser Ile His Val Gly Val Arg Cys Ile Glu Met Leu Ile Glu Ser Thr
                210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
                260                 265                 270

Val Pro Pro Lys Pro Trp Thr Gly Ile Thr Gly Gly Gly Tyr Trp Ala
                275                 280                 285

Asn Gly Arg Arg Pro Leu Ala Leu Val Arg Thr His Ser Lys Lys Ala
                290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
                355                 360                 365

Met Asn Pro Glu Ala Leu Thr Ala Trp Lys Arg Ala Ala Ala Val
                370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
                420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
                450                 455                 460
```

```
Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
        500                 505                 510

Ala Phe Cys Phe Glu Tyr Ala Gly Val Gln His His Gly Leu Ser Tyr
    515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
        580                 585                 590

Glu Val Val Thr Val Thr Asp Glu Asn Thr Gly Glu Ile Ser Glu Lys
    595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
        660                 665                 670

Ala Ala Gly Tyr Met Ala Lys Leu Ile Trp Glu Ser Val Ser Val Thr
    675                 680                 685

Val Val Ala Ala Val Glu Ala Met Asn Trp Leu Lys Ser Ala Ala Lys
690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
        740                 745                 750

Gly Gln Phe Arg Leu Gln Pro Thr Ile Asn Thr Asn Lys Asp Ser Glu
    755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
        820                 825                 830

Val Asp Thr Tyr Glu Ser Cys Asp Val Leu Ala Asp Phe Tyr Asp Gln
    835                 840                 845

Phe Ala Asp Gln Leu His Glu Ser Gln Leu Asp Lys Met Pro Ala Leu
850                 855                 860

Pro Ala Lys Gly Asn Leu Asn Leu Arg Asp Ile Leu Glu Ser Asp Phe
865                 870                 875                 880

Ala Phe Ala
```

<210> SEQ ID NO 242
<211> LENGTH: 48
<212> TYPE: DNA
<213> ORGANISM: Artificial Sequence
<220> FEATURE:
<223> OTHER INFORMATION: synthetic Enterobacteria phage T7 stem loop
      terminator seed sequence
<220> FEATURE:
<221> NAME/KEY: modified_base
<222> LOCATION: (3)...(6)
<223> OTHER INFORMATION: n = g, a, c or t

<400> SEQUENCE: 242
tannnnaacc sswwssssss tcwwwwcgss sssswwssgg tttttttgt                48

<210> SEQ ID NO 243
<211> LENGTH: 29
<212> TYPE: DNA
<213> ORGANISM: Artificial Sequence
<220> FEATURE:
<223> OTHER INFORMATION: synthetic Enterobacteria phage T7 terminator 52

<400> SEQUENCE: 243
tataaaacgg ggggctaggg gttttttgt                                      29

<210> SEQ ID NO 244
<211> LENGTH: 48
<212> TYPE: DNA
<213> ORGANISM: Artificial Sequence
<220> FEATURE:
<223> OTHER INFORMATION: synthetic Enterobacteria phage T7 terminator 23

<400> SEQUENCE: 244
tactcgaacc cctagcccgc tcttatcggg cggctagggg tttttttgt                48

<210> SEQ ID NO 245
<211> LENGTH: 37
<212> TYPE: DNA
<213> ORGANISM: Artificial Sequence
<220> FEATURE:
<223> OTHER INFORMATION: synthetic Enterobacteria phage T7 terminator 72

<400> SEQUENCE: 245
tagcagaacc gctaacgggg gcgaaggggt tttttgt                             37

<210> SEQ ID NO 246
<211> LENGTH: 48
<212> TYPE: DNA
<213> ORGANISM: Artificial Sequence
<220> FEATURE:
<223> OTHER INFORMATION: synthetic Enterobacteria phage T7 terminator 48

<400> SEQUENCE: 246
tactcgaacc cctagcccgc tcttatcggg cggctagggg tttttttgt                48

<210> SEQ ID NO 247
<211> LENGTH: 29
<212> TYPE: DNA
<213> ORGANISM: Artificial Sequence
<220> FEATURE:
<223> OTHER INFORMATION: synthetic Enterobacteria phage T7 terminator 1

<400> SEQUENCE: 247
tacatatcgg gggggtaggg gttttttgt                                      29

<210> SEQ ID NO 248
<211> LENGTH: 29
<212> TYPE: DNA
<213> ORGANISM: Artificial Sequence
<220> FEATURE:
<223> OTHER INFORMATION: synthetic Enterobacteria phage T7 terminator 2

<400> SEQUENCE: 248
tacatatcgg gggggtaggg gttttttgt                                      29

<210> SEQ ID NO 249
<211> LENGTH: 48
<212> TYPE: DNA
<213> ORGANISM: Artificial Sequence
<220> FEATURE:
<223> OTHER INFORMATION: synthetic Enterobacteria phage T7 wild type
      (WT) terminator

<400> SEQUENCE: 249
tagcataacc ccttggggcc tctaaacggg tcttgagggg ttttttgt                 48

<210> SEQ ID NO 250
<211> LENGTH: 47
<212> TYPE: DNA
<213> ORGANISM: Artificial Sequence
<220> FEATURE:
<223> OTHER INFORMATION: synthetic Enterobacteria phage T7 terminator 31

<400> SEQUENCE: 250
taccctaacc ccttccccgg tcaatcgggg cggatggggt tttttgt                  47

<210> SEQ ID NO 251
<211> LENGTH: 47
<212> TYPE: DNA
<213> ORGANISM: Artificial Sequence
<220> FEATURE:
<223> OTHER INFORMATION: synthetic Enterobacteria phage T7 terminator 58

<400> SEQUENCE: 251
tagaccaacc ccttgcggcc tcaatcgggg gggatggggt tttttgt                  47

<210> SEQ ID NO 252
<211> LENGTH: 37
<212> TYPE: DNA
<213> ORGANISM: Artificial Sequence
<220> FEATURE:
<223> OTHER INFORMATION: synthetic Enterobacteria phage T7 terminator 25

<400> SEQUENCE: 252
tactctaacc ccatcggccg tcttaggggt tttttgt                             37

<210> SEQ ID NO 253
<211> LENGTH: 48
<212> TYPE: DNA
<213> ORGANISM: Artificial Sequence
<220> FEATURE:
<223> OTHER INFORMATION: synthetic Enterobacteria phage T7 terminator 17

<400> SEQUENCE: 253
tacctcaacc ccttccgccc tcatatcgcg gggcatgcgg ttttttgt                 48

<210> SEQ ID NO 254
<211> LENGTH: 39
<212> TYPE: PRT
<213> ORGANISM: Artificial Sequence
<220> FEATURE:
<223> OTHER INFORMATION: synthetic Enterobacteria phage T7 RNA polymerase (RNAP) specificity loop sequence

<400> SEQUENCE: 254

Val Trp Gln Glu Tyr Lys Lys Pro Ile Gln Thr Arg Leu Asn Leu Met
1               5                   10                  15

Phe Leu Gly Gln Phe Arg Leu Gln Pro Thr Ile Asn Thr Asn Lys Asp
            20                  25                  30

Ser Glu Ile Asp Ala His Lys
        35

<210> SEQ ID NO 255
<211> LENGTH: 39
<212> TYPE: PRT
<213> ORGANISM: Artificial Sequence
<220> FEATURE:
<223> OTHER INFORMATION: synthetic Enterobacteria phage T3 RNA
      polymerase (RNAP) specificity loop sequence

<400> SEQUENCE: 255

Val Trp Gln Glu Tyr Lys Lys Pro Ile Gln Lys Arg Leu Asp Met Ile
1               5                   10                  15

Phe Leu Gly Gln Phe Arg Leu Gln Pro Thr Ile Asn Thr Asn Lys Asp
            20                  25                  30

Ser Glu Ile Asp Ala His Lys
        35

<210> SEQ ID NO 256
<211> LENGTH: 23
<212> TYPE: DNA
<213> ORGANISM: Artificial Sequence
<220> FEATURE:
<223> OTHER INFORMATION: synthetic Enterobacteria phage T3 RNA
      polymerase (RNAP) promoter sequence

<400> SEQUENCE: 256
taataaccct cactataggg aga                                          23

<210> SEQ ID NO 257
<211> LENGTH: 39
<212> TYPE: PRT
<213> ORGANISM: Artificial Sequence
<220> FEATURE:
<223> OTHER INFORMATION: synthetic Enterobacteria phage K1F RNA
      polymerase (RNAP) specificity loop sequence

<400> SEQUENCE: 257

Val Trp Gln Glu Tyr Lys Lys Pro Ile Gln Thr Arg Leu Asn Leu Met
1               5                   10                  15

Phe Leu Gly Ser Phe Asn Leu Gln Pro Thr Val Asn Thr Asn Lys Asp
            20                  25                  30

Ser Glu Ile Asp Ala His Lys
        35

<210> SEQ ID NO 258
<211> LENGTH: 23
<212> TYPE: DNA
<213> ORGANISM: Artificial Sequence
<220> FEATURE:
<223> OTHER INFORMATION: synthetic Enterobacteria phage K1F RNA
      polymerase (RNAP) promoter sequence

<400> SEQUENCE: 258
taataactat cactataggg aga                                          23

<210> SEQ ID NO 259
<211> LENGTH: 39
<212> TYPE: PRT
<213> ORGANISM: Artificial Sequence
<220> FEATURE:
<223> OTHER INFORMATION: synthetic Enterobacteria phage N4 RNA
      polymerase (RNAP) specificity loop sequence

<400> SEQUENCE: 259

Val Trp Gln Glu Tyr Lys Lys Pro Ile Gln Thr Arg Ile Asp Cys Val
1               5                   10                  15

Ile Leu Gly Thr His Arg Met Ala Leu Thr Ile Asn Thr Asn Lys Asp
            20                  25                  30

Ser Glu Ile Asp Ala His Lys
        35

<210> SEQ ID NO 260
<211> LENGTH: 23
<212> TYPE: DNA
<213> ORGANISM: Artificial Sequence
<220> FEATURE:
<223> OTHER INFORMATION: synthetic Enterobacteria phage N4 RNA
      polymerase (RNAP) promoter sequence

<400> SEQUENCE: 260
taataaccca cactataggg aga                                           23

<210> SEQ ID NO 261
<211> LENGTH: 498
<212> TYPE: DNA
<213> ORGANISM: Salmonella typhimurium
<220> FEATURE:
<223> OTHER INFORMATION: transcriptional activator sicA

<400> SEQUENCE: 261
atggattatc aaaataatgt cagcgaagaa cgtgttgcgg aaatgatttg ggatgccgtt    60
agtgaaggcg ccacgctaaa agacgttcat gggatccctc aagatatgat ggacggttta   120
tatgctcatg cttatgagtt ttataaccag ggacgactgg atgaagctga cgttctttt   180 cgtttcttat gcatttatga tttttacaat cccgattaca ccatgggact ggcggcagta   240
tgccaactga aaaacaatt tcagaaagca tgtgaccttt atgcagtagc gtttacgtta   300
cttaaaaatg attatcgccc cgttttttt accgggcagt gtcaattatt aatgcgtaag   360
gcagcaaaag ccagacagtg ttttgaactt gtcaatgaac gtactgaaga tgagtctctg   420
cgggcaaaag cgttggtcta tctggaggcg ctaaaaacgg cggagacaga gcagcacagt   480
gaacaagaaa aggaataa                                                 498

<210> SEQ ID NO 262
<211> LENGTH: 498
<212> TYPE: DNA
<213> ORGANISM: Artificial Sequence
<220> FEATURE:
<223> OTHER INFORMATION: synthetic Salmonella typhimurium mutant
      transcriptional activator sicA*

<400> SEQUENCE: 262
atggattatc aaaataatgt cagcgaagaa cgtgttgcgg aaatgatttg ggatgccgtt    60
agtgaaggcg ccacgctaaa agacgttcat gggatccctc aagatatgat ggacggttta   120
tatgctcatg cttatgagtt ttataaccag ggacgactgg atgaagctga cgttctttt   180 cgttacttat gcatttatga tttttacaat cccgattaca ccatgggact ggcggcagta   240

```
tgccaactga aaaaacaatt tcagaaagca tgtgaccttt atgcagtagc gtttacgtta    300
cttaaaaatg attatcgccc cgttttttt  accgggcagt gtcaattatt aatgcgtaag    360
gcagcaaaag ccagacagtg ttttgaactt gtcaatgaac gtactgaaga tgagtctctg    420
cgggcaaaag cgttggtcta tctggaggcg ctaaaaacgg cggagacaga gcagcacagt    480
gaacaagaaa aggaataa                                                  498
```

<210> SEQ ID NO 263
<211> LENGTH: 750
<212> TYPE: DNA
<213> ORGANISM: Salmonella typhimurium
<220> FEATURE:
<223> OTHER INFORMATION: transcriptional activator invF with new start
      codon

<400> SEQUENCE: 263

```
atgctaaata cgcaggaagt acttaaagaa ggagagaagc ggaaaatccg cagcccggaa     60
gcatggttta tacagacgtg ttccgcgcaa aagctgcata tgtcattttc tgaaagccga    120
cacaatgaaa attgcctgat tcaggaaggc gcgctgcttt tttgcgagca ggccgttgtc    180
gcaccagtat caggagacct ggttttttcga ccgttaaaaa ttgaagtact cagcaaatta    240 ctggcatttta tcgatggcgc aggattagtg gacacgacat atgctgaatc cgataaatgg    300
gttttgctga gtcctgagtt tcgcgctatt tgcaagatc gtaaacgctg cgagtactgg    360
tttttgcagc aaattattac gccttctccg gccttcaata aggtactggc gctgttacga    420
aaaagcgaga gttactggtt ggttggctat ttactcgctc agtcaaccag cggcaacacg    480
atgagaatgc tgggagaaga ctatggcgtt tcttataccc attttcgtcg tttgtgcagc    540
agagcgttgg gcgaaaaagc gaagagtgaa ttacgaaact ggcgtatggc gcaatcgctg    600
ctgaatagtg tagaaggcca cgagaacatc acccaattag ccgttaatca tggttactca    660
tcgccttcac attttctag  tgagatcaaa gagctgatcg gcgtttcgcc gcggaaatta    720
tcaaatatta ttcaattggc agacaaatga                                    750
```

<210> SEQ ID NO 264
<211> LENGTH: 163
<212> TYPE: DNA
<213> ORGANISM: Artificial Sequence
<220> FEATURE:
<223> OTHER INFORMATION: synthetic promoter psicA

<400> SEQUENCE: 264

```
ccacaagaaa cgaggtacgg cattgagccg cgtaaggcag tagcgatgta ttcattgggc     60
gttttttgaa tgttcactaa ccaccgtcgg ggtttaataa ctgcatcaga taaacgcagt    120
cgttaagttc tacaaagtcg gtgacagata acaggagtaa gta                     163
```

<210> SEQ ID NO 265
<211> LENGTH: 468
<212> TYPE: DNA
<213> ORGANISM: Shigella flexneri
<220> FEATURE:
<223> OTHER INFORMATION: transcriptional activator ipgC

<400> SEQUENCE: 265

```
atgtctttaa atatcaccga aaatgaaagc atctctactg cagtaattga tgcaattaac     60
tctggcgcta cactgaaaga tattaatgca attcctgatg atatgatgga tgacatttat    120
tcatatgctt atgactttta caacaaagga agaatagagg aagctgaagt tttcttcagg    180
```

```
ttttatgta tatacgactt ttacaatgta gactacatta tgggactcgc agctatttat      240
cagataaaag aacagttcca acaagcagca gacctttatg ctgtcgcttt tgcattagga      300
aaaaatgact atacaccagt attccatact ggacaatgtc agcttcggtt gaaagccccc      360
ttaaaagcta aagagtgctt cgaactcgta attcaacaca gcaatgatga aaattaaaa       420 ataaaagcac aatcatactt ggacgcaatt caggatatca aggagtaa                   468
```

<210> SEQ ID NO 266
<211> LENGTH: 756
<212> TYPE: DNA
<213> ORGANISM: Artificial Sequence
<220> FEATURE:
<223> OTHER INFORMATION: synthetic codon optimized Shigella flexneri mxiE

<400> SEQUENCE: 266

```
atgagtaaat ataaaggcct gaacaccagc aacatgttct acatctacag ctctggtcat      60
gaaccggtga acgttgaact ggtgaaagat aaagaacgta acatcatcga actggcaccg     120
gcgtggaaag cttttttctt tgtgcgtaac cagaacatca aattcagcga taacgttaac     180
taccactacc gcttcaacat caactcttgc gcaaaattcc tggcgttttg ggattatttt     240
agcggcgccc tggttgaaca ttctcacgca gaaaaatgca tccatttcta ccacgaaaac     300
gatctgcgtg atagctgtaa tacgaatct atgctggata aactgatgct gcgcttcatt      360
tttagtagcg atcagaacgt gtctaatgcc ctggcaatga tccgtatgac cgaaagttat     420
catctggttc tgtacctgct gcgtacgatt gaaaagaaa aagaagtgcg catcaaaagc      480
ctgaccgaac actatggcgt ttctgaagcg tactttcgta gtctgtgtcg caaagcgctg     540
ggtgccaaag tgaaagaaca gctgaacacg tggcgcctgg tgaatggcct gctggatgtt     600
ttcctgcata ccagaccat tacgagcgcg gccatgaaca tggttatgc gtctaccagt       660 cacttcagca tgaaattaa aacgcgtctg ggctttagtg cccgcgaact gagcaacatc      720
accttcctgg tgaagaaaat taatgaaaaa atctaa                               756
```

<210> SEQ ID NO 267
<211> LENGTH: 350
<212> TYPE: DNA
<213> ORGANISM: Artificial Sequence
<220> FEATURE:
<223> OTHER INFORMATION: synthetic promoter pipaH9.8

<400> SEQUENCE: 267

```
gcgaaaatga catcaaaaac gccattaacc tgatgttctg gggaatataa atgtcaggct      60
agggtcaaaa atcgtggcgt tgacaaaatg gctgcgttac gtcattgagc atatccagga     120
ctggccggca aaccgggtac gcgatctgtt gccttggaaa gttgatctga cctctcagta     180
aatatcaata cggttctgac gagccgctta ccgttcaaat atgaagtacg atgtttaact     240
aaccgaaaaa caagaacaat acggtgcaaa caggccattc acggttaact gaaacagtat     300
cgttttttta cagccaattt tgtttatcct tattataata aaaaagtgct                 350
```

<210> SEQ ID NO 268
<211> LENGTH: 350
<212> TYPE: DNA
<213> ORGANISM: Artificial Sequence
<220> FEATURE:
<223> OTHER INFORMATION: synthetic promoter pipaH9.8* with mutation

<400> SEQUENCE: 268

```
gcgaaaatga catcaaaaac gccattaacc tgatgttctg gggaatataa atgtcaggct    60
agggtcaaaa atcgtggcgt tgacaaaatg gctgcgttac gtcattgagc atatccagga   120
ctggccggca aaccgggtac gcgatctgtt gccttggaaa gttgatctga cctctcagta   180
aatatcaata cggttctgac gagccgctta ccgttcaaat atgaagtacg atgtttaact   240
aaccgaaaaa caagaacaat acggtgcaaa caggccattc acggttaact gaaacagtat   300
cgttttttta cagccaattt tgtttatcct tattaagata aaaagtgct                350
```

<210> SEQ ID NO 269
<211> LENGTH: 438
<212> TYPE: DNA
<213> ORGANISM: Pseudomonas aeruginosa
<220> FEATURE:
<223> OTHER INFORMATION: transcriptional activator exsC

<400> SEQUENCE: 269

```
atggatttaa cgagcaaggt caaccgactg cttgccgagt tcgcaggccg tatcggtttg    60
ccttccctgt ccctcgacga ggagggcatg gcgagcctcc tgttcgacga acaggtgggc   120
gtcaccctgt tgctgctcgc cgagcgcgag cgtctgttgc tggaggccga tgtggcgggc   180
atcgatgtgc tgggcgaggg gatctttcgc cagctcgcca gcttcaaccg ccattggcac   240
cgtttcgatc tgcatttcgg cttcgacgag ctgaccggca aggtccagtt gtatgcgcag   300
attctcgcag cgcaactgac cctcgaatgc ttcgaggcga ccttggccaa tctgctcgat   360
cacgccgagt tctggcagcg cctgctgccg tgcgacagtg atcgcgaggc ggtcgctgcg   420
gtcggcatga gggtttga                                                  438
```

<210> SEQ ID NO 270
<211> LENGTH: 831
<212> TYPE: DNA
<213> ORGANISM: Pseudomonas aeruginosa
<220> FEATURE:
<223> OTHER INFORMATION: transcriptional activator exsD

<400> SEQUENCE: 270

```
atggagcagg aagacgataa gcagtactcc cgagaagcgg tgttcgctgg caggcgggta    60
tccgtggtgg gctcggacgc ccgctcgcgg ggtcgggtgc cgggttacgc atcgagcagt   120
ttgtatcgtg agtccggaat catcagtgcg cggcaactgg cgttgctgca gcggatgctg   180
ccgcgcctgc ggctggagca actgttccgc tgcgagtggt tgcagcagcg cctggcgcgc   240
ggcctggcgc tggggcgcga agaggtgcgg cagattctcc tctgcgcggc gcaggacgac   300
gacggctggt gctccgaact gggcgaccgg gtcaacctcg ccgtgccgca gtcgatgatc   360
gactgggtcc tgctgccggt ctatggctgg tgggaaagcc tgctcgacca ggcgatcccc   420
ggctggcgcc tgtcgctggt ggagctggag acccagtccc ggcaactgcg agtcaagtcc   480
gaattctggt cccgcgtggc cgagctggag ccggagcagg cccgcgagga actggccagg   540
gtcgccaagt gccaggcgcg cacccaggaa caggtggccg aactggccgg caagctggag   600
acggcttcgg cactggcgaa gagcgcctgg ccgaactggc agcggggcat ggcgacgctg   660
ctcgccagcg gcgggctggc cggcttcgag ccgatccccg aggtcctcga atgcctctgg   720
caacctctct gccggctgga cgacgacgtc ggcgcggcgg acgccgtcca ggcctggctg   780
cacgaacgca acctgtgcca ggcacaggat cacttctact ggcagagctg a             831
```

<210> SEQ ID NO 271

```
<211> LENGTH: 837
<212> TYPE: DNA
<213> ORGANISM: Pseudomonas aeruginosa
<220> FEATURE:
<223> OTHER INFORMATION: transcriptional activator exsA

<400> SEQUENCE: 271
atgcaaggag ccaaatctct tggccgaaag cagataacgt cttgtcattg gaacattcca      60
actttcgaat acagggtaaa caaggaagag ggcgtatatg ttctgctcga gggcgaactg     120
accgtccagg acatcgattc cacttttgc ctggcgcctg gcgagttgct tttcgtccgc      180
cgcggaagct atgtcgtaag taccaaggga aggacagcc gaatactctg gattccatta     240
tctgcccagt ttctacaagg cttcgtccag cgcttcggcg cgctgttgag tgaagtcgag     300
cgttgcgacg agcccgtgcc gggcatcatc gcgttcgctg ccacgcctct gctggccggt     360
tgcgtcaagg ggttgaagga attgcttgtg catgagcatc cgccgatgct cgcctgcctg     420
aagatcgagg agttgctgat gctcttcgcg ttcagtccgc aggggccgct gctgatgtcg     480
gtcctgcggc aactgagcaa ccggcatgtc gagcgtctgc agctattcat ggagaagcac     540
tacctcaacg agtggaagct gtccgacttc tcccgcgagt tcggcatggg gctgaccacc     600
ttcaaggagc tgttcggcag tgtctatggg gtttcgccgc gcgcctggat cagcgagcgg     660
agaatcctct atgcccatca gttgctgctc aacagcgaca tgagcatcgt cgacatcgcc     720
atggaggcgg gcttttccag tcagtcctat ttcacccaga gctatcgccg ccgtttcggc     780
tgcacgccga ccgctcgcg gcaggggaag gacgaatgcc gggctaaaaa taactga        837

<210> SEQ ID NO 272
<211> LENGTH: 80
<212> TYPE: DNA
<213> ORGANISM: Artificial Sequence
<220> FEATURE:
<223> OTHER INFORMATION: synthetic pesxD promoter

<400> SEQUENCE: 272
gaaggacgaa tgccgggcta aaataactg acgttttttg aaagcccggt agcggctgca      60
tgagtagaat cggcccaaat                                                 80

<210> SEQ ID NO 273
<211> LENGTH: 80
<212> TYPE: DNA
<213> ORGANISM: Artificial Sequence
<220> FEATURE:
<223> OTHER INFORMATION: synthetic pexsC promoter

<400> SEQUENCE: 273
gatgtggctt ttttcttaaa agaaaagtct ctcagtgaca aaagcgatgc atagcccggt      60
gctagcatgc gctgagcttt                                                 80

<210> SEQ ID NO 274
<211> LENGTH: 702
<212> TYPE: DNA
<213> ORGANISM: Artificial Sequence
<220> FEATURE:
<223> OTHER INFORMATION: synthetic red fluorescence protein (rfp, RFP)

<400> SEQUENCE: 274
atggcttcct ccgaagacgt tatcaaagag ttcatgcgtt tcaaagttcg tatggaaggt      60
tccgttaacg gtcacgagtt cgaaatcgaa ggtgaaggtg aaggtcgtcc gtacgaaggt     120
acgcagaccg ctaaactgaa agttaccaaa ggtggtccgc tgccgttcgc ttgggacatc     180
```

```
ctgtccccgc agttccagta cggttccaaa gcttacgtta acacccggc tgacatcccg      240 gactacctga aactgtcctt cccggaaggt ttcaaatggg aacgtgttat gaacttcgaa      300
gacggtggtg ttgttaccgt tacccaggac tcctccctgc aagacggtga gttcatctac      360
aaagttaaac tgcgtggtac taacttcccg tccgacggtc cggttatgca gaaaaaaacc      420
atgggttggg aagcttccac cgaacgtatg tacccggaag acggtgctct gaaaggtgaa      480
atcaaaatgc gtctgaaact gaaagacggt ggtcactacg acgctgaagt taaaaccacc      540
tacatggcta aaaaccggt tcagctgccg ggtgcttaca aaccgacat caaactggac       600 atcacctccc acaacgaaga ctacaccatc gttgaacagt acgaacgtgc tgaaggtcgt      660
cactccaccg gtgctgcagc aaacgacgaa aactacgctt aa                        702
```

<210> SEQ ID NO 275
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 275

```
agttcgatga gagcgataac cctctacaaa taattttgtt taa                        43
```

<210> SEQ ID NO 276
<211> LENGTH: 42
<212> TYPE: DNA
<213> ORGANISM: Artificial Sequence
<220> FEATURE:
<223> OTHER INFORMATION: synthetic T5 phage buffer sequence

<400> SEQUENCE: 276

```
ataaattgat aaacaaaaac ctctacaaat aattttgttt aa                         42
```

<210> SEQ ID NO 277
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 277

```
ataaatttga gagaggagtt cctctacaaa taattttgtt taa                        43
```

<210> SEQ ID NO 278
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 278

```
attaaagagg agaaattaac cctctacaaa taattttgtt taa                        43
```

<210> SEQ ID NO 279
<211> LENGTH: 43
<212> TYPE: DNA
<213> ORGANISM: Artificial Sequence
<220> FEATURE:
<223> OTHER INFORMATION: synthetic T7 phage buffer sequence

<400> SEQUENCE: 279

```
aaacctaatg gatcgacctt cctctacaaa taattttgtt taa                        43
```

```
<210> SEQ ID NO 280
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 280
atcgagaggg acacggcgac ctctacaaat aattttgttt aa                        42

<210> SEQ ID NO 281
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 281
gctaggtaac actagcagcc ctctacaaat aattttgttt aa                        42

<210> SEQ ID NO 282
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 282
atgaaacgac agtgagtcac ctctacaaat aattttgttt aa                        42

<210> SEQ ID NO 283
<211> LENGTH: 43
<212> TYPE: DNA
<213> ORGANISM: Artificial Sequence
<220> FEATURE:
<223> OTHER INFORMATION: synthetic T7 phage buffer sequence

<400> SEQUENCE: 283
agggagacca caacggtttc cctctacaaa taattttgtt taa                       43

<210> SEQ ID NO 284
<211> LENGTH: 43
<212> TYPE: DNA
<213> ORGANISM: Artificial Sequence
<220> FEATURE:
<223> OTHER INFORMATION: synthetic high-transcription escape buffer
      sequence

<400> SEQUENCE: 284
attaaaaaac ctgctaggat cctctacaaa taattttgtt taa                       43

<210> SEQ ID NO 285
<211> LENGTH: 43
<212> TYPE: DNA
<213> ORGANISM: Artificial Sequence
<220> FEATURE:
<223> OTHER INFORMATION: synthetic high-transcription escape buffer
      sequence

<400> SEQUENCE: 285
ataaaggaaa acggtcaggt cctctacaaa taattttgtt taa                       43

<210> SEQ ID NO 286
<211> LENGTH: 43
<212> TYPE: DNA
<213> ORGANISM: Artificial Sequence
```

```
<220> FEATURE:
<223> OTHER INFORMATION: synthetic high-transcription escape buffer
      sequence

<400> SEQUENCE: 286
ataggttaaa agcctgtcat cctctacaaa taattttgtt taa                    43

<210> SEQ ID NO 287
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 287
acaataaaaa atcatttaca tgtttcctct acaaataatt ttgtttaa               48

<210> SEQ ID NO 288
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 288
agaagcagcg cgcaaaaatc agctgcctct acaaataatt ttgtttaa               48

<210> SEQ ID NO 289
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 289
atgagttcat ttcagacagg caaatcctct acaaataatt ttgtttaa               48

<210> SEQ ID NO 290
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 290
aacttgcagt tatttactgt gattacctct acaaataatt ttgtttaa               48

<210> SEQ ID NO 291
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 291
agccacaaaa aaagtcatgt tggttcctct acaaataatt ttgtttaa               48

<210> SEQ ID NO 292
<211> LENGTH: 53
<212> TYPE: DNA
<213> ORGANISM: Artificial Sequence
<220> FEATURE:
<223> OTHER INFORMATION: synthetic carbon utilization buffer sequence

<400> SEQUENCE: 292
acacagtcac ttatctttta gttaaaaggt cctctacaaa taattttgtt taa         53
```

<210> SEQ ID NO 293
<211> LENGTH: 43
<212> TYPE: DNA
<213> ORGANISM: Artificial Sequence
<220> FEATURE:
<223> OTHER INFORMATION: synthetic anti-escaping buffer sequence

<400> SEQUENCE: 293
atccggaatc ctcttcccgg cctctacaaa taattttgtt taa                    43

<210> SEQ ID NO 294
<211> LENGTH: 48
<212> TYPE: DNA
<213> ORGANISM: Artificial Sequence
<220> FEATURE:
<223> OTHER INFORMATION: synthetic anti-escaping buffer sequence

<400> SEQUENCE: 294
aacaaaataa aaaggagtcg ctcaccctct acaaataatt ttgtttaa               48

<210> SEQ ID NO 295
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 295
agttcgatga gagcgataac agttccagat tcaggaacta taa                    43

<210> SEQ ID NO 296
<211> LENGTH: 42
<212> TYPE: DNA
<213> ORGANISM: Artificial Sequence
<220> FEATURE:
<223> OTHER INFORMATION: synthetic T5 phage buffer sequence

<400> SEQUENCE: 296
ataaattgat aaacaaaaaa gttccagatt caggaactat aa                     42

<210> SEQ ID NO 297
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 297
ataaatttga gagaggagtt agttccagat tcaggaacta taa                    43

<210> SEQ ID NO 298
<211> LENGTH: 43
<212> TYPE: DNA
<213> ORGANISM: Artificial Sequence
<220> FEATURE:
<223> OTHER INFORMATION: synthetic T5 phage buffer sequence

<400> SEQUENCE: 298
attaaagagg agaaattaac agttccagat tcaggaacta taa                    43

<210> SEQ ID NO 299
<211> LENGTH: 43
<212> TYPE: DNA
<213> ORGANISM: Artificial Sequence
<220> FEATURE:

```
<223> OTHER INFORMATION: synthetic T5 phage buffer sequence

<400> SEQUENCE: 299
aaacctaatg gatcgacctt agttccagat tcaggaacta taa          43

<210> SEQ ID NO 300
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 300
atcgagaggg acacggcgaa gttccagatt caggaactat aa           42

<210> SEQ ID NO 301
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 301
gctaggtaac actagcagca gttccagatt caggaactat aa           42

<210> SEQ ID NO 302
<211> LENGTH: 42
<212> TYPE: DNA
<213> ORGANISM: Artificial Sequence
<220> FEATURE:
<223> OTHER INFORMATION: synthetic T7 phage buffer sequence

<400> SEQUENCE: 302
atgaaacgac agtgagtcaa gttccagatt caggaactat aa           42

<210> SEQ ID NO 303
<211> LENGTH: 43
<212> TYPE: DNA
<213> ORGANISM: Artificial Sequence
<220> FEATURE:
<223> OTHER INFORMATION: synthetic T7 phage buffer sequence

<400> SEQUENCE: 303
agggagacca caacggtttc agttccagat tcaggaacta taa          43

<210> SEQ ID NO 304
<211> LENGTH: 43
<212> TYPE: DNA
<213> ORGANISM: Artificial Sequence
<220> FEATURE:
<223> OTHER INFORMATION: synthetic high-transcription escape buffer
      sequence

<400> SEQUENCE: 304
attaaaaaac ctgctaggat agttccagat tcaggaacta taa          43

<210> SEQ ID NO 305
<211> LENGTH: 43
<212> TYPE: DNA
<213> ORGANISM: Artificial Sequence
<220> FEATURE:
<223> OTHER INFORMATION: synthetic high-transcription escape buffer
      sequence

<400> SEQUENCE: 305
ataaaggaaa acggtcaggt agttccagat tcaggaacta taa          43
```

<210> SEQ ID NO 306
<211> LENGTH: 43
<212> TYPE: DNA
<213> ORGANISM: Artificial Sequence
<220> FEATURE:
<223> OTHER INFORMATION: synthetic high-transcription escape buffer
      sequence

<400> SEQUENCE: 306
ataggttaaa agcctgtcat agttccagat tcaggaacta taa                    43

<210> SEQ ID NO 307
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 307
acaataaaaa atcatttaca tgtttagttc cagattcagg aactataa               48

<210> SEQ ID NO 308
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 308
agaagcagcg cgcaaaaatc agctgagttc cagattcagg aactataa               48

<210> SEQ ID NO 309
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 309
atgagttcat ttcagacagg caaatagttc cagattcagg aactataa               48

<210> SEQ ID NO 310
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 310
aacttgcagt tatttactgt gattaagttc cagattcagg aactataa               48

<210> SEQ ID NO 311
<211> LENGTH: 48
<212> TYPE: DNA
<213> ORGANISM: Artificial Sequence
<220> FEATURE:
<223> OTHER INFORMATION: synthetic carbon utilization buffer sequence

<400> SEQUENCE: 311
agccacaaaa aaagtcatgt tggttagttc cagattcagg aactataa               48

<210> SEQ ID NO 312
<211> LENGTH: 53
<212> TYPE: DNA
<213> ORGANISM: Artificial Sequence

```
<220> FEATURE:
<223> OTHER INFORMATION: synthetic carbon utilization buffer sequence

<400> SEQUENCE: 312
acacagtcac ttatctttta gttaaaaggt agttccagat tcaggaacta taa         53

<210> SEQ ID NO 313
<211> LENGTH: 43
<212> TYPE: DNA
<213> ORGANISM: Artificial Sequence
<220> FEATURE:
<223> OTHER INFORMATION: synthetic anti-escaping buffer sequence

<400> SEQUENCE: 313
atccggaatc ctcttcccgg agttccagat tcaggaacta taa                    43

<210> SEQ ID NO 314
<211> LENGTH: 48
<212> TYPE: DNA
<213> ORGANISM: Artificial Sequence
<220> FEATURE:
<223> OTHER INFORMATION: synthetic anti-escaping buffer sequence

<400> SEQUENCE: 314
aacaaaataa aaaggagtcg ctcacagttc cagattcagg aactataa               48

<210> SEQ ID NO 315
<211> LENGTH: 30
<212> TYPE: DNA
<213> ORGANISM: Artificial Sequence
<220> FEATURE:
<223> OTHER INFORMATION: synthetic stem loops buffer sequence

<400> SEQUENCE: 315
gatcaccagg gggatccccc ggtgaaggat                                   30

<210> SEQ ID NO 316
<211> LENGTH: 38
<212> TYPE: DNA
<213> ORGANISM: Artificial Sequence
<220> FEATURE:
<223> OTHER INFORMATION: synthetic stem loops buffer sequence

<400> SEQUENCE: 316
gatcgcccac cggcagctgc cggtgggcga tcaaggat                          38

<210> SEQ ID NO 317
<211> LENGTH: 45
<212> TYPE: DNA
<213> ORGANISM: Artificial Sequence
<220> FEATURE:
<223> OTHER INFORMATION: synthetic stem loops buffer sequence

<400> SEQUENCE: 317
gatcatcggt agagttaata ttgagcagat cccccggtga aggat                  45

<210> SEQ ID NO 318
<211> LENGTH: 36
<212> TYPE: DNA
<213> ORGANISM: Artificial Sequence
<220> FEATURE:
<223> OTHER INFORMATION: synthetic stem loops buffer sequence

<400> SEQUENCE: 318
attgatctgg ttattaaagg taatcgggtc atttta                            36
```

<210> SEQ ID NO 319
<211> LENGTH: 41
<212> TYPE: DNA
<213> ORGANISM: Artificial Sequence
<220> FEATURE:
<223> OTHER INFORMATION: synthetic stem loops buffer sequence

<400> SEQUENCE: 319
gttctccacg ggtgggatga gcccctcgtg gtggaaatgc g       41

<210> SEQ ID NO 320
<211> LENGTH: 27
<212> TYPE: DNA
<213> ORGANISM: Artificial Sequence
<220> FEATURE:
<223> OTHER INFORMATION: synthetic stem loops buffer sequence

<400> SEQUENCE: 320
agcatgaggt aaagtgtcat gcaccaa       27

<210> SEQ ID NO 321
<211> LENGTH: 38
<212> TYPE: DNA
<213> ORGANISM: Artificial Sequence
<220> FEATURE:
<223> OTHER INFORMATION: synthetic stem loops buffer sequence

<400> SEQUENCE: 321
acgtcgactt atctcgagtg agatattgtt gacggtac       38

<210> SEQ ID NO 322
<211> LENGTH: 37
<212> TYPE: DNA
<213> ORGANISM: Artificial Sequence
<220> FEATURE:
<223> OTHER INFORMATION: synthetic stem loops buffer sequence

<400> SEQUENCE: 322
acgtcgactt atctcgagtg agataagttg acggtac       37

<210> SEQ ID NO 323
<211> LENGTH: 51
<212> TYPE: DNA
<213> ORGANISM: Artificial Sequence
<220> FEATURE:
<223> OTHER INFORMATION: synthetic stem loops buffer sequence

<400> SEQUENCE: 323
acgtcgactt atctcgagac tgcagttcaa tagagatatt gttgacggta c       51

<210> SEQ ID NO 324
<211> LENGTH: 52
<212> TYPE: DNA
<213> ORGANISM: Artificial Sequence
<220> FEATURE:
<223> OTHER INFORMATION: synthetic stem loops (ribozyme) buffer sequence

<400> SEQUENCE: 324
gactgtcacc ggatgtgctt tccggtctga tgagtccgtg aggacgaaac ag       52

<210> SEQ ID NO 325
<211> LENGTH: 53
<212> TYPE: DNA
<213> ORGANISM: Artificial Sequence
<220> FEATURE:
<223> OTHER INFORMATION: synthetic stem loops buffer sequence

<400> SEQUENCE: 325
gatcaccagg gggatccccc ggtgaaggat cctctacaaa taattttgtt taa         53

<210> SEQ ID NO 326
<211> LENGTH: 61
<212> TYPE: DNA
<213> ORGANISM: Artificial Sequence
<220> FEATURE:
<223> OTHER INFORMATION: synthetic stem loops buffer sequence

<400> SEQUENCE: 326
gatcgcccac cggcagctgc cggtgggcga tcaaggatcc tctacaaata attttgttta    60
a                                                                    61

<210> SEQ ID NO 327
<211> LENGTH: 68
<212> TYPE: DNA
<213> ORGANISM: Artificial Sequence
<220> FEATURE:
<223> OTHER INFORMATION: synthetic stem loops buffer sequence

<400> SEQUENCE: 327
gatcatcggt agagttaata ttgagcagat cccccggtga aggatcctct acaaataatt    60
ttgtttaa                                                             68

<210> SEQ ID NO 328
<211> LENGTH: 59
<212> TYPE: DNA
<213> ORGANISM: Artificial Sequence
<220> FEATURE:
<223> OTHER INFORMATION: synthetic stem loops buffer sequence

<400> SEQUENCE: 328
attgatctgg ttattaaagg taatcgggtc attttacctc tacaaataat tttgtttaa    59

<210> SEQ ID NO 329
<211> LENGTH: 64
<212> TYPE: DNA
<213> ORGANISM: Artificial Sequence
<220> FEATURE:
<223> OTHER INFORMATION: synthetic stem loops buffer sequence

<400> SEQUENCE: 329
gttctccacg ggtgggatga gcccctcgtg gtggaaatgc gcctctacaa ataattttgt    60
ttaa                                                                 64

<210> SEQ ID NO 330
<211> LENGTH: 50
<212> TYPE: DNA
<213> ORGANISM: Artificial Sequence
<220> FEATURE:
<223> OTHER INFORMATION: synthetic stem loops buffer sequence

<400> SEQUENCE: 330
agcatgaggt aaagtgtcat gcaccaacct ctacaaataa ttttgtttaa              50

<210> SEQ ID NO 331
<211> LENGTH: 61
<212> TYPE: DNA
<213> ORGANISM: Artificial Sequence
<220> FEATURE:
<223> OTHER INFORMATION: synthetic stem loops buffer sequence

```
<400> SEQUENCE: 331
acgtcgactt atctcgagtg agatattgtt gacggtaccc tctacaaata attttgttta      60
a                                                                      61

<210> SEQ ID NO 332
<211> LENGTH: 60
<212> TYPE: DNA
<213> ORGANISM: Artificial Sequence
<220> FEATURE:
<223> OTHER INFORMATION: synthetic stem loops buffer sequence

<400> SEQUENCE: 332
acgtcgactt atctcgagtg agataagttg acggtaccct ctacaaataa ttttgtttaa      60

<210> SEQ ID NO 333
<211> LENGTH: 74
<212> TYPE: DNA
<213> ORGANISM: Artificial Sequence
<220> FEATURE:
<223> OTHER INFORMATION: synthetic stem loops buffer sequence

<400> SEQUENCE: 333
acgtcgactt atctcgagac tgcagttcaa tagagatatt gttgacggta ccctctacaa      60
ataattttgt ttaa                                                        74

<210> SEQ ID NO 334
<211> LENGTH: 75
<212> TYPE: DNA
<213> ORGANISM: Artificial Sequence
<220> FEATURE:
<223> OTHER INFORMATION: synthetic stem loops (ribozyme) buffer sequence

<400> SEQUENCE: 334
gactgtcacc ggatgtgctt tccggtctga tgagtccgtg aggacgaaac agcctctaca      60
aataattttg tttaa                                                       75

<210> SEQ ID NO 335
<211> LENGTH: 72
<212> TYPE: DNA
<213> ORGANISM: Artificial Sequence
<220> FEATURE:
<223> OTHER INFORMATION: synthetic Ptac controller #1 promoter sequence,
      Ptac (SBa_00512 sequence

<400> SEQUENCE: 335
tattctgaaa tgagctgttg acaattaatc atcggctcgt ataatgtgtg gaattgtgag      60
cggataacaa tt                                                          72

<210> SEQ ID NO 336
<211> LENGTH: 75
<212> TYPE: DNA
<213> ORGANISM: Artificial Sequence
<220> FEATURE:
<223> OTHER INFORMATION: synthetic controller #3 promoter sequence, Ptac
      plus OR1 and OR2 (SBa_000506) sequence

<400> SEQUENCE: 336
tattaacacc gtgcgtgttg acagctatac ctctggcggt tataatgcta gcggaattgt      60
gagcggataa caatt                                                       75

<210> SEQ ID NO 337
<211> LENGTH: 36
```

<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (21)...(28)
<223> OTHER INFORMATION: n = g, a, c or t

<400> SEQUENCE: 337
cttgggcacg cgtccattaa nnaggannaa ttaagc     36

<210> SEQ ID NO 338
<211> LENGTH: 36
<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (19)...(26)
<223> OTHER INFORMATION: n = g, a, c or t

<400> SEQUENCE: 338
tgggcacgcg tccattaann aggannaatt attagc     36

<210> SEQ ID NO 339
<211> LENGTH: 36
<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (23)...(30)
<223> OTHER INFORMATION: n = g, a, c or t

<400> SEQUENCE: 339
tacttgggca cgcgtccatt aannaggann aatagc     36

<210> SEQ ID NO 340
<211> LENGTH: 36
<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (21)...(28)
<223> OTHER INFORMATION: n = g, a, c or t

<400> SEQUENCE: 340
cttgggcacg cgtccattaa naaggagnaa ttaagc     36

<210> SEQ ID NO 341
<211> LENGTH: 36
<212> TYPE: DNA
<213> ORGANISM: Artificial Sequence
<220> FEATURE:
<223> OTHER INFORMATION: synthetic randomized sequence
<220> FEATURE:
<221> NAME/KEY: modified_base
<222> LOCATION: (20)...(29)
<223> OTHER INFORMATION: n = g, a, c or t

<400> SEQUENCE: 341
cttgggcacg cgtccattan taaggaggna ttaagc     36

<210> SEQ ID NO 342

```
<211> LENGTH: 34
<212> TYPE: DNA
<213> ORGANISM: Artificial Sequence
<220> FEATURE:
<223> OTHER INFORMATION: synthetic weak ribosome binding site (RBS)
      (SBa_000507)

<400> SEQUENCE: 342
tatccaaacc agtagctcaa ttggagtcgt ctat                               34

<210> SEQ ID NO 343
<211> LENGTH: 123
<212> TYPE: DNA
<213> ORGANISM: Artificial Sequence
<220> FEATURE:
<223> OTHER INFORMATION: synthetic N-terminal degradation tag
      (SBa_000509)

<400> SEQUENCE: 343
ttgtttatca agcctgcgga tctccgcgaa attgtgactt ttccgctatt tagcgatctt    60
gttcagtgtg gctttccttc accggcagca gattacgttg aacagcgcat cgatctgggt   120
ggc                                                                123

<210> SEQ ID NO 344
<211> LENGTH: 41
<212> TYPE: DNA
<213> ORGANISM: Artificial Sequence
<220> FEATURE:
<223> OTHER INFORMATION: synthetic Enterobacteria phage T7 terminator
      seed sequence
<220> FEATURE:
<221> NAME/KEY: modified_base
<222> LOCATION: (3)...(16)
<223> OTHER INFORMATION: n = g, a, c or t

<400> SEQUENCE: 344
tannnaaccs swwssnssss tcwwwcgsss ssswwssgtt t                       41

<210> SEQ ID NO 345
<211> LENGTH: 15
<212> TYPE: DNA
<213> ORGANISM: Artificial Sequence
<220> FEATURE:
<223> OTHER INFORMATION: synthetic replacement sequence for 15bp
      upstream of start codon
<220> FEATURE:
<221> NAME/KEY: modified_base
<222> LOCATION: (1)...(15)
<223> OTHER INFORMATION: n = g, a, c or t

<400> SEQUENCE: 345
nnnaggaggn nnnnn                                                    15
```